US011040985B2

(12) United States Patent
Stafford et al.

(10) Patent No.: US 11,040,985 B2
(45) Date of Patent: Jun. 22, 2021

(54) CHEMICAL COMPOUNDS AS INHIBITORS OF INTERLEUKIN-1 ACTIVITY

(71) Applicant: Genentech, Inc., South San Francisco, CA (US)

(72) Inventors: Jeffrey A. Stafford, San Diego, CA (US); James M. Veal, Apex, NC (US); Lynnie Lin Trzoss, San Diego, CA (US); Christopher McBride, San Diego, CA (US)

(73) Assignee: Genentech, Inc., South San Francisco, CA (US)

( * ) Notice: Subject to any disclaimer, the term of this patent is extended or adjusted under 35 U.S.C. 154(b) by 21 days.

(21) Appl. No.: 16/513,621

(22) Filed: Jul. 16, 2019

(65) Prior Publication Data

US 2019/0337965 A1     Nov. 7, 2019

Related U.S. Application Data

(63) Continuation of application No. PCT/US2018/014728, filed on Jan. 22, 2018.

(60) Provisional application No. 62/449,431, filed on Jan. 23, 2017, provisional application No. 62/492,813, filed on May 1, 2017.

(51) Int. Cl.
*C07D 498/04* (2006.01)
*A61P 37/02* (2006.01)

(52) U.S. Cl.
CPC ............ *C07D 498/04* (2013.01); *A61P 37/02* (2018.01)

(58) Field of Classification Search
CPC ................................ C07D 498/04; A61P 37/02
See application file for complete search history.

(56) References Cited

U.S. PATENT DOCUMENTS

| 6,147,115 A | 11/2000 | Crowell et al. |
| 10,538,487 B2 | 1/2020 | O'Neill et al. |
| 2014/0221340 A1 | 7/2014 | Yamamoto et al. |
| 2019/0119203 A1 | 4/2019 | Glick et al. |
| 2019/0119224 A1 | 4/2019 | Glick et al. |
| 2019/0119241 A1 | 4/2019 | Glick et al. |

FOREIGN PATENT DOCUMENTS

| WO | 1998/032733 | 7/1998 |
| WO | 2001/019390 A1 | 3/2001 |
| WO | 2003/045400 A1 | 6/2003 |
| WO | 2011/102149 A1 | 8/2011 |
| WO | 2016/131098 A1 | 8/2016 |
| WO | 2017/140778 | 8/2017 |
| WO | 2017/184604 | 10/2017 |
| WO | 2017/184623 | 10/2017 |
| WO | 2017/184624 | 10/2017 |
| WO | 2018/215818 A1 | 11/2018 |
| WO | 2019/008025 A1 | 1/2019 |
| WO | 2019/008029 A1 | 1/2019 |
| WO | 2019/034686 | 2/2019 |
| WO | 2019/034688 A1 | 2/2019 |
| WO | 2019/034690 A1 | 2/2019 |
| WO | 2019/034692 A1 | 2/2019 |
| WO | 2019/034693 | 2/2019 |
| WO | 2019/034696 | 2/2019 |
| WO | 2019/034697 | 2/2019 |
| WO | 2019/092170 A1 | 5/2019 |
| WO | 2019/092171 | 5/2019 |
| WO | 2019/092172 | 5/2019 |
| WO | 2019/121691 | 6/2019 |
| WO | 2019/166619 | 9/2019 |
| WO | 2019/166621 | 9/2019 |
| WO | 2019/166623 | 9/2019 |
| WO | 2019/206871 | 10/2019 |
| WO | 2020/010143 | 1/2020 |
| WO | 2020/035464 | 2/2020 |
| WO | 2020/035465 | 2/2020 |
| WO | 2020/035466 | 2/2020 |
| WO | 2020/079207 | 4/2020 |
| WO | 2020/086732 | 4/2020 |
| WO | 2020/104657 | 5/2020 |

OTHER PUBLICATIONS

International Preliminary Report on Patentability—PCT/US2018/014728, pp. 1-6, dated Jul. 23, 2019.
International Search Report—PCT/US2018/014728, pp. 1-5, dated Mar. 20, 2018.
Baldwin et al., "Inhibiting the Inflammasome: A Chemical Perspective" J. Med. Chem. 59:1691-1710 (2016).
Hill et al., "Sulfonylureas as Concomitant Insulin Secretagogues and NLRP3 Inflammasome Inhibitors" Chem. Med. Chem. 12:1449-1457 ( 2017).
Shah et al., "Analysis of Pfizer Compounds in EPA's ToxCast Chemicals-Assay Space" Chem. Res. Toxicol. 27:86-98 ( 2014).
Howbert, J.J., et al., "Novel agents effective against solid tumors: The Diarylsulfonylureas. Synthesis, Activities, and Analysis of Quantitative Structure-Activity Relationships" J MED CHEM 33(9):2393-2407 (Sep. 1, 1990).

*Primary Examiner* — Rebecca L Anderson
(74) *Attorney, Agent, or Firm* — Katherine J. Mackenzie

(57) ABSTRACT

The present disclosure relates to novel sulfonylurea and sulfonyl thiourea compounds and related compounds and their use in treating a disease or condition responsive to modulation of cytokines such as IL-1β and IL-18, modulation of NLRP3 or inhibition of the activation of NLRP3 or related components of the inflammatory process.

74 Claims, 6 Drawing Sheets

CHEMICAL COMPOUNDS AS INHIBITORS OF INTERLEUKIN-1 ACTIVITY

CROSS REFERENCE TO RELATED APPLICATIONS

This application is a continuation of International Patent Application No. PCT/US2018/014728, filed Jan. 22, 2018, which claims the benefit of U.S. Provisional Application No. 62/449,431, filed Jan. 23, 2017 and of U.S. Provisional Application No. 62/492,813, filed May 1, 2017, the contents of which are incorporated herein by reference in their entireties.

FIELD OF DISCLOSURE

The present disclosure relates to novel sulfonylurea and sulfonyl thiourea compounds and related compounds and their use in treating a disease or condition responsive to modulation of cytokines such as IL-1β and IL-18, modulation of NLRP3, or inhibition of the activation of NLRP3 or related components of the inflammatory process.

BACKGROUND

The NOD-like receptor (NLR) family, pyrin domain-containing protein 3 (NLRP3) inflammasome is a component of the inflammatory process, and its aberrant activation is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular receptor protein that senses certain inflammatory signals. Upon activation, NLRP3 binds to apoptosis-associated speck-like protein containing a caspase activation and recruitment domain (ASC). The NLRP3-ASC complex then polymerizes to form a large aggregate known as an ASC speck. Polymerized NLRP3-ASC in turn interacts with the cysteine protease caspase-1 to form a complex termed the inflammasome. This results in the activation of caspase-1, which cleaves the proinflammatory cytokines IL-1β and IL-18 to their active forms and mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergize with IL-23 to induce IL-17 production by memory CD4 Th17 cells and by γδ T cells in the absence of T cell receptor engagement. IL-18 and IL-12 also synergize to induce IFN-γ production from memory T cells and NK cell driving a Th1 response.

Other intracellular pattern recognition receptors (PRRs) are also capable of forming inflammasomes. These include other NLR family members such as NLRP1 and NLRC4, as well as non-NLR PRRs such as the double-stranded DNA (dsDNA) sensors absent in melanoma 2 (AIM2) and interferon, gamma inducible protein 16 (IFI16). NLRP3-dependent IL-1β processing can also be activated by an indirect, non-canonical pathway downstream of caspase-11.

The inherited CAPS diseases Muckle-Wells syndrome (MWS), familial cold autoinflammatory syndrome and neonatal-onset multisystem inflammatory disease are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using mice with constitutive NLRP3 activation, but there have also been insights into the specific activation of NLRP3 in these diseases. In type 2 diabetes, the deposition of islet amyloid polypeptide in the pancreas activates NLRP3 and IL-1β signaling, resulting in cell death and inflammation.

There is a need to provide compounds with improved pharmacological and/or physiological and or physicochemical properties and/or those that provide a useful alternative to known compounds.

SUMMARY

The present disclosure provides compounds that are effective in the inhibition of an inflammasome, such as the NLRP3 inflammasome. The compounds are also effective in modulating of interleukins. The disclosed compounds have desirable molecular weights, physico-chemical properties, and lipophilicity, which are features that help with achieving therapeutic efficacy and decreasing unintended liabilities.

The present disclosure provides compounds of Formula I:

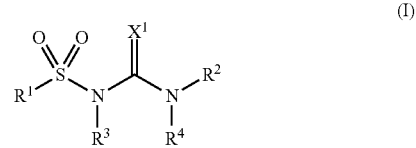

and pharmaceutically acceptable salts, prodrugs, solvates, hydrates, isomers, or tautomers thereof, wherein:

$X^1$ is O, S,

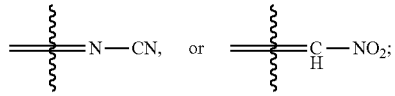

$R^1$ is selected from the group consisting of an optionally substituted $C_1$-$C_6$alkyl, optionally substituted $C_1$-$C_6$alkenyl, optionally substituted $C_1$-$C_6$alkynyl, —$(CH_2)_m$—O—$(CH_2)_m$—$CH_3$,

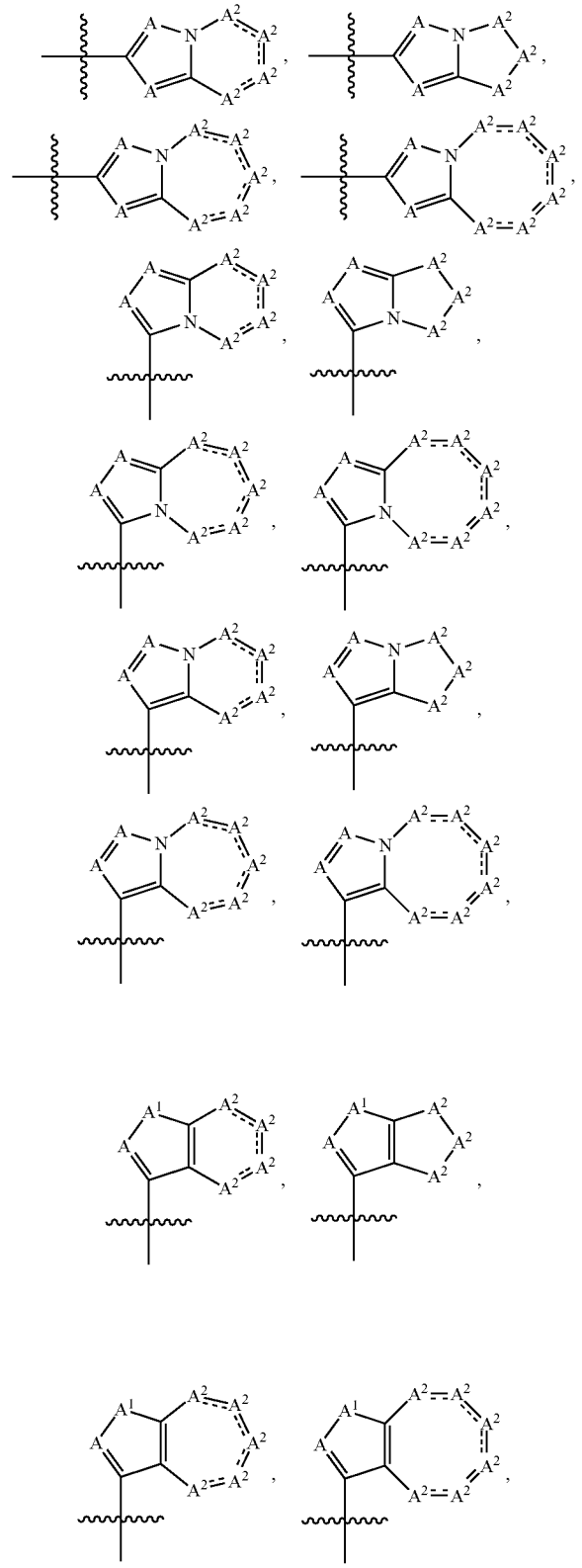

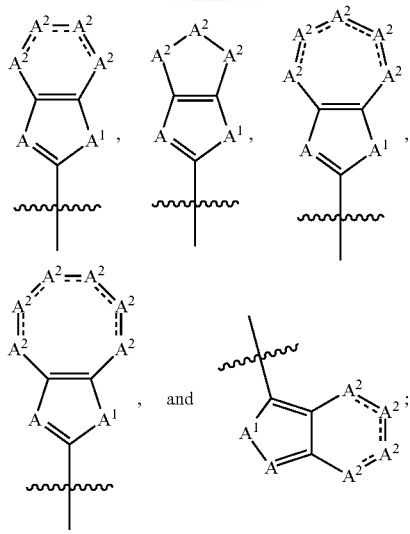

wherein ═══ represents a single bond or a double bond provided that the ring comprising one or more $A^2$ is a non-aromatic ring;

each A is independently $CR^5$ or N;

$A^1$ is $NR^5$, O, S, or C(O);

each $A^2$ is independently $CR^5$, $C(R^5)_2$, N, $NR^5$, O, S, or $S(O)_2$;

$R^2$ is

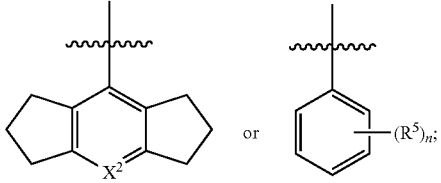

$X^2$ is N or $CR^5$;

$R^3$ and $R^4$ are H;

each $R^5$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; or two $R^5$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; or two geminal $R^5$ can form an oxo group;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^5$, O, S, or $S(O)_2$.

The present disclosure provides compounds of Formula Ia:

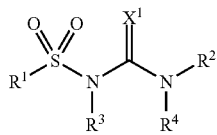
(Ia)

and pharmaceutically acceptable salts, prodrugs, solvates, hydrates, isomers, and tautomers thereof, wherein:

$X^1$ is O, S,

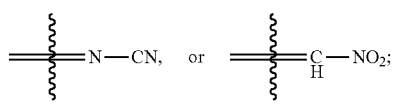

$R^1$ is selected from the group consisting of an optionally substituted $C_1$-$C_6$alkyl, optionally substituted $C_1$-$C_6$alkenyl, optionally substituted $C_1$-$C_6$alkynyl, —(CH$_2$)$_m$—O —(CH$_2$)$_m$—CH$_3$,

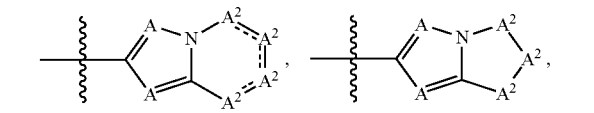

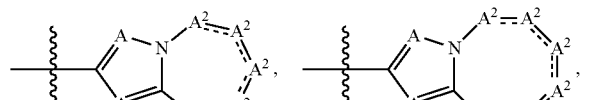

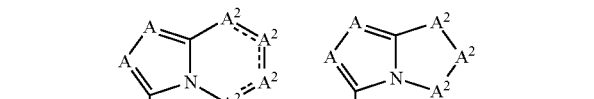

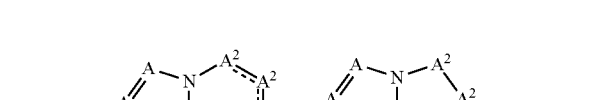

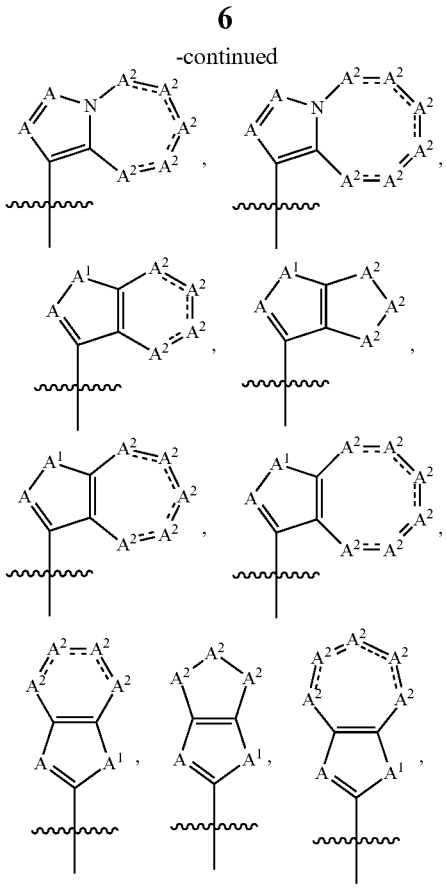

each A is independently $CR^{5a}$ or N;
$A^1$ is $NR^{5a}$, O, S, or C(O);
each $A^2$ is independently $CR^{5a}$, $C(R^{5a})_2$, N, $NR^{5a}$, O, S, or $S(O)_2$;
$R^2$ is

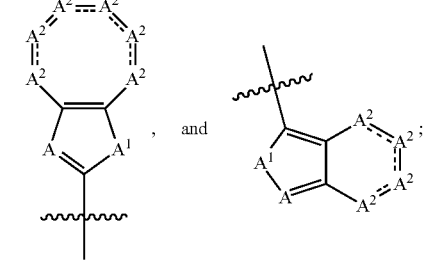

$X^2$ is N or $CR^{5b}$;
$R^3$ and $R^4$ are H;
each $R^{5a}$ is independently H, D, halogen, OH, CN, —NO$_2$, —SR$^6$, —OR$^6$, —NHR$^6$, —NR$^6$R$^7$, —S(O)$_2$N(R$^6$)$_2$—, —S(O)$_2$R$^6$, —C(O)R$^6$, —C(O)OR$^6$, —C(O)NR$^6$R$^7$, —NR$^6$S(O)$_2$R$^7$, —S(O)R$^6$, —S(O)NR$^6$R$^7$, —NR$^6$S(O)R$^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; or two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; or two geminal $R^{5a}$ can form an oxo group;

each $R^{5b}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; or two $R^{5b}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^{5a}$, O, S, or $S(O)_2$.

The present disclosure provides compounds of Formula Ib:

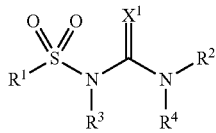

(Ib)

and pharmaceutically acceptable salts, prodrugs, solvates, hydrates, isomers, and tautomers thereof, wherein:

$X^1$ is O, S,

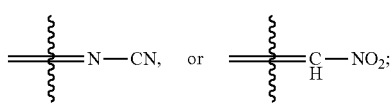

$R^1$ is selected from the group consisting of an optionally substituted $C_1$-$C_6$alkyl, optionally substituted $C_1$-$C_6$alkenyl, optionally substituted $C_1$-$C_6$alkynyl, —$(CH_2)_m$—O—$(CH_2)_m$—$CH_3$,

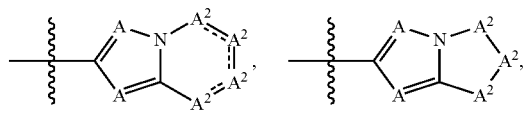

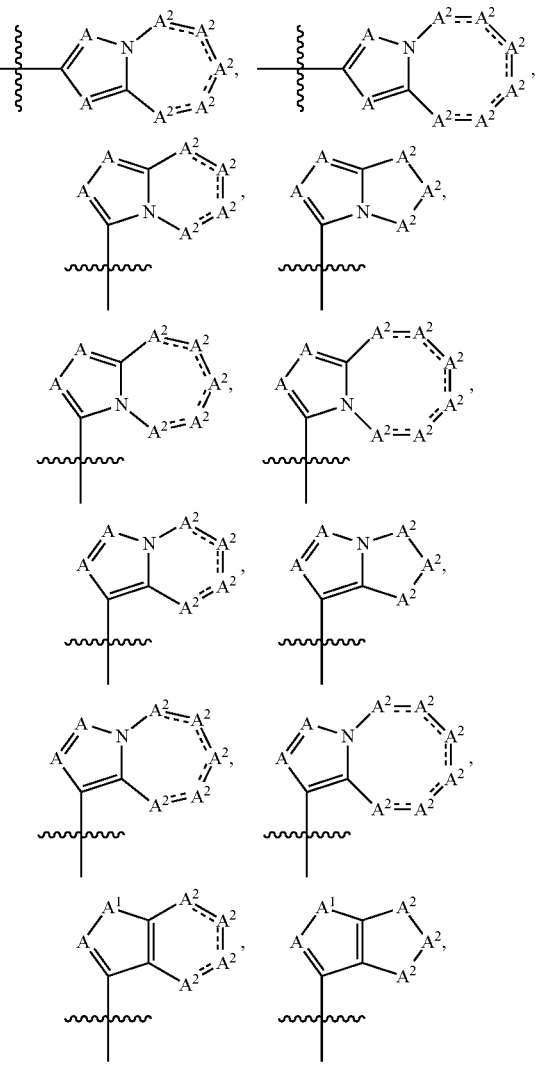

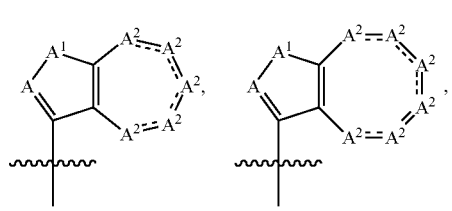

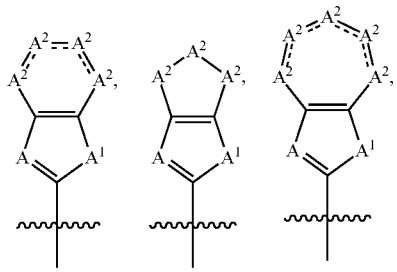

-continued

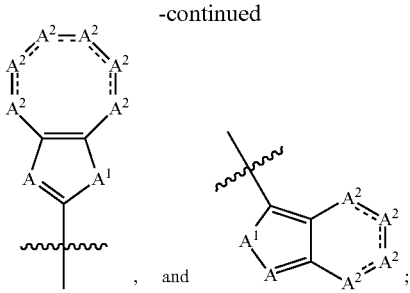

wherein ═ represents a single bond or a double bond provided that the ring comprising one or more $A^2$ is a non-aromatic ring;

each A is independently $CR^{5a}$ or N;

$A^1$ is $NR^{5a}$, O, S, or C(O);

each $A^2$ is independently $CR^{5a}$, $C(R^{5a})_2$, N, $NR^{5a}$, O, S, or $S(O)_2$;

$R^2$ is

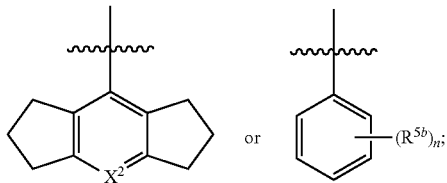

$X^2$ is N or $CR^{5b}$;

$R^3$ and $R^4$ are H;

each $R^{5a}$ is independently H, D, halogen, OH, CN, $-NO_2$, $-SR^6$, $-OR^6$, $-NHR^6$, $-NR^6R^7$, $-S(O)_2N(R^6)_2-$, $-S(O)_2R^6$, $-C(O)R^6$, $-C(O)OR^6$, $-C(O)NR^6R^7$, $-NR^6S(O)_2R^7$, $-S(O)R^6$, $-S(O)NR^6R^7$, $-NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2-C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2-C_3$-$C_8$cycloalkyl are optionally substituted with D, halogen, $C_1$-$C_6$alkyl, $-OR^6$, $-NH_2$, $-NH(C_1$-$C_6$alkyl), or $-N(C_1$-$C_6$alkyl)$_2$; or two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; wherein the $C_3$-$C_8$cycloalkyl, heterocyclyl, aryl, or heteroaryl are optionally substituted with D, halogen, $C_1$-$C_6$alkyl, $-OR^6$, $-NH_2$, $NH(C_1$-$C_6$alkyl), or $N(C_1$-$C_6$alkyl)$_2$; or two geminal $R^{5a}$ can form an oxo group;

each $R^{5b}$ is independently H, D, halogen, OH, CN, $-NO_2$, $-SR^6$, $-OR^6$, $-NHR^6$, $-NR^6R^7$, $-S(O)_2N(R^6)_2-$, $-S(O)_2R^6$, $-C(O)R^6$, $-C(O)OR^6$, $-C(O)NR^6R^7$, $-NR^6S(O)_2R^7$, $-S(O)R^6$, $-S(O)NR^6R^7$, $-NR^6S(O)R^7$, $C_1$-$C_6$alkyl, $C_2$-$C_6$alkenyl, $C_4$-$C_8$cycloalkenyl, or $C_2$-$C_6$alkynyl; wherein the $C_1$-$C_6$alkyl, $C_2$-$C_6$alkenyl, $C_4$-$C_8$cycloalkenyl, and $C_2$-$C_6$alkynyl are optionally substituted with D, halogen, $-OR^6$, $-NH_2$, $-NH(C_1$-$C_6$alkyl), or $-N(C_1$-$C_6$alkyl)$_2$;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; wherein the $C_1$-$C_6$alkyl, $C_2$-$C_8$alkenyl, $C_4$-$C_8$cycloalkenyl, $C_2$-$C_6$alkynyl, $C_3$-$C_8$cycloalkyl, heterocyclyl, aryl, and heteroaryl are optionally substituted with D, halogen, $C_1$-$C_6$alkyl, $-OH$, $-O-C_1$-$C_6$alkyl, $-NH_2$, $-NH(C_1$-$C_6$alkyl), or $-N(C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^{5a}$, O, S, or $S(O)_2$.

The present disclosure provides compounds of Formula Ic:

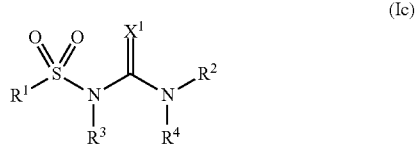

(Ic)

and pharmaceutically acceptable salts, prodrugs, solvates, hydrates, isomers, and tautomers thereof, wherein:

$X^1$ is O, S,

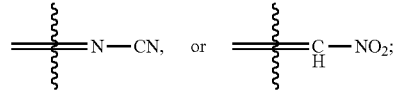

$R^1$ is selected from the group consisting of an optionally substituted $C_1$-$C_6$alkyl, optionally substituted $C_1$-$C_6$alkenyl, optionally substituted $C_1$-$C_6$alkynyl, $-(CH_2)_m-O-(CH_2)_m-CH_3$,

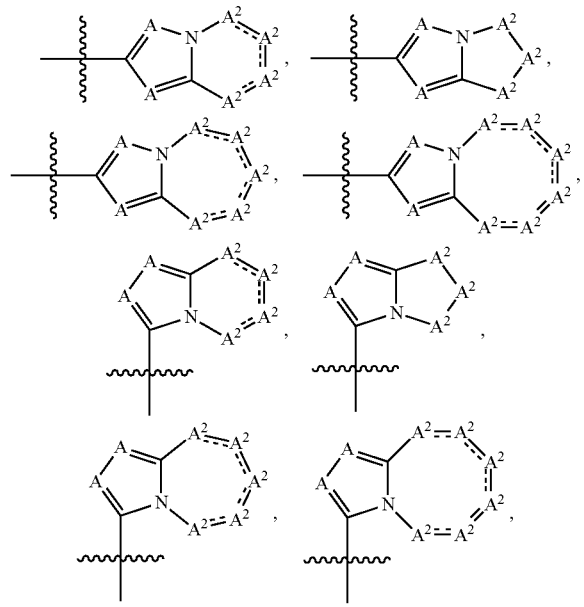

-continued

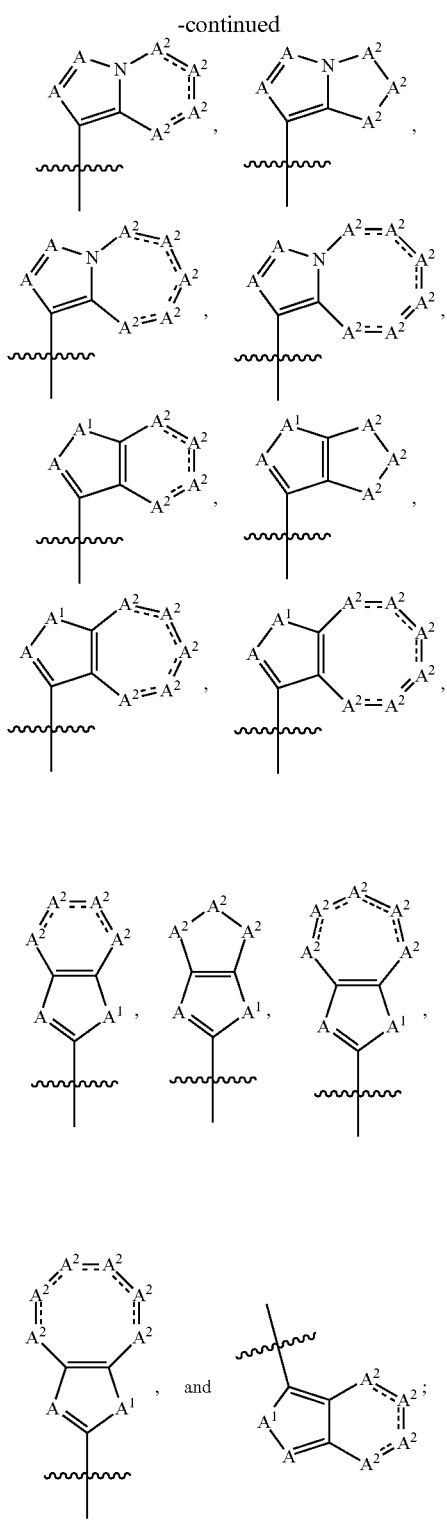

wherein === represents a single bond or a double bond provided that the ring comprising one or more $A^2$ is a non-aromatic ring;

each A is independently $CR^{5a}$ or N;

$A^1$ is $NR^{5a}$, O, S, or C(O);

each $A^2$ is independently $CR^{5a}$, $C(R^{5a})_2$, N, $NR^{5a}$, O, S, or $S(O)_2$;

$R^2$ is

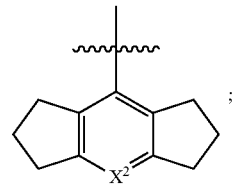

$X^2$ is N or $CR^{5b}$;

$R^3$ and $R^4$ are H;

each $R^{5a}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; wherein the $C_3$-$C_8$cycloalkyl, heterocyclyl, aryl, or heteroaryl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two geminal $R^{5a}$ can form an oxo group;

each $R^{5b}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, or $C_2$-$C_6$alkynyl; wherein the $C_1$-$C_6$alkyl, $C_2$-$C_6$alkenyl, $C_4$-$C_8$cycloalkenyl, and $C_2$-$C_6$alkynyl are optionally substituted with D, halogen, —$OR^6$, —$NH_2$, —NH($C_1$-$C_6$alkyl), or —N($C_1$-$C_6$alkyl)$_2$;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; wherein the $C_1$-$C_6$alkyl, $C_2$-$C_8$alkenyl, $C_4$-$C_8$cycloalkenyl, $C_2$-$C_6$alkynyl, $C_3$-$C_8$cycloalkyl, heterocyclyl, aryl, and heteroaryl are optionally substituted with D, halogen, $C_1$-$C_6$alkyl, —OH, —O—$C_1$-$C_6$alkyl, —$NH_2$, —NH($C_1$-$C_6$alkyl), or —N($C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^{5a}$, O, S, or $S(O)_2$.

The present disclosure provides compounds of Formula Id:

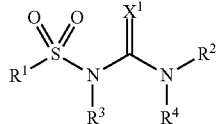
(Id)

and pharmaceutically acceptable salts, prodrugs, solvates, hydrates, isomers, and tautomers thereof, wherein:

$X^1$ is O, S,

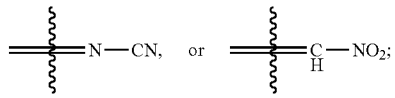

$R^1$ is selected from the group consisting of an optionally substituted $C_1$-$C_6$alkyl, optionally substituted $C_1$-$C_6$alkynyl, —$(CH_2)_m$—O—$(CH_2)_m$—$CH_3$,

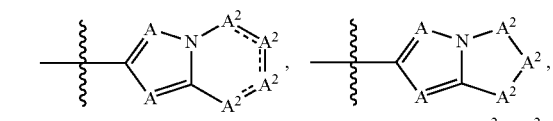

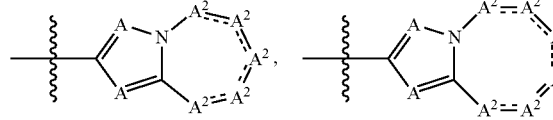

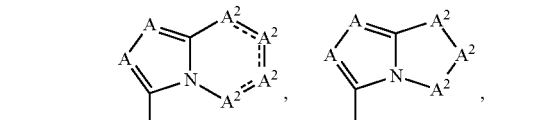

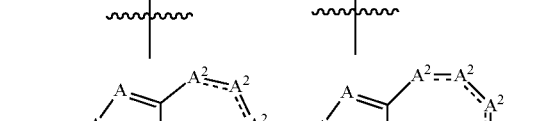

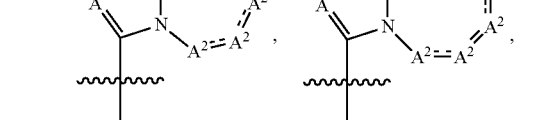

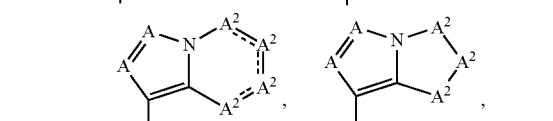

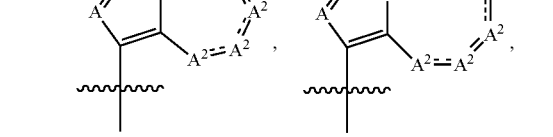

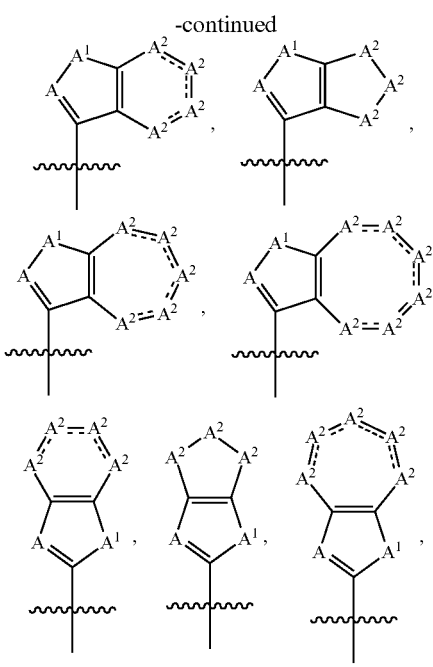

wherein ═══ represents a single bond or a double bond provided that the ring comprising one or more $A^2$ is a non-aromatic ring;

each A is independently $CR^{5a}$ or N;

$A^1$ is $NR^{5a}$, O, S, or C(O);

each $A^2$ is independently $CR^{5a}$, $C(R^{5a})_2$, N, $NR^{5a}$, O, S, or $S(O)_2$;

$R^2$ is

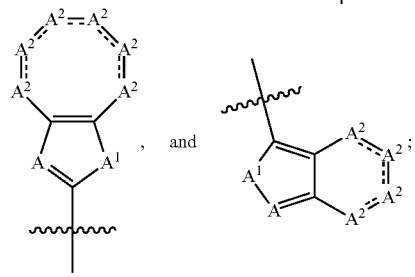

$R^3$ and $R^4$ are H;

each $R^{5a}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, halogen, $C_1$-$C_6$alkyl, —$OR^6$, —$NH_2$, NH($C_1$-$C_6$alkyl), or N($C_1$-$C_6$alkyl)$_2$; or two R$^{5a}$ together with the atoms to which they are attached can form C$_3$-C$_8$cycloalkyl, heterocyclyl, aryl, or heteroaryl; wherein the heterocyclyl and heteroaryl contain 1-3 heteroatoms selected from the group consisting of N, S, P and O; wherein the C$_3$-C$_8$cycloalkyl, heterocyclyl, aryl, or heteroaryl are optionally substituted with D, halogen, C$_1$-C$_6$alkyl, —OR$^6$, —NH$_2$, —NH(C$_1$-C$_6$alkyl), or —N(C$_1$-C$_6$alkyl)$_2$; or two geminal R$^{5a}$ can form an oxo group;

each R$^{5b}$ is independently H, D, halogen, OH, CN, —NO$_2$, —SR$^6$, —OR$^6$, —NHR$^6$, —NR$^6$R$^7$, —S(O)$_2$N(R$^6$)$_2$—, —S(O)$_2$R$^6$, —C(O)R$^6$, —C(O)OR$^6$, —C(O)NR$^6$R$^7$, —NR$^6$S(O)$_2$R$^7$, —S(O)R$^6$, —S(O)NR$^6$R$^7$, —NR$^6$S(O)R$^7$, C$_1$-C$_6$alkyl, C$_2$-C$_6$alkenyl, C$_4$-C$_8$cycloalkenyl, or C$_2$-C$_6$alkynyl; wherein the C$_1$-C$_6$alkyl, C$_2$-C$_6$alkenyl, C$_4$-C$_8$cycloalkenyl, and C$_2$-C$_6$alkynyl are optionally substituted with D, halogen, —OR$^6$, —NH$_2$, —NH(C$_1$-C$_6$alkyl), or —N(C$_1$-C$_6$alkyl)$_2$;

R$^6$ and R$^7$ are independently, at each occurrence H, D, C$_1$-C$_8$alkyl, C$_2$-C$_8$alkenyl, C$_4$-C$_8$cycloalkenyl, C$_2$-C$_8$alkynyl, C$_3$-C$_8$cycloalkyl, heterocyclyl, aryl, or heteroaryl; wherein the heterocyclyl and heteroaryl contain 1-5 heteroatoms selected from the group consisting of N, S, P and O; wherein the C$_1$-C$_6$alkyl, C$_2$-C$_5$alkenyl, C$_4$-C$_8$cycloalkenyl, C$_2$-C$_6$alkynyl, C$_3$-C$_8$cycloalkyl, heterocyclyl, aryl, and heteroaryl are optionally substituted with D, halogen, C$_1$-C$_6$alkyl, —OH, —O—C$_1$-C$_6$alkyl, —NH$_2$, —NH(C$_1$-C$_6$alkyl), or —N(C$_1$-C$_6$alkyl)$_2$; or R$^6$ and R$^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or A$^1$ is an imidazole, then at least one A$^2$ is N, NR$^{5a}$, O, S, or S(O)$_2$.

The present disclosure provides compounds of Formula Ie:

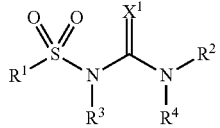

(Ie)

and pharmaceutically acceptable salts, prodrugs, solvates, hydrates, isomers, and tautomers thereof, wherein:

X$^1$ is O or S;

R$^1$ is selected from the group consisting of

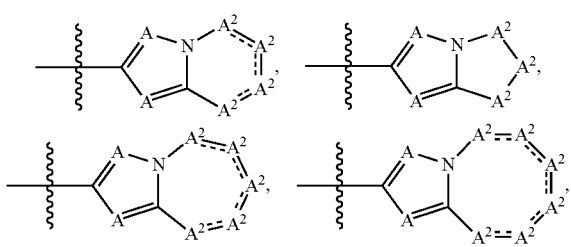

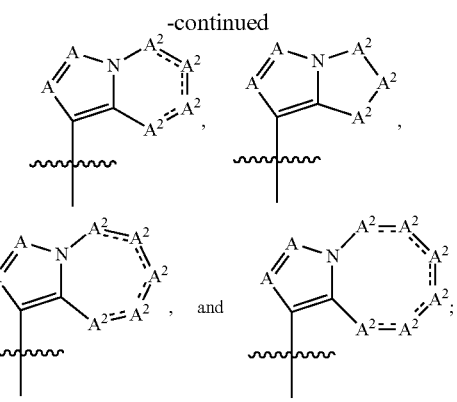

wherein ═══ represents a single bond or a double bond provided that the ring comprising one or more A$^2$ is a non-aromatic ring;

each A is independently CR$^{5a1}$ or N;

each A$^2$ is independently CR$^{5a2}$, C(R$^{5a2}$)$_2$, N, NR$^{5a2}$, O, S, or S(O)$_2$;

R$^2$ is

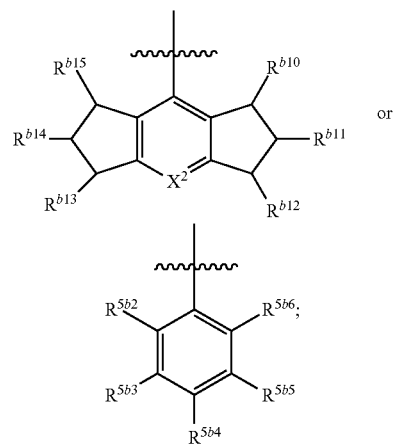

X$^2$ is N or CR$^{5b1}$;

each R$^{b10}$, R$^{b11}$, R$^{b12}$, R$^{b13}$, R$^{b14}$, and R$^{b15}$ is independently H, —OH, or oxo;

R$^3$ and R$^4$ are H;

each R$^{5a1}$ is independently H, D, halogen, OH, CN, —NO$_2$, —SR$^6$, —OR$^6$, —NHR$^6$, —NR$^6$R$^7$, —NR$^6$C(O)R$^6$, —NR$^6$C(O)OR$^6$, —NR$^6$C(O)NR$^6$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, or —NR$^6$C(O)R$^6$;

each R$^{5a2}$ is independently H, D, halogen, OH, CN, —NO$_2$, —SR$^6$, —OR$^6$, —NHR$^6$, —NR$^6$R$^7$, —C(O)R$^6$, —S(O)$_2$R$^6$, —C(O)OR$^6$, —C(O)NR$^6$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, —$NR^6C(O)R^6$, —$NR^6C(O)NR^6$, —$NR^6C(O)R^6$, or —$NR^6S(O)_2R^6$; or two $R^{5a2}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)_2$, —$S(O)_2$—$R^6$, —$COR^6$, —$NR^6C(O)OR^6$, —$NR^6C(O)R^6$, —$NR^6C(O)NR^6$, or —$NR^6S(O)_2R^6$; or two geminal $R^{5a2}$ can form an oxo group;

$R^{5b1}$ is H, D, halogen, —CN—$OR^6$, or $C_1$-$C_6$alkyl, $C_3$-$C_8$cycloalkyl, —$C(O)NR^6$, —$C(O)OR^6$; wherein the $C_1$-$C_6$alkyl, and $C_3$-$C_8$cycloalkyl, are optionally substituted with D, halogen, —CN, —$OR^6$, —$NH_2$, —$NH(C_1$-$C_6$alkyl), or —$N(C_1$-$C_6$alkyl)_2$;

each $R^{5b2}$, $R^{5b3}$, $R^{5b4}$, $R^{5b5}$, and $R^{5b6}$ is independently H, D, halogen, OH, —CN, —$NO_2$, —$SR^6$, —$OR^6$, —$NHR^6$, —$NR^6R^7$, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, —CN, —$OR^6$, —$NH_2$, —$NH(C_1$-$C_6$alkyl), or —$N(C_1$-$C_6$alkyl)_2$; or two adjacent $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, —CN, $C_1$-$C_6$alkyl, —$OR^6$, —$NH_2$, —$NH(C_1$-$C_6$alkyl), or —$N(C_1$-$C_6$alkyl)_2$; and $R^6$ and $R^7$ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_8$alkyl, $C_2$-$C_5$alkenyl, $C_2$-$C_8$alkynyl, $C_3$-$C_8$cycloalkyl, $C_4$-$C_8$cycloalkenyl, heterocyclyl, aryl, and heteroaryl are optionally substituted with D, —CN, halogen, $C_1$-$C_6$alkyl, —OH, —O—$C_1$-$C_6$alkyl, —$NH_2$, —$NH(C_1$-$C_6$alkyl), or —$N(C_1$-$C_6$alkyl)_2$; or $R^6$ and $R^7$ together with the atom to which they are attached can form heterocyclyl or heteroaryl containing 1-3 heteroatoms selected from the group consisting of N, S, P and O; provided that when the ring comprising A and/or $A^1$ is an imidazole, then at least one $A^2$ is N, $NR^{5a2}$, O, S, or $S(O)_2$.

The present disclosure provides compounds of Formula If:

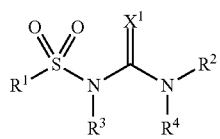

(If)

and pharmaceutically acceptable salts, prodrugs, solvates, hydrates, isomers, and tautomers thereof, wherein:
$X^1$ is O or S;
$R^1$ is selected from the group consisting of

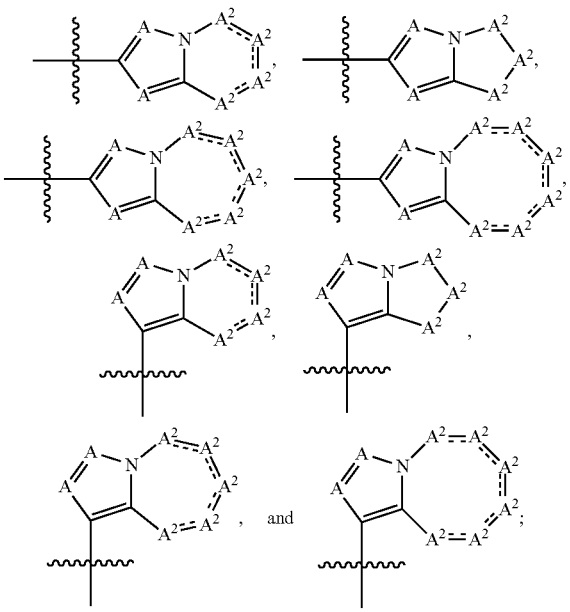

wherein === represents a single bond or a double bond provided that the ring comprising one or more $A^2$ is a non-aromatic ring;

each A is independently $CR^{5a1}$ or N;
each $A^2$ is independently $CR^{5a2}$, $C(R^{5a2})_2$, N, $NR^{5a2}$, O, S, or $S(O)_2$;

$R^2$ is

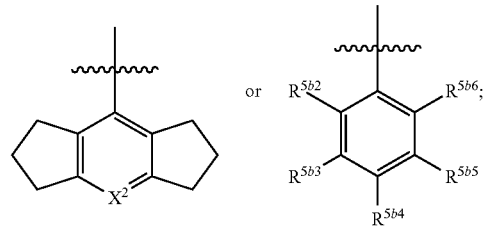

$X^2$ is N or $CR^{5b1}$;
$R^3$ and $R^4$ are H;
each $R^{5a1}$ is independently H, D, halogen, OH, CN, —$NO_2$, —$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, or —$NR^6C(O)R^6$;

each $R^{5a2}$ is independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—

$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, —$NR^6C(O)R^6$, —$NR^6C(O)NR^6$, —$NR^6C(O)R^6$, or —$NR^6S(O)_2R^6$; or two $R^{5a2}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)_2$, —$S(O)_2$—$R^6$, —$COR^6$, —$NR^6C(O)OR^6$, —$NR^6C(O)R^6$, —$NR^6C(O)NR^6$, or —$NR^6S(O)_2R^6$; or two geminal $R^{5a2}$ can form an oxo group;

$R^{5b1}$ is H, D, halogen, —CN—$OR^6$, or $C_1$-$C_6$alkyl, $C_3$-$C_8$cycloalkyl, —$C(O)NR^6$, —$C(O)OR^6$; wherein the $C_1$-$C_6$alkyl, and $C_3$-$C_8$cycloalkyl, are optionally substituted with D, halogen, —CN, —$OR^6$, —$NH_2$, —$NH(C_1$-$C_6$alkyl), or —$N(C_1$-$C_6$alkyl)_2$;

each $R^{5b2}$, $R^{5b3}$, $R^{5b4}$, $R^{5b5}$, and $R^{5b6}$ is independently H, D, halogen, OH, —CN, —$NO_2$, —$SR^6$, —$OR^6$, —$NHR^6$, —$NR^6R^7$, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, —CN, —$OR^6$, —$NH_2$, —$NH(C_1$-$C_6$alkyl), or —$N(C_1$-$C_6$alkyl)_2$; or two adjacent $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, —CN, $C_1$-$C_6$alkyl, —$OR^6$, —$NH_2$, —$NH(C_1$-$C_6$alkyl), or —$N(C_1$-$C_6$alkyl)_2$; and $R^6$ and $R^7$ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, and heteroaryl are optionally substituted with D, —CN, halogen, $C_1$-$C_6$alkyl, —OH, —O—$C_1$-$C_6$alkyl, —$NH_2$, —$NH(C_1$-$C_6$alkyl), or —$N(C_1$-$C_6$alkyl)_2$; or $R^6$ and $R^7$ together with the atom to which they are attached can form heterocyclyl or heteroaryl containing 1-3 heteroatoms selected from the group consisting of N, S, P and O;

provided that when the ring comprising A and/or $A^1$ is an imidazole, then at least one $A^2$ is N, $NR^{5a2}$, O, S, or $S(O)_2$.

The present disclosure provides compounds of Formula Ig:

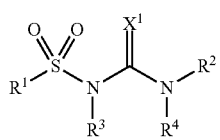

(Ig)

and pharmaceutically acceptable salts, prodrugs, solvates, hydrates, isomers, and tautomers thereof, wherein:

$X^1$ is O or S;

$R^1$ is selected from the group consisting of

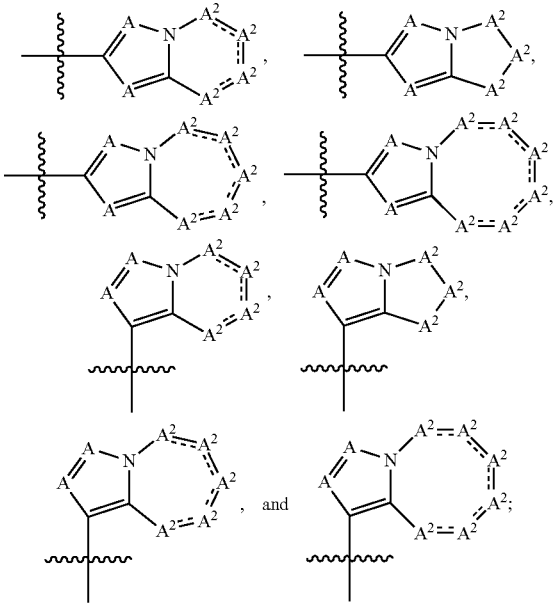

wherein === represents a single bond or a double bond provided that the ring comprising one or more $A^2$ is a non-aromatic ring;

each A is independently $CR^{5a1}$ or N;

each $A^2$ is independently $CR^{5a2}$, $C(R^{5a2})_2$, N, $NR^{5a2}$, O, S, or $S(O)_2$;

$R^2$ is

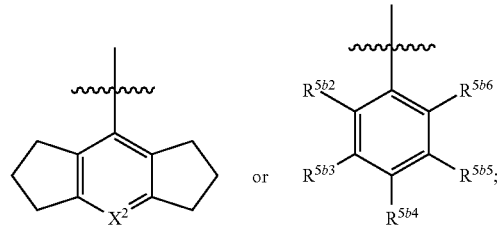

$X^2$ is N or $CR^{5b1}$;

$R^3$ and $R^4$ are H;

each $R^{5a1}$ is independently H, D, halogen, OH, CN, —$NO_2$—$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, or —$NR^6C(O)R^6$;

each $R^{5a2}$ is independently H, D, halogen, OH, CN, —$NO_2$, —$SR^6$, —$OR^6$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl;

wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NR^6C(O)OR^6$, —$NR^6C(O)R^6$, —$NR^6C(O)NR^6$, —$NR^6C(O)R^6$, or —$NR^6S(O)_2R^6$; or two $R^{5a2}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$S(O)_2$—$R^6$; —$COR^6$, —$NR^6C(O)OR^6$, —$NR^6C(O)R^6$, —$NR^6C(O)NR^6$, or —$NR^6S(O)_2R^6$; or two geminal $R^{5a2}$ can form an oxo group;

$R^{5b1}$ is H, D, halogen, —CN—$OR^6$, or $C_1$-$C_6$alkyl, $C_3$-$C_8$cycloalkyl, —$C(O)NR^6$, —$C(O)OR^6$; wherein the $C_1$-$C_6$alkyl, and $C_3$-$C_8$cycloalkyl, are optionally substituted with D, halogen, —CN, —$OR^6$, —$NH_2$, —$NH(C_1$-$C_6$alkyl), or —$N(C_1$-$C_6$alkyl)$_2$;

each $R^{5b2}$, $R^{5b3}$, $R^{5b4}$, $R^{5b5}$, and $R^{5b6}$ is independently H, D, halogen, OH, —CN, —$NO_2$, —$SR^6$, —$OR^6$, —$NHR^6$, —$NR^6R^7$, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, —CN, —$OR^6$, —$NH_2$, —$NH(C_1$-$C_6$alkyl), or —$N(C_1$-$C_6$alkyl)$_2$; or two adjacent $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, —CN, $C_1$-$C_6$alkyl, —$OR^6$, —$NH_2$, —$NH(C_1$-$C_6$alkyl), or —$N(C_1$-$C_6$alkyl)$_2$; and $R^6$ and $R^7$ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, and heteroaryl are optionally substituted with D, —CN, halogen, $C_1$-$C_6$alkyl, —OH, —O—$C_1$-$C_6$alkyl, —$NH_2$, —$NH(C_1$-$C_6$alkyl), or —$N(C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

provided that when the ring comprising A and/or $A^1$ is an imidazole, then at least one $A^2$ is N, $NR^{5a2}$, O, S, or $S(O)_2$.

The present disclosure provides compounds of Formula Ih:

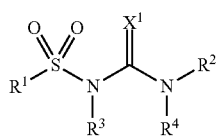

(Ih)

and pharmaceutically acceptable salts, prodrugs, solvates, hydrates, isomers, and tautomers thereof, wherein:
$X^1$ is O or S;
$R^1$ is selected from the group consisting of

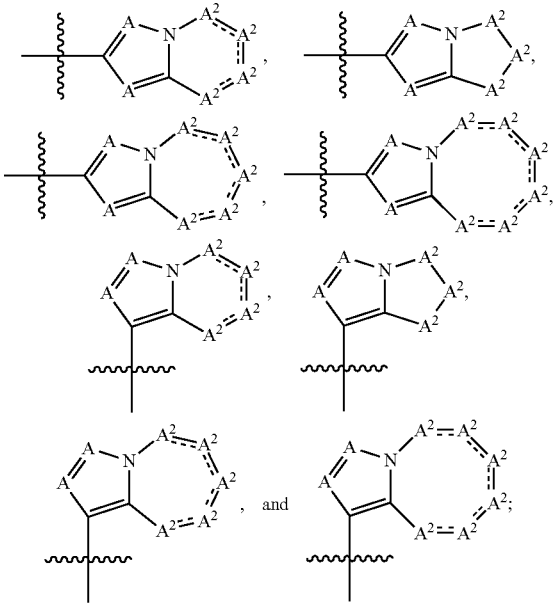

, and wherein === represents a single bond or a double bond provided that the ring comprising one or more $A^2$ is a non-aromatic ring;
each A is independently $CR^{5a1}$ or N;
each $A^2$ is independently $CR^{5a2}$, $C(R^{5a2})_2$, N, $NR^{5a2}$, O, S, or $S(O)_2$;
$R^2$ is

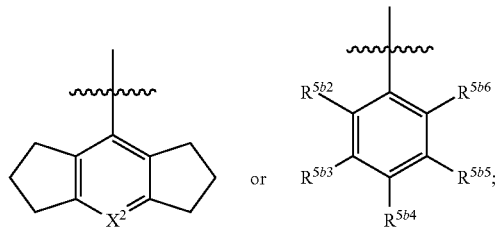

or $X^2$ is N or $CR^{5b1}$;
$R^3$ and $R^4$ are H;
each $R^{5a1}$ is independently H, D, halogen, —OH, —CN, —$NO_2$, —$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$;

each $R^{5a2}$ is independently H, D, halogen, OH, —CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—

$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$, —$NR^6C(O)NR^6$, —$NR^6C(O)R^6$, or —$NR^6S(O)_2R^6$;

wherein at least one $R^{5a2}$ is —$NHR^6$, —$NR^6R^7$, $C_1$-$C_6$alkyl, or heterocyclyl containing N; wherein the $C_1$-$C_6$alkyl is substituted with —$NH_2$, —$NH(C_1$-$C_6$alkyl), or —$N(C_1$-$C_6$alkyl)$_2$, and wherein the heterocyclyl is optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$, —$NR^6C(O)NR^6$, —$NR^6C(O)R^6$, or —$NR^6S(O)_2R^6$;

$R^{5b1}$ is H, D, halogen, —CN—$OR^6$, or $C_1$-$C_6$alkyl, $C_3$-$C_8$cycloalkyl, —$C(O)NR^6$, —$C(O)OR^6$; wherein the $C_1$-$C_6$alkyl, and $C_3$-$C_8$cycloalkyl, are optionally substituted with D, halogen, —CN, —$OR^6$, —$NH_2$, —$NH(C_1$-$C_6$alkyl), or —$N(C_1$-$C_6$alkyl)$_2$;

each $R^{5b2}$, $R^{5b3}$, $R^{5b4}$, $R^{5b5}$, and $R^{5b6}$ is independently H, D, halogen, OH, —CN, —$NO_2$, —$SR^6$, —$OR^6$, —$NHR^6$, —$NR^6R^7$, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, —CN, —$OR^6$, —$NH_2$, —$NH(C_1$-$C_6$alkyl), or —$N(C_1$-$C_6$alkyl)$_2$; or two adjacent $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, —CN, $C_1$-$C_6$alkyl, —$OR^6$, —$NH_2$, —$NH(C_1$-$C_6$alkyl), or —$N(C_1$-$C_6$alkyl)$_2$; and $R^6$ and $R^7$ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, and heteroaryl are optionally substituted with D, —CN, halogen, $C_1$-$C_6$alkyl, —OH, —O—$C_1$-$C_6$alkyl, —$NH_2$, —$NH(C_1$-$C_6$alkyl), or —$N(C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

provided that when the ring comprising A and/or $A^1$ is an imidazole, then at least one $A^2$ is N, $NR^{5a2}$, O, S, or $S(O)_2$.

The present disclosure provides a pharmaceutical composition comprising a compound of the present disclosure, and pharmaceutically acceptable salts, prodrugs, solvates, hydrates, isomers, and tautomers thereof, and a pharmaceutically acceptable carrier, diluent and/or excipient.

The present disclosure provides a method of treatment or prevention of a disease, disorder or condition including the step of administering an effective amount of a compound of the present disclosure, and pharmaceutically acceptable salts, prodrugs, solvates, hydrates, isomers, and tautomers thereof to thereby treat or prevent the disease, disorder or condition in a subject in need thereof.

The present disclosure provides a compound of the present disclosure, and pharmaceutically acceptable salts, prodrugs, solvates, hydrates, isomers, and tautomers thereof, or the pharmaceutical composition of the present disclosure for use in the treatment or prevention of a disease, disorder or condition in a subject in need thereof.

The present disclosure provides for use of a compound of the present disclosure, and pharmaceutically acceptable salts, prodrugs, solvates, hydrates, isomers, and tautomers thereof, for the treatment or prevention of a disease, disorder or condition in a subject in need thereof.

The present disclosure provides for use of a compound of the present disclosure, and pharmaceutically acceptable salts, prodrugs, solvates, hydrates, isomers, and tautomers thereof, in the manufacture of a medicament for the treatment or prevention of a disease, disorder or condition.

In certain embodiments, the disease, disorder or condition is responsive to inhibition of an inflammasome.

In certain embodiments, the disease, disorder or condition is responsive to inhibition of activation of the NLRP3 inflammasome.

In certain embodiments, the disease, disorder or condition is a disease, disorder or condition of the immune system, the liver, the lung, the skin, the cardiovascular system, the renal system, the gastrointestinal tract, the respiratory system, the endocrine system, the central nervous system, or is a cancer or other malignancy, or is caused by or associated with a pathogen.

The present disclosure provides a method of modulating the activity of a biological target comprising the step of exposing the biological target to a compound of the present disclosure, and pharmaceutically acceptable salts thereof.

The biological target may be selected from the group consisting of the NLRP3 inflammasome, IL-6, IL-1β, IL-17, IL-18, IL-1α, IL-37, IL-22, IL-33 and Th17 cells.

DETAILED DESCRIPTION

Figure 1:
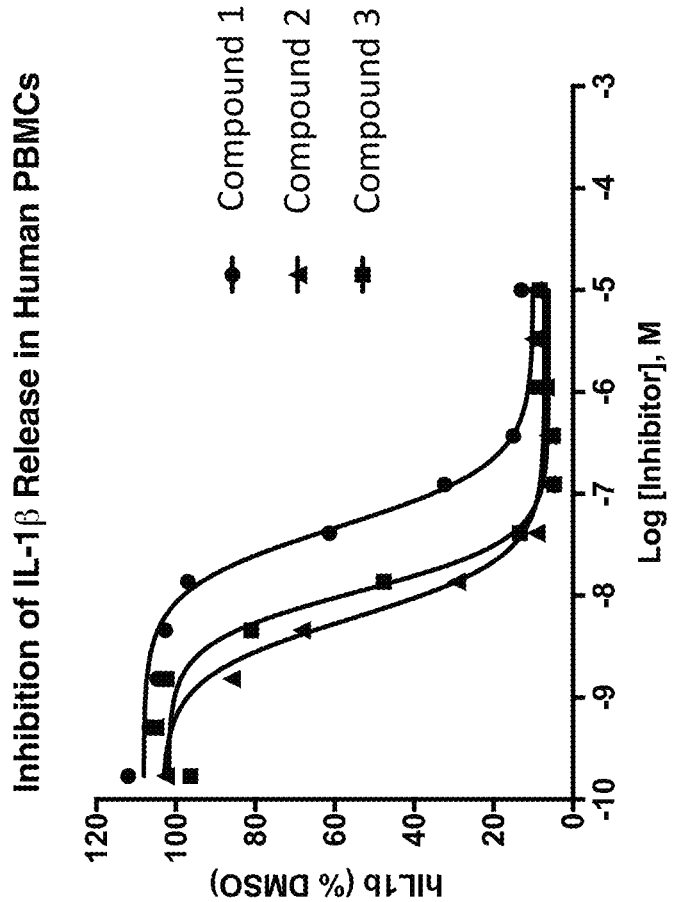
FIG. 1 shows inhibition of IL-1β production in peripheral blood mononucleocytes (PBMCs) as a result of treatment with Compound 1, Compound 2, or Compound 3.

As used above, and throughout this disclosure, the following terms, unless otherwise indicated, shall be understood to have the following meanings. If a term is missing, the conventional term as known to one skilled in the art controls.

As used herein, the terms "including," "containing," and "comprising" are used in their open, non-limiting sense.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

A "patient" is a mammal, e.g., a human, mouse, rat, guinea pig, dog, cat, horse, cow, pig, or non-human primate, such as a monkey, chimpanzee, baboon or rhesus. "Patient" includes both human and animals.

The term "inhibitor" refers to a molecule such as a compound, a drug, enzyme, or a hormone that blocks or otherwise interferes with a particular biologic activity.

The terms "effective amount" or "therapeutically effective amount" when used in connection with a compound refer to a sufficient amount of the compound to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective amount" in any individual case may be determined by one of ordinary skill in the art using routine experimentation. Thus, the expression "effective amount" generally refers to the quantity for which the active substance has therapeutic effects. In the present case the active substance is the inhibitor of the inflammasome.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying causes of symptoms, inhibiting the disorder or disease, e.g., arresting the development of the disorder or disease, relieving the disorder or disease, causing regression of the disorder or disease, relieving a condition caused by the disease or disorder, or stopping or alleviating the symptoms of the disease or disorder.

The term "disorder" is used in this disclosure to mean, and is used interchangeably with, the terms disease, condition, or illness, unless otherwise indicated.

By using the terms "pharmaceutically acceptable" or "pharmacologically acceptable" it is intended to mean a material which is not biologically, or otherwise, undesirable—the material may be administered to an individual without causing any substantially undesirable biological effects or interacting in a deleterious manner with any of the components of the composition in which it is contained.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject. Excipients should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, spray-dried dispersions, and the like.

The term "pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals. Examples of mammals include, but are not limited to, any member of the class Mammalia: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present disclosure, the mammal is a human.

The present disclosure also includes "prodrugs" of compounds. The term "prodrug" means a compound which is convertible in vivo by metabolic means (e.g., by hydrolysis) to a disclosed compound or active ingredient. Prodrugs can be prepared by techniques known to one skilled in the art. These techniques generally modify appropriate functional, e.g., a hydroxy, amino, carboxylic, etc., groups in a given compound. These modified functional groups, however, regenerate original functional groups by routine manipulation or in vivo. Examples of prodrugs include, but are not limited to esters (e.g., acetate, formate, and benzoate derivatives), carbamates (e.g., N,N-dimethylaminocarbonyl) of hydroxy or amino functional groups in compounds of the present disclosure, amides (e.g., trifluoroacetylamino, acetylamino, and the like), and the like. Since prodrugs are known to enhance numerous desirable qualities of pharmaceuticals (e.g., solubility, bioavailability, manufacturing, transport, pharmacodynamics, etc.), the compounds of the present disclosure may be delivered in prodrug form. Prodrugs, for instance, may be bioavailable by oral administration even when the parent drug is not. Thus, the present disclosure is intended to cover prodrugs of the presently claimed compounds, methods of delivering the same, and compositions containing the same. Generally speaking, prodrugs are derivatives of per se drugs that after administration undergo conversion or metabolism to the physiologically active species. The conversion may be spontaneous, such as hydrolysis in the physiological environment, or may be enzyme-catalyzed. Prodrugs include compounds that can be oxidized, reduced, aminated, deaminated, hydroxylated, dehydroxylated, hydrolyzed, esterified, alkylated, dealkylated, acylated, deacylated, phosphorylated, and/or dephosphorylated to produce the active compound.

The term "$IC_{50}$", as used herein, refers to concentrations at which a measurable activity, phenotype or response, for example growth or proliferation of cells such as tumor cells, is inhibited by 50%. $IC_{50}$ values can be estimated from an appropriate dose-response curve, for example by eye or by using appropriate curve fitting or statistical software. More accurately, $IC_{50}$ values may be determined using non-linear regression analysis.

The terms "administered", "administration", or "administering" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body, including an animal, in need of treatment by bringing such individual in contact with, or otherwise exposing such individual to, such compound.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, or branched. As used herein, "lower alkyl" means an alkyl having from 1 to 6 carbon atoms.

As used herein, an "alkenyl" includes an unbranched or branched hydrocarbon chain containing 2-12 carbon atoms. The "alkenyl" group contains at least one double bond. The double bond of an alkenyl group can be unconjugated or conjugated to another unsaturated group. Examples of alkenyl groups include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted. Alkenyl, as defined herein, may also be branched or straight.

As used herein, "alkynyl" includes an unbranched or branched unsaturated hydrocarbon chain containing 2-12 carbon atoms. The "alkynyl" group contains at least one triple bond. The triple bond of an alkynyl group can be unconjugated or conjugated to another unsaturated group. Examples of alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "hydroxyl" or "hydroxy" means an OH group;

The term "alkoxy" as used herein refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

It should also be noted that any carbon as well as heteroatom with unsatisfied valences in the text, schemes, examples and Tables herein is assumed to have the sufficient number of hydrogen atom(s) to satisfy the valences.

As used herein, references to hydrogen may also refer to a deuterium substitution if desired. The term "deuterium" as used herein means a stable isotope of hydrogen having odd numbers of protons and neutrons.

The term "halo" or "halogen" refers to fluorine, chlorine, bromine, or iodine.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amino" as used herein means a substituent containing at least one nitrogen atom. Specifically, $NH_2$, —NH(alkyl) or alkylamino, —N(alkyl)$_2$ or dialkylamino, amide, carboxamide, urea, and sulfamide substituents are included in the term "amino".

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 18 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. The substituents can themselves be optionally substituted. Examples include, but are not limited to, benzothiophene, furyl, thienyl, pyrrolyl, pyridyl, pyrazinyl, pyrazolyl, pyridazinyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, benzoimidazolyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]

pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring.

As used herein, the term "cycloalkyl" refers to a saturated or partially saturated, monocyclic, fused or spiro polycyclic, carbocycle having from 3 to 18 carbon atoms per ring. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

As used herein, the term "cycloalkenyl" refers to a partially saturated, monocyclic, fused or spiro polycyclic, carbocycle having from 3 to 18 carbon atoms per ring and contains at least one double bond. The cycloalkenyl ring may be optionally substituted by one or more substituents, e.g., 1 to 5 substituents, at any point of attachment. The substituents can themselves be optionally substituted.

As used herein, the term "heterocycloalkyl" or "heterocyclyl" refers to a saturated or partially unsaturated and non-aromatic monocyclic, or fused or spiro, polycyclic, ring structure of 4- to 18 atoms containing carbon and heteroatoms taken from oxygen, nitrogen, or sulfur and wherein there is not delocalized π-electrons (aromaticity) shared among the ring carbon or heteroatoms. The heterocycloalkyl or heterocyclyl ring structure may be substituted by one or more substituents. The substituents can themselves be optionally substituted. Examples of heterocycloalkyl or heterocyclyl rings include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, homotropanyl, dihydrothiophen-2(3H)-onyl, tetrahydrothiophene 1,1-dioxide, 2,5-dihydro-1H-pyrrolyl, imidazolidin-2-one, pyrrolidin-2-one, dihydrofuran-2(3H)-one, 1,3-dioxolan-2-one, isothiazolidine 1,1-dioxide, 4,5-dihydro-1H-imidazolyl, 4,5-dihydrooxazolyl, oxiranyl, pyrazolidinyl, 4H-1,4-thiazinyl, thiomorpholinyl, 1,2,3,4-tetrahydropyridinyl, 1,2,3,4-tetrahydropyrazinyl, 1,3-oxazinan-2-one, tetrahydro-2H-thiopyran 1,1-dioxide, 7-oxabicyclo[2.2.1]heptanyl, 1,2-thiazepane 1,1-dioxide, octahydro-2H-quinolizinyl, 1,3-diazabicyclo[2.2.2]octanyl, 2,3-dihydrobenzo[b][1,4]dioxine, 3-azabicyclo[3.2.1]octanyl, 8-azabicyclo[4.5]decane, 8-oxa-3-azabicyclo[3.2.1]octanyl, 2-azabicyclo[2.2.1]heptane, 2,8-diazaspiro[5.5]undecanyl, 2-azaspiro[5.5]undecanyl, 3-azaspiro[5.5]undecanyl, decahydroisoquinolinyl, 1-oxa-8-azaspiro[4.5]decanyl, 8-azabicyclo[3.2.1]octanyl, 1,4'-bipiperidinyl, azepanyl, 8-oxa-3-azabicyclo[3.2.1]octanyl, 3,4-dihydro-2H-benzo[b][1,4]oxazinyl, 5,6,7,8-tetrahydroimidazo[1,2-a]pyridinyl, 1,4-diazepanyl, phenoxathiinyl, benzo[d][1,3]dioxolyl, 2,3-dihydrobenzofuranyl, 2,3-dihydrobenzo[b][1,4]dioxinyl, 4-(piperidin-4-yl)morpholinyl, 3-azaspiro[5.5]undecanyl, decahydroquinolinyl, piperazin-2-one, 1-(pyrrolidin-2-ylmethyl)pyrrolidinyl, 1,3'-bipyrrolidinyl, and 6,7,8,9-tetrahydro-1H,5H-pyrazolo[1,2-a][1,2]diazepinyl.

Numerical ranges, as used herein, are intended to include sequential integers. For example, a range expressed as "from 0 to 5" would include 0, 1, 2, 3, 4 and 5.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, oxo, -halogen, $C_1$-$C_6$ alkyl, $C_1$-$C_6$alkoxy, $C_1$-$C_6$ haloalkyl, $C_1$-$C_6$ haloalkoxy, —$OC_1$-$C_6$ alkenyl, —$OC_1$-$C_6$alkynyl, —$C_1$-$C_6$ alkenyl, —$C_1$-$C_6$ alkynyl, —OH, CN (cyano), —$CH_2CN$, —OP(O)(OH)$_2$, —C(O)OH, —OC(O)$C_1$-$C_6$ alkyl, —C(O)$C_1$-$C_6$ alkyl, —C(O)—$C_0$-$C_6$ alkylenyl-cycloalkyl, —C(O)—$C_0$-$C_6$ alkylenyl-heterocycloalkyl, —C(O)—$C_0$-$C_6$ alkylenyl-aryl, —C(O)—$C_0$-$C_6$ alkylenyl-heteroaryl, —OC(O)O$C_1$-$C_6$ alkyl, $NH_2$, NH($C_1$-$C_6$ alkyl), N($C_1$-$C_6$ alkyl)$_2$, —C(O)$NH_2$, —C(O)NH($C_1$-$C_6$ alkyl), —C(O)N($C_1$-$C_6$alkyl)$_2$, —C(O)NH cycloalkyl, —C(O)N($C_1$-$C_6$ alkyl)cycloalkyl, —C(O)NHheterocycloalkyl, —C(O)N($C_1$-$C_6$ alkyl)heterocycloalkyl, —C(O)NHaryl, —C(O)N($C_1$-$C_6$ alkyl)aryl, —C(O)NHheteroaryl, —C(O)N($C_1$-$C_6$ alkyl)heteroaryl, —S(O)$_2$—$C_1$-$C_6$ alkyl, —S(O)$_2$—$C_1$-$C_6$ haloalkyl, —S(O)$_2$— cycloalkyl, —S(O)$_2$-heterocycloalkyl, —S(O)$_2$— aryl, —S(O)$_2$-heteroaryl —$C_0$-$C_6$ alkylenyl-S(O)$_2$$NH_2$, —S(O)$_2$$NHC_1$-$C_6$ alkyl, —S(O)$_2$N($C_1$-$C_6$ alkyl)$_2$, —S(O)$_2$NHcycloalkyl, —S(O)$_2$NHheterocycloalkyl, —S(O)$_2$NHaryl, —S(O)$_2$NHhetereoaryl, —NHS(O)$_2$$C_1$-$C_6$ alkyl, —N($C_1$-$C_6$ alkyl)S(O)$_2$($C_1$-$C_6$ alkyl), —NHS(O)$_2$aryl, —N($C_1$-$C_6$ alkyl)S(O)$_2$ aryl, —NHS(O)$_2$ heteroaryl, —N($C_1$-$C_6$alkyl)S(O)$_2$ heteroaryl, —NHS(O)$_2$ cycloalkyl, —N($C_1$-$C_6$ alkyl)S(O)$_2$ cycloalkyl, —NHS(O)$_2$ heterocycloalkyl, —N($C_1$-$C_6$ alkyl)S(O)$_2$ heterocycloalkyl, —N($C_1$-$C_6$ alkyl)S(O)$_2$ aryl, —$C_0$-$C_6$ alkylenyl-aryl, —$C_0$-$C_6$ alkylenyl-heteroaryl, —$C_0$-$C_6$ alkylenyl-cycloalkyl, —$C_0$-$C_6$ alkylenyl-heterocycloalkyl, —O-aryl, —NH-aryl, and N($C_1$-$C_6$ alkyl)aryl. The substituents can themselves be optionally substituted. When a multifunctional moiety is shown, the point of attachment to the core is indicated by a line, e.g., (cycloalkyloxy)alkyl-refers to alkyl being the point of attachment to the core while cycloalkyl is attached to alkyl via the oxy group. "Optionally substituted" also refers to "substituted" or "unsubstituted", with the meanings described above.

The term "oxa" as used herein refers to an "—O—" group.

The term "oxo" as used herein refers to an "=O" group.

The term "solvate" refers to a complex of variable stoichiometry formed by a solute and solvent. Such solvents for the purpose of the present disclosure may not interfere with the biological activity of the solute. Examples of suitable solvents include, but are not limited to, water, methanol, ethanol, and acetic acid. Solvates wherein water is the solvent molecule are typically referred to as hydrates. Hydrates include compositions containing stoichiometric amounts of water, as well as compositions containing variable amounts of water.

The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula with an amount of acid or base, such as an equivalent amount, in a medium such as one in which the salt precipitates or in an aqueous medium followed by lyophilization.

In another embodiment of the present disclosure, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Compounds of the various Formulae, and salts, solvates, esters and prodrugs thereof, may exist in their tautomeric form (for example, as an amide or imino ether). All such tautomeric forms are contemplated herein as part of the present disclosure.

The compounds of the various Formulae may contain asymmetric or chiral centers, and, therefore, exist in different stereoisomeric forms. It is intended that all stereoisomeric forms of the compounds of the various Formulae as well as mixtures thereof, including racemic mixtures, form part of the present disclosure. In addition, the present disclosure embraces all geometric and positional isomers. For example, if a compound of the various Formulae incorporates a double bond or a fused ring, both the cis- and trans-forms, as well as mixtures, are embraced within the scope of the present disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulae may be atropisomers (e.g., substituted biaryls) and are considered as part of the present disclosure. Enantiomers can also be separated by use of a chiral HPLC column.

It is also possible that the compounds of Formula (I) may exist in different tautomeric forms, and all such forms are embraced within the scope of the present disclosure. Also, for example, all keto-enol and imine-enamine forms of the compounds are included in the present disclosure.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of the present disclosure, as are positional isomers (such as, for example, 4-pyridyl and 3-pyridyl). (For example, if a compound of the various Formulae incorporates a double bond or a fused ring, both the cis- and trans-forms, as well as mixtures, are embraced within the scope of the present disclosure. Also, for example, all keto-enol and imine-enamine forms of the compounds are included in the present disclosure.) Individual stereoisomers of the compounds of the present disclosure may, for example, be substantially free of other isomers, or may be admixed, for example, as racemates or with all other, or other selected, stereoisomers. The chiral centers of the present disclosure can have the S or R configuration as defined by the IUPAC 1974 Recommendations.

The present disclosure also embraces isotopically-labelled compounds of the present disclosure which are identical to those recited herein, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorus, fluorine and chlorine, such as $^{2}H$ (or D), $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the various Formulae (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of the various Formulae can generally be prepared by following procedures analogous to those disclosed in the Schemes and/or in the Examples herein below, by substituting an appropriate isotopically labelled reagent for a non-isotopically labelled reagent.

In some embodiments, the compound comprises at least one deuterium atom. For example, one or more hydrogen atoms in a compound of the present disclosure can be replaced or substituted by deuterium. In some embodiments, the compound comprises two or more deuterium atoms. In some embodiments, the compound comprises 1, 2, 3, 4, 5, 6, 7, 8, 9, 10, 11 or 12 deuterium atoms.

The compounds of Formula (I) may form salts which are also within the scope of the present disclosure. Reference to a compound of the Formula herein is understood to include reference to salts thereof, unless otherwise indicated.

The present disclosure is directed to compounds as described herein and pharmaceutically acceptable salts, enantiomers, hydrates, solvates, prodrugs, isomers, or tautomers thereof, and pharmaceutical compositions comprising one or more compounds as described herein, or pharmaceutically acceptable salts, enantiomers, hydrates, solvates, prodrugs, isomers, or tautomers thereof.

In the present disclosure, reference to Formula (1b) includes reference to Formula (1b)-1 and similarly for Formula (Ic), (Id), and (Ig). In the present disclosure, reference to, e.g., Formula 1b-1g includes reference to Formula (1b)-1, (Ic)-1, (Id)-1, (1g)-1, and (Ih)-1

Compounds

The present disclosure provides a compound having the structure of Formula (I),

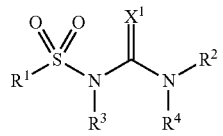

(I)

and pharmaceutically acceptable salts, enantiomers, hydrates, solvates, prodrugs, isomers, and tautomers thereof, where $X^1$, $R^1$, $R^2$, $R^3$, and $R^4$ are as described above.

The present disclosure provides a compound having the structure of Formula (Ia),

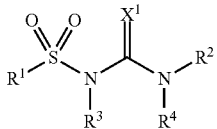

(Ia)

and pharmaceutically acceptable salts, enantiomers, hydrates, solvates, prodrugs, isomers, and tautomers thereof, where $X^1$, $R^1$, $R^2$, $R^3$, and $R^4$ are as described above.

The present disclosure provides a compound having the structure of Formula (Ib),

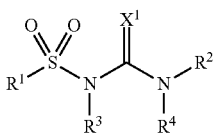

(Ib)

and pharmaceutically acceptable salts, enantiomers, hydrates, solvates, prodrugs, isomers, and tautomers thereof, where $X^1$, $R^1$, $R^2$, $R^3$, and $R^4$ are as described above.

In certain embodiments, the present disclosure provides a compound having the structure of Formula (Ib), which is of the Formula (Ib)-1:

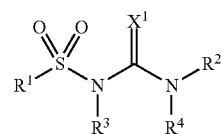

(Ib)-1 and pharmaceutically acceptable salts, prodrugs, solvates, hydrates, isomers, and tautomers thereof,
wherein:
$X^1$ is O, S,

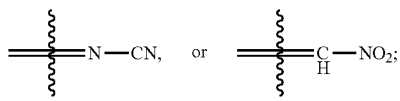

$R^1$ is selected from the group consisting of

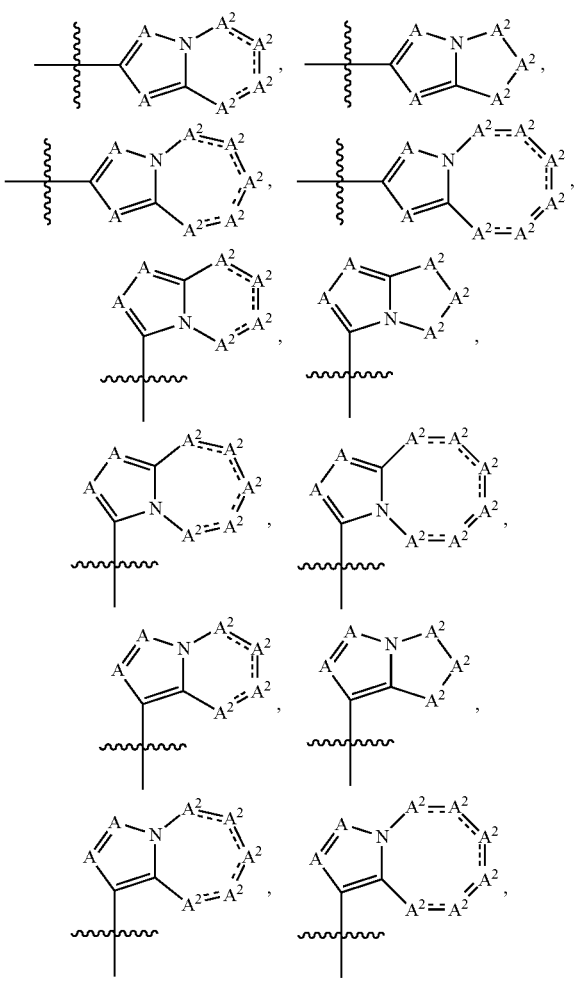

-continued

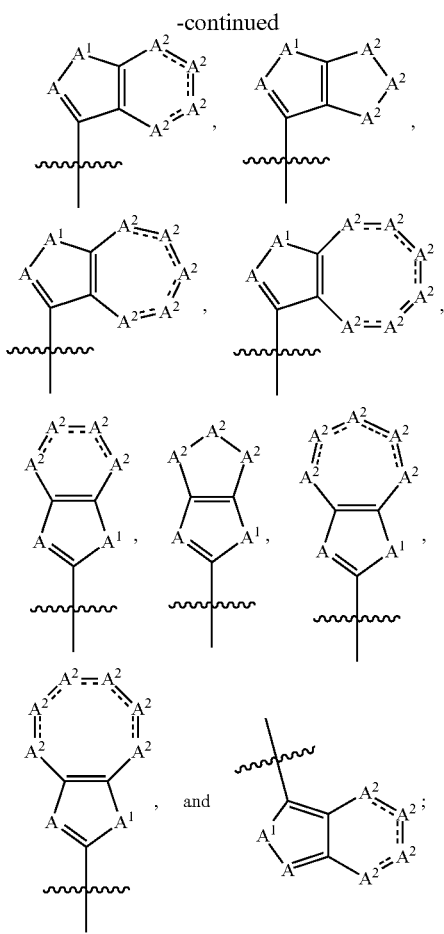

wherein ═ represents a single bond or a double bond provided that the ring comprising one or more $A^2$ is a non-aromatic ring;

each A is independently $CR^{5a}$ or N;

$A^1$ is $NR^{5a}$, O, S, or C(O);

each $A^2$ is independently $CR^{5a}$, $C(R^{5a})_2$, N, $NR^{5a}$, O, S, or $S(O)_2$;

$R^2$ is

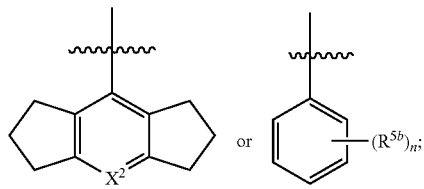

$X^2$ is N or $CR^{5b}$;

$R^3$ and $R^4$ are H;

each $R^{5a}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; wherein the $C_3$-$C_8$cycloalkyl, heterocyclyl, aryl, or heteroaryl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two geminal $R^{5a}$ can form an oxo group;

each $R^{5b}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, or $C_2$-$C_6$alkynyl; wherein the $C_1$-$C_6$alkyl, $C_2$-$C_6$alkenyl, $C_4$-$C_8$cycloalkenyl, and $C_2$-$C_6$alkynyl are optionally substituted with D, halogen, —$OR^6$, —$NH_2$, —NH($C_1$-$C_6$alkyl), or —N($C_1$-$C_6$alkyl)$_2$;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; wherein the $C_1$-$C_6$alkyl, $C_2$-$C_8$alkenyl, $C_4$-$C_8$cycloalkenyl, $C_2$-$C_6$alkynyl, $C_3$-$C_8$cycloalkyl, heterocyclyl, aryl, and heteroaryl are optionally substituted with D, halogen, $C_1$-$C_6$alkyl, —OH, —O—$C_1$-$C_6$alkyl, —$NH_2$, —NH($C_1$-$C_6$alkyl), or —N($C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^{5a}$, O, S, or $S(O)_2$.

The present disclosure provides a compound having the structure of Formula (Ic),

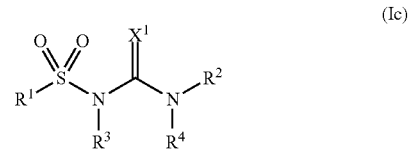

and pharmaceutically acceptable salts, enantiomers, hydrates, solvates, prodrugs, isomers, and tautomers thereof, where $X^1$, $R^1$, $R^2$, $R^3$, and $R^4$ are as described above.

In certain embodiments, the present disclosure provides a compound having the structure of Formula (Ic), which is of the Formula (Ic)-1:

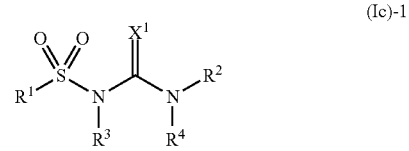

and pharmaceutically acceptable salts, prodrugs, solvates, hydrates, isomers, and tautomers thereof, wherein:

$X^1$ is O, S, 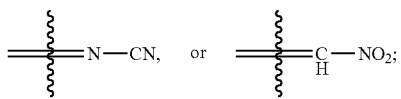

$R^1$ is selected from the group consisting of

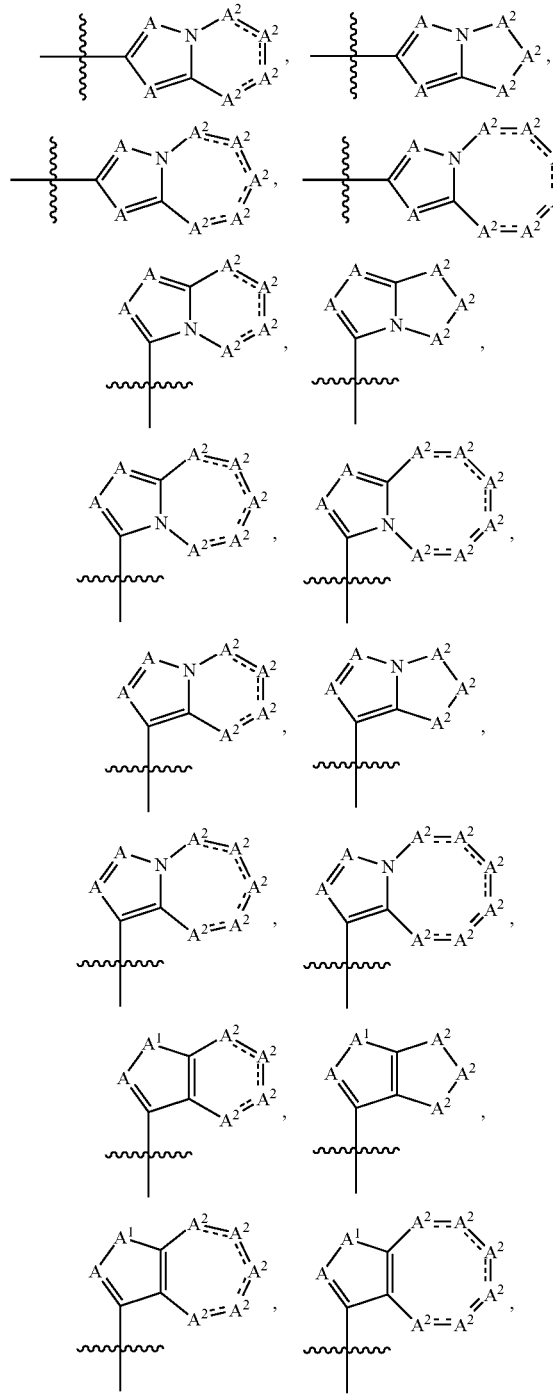

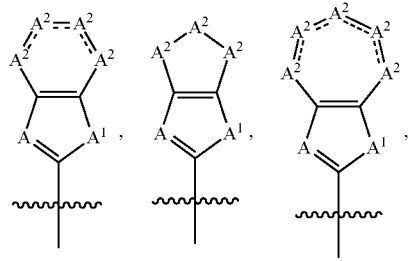

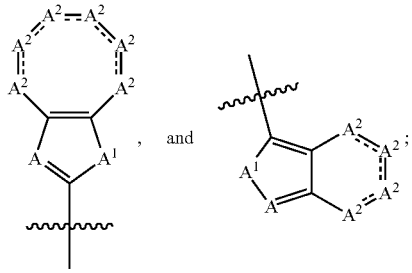

wherein ═══ represents a single bond or a double bond provided that the ring comprising one or more $A^2$ is a non-aromatic ring;

each A is independently $CR^{5a}$ or N;

$A^1$ is $NR^{5a}$, O, S, or C(O);

each $A^2$ is independently $CR^{5a}$, $C(R^{5a})_2$, N, $NR^{5a}$, O, S, or $S(O)_2$;

$R^2$ is

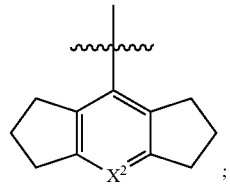

$X^2$ is N or $CR^{5b}$;

$R^3$ and $R^4$ are H;

each $R^{5a}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; wherein the $C_3$-$C_8$cycloalkyl, heterocyclyl, aryl, or heteroaryl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two geminal $R^{5a}$ can form an oxo group;

each $R^{5b}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —C(O)

NR$^6$R$^7$, —NR$^6$S(O)$_2$R$^7$, —S(O)R$^6$, —S(O)NR$^6$R$^7$, —NR$^6$S(O)R$^7$, C$_1$-C$_6$alkyl, C$_2$-C$_6$alkenyl, C$_4$-C$_8$cycloalkenyl, or C$_2$-C$_6$alkynyl; wherein the C$_1$-C$_6$alkyl, C$_2$-C$_6$alkenyl, C$_4$-C$_8$cycloalkenyl, and C$_2$-C$_6$alkynyl are optionally substituted with D, halogen, —OR$^6$, —NH$_2$, —NH(C$_1$-C$_6$alkyl), or —N(C$_1$-C$_6$alkyl)$_2$;

R$^6$ and R$^7$ are independently, at each occurrence H, D, C$_1$-C$_8$alkyl, C$_2$-C$_8$alkenyl, C$_4$-C$_8$cycloalkenyl, C$_2$-C$_8$alkynyl, C$_3$-C$_8$cycloalkyl, heterocyclyl, aryl, or heteroaryl; wherein the heterocyclyl and heteroaryl contain 1-5 heteroatoms selected from the group consisting of N, S, P and O; wherein the C$_1$-C$_6$alkyl, C$_2$-C$_8$alkenyl, C$_4$-C$_8$cycloalkenyl, C$_2$-C$_6$alkynyl, C$_3$-C$_8$cycloalkyl, heterocyclyl, aryl, and heteroaryl are optionally substituted with D, halogen, C$_1$-C$_6$alkyl, —OH, —O—C$_1$-C$_6$alkyl, —NH$_2$, —NH(C$_1$-C$_6$alkyl), or —N(C$_1$-C$_6$alkyl)$_2$; or R$^6$ and R$^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or A$^1$ is an imidazole, then at least one A$^2$ is N, NR$^{5a}$, O, S, or S(O)$_2$.

The present disclosure provides a compound having the structure of Formula (Id),

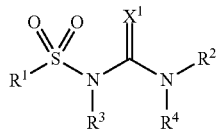

(Id)

and pharmaceutically acceptable salts, enantiomers, hydrates, solvates, prodrugs, isomers, and tautomers thereof, where X$^1$, R$^1$, R$^2$, R$^3$, and R$^4$ are as described above.

In certain embodiments, the present disclosure provides a compound having the structure of Formula (Id), which is of the Formula (Id)-1:

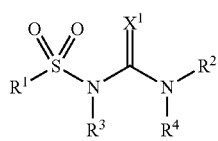

(Id)-1 and pharmaceutically acceptable salts, prodrugs, solvates, hydrates, isomers, and tautomers thereof, wherein:

X$^1$ is O, S,

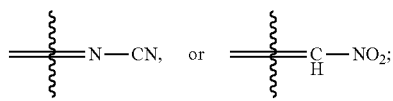

R$^1$ is selected from the group consisting of

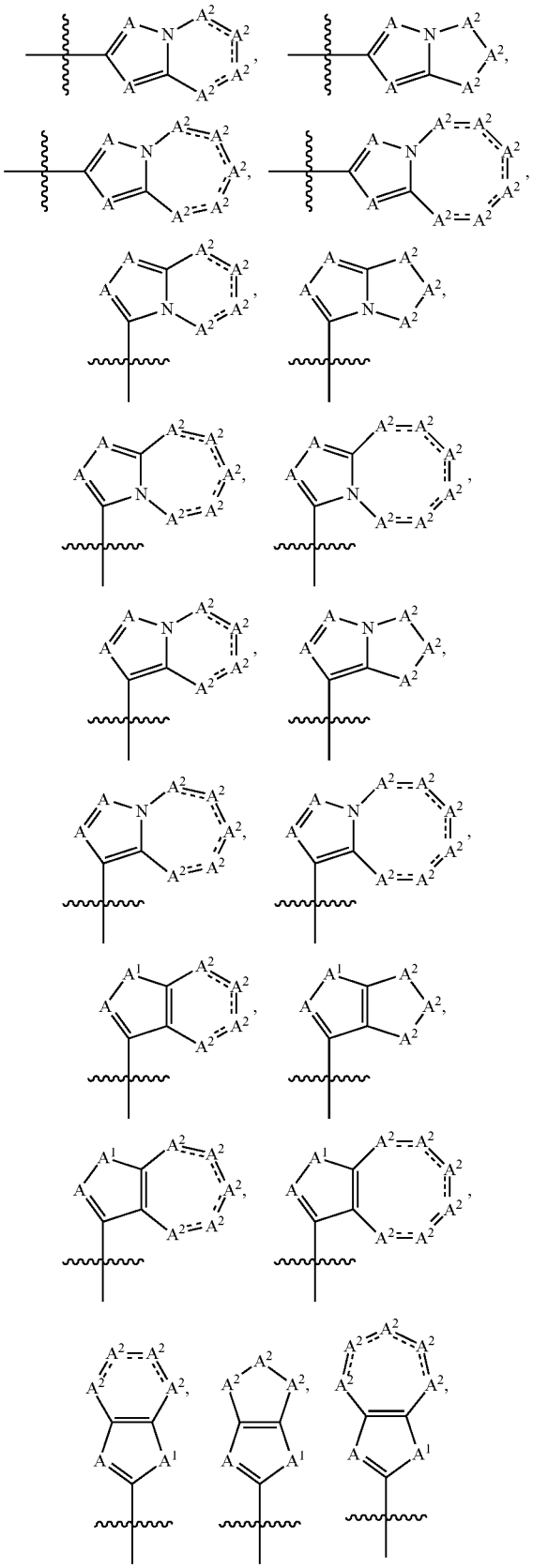

-continued

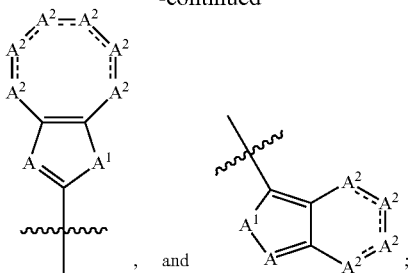
, and wherein === represents a single bond or a double bond provided that the ring comprising one or more $A^2$ is a non-aromatic ring;

each A is independently $CR^{5a}$ or N;

$A^1$ is $NR^{5a}$, O, S, or C(O);

each $A^2$ is independently $CR^{5a}$, $C(R^{5a})_2$, N, $NR^{5a}$, O, S, or $S(O)_2$;

$R^2$ is

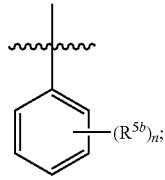

$R^3$ and $R^4$ are H;

each $R^{5a}$ is independently H, D, halogen, OH, CN, —$NO_2$—$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, halogen, $C_1$-$C_6$alkyl, —$OR^6$, —$NH_2$, —$NH(C_1$-$C_6$alkyl), or —$N(C_1$-$C_6$alkyl)$_2$; or two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; wherein the $C_3$-$C_8$cycloalkyl, heterocyclyl, aryl, or heteroaryl are optionally substituted with D, halogen, $C_1$-$C_6$alkyl, —$OR^6$, —$NH_2$, $NH(C_1$-$C_6$alkyl), or $N(C_1$-$C_6$alkyl)$_2$; or two geminal $R^{5a}$ can form an oxo group;

each $R^{5b}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, or $C_2$-$C_6$alkynyl; wherein the $C_1$-$C_6$alkyl, $C_2$-$C_6$alkenyl, $C_4$-$C_8$cycloalkenyl, and $C_2$-$C_6$alkynyl are optionally substituted with D, halogen, —$OR^6$, —$NH_2$, —$NH(C_1$-$C_6$alkyl), or —$N(C_1$-$C_6$alkyl)$_2$;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; wherein the $C_1$-$C_6$alkyl, $C_2$-$C_8$alkenyl, $C_4$-$C_8$cycloalkenyl, $C_2$-$C_6$alkynyl, $C_3$-$C_8$cycloalkyl, heterocyclyl, aryl, and heteroaryl are optionally substituted with D, halogen, $C_1$-$C_6$alkyl, —OH, —O—$C_1$-$C_6$alkyl, —$NH_2$, —$NH(C_1$-$C_6$alkyl), or —$N(C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^{5a}$, O, S, or $S(O)_2$.

The present disclosure provides a compound having the structure of Formula (Ie),

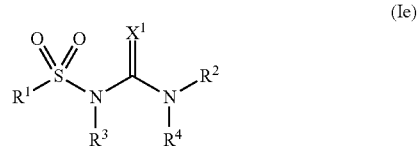

and pharmaceutically acceptable salts, enantiomers, hydrates, solvates, prodrugs, isomers, and tautomers thereof, where $X^1$, $R^1$, $R^2$, $R^3$, and $R^4$ are as described above.

The present disclosure provides a compound having the structure of Formula (If),

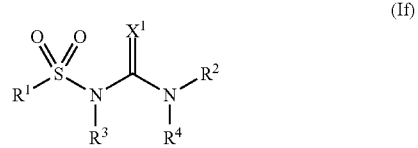

and pharmaceutically acceptable salts, enantiomers, hydrates, solvates, prodrugs, isomers, and tautomers thereof, where $X^1$, $R^1$, $R^2$, $R^3$, and $R^4$ are as described above.

The present disclosure provides a compound having the structure of Formula (Ig),

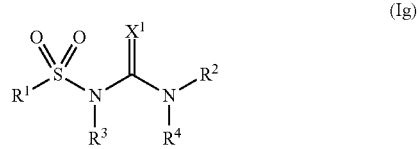

and pharmaceutically acceptable salts, enantiomers, hydrates, solvates, prodrugs, isomers, and tautomers thereof, where $X^1$, $R^1$, $R^2$, $R^3$, and $R^4$ are as described above. Compounds of Formula (If) do not contain a basic amino group in the $R^1$ substituent. The sulfonylurea moiety within compounds of Formula (Ig) renders pka values for these compounds in the range of 5.2-6.2, characterizing them as weak organic acids. Compounds of this structure may display low volumes of distribution in vivo and may exhibit high plasma protein binding.

In certain embodiments, the present disclosure provides a compound having the structure of Formula (Ig), which is of the Formula (Ig)-1:

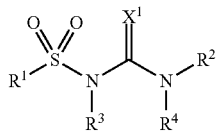

and pharmaceutically acceptable salts, prodrugs, solvates, hydrates, isomers, and tautomers thereof,
wherein:
$X^1$ is O or S;
$R^1$ is selected from the group consisting of

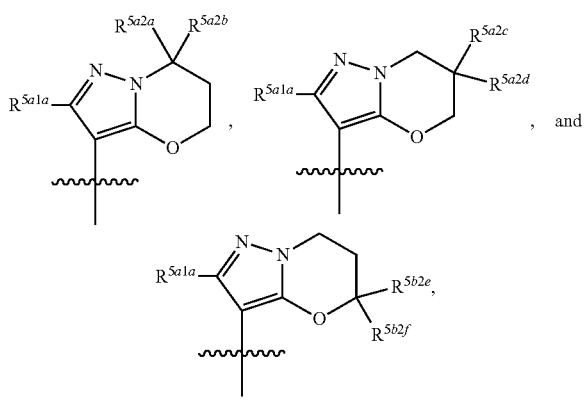

$R^2$ is

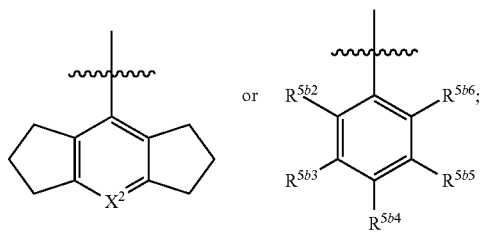

$X^2$ is N or $CR^{5b1}$;
$R^3$ and $R^4$ are H;
$R^{5a1a}$ is H, D, halogen, OH, CN, $-NO_2$, $-SR^6$, $-OR^6$, $-NHR^6$, $-NR^6R^7$, $-NR^6C(O)R^6$, $-NR^6C(O)OR^6$, $-NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2$-$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2$-$C_3$-$C_8$cycloalkyl are optionally substituted with D, $-CN$, halogen, $C_1$-$C_6$alkyl, $-OR^6$, $-NH_2$, $-NH(C_1$-$C_6$alkyl), $N(C_1$-$C_6$alkyl)$_2$, $-NR^6C(O)OR^6$, or $-NR^6C(O)R^6$;
$R^{5a2a}$, $R^{5a2b}$, $R^{5a2c}$, $R^{5a2d}$, $R^{5a2e}$, and $R^{5a2f}$ are selected from independently H, D, halogen, OH, CN, $-NO_2$, $-SR^6$, $-OR^6$, $-C(O)R^6$, $-S(O)_2R^6$, $-C(O)OR^6$, $-C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2$-$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2$-$C_3$-$C_8$cycloalkyl are optionally substituted with D, $-CN$, halogen, $C_1$-$C_6$alkyl, $-OR^6$, $-NR^6C(O)OR^6$, $-NR^6C(O)R^6$, $-NR^6C(O)NR^6$, $-NR^6C(O)R^6$, $-NS(O)_2R^6$; or
two $R^{5a2a}$, $R^{5a2b}$, $R^{5a2c}$, $R^{5a2d}$, $R^{5a2e}$, and $R^{5a2f}$ which are germinal, together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, $-OR^6$, $-S(O)_2$-$R^6$; $-COR^6$, $-NR^6C(O)OR^6$, $-NR^6C(O)R^6$, $-NR^6C(O)NR^6$, or $-NS(O)_2R^6$; or
two geminal $R^{5a2a}$, $R^{5a2b}$, $R^{5a2c}$, $R^{5a2d}$, $R^{5a2e}$, and $R^{5a2f}$ can form an oxo group;
$R^{5b1}$ is H, D, halogen, $-CN$, $-OR^6$, or $C_1$-$C_6$alkyl, $C_3$-$C_8$cycloalkyl, $-C(O)NR^6$, $-C(O)OR^6$; wherein the $C_1$-$C_6$alkyl, and $C_3$-$C_8$cycloalkyl, are optionally substituted with D, halogen, $-CN$, $-OR^6$, $-NH_2$, $-NH(C_1$-$C_6$alkyl), or $-N(C_1$-$C_6$alkyl)$_2$;
each $R^{5b2}$, $R^{5b3}$, $R^{5b4}$, $R^{5b5}$, and $R^{5b6}$ is independently H, D, halogen, OH, $-CN$, $-NO_2$, $-SR^6$, $-OR^6$, $-NHR^6$, $-NR^6R^7$, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, $-CN$, $-OR^6$, $-NH_2$, $-NH(C_1$-$C_6$alkyl), or $-N(C_1$-$C_6$alkyl)$_2$; or
two adjacent $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, $-CN$, $C_1$-$C_6$alkyl, $-OR^6$, $-NH_2$, $-NH(C_1$-$C_6$alkyl), or $-N(C_1$-$C_6$alkyl)$_2$; and
$R^6$ and $R^7$ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, and heteroaryl are optionally substituted with D, $-CN$, halogen, $C_1$-$C_6$alkyl, $-OH$, $-O$-$C_1$-$C_6$alkyl, $-NH_2$, $-NH(C_1$-$C_6$alkyl), or $-N(C_1$-$C_6$alkyl)$_2$; or
$R^6$ and $R^7$ together with the atom to which they are attached can form heterocyclyl or heteroaryl containing 1-3 heteroatoms selected from the group consisting of N, S, P and O.

The present disclosure provides a compound having the structure of Formula (Ih),

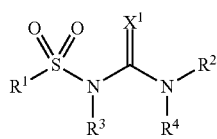

and pharmaceutically acceptable salts, enantiomers, hydrates, solvates, prodrugs, isomers, and tautomers thereof, where $X^1$, $R^5$, $R^2$, $R^3$, and $R^4$ are as described above.

Compounds of Formula (Ih) contain a basic amino group. Incorporation of a basic amino group to a compound of Formula (Ih), which also bears the acidic sulfonylurea moiety, would be expected to exist as a zwitterion, having a net zero charge. Zwitterionic compounds can have different physicochemical properties than weak organic acids. Notably, there may be increased volumes of distribution in vivo as well as lowered plasma protein binding. In certain embodiments of Formula Ih, one or two $R^{5a2}$ are —NHR$^6$, —NR$^6$R$^7$, C$_1$-C$_6$alkyl, or heterocyclyl containing N; wherein the C$_1$-C$_6$alkyl is substituted with —NH$_2$, —NH(C$_1$-C$_6$alkyl), or —N(C$_1$-C$_6$alkyl)$_2$, and wherein the heterocyclyl is optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, or —NR$^6$C(O)R$^6$, —NR$^6$C(O)NR$^6$, —NR$^6$C(O)R$^6$, or —NR$^6$S(O)$_2$R$^6$. In certain embodiments of Formula Ih, one $R^{5a2}$ is —NHR$^6$, —NR$^6$R$^7$, C$_1$-C$_6$alkyl, or heterocyclyl containing N; wherein the C$_1$-C$_6$alkyl is substituted with —NH$_2$, —NH(C$_1$-C$_6$alkyl), or —N(C$_1$-C$_6$alkyl)$_2$, and wherein the heterocyclyl is optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, or —NR$^6$C(O)R$^6$, —NR$^6$C(O)NR$^6$, —NR$^6$C(O)R$^6$, or —NR$^6$S(O)$_2$R$^6$.

In certain embodiments, the present disclosure provides a compound having the structure of Formula (Ih), which is of the Formula (Ih)-1:

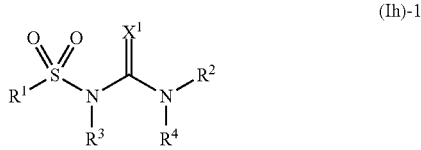

(Ih)-1 and pharmaceutically acceptable salts, prodrugs, solvates, hydrates, isomers, and tautomers thereof,
wherein:
$X^1$ is O or S;
$R^1$ is selected from the group consisting of

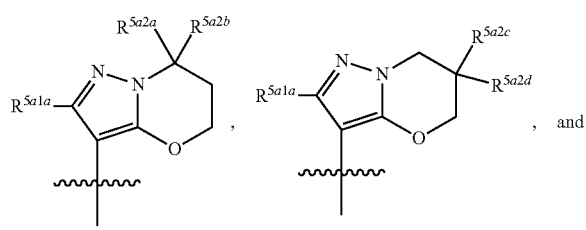

, and

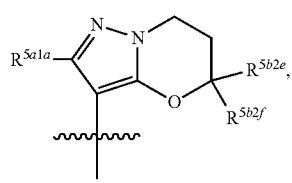

$R^2$ is

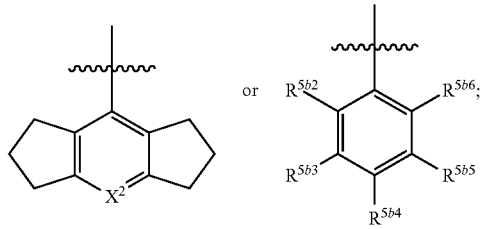

$X^2$ is N or CR$^{5b1}$;
$R^3$ and $R^4$ are H;
$R^{5a1a}$ is H, D, halogen, OH, CN, —NO$_2$—SR$^6$, —OR$^6$, —NHR$^6$, —NR$^6$R$^7$, —NR$^6$C(O)R$^6$, —NR$^6$C(O)OR$^6$, —NR$^6$C(O)NR$^6$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, —CN, halogen, C$_1$-C$_6$alkyl, —OR$^6$, —NH$_2$, —NH(C$_1$-C$_6$alkyl), N(C$_1$-C$_6$alkyl)$_2$, —NR$^6$C(O)OR$^6$, or —NR$^6$C(O)R$^6$;

each $R^{5a2a}$, $R^{5a2b}$, $R^{5a2c}$, $R^{5a2d}$, $R^{5a2e}$, and $R^{5a2f}$ are independently selected from H, —NHR$^6$, —NR$^6$R$^7$, C$_1$-C$_6$alkyl, and heterocyclyl containing N; wherein the C$_1$-C$_6$alkyl is substituted with —NH2, —NH(C$_1$-C$_6$alkyl), or —N(C$_1$-C$_6$alkyl)$_2$, and wherein the heterocyclyl is optionally substituted with with D, —CN, halogen, C$_1$-C$_6$alkyl, —OR$^6$, —NH2, —NH(C$_1$-C$_6$alkyl), —N(C$_1$-C$_6$alkyl)$_2$, —NR$^6$C(O)OR$^6$, or —NR$^6$C(O)R$^6$, —NR$^6$C(O)NR$^6$, —NR$^6$C(O)R$^6$, or —NR$^6$S(O)$_2$R$^6$;

$R^{5b1}$ is H, D, halogen, —CN—OR$^6$, or C$_1$-C$_6$alkyl, C$_3$-C$_8$cycloalkyl, —C(O)NR$^6$, —C(O)OR$^6$; wherein the C$_1$-C$_6$alkyl, and C$_3$-C$_8$cycloalkyl, are optionally substituted with D, halogen, —CN, —OR$^6$, —NH$_2$, —NH(C$_1$-C$_6$alkyl), or —N(C$_1$-C$_6$alkyl)$_2$;

each $R^{5b2}$, $R^{5b3}$, $R^{5b4}$, $R^{5b5}$, and $R^{5b6}$ is independently H, D, halogen, OH, —CN, —NO$_2$, —SR$^6$, —OR$^6$, —NHR$^6$, —NR$^6$R$^7$, C$_1$-C$_6$alkyl, C$_2$-C$_6$alkenyl, C$_4$-C$_8$cycloalkenyl, C$_3$-C$_8$cycloalkyl, or C$_2$-C$_6$alkynyl; wherein the C$_1$-C$_6$alkyl, C$_2$-C$_6$alkenyl, C$_4$-C$_8$cycloalkenyl, C$_3$-C$_8$cycloalkyl, and C$_2$-C$_6$alkynyl are optionally substituted with D, halogen, —CN, —OR$^6$, —NH$_2$, —NH(C$_1$-C$_6$alkyl), or —N(C$_1$-C$_6$alkyl)$_2$; or two adjacent $R^{5b2}$, $R^{5b3}$, $R^{5b4}$, $R^{5b5}$, and $R^{5b6}$ together with the atoms to which they are attached can form C$_3$-C$_8$cycloalkyl, heterocyclyl, aryl, or heteroaryl, wherein C$_3$-C$_8$cycloalkyl, heterocyclyl, aryl, or heteroaryl are optionally substituted with halogen, —CN, C$_1$-C$_6$alkyl, —OR$^6$, —NH2, —NH(C$_1$-C$_6$alkyl), or —N(C$_1$-C$_6$alkyl)$_2$; and $R^6$ and $R^7$ are independently, at each occurrence, H, D, C$_1$-C$_8$alkyl, C$_2$-C$_8$alkenyl, C$_2$-C$_8$alkynyl, C$_3$-C$_8$cycloalkyl, C$_4$-C$_8$cycloalkenyl, heterocyclyl, aryl, or heteroaryl; wherein the heterocyclyl and heteroaryl contain 1-5 heteroatoms selected from the group consisting of N, S, P and O; wherein the C$_1$-C$_8$alkyl, C$_2$-C$_8$alkenyl, C$_2$-C$_8$alkynyl, C$_3$-C$_8$cycloalkyl, C$_4$-C$_8$cycloalkenyl, heterocyclyl, aryl, and heteroaryl are optionally substituted with D, —CN, halogen, C$_1$-C$_6$alkyl, —OH, —O—C$_1$-C$_6$alkyl, —NH2, —NH(C$_1$-C$_6$alkyl), or —N(C$_1$-C$_6$alkyl)$_2$; or $R^6$ and $R^7$ together with the atom to which they are attached can form heterocyclyl or heteroaryl containing 1-3 heteroatoms selected from the group consisting of N, S, P and O.

In certain embodiments of Formula I, when $R^1$ is

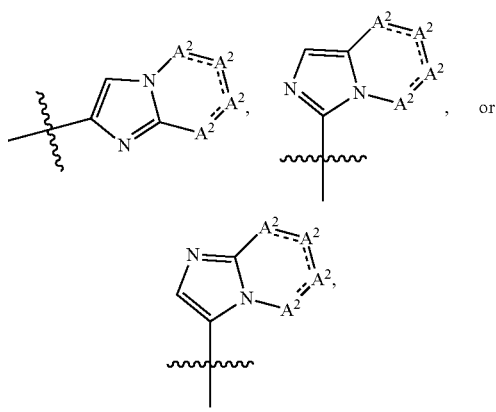

then at least one $A^2$ is N, $NR^5$, O, S, or $S(O)_2$. In certain embodiments of Formulae Ia-Id, when $R^1$ is

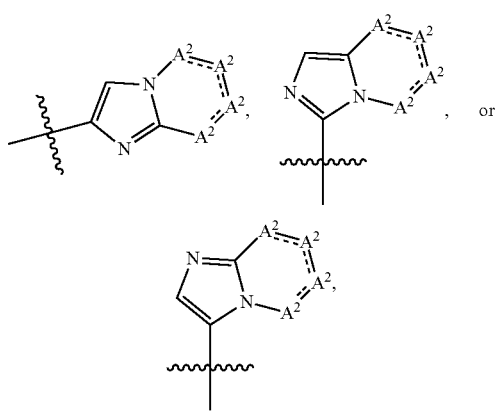

then at least one $A^2$ is N, $NR^{5a}$, O, S, or $S(O)_2$.

In certain embodiments of the formulae described herein, $X^1$ is O. In certain embodiments, $X^1$ is S. In certain embodiments, $X^1$ is

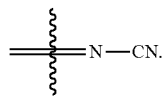

In certain embodiments, $X^1$ is

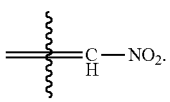

In certain embodiments of the formulae described herein, $R^2$ is

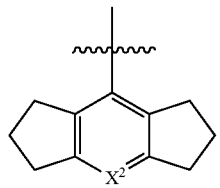

In certain embodiments of Formula I, $R^2$ is

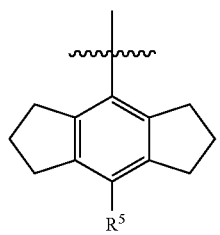

In certain embodiments of Formulae Ia-Id, $R^2$ is

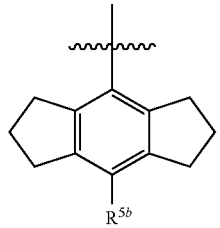

In certain embodiments, $R^2$ is

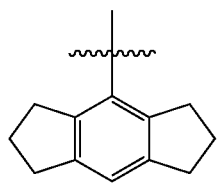

In certain embodiments, $R^2$ is

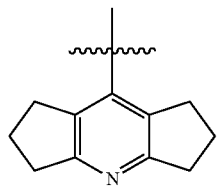

In certain embodiments of the formula described herein, $R^2$ is

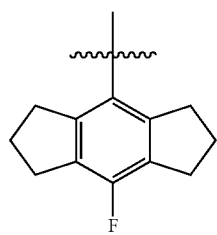

In certain embodiments of Formula I, $R^5$ is H, D, halogen, CN, —$OR^6$, or $C_1$-$C_6$alkyl. In certain embodiments, $R^5$ is H, halogen, or $C_1$-$C_6$alkyl. In certain embodiments, $R^5$ is H, halogen, or methyl. In certain embodiments, $R^5$ is H, fluoro, chloro, or methyl. In certain embodiments, $R^5$ is H. In certain embodiments, $R^5$ is halogen. In certain embodiments, $R^5$ is fluoro. In certain embodiments, $R^5$ is chloro. In certain embodiments, $R^5$ is methyl.

In certain embodiments of Formulae Ia-Id, $R^{5b}$ is H, D, halogen, CN, —$OR^6$, or $C_1$-$C_6$alkyl. In certain embodiments, $R^{5b}$ is H, halogen, or $C_1$-$C_6$alkyl. In certain embodiments, $R^{5b}$ is H, halogen, or methyl. In certain embodiments, $R^{5b}$ is H, fluoro, chloro, or methyl. In certain embodiments, $R^{5b}$ is H. In certain embodiments, $R^{5b}$ is halogen. In certain embodiments, $R^{5b}$ is fluoro. In certain embodiments, $R^{5b}$ is chloro. In certain embodiments, $R^{5b}$ is methyl.

In certain embodiments of Formula I, $R^2$ is

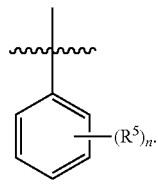

In certain embodiments of Formula Ia-Id, $R^2$ is

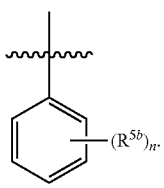

In certain embodiments, n is zero, one, or two.

In certain embodiments of Formula I, each $R^5$ is independently H, halogen, OH, CN, —$NO_2$, —$OR^6$, $C_1$-$C_6$alkyl, $C_2$-$C_6$alkenyl, $C_4$-$C_8$cycloalkenyl, or $C_3$-$C_8$cycloalkyl. In certain embodiments, each $R^5$ is independently selected from the group consisting of H, halogen, $C_1$-$C_6$alkyl, $C_3$-$C_8$cycloalkyl, and —CN.

In certain embodiments of Formulae Ia-Id, each $R^{5b}$ is independently H, halogen, OH, CN, —$NO_2$, —$OR^6$, $C_1$-$C_6$alkyl, $C_2$-$C_6$alkenyl, $C_4$-$C_8$cycloalkenyl, or $C_3$-$C_8$cycloalkyl. In certain embodiments, each $R^{5b}$ is independently selected from the group consisting of H, halogen, $C_1$-$C_6$alkyl, $C_3$-$C_8$cycloalkyl, and —CN.

In certain embodiments of Formula I, $R^2$ is

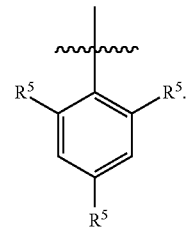

In certain embodiments of Formulae Ia-Id, $R^2$ is

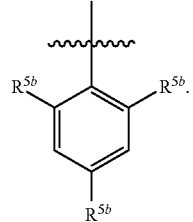

In certain embodiments of Formula I, $R^2$ is

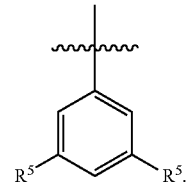

In certain embodiments of Formulae Ia-Id, $R^2$ is

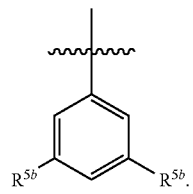

In certain embodiments of the formulae described herein, $R^2$ is selected from the group consisting of

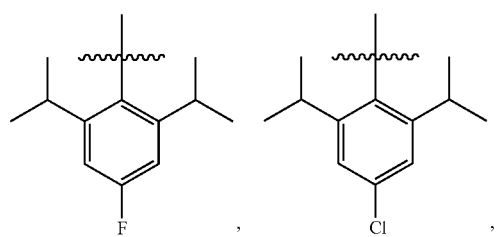

-continued

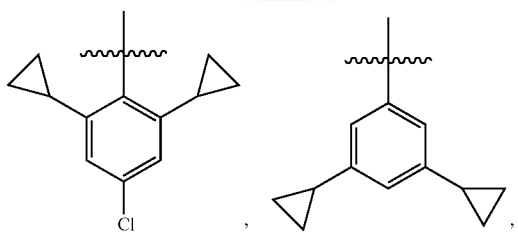

In certain embodiments, wherein R² is selected from the group consisting of

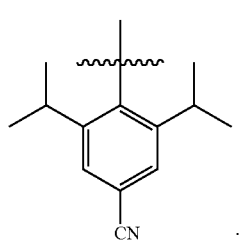

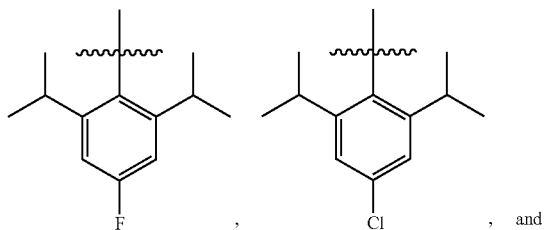

In certain embodiments, R² is

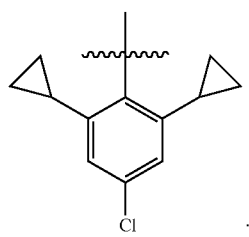

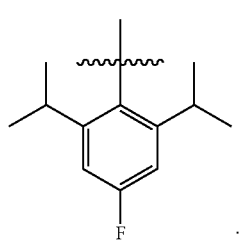 [SMILES: *c1c(C(C)C)cc(F)cc1C(C)C]

In certain embodiments of the formula Ie-Ih, R² is

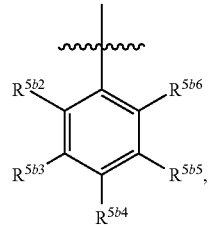

wherein at least one of $R^{5b2}$, $R^{5b3}$, $R^{5b4}$, $R^{5b5}$, and $R^{5b6}$ is $C_1$-$C_6$alkyl or $C_3$-$C_8$cycloalkyl, wherein the $C_1$-$C_6$alkyl and $C_3$-$C_8$cycloalkyl are optionally substituted with D, halogen, —CN, —OR⁶, —NH₂, —NH($C_1$-$C_6$alkyl), or —N($C_1$-$C_6$alkyl)₂. In certain embodiments, at least one of $R^{5b2}$, $R^{5b3}$, $R^{5b4}$, $R^{5b5}$, and $R^{5b6}$ is $C_1$-$C_6$alkyl or $C_3$-$C_8$cycloalkyl, wherein the $C_1$-$C_6$alkyl and $C_3$-$C_8$cycloalkyl are optionally substituted with halogen.

In certain embodiments of the formulae described herein, R¹ is an optionally substituted $C_1$-$C_6$alkyl. In certain embodiments, R¹ is $C_1$-$C_6$alkyl. In certain embodiments, R¹ is $C_1$-$C_8$alkyl. In certain embodiments, R¹ is methyl. In certain embodiments, R¹ is an optionally substituted $C_1$-$C_6$alkenyl. In certain embodiments, R¹ is an optionally substituted $C_1$-$C_6$alkynyl. In certain embodiments, R¹ is —(CH₂)$_m$—O—(CH₂)$_m$—CH₃, each m is independently an integer from one to 4.

In certain embodiments of the formulae described herein, R¹ is selected from the group consisting

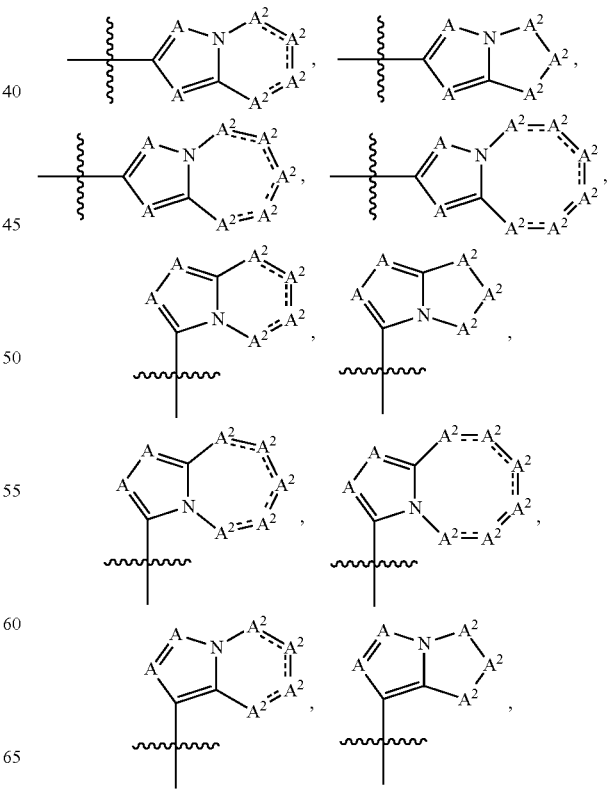

-continued
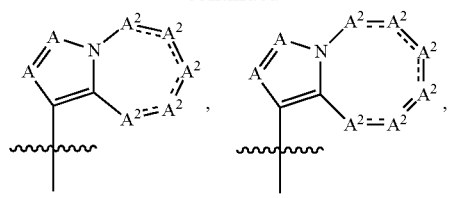
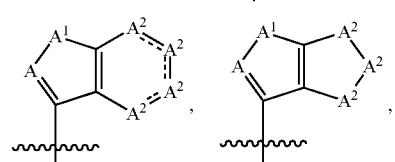
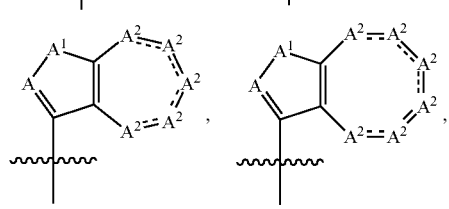
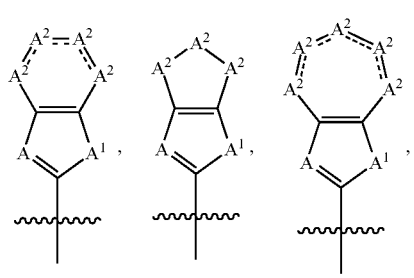
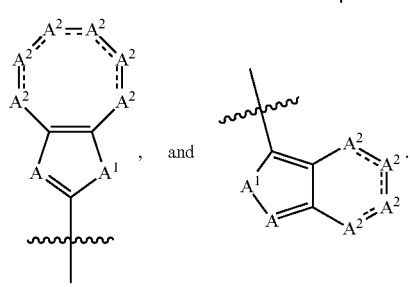
and
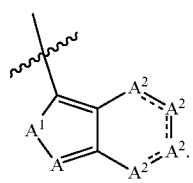
In certain embodiments of the formulae described herein, R¹ is
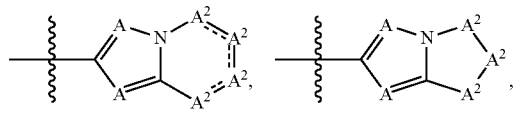
In certain embodiments of the formulae described herein, R¹ is
-continued
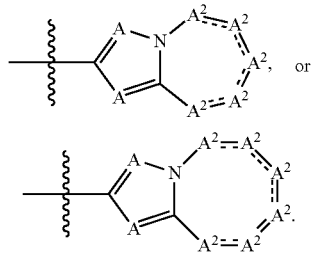
In certain embodiments of the formulae described herein, R¹ is
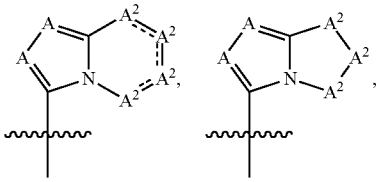
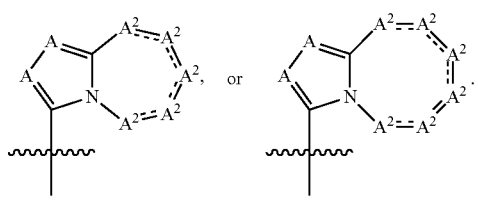
In certain embodiments of the formulae described herein, R¹ is
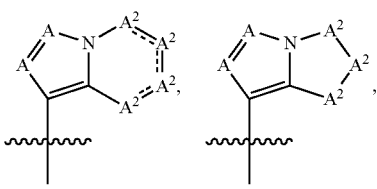
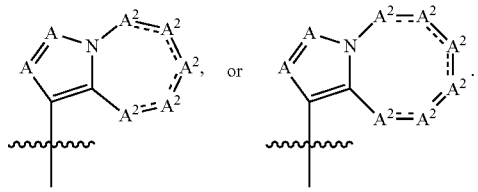
In certain embodiments of the formulae described herein, R¹ is
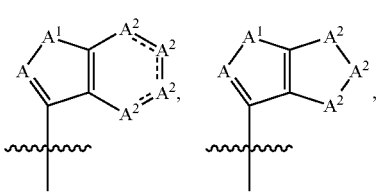

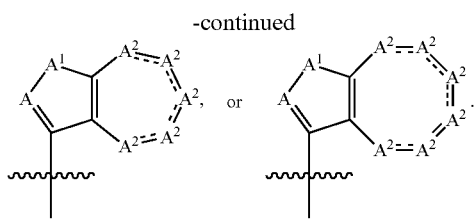

In certain embodiments of the formulae described herein, $R^1$ is

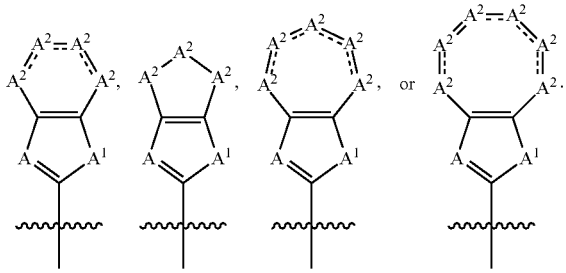

In certain embodiments of the formulae described herein, $R^1$ is

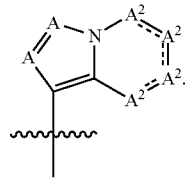

In certain embodiments, $R^1$ is

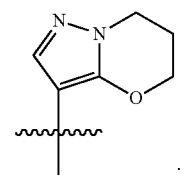 [SMILES: *c1cnn2c1OCCC2]

In certain embodiments, $R^1$ is

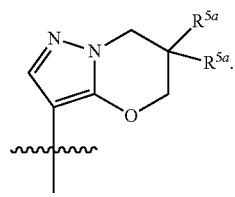

In certain embodiments of the formulae described herein, the ═ are single bonds in the ring comprising $A^2$, thereby forming a saturated ring. In certain embodiments, one to two ═ are double bonds in the ring comprising $A^2$, thereby forming an unsaturated ring.

In certain embodiments of Formula I, A is $CR^5$. In certain embodiments of Formulae Ia-Id, A is $CR^{5a}$. In certain embodiments of the formulae described herein, A is N.

In certain embodiments of Formula I, $A^1$ is $NR^5$. In certain embodiments of Formulae Ia-Id, $A^1$ is $NR^{5a}$. In certain embodiments of the formulae described herein, $A^1$ is O. In certain embodiments of the formulae described herein, $A^1$ is S. In certain embodiments of the formulae described herein, $A^1$ is C(O).

In certain embodiments of the formulae described herein, each $A^2$ is independently $CH_2$ or O. In certain embodiments, each $A^2$ is $CH_2$.

In certain embodiments of Formula I, one A is $CR^5$ and the other A is N. In certain embodiments, each $A^2$ is independently $C(R^5)_2$, $NR^5$, or O.

In certain embodiments of Formulae Ia-Id, one A is $CR^{5a}$ and the other A is N. In certain embodiments, each $A^2$ is independently $C(R^{5a})_2$, $NR^{5a}$, or O.

In certain embodiments of Formula I, $R^5$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl. In certain embodiments, the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl is optionally substituted.

In certain embodiments of Formula Ia, each $R^{5a}$ is independently H, D, halogen, OH, CN, —$NO_2$—$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl. In certain embodiments, the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl is optionally substituted.

In certain embodiments of Formula Ia, each $R^{5b}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl. In certain embodiments, the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, or heteroaryl is optionally substituted.

In certain embodiments of Formula I, two $R^5$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O. In certain embodiments, the $C_3$-$C_8$cycloalkyl, heterocyclyl, aryl, or heteroaryl is optionally substituted.

In certain embodiments of Formulae Ia-Id, two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O. In certain embodiments, the $C_3$-$C_8$cycloalkyl, heterocyclyl, aryl, or heteroaryl is optionally substituted. In certain embodiments, the $C_3$-$C_8$cycloalkyl, heterocyclyl, aryl, or heteroaryl is optionally substituted with D, halogen, $C_1$-$C_6$alkyl, —OH, —$NH_2$, $NH(C_1$-$C_6$alkyl), or $N(C_1$-$C_6$alkyl)$_2$. In certain embodiments, two $R^{5a}$ together with the atoms to which they are attached can form $C_3$-$C_8$cycloalkyl, optionally substituted with D, halogen, $C_1$-$C_6$alkyl, —$OR^6$, —$NH_2$, —$NH(C_1$-$C_6$alkyl), or —$N(C_1$-$C_6$alkyl)$_2$.

In certain embodiments of the formulae described herein, two geminal $R^5$ can form an oxo group. In certain embodiments of Formula Ia-Id, two geminal $R^{5a}$ can form an oxo group.

In certain embodiments of Formulae Ib-Id, each $R^{5a}$ is independently H, D, halogen, OH, CN, —NO$_2$, —SR$^6$, —OR$^6$, —NHR$^6$, —NR$^6$R$^7$, —S(O)$_2$N(R$^6$)$_2$—, —S(O)$_2$R$^6$, —C(O)R$^6$, —C(O)OR$^6$, —C(O)NR$^6$R$^7$, —NR$^6$S(O)$_2$R$^7$, —S(O)R$^6$, —S(O)NR$^6$R$^7$, —NR$^6$S(O)R$^7$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, halogen, C$_1$-C$_6$alkyl, —OH, —NH$_2$, —NH(C$_1$-C$_6$alkyl), or —N(C$_1$-C$_6$alkyl)$_2$. In certain embodiments, $R^{5a}$ is C$_1$-C$_6$alkyl optionally substituted with D, halogen, C$_1$-C$_6$alkyl, —OR$^6$, —NH$_2$, NH(C$_1$-C$_6$alkyl), or N(C$_1$-C$_6$alkyl)$_2$. In certain embodiments, $R^{5a}$ is heterocyclyl optionally substituted with D, halogen, C$_1$-C$_6$alkyl, —OH, —NH$_2$, —NH(C$_1$-C$_6$alkyl), or —N(C$_1$-C$_6$alkyl)$_2$.

In certain embodiments of Formulae Ib-Id, two $R^{5a}$ together with the atoms to which they are attached can form C$_3$-C$_8$cycloalkyl, heterocyclyl, aryl, or heteroaryl; wherein the heterocyclyl and heteroaryl contain 1-3 heteroatoms selected from the group consisting of N, S, P and O; wherein the C$_3$-C$_8$cycloalkyl, heterocyclyl, aryl, or heteroaryl are optionally substituted with D, halogen, C$_1$-C$_6$alkyl, —OH, —NH$_2$, —NH(C$_1$-C$_6$alkyl), or —N(C$_1$-C$_6$alkyl)$_2$. In certain embodiments, two $R^{5a}$ together with the atoms to which they are attached can form C$_3$-C$_8$cycloalkyl, optionally substituted with D, halogen, C$_1$-C$_6$alkyl, —OR$^6$, —NH$_2$, —NH(C$_1$-C$_6$alkyl), or —N(C$_1$-C$_6$alkyl)$_2$.

In certain embodiments of Formulae Ib-Id, two geminal $R^{5a}$ can form an oxo group.

In certain embodiments of Formulae Ib-Id, each $R^{5b}$ is independently H, D, halogen, OH, CN, —NO$_2$, —SR$^6$, —OR$^6$, —NHR$^6$, —NR$^6$R$^7$, —S(O)$_2$N(R$^6$)$_2$—, —S(O)$_2$R$^6$, —C(O)R$^6$, —C(O)OR$^6$, —C(O)NR$^6$R$^7$, —NR$^6$S(O)$_2$R$^7$, —S(O)R$^6$, —S(O)NR$^6$R$^7$, —NR$^6$S(O)R$^7$, C$_1$-C$_6$alkyl, C$_2$-C$_6$alkenyl, C$_4$-C$_8$cycloalkenyl, or C$_2$-C$_6$alkynyl; wherein the C$_1$-C$_6$alkyl, C$_2$-C$_6$alkenyl, C$_4$-C$_8$cycloalkenyl, and C$_2$-C$_6$alkynyl are optionally substituted with D, halogen, —OR$^6$, —NH$_2$, —NH(C$_1$-C$_6$alkyl), or —N(C$_1$-C$_6$alkyl)$_2$.

In certain embodiments of Formula I, each $R^5$ is independently H, —NHR$^6$, or —NR$^6$R$^7$. In certain embodiments, each $A^2$ is independently C(R$^5$)$_2$ or O; and each $R^5$ is independently H, —NHR$^6$, or —NR$^6$R$^7$.

In certain embodiments of Formulae Ia-Id, each $R^{5a}$ is independently H, —NHR$^6$, —NR$^6$R$^7$, C$_1$-C$_6$alkyl, or heterocyclyl containing N, wherein the C$_1$-C$_6$alkyl is substituted with —NH$_2$, —NH(C$_1$-C$_6$alkyl), or —N(C$_1$-C$_6$alkyl)$_2$, and wherein the heterocyclyl is optionally substituted with D, halogen, C$_1$-C$_6$alkyl, —OR$^6$, —NH$_2$, —NH(C$_1$-C$_6$alkyl), or —N(C$_1$-C$_6$alkyl)$_2$. In certain embodiments, each $A^2$ is independently C(R$^{5a}$)$_2$ or O; and each $R^{5a}$ is independently H, —NHR$^6$, —NR$^6$R$^7$, C$_1$-C$_6$alkyl, or heterocyclyl containing N, wherein the C$_1$-C$_6$alkyl is substituted with —NH$_2$, —NH(C$_1$-C$_6$alkyl), or —N(C$_1$-C$_6$alkyl)$_2$, and wherein the heterocyclyl is optionally substituted with D, halogen, C$_1$-C$_6$alkyl, —OR$^6$, —NH$_2$, —NH(C$_1$-C$_6$alkyl), or —N(C$_1$-C$_6$alkyl)$_2$.

In certain embodiments of the formulae described herein, $R^1$ is selected from the group consisting of

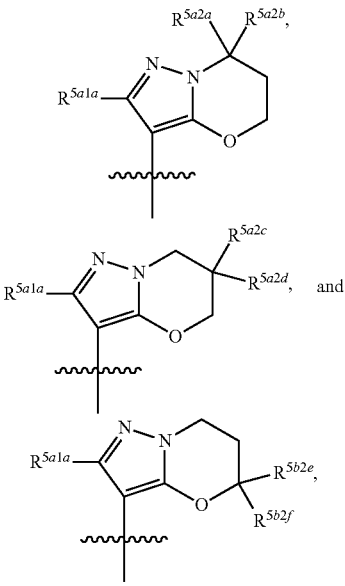

wherein $R^{5a1a}$ is H, D, halogen, OH, CN, —NO$_2$, —SR$^6$, —OR$^6$, —NHR$^6$, —NR$^6$R$^7$, —NR$^6$C(O)R$^6$, —NR$^6$C(O)OR$^6$, —NR$^6$C(O)NR$^6$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, or —NR$^6$C(O)R$^6$; and $R^{5a2a}$, $R^{5a2b}$, $R^{5a2c}$, $R^{5a2d}$, $R^{5a2e}$, and $R^{5a2f}$ are selected from independently H, —NHR$^6$, —NR$^6$R$^7$, C$_1$-C$_6$alkyl, or heterocyclyl containing N, wherein the C$_1$-C$_6$alkyl is substituted with —NH$_2$, —NH(C$_1$-C$_6$alkyl), or —N(C$_1$-C$_6$alkyl)$_2$, and wherein the heterocyclyl is optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, or —NR$^6$C(O)R$^6$, —NR$^6$C(O)NR$^6$, —NR$^6$C(O)R$^6$, or —NR$^6$S(O)$_2$R$^6$.

In certain embodiments of the formulae described herein, $R^6$ and $R^7$ are independently, at each occurrence H, D, C$_1$-C$_8$alkyl, C$_2$-C$_8$alkenyl, C$_4$-C$_8$cycloalkenyl, C$_2$-C$_8$alkynyl, C$_3$-C$_8$cycloalkyl, heterocyclyl, aryl, or heteroaryl, wherein the heterocyclyl and heteroaryl contain 1-5 heteroatoms selected from the group consisting of N, S, P and O. In certain embodiments, the C$_1$-C$_8$alkyl, C$_2$-C$_8$alkenyl, C$_4$-C$_8$cycloalkenyl, C$_2$-C$_8$alkynyl, C$_3$-C$_8$cycloalkyl, heterocyclyl, aryl, or heteroaryl is optionally substituted.

In certain embodiments of the formulae described herein, $R^6$ and $R^7$ together with the atom to which they are attached can form heterocyclyl or heteroaryl containing 1-3 heteroatoms selected from the group consisting of N, S, P and O. In certain embodiments, the heterocyclyl or heteroaryl is optionally substituted.

In certain embodiments of Formulae Ib-Id, $R^6$ and $R^7$ are independently, at each occurrence H, D, C$_1$-C$_8$alkyl, C$_2$-C$_8$alkenyl, C$_4$-C$_8$cycloalkenyl, C$_2$-C$_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; wherein the $C_1$-$C_6$alkyl, $C_2$-$C_8$alkenyl, $C_4$-$C_8$cycloalkenyl, $C_2$-$C_6$alkynyl, $C_3$-$C_8$cycloalkyl, heterocyclyl, aryl, and heteroaryl are optionally substituted with D, halogen, $C_1$-$C_6$alkyl, —OH, —O—$C_1$-$C_6$alkyl, —NH$_2$, —NH($C_1$-$C_6$alkyl), or —N($C_1$-$C_6$alkyl)$_2$. In certain embodiments, $R^6$ is $C_1$-$C_6$alkyl optionally substituted with D, halogen, $C_1$-$C_6$alkyl, —OH, —NH$_2$, —NH($C_1$-$C_6$alkyl), or —N($C_1$-$C_6$alkyl)$_2$. In certain embodiments, $R^7$ is $C_1$-$C_6$alkyl optionally substituted with D, halogen, $C_1$-$C_6$alkyl, —OH, —NH$_2$, —NH($C_1$-$C_6$alkyl), or —N($C_1$-$C_6$alkyl)$_2$.

As described above in Formula Ie, $R^2$ can be

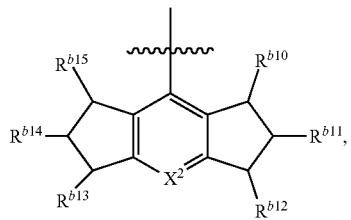

wherein each $R^{b10}$, $R^{b11}$, $R^{b12}$, $R^{b13}$, $R^{b14}$, and $R^{b15}$ is independently H, —OH, or oxo. In certain embodiments, one of $R^{b10}$, $R^{b11}$, $R^{b12}$, $R^{b13}$, $R^{b14}$, and $R^{b15}$ is —OH or oxo and the rest are H. In certain embodiments, one of $R^{b10}$, $R^{b11}$, $R^{b12}$, $R^{b13}$, $R^{b14}$, and $R^{b15}$ is —OH and the rest are H. In certain embodiments, one of $R^{b10}$, $R^{b11}$, $R^{b12}$, $R^{b13}$, $R^{b14}$, and $R^{b15}$ is oxo and the rest are H.

As described above in Formula Ie-Ih, $X^1$ is O or S. In certain embodiments of Formula Ie-Ig, $X^1$ is O. In certain embodiments, $X^1$ is S.

As described above in Formula Ie-Ih, $R^2$ is

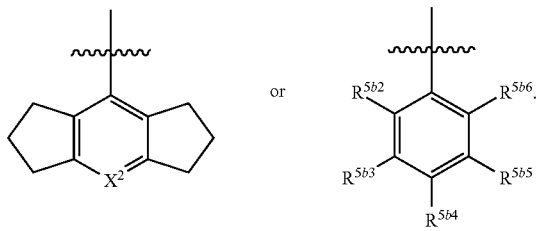

In certain embodiments of Formula Ie-Ih, $R^2$ is

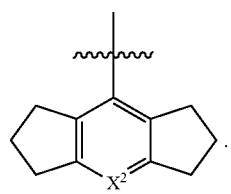

As described above in Formula Ie-Ih, $X^2$ is N or $CR^{5b1}$. In certain embodiments of Formula Ie-Ih, $X^2$ is $CR^{5b1}$. In certain embodiments, $X^2$ is N.

As described above in Formula Ie-Ih, $R^{5b1}$ is H, D, halogen, —CN, —OR$^6$, or $C_1$-$C_6$alkyl, $C_3$-$C_8$cycloalkyl, —C(O)NR$^6$, —C(O)OR$^6$; wherein the $C_1$-$C_6$alkyl, and $C_3$-$C_8$cycloalkyl, are optionally substituted with D, halogen, —CN, —OR$^6$, —NH$_2$, —NH($C_1$-$C_6$alkyl), or —N($C_1$-$C_6$alkyl)$_2$.

In certain embodiments of Formula Ie-Ih, $R^{5b1}$ is H, halogen, or $C_1$-$C_6$alkyl. In certain embodiments, $R^{5b1}$ is H, halogen, or methyl. In certain embodiments, $R^{5b1}$ is H, fluoro, chloro, or methyl. In certain embodiments, $R^{5b1}$ is H. In certain embodiments, $R^{5b1}$ is halogen. In certain embodiments, $R^{5b1}$ is fluoro. In certain embodiments, $R^{5b1}$ is chloro. In certain embodiments, $R^{5b1}$ is methyl. In certain embodiments of Formula Ie-Ih, $R^{5b1}$ is an optionally substituted $C_1$-$C_6$alkyl. In certain embodiments, $R^{5b1}$ is $C_1$-$C_6$alkyl, optionally substituted with halogen. In certain embodiments, $R^{5b1}$ is —OR$^6$. In certain embodiments, $R^{5b1}$ is —OH.

In certain embodiments of Formula Ie-Ih, $R^2$ is $R^2$ is

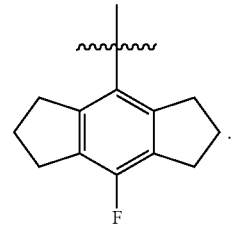

In certain embodiments, $R^2$ is

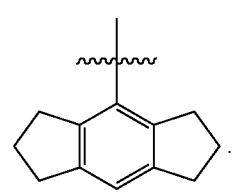 [SMILES: *c1c2c(cc3c1CCC3)CCC2]

In certain embodiments of Formula Ie-Ih, $R^2$ is

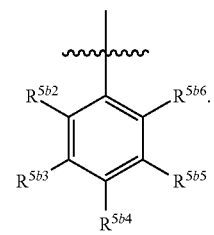

As described above in Formula Ie-Ih, each $R^{5b2}$, $R^{5b3}$, $R^{5b4}$, $R^{5b5}$, and $R^{5b6}$ is independently H, D, halogen, OH, —CN, —NO$_2$, —SR$^6$, —OR$^6$, —NHR$^6$, —NR$^6$R$^7$, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, —CN, —OR$^6$, —NH$_2$, —NH($C_1$-$C_6$alkyl), or —N($C_1$-$C_6$alkyl)$_2$; or two adjacent $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, —CN, $C_1$-$C_6$alkyl, —OR$^6$, —NH$_2$, —NH($C_1$-$C_6$alkyl), or —N($C_1$-$C_6$alkyl)$_2$.

In certain embodiments, each $R^{5b2}$, $R^{5b3}$, $R^{5b4}$, $R^{5b5}$, and $R^{5b6}$ is independently H, D, halogen, OH, CN, —NO$_2$, —OR$^6$, C$_1$-C$_6$alkyl, C$_2$-C$_6$alkenyl, C$_4$-C$_8$cycloalkenyl, or C$_3$-C$_8$cycloalkyl. In certain embodiments, each R$^{5b2}$, R$^{5b3}$, R$^{5b4}$, R$^{5b5}$, and R$^{5b6}$ is independently selected from the group consisting of H, D, halogen, C$_1$-C$_6$alkyl, C$_3$-C$_8$cycloalkyl, and —CN. In certain embodiments, at least one of R$^{5b2}$, R$^{5b3}$, R$^{5b4}$, R$^{5b5}$, and R$^{5b6}$ is not hydrogen. In certain embodiments, one of R$^{5b2}$, R$^{5b3}$, R$^{5b4}$, R$^{5b5}$, and R$^{5b6}$ is —OR$^6$. In certain embodiments, one of R$^{5b2}$, R$^{5b3}$, R$^{5b4}$, R$^{5b5}$, and R$^{5b6}$ is —OH.

In certain embodiments of Formula Ie-Ih, R$^2$ is

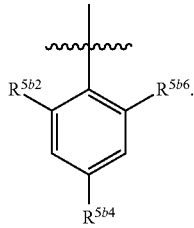

In certain embodiments of Formula Ie-Ih, R$^2$ is

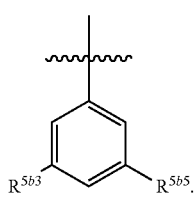

In certain embodiments of Formula Ie-Ih, R$^2$ is selected from the group consisting of

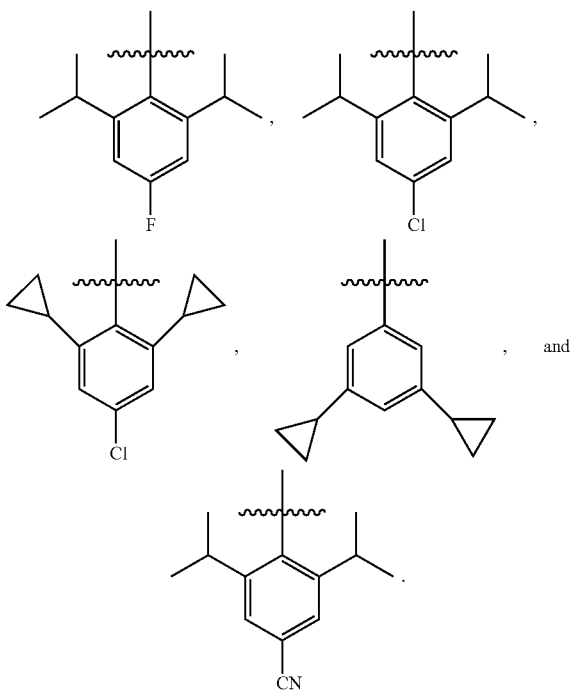

In certain embodiments, wherein R$^2$ is selected from the group consisting of

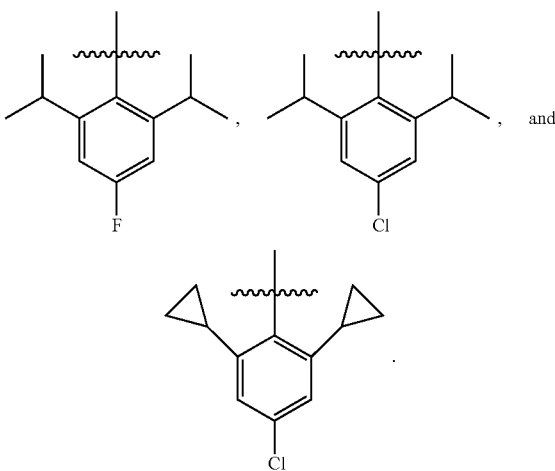

In certain embodiments, R$^2$ is

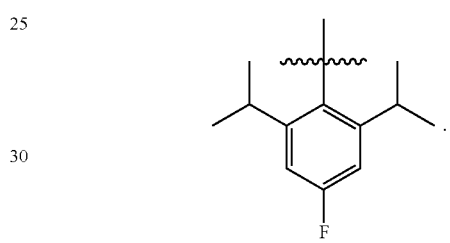

In certain embodiments of Formula Ie-Ih, two adjacent R$^{5b2}$, R$^{5b3}$, R$^{5b4}$, R$^{5b5}$, and R$^{5b6}$ together with the atoms to which they are attached can form C$_3$-C$_8$cycloalkyl, heterocyclyl, aryl, or heteroaryl, wherein C$_3$-C$_8$cycloalkyl, heterocyclyl, aryl, or heteroaryl are optionally substituted with halogen, C$_1$-C$_6$alkyl, —OR$^6$, —NH$_2$, —NH(C$_1$-C$_6$alkyl), or —N(C$_1$-C$_6$alkyl)$_2$. In certain embodiments, two adjacent R$^{5b2}$, R$^{5b3}$, R$^{5b4}$, R$^{5b5}$, and R$^{5b6}$ together with the atoms to which they are attached can form C$_3$-C$_8$cycloalkyl or heterocyclyl, wherein C$_3$-C$_8$cycloalkyl and heterocyclyl are optionally substituted with halogen, C$_1$-C$_6$alkyl, —OR$^6$, —NH$_2$, —NH(C$_1$-C$_6$alkyl), or —N(C$_1$-C$_6$alkyl)$_2$.

In certain embodiments of Formula Ie-Ih, R$^2$ is

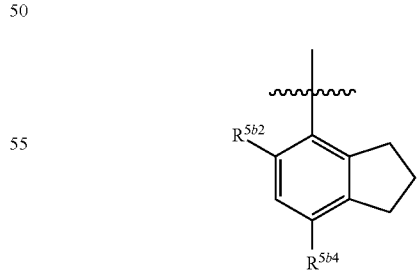

In certain embodiments, each R$^{5b2}$ and R$^{5b4}$ is selected from the group consisting of H, D, halogen, C$_1$-C$_6$alkyl, C$_3$-C$_8$cycloalkyl, and —CN.

In certain embodiments of Formula Ie-Ih, R$^2$ is

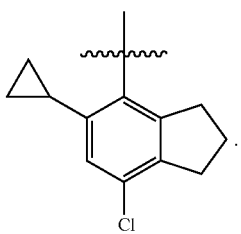 [SMILES: *c1c(C2CC2)cc(Cl)c2c1CCC2]

As described above in Formula Ie-Ih, $R^1$ is selected from the group consisting of

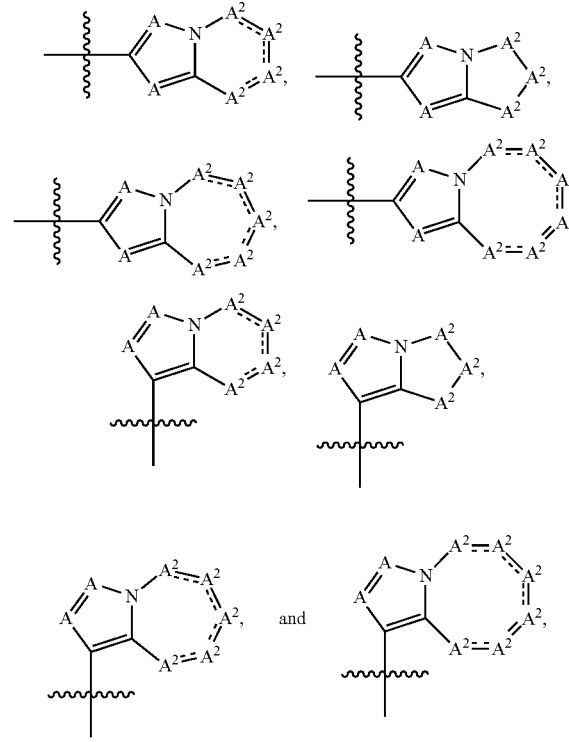

wherein === represents a single bond or a double bond provided that the ring comprising one or more $A^2$ is a non-aromatic ring.

In certain embodiments of Formula Ie-Ih, === represents a single bond. In certain embodiments of Formula Ie-Ih, === represents a double bond. In certain embodiments, the === are single bonds in the ring comprising $A^2$, thereby forming a saturated ring.

In certain embodiments of Formula Ie-Ih, $R^1$ is

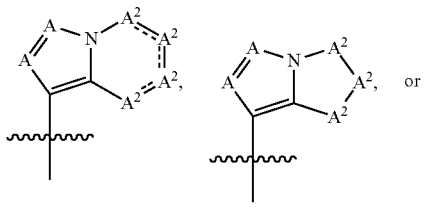

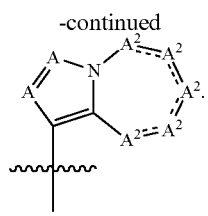

In certain embodiments, $R^1$ is

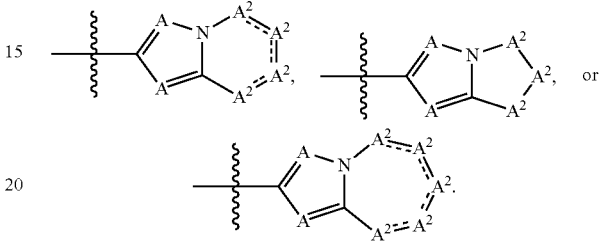

As described above in Formula Ie-Ih, each A is independently $CR^{5a1}$ or N; and each $A^2$ is independently $CR^{5a2}$, $C(R^{5a2})_2$, N, $NR^{5a2}$, O, S, or $S(O)_2$.

In certain embodiments of Formula Ie-Ih, one A is $CR^{5a1}$ and the other A is N. In certain embodiments, each $A^2$ is independently $C(R^{5a2})_2$, $NR^{5a2}$, or O.

As described above in Formula Ie-Ih, each $R^{5a1}$ is independently H, D, halogen, OH, CN, $-NO_2$, $-SR^6$, $-OR^6$, $-NHR^6$, $-NR^6R^7$, $-NR^6C(O)R^6$, $-NR^6C(O)OR^6$, $-NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2$-$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2$-$C_3$-$C_8$cycloalkyl are optionally substituted with D, $-CN$, halogen, $C_1$-$C_6$alkyl, $-OR^6$, $-NH_2$, $-NH(C_1$-$C_6$alkyl), $-N(C_1$-$C_6$alkyl)$_2$, $-NR^6C(O)OR^6$, or $-NR^6C(O)R^6$.

In certain embodiments of Formula Ie-Ih, each $R^{5a1}$ is independently H, halogen, OH, $-OR^6$, $-NHR^6$, $-NR^6R^7$, $C_1$-$C_6$alkyl, $C_3$-$C_8$cycloalkyl, or heterocyclyl, wherein the $C_1$-$C_6$alkyl, $C_3$-$C_8$cycloalkyl, and heterocyclyl are optionally substituted with halogen, $C_1$-$C_6$alkyl, $-OR^6$, $-NH_2$, $-NH(C_1$-$C_6$alkyl), $-N(C_1$-$C_6$alkyl)$_2$, $-NR^6C(O)OR^6$, or $-NR^6C(O)R^6$.

As described above in Formula Ie-Ih, each $R^{5a2}$ is independently H, D, halogen, OH, CN, $-NO_2$, $-SR^6$, $-OR^6$, $-NHR^6$, $-NR^6R^7$, $-C(O)R^6$, $-S(O)_2R^6$, $-C(O)OR^6$, $-C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2$-$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2$-$C_3$-$C_8$cycloalkyl are optionally substituted with D, $-CN$, halogen, $C_1$-$C_6$alkyl, $-OR^6$, $-NH_2$, $-NH(C_1$-$C_6$alkyl), $-N(C_1$-$C_6$alkyl)$_2$, $-NR^6C(O)OR^6$, $-NR^6C(O)R^6$, $NR^6C(O)NR^6$, $-NR^6C(O)R^6$, or $-NR^6S(O)_2R^6$; or two $R^{5a2}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or two geminal $R^{5a2}$ can form an oxo group;

In certain embodiments of Formula Ie, If and Ig, each $R^{5a2}$ is independently H, halogen, OH, —$OR^6$, $C_1$-$C_6$alkyl, $C_3$-$C_8$cycloalkyl, or heterocyclyl; wherein the $C_1$-$C_6$alkyl, $C_3$-$C_8$cycloalkyl, and heterocyclyl are optionally substituted with halogen, $C_1$-$C_6$alkyl, —$OR^6$, —$NR^6C(O)OR^6$, or —$NR^6C(O)R^6$.

In certain embodiments of Formula Ie, If, and Ih, each $R^{5a2}$ is independently H, halogen, OH, —$OR^6$, —$NHR^6$, —$NR^6R^7$, $C_1$-$C_6$alkyl, $C_3$-$C_8$cycloalkyl, or heterocyclyl; wherein the $C_1$-$C_6$alkyl, $C_3$-$C_8$cycloalkyl, and heterocyclyl are optionally substituted with halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$.

In certain embodiments of Formula Ie, If, and Ih, each $R^{5a2}$ is independently H, —$NHR^6$, or $C_1$-$C_6$alkyl; wherein the $C_1$-$C_6$alkyl is substituted with —$NH_2$, —$NH(C_1$-$C_6$alkyl), or —$N(C_1$-$C_6$alkyl)$_2$. In certain embodiments, each $R^{5a2}$ is independently H, or heterocyclyl containing N; wherein the heterocyclyl is optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$, —$NR^6C(O)NR^6$, —$NR^6C(O)R^6$, or —$NR^6S(O)_2R^6$.

In certain embodiments of Formula Ie, If, each $A^2$ is independently $C(R^{5a2})_2$ or O; and each $R^{5a2}$ is independently H, —$NHR^6$, —$NR^6R^7$, $C_1$-$C_6$alkyl, or heterocyclyl containing N; wherein the $C_1$-$C_6$alkyl is substituted with —$NH_2$, —$NH(C_1$-$C_6$alkyl), or —$N(C_1$-$C_6$alkyl)$_2$, and wherein the heterocyclyl is optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$, —$NR^6C(O)NR^6$, —$NR^6C(O)R^6$, or —$NR^6S(O)_2R^6$.

In certain embodiments of Formula Ie-Ih, two geminal $R^{5a2}$ can form an oxo group.

In certain embodiments of Formula Ie-If, $R^1$ is selected from the group consisting of

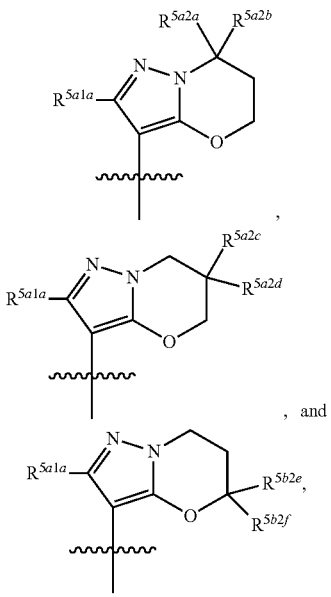

, and wherein $R^{5a1a}$ is H, D, halogen, OH, CN, —$NO_2$, —$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$;

$R^{5a2a}$, $R^{5a2b}$, $R^{5a2c}$, $R^{5a2d}$, $R^{5a2e}$, and $R^{5a2f}$ are selected from independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S(O)_2R^6$; or two $R^{5a2a}$, $R^{5a2b}$, $R^{5a2c}$, $R^{5a2d}$, $R^{5a2e}$, and $R^{5a2f}$ which are germinal together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or two geminal $R^{5a2a}$, $R^{5a2b}$, $R^{5a2c}$, $R^{5a2d}$, $R^{5a2e}$, and $R^{5a2f}$ can form an oxo group.

In certain embodiments of Formula Ie-Ig, $R^1$ is selected from the group consisting of

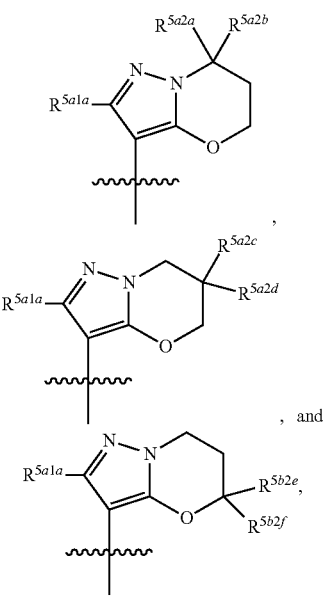

, and wherein $R^{5a1a}$ is H, D, halogen, OH, CN, —$NO_2$—$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, or —$NR^6C(O)R^6$;

$R^{5a2a}$, $R^{5a2b}$, $R^{5a2c}$, $R^{5a2d}$, $R^{5a2e}$, and $R^{5a2f}$ are selected from H, D, halogen, OH, CN, —$NO_2$, —$SR^6$, —$OR^6$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NR^6C(O)OR^6$, —$NR^6C(O)R^6$, —$NR^6C(O)NR^6$, —$NR^6C(O)R^6$, or —$NR^6S(O)_2R^6$; or two $R^{5a2a}$, $R^{5a2b}$, $R^{5a2c}$, $R^{5a2d}$, $R^{5a2e}$, and $R^{5a2f}$ which are germinal, together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$S(O)_2$—$R^6$; —$COR^6$, $NR^6C(O)OR^6$, —$NR^6C(O)R^6$, —$NR^6C(O)NR^6$, or —$NR^6S(O)_2R^6$; or two geminal $R^{5a2a}$, $R^{5a2b}$, $R^{5a2c}$, $R^{5a2d}$, $R^{5a2e}$, and $R^{5a2f}$ can form an oxo group.

In certain embodiments of Formula Ie-If and Ih, $R^1$ is selected from the group consisting of

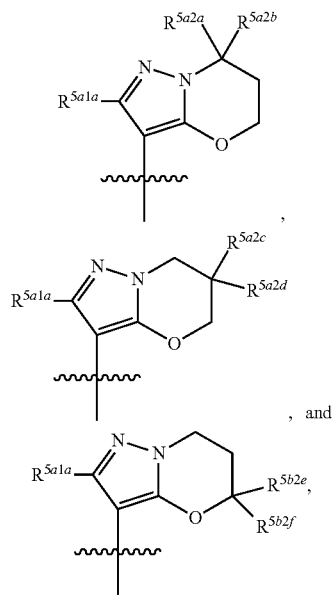

, and wherein $R^{5a1a}$ is H, D, halogen, OH, CN, —$NO_2$, —$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, or —$NR^6C(O)R^6$; and $R^{5a2a}$, $R^{5a2b}$, $R^{5a2c}$, $R^{5a2d}$, $R^{5a2e}$, and $R^{5a2f}$ are selected from independently H, —$NHR^6$, —$NR^6R^7$, $C_1$-$C_6$alkyl, or heterocyclyl containing N; wherein the $C_1$-$C_6$alkyl is substituted with —$NH_2$, —$NH(C_1$-$C_6$alkyl), or —$N(C_1$-$C_6$alkyl)_2$, and wherein the heterocyclyl is optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, or —$NR^6C(O)R^6$, —$NR^6C(O)NR^6$, —$NR^6C(O)R^6$, or —$NR^6S(O)_2R^6$.

In certain embodiments of the formulae described herein, $R^1$ is

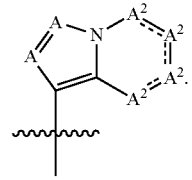

In certain embodiments, one A is $CR^{5a1}$ and the other A is N. In certain embodiments, each $A^2$ is independently $C(R^{5a2})_2$, $NR^{5a2}$, or O. In certain embodiments, wherein each $R^{5a2}$ is independently H, halogen, OH, —$OR^6$, —$NHR^6$, —$NR^6R^7$, $C_1$-$C_6$alkyl, $C_3$-$C_8$cycloalkyl, heterocyclyl, aryl, heteroaryl, or —$CH_2$—$C_3$-$C_8$cycloalkyl. In certain embodiments, wherein two $R^{5a2}$ together with the atoms to which they are attached can form $C_3$-$C_8$cycloalkyl or heterocyclyl.

In certain embodiments of the formulae described herein, $R^1$ is

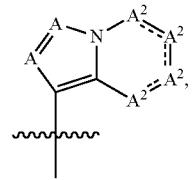

which is a formula of

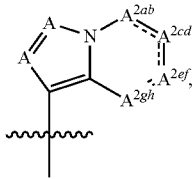

wherein:

$A^{2ab}$ is selected from $CR^{5a2}$, $C(R^{5a2a})(R^{5a2b})$, N, $NR^{5a2}$, O, S, or $S(O)_2$;

$A^{2cd}$ is selected from $CR^{5a2}$, $C(R^{5a2c})(R^{5a2d})$, N, $NR^{5a2}$, O, S, or $S(O)_2$;

$A^{2ef}$ is selected from $CR^{5a2}$, $C(R^{5a2e})(R^{5a2f})$, N, $NR^{5a2}$, O, S, or $S(O)_2$;

$A^{2gh}$ is selected from $CR^{5a2}$, $C(R^{5a2g})(R^{5a2h})$, N, $NR^{5a2}$, O, S, or $S(O)_2$;

each $R^{5a2a}$, $R^{5a2b}$, $R^{5a2c}$, $R^{5a2d}$, $R^{5a2e}$, $R^{5a2f}$, $R^{5a2g}$, and $R^{5a2h}$ are independently H, D, halogen, OH, CN, $-NO_2$, $-SR^6$, $-OR^6$, $-NHR^6$, $-NR^6R^7$, $-C(O)R^6$, $-S(O)_2R^6$, $-C(O)OR^6$, $-C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2$-$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2$-$C_3$-$C_8$cycloalkyl are optionally substituted with D, $-CN$, halogen, $C_1$-$C_6$alkyl, $-OR^6$, $-NH_2$, $-NH(C_1$-$C_6$alkyl), $-N(C_1$-$C_6$alkyl)$_2$, $-NR^6C(O)OR^6$, $-NR^6C(O)R^6$, $-NR^6C(O)NR^6$, $-NR^6C(O)R^6$, or $-NR^6S(O)_2R^6$; or two $R^{5a2a}$, $R^{5a2b}$, $R^{5a2c}$, $R^{5a2d}$, $R^{5a2e}$, $R^{5a2f}$, $R^{5a2g}$, and $R^{5a2h}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, $-OR^6$, $-NH_2$, $-NH(C_1$-$C_6$alkyl), $-N(C_1$-$C_6$alkyl)$_2$, $-S(O)_2$-$R^6$, $-COR^6$, $-NR^6C(O)OR^6$, $-NR^6C(O)R^6$, $-NR^6C(O)NR^6$, or $-NR^6S(O)_2R^6$; or two geminal $R^{5a2a}$, $R^{5a2b}$, $R^{5a2c}$, $R^{5a2d}$, $R^{5a2e}$, $R^{5a2f}$, $R^{5a2g}$, and $R^{5a2h}$ can form an oxo group.

In certain embodiments of the formulae described herein, $R^1$ is

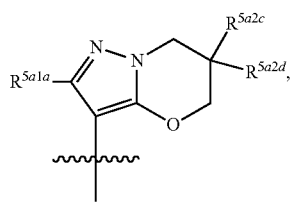

wherein wherein $R^{5a1a}$ is H, D, halogen, OH, CN, $-NO_2$, $-SR^6$, $-OR^6$, $-NHR^6$, $-NR^6R^7$, $-NR^6C(O)R^6$, $-NR^6C(O)OR^6$, $-NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2$-$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2$-$C_3$-$C_8$cycloalkyl are optionally substituted with D, $-CN$, halogen, $C_1$-$C_6$alkyl, $-OR^6$, $-NH_2$, $-NH(C_1$-$C_6$alkyl), $-N(C_1$-$C_6$alkyl)$_2$, $-NR^6C(O)OR^6$, or $-NR^6C(O)R^6$;

$R^{5a2c}$ and $R^{5a2d}$ are each independently H, D, halogen, OH, CN, $-NO_2$, $-SR^6$, $-OR^6$, $-NHR^6$, $-NR^6R^7$, $-C(O)R^6$, $-S(O)_2R^6$, $-C(O)OR^6$, $-C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2$-$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2$-$C_3$-$C_8$cycloalkyl are optionally substituted with D, $-CN$, halogen, $C_1$-$C_6$alkyl, $-OR^6$, $-NH_2$, $-NH(C_1$-$C_6$alkyl), $-N(C_1$-$C_6$alkyl)$_2$, $-NR^6C(O)OR^6$, $-NR^6C(O)R^6$, $-NR^6C(O)NR^6$, $-NR^6C(O)R^6$, or $-NR^6S(O)_2R^6$; or $R^{5a2c}$ and $R^{5a2d}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, $-OR^6$, $-NH_2$, $-NH(C_1$-$C_6$alkyl), $-N(C_1$-$C_6$alkyl)$_2$, $-S(O)_2$-$R^6$, $-COR^6$, $-NR^6C(O)OR^6$, $-NR^6C(O)R^6$, $-NR^6C(O)NR^6$, or $-NR^6S(O)_2R^6$; or $R^{5a2c}$ and $R^{5a2d}$ can form an oxo group.

In certain embodiments, each $R^{5a2c}$ and $R^{5a2d}$ is independently H, halogen, OH, $-OR^6$, $-NHR^6$, $-NR^6R^7$, $C_1$-$C_6$alkyl, $C_3$-$C_8$cycloalkyl, heterocyclyl, aryl, heteroaryl, or $-CH_2$-$C_3$-$C_8$cycloalkyl. In certain embodiments, each $R^{5a2c}$ and $R^{5a2d}$ is independently H, halogen, OH, $-OR^6$, $-NHR^6$, or $-NR^6R^7$. In certain embodiments, one of $R^{5a2c}$ and $R^{5a2d}$ is H and the other is independently halogen, OH, $-OR^6$, $-NHR^6$, or $-NR^6R^7$. In certain embodiments, $R^{5a2c}$ and $R^{5a2d}$ together with the atoms to which they are attached can form $C_3$-$C_8$cycloalkyl or heterocyclyl.

In certain embodiments of the formulae described herein, $R^1$ is.

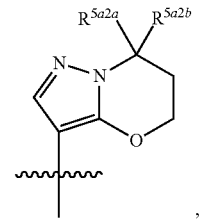

wherein $R^{5a2a}$ and $R^{5a2b}$ are each independently H, D, halogen, OH, CN, $-NO_2$, $-SR^6$, $-OR^6$, $-NHR^6$, $-NR^6R^7$, $-C(O)R^6$, $-S(O)_2R^6$, $-C(O)OR^6$, $-C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2$-$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2$-$C_3$-$C_8$cycloalkyl are optionally substituted with D, $-CN$, halogen, $C_1$-$C_6$alkyl, $-OR^6$, $-NH_2$, $-NH(C_1$-$C_6$alkyl), $-N(C_1$-$C_6$alkyl)$_2$, $-NR^6C(O)OR^6$, $-NR^6C(O)R^6$, $NR^6C(O)NR^6$, $-NR^6C(O)R^6$, or $-NR^6S(O)_2R^6$; or $R^{5a2a}$ and $R^{5a2b}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, $-OR^6$, $-NH_2$, $-NH(C_1$-$C_6$alkyl), $-N(C_1$-$C_6$alkyl)$_2$, $-S(O)_2$-$R^6$, $-COR^6$, $-NR^6C(O)OR^6$, $-NR^6C(O)R^6$, $-NR^6C(O)NR^6$, or $-NR^6S(O)_2R^6$; or $R^{5a2a}$ and $R^{5a2b}$ can form an oxo group.

In certain embodiments, each $R^{5a2a}$ and $R^{5a2b}$ is independently H, halogen, OH, $-OR^6$, $-NHR^6$, $-NR^6R^7$, $C_1$-$C_6$alkyl, $C_3$-$C_8$cycloalkyl, heterocyclyl, aryl, heteroaryl, or $-CH_2$-$C_3$-$C_8$cycloalkyl. In certain embodiments, each $R^{5a2a}$ and $R^{5a2b}$ is independently H, halogen, OH, $-OR^6$, $-NHR^6$, or $-NR^6R^7$. In certain embodiments, one of $R^{5a2a}$ and $R^{5a2b}$ is H and the other is independently halogen, OH, $-OR^6$, $-NHR^6$, or $-NR^6R^7$. In certain embodiments, $R^{5a2a}$ and $R^{5a2b}$ together with the atoms to which they are attached can form $C_3$-$C_8$cycloalkyl or heterocyclyl.

In certain embodiments of the formulae described herein, R¹ is.

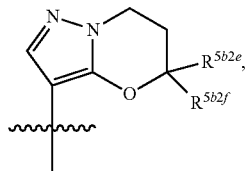

wherein

R$^{5a2e}$ and R$^{5a2f}$ are each independently independently H, D, halogen, OH, CN, —NO$_2$, —SR$^6$, —OR$^6$, —NHR$^6$, —NR$^6$R$^7$, —C(O)R$^6$, —S(O)$_2$R$^6$, —C(O)OR$^6$, —C(O)NR$^6$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, —NR$^6$C(O)R$^6$, NR$^6$C(O)NR$^6$, —NR$^6$C(O)R$^6$, or —NR$^6$S(O)$_2$R$^6$; or R$^{5a2e}$ and R$^{5a2f}$ together with the atoms to which they are attached can form C$_3$-C$_8$cycloalkyl or heterocyclyl; wherein the heterocyclyl contains 1-3 heteroatoms selected from the group consisting of N, S, P and O; wherein the C$_3$-C$_8$cycloalkyl and heterocyclyl are optionally substituted with D, halogen, C$_1$-C$_6$alkyl, —OR$^6$, —NH$_2$, —NH(C$_1$-C$_6$alkyl), —N(C$_1$-C$_6$alkyl)$_2$, —S(O)$_2$—R$^6$, —COR$^6$, —NR$^6$C(O)OR$^6$, —NR$^6$C(O)R$^6$, —NR$^6$C(O)NR$^6$, or —NR$^6$S(O)$_2$R$^6$; or R$^{5a2e}$ and R$^{5a2f}$ can form an oxo group.

In certain embodiments, each R$^{5a2e}$ and R$^{5a2f}$ is independently H, halogen, OH, —OR$^6$, —NHR$^6$, —NR$^6$R$^7$, C$_1$-C$_6$alkyl, C$_3$-C$_8$cycloalkyl, heterocyclyl, aryl, heteroaryl, or —CH$_2$—C$_3$-C$_8$cycloalkyl. In certain embodiments, each R$^{5a2e}$ and R$^{5a2f}$ is independently H, halogen, OH, —OR$^6$, —NHR$^6$, or —NR$^6$R$^7$. In certain embodiments, one of R$^{5a2e}$ and R$^{5a2f}$ is H and the other is independently halogen, OH, —OR$^6$, —NHR$^6$, or —NR$^6$R$^7$. In certain embodiments, R$^{5a2e}$ and R$^{5a2f}$ together with the atoms to which they are attached can form C$_3$-C$_8$cycloalkyl or heterocyclyl.

In certain embodiments of the formulae described herein, R¹ is.

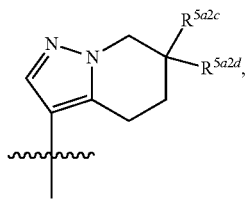

wherein

R$^{5a2c}$ and R$^{5a2d}$ are each independently H, D, halogen, OH, CN, —NO$_2$, —SR$^6$, —OR$^6$, —NHR$^6$, —NR$^6$R$^7$, —C(O)R$^6$, —S(O)$_2$R$^6$, —C(O)OR$^6$, —C(O)NR$^6$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, —NR$^6$C(O)R$^6$, NR$^6$C(O)NR$^6$, —NR$^6$C(O)R$^6$, or —NR$^6$S(O)$_2$R$^6$; or R$^{5a2c}$ and R$^{5a2d}$ together with the atoms to which they are attached can form C$_3$-C$_8$cycloalkyl or heterocyclyl; wherein the heterocyclyl contains 1-3 heteroatoms selected from the group consisting of N, S, P and O; wherein the C$_3$-C$_8$cycloalkyl and heterocyclyl are optionally substituted with D, halogen, C$_1$-C$_6$alkyl, —OR$^6$, —NH$_2$, —NH(C$_1$-C$_6$alkyl), —N(C$_1$-C$_6$alkyl)$_2$, —S(O)$_2$—R$^6$, —COR$^6$, —NR$^6$C(O)OR$^6$, —NR$^6$C(O)R$^6$, —NR$^6$C(O)NR$^6$, or —NR$^6$S(O)$_2$R$^6$; or R$^{5a2c}$ and R$^{5a2d}$ can form an oxo group.

In certain embodiments, each R$^{5a2c}$ and R$^{5a2d}$ is independently H, halogen, OH, —OR$^6$, —NHR$^6$, —NR$^6$R$^7$, C$_1$-C$_6$alkyl, C$_3$-C$_8$cycloalkyl, heterocyclyl, aryl, heteroaryl, or —CH$_2$—C$_3$-C$_8$cycloalkyl. In certain embodiments, each R$^{5a2c}$ and R$^{5a2d}$ is independently H, halogen, OH, —OR$^6$, —NHR$^6$, or —NR$^6$R$^7$. In certain embodiments, one of R$^{5a2c}$ and R$^{5a2d}$ is H and the other is independently halogen, OH, —OR$^6$, —NHR$^6$, or —NR$^6$R$^7$. In certain embodiments, R$^{5a2c}$ and R$^{5a2d}$ together with the atoms to which they are attached can form C$_3$-C$_8$cycloalkyl or heterocyclyl.

In certain embodiments of the formulae described herein, R¹ is selected from the group consisting of

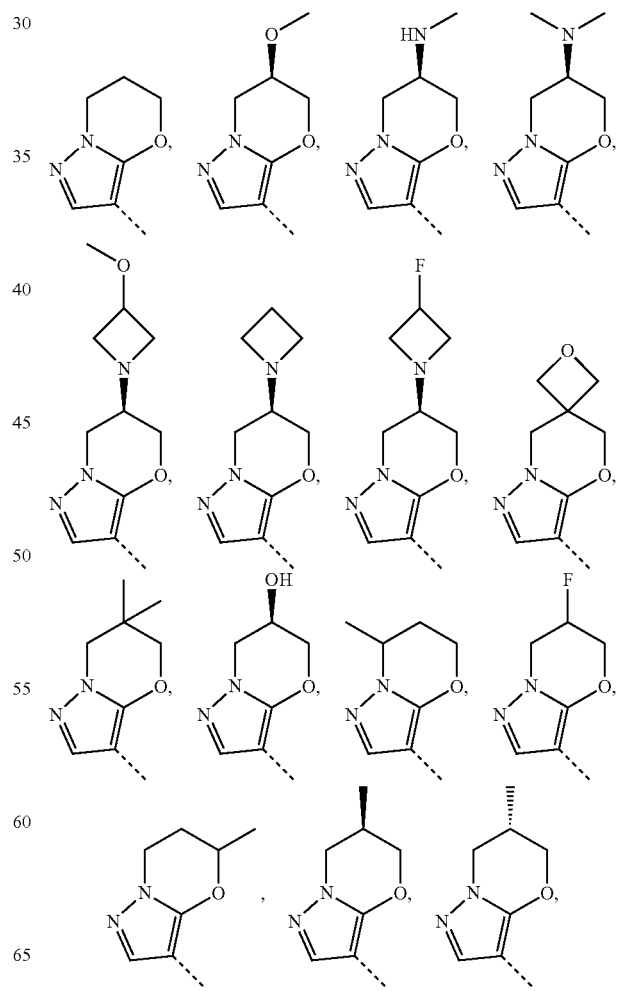

73

-continued

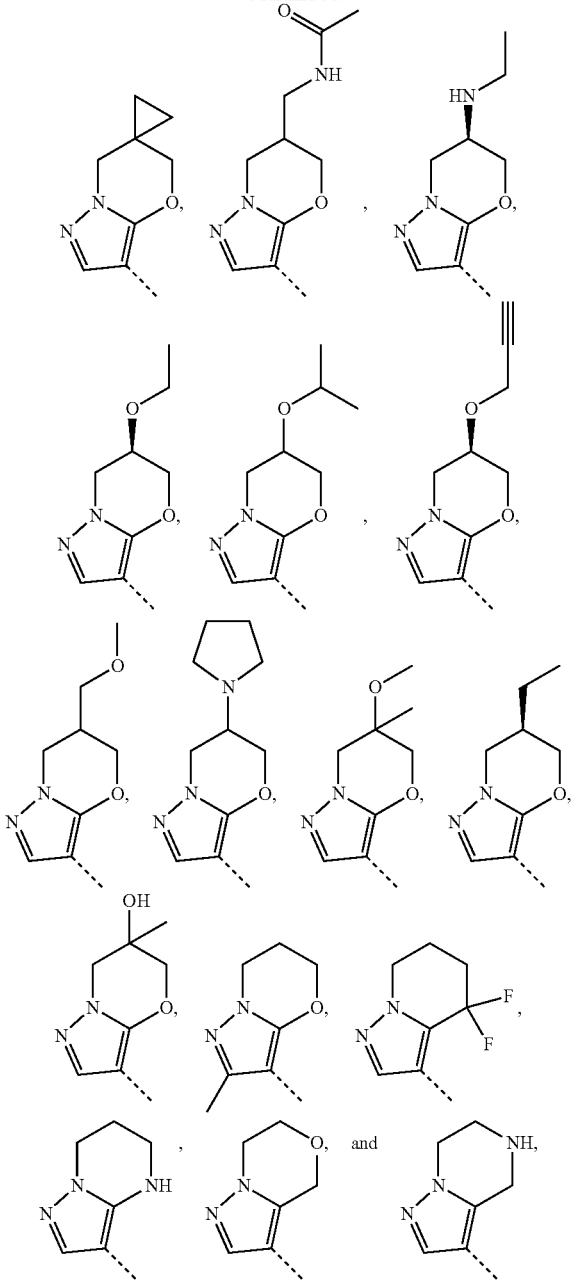

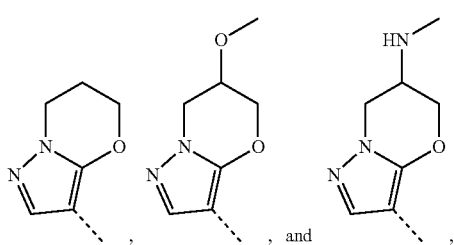

wherein - - - is connection to the rest of the compound.

In certain embodiments in the formulae described herein, R¹ is selected from the group consisting of

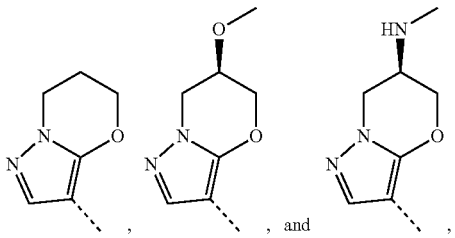

wherein - - - is connection to the rest of the compound.

74

In certain embodiments of the formulae described herein, R¹ is selected from the group consisting of


wherein - - - is connection to the rest of the compound.

In certain embodiments of the formulae described herein, R¹ is


In certain embodiments, one A is $CR^{5a1}$ and the other A is N. In certain embodiments, each $A^2$ is independently $C(R^{5a2})_2$, $NR^{5a2}$, or O. In certain embodiments, wherein each $R^{5a2}$ is independently H, halogen, OH, —$OR^6$, —$NHR^6$, —$NR^6R^7$, $C_1$-$C_6$alkyl, $C_3$-$C_8$cycloalkyl, heterocyclyl, aryl, heteroaryl, or —$CH_2$—$C_3$-$C_8$cycloalkyl. In certain embodiments, wherein two $R^{5a2}$ together with the atoms to which they are attached can form $C_3$-$C_8$cycloalkyl or heterocyclyl.

In certain embodiments of the formulae described herein, R¹ is

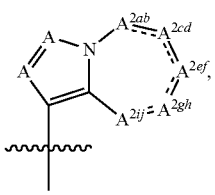

which is a formula of wherein.

$A^{2ab}$ is selected from $CR^{5a2}$, $C(R^{5a2a})(R^{5a2b})$, N, $NR^{5a2}$, O, S, or $S(O)_2$;

$A^{2cd}$ is selected from $CR^{5a2}$, $C(R^{5a2c})(R^{5a2d})$, N, $NR^{5a2}$, O, S, or $S(O)_2$;

$A^{2ef}$ is selected from $CR^{5a2}$, $C(R^{5a2e})(R^{5a2f})$, N, $NR^{5a2}$, O, S, or $S(O)_2$;

$A^{2gh}$ is selected from $CR^{5a2}$, $C(R^{5a2g})(R^{5a2h})$, N, $NR^{5a2}$, O, S, or $S(O)_2$;

$A^{2ij}$ is selected from $CR^{5a2}$, $C(R^{5a2i})(R^{5a2j})$, N, $NR^{5a2}$, O, S, or $S(O)_2$;

each $R^{5a2a}$, $R^{5a2b}$, $R^{5a2c}$, $R^{5a2d}$, $R^{5a2e}$, $R^{5a2f}$, $R^{5a2g}$, $R^{5a2h}$, $R^{5a2i}$, and $R^{5a2j}$ are independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S(O)_2R^6$; or two $R^{5a2a}$, $R^{5a2b}$, $R^{5a2c}$, $R^{5a2d}$, $R^{5a2e}$, $R^{5a2f}$, $R^{5a2g}$, $R^{5a2h}$, $R^{5a2i}$, and $R^{5a2j}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or two geminal $R^{5a2a}$, $R^{5a2b}$, $R^{5a2c}$, $R^{5a2d}$, $R^{5a2e}$, $R^{5a2f}$, $R^{5a2g}$, $R^{5a2h}$, $R^{5a2i}$, and $R^{5a2j}$ can form an oxo group.

In certain embodiments the formulae described herein, $R^1$ is

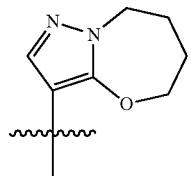

In certain embodiments of the formulae described herein, $R^1$ is

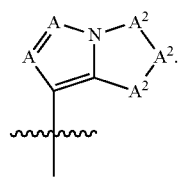

In certain embodiments, one A is $CR^{5a1}$ and the other A is N. In certain embodiments, each $A^2$ is independently $C(R^{5a2})_2$, $NR^{5a2}$, or O. In certain embodiments, wherein each $R^{5a2}$ is independently H, halogen, OH, —$OR^6$, —$NHR^6$, —$NR^6R^7$, $C_1$-$C_6$alkyl, $C_3$-$C_8$cycloalkyl, heterocyclyl, aryl, heteroaryl, or —$CH_2$—$C_3$-$C_8$cycloalkyl. In certain embodiments, wherein two $R^{5a2}$ together with the atoms to which they are attached can form $C_3$-$C_8$cycloalkyl or heterocyclyl.

In certain embodiments the formulae described herein, $R^1$ is

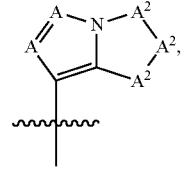

which is a formula of

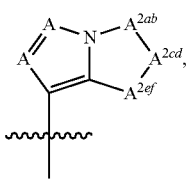

wherein.

$A^{2ab}$ is selected from $C(R^{5a2a})(R^{5a2b})$, $NR^{5a2}$, O, S, or $S(O)_2$;

$A^{2cd}$ is selected from $C(R^{5a2c})(R^{5a2d})$, $NR^{5a2}$, O, S, or $S(O)_2$;

$A^{2ef}$ is selected from $C(R^{5a2e})(R^{5a2f})$, $NR^{5a2}$, O, S, or $S(O)_2$;

each $R^{5a2a}$, $R^{5a2b}$, $R^{5a2c}$, $R^{5a2d}$, $R^{5a2e}$, and $R^{5a2f}$ are independently H, D, halogen, OH, CN, —$NO_2$—$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S(O)_2R^6$; or two $R^{5a2a}$, $R^{5a2b}$, $R^{5a2c}$, $R^{5a2d}$, $R^{5a2e}$, and $R^{5a2f}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or two geminal $R^{5a2a}$, $R^{5a2b}$, $R^{5a2c}$, $R^{5a2d}$, $R^{5a2e}$, and $R^{5a2f}$ can form an oxo group.

In certain embodiments the formulae described herein, $R^1$ is

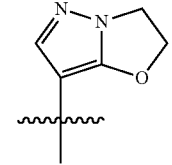

In certain embodiments of the formulae described herein, $R^1$ is

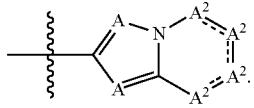

In certain embodiments, one A is $CR^{5a1}$ and the other A is N. In certain embodiments, each $A^2$ is independently $C(R^{5a2})_2$, $NR^{5a2}$, or O. In certain embodiments, wherein each $R^{5a2}$ is independently H, halogen, OH, —$OR^6$, —$NHR^6$, —$NR^6R^7$, $C_1$-$C_6$alkyl, $C_3$-$C_8$cycloalkyl, heterocyclyl, aryl, heteroaryl, or —$CH_2$—$C_3$-$C_8$cycloalkyl. In certain embodiments, wherein two $R^{5a2}$ together with the atoms to which they are attached can form $C_3$-$C_8$cycloalkyl or heterocyclyl.

In certain embodiments the formulae described herein, $R^1$ is

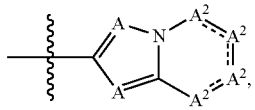

which is a formula of

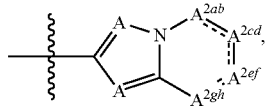

wherein.

$A^{2ab}$ is selected from $CR^{5a2}$, $C(R^{5a2a})(R^{5a2b})$, N, $NR^{5a2}$, O, S, or $S(O)_2$;

$A^{2cd}$ is selected from $CR^{5a2}$, $C(R^{5a2c})(R^{5a2d})$, N, $NR^{5a2}$, O, S, or $S(O)_2$;

$A^{2ef}$ is selected from $CR^{5a2}$, $C(R^{5a2e})(R^{5a2f})$, N, $NR^{5a2}$, O, S, or $S(O)_2$;

$A^{2gh}$ is selected from $CR^{5a2}$, $C(R^{5a2g})(R^{5a2h})$, N, $NR^{5a2}$, O, S, or $S(O)_2$;

each $R^{5a2a}$, $R^{5a2b}$, $R^{5a2c}$, $R^{5a2d}$, $R^{5a2e}$, $R^{5a2f}$, $R^{5a2g}$, and $R^{5a2h}$ are independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl$)_2$, —$NR^6C(O)OR^6$, —$NR^6C(O)R^6$, $NR^6C(O)NR^6$, —$NR^6C(O)R^6$, or —$NR^6S(O)_2R^6$ or two $R^{5a2a}$, $R^{5a2b}$, $R^{5a2c}$, $R^{5a2d}$, $R^{5a2e}$, $R^{5a2f}$, $R^{5a2g}$, and $R^{5a2h}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl$)_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$ or two geminal $R^{5a2a}$, $R^{5a2b}$, $R^{5a2c}$, $R^{5a2d}$, $R^{5a2e}$, $R^{5a2f}$, $R^{5a2g}$, and $R^{5a2h}$ can form an oxo group.

The present disclosure provides a compound of formula Ie-If, wherein $X^1$ is O;

$R^1$ is selected from the group consisting of

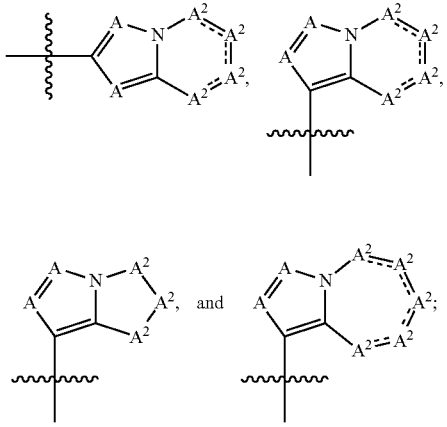

wherein — represents a single bond;

each $A^2$ is independently $C(R^{5a2})_2$ or O;

$X^2$ is $CR^{5b1}$;

each $R^{5a1}$ is independently H or $C_1$-$C_6$alkyl; wherein the $C_1$-$C_6$alkyl is optionally substituted with D, halogen, —$OR^6$, —$NH_2$, $NH(C_1$-$C_6$alkyl), $N(C_1$-$C_6$alkyl$)_2$, —$NR^6C(O)OR^6$, or —$NR^6C(O)R^6$;

each $R^{5a2}$ is independently H, halogen, OH, —$OR^6$, —$NHR^6$, —$NR^6R^7$, $C_1$-$C_6$alkyl, or heterocyclyl; wherein the $C_1$-$C_6$alkyl and heterocyclyl are optionally substituted with D, halogen, —$OR^6$, —$NH_2$, —$NH(C_1$-$C_6$alkyl), —$N(C_1$-$C_6$alkyl$)_2$, —$NR^6C(O)OR^6$, or —$NR^6C(O)R^6$; or two $R^{5a2}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl$)_2$, or —$S(O)_2$—$R^6$; or two geminal $R^{5a2}$ can form an oxo group;

$R^{5b1}$ is H, D, halogen, or $C_1$-$C_6$alkyl;

each $R^{5b2}$, $R^{5b3}$, $R^{5b4}$, $R^{5b5}$, and $R^{5b6}$ is independently H, D, halogen, —CN, —$OR^6$, $C_1$-$C_6$alkyl, or $C_3$-$C_8$cycloalkyl; wherein the $C_1$-$C_6$alkyl, and $C_3$-$C_8$cycloalkyl, are optionally substituted with D, halogen, —$OR^6$, —$NH_2$, —$NH(C_1$-$C_6$alkyl), or —$N(C_1$-$C_6$alkyl$)_2$; or two $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, or heteroaryl, wherein $C_3$-$C_8$cycloalkyl, heterocyclyl, or heteroaryl are optionally substituted with halogen or $C_1$-$C_6$alkyl; and $R^6$ and $R^7$ are independently, at each occurrence, H, D, $C_1$-$C_8$alkyl, $C_2$-$C_8$alkynyl, or aryl; wherein the $C_1$-$C_8$alkyl, $C_2$-$C_8$alkynyl, and aryl, are optionally substituted with D, halogen or $C_1$-$C_6$alkyl.

In certain embodiments, the compound is of formula:

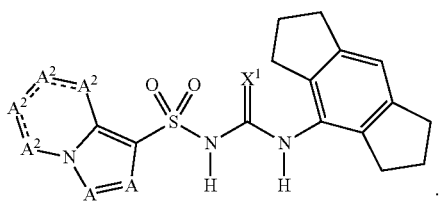

In certain embodiments, the compound is of formula:

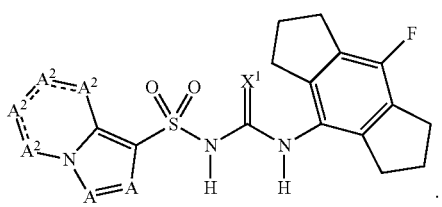

In certain embodiments of formula (I), $X^1$ is O and $R^2$ is

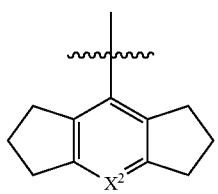

In certain embodiments of formula (I), $X^1$ is O and $R^1$ is

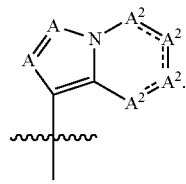

In certain embodiments of formula (I), $R^1$ is

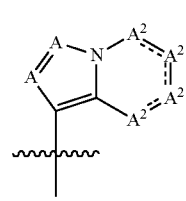

and $R^2$ is

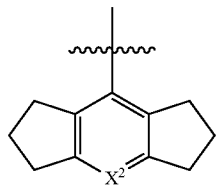

In some embodiments, the present disclosure provides a compound of formula (I),

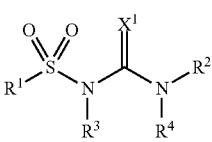

(I)

having one, two, or three of the following features:
a) X is O;
b) $R^1$ is

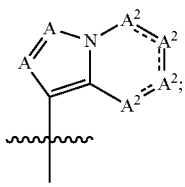

c) $R^2$ is

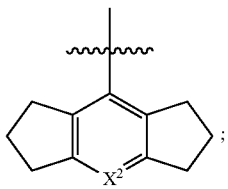

d) $X^2$ is CH or CF.

In some embodiments, the present disclosure provides a compound of formula (I),

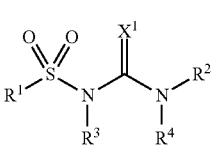

(I)

having one, two, or three of the following features:
a) X is O;
b) $R^1$ is

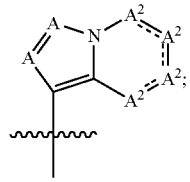

c) $R^2$ is

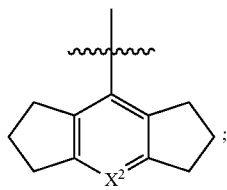

d) $X^2$ is CH.

In some embodiments, the present disclosure provides a compound of formula (I),

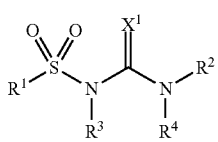

(I)

having one, two, or three of the following features:
a) X is S;
b) $R^1$ is

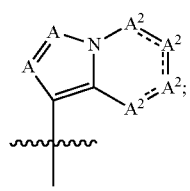

c) $R^2$ is

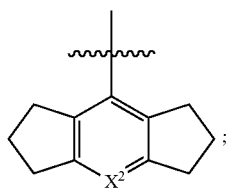

d) $X^2$ is CH.

In some embodiments, the present disclosure provides a compound of formula (I),

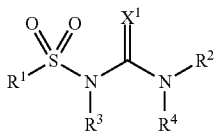

(I)

having one, two, or three of the following features:
a) X is S;
b) $R^1$ is methyl;
c) $R^2$ is

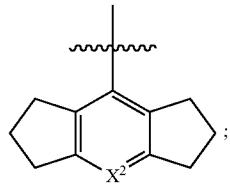

d) $X^2$ is CH.

In some embodiments, the present disclosure provides a compound of formula (I),

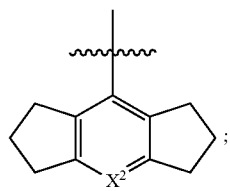

(I)

having one, two, or three of the following features:
a) X is S;
b) $R^1$ is methyl;
c) $R^2$ is

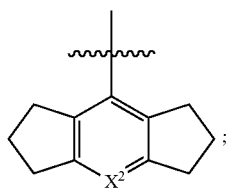

d) $X^2$ is CH.

In some embodiments, the present disclosure provides a compound of formula (I),

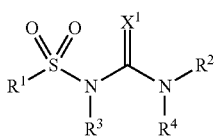

(I)

having one, two, or three of the following features:
a) X is O;
b) $R^1$ is

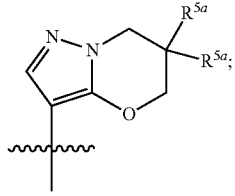

c) $R^2$ is

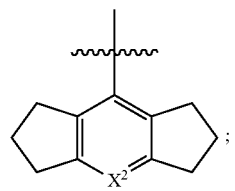

d) $X^2$ is CH.

In some embodiments, the present disclosure provides a compound of formula Ie-If,

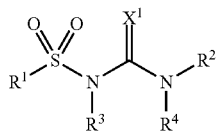
(Ie)

having one, two, or three of the following features:
a) X is O;
b) $R^1$ is

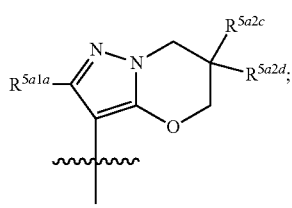

c) one of $R^{5a2c}$ and $R^{5a2d}$ is H and the other is independently halogen, OH, —$OR^6$, —$NHR^6$, or —$NR^6R^7$;
d) $R^2$ is

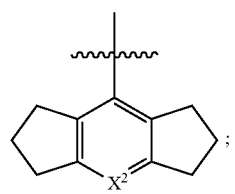

e) $X^2$ is CH or CF.

In some embodiments, the present disclosure provides a compound of formula (I),

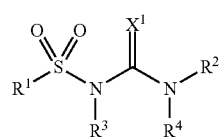
(I)

having one, two, or three of the following features:
a) X is O;
b) $R^1$ is

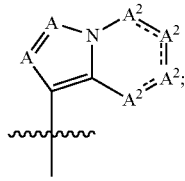

c) $R^2$ is

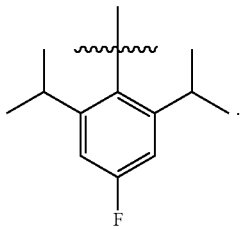 [SMILES: *c1c(C(C)C)cc(F)cc1C(C)C]

In certain embodiments, the present disclosure provides for

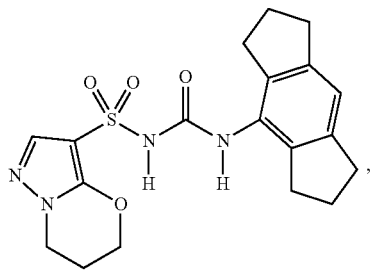 [SMILES: O=C(Nc1c2c(cc3c1CCC3)CCC2)NS(=O)(=O)c1cnn2c1OCCC2]

N-((1,2,3,5,6,7-hexahydro-s-indacen-4-yl)carbamoyl)-6,7-dihydro-5H-pyrazolo[5,1-b][1,3]oxazine-3-sulfonamide and pharmaceutically acceptable salts thereof.

In certain embodiments, the present disclosure provides for

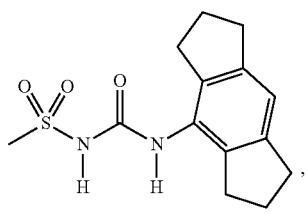 [SMILES: CS(=O)(=O)NC(=O)Nc1c2c(cc3c1CCC3)CCC2]

N-((1,2,3,5,6,7-hexahydro-s-indacen-4-yl)carbamoyl)methanesulfonamide and pharmaceutically acceptable salts thereof.

In certain embodiments, the present disclosure provides for

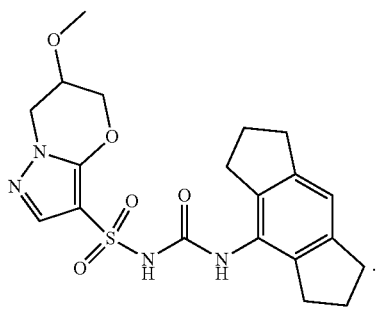 [SMILES: COC1COc2c(S(=O)(=O)NC(=O)Nc3c4c(cc5c3CCC5)CCC4)cnn2C1]

and pharmaceutically acceptable salts thereof.

In certain embodiments, the present disclosure provides for

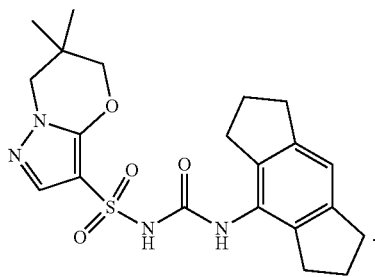 [SMILES: CC1(C)COc2c(S(=O)(=O)NC(=O)Nc3c4c(cc5c3CCC5)CCC4)cnn2C1]

and pharmaceutically acceptable salts thereof.

In certain embodiments, the present disclosure provides for

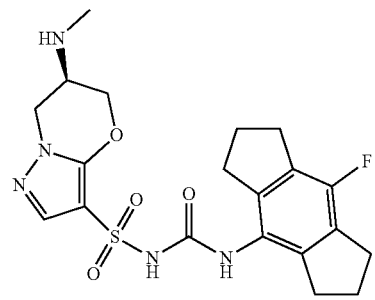 [SMILES: CN[C@H]1COc2c(S(=O)(=O)NC(=O)Nc3c4c(c(F)c5c3CCC5)CCC4)cnn2C1]

and pharmaceutically acceptable salts thereof.

In certain embodiments, the present disclosure provides for

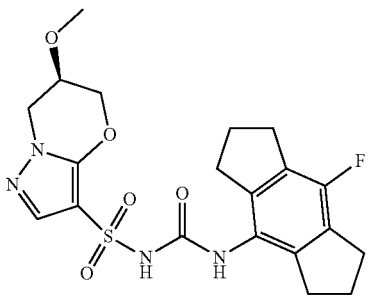 [SMILES: CO[C@H]1COc2c(S(=O)(=O)NC(=O)Nc3c4c(c(F)c5c3CCC5)CCC4)cnn2C1]

and pharmaceutically acceptable salts thereof.

In certain embodiments, the present disclosure provides for

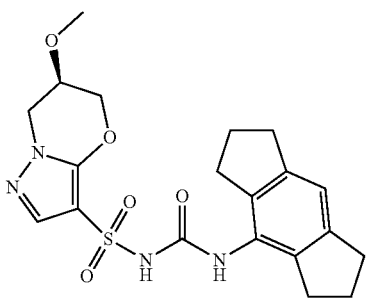 [SMILES: CO[C@H]1COc2c(S(=O)(=O)NC(=O)Nc3c4c(cc5c3CCC5)CCC4)cnn2C1]

and pharmaceutically acceptable salts thereof.

In certain embodiments, the present disclosure provides for

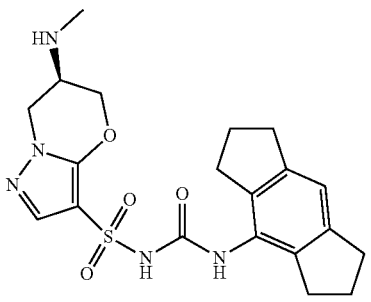 [SMILES: CN[C@H]1COc2c(S(=O)(=O)NC(=O)Nc3c4c(cc5c3CCC5)CCC4)cnn2C1]

and pharmaceutically acceptable salts thereof.

In certain embodiments, the present disclosure provides for

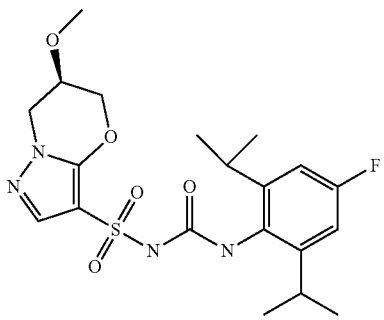 [SMILES: CN[C@H]1COc2c(S(=O)(=O)NC(=O)Nc3c(C(C)C)cc(F)cc3C(C)C)cnn2C1]

and pharmaceutically acceptable salts thereof.

In certain embodiments, the present disclosure provides for
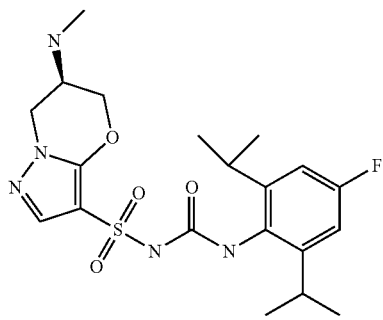
and pharmaceutically acceptable salts thereof.
In certain embodiments, the present disclosure provide for a compound, and pharmaceutically acceptable salts, prodrugs, solvates, hydrates, isomers, and tautomers thereof, selected from the group consisting of:
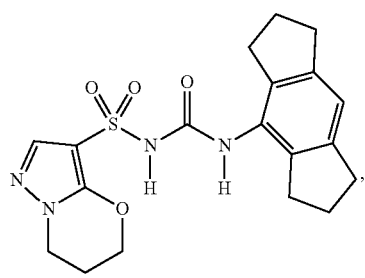
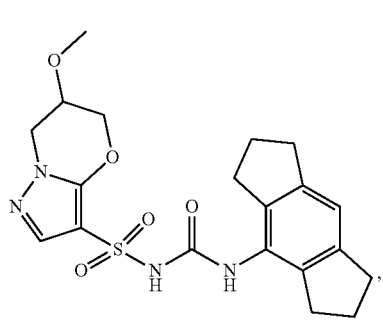
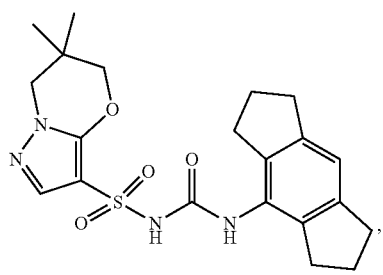
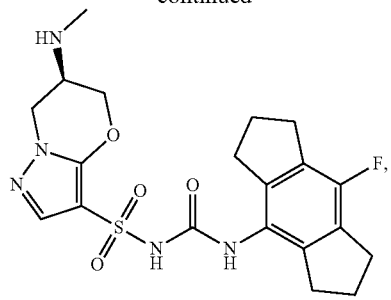
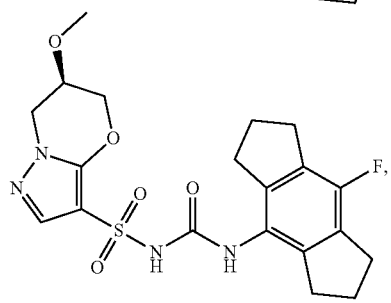
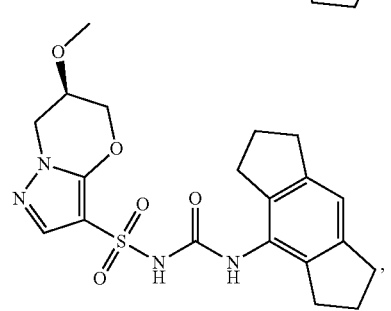
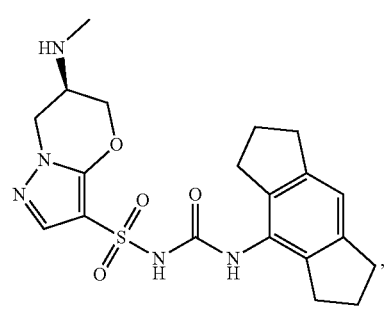
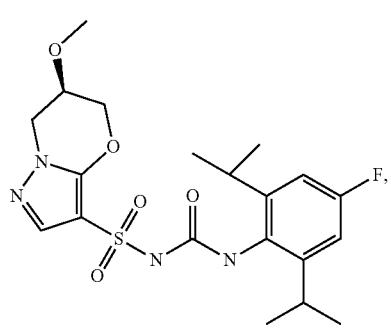

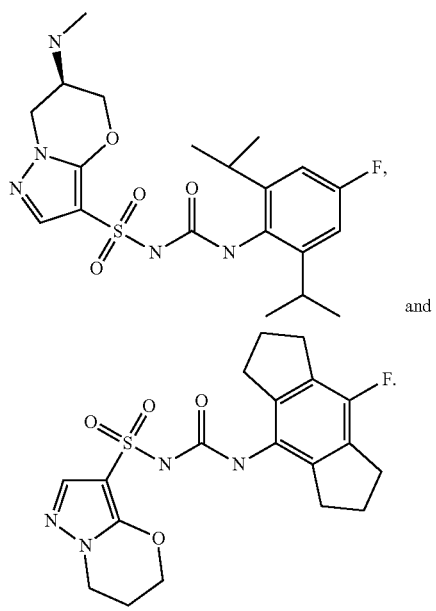
and
In certain embodiments, the present disclosure provide for a compound, and pharmaceutically acceptable salts, prodrugs, solvates, hydrates, isomers, and tautomers thereof, selected from the group consisting of:
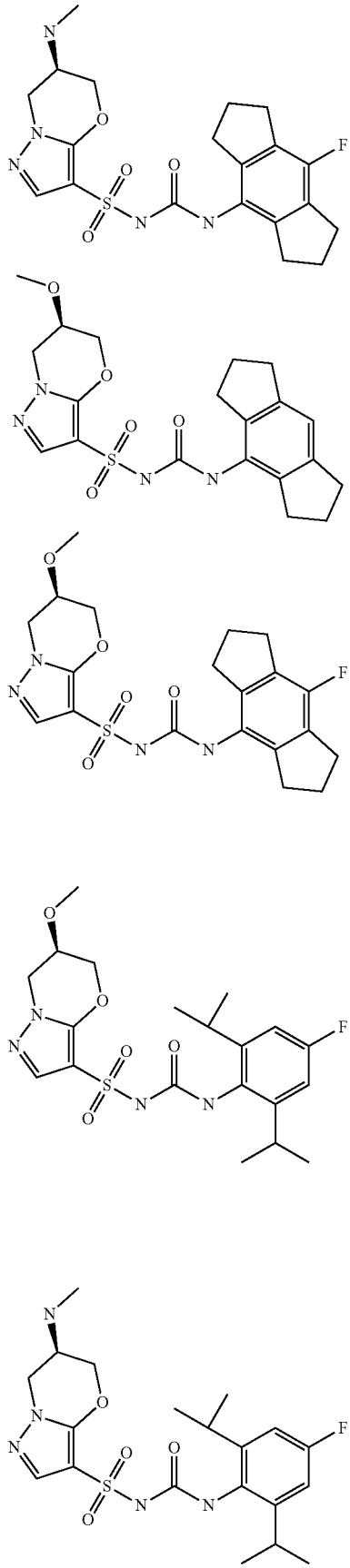

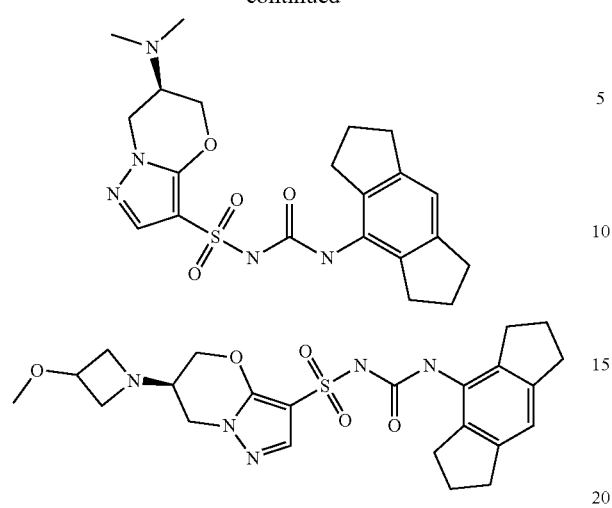
In certain embodiments, the present disclosure provides for the following compounds, and pharmaceutically acceptable salts, prodrugs, solvates, hydrates, isomers, and tautomers thereof:
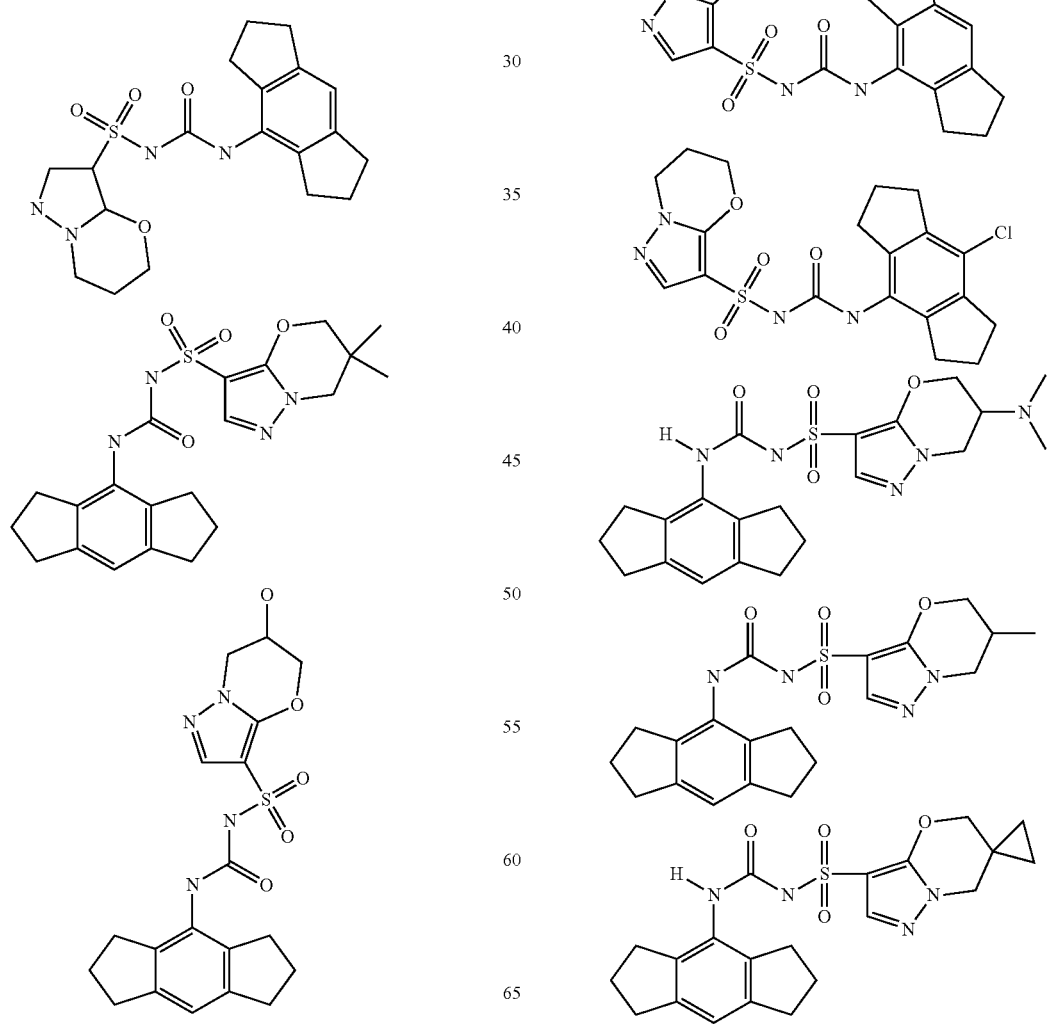

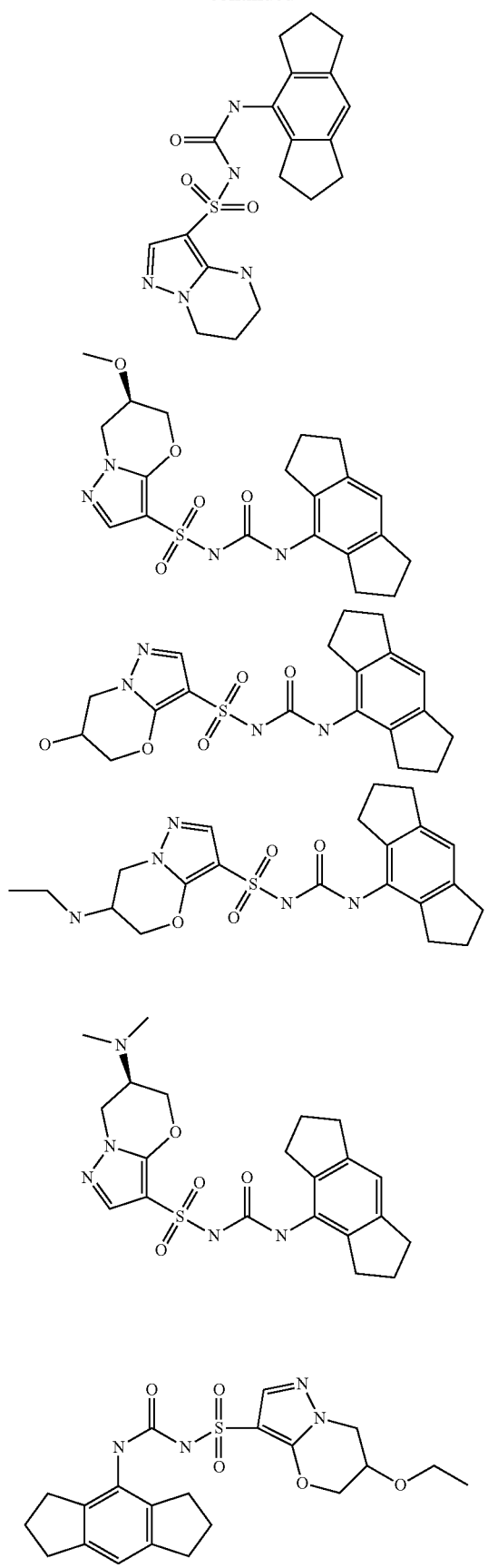
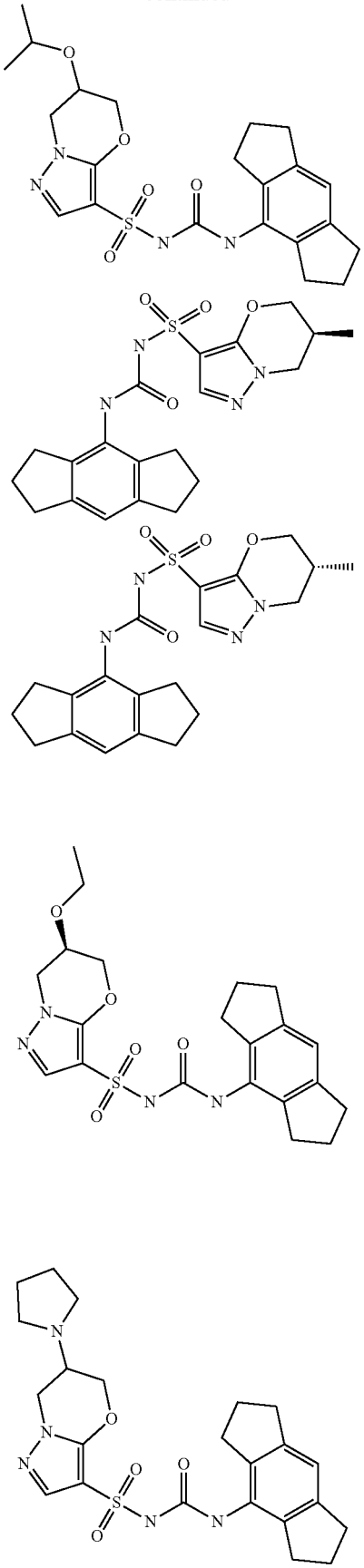

95
-continued
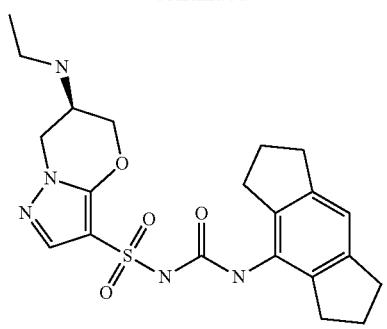
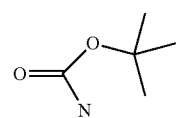
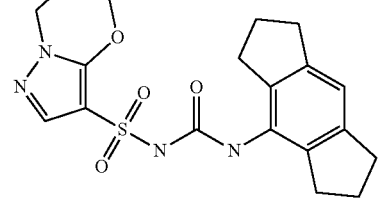
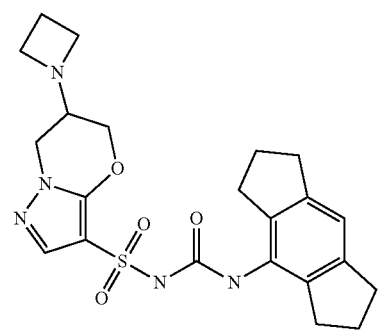
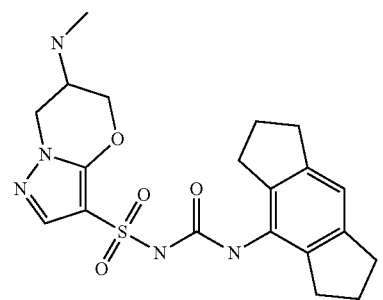
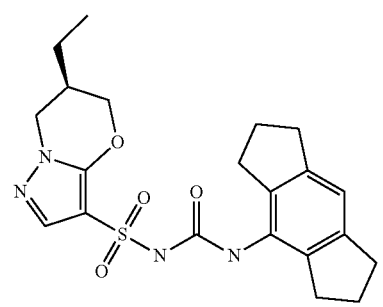
96
-continued
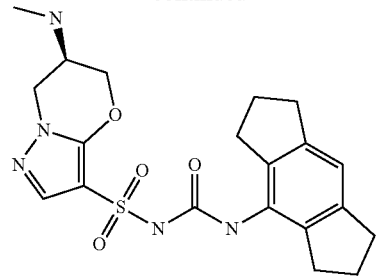
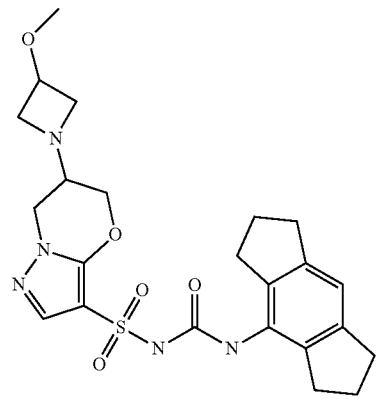
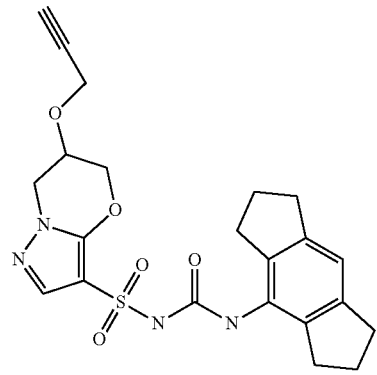
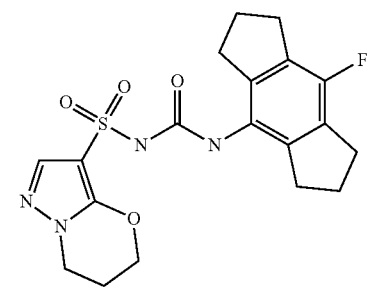
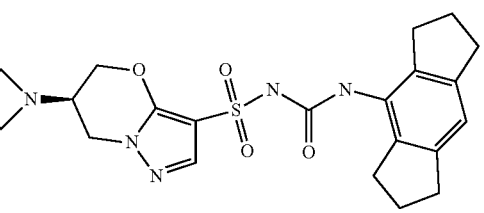

97
-continued
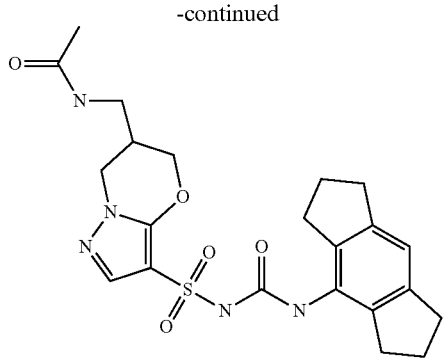
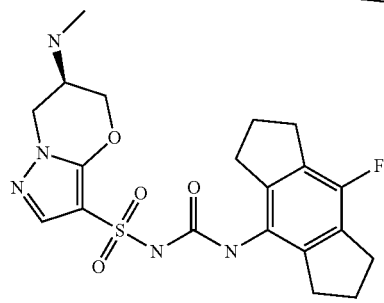
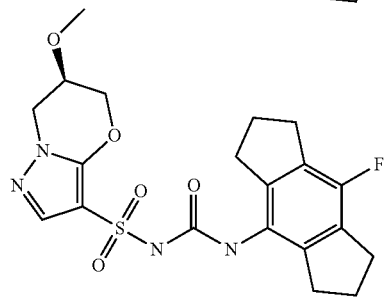
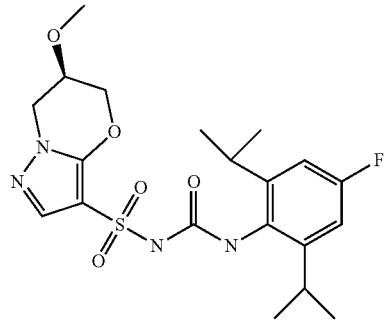
In certain embodiments, the present disclosure provides for the following compounds, and pharmaceutically acceptable salts, prodrugs, solvates, hydrates, isomers, and tautomers thereof:
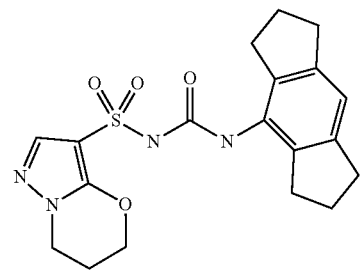
98
-continued
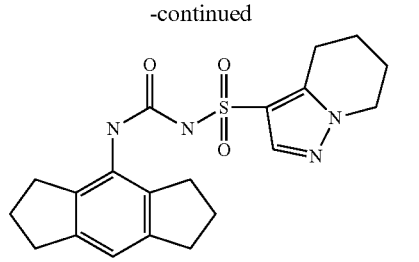
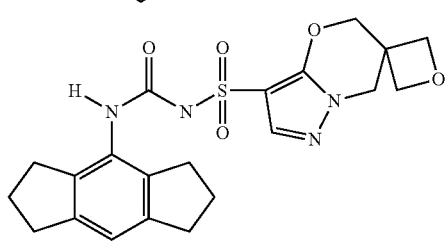
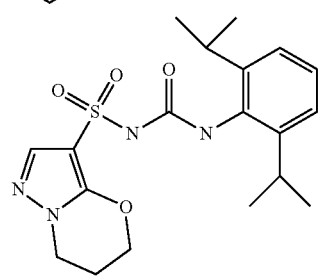
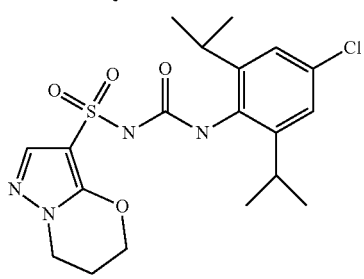
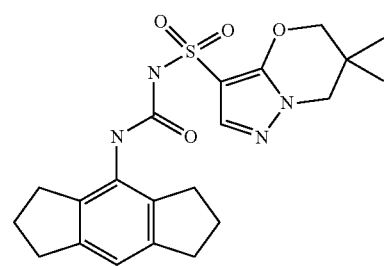
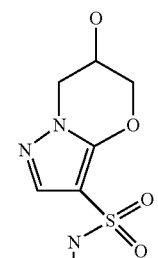
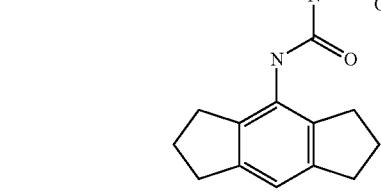

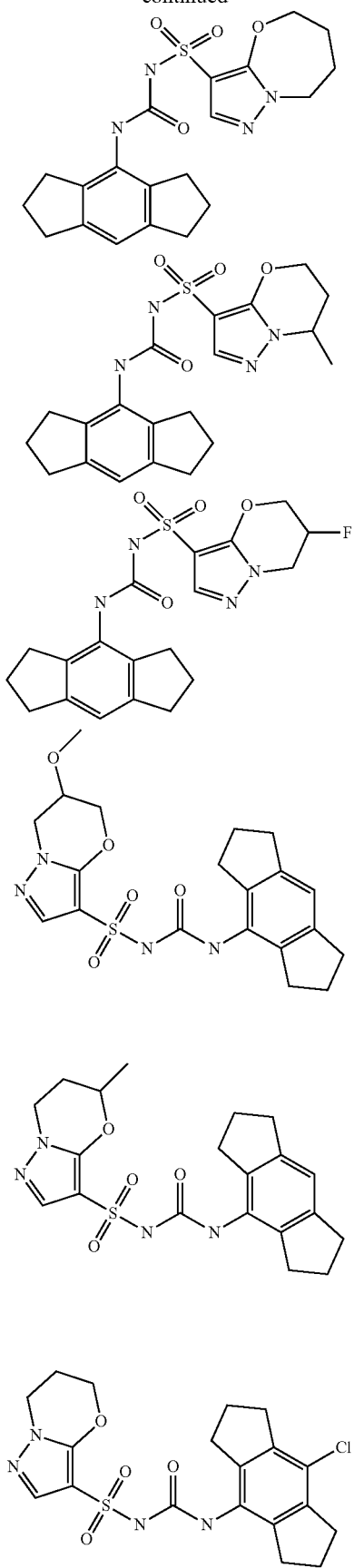
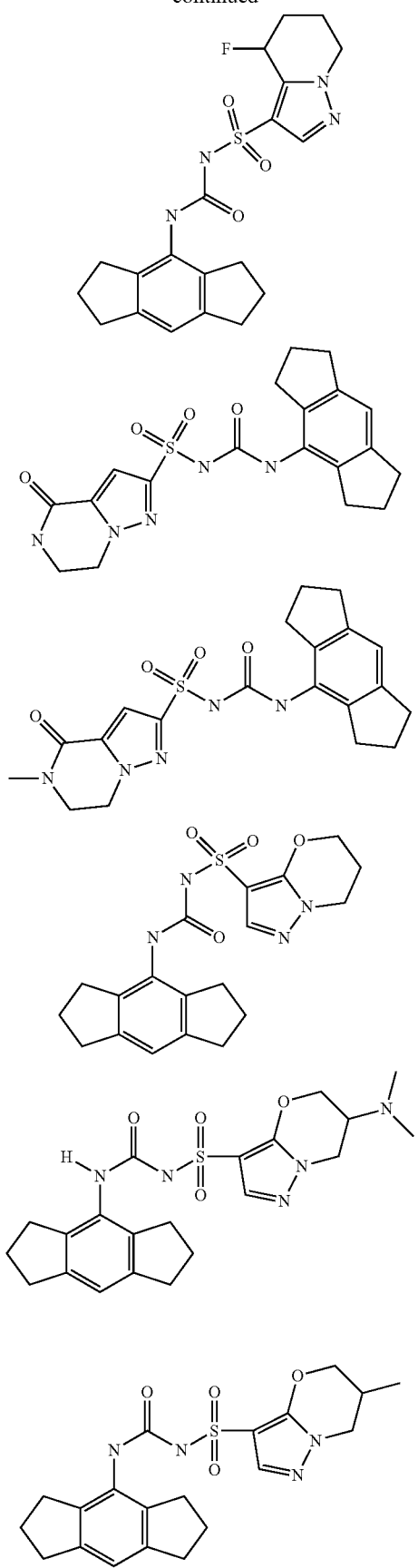

101
-continued
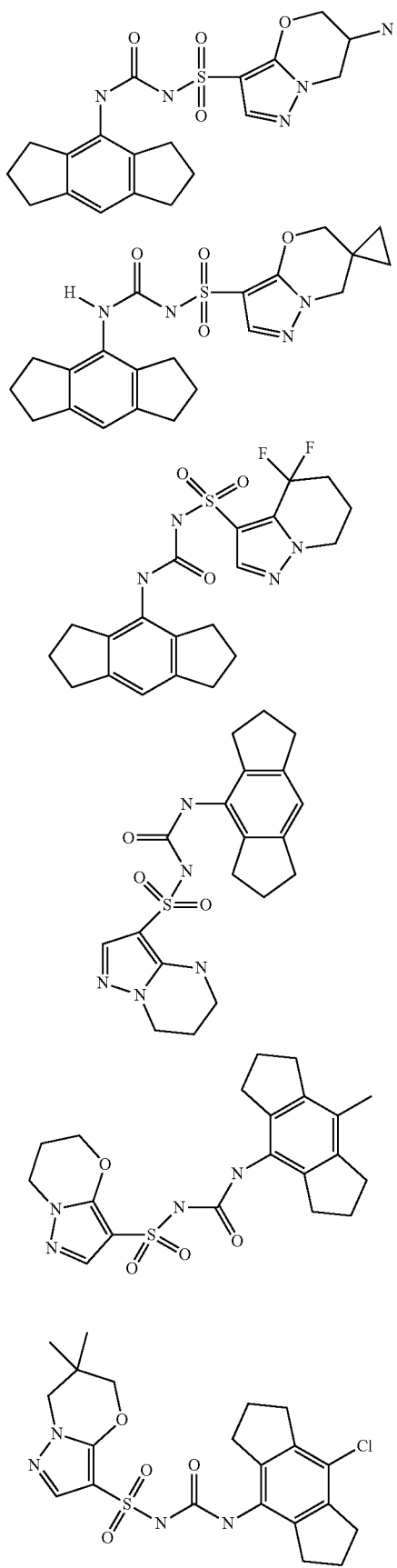
102
-continued
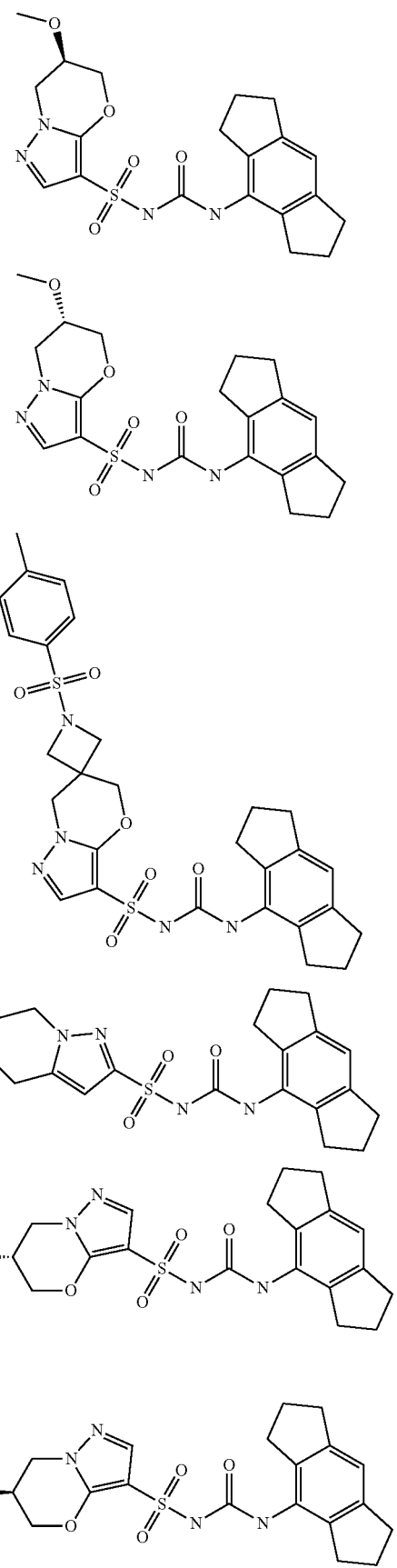

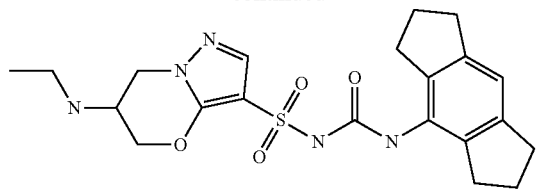
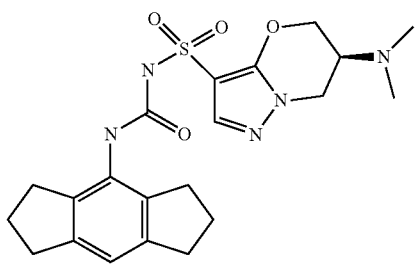
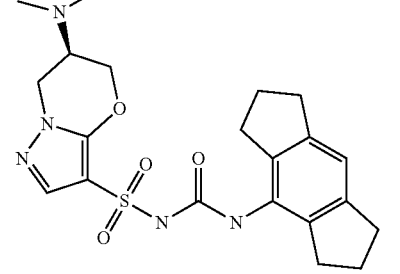
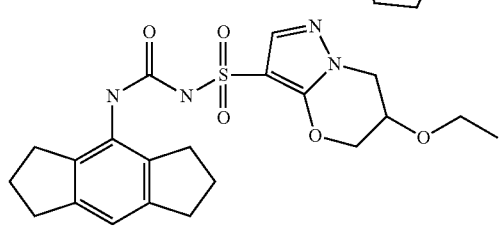
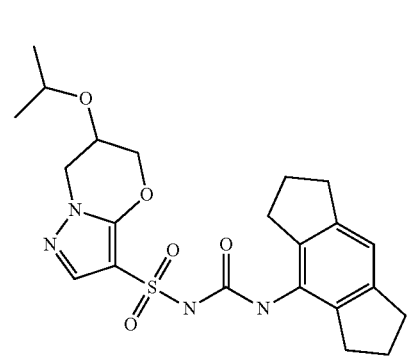
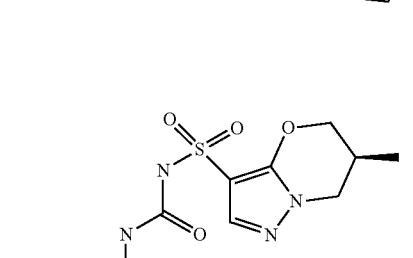
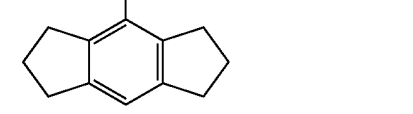
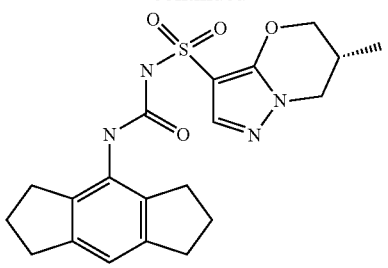
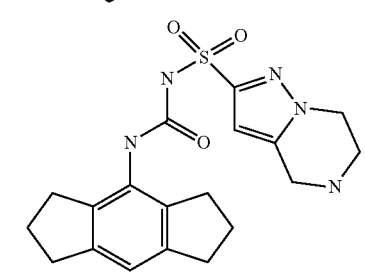
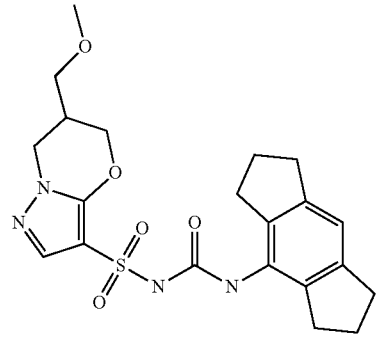
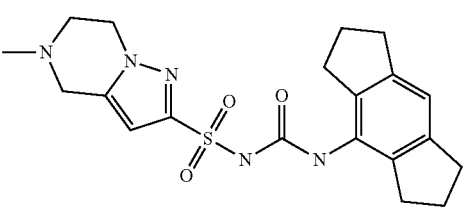
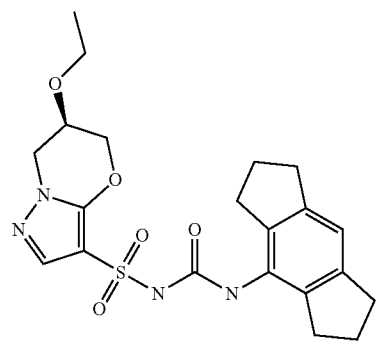
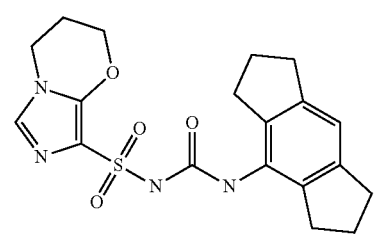

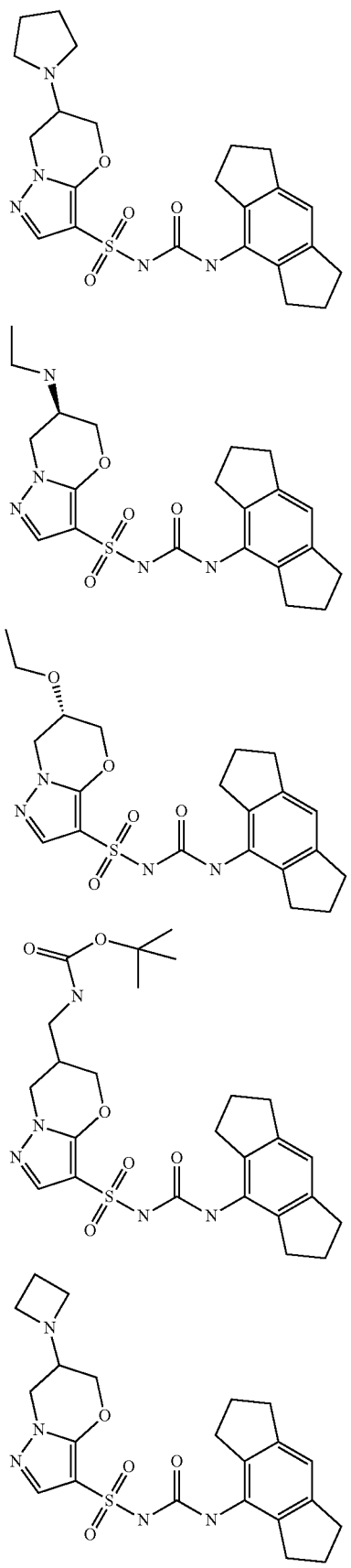
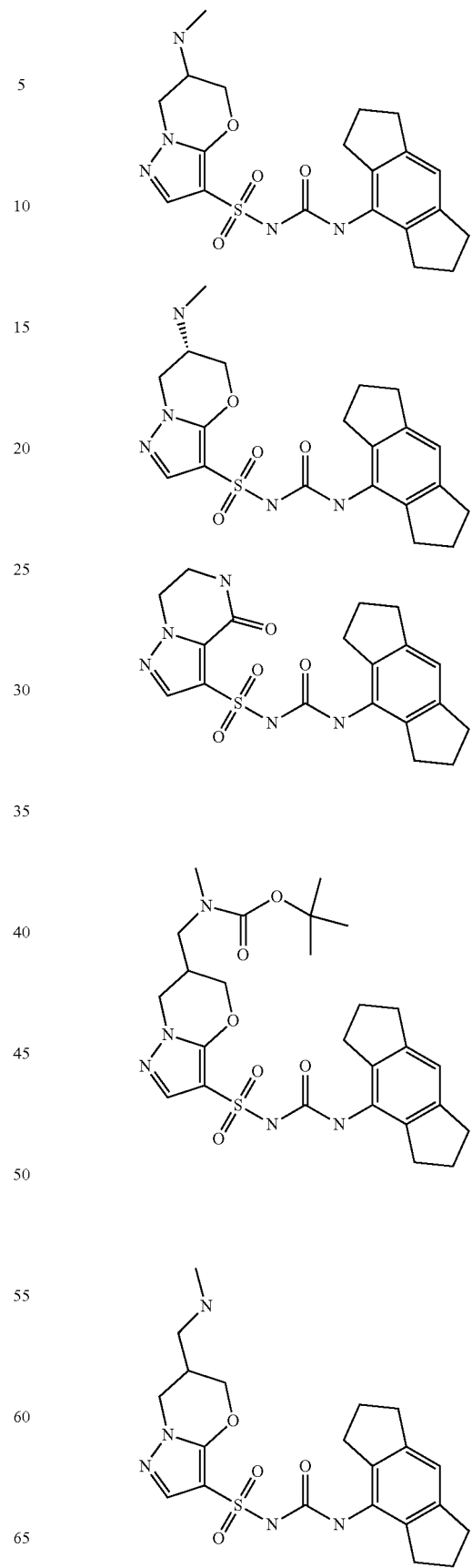

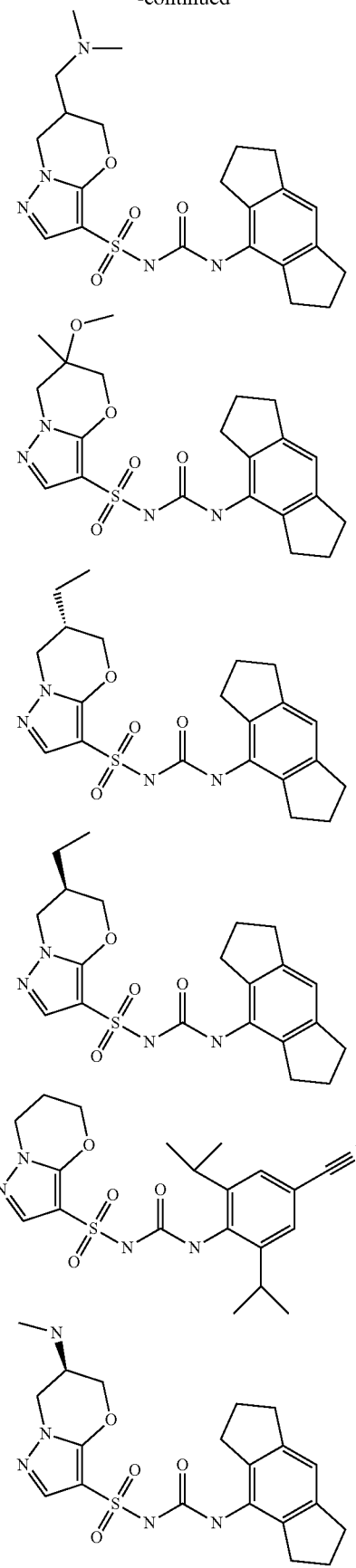
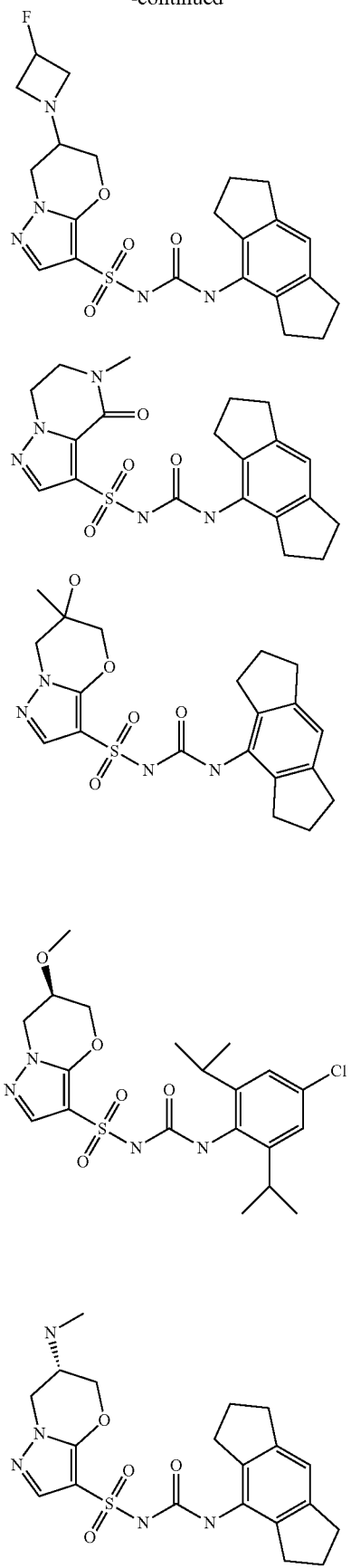

109
-continued
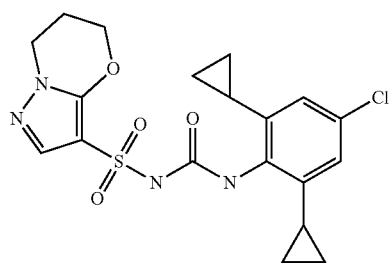
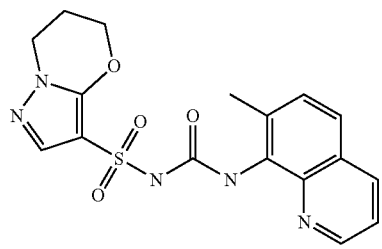
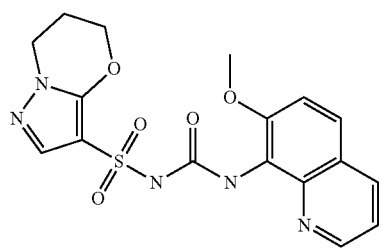
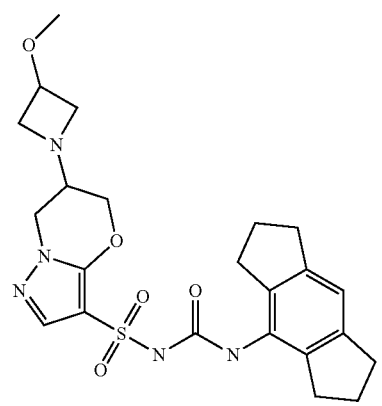
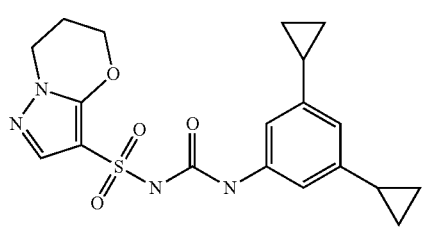
110
-continued
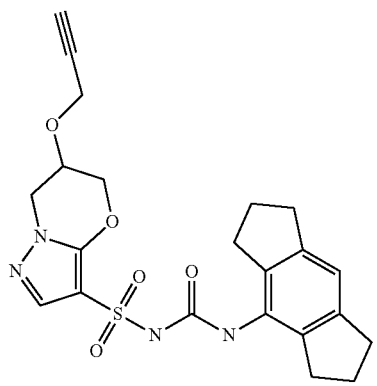
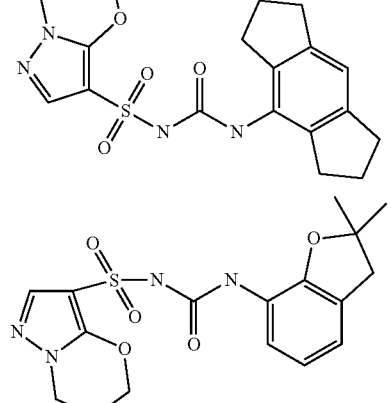
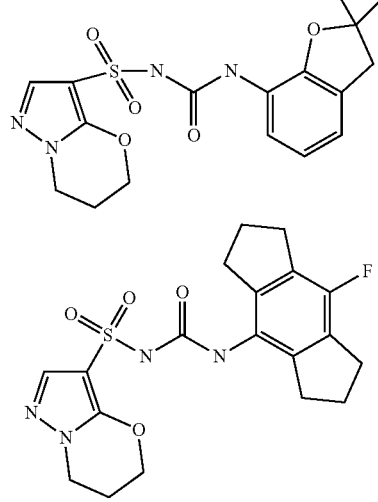
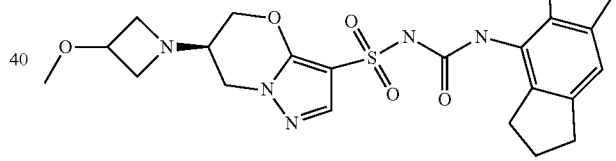
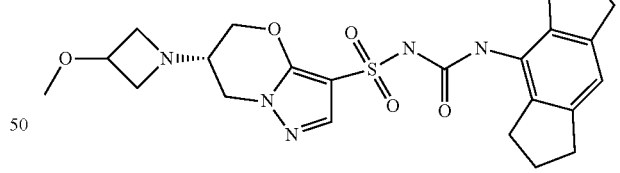
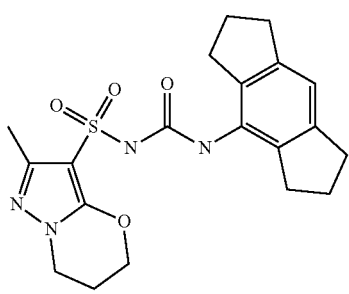

111
-continued
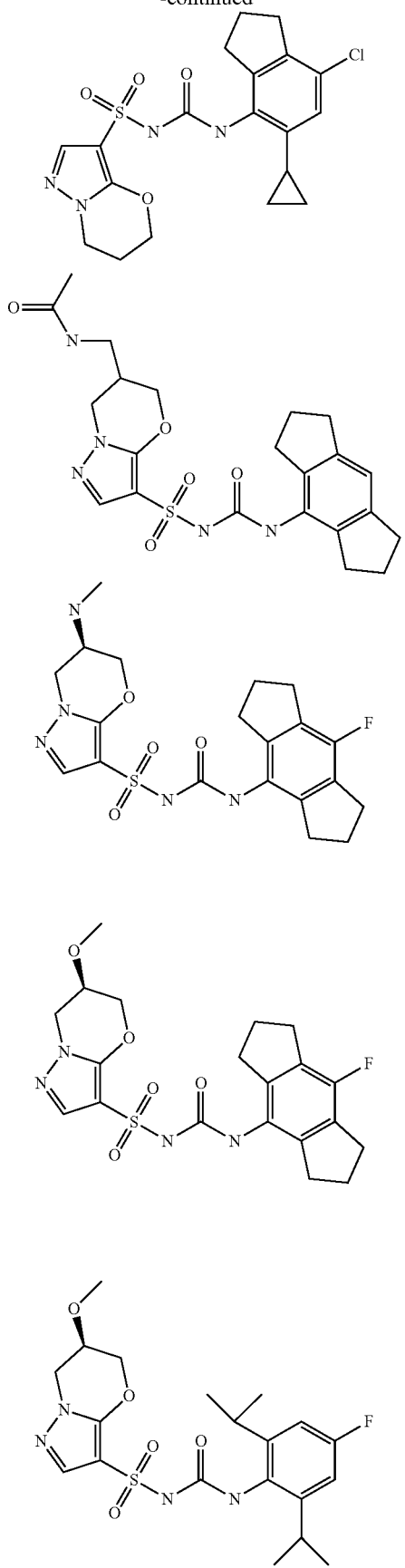
112
-continued
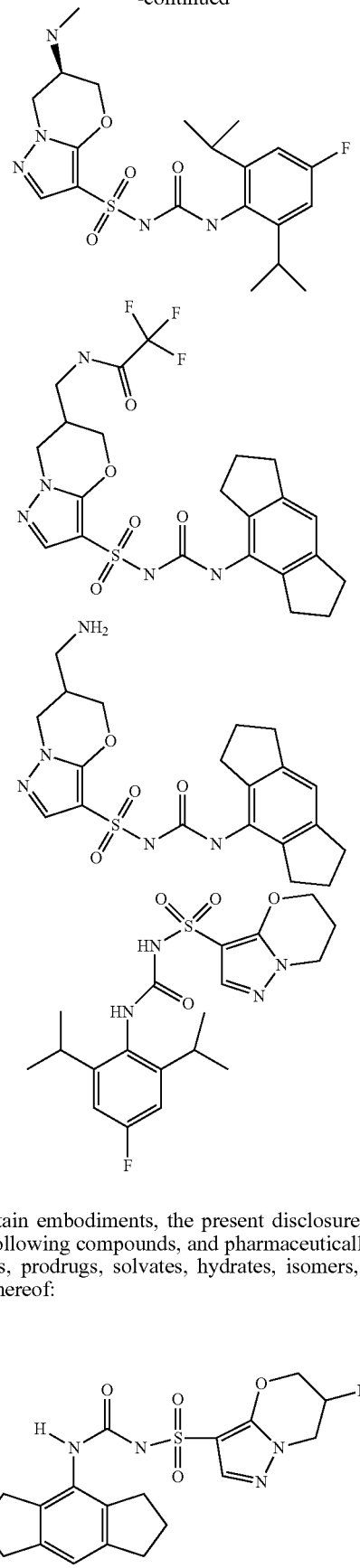
In certain embodiments, the present disclosure provides for the following compounds, and pharmaceutically acceptable salts, prodrugs, solvates, hydrates, isomers, and tautomers thereof:

113
-continued
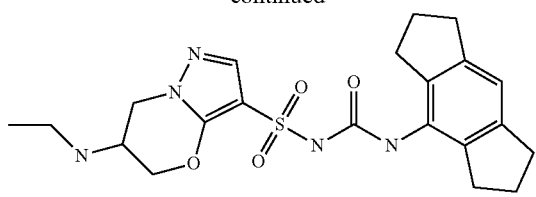
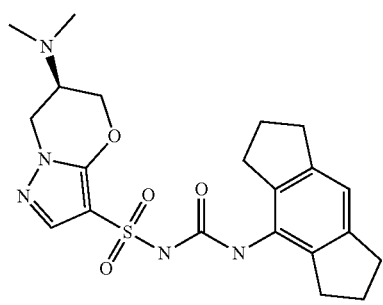
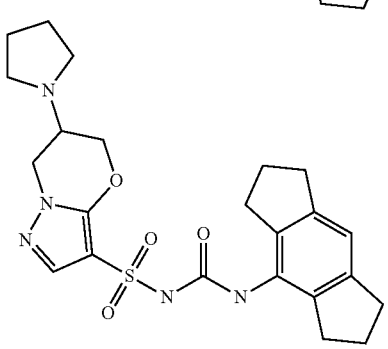
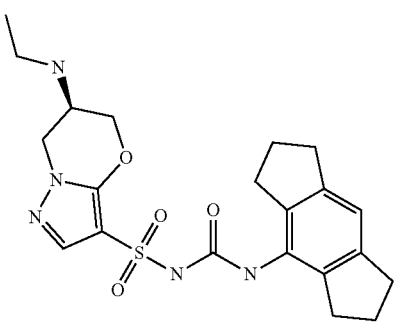
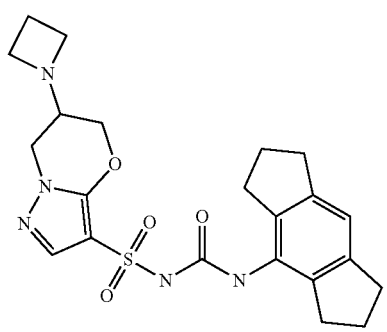
114
-continued
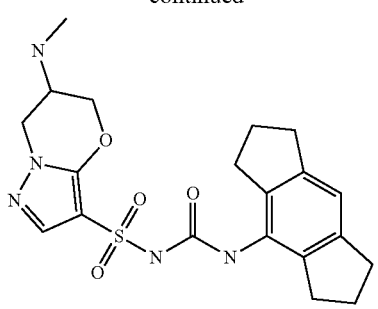
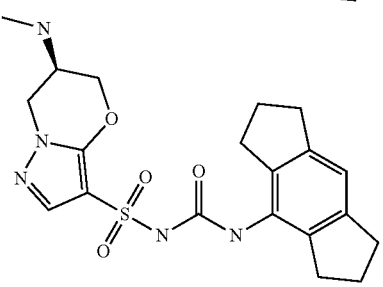
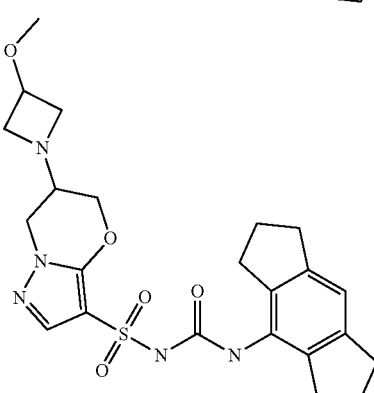
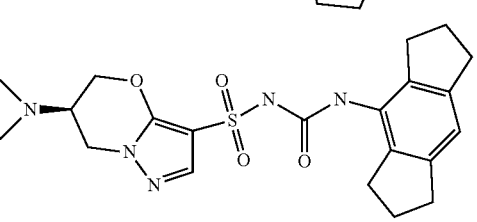
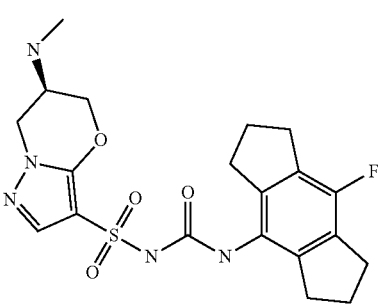
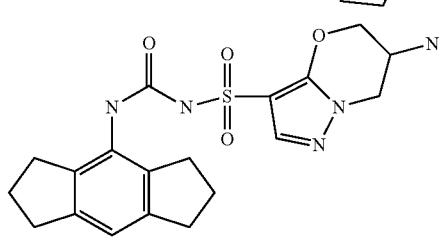

115
-continued
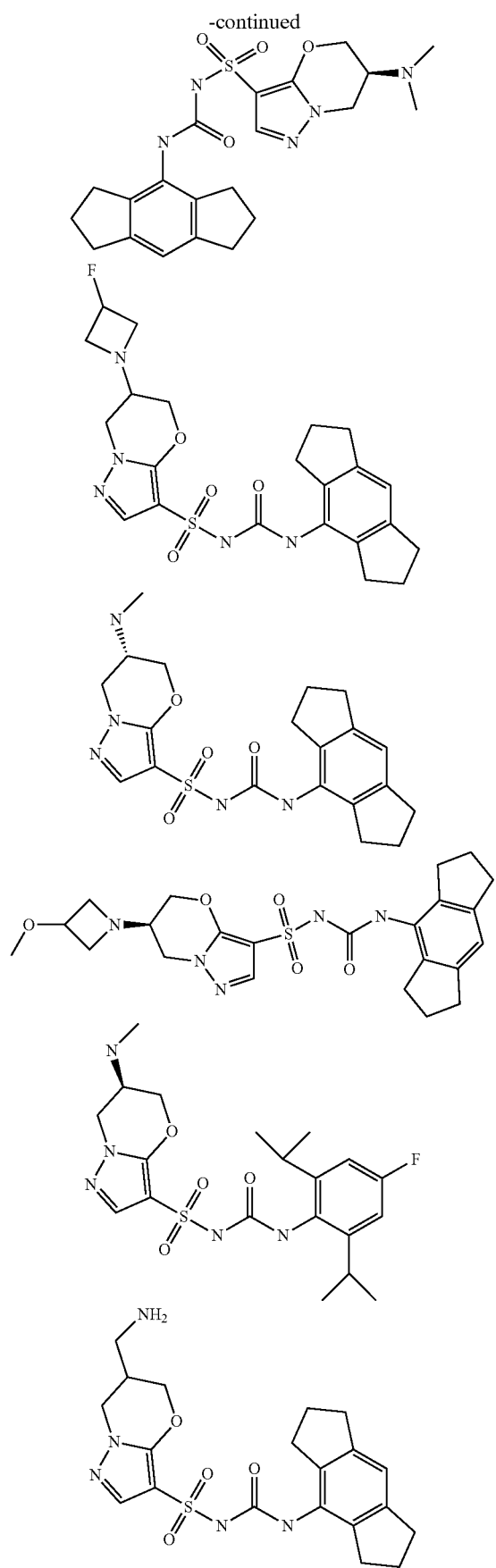
116
-continued
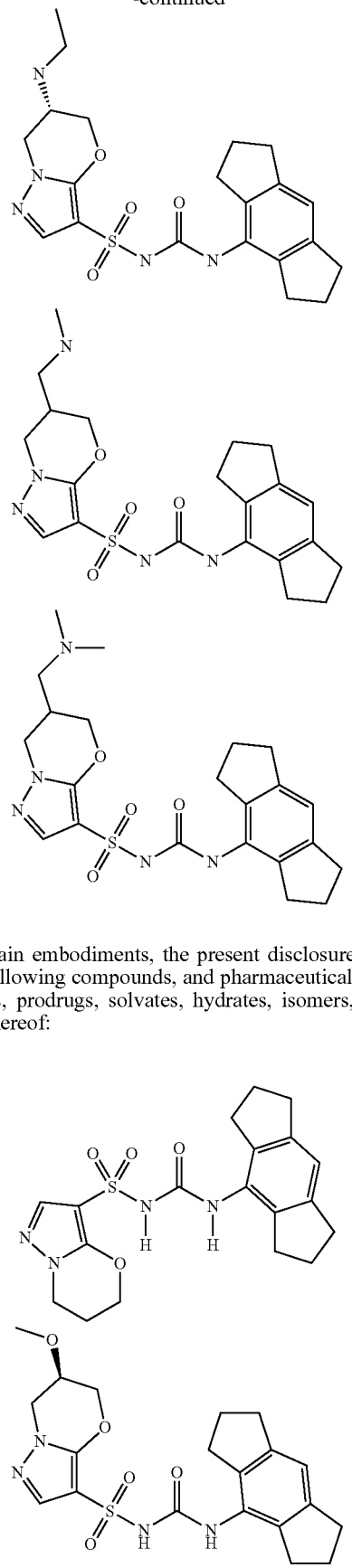
In certain embodiments, the present disclosure provides for the following compounds, and pharmaceutically acceptable salts, prodrugs, solvates, hydrates, isomers, and tautomers thereof:

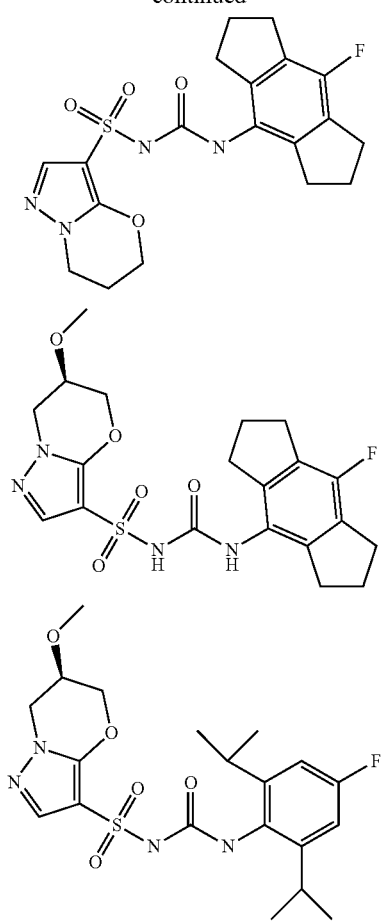
In certain embodiments, the present disclosure provides for the following compounds, and pharmaceutically acceptable salts, prodrugs, solvates, hydrates, isomers, and tautomers thereof:
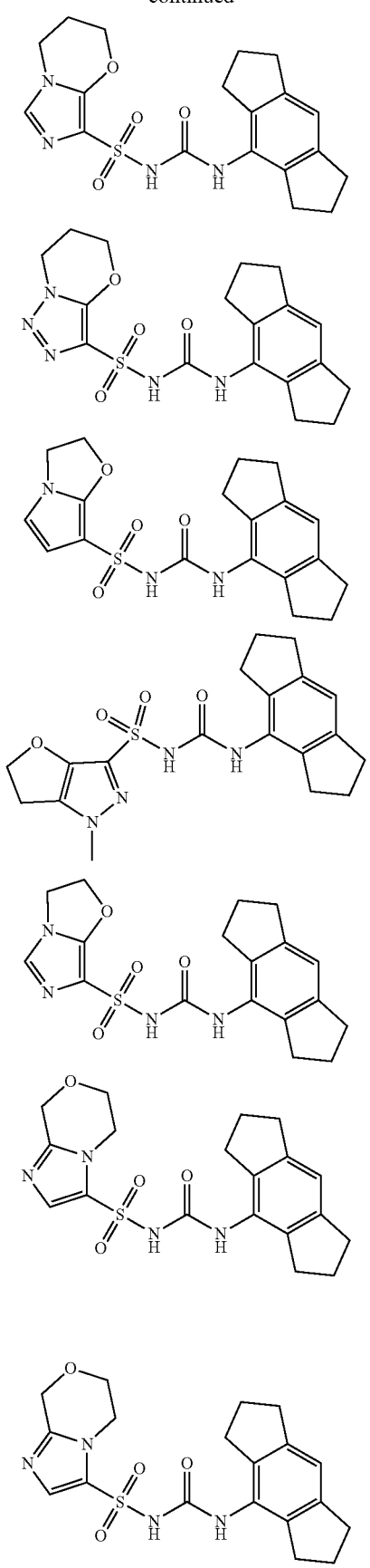

119
-continued
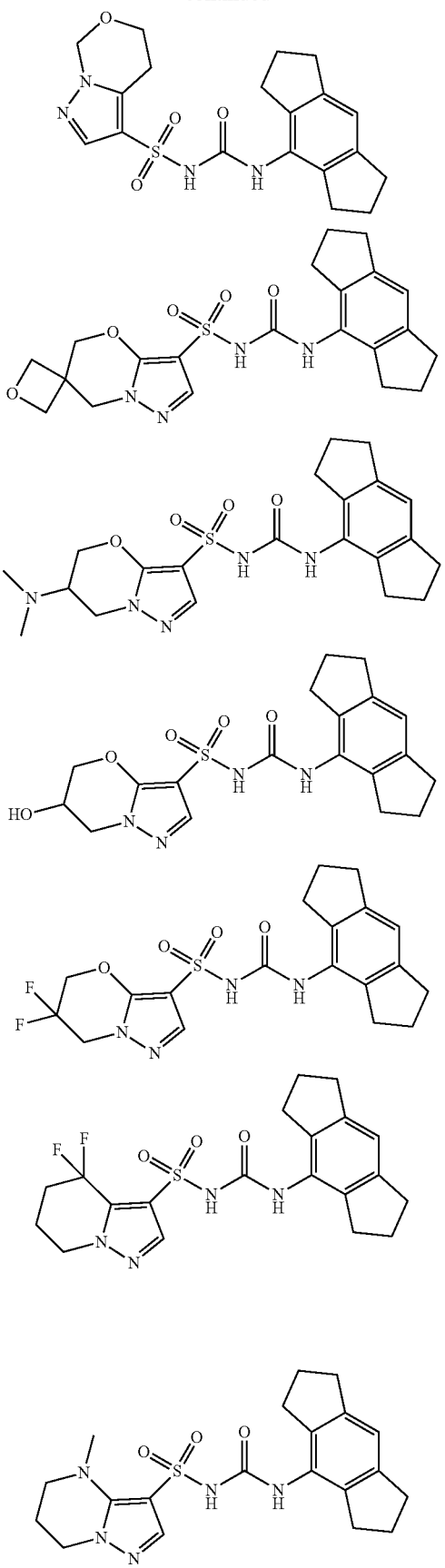
120
-continued
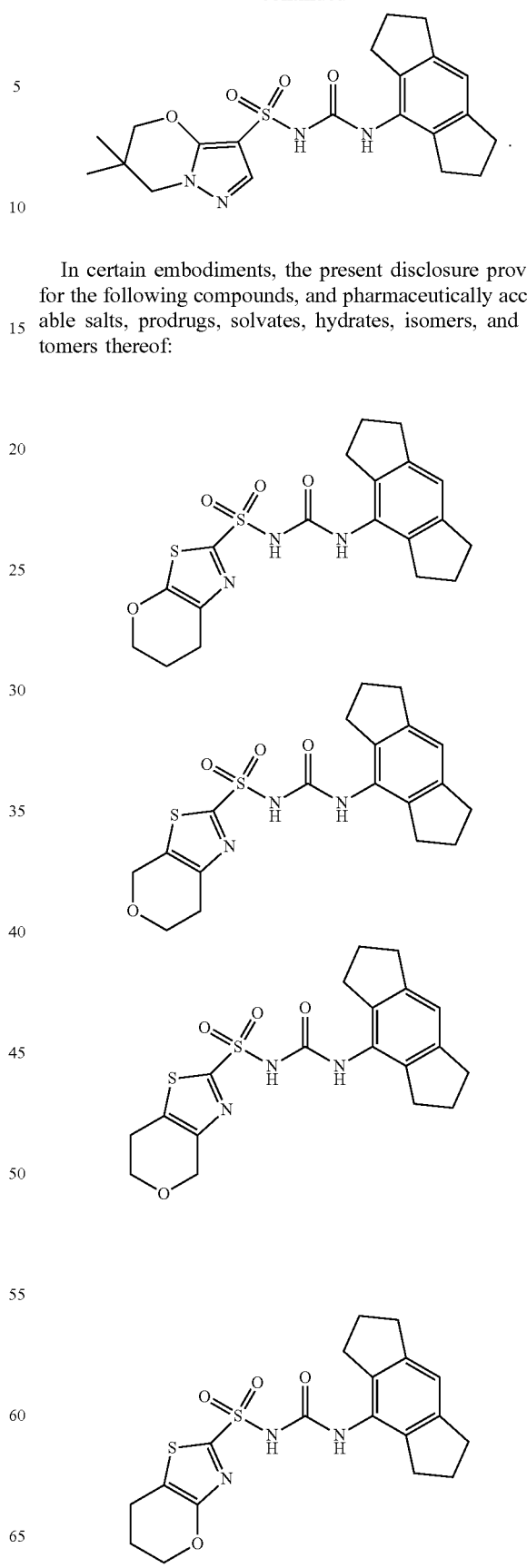
In certain embodiments, the present disclosure provides for the following compounds, and pharmaceutically acceptable salts, prodrugs, solvates, hydrates, isomers, and tautomers thereof:

121
-continued
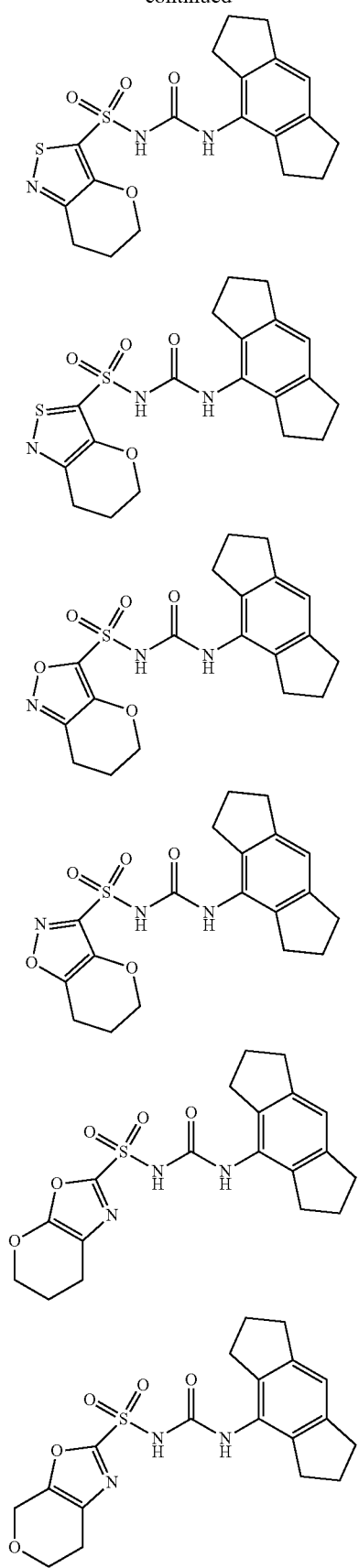
122
-continued
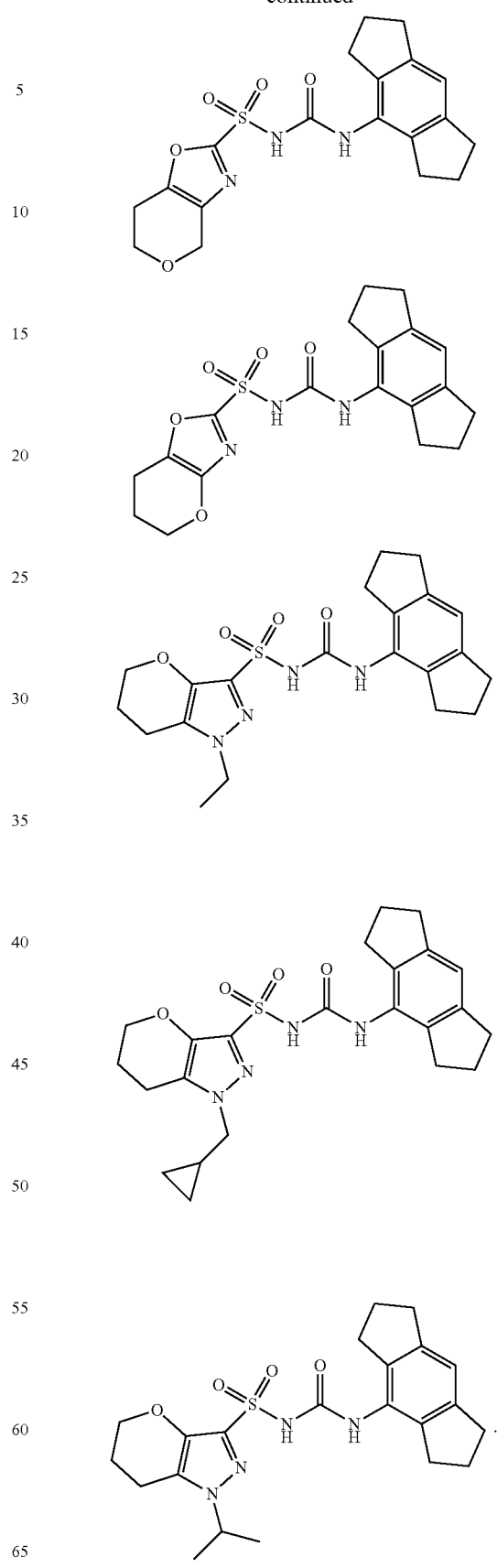

In certain embodiments, the present disclosure provides for the following compounds, and pharmaceutically acceptable salts thereof:
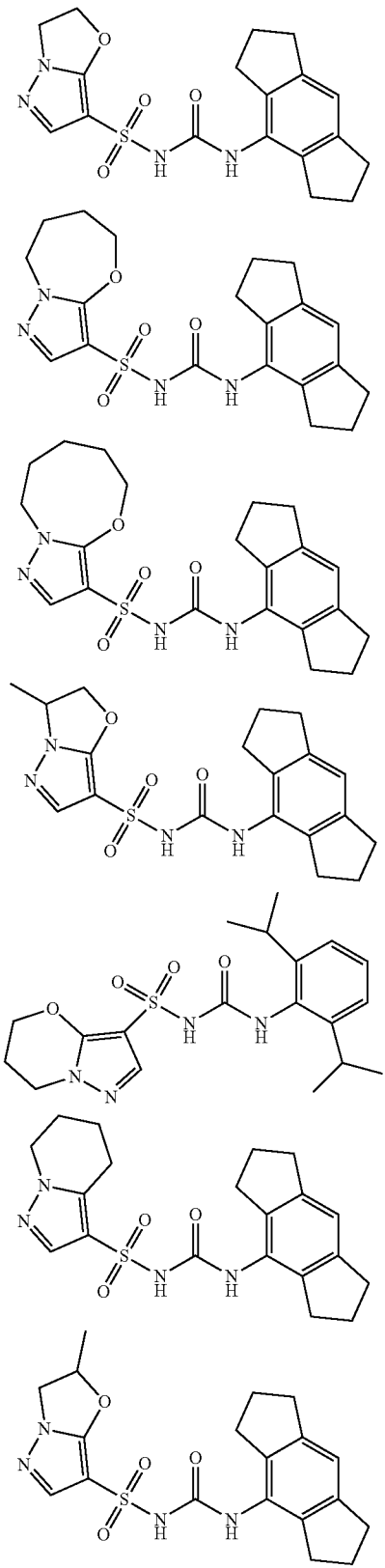
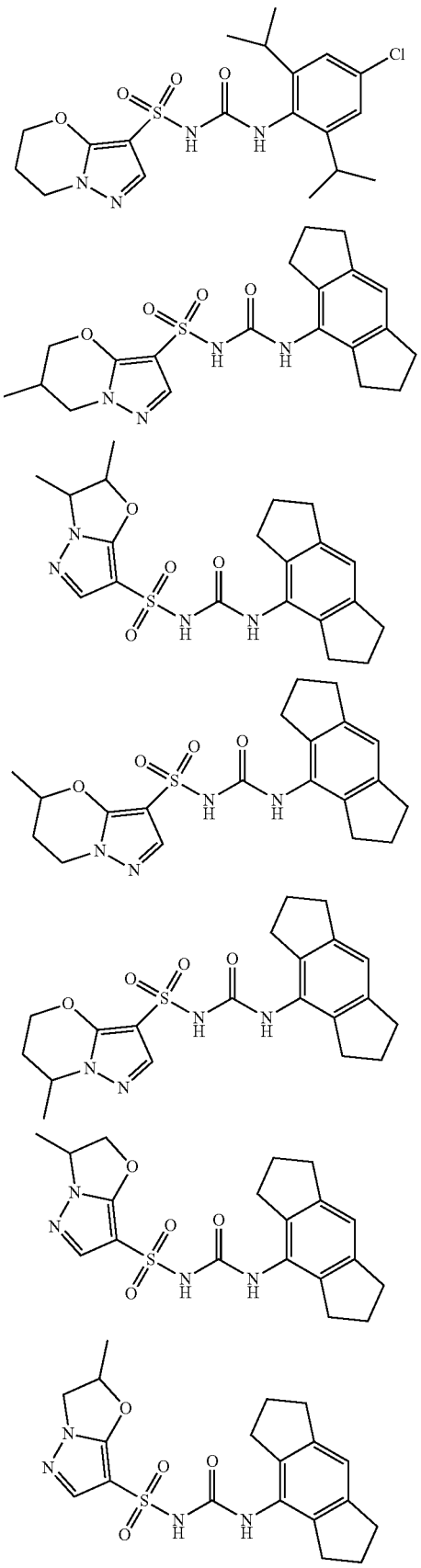

-continued
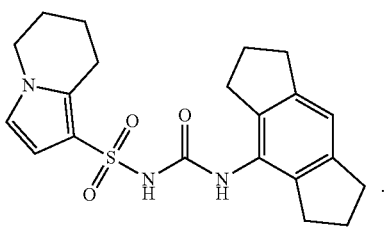
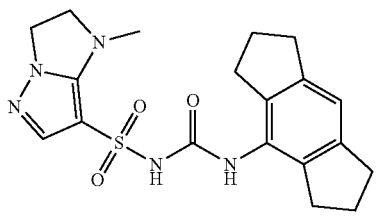
In certain embodiments, the present disclosure provides for the following compounds, and pharmaceutically acceptable salts thereof:
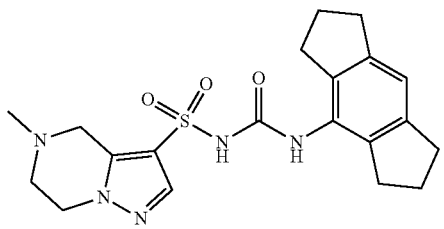
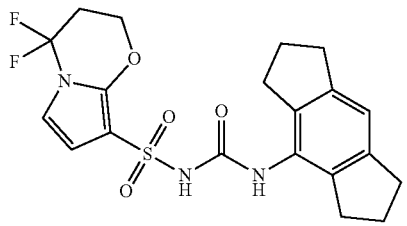
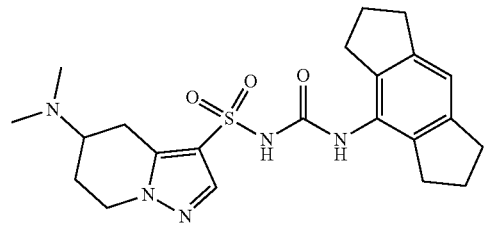
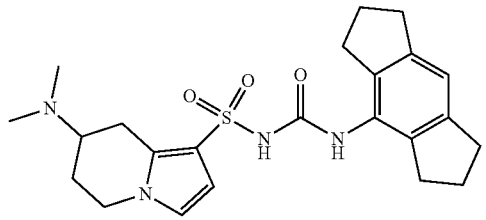
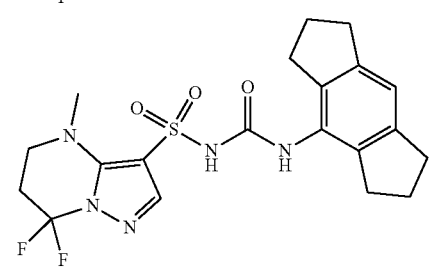
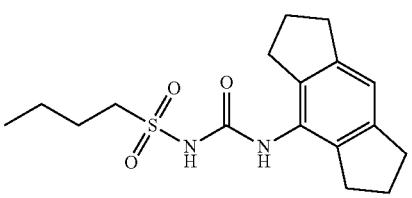
In certain embodiments, the present disclosure provides for the following compounds, and pharmaceutically acceptable salts, prodrugs, solvates, hydrates, isomers, and tautomers thereof:
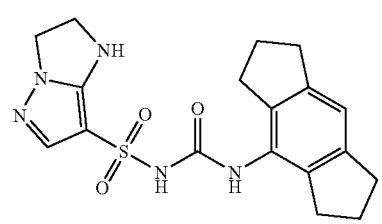
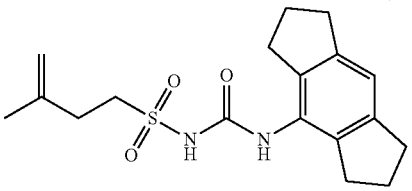

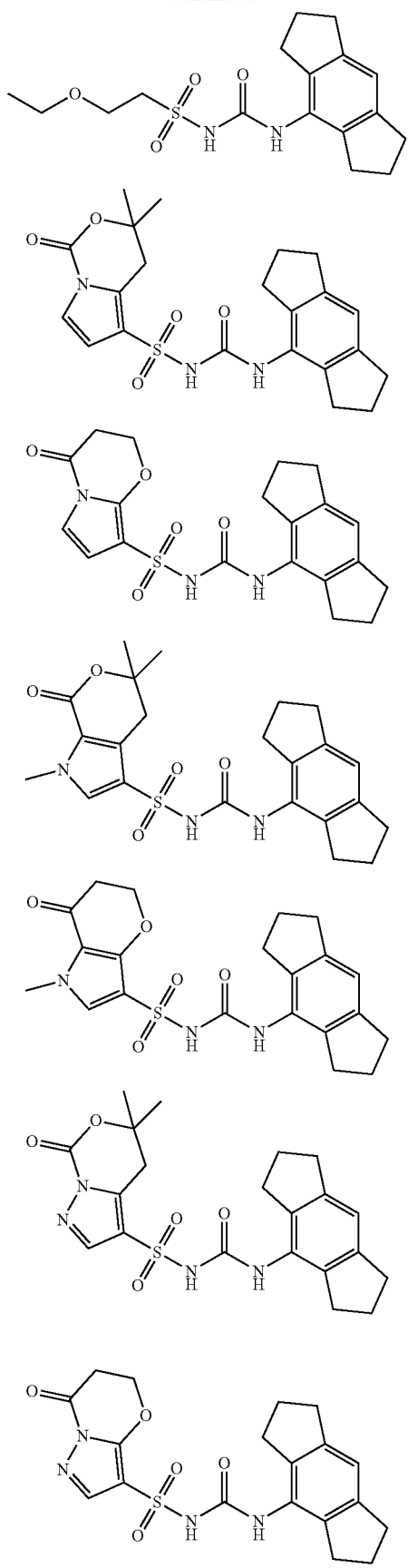
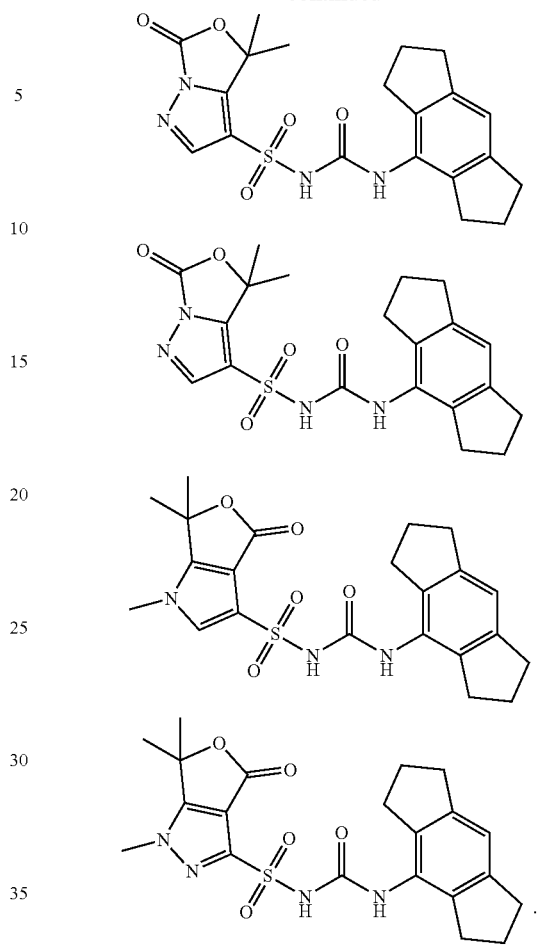
In certain embodiments, the present disclosure provides for the following compounds, and pharmaceutically acceptable salts, prodrugs, solvates, hydrates, isomers, and tautomers thereof:
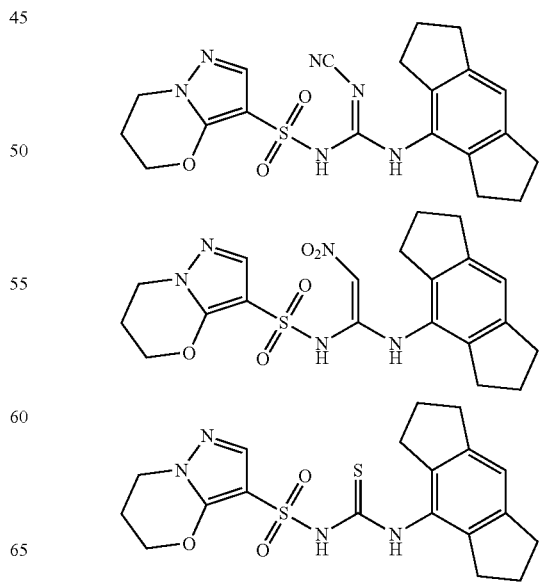

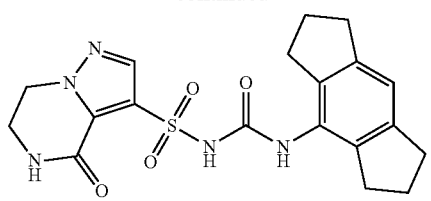
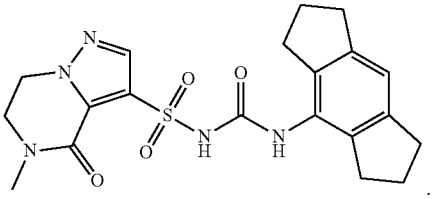
In certain embodiments, the present disclosure provides for the following compounds, and pharmaceutically acceptable salts, prodrugs, solvates, hydrates, isomers, and tautomers thereof:
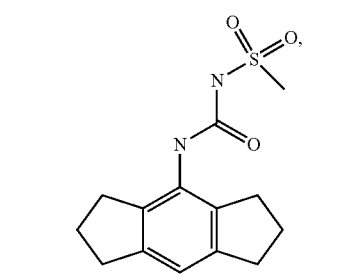
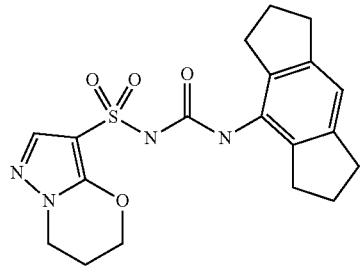
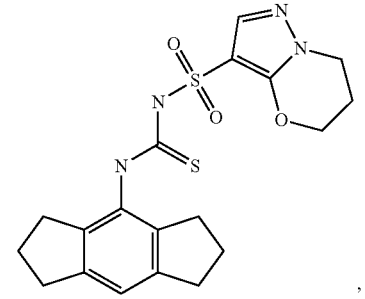
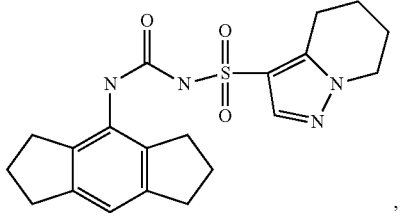
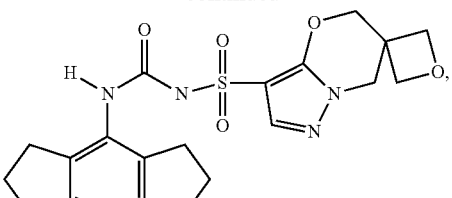
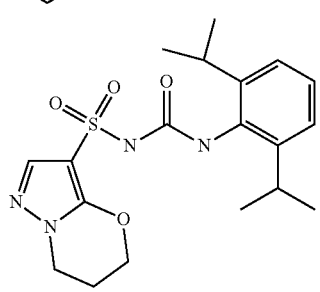
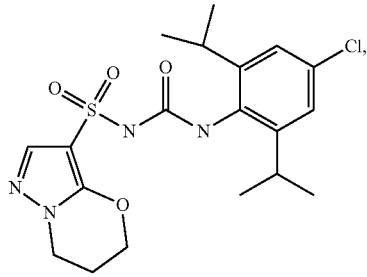
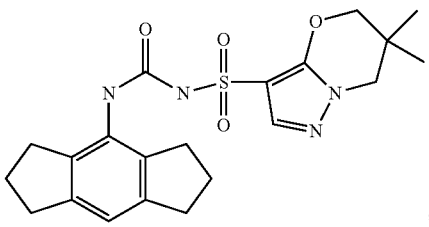
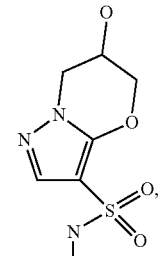
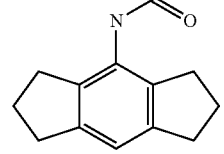
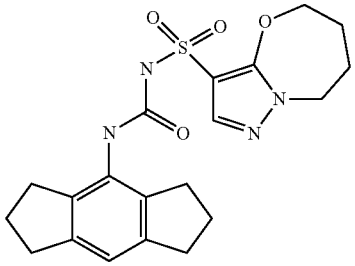

131
-continued
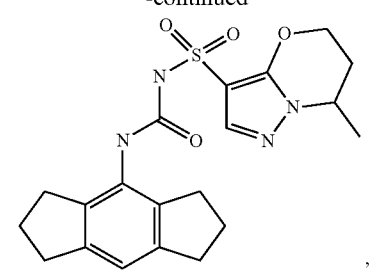
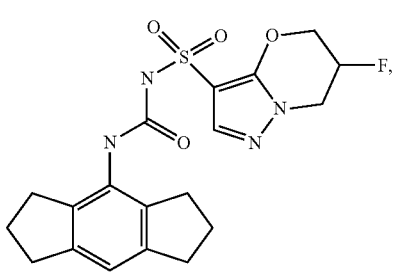
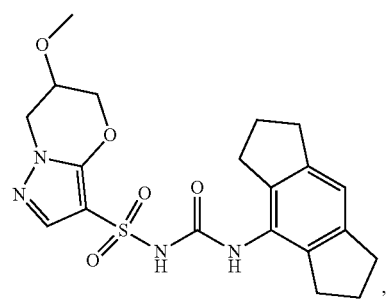
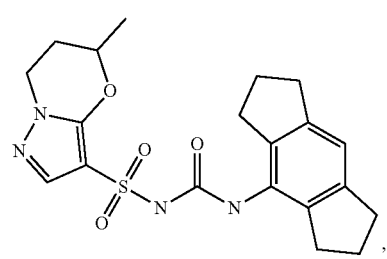
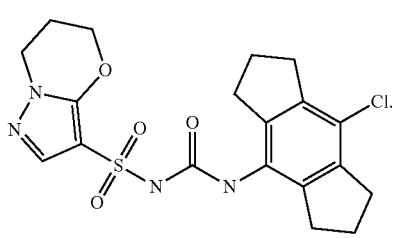
132
In certain embodiments, the present disclosure provides for the following compounds, and pharmaceutically acceptable salts, prodrugs, solvates, hydrates, isomers, and tautomers thereof:
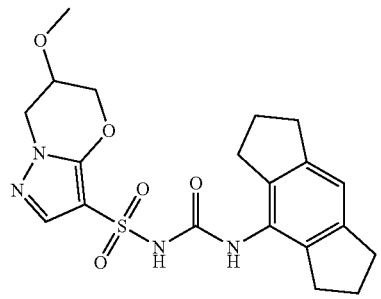
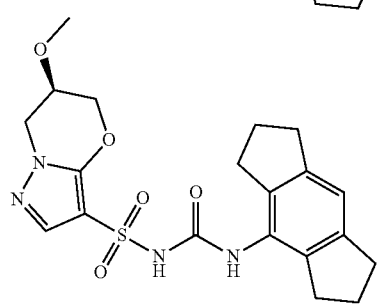
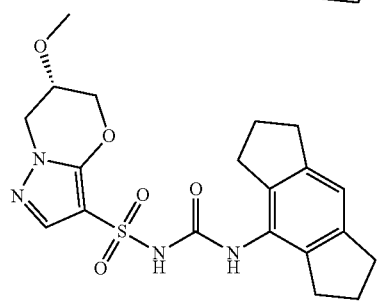
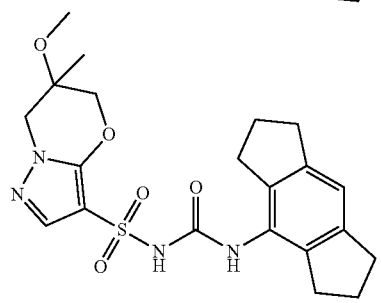
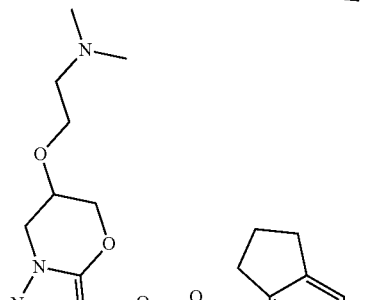
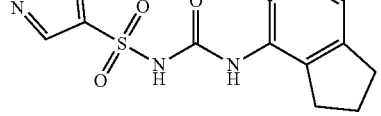

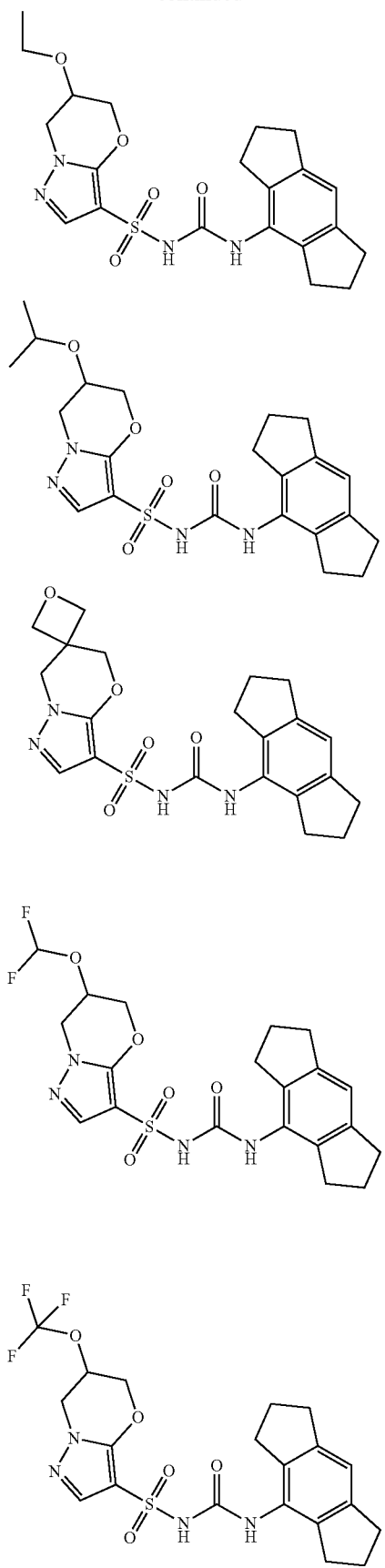
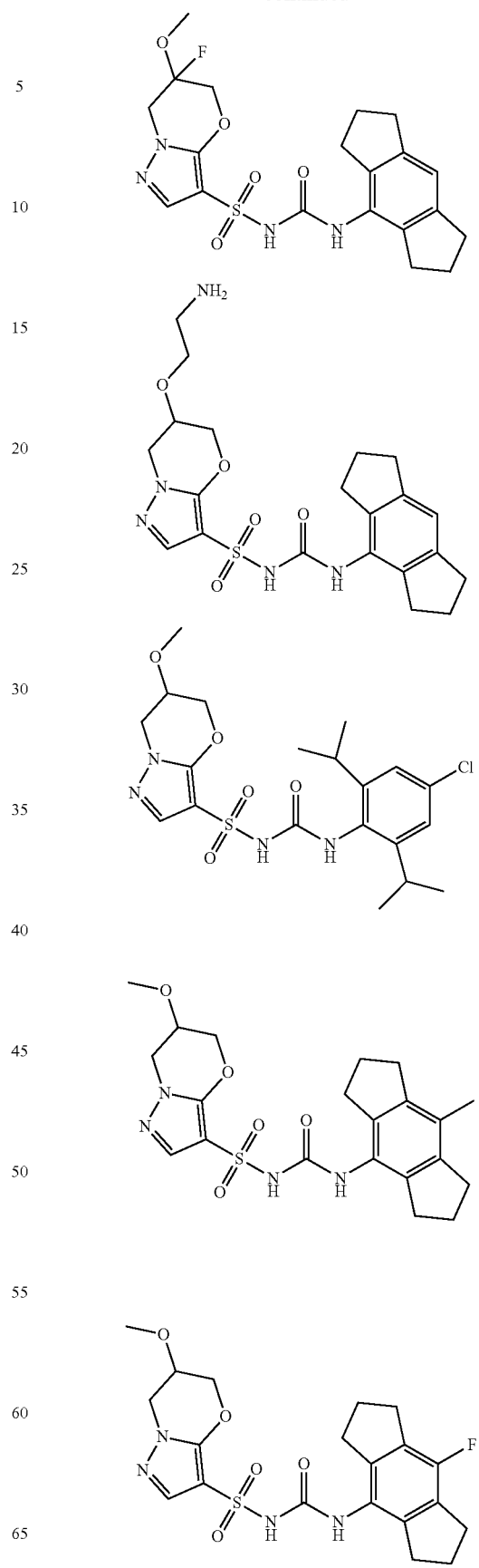

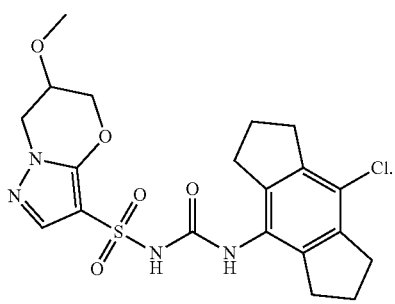
In certain embodiments, the present disclosure provides for the following compounds, and pharmaceutically acceptable salts, prodrugs, solvates, hydrates, isomers, and tautomers thereof:
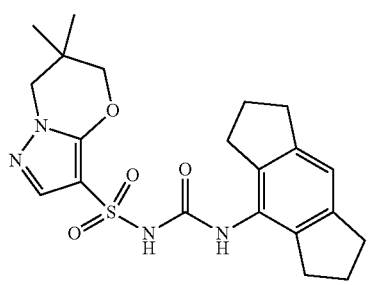
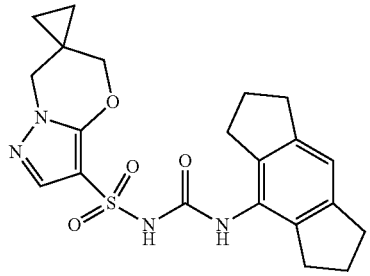
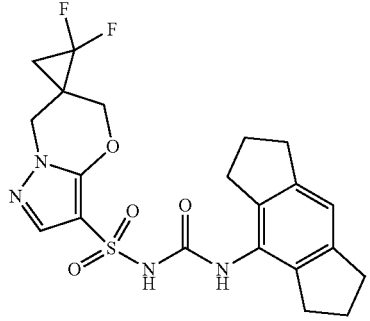
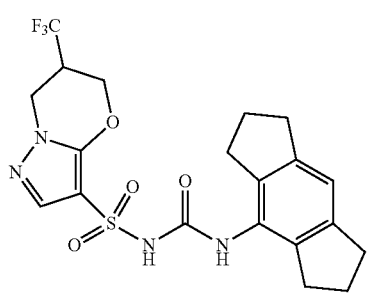
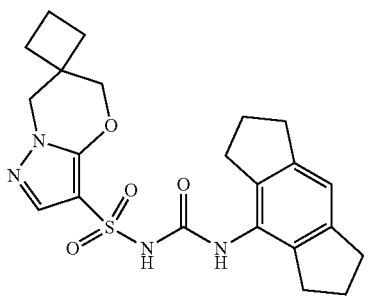
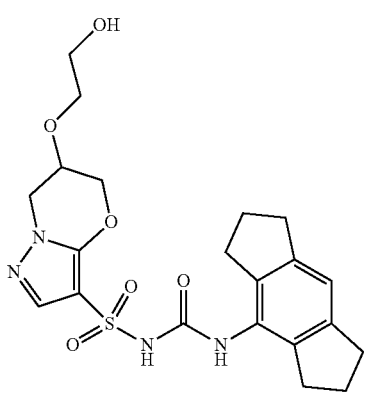
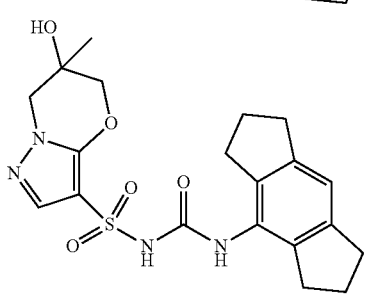
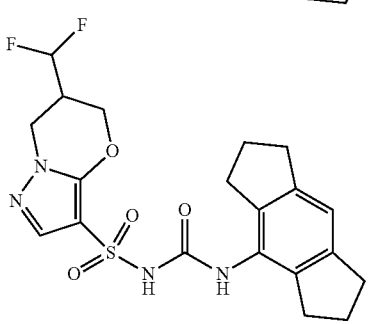
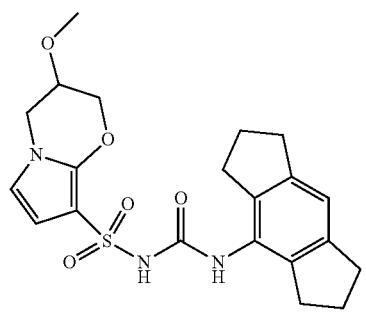

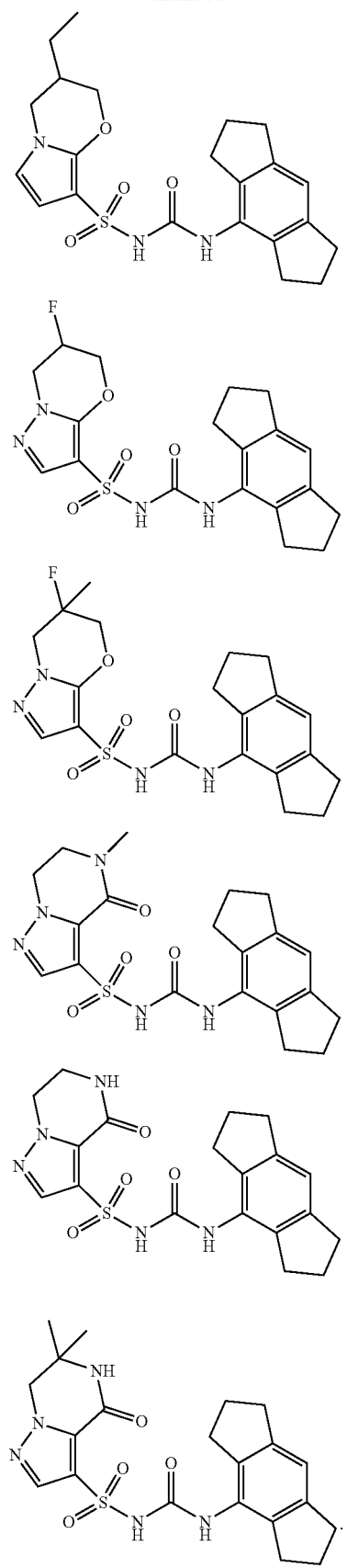
In certain embodiments, the present disclosure provides for the following compounds, and pharmaceutically acceptable salts, prodrugs, solvates, hydrates, isomers, and tautomers thereof
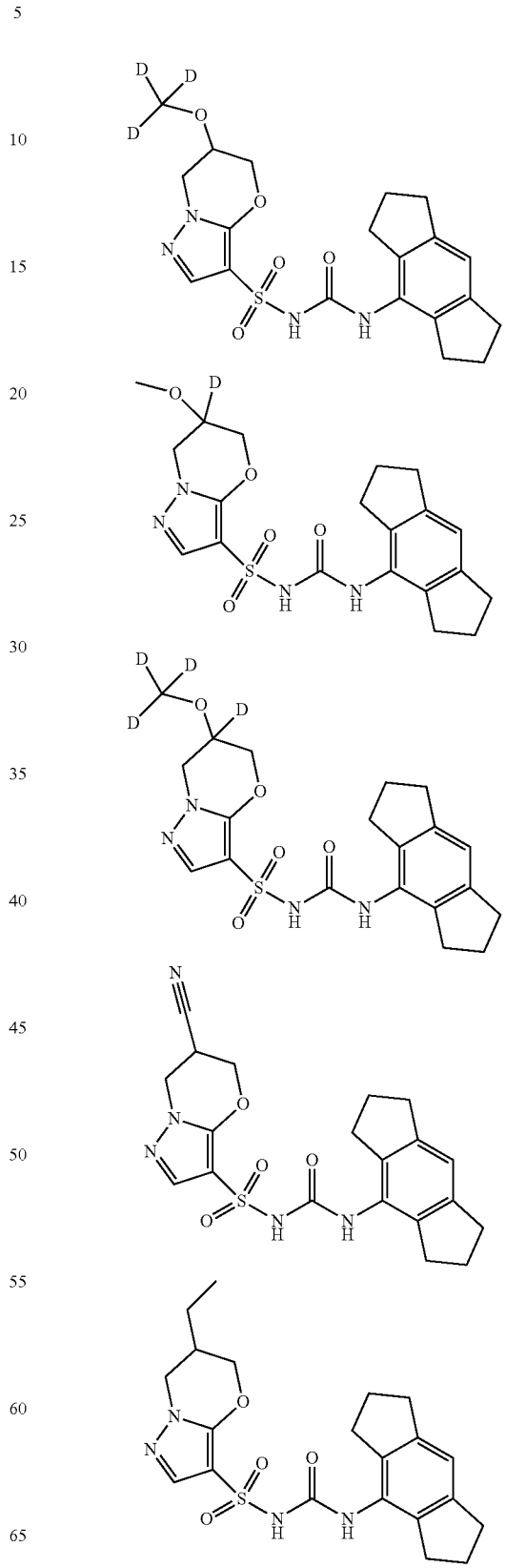

-continued
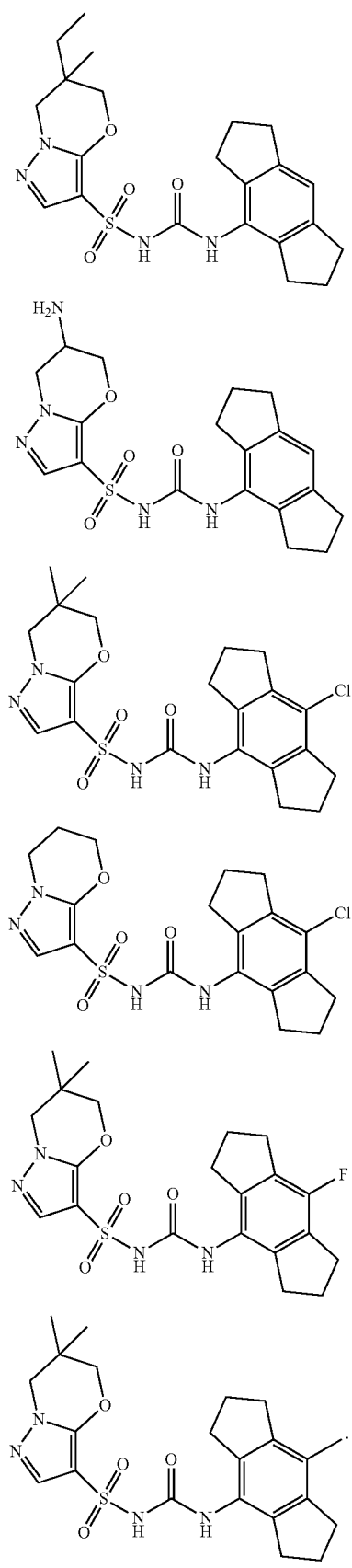
In certain embodiments, the present disclosure provides for the following compounds, and pharmaceutically acceptable salts, prodrugs, solvates, hydrates, isomers, and tautomers thereof:
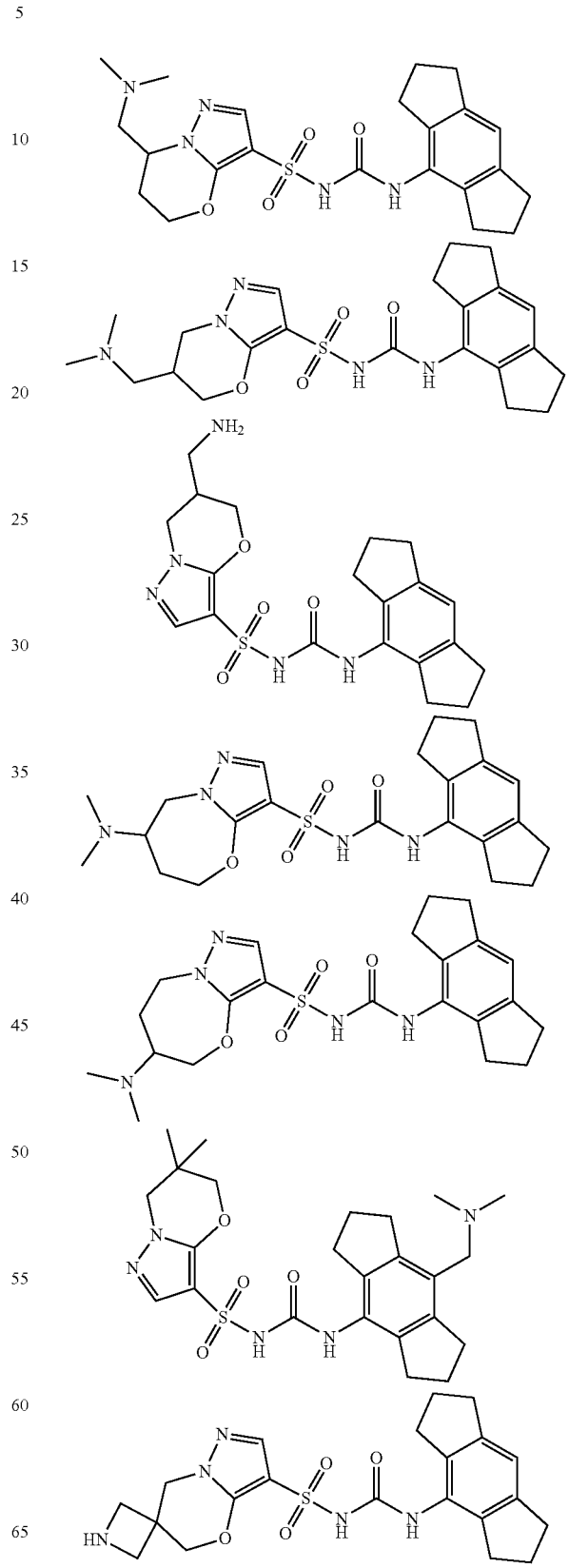

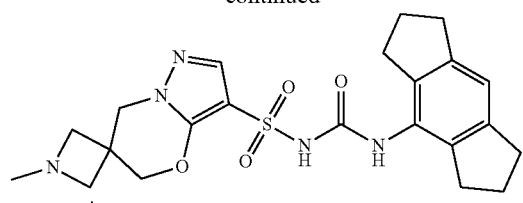
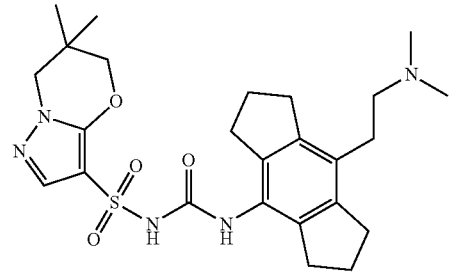
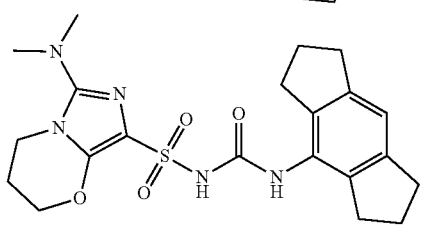
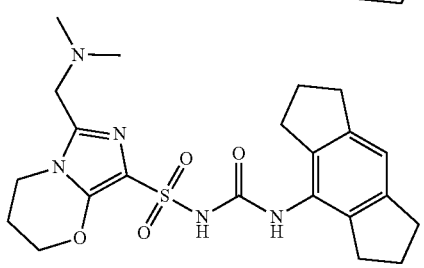
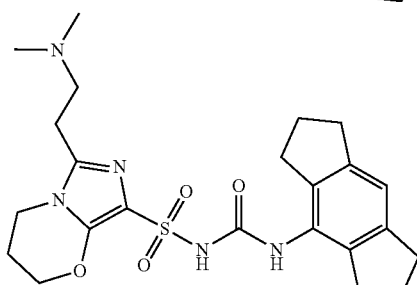
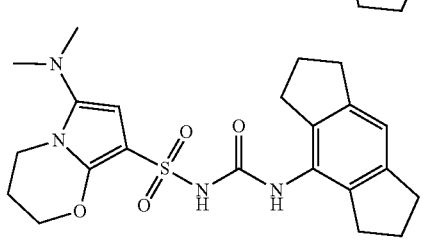
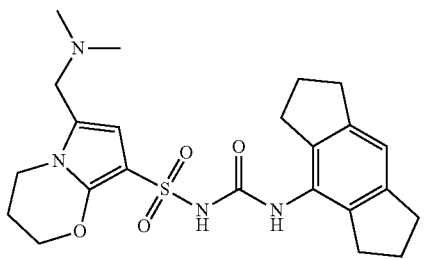
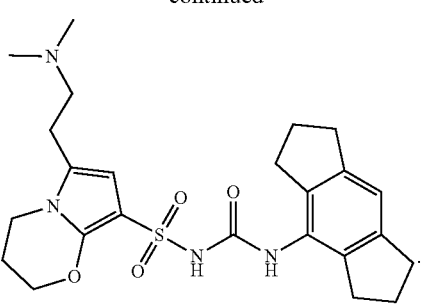
In certain embodiments, the present disclosure provides for the following compounds, and pharmaceutically acceptable salts, prodrugs, solvates, hydrates, isomers, and tautomers thereof:
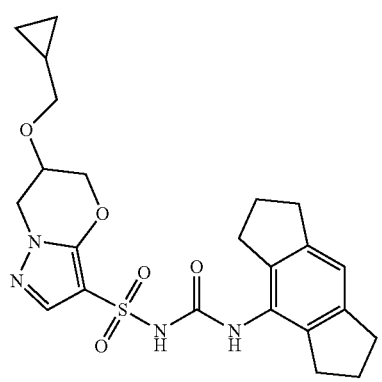
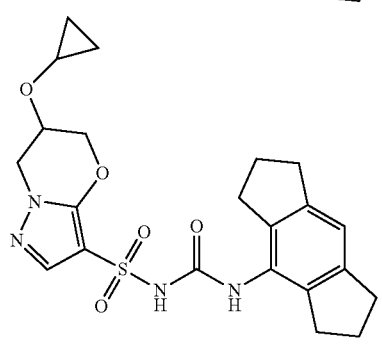
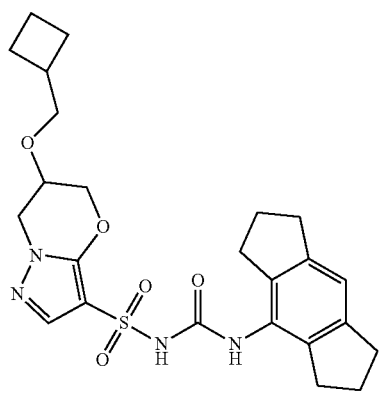

143
-continued
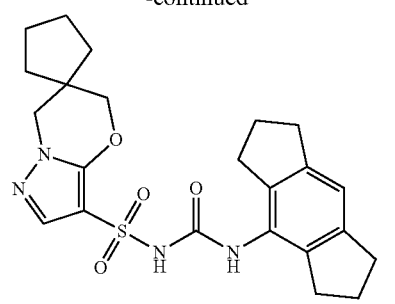
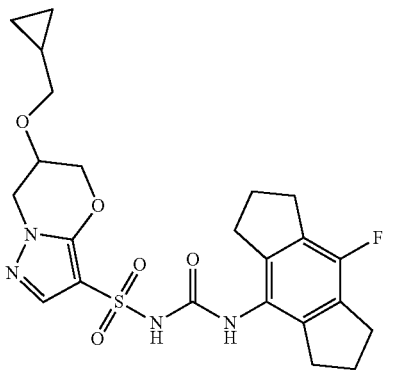
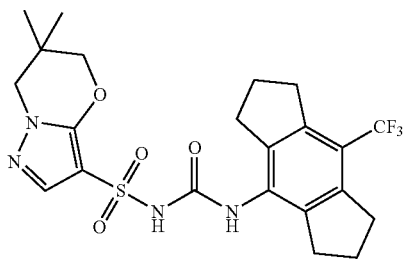
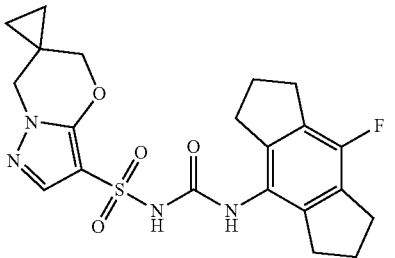
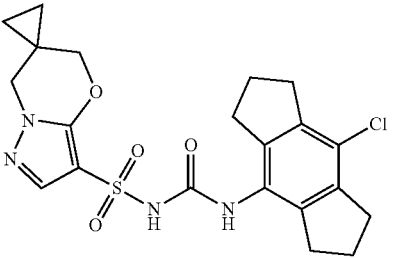
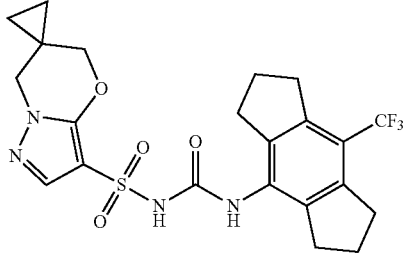
144
-continued
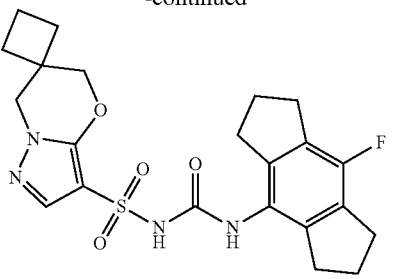
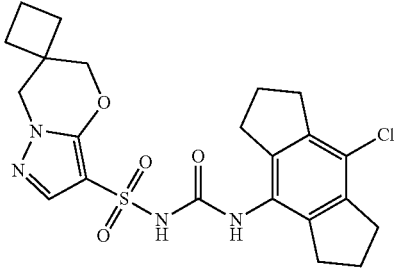
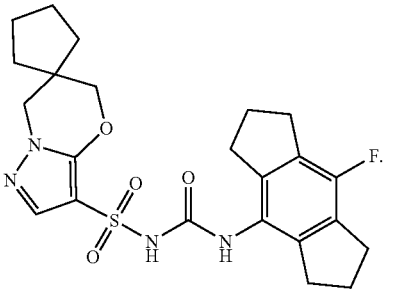 [SMILES: O=C(Nc1c2c(c(F)c3c1CCC3)CCC2)NS(=O)(=O)c1cnn2c1OCC1(CCCC1)C2]
In certain embodiments, the present disclosure provides for the following compounds, and pharmaceutically acceptable salts, prodrugs, solvates, hydrates, isomers, and tautomers thereof:
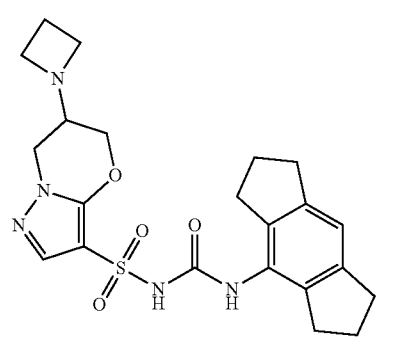
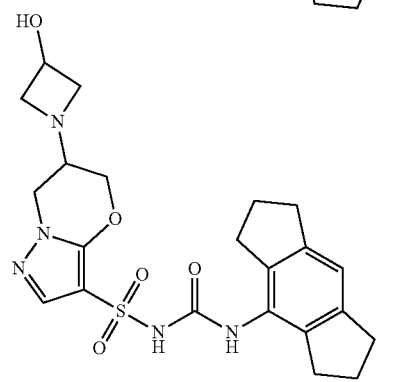

145
-continued
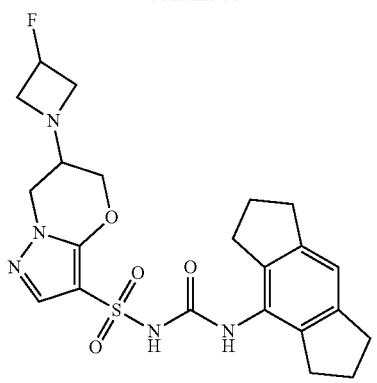
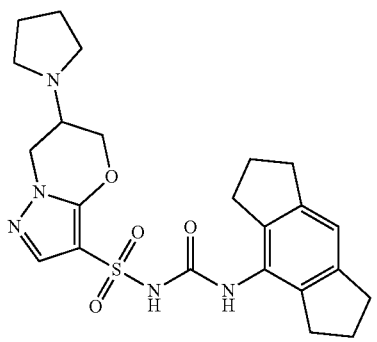
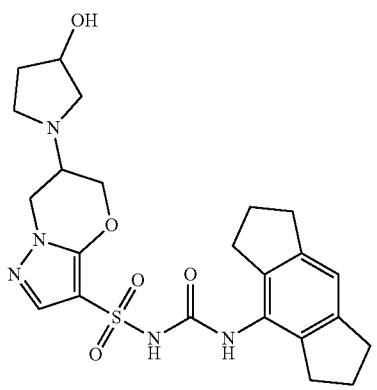
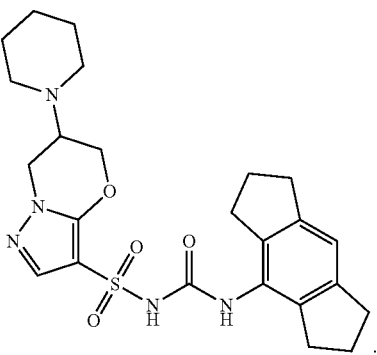 [SMILES: O=C(Nc1c2c(cc3c1CCC3)CCC2)NS(=O)(=O)c1cnn2c1OCC(N1CCCCC1)C2]
146
In certain embodiments, the present disclosure provides for the following compounds, and pharmaceutically acceptable salts, prodrugs, solvates, hydrates, isomers, and tautomers thereof:
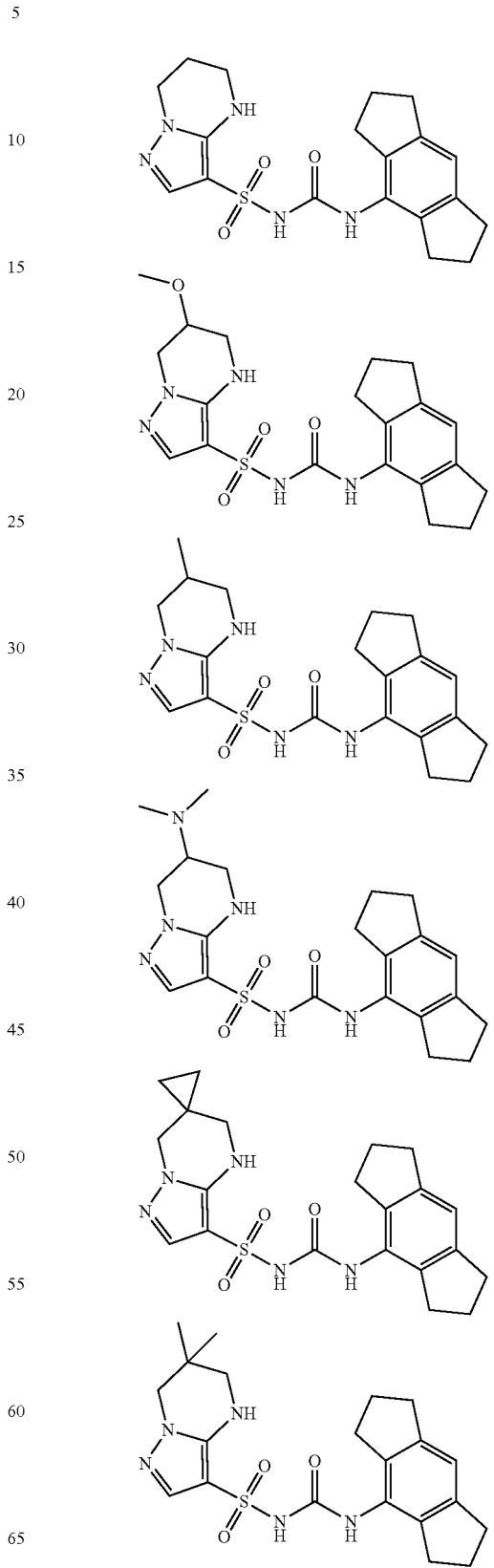

-continued

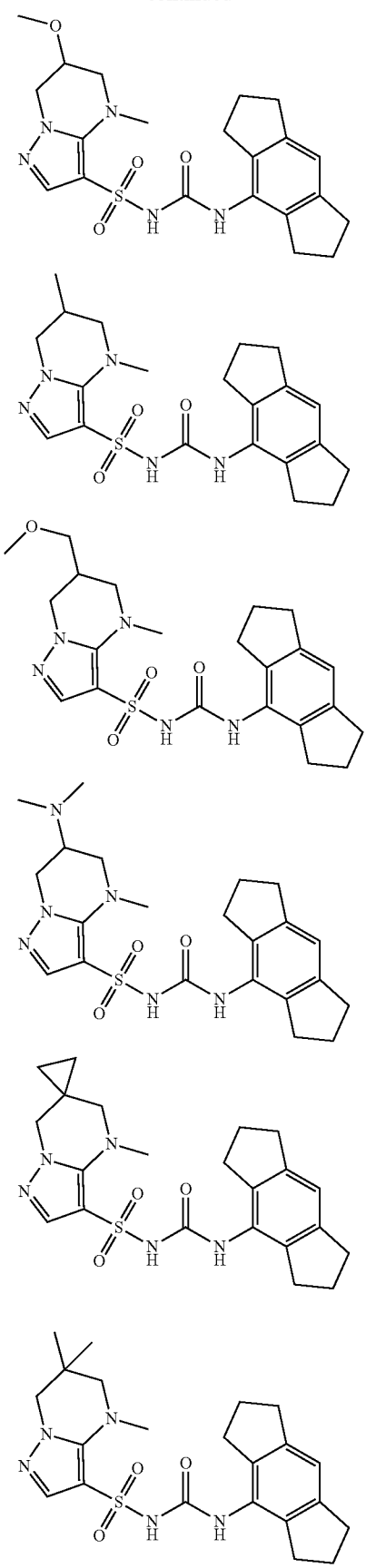 [SMILES: COC1CN(C)c2c(S(=O)(=O)NC(=O)Nc3c4c(cc5c3CCC5)CCC4)cnn2C1 ; CC1CN(C)c2c(S(=O)(=O)NC(=O)Nc3c4c(cc5c3CCC5)CCC4)cnn2C1 ; COCC1CN(C)c2c(S(=O)(=O)NC(=O)Nc3c4c(cc5c3CCC5)CCC4)cnn2C1 ; CN1CC(N(C)C)Cn2ncc(S(=O)(=O)NC(=O)Nc3c4c(cc5c3CCC5)CCC4)c21 ; CN1CC2(CC2)Cn2ncc(S(=O)(=O)NC(=O)Nc3c4c(cc5c3CCC5)CCC4)c21 ; CN1CC(C)(C)Cn2ncc(S(=O)(=O)NC(=O)Nc3c4c(cc5c3CCC5)CCC4)c21]

-continued

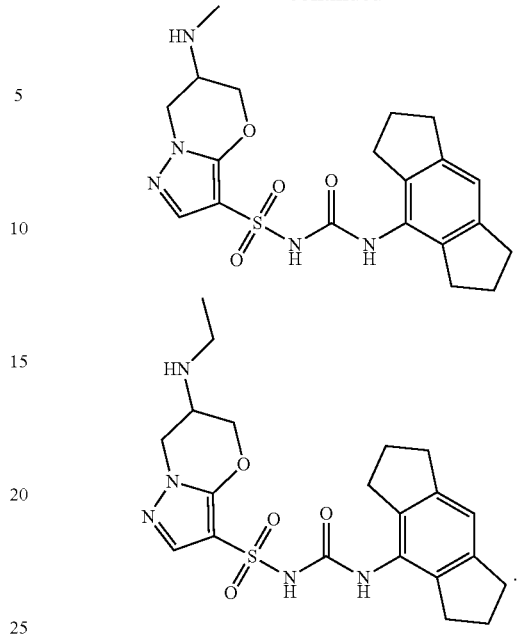

Unless otherwise stated, structures depicted herein are also meant to include compounds which differ only in the presence of one or more isotopically enriched atoms. For example, compounds having the present structure except for the replacement of a hydrogen atom by deuterium or tritium, or the replacement of a carbon atom by $^{13}C$ or $^{14}C$, or the replacement of a nitrogen atom by $^{15}N$, or the replacement of an oxygen atom with $^{17}O$ or $^{18}O$ are within the scope of the present disclosure. Such isotopically labeled compounds are useful as research or diagnostic tools.

Methods of Treatment

The disclosed compounds (e.g., compounds of formula I, Ia, Ib, Ic, Id, Ie, If, Ig, and Ih), and their pharmaceutically acceptable salts have activity as pharmaceuticals, as discussed herein.

The present disclosure provides a method of treatment or prevention of a disease, disorder or condition including the step of administering an effective amount of a compound of the present disclosure, and pharmaceutically acceptable salts, prodrugs, solvates, hydrates, isomers, and tautomers thereof to thereby treat or prevent the disease, disorder or condition in a subject in need thereof.

The present disclosure provides a compound of the present disclosure, and pharmaceutically acceptable salts, prodrugs, solvates, hydrates, isomers, and tautomers thereof, or the pharmaceutical composition of the present disclosure for use in the treatment or prevention of a disease, disorder or condition in a subject in need thereof.

The present disclosure provides for use of a compound of the present disclosure, and pharmaceutically acceptable salts, prodrugs, solvates, hydrates, isomers, and tautomers thereof, for the treatment or prevention of a disease, disorder or condition in a subject in need thereof.

The present disclosure provides for use of a compound of the present disclosure, and pharmaceutically acceptable salts, prodrugs, solvates, hydrates, isomers, and tautomers thereof, in the manufacture of a medicament for the treatment or prevention of a disease, disorder or condition.

In certain embodiments, the disease, disorder or condition is one which is responsive to inhibition of activation of an inflammasome. In one particular embodiment, the disease, disorder or condition is one which is responsive to inhibition of activation of the NLRP3 inflammasome.

According to this embodiment, the compound of the present disclosure, or pharmaceutically effective salt, solvate or prodrug thereof is a specific inhibitor of NLRP3.

In a further embodiment, the disease, disorder or condition is responsive to modulation of one or more of IL-6, IL-1β, IL-17, IL-18, IL-1α, IL-37, IL-22, IL-33, and Th17 cells. In certain embodiments, the disease, disorder or condition is responsive to modulation of one or more of IL-1β and IL-18.

In one embodiment, the modulation is inhibition of one or more of IL-6, IL-1β, IL-17, IL-18, IL-1α, IL-37, IL-22, and IL-33. In one embodiment, the modulation is inhibition of one or more of IL-1β and IL-18.

In one embodiment, the modulation of Th17 cells is by inhibition of production and/or secretion of IL-17.

In general embodiments, the disease, disorder or condition is a disease, disorder or condition of the immune system, the cardiovascular system, the endocrine system, the gastrointestinal tract, the renal system, the respiratory system, the central nervous system, is a cancer or other malignancy and/or is caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is Type I diabetes which is an autoimmune disease and a disease of the endocrine system.

In one embodiment, the disease, disorder or condition is of the immune system. In particular embodiments, the disease, disorder or condition is an inflammatory disease, disorder or condition or an autoimmune disease, disorder or condition.

In one embodiment, the disease, disorder or condition is of the liver.

In one embodiment, the disease, disorder or condition is of the lung.

In one embodiment, the disease, disorder or condition is of the skin.

In one embodiment, the disease, disorder or condition is of the cardiovascular system.

In one embodiment, the disease, disorder or condition is a cancer, tumor or other malignancy. As used herein, cancers tumors and malignancies, refer to diseases, disorders or conditions, or to cells or tissues associated with the diseases, disorders or conditions, characterized by aberrant or abnormal cell proliferation, differentiation and/or migration often accompanied by an aberrant or abnormal molecular phenotype that includes one or more genetic mutations or other genetic changes associated with oncogenesis, expression of tumor markers, loss of tumor suppressor expression or activity and/or aberrant or abnormal cell surface marker expression. In general embodiments, cancers, tumors and malignancies may include sarcomas, lymphomas, leukemias, solid tumors, blastomas, gliomas, carcinomas, melanomas and metastatic cancers, although without limitation thereto. A more comprehensive listing of cancers tumors and malignancies may be found at the National Cancer Institutes website http://www.cancer.gov/cancertopics/types/alphalist, which is hereby incorporated by reference in its entirety.

In one embodiment, the disease, disorder or condition is of the renal system.

In one embodiment, the disease, disorder or condition is of the gastro-intestinal tract.

In one embodiment, the disease, disorder or condition is of the respiratory system.

In a further embodiment, the disease, disorder or condition is of the endocrine system.

In one embodiment, the disease, disorder or condition is of the central nervous system (CNS).

In one embodiment, the disease, disorder or condition is caused by, or is associated with, a pathogen. The pathogen may be a virus, a bacterium, a protist, a worm or a fungus or any other organism capable of infecting a mammal, although without limitation thereto.

Non-limiting examples of viruses include influenza virus, cytomegalovirus, Epstein Barr Virus, human immunodeficiency virus (HIV), alphavirus such as Chikungunya and Ross River virus, flaviviruses such as Dengue virus, Zika virus and papillomavirus, although without limitation thereto.

Non-limiting examples of pathogenic bacteria include *Staphylococcus aureus, Helicobacter pylori, Bacillus anthracis, Bordatella pertussis, Corynebacterium diptheriae, Clostridium tetani, Clostridium botulinum, Streptococcus pneumoniae, Streptococcus pyogenes, Listeria monocytogenes, Hemophilus influenzae, Pasteureiia multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* and *Yersinia pestis*, although without limitation thereto.

Non-limiting examples of protists include *Plasmodium, Babesia, Giardia, Entamoeba, Leishmania* and *Trypanosomes*, although without limitation thereto.

Non-limiting examples of worms include helminths inclusive of schistisimes, roundworms, tapeworms and flukes, although without limitation thereto.

Non-limiting examples of fungi include *Candida* and *Aspergillus* species, although without limitation thereto.

In particular embodiments, the disease, disorder or condition is selected from the group consisting of constitutive inflammation including the cryopyrin-associated periodic syndromes (CAPS): Muckle-Wells syndrome (MWS), familial cold autoinflammatory syndrome (FCAS) and neonatal-onset multisystem inflammatory disease (NOMID); including autoinflammatory diseases: familial Mediterranean fever (FMF), TNF receptor associated periodic syndrome (TRAPS), mevalonate kinase deficiency (MKD), hyperimmunoglobulinemia D and periodic fever syndrome (H IDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, and developmental delay (SIFD); Sweet s syndrome, chronic nonbacterial osteomyelitis (CNO), chronic recurrent multifocal osteomyelitis (CRMO) and synovitis, acne, pustulosis, hyperostosis, osteitis syndrome (SAPHO); autoimmune diseases including multiple sclerosis (MS), type-1 diabetes, psoriasis, rheumatoid arthritis, Behcet's disease, Sjogren's syndrome and Schnitzler syndrome; respiratory diseases including idiopathic pulmonary fibrosis (IPF), chronic obstructive pulmonary disorder (COPD), steroid-resistant asthma, asbestosis, silicosis and cystic fibrosis; central nervous system diseases including Parkinson's disease, Alzheimer's disease, motor neuron disease, Huntington's disease, cerebral malaria and brain injury from pneumococcal meningitis; metabolic diseases including Type 2 diabetes, atherosclerosis, obesity, gout, pseudo-gout; ocular diseases including those of the ocular epithelium, age-related macular degeneration (AMD), corneal infection, uveitis and dry eye; kidney disease including chronic kidney disease, oxalate nephropathy and diabetic nephropathy; liver disease including non-alcoholic steatohepatitis and alcoholic liver disease; inflammatory reactions in skin including contact hypersensitivity and sunburn; inflammatory reactions in the joints including osteoarthritis, systemic juvenile idiopathic arthritis, adult-onset Still's disease, relapsing polychondritis; viral infections including alpha virus (Chikungunya, Ross River) and flavivirus (Dengue and Zika Virus), flu, HIV; hidradenitis suppurativa (HS) and other cyst-causing skin diseases; cancers including lung cancer metastasis, pancreatic cancers, gastric cancers, myelodisplastic syndrome, leukemia; polymyositis; stroke; myocardial infarction; Graft versus Host Disease; hypertension; colitis; helminth infection; bacterial infection; abdominal aortic aneurism; wound healing; depression, psychological stress; pericarditis including Dressler's syndrome, ischaemia reperfusion injury and any disease where an individual has been determined to carry a germline or somatic non-silent mutation in NLRP3.

In one non-limiting example of those described, the disease, disorder or condition being treated is NASH. NLRP3 inflammasome activation is central to inflammatory recruitment in NASH, and inhibition of NLRP3 may both prevent and reverse liver fibrosis. Compounds of the present disclosure, by interrupting the function of NLRP3 inflammasomes in liver tissue, can cause histological reductions in liver inflammation, decreased recruitment of macrophages and neutrophils, and suppression of NF-κB activation. Inhibition of the NLRP3 can reduce hepatic expression of pro-IL-1β and normalized hepatic and circulating IL-1β, IL-6 and MCP-1 levels thereby assisting in treatment of the disease.

In a further non-limiting example of those described, the disease, disorder or condition being treated is severe steroid resistant (SSR) asthma. Respiratory infections induce an NLRP3 inflammasome/caspase-1/IL-1β signaling axis in the lungs that promotes SSR asthma. The NLRP3 inflammasome recruits, and activates, pro-caspase-1 to induce IL-1β responses. NLRP3 inflammasome-induced IL-β responses are therefore important in the control of infections, however, excessive activation results in aberrant inflammation and has been associated with the pathogenesis of SSR asthma and COPD. The administration of compounds of the present disclosure that target specific disease processes, are more therapeutically attractive than non-specifically inhibiting inflammatory responses with steroids or IL-1β. Targeting the NLRP3 inflammasome/caspase-1/IL-1β signaling axis with the compounds of the present disclosure may therefore be useful in the treatment of SSR asthma and other steroid-resistant inflammatory conditions.

In one further non-limiting example of those described, the disease, disorder or condition being treated is Parkinson's disease. Parkinson's is the most common neurodegenerative movement disorder and is characterized by a selective loss of dopaminergic neurons, accompanied by the accumulation of mis-folded a-synuclein (Syn) into Lewy bodies that are pathological hallmarks of the disease. Chronic microglial neuroinflammation is evident early in the disease, and has been proposed to drive pathology.

A central role for microglial NLRP3 is postulated in Parkinson's progression. The NLRP3 inflammasome is activated by fibrillar Syn via a Syk kinase dependent mechanism, and also occurs in the absence of Syn pathology at the early stages of dopaminergic degeneration, and drives neuronal loss. The compounds of the present disclosure may block NLRP3 inflammasome activation by fibrillar Syn or mitochondrial dysfunction and thereby confer effective neuroprotection of the nigrostriatal dopaminergic system and assist with treatment of Parkinson's.

In certain embodiments, the method treats or prevents a disease or disorder, including, but not limited to, a bacterial infection, a viral infection, a fungal infection, inflammatory bowel disease, celiac disease, colitis, intestinal hyperplasia, cancer, metabolic syndrome, obesity, rheumatoid arthritis, liver disease, liver fibrosis, hepatic steatosis, fatty liver disease, non-alcoholic fatty liver disease (NAFLD), and non-alcoholic steatohepatitis (NASH).

In certain embodiments, the disease, disorder or condition is selected from the group consisting of NASH (nonalcoholic steatohepatitis); CAPS (Cryopyrin Associated Periodic Syndromes); IPF (Idiopathic pulmonary fibrosis); MI (R/I) (myocardial infarction and reperfusion injury); Gout; I/O (immuno-oncology); Asthma; IBD (inflammatory bowel disease); Renal fibrosis; adult onset Still's disease; systemic juvenile idiopathic arthritis; tumour necrosis factor receptor-associated periodic syndrome (TRAPS); colchicine-resistant familial Mediterranean fever (FMF); hyper IgD syndrome (HIDS)/Mevalonate Kinase Deficiency (MKD); traumatic brain injury; Parkinson's Disease; moderate to severe inflammatory acne; acute non-anterior non-infectious uveitis (NIU); AD (Alzheimer's disease); COPD (Chronic Obstructive Pulmonary Disease); Sepsis; MS (multiple sclerosis); Behcet's disease; RA (rheumatoid arthritis); erosive osteoarthritis; T1D (Type 1 diabetes); T2D (Type 2 diabetes); Obesity; osteoporosis; cystic fibrosis; alcoholic liver disease; aging; HCC (hepatocellular carcinoma); depression; endometriosis; pyoderma gangrenosum ("PG"), a rare ulcerative skin disease; Lupus Nephritis; Epilepsy; ischemic stroke; deafness; sickle cell disease; SLE (Systemic Lupus Erythematosus); and Spinal cord injury.

For the above-mentioned therapeutic uses the dosage administered will, of course, vary with the compound employed, the mode of administration, the treatment desired and the disorder indicated. For example, the daily dosage of the compound of the present disclosure, if inhaled, may be in the range from about 0.05 micrograms per kilogram body weight (μg/kg) to about 100 micrograms per kilogram body weight (μg/kg). Alternatively, if the compound is administered orally, then the daily dosage of the compound of the present disclosure may be in the range from about 0.01 micrograms per kilogram body weight (μg/kg) to about 100 milligrams per kilogram body weight (mg/kg).

Pharmaceutical Compositions

The disclosed compounds (e.g., compounds of formula I, Ia, Ib, Ic, Id, Ie, If, Ig, and Ih), and pharmaceutically acceptable salts thereof may be used on their own but will generally be administered in the form of a pharmaceutical composition in which the disclosed compound/salt (e.g., compounds of formula I, Ia, Ib, Ic, Id, Ie, If, Ig, and Ih and salts thereof) (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988, which is hereby incorporated by reference in its entirety.

Depending on the mode of administration, the pharmaceutical composition will comprise from about 0.05 to about 99% w (percent by weight), more particularly from about 0.05 to about 80% w, still more particularly from about 0.10 to about 70% w, and even more particularly from about 0.10 to about 50% w, of active ingredient, all percentages by weight being based on total composition.

The present disclosure also provides a pharmaceutical composition comprising a disclosed compound (e.g., compound of formula I, Ia, Ib, Ic, Id, Ie, If, Ig, and Ih), or a pharmaceutically acceptable salt thereof as hereinbefore defined, in association with a pharmaceutically acceptable adjuvant, diluent or carrier.

The present disclosure further provides a process for the preparation of a pharmaceutical composition of the present disclosure which comprises mixing a disclosed compound (e.g., compound of formula I, Ia, Ib, Ic, Id, Ie, If, Ig, and Ih), or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the present disclosure (including pharmaceutically acceptable salts) may be administered by oral or nasal inhalation. For inhalation, the compound is desirably finely divided. The finely divided compound preferably has a mass median diameter of less than 10 micrometres (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the present disclosure may also be administered by means of a dry powder inhaler. The inhaler may be a single or a multi dose inhaler, and may be a breath actuated dry powder inhaler.

One possibility is to mix the finely divided compound of the present disclosure with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatin capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

Another possibility is to process the compound as an amorphous dispersion in a polymer matrix such as hydroxypropyl methylcellulose (HPMC) or hydroxypropyl methylcellulose acetate succinate (HPMCAS). As the name suggests, spray-dried dispersions (SDDs) are obtained by dissolving drug and polymer in an organic solvent, atomizing the resulting solution into droplets, and evaporation to dried solid particles. SDDs are usually amenable for use a variety of final oral dosage forms, including capsules and tablets.

For oral administration the compound of the present disclosure may be admixed with an adjuvant or a carrier, for example, lactose, saccharose, sorbitol, mannitol; a starch, for example, potato starch, corn starch or amylopectin; a cellulose derivative; a binder, for example, gelatin or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatin, talcum and titanium dioxide. Alternatively, the tablet may be coated with a suitable polymer dissolved in a readily volatile organic solvent.

For the preparation of soft gelatin capsules, the compound of the present disclosure may be admixed with, for example, a vegetable oil or polyethylene glycol. Hard gelatin capsules may contain granules of the compound using either the above-mentioned excipients for tablets. Also liquid or semi-solid formulations of the compound of the present disclosure may be filled into hard gelatin capsules.

Liquid preparations for oral application may be in the form of syrups or suspensions, for example, solutions containing the compound of the present disclosure, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

Combination Therapy

The compounds of the present disclosure (that is, compounds of formula I, Ia, Ib, Ic, Id, Ie, If, Ig, and Ih, and pharmaceutically acceptable salts thereof) may also be administered in conjunction with other compounds used for the treatment of the above conditions.

The present disclosure therefore further relates to combination therapies wherein a compound of the present disclosure or a pharmaceutical composition or formulation comprising a compound of the present disclosure is administered concurrently or sequentially or as a combined preparation with another therapeutic agent or agents, for the treatment of one or more of the conditions listed.

Methods of Synthesizing the Compounds

The compounds of the present disclosure may be made by a variety of methods, including standard chemistry. One suitable synthetic route is depicted in the Scheme provided below.

The compounds of the present disclosure (e.g., compound of formula I, Ia, Ib, Ic, Id, Ie, Lf, Ig, and Ih), or a pharmaceutically acceptable salt, enantiomer, hydrate, solvate, prodrug, isomer, or tautomer thereof, may be prepared by methods known in the art of organic synthesis as set forth in part by the following synthetic scheme. In the scheme described below, it is well understood that protecting groups for sensitive or reactive groups are employed where necessary in accordance with general principles or chemistry.

Protecting groups are manipulated according to standard methods of organic synthesis (T. W. Greene and P. G. M. Wuts, "Protective Groups in Organic Synthesis", Third edition, Wiley, New York 1999, which is hereby incorporated by reference in its entirety). These groups are removed at a convenient stage of the compound synthesis using methods that are readily apparent to those skilled in the art. The selection processes, as well as the reaction conditions and order of their execution, shall be consistent with the preparation of disclosed compounds (e.g., compounds of formula I, Ia, Ib, Ic, Id, Ie, If, Ig, and Ih).

Those skilled in the art will recognize if a stereocenter exists in the compounds of Formula (I). Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994), which is hereby incorporated by reference in its entirety.

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. Illustrative methods include but are not limited to those methods described below. Compounds of the present disclosure can be synthesized by following the steps outlined in Scheme 1. Starting materials are either commercially available or made by known procedures in the reported literature or as illustrated.

Formula I, Ia, Ib, Ic, Id, Ie, If, Ig, and Ih can be prepared according to the general procedures outlined in Scheme 1. In Method A, disclosed compounds (e.g., compounds of formula I, Ia, Ib, Ic, Id, Ie, If, Ig, and Ih) are readily accessible from reaction of sulfonyl isocyanate or isothiocyanate (compound A-1) and an amine (compound A-2). In certain embodiments, compound A-2 is treated with a base in an appropriate solvent. Then, compound A-1 is added to compound A-2. The reaction is performed in a suitable solvent (e.g., tetrahydrofuran or dichloromethane) at room temperature to reflux.

With continued reference to Scheme 1, in Method B, compounds of Formula (I) are readily accessible from reaction of an isocyanate or isothiocyanate (compound B-1) and a sulfonamide (compound B-2). In certain embodiments, compound B-2 is treated with a base in an appropriate solvent. Then, compound B-1 is added to compound B-2. The reaction is performed in a suitable solvent (e.g., tetrahydrofuran or dichloromethane) at room temperature to reflux.

Scheme 1

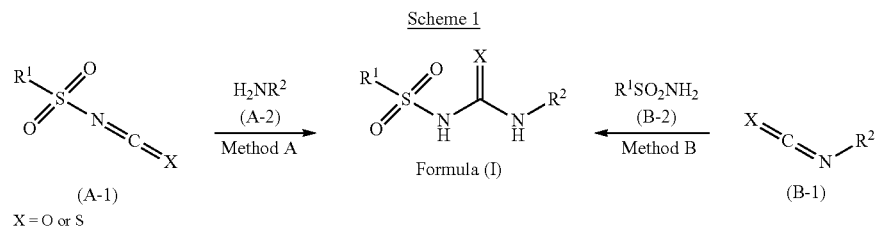

Example Embodiments

Embodiment I-1. A compound of formula I:

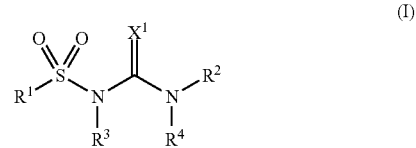

(I)

or a pharmaceutically acceptable salt, prodrug, solvate, hydrate, isomer, or tautomer thereof, wherein:

$X^1$ is O, S,

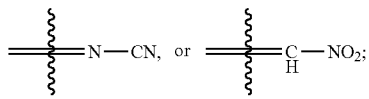

$R^1$ is selected from the group consisting of an optionally substituted $C_1$-$C_6$alkyl, optionally substituted $C_1$-$C_6$alkenyl, optionally substituted $C_1$-$C_6$alkynyl, —$(CH_2)_m$—O—$(CH_2)_m$—$CH_3$,

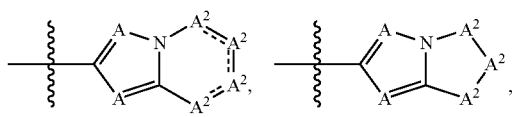

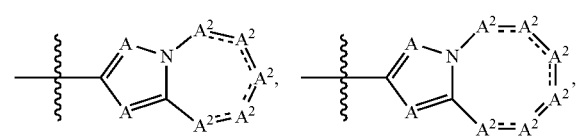

-continued

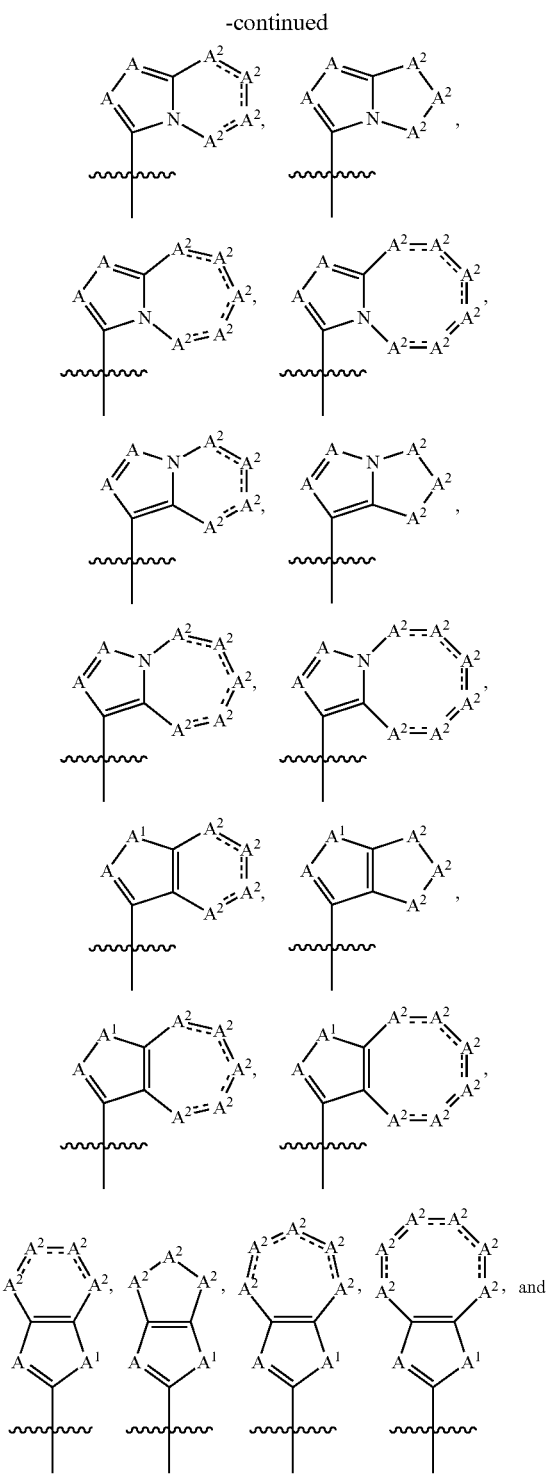

wherein ═ represents a single bond or a double bond provided that the ring comprising one or more $A^2$ is a non-aromatic ring;

each A is independently $CR^5$ or N;

$A^1$ is $NR^5$, O, S, or C(O);

each $A^2$ is independently $CR^5$, $C(R^5)_2$, N, $NR^5$, O, S, or $S(O)_2$;

$R^2$ is

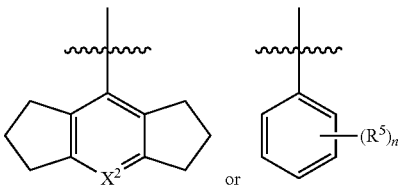

$X^2$ is N or $CR^5$;

$R^3$ and $R^4$ are H;

each $R^5$ is independently H, D, halogen, OH, CN, $-NO_2$, $-SR^6$, $-OR^6$, $-NHR^6$, $-NR^6R^7$, $-S(O)_2N(R^6)_2-$, $-S(O)_2R^6$, $-C(O)R^6$, $-C(O)OR^6$, $-C(O)NR^6R^7$, $-NR^6S(O)_2R^7$, $-S(O)R^6$, $-S(O)NR^6R^7$, $-NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2-C_3$-$C_8$cycloalkyl; or two $R^5$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; or two geminal $R^5$ can form an oxo group;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^5$, O, S, or $S(O)_2$.

Embodiment I-2. The compound of Embodiment I-1, wherein $X^1$ is O.

Embodiment I-3. The compound of Embodiment I-1, wherein $X^1$ is S.

Embodiment I-4. The compound of any one of Embodiments I-1 to I-3, wherein $R^2$ is

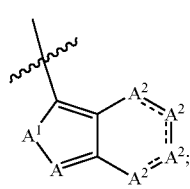

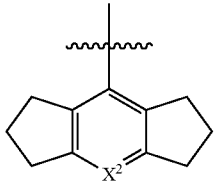

Embodiment I-5. The compound of any one of Embodiments I-1 to I-3, wherein R² is

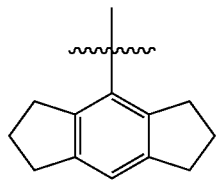

Embodiment I-6. The compound of any one of Embodiments I-1 to I-5, wherein the ═ are single bonds in the ring comprising A², thereby forming a saturated ring.

Embodiment I-7. The compound of any one of Embodiments I-1 to I-5, wherein R¹ is

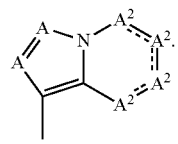

Embodiment I-8. The compound of Embodiment I-7, wherein each A² is independently CH₂ or O.

Embodiment I-9. The compound of any one of Embodiments I-1 to I-5, wherein R¹ is

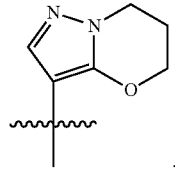

Embodiment I-10. The compound of any one of Embodiments I-1 to I-5, wherein R¹ is methyl.

Embodiment I-11. The compound of any one of Embodiments I-1 to I-9, wherein the compound is of formula:

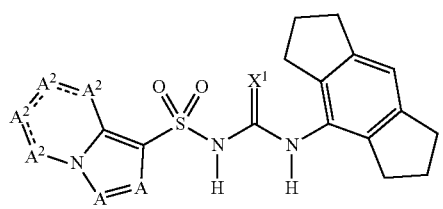

Embodiment I-12. The compound of Embodiment I-1, which is

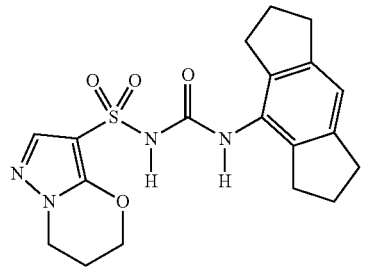

N-((1,2,3,5,6,7-hexahydro-s-indacen-4-yl)carbamoyl)-6,7-dihydro-5H-pyrazolo[5,1-b][1,3]oxazine-3-sulfonamide.

Embodiment I-13. The compound of Embodiment I-1, which is

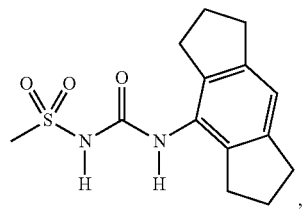 [SMILES: CS(=O)(=O)NC(=O)Nc1c2c(cc3c1CCC3)CCC2]

N-((1,2,3,5,6,7-hexahydro-s-indacen-4-yl)carbamoyl)methanesulfonamide.

Embodiment I-14. The compound of Embodiment I-1, which is selected from the group consisting of

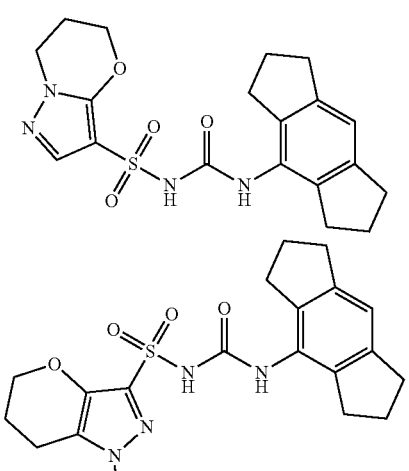

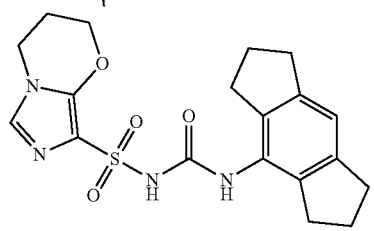

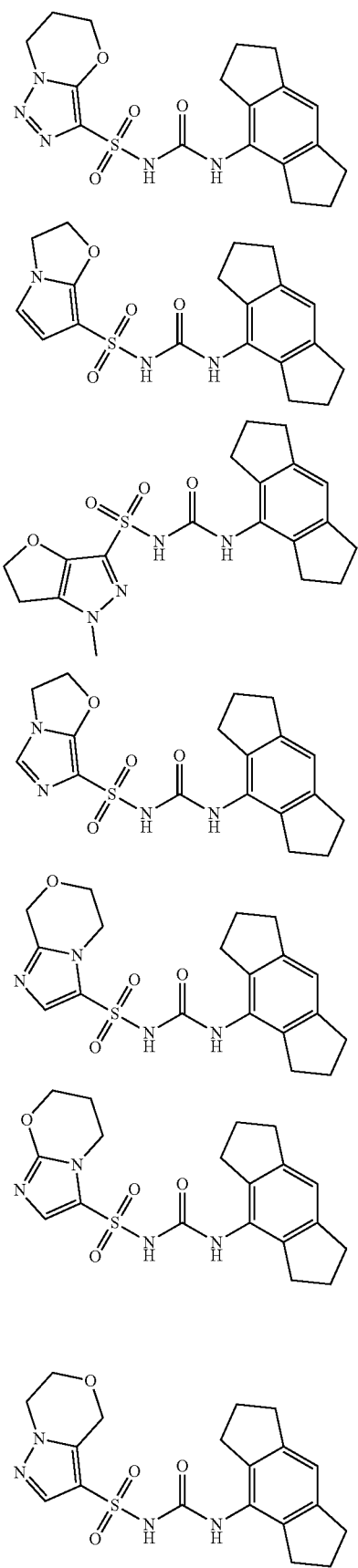
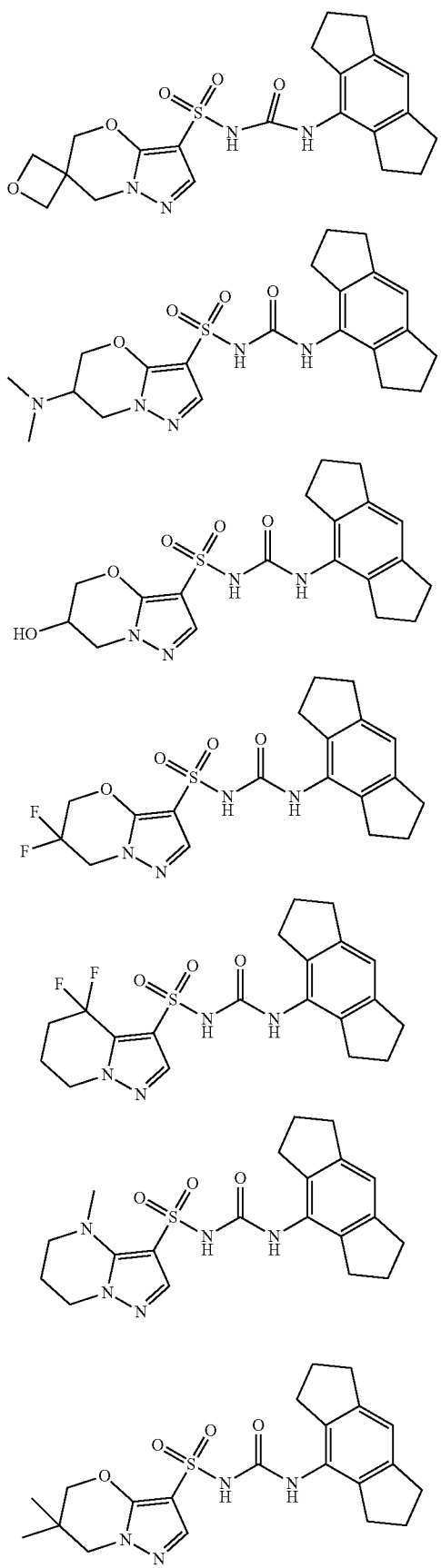

163 -continued
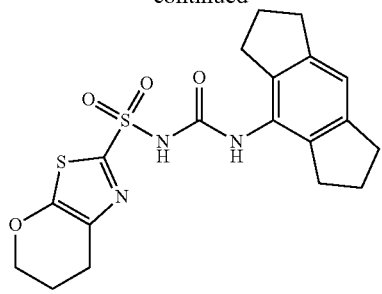
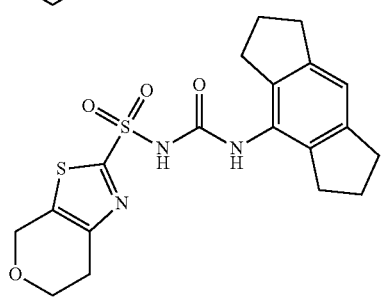
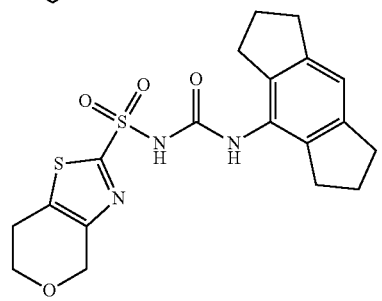
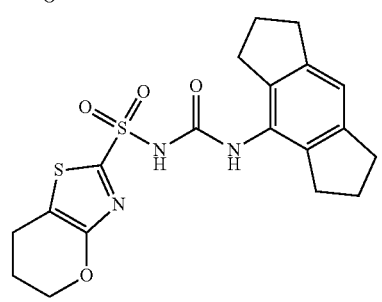
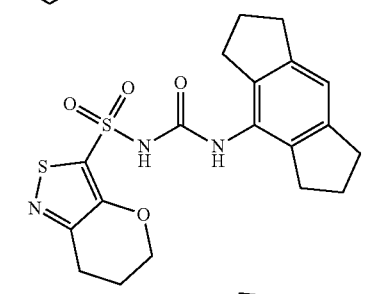
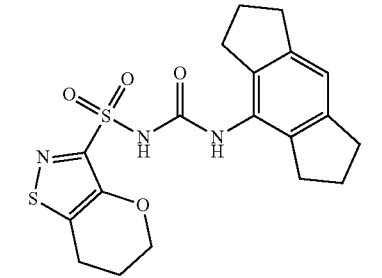
164 -continued
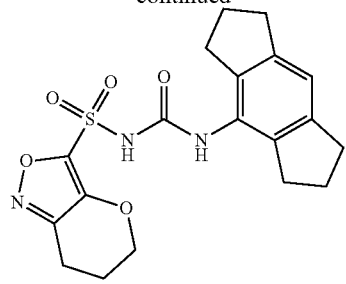
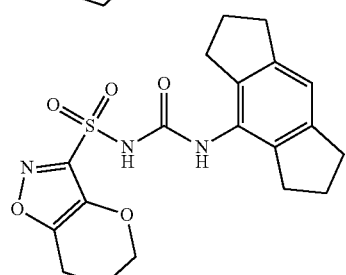
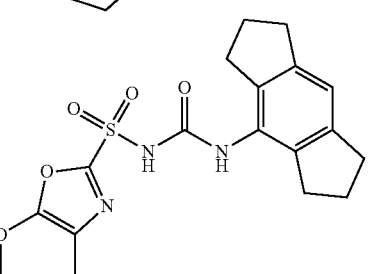
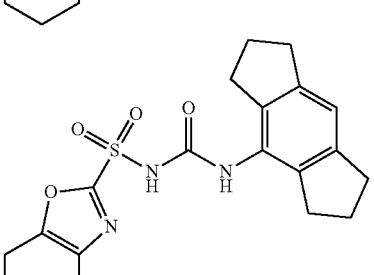
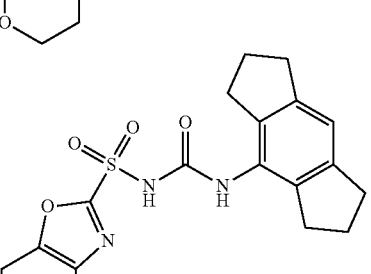
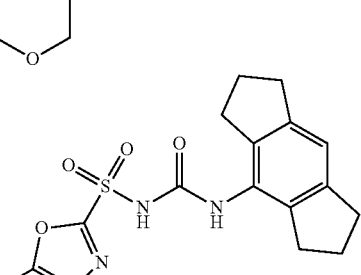

165
-continued
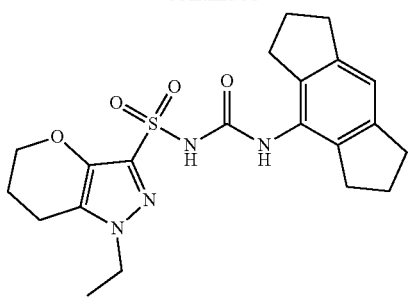
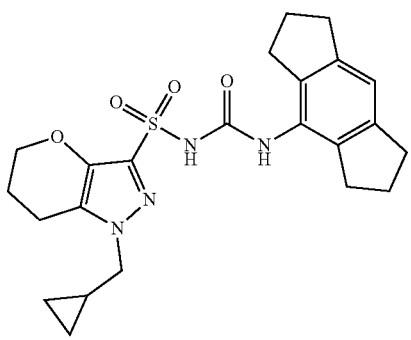
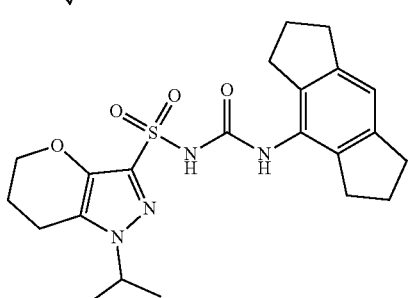
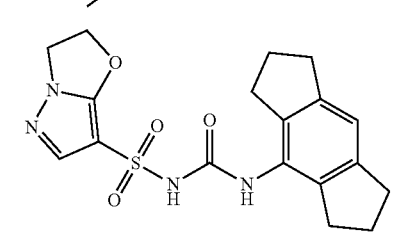
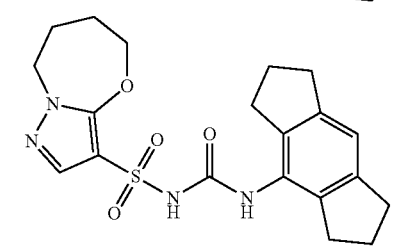
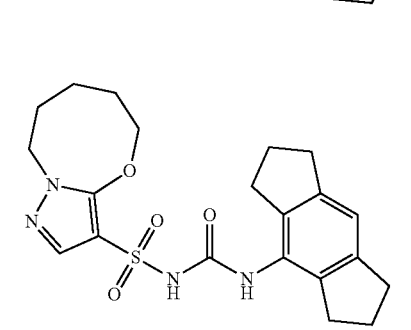
166
-continued
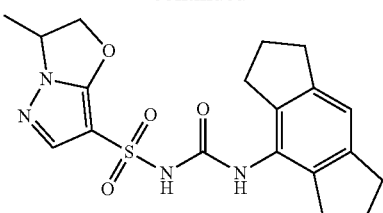
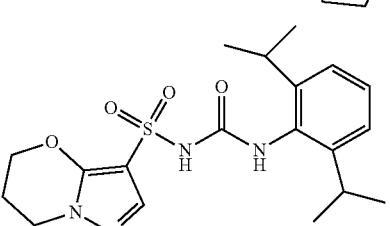
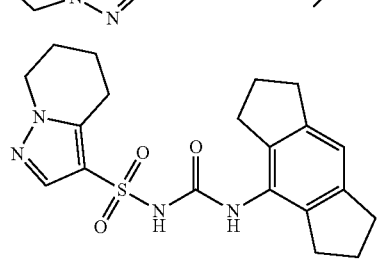
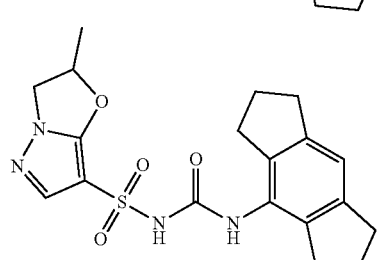
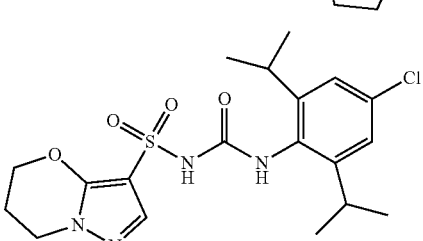
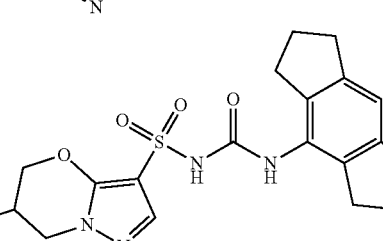
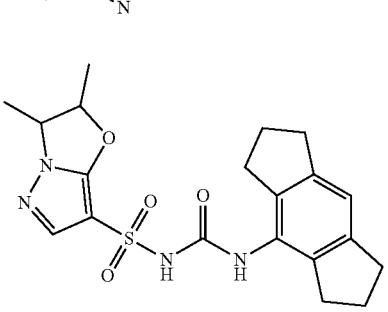

167
-continued
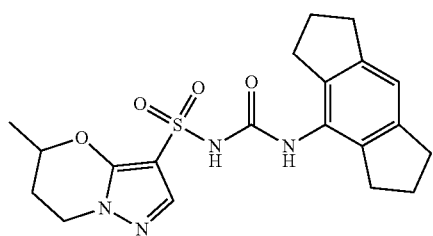
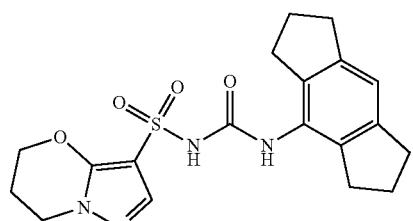
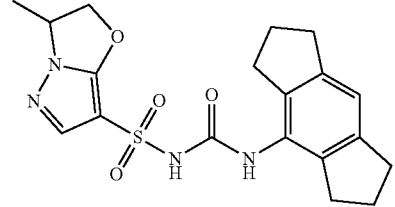
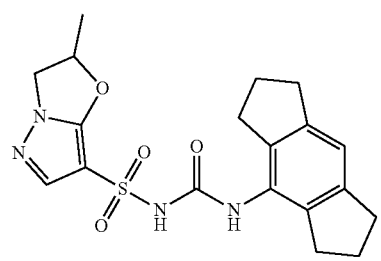
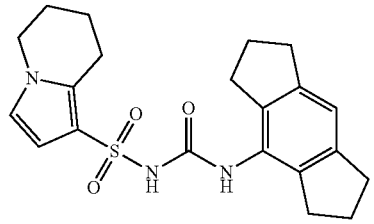
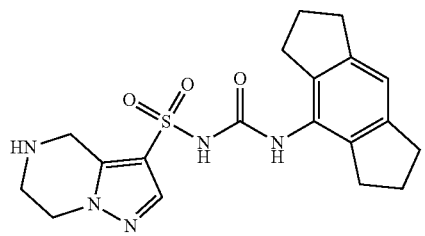
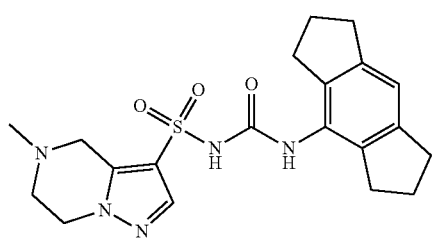
168
-continued
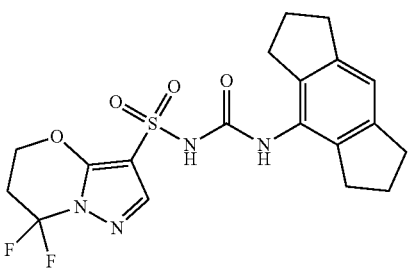
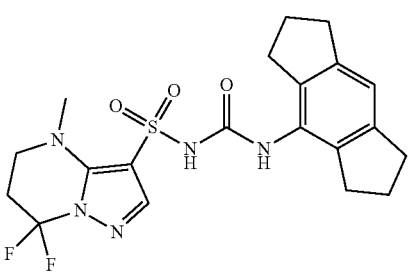
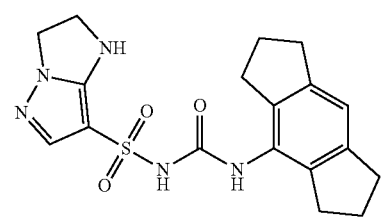
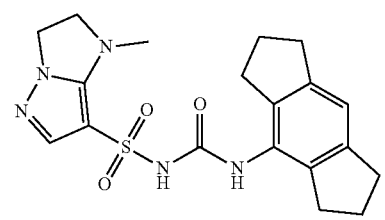
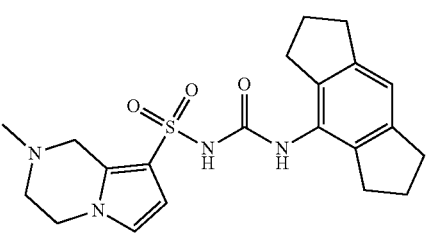
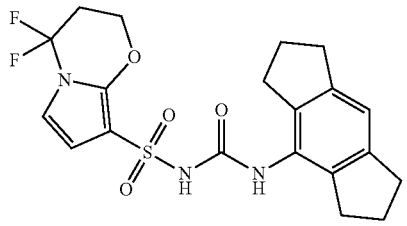
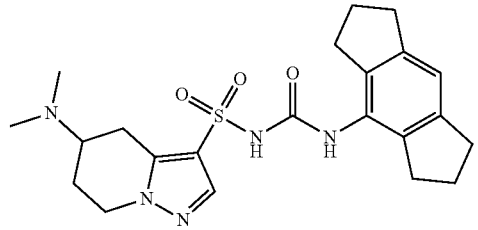

169
-continued
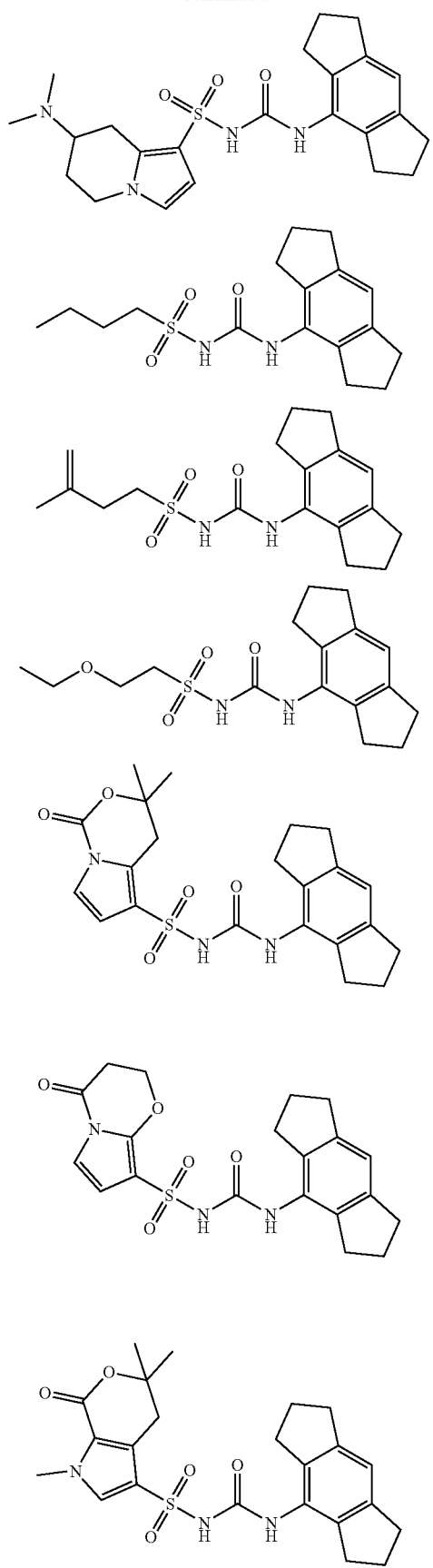
170
-continued
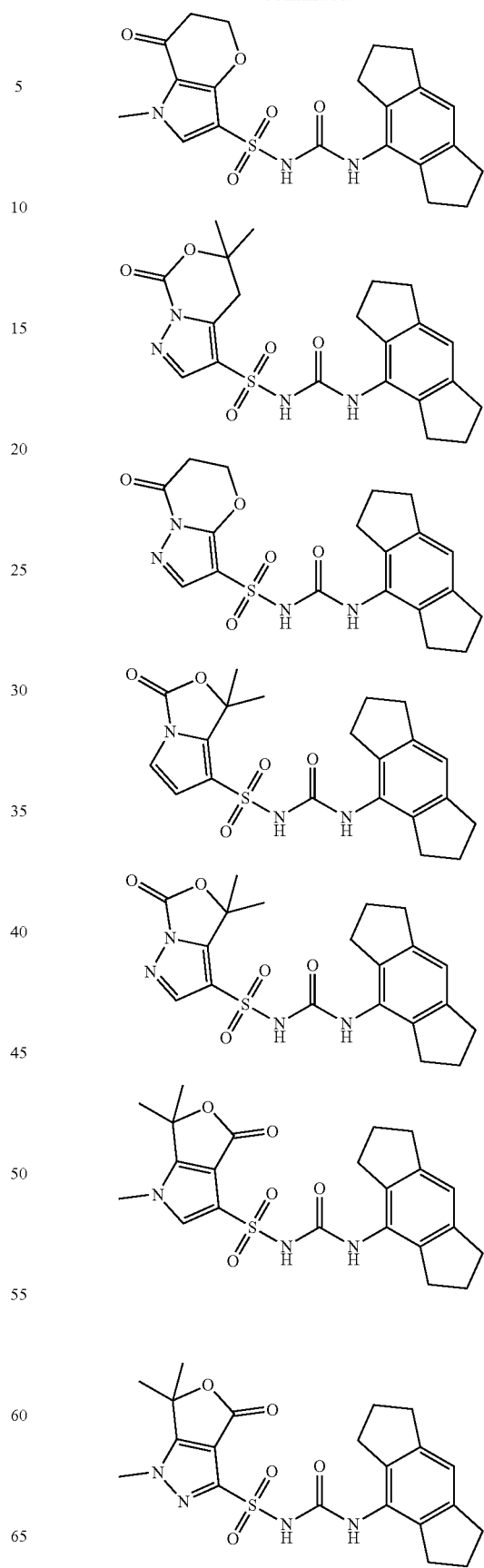

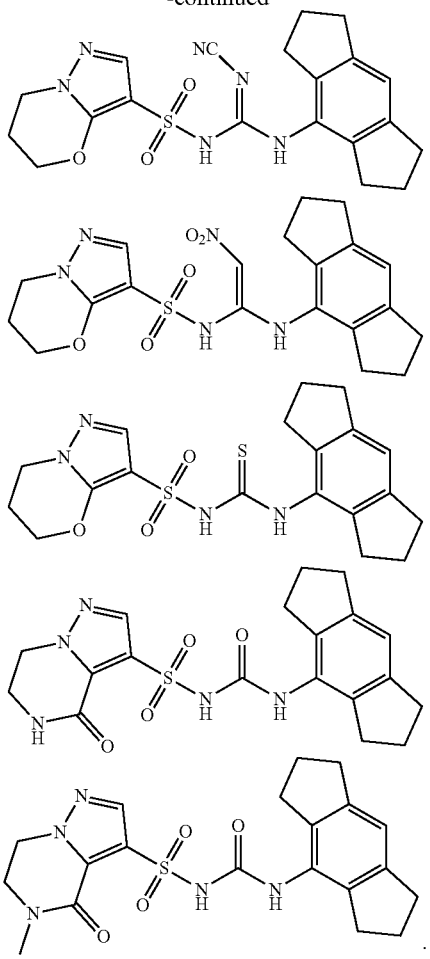

Embodiment I-15. A pharmaceutical composition comprising a compound of any one of Embodiments I-1 to I-14 and a pharmaceutically acceptable carrier.

Embodiment I-16. A method of treatment or prevention of a disease, disorder or condition including the step of administering an effective amount of a compound of any one of Embodiments I-1 to I-14, or a pharmaceutically acceptable salt, prodrug, solvate, hydrate, isomer, or tautomer thereof, to thereby treat or prevent the disease disorder or condition.

Embodiment I-17. The method of Embodiment I-16, wherein the disease, disorder or condition is responsive to inhibition of inflammasome.

Embodiment I-18. The method of Embodiment I-16 or I-17, wherein the disease, disorder or condition is one which is responsive to inhibition of activation of the NLRP3 inflammasome.

Embodiment I-19. The method of Embodiment I-16 or I-17, wherein the disease, disorder or condition is responsive to modulation of one or more of IL-6, IL-1β, IL-17, IL-18, IL-1α, IL-37, IL-22, IL-33 and Th17 cells.

Embodiment I-20. The method of any one of Embodiments I-16 to I-19, wherein the disease, disorder or condition is a disease, disorder or condition of the immune system.

Embodiment I-21. The method of any one of Embodiments I-16 to I-19, wherein the disease, disorder or condition is an inflammatory disease disorder or condition or an autoimmune disease disorder or condition.

Embodiment I-22. The method of any one of Embodiments I-16 to I-19, wherein the disease, disorder or condition is a disease, disorder or condition of the liver.

Embodiment I-23. The method of any one of Embodiments I-16 to I-19, wherein the disease, disorder or condition is a disease, disorder or condition of the lung.

Embodiment I-24. The method of any one of Embodiments I-16 to I-19, wherein the disease, disorder or condition is a disease, disorder or condition of the skin.

Embodiment I-25. The method of any one of Embodiments I-16 to I-19, wherein the disease, disorder or condition is a disease, disorder or condition of the cardiovascular system.

Embodiment I-26. The method of any one of Embodiments I-16 to I-19, wherein the disease, disorder or condition is a cancer, tumor or other malignancy.

Embodiment I-27. The method of any one of Embodiments I-16 to I-19, wherein the disease, disorder or condition is a disease, disorder or condition is of the renal system.

Embodiment I-28. The method of any one of Embodiments I-16 to I-19, wherein the disease, disorder or condition is a disease, disorder or condition is of the gastrointestinal tract.

Embodiment I-29. The method of any one of Embodiments I-16 to I-19, wherein the disease, disorder or condition is a disease, disorder or condition is of the respiratory system.

Embodiment I-30. The method of any one of Embodiments I-16 to I-19, wherein the disease, disorder or condition is a disease, disorder or condition is of the endocrine system.

Embodiment I-31. The method of any one of Embodiments I-16 to I-19, wherein the disease, disorder or condition is a disease, disorder or condition is of the central nervous system (CNS).

Embodiment I-32. The method of any one of Embodiments I-16 to I-19, wherein the disease, disorder or condition is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), corneal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

Embodiment I-33. The method of Embodiment I-15, wherein the disorder is selected from the group consisting of a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), and non-alcoholic steatohepatitis (NASH).

Embodiment I-34. The method of Embodiment I-33, wherein the disorder is non-alcoholic steatohepatitis (NASH).

Embodiment I-35. The method of any one of Embodiments I-16 to I-34, wherein the treatment or prevention of the disease, disorder or condition is performed on a mammal.

Embodiment I-36. The method of Embodiment I-35, wherein the mammal is a human subject.

Embodiment I-37. A method of modulating the activity of a biological target comprising the step of exposing the biological target to a compound of any one of Embodiments I-1 to I-14, or a pharmaceutically effective salt, solvate or prodrug thereof.

Embodiment I-38. The method of Embodiment I-37, wherein the biological target may be selected from the group consisting of the NLRP3 inflammasome, IL-6, IL-1β, IL-17, IL-18, IL-1α, IL-37, IL-22, IL-33 and Th17 cells.

Embodiment I-39. Use of a compound of any one of Embodiments I-1 to I-14 in the treatment of a disease, disorder or condition that is responsive to inhibition of inflammasome.

Embodiment I-40. A compound of any one of Embodiments I-1 to I-14 for use in the manufacture of a medicament for treating a disease, disorder or condition that is responsive to inhibition of inflammasome.

Embodiment II-1. A compound of formula Ia:

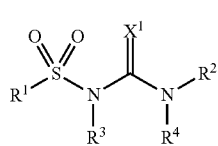

(Ia)

or a pharmaceutically acceptable salt, prodrug, solvate, hydrate, isomer, or tautomer thereof, wherein:

$X^1$ is O, S,

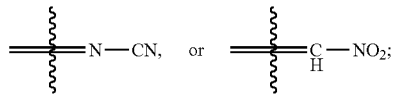

$R^1$ is selected from the group consisting of an optionally substituted $C_1$-$C_6$alkyl, optionally substituted $C_1$-$C_6$alkenyl, optionally substituted $C_1$-$C_6$alkynyl, —$(CH_2)_m$—O—$(CH_2)_m$—$CH_3$,

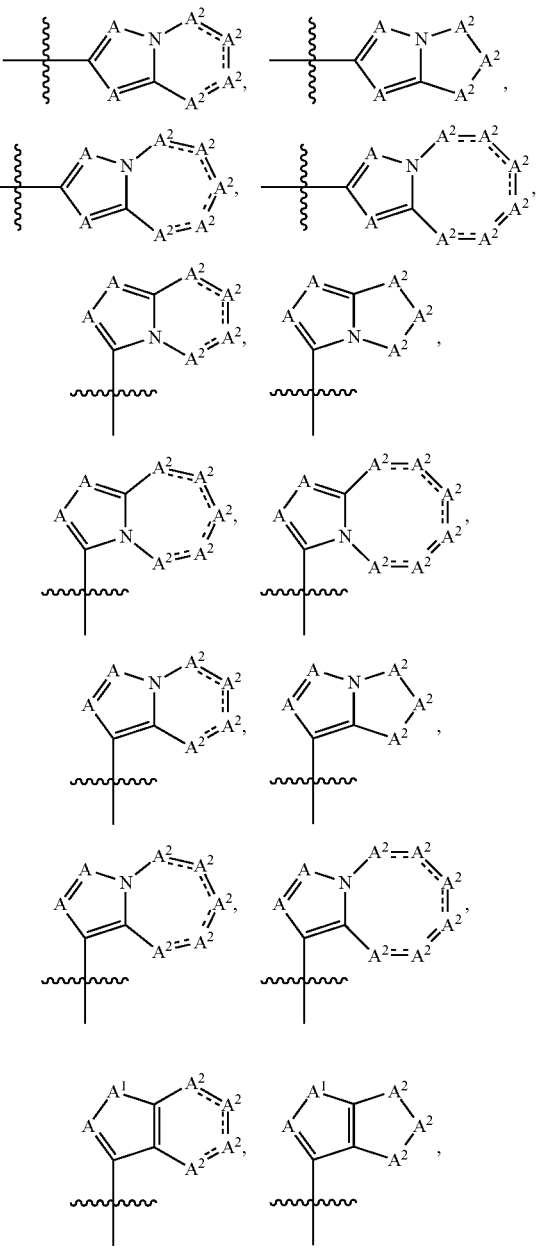

-continued

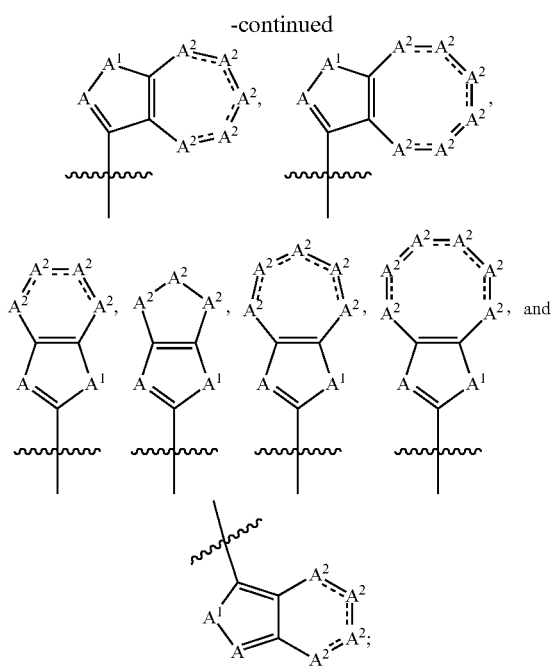

wherein ═ represents a single bond or a double bond provided that the ring comprising one or more A² is a non-aromatic ring;

each A is independently CR$^{5a}$ or N;

A¹ is NR$^{5a}$, O, S, or C(O);

each A² is independently CR$^{5a}$, C(R$^{5a}$)$_2$, N, NR$^{5a}$, O, S, or S(O)$_2$;

R² is

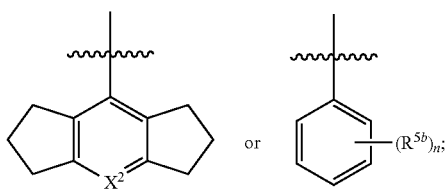

X² is N or CR$^{5b}$;

R³ and R⁴ are H;

each R$^{5a}$ is independently H, D, halogen, OH, CN, —NO$_2$, —SR⁶, —OR⁶, —NHR⁶, —NR⁶R⁷, —S(O)$_2$N(R⁶)$_2$—, —S(O)$_2$R⁶, —C(O)R⁶, —C(O)OR⁶, —C(O)NR⁶R⁷, —NR⁶S(O)$_2$R⁷, —S(O)R⁶, —S(O)NR⁶R⁷, —NR⁶S(O)R⁷, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; or two R$^{5a}$ together with the atoms to which they are attached can form C$_3$-C$_8$cycloalkyl, heterocyclyl, aryl, or heteroaryl; wherein the heterocyclyl and heteroaryl contain 1-3 heteroatoms selected from the group consisting of N, S, P and O; or two geminal R$^{5a}$ can form an oxo group;

each R$^{5b}$ is independently H, D, halogen, OH, CN, —NO$_2$, —SR⁶, —OR⁶, —NHR⁶, —NR⁶R⁷, —S(O)$_2$N(R⁶)$_2$—, —S(O)$_2$R⁶, —C(O)R⁶, —C(O)OR⁶, —C(O)NR⁶R⁷, —NR⁶S(O)$_2$R⁷, —S(O)R⁶, —S(O)NR⁶R⁷, —NR⁶S(O)R⁷, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; or two R$^{5b}$ together with the atoms to which they are attached can form C$_3$-C$_8$cycloalkyl, heterocyclyl, aryl, or heteroaryl; wherein the heterocyclyl and heteroaryl contain 1-3 heteroatoms selected from the group consisting of N, S, P and O;

R⁶ and R⁷ are independently, at each occurrence H, D, C$_1$-C$_8$alkyl, C$_2$-C$_8$alkenyl, C$_4$-C$_8$cycloalkenyl, C$_2$-C$_8$alkynyl, C$_3$-C$_8$cycloalkyl, heterocyclyl, aryl, or heteroaryl; wherein the heterocyclyl and heteroaryl contain 1-5 heteroatoms selected from the group consisting of N, S, P and O; or R⁶ and R⁷ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or A¹ is an imidazole, then at least one A² is N, NR$^{5a}$, O, S, or S(O)$_2$.

Embodiment II-2. A compound of formula Ib:

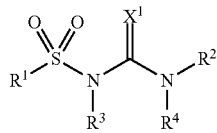

(Ib)

or a pharmaceutically acceptable salt, prodrug, solvate, hydrate, isomer, or tautomer thereof, wherein:

X¹ is O, S,

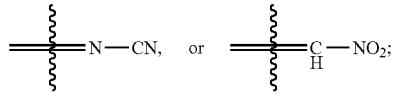

R¹ is selected from the group consisting of an optionally substituted C$_1$-C$_6$alkyl, optionally substituted C$_1$-C$_6$alkenyl, optionally substituted C$_1$-C$_6$alkynyl, —(CH$_2$)$_m$—O—(CH$_2$)$_m$—CH$_3$,

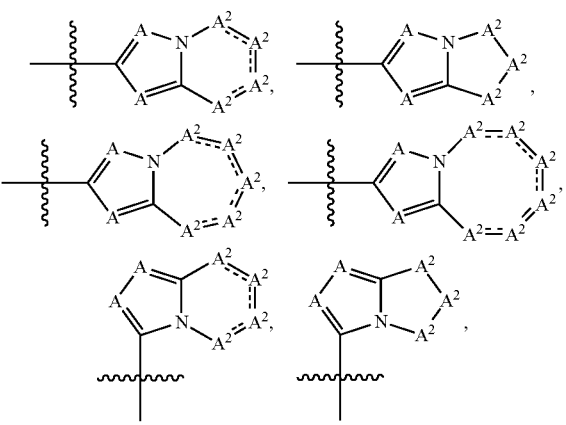

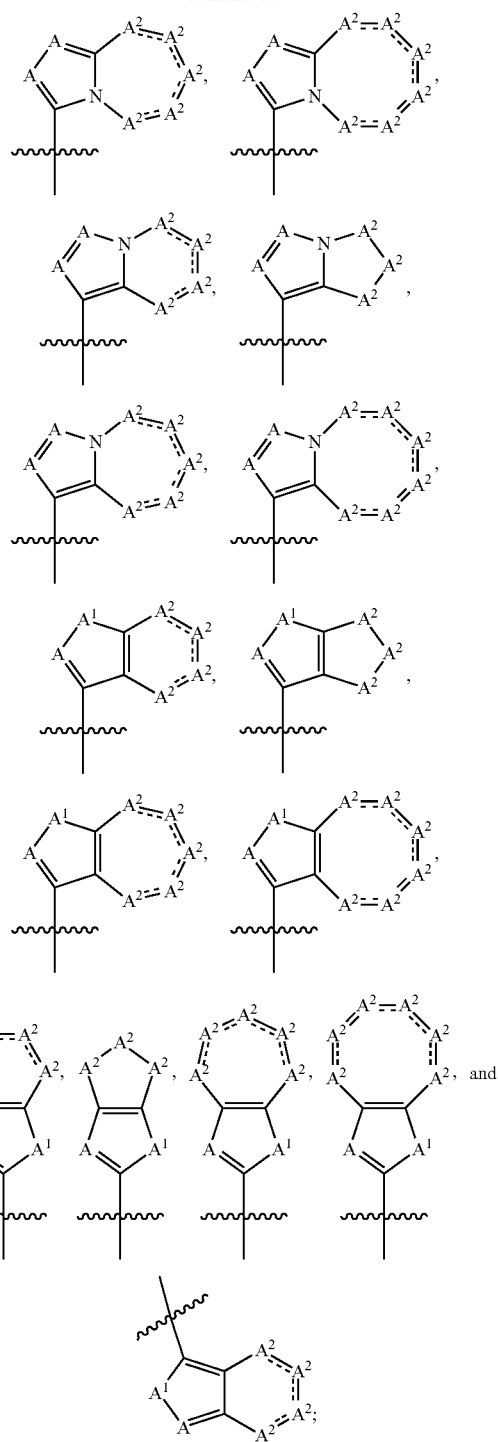

wherein ⚌ represents a single bond or a double bond provided that the ring comprising one or more $A^2$ is a non-aromatic ring;

each A is independently $CR^{5a}$ or N;

$A^1$ is $NR^{5a}$, O, S, or C(O);

each $A^2$ is independently $CR^{5a}$, $C(R^{5a})_2$, N, $NR^{5a}$, O, S, or $S(O)_2$;

$R^2$ is

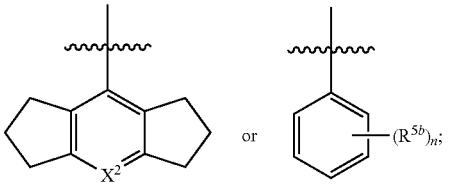

$X^2$ is N or $CR^{5b}$;

$R^3$ and $R^4$ are H;

each $R^{5a}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; wherein the $C_3$-$C_8$cycloalkyl, heterocyclyl, aryl, or heteroaryl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two geminal $R^{5a}$ can form an oxo group;

each $R^{5b}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, or $C_2$-$C_6$alkynyl; wherein the $C_1$-$C_6$alkyl, $C_2$-$C_6$alkenyl, $C_4$-$C_8$cycloalkenyl, and $C_2$-$C_6$alkynyl are optionally substituted with D, halogen, —$OR^6$, —$NH_2$, —NH($C_1$-$C_6$alkyl), or —N($C_1$-$C_6$alkyl)$_2$;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; wherein the $C_1$-$C_6$alkyl, $C_2$-$C_8$alkenyl, $C_4$-$C_8$cycloalkenyl, $C_2$-$C_6$alkynyl, $C_3$-$C_8$cycloalkyl, heterocyclyl, aryl, and heteroaryl are optionally substituted with D, halogen, $C_1$-$C_6$alkyl, —OH, —O—$C_1$-$C_6$alkyl, —$NH_2$, —NH($C_1$-$C_6$alkyl), or —N($C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^{5a}$, O, S, or $S(O)_2$.

Embodiment II-3. A compound of formula Ic:

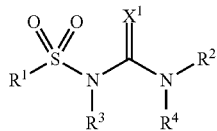
(Ic)

or a pharmaceutically acceptable salt, prodrug, solvate, hydrate, isomer, or tautomer thereof,
wherein:
$X^1$ is O, S,

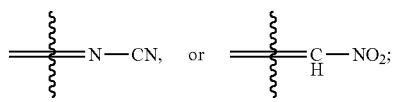

$R^1$ is selected from the group consisting of an optionally substituted $C_1$-$C_6$alkyl, optionally substituted $C_1$-$C_6$alkenyl, optionally substituted $C_1$-$C_6$alkynyl, —$(CH_2)_m$—O—$(CH_2)_m$—$CH_3$,

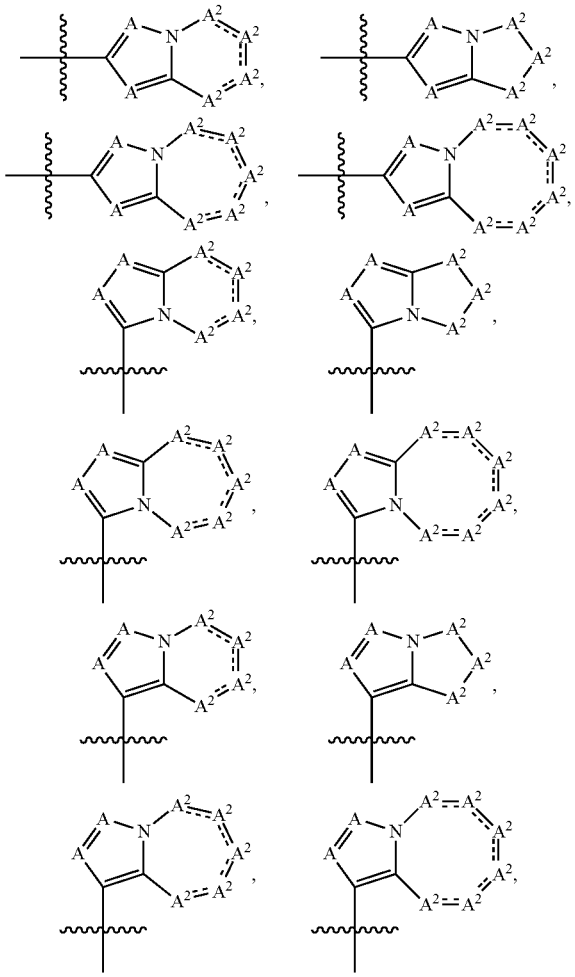

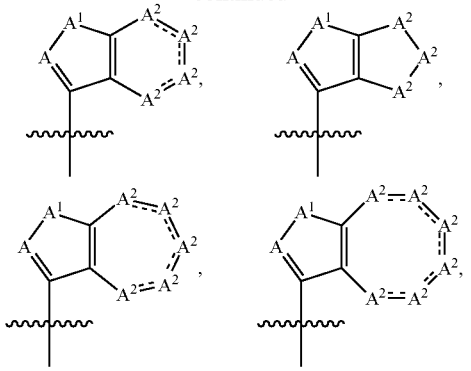

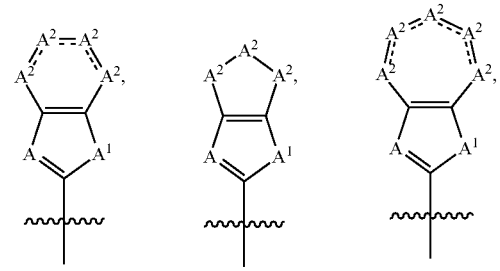

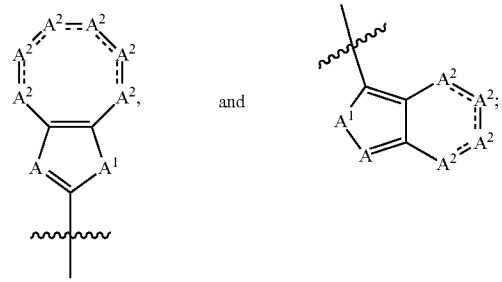

wherein ═ represents a single bond or a double bond provided that the ring comprising one or more $A^2$ is a non-aromatic ring;
each A is independently $CR^{5a}$ or N;
$A^1$ is $NR^{5a}$, O, S, or C(O);
each $A^2$ is independently $CR^{5a}$, $C(R^{5a})_2$, N, $NR^{5a}$, O, S, or $S(O)_2$; $R^2$ is

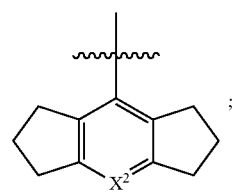

$X^2$ is N or $CR^{5b}$;
$R^3$ and $R^4$ are H;
each $R^{5a}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two $R^{5a}$ together with the atoms to which they are attached can form $C_3$-$C_8$cycloalkyl, heterocyclyl, aryl, or heteroaryl; wherein the heterocyclyl and heteroaryl contain 1-3 heteroatoms selected from the group consisting of N, S, P and O; wherein the $C_3$-$C_8$cycloalkyl, heterocyclyl, aryl, or heteroaryl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two geminal $R^{5a}$ can form an oxo group;

each $R^{5b}$ is independently H, D, halogen, OH, CN, —$NO_2$, —$SR^6$, —$OR^6$, —$NHR^6$, —$NR^6R^7$, —$S(O)_2N(R^6)_2$—, —$S(O)_2R^6$, —$C(O)R^6$, —$C(O)OR^6$, —$C(O)NR^6R^7$, —$NR^6S(O)_2R^7$, —$S(O)R^6$, —$S(O)NR^6R^7$, —$NR^6S(O)R^7$, $C_1$-$C_6$alkyl, $C_2$-$C_6$alkenyl, $C_4$-$C_8$cycloalkenyl, or $C_2$-$C_6$alkynyl; wherein the $C_1$-$C_6$alkyl, $C_2$-$C_6$alkenyl, $C_4$-$C_8$cycloalkenyl, and $C_2$-$C_6$alkynyl are optionally substituted with D, halogen, —$OR^6$, —$NH_2$, —NH($C_1$-$C_6$alkyl), or —N($C_1$-$C_6$alkyl)$_2$;

$R^6$ and $R^7$ are independently, at each occurrence H, D, $C_1$-$C_8$alkyl, $C_2$-$C_8$alkenyl, $C_4$-$C_8$cycloalkenyl, $C_2$-$C_8$alkynyl, $C_3$-$C_8$cycloalkyl, heterocyclyl, aryl, or heteroaryl; wherein the heterocyclyl and heteroaryl contain 1-5 heteroatoms selected from the group consisting of N, S, P and O; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, and heteroaryl are optionally substituted with D, halogen, $C_1$-$C_6$alkyl, —OH, —O—$C_1$-$C_6$alkyl, —$NH_2$, —NH($C_1$-$C_6$alkyl), or —N($C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or $A^1$ is an imidazole, then at least one $A^2$ is N, $NR^{5a}$, O, S, or $S(O)_2$.

Embodiment II-4. A compound of formula Id:

(Id)

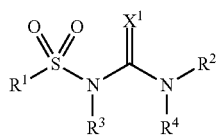

or a pharmaceutically acceptable salt, prodrug, solvate, hydrate, isomer, or tautomer thereof, wherein:

$X^1$ is O, S,

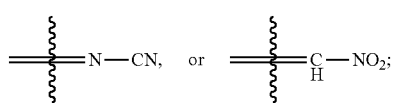

$R^1$ is selected from the group consisting of an optionally substituted $C_1$-$C_6$alkyl, optionally substituted $C_1$-$C_6$alkynyl, —$(CH_2)_m$—O—$(CH_2)_m$—$CH_3$,

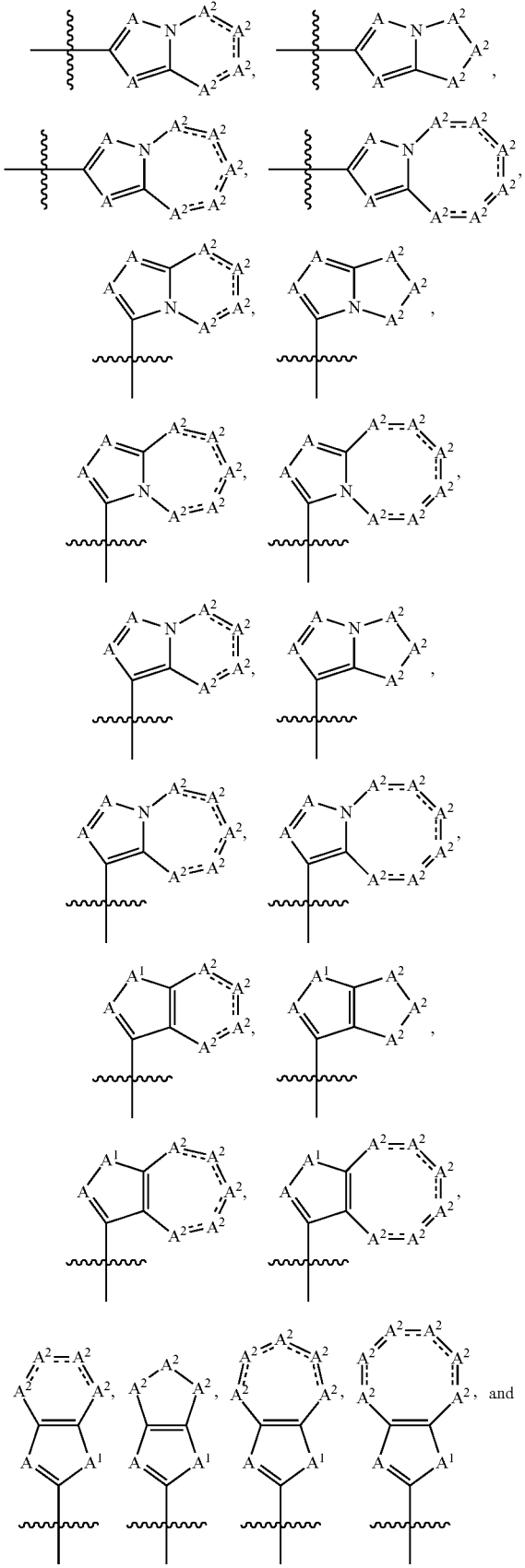

-continued

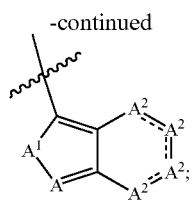

wherein ═ represents a single bond or a double bond provided that the ring comprising one or more A² is a non-aromatic ring;

each A is independently CR$^{5a}$ or N;

A¹ is NR$^{5a}$, O, S, or C(O);

each A² is independently CR$^{5a}$, C(R$^{5a}$)$_2$, N, NR$^{5a}$, O, S, or S(O)$_2$;

R² is

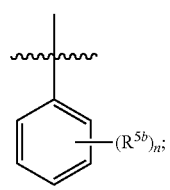

R³ and R⁴ are H;

each R$^{5a}$ is independently H, D, halogen, OH, CN, —NO$_2$, —SR⁶, —OR⁶, —NHR⁶, —NR⁶R⁷, —S(O)$_2$N(R⁶)$_2$—, —S(O)$_2$R⁶, —C(O)R⁶, —C(O)OR⁶, —C(O)NR⁶R⁷, —NR⁶S(O)$_2$R⁷, —S(O)R⁶, —S(O)NR⁶R⁷, —NR⁶S(O)R⁷, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, halogen, C$_1$-C$_6$alkyl, —OR⁶, —NH$_2$, —NH(C$_1$-C$_6$alkyl), or —N(C$_1$-C$_6$alkyl)$_2$; or two R$^{5a}$ together with the atoms to which they are attached can form C$_3$-C$_8$cycloalkyl, heterocyclyl, aryl, or heteroaryl; wherein the heterocyclyl and heteroaryl contain 1-3 heteroatoms selected from the group consisting of N, S, P and O; wherein the C$_3$-C$_8$cycloalkyl, heterocyclyl, aryl, or heteroaryl are optionally substituted with D, halogen, C$_1$-C$_6$alkyl, —OR⁶, —NH$_2$, —NH(C$_1$-C$_6$alkyl), or —N(C$_1$-C$_6$alkyl)$_2$; or two geminal R$^{5a}$ can form an oxo group;

each R$^{5b}$ is independently H, D, halogen, OH, CN, —NO$_2$—SR⁶, —OR⁶, —NHR⁶, —NR⁶R⁷, —S(O)$_2$N(R⁶)$_2$—, —S(O)$_2$R⁶, —C(O)R⁶, —C(O)OR⁶, —C(O)NR⁶R⁷, —NR⁶S(O)$_2$R⁷, —S(O)R⁶, —S(O)NR⁶R⁷, —NR⁶S(O)R⁷, C$_1$-C$_6$alkyl, C$_2$-C$_6$alkenyl, C$_4$-C$_8$cycloalkenyl, or C$_2$-C$_6$alkynyl; wherein the C$_1$-C$_6$alkyl, C$_2$-C$_6$alkenyl, C$_4$-C$_8$cycloalkenyl, and C$_2$-C$_6$alkynyl are optionally substituted with D, halogen, —OR⁶, —NH$_2$, —NH(C$_1$-C$_6$alkyl), or —N(C$_1$-C$_6$alkyl)$_2$;

R⁶ and R⁷ are independently, at each occurrence H, D, C$_1$-C$_8$alkyl, C$_2$-C$_8$alkenyl, C$_4$-C$_8$cycloalkenyl, C$_2$-C$_8$alkynyl, C$_3$-C$_8$cycloalkyl, heterocyclyl, aryl, or heteroaryl; wherein the heterocyclyl and heteroaryl contain 1-5 heteroatoms selected from the group consisting of N, S, P and O; wherein the C$_1$-C$_8$alkyl, C$_2$-C$_8$alkenyl, C$_4$-C$_8$cycloalkenyl, C$_2$-C$_6$alkynyl, C$_3$-C$_8$cycloalkyl, heterocyclyl, aryl, and heteroaryl are optionally substituted with D, halogen, C$_1$-C$_6$alkyl, —OH, —O—C$_1$-C$_6$alkyl, —NH$_2$, —NH(C$_1$-C$_6$alkyl), or —N(C$_1$-C$_6$alkyl)$_2$; or R⁶ and R⁷ together with the atom to which they are attached can form heterocyclyl or heteroaryl containing 1-3 heteroatoms selected from the group consisting of N, S, P and O;

each m is independently an integer from one to 4; and n is an integer from zero to 5;

provided that when the ring comprising A and/or A¹ is an imidazole, then at least one A² is N, NR$^{5a}$, O, S, or S(O)$_2$.

Embodiment II-5. The compound of any one of Embodiments II-1 to II-4, wherein R¹ is selected from the group consisting of:

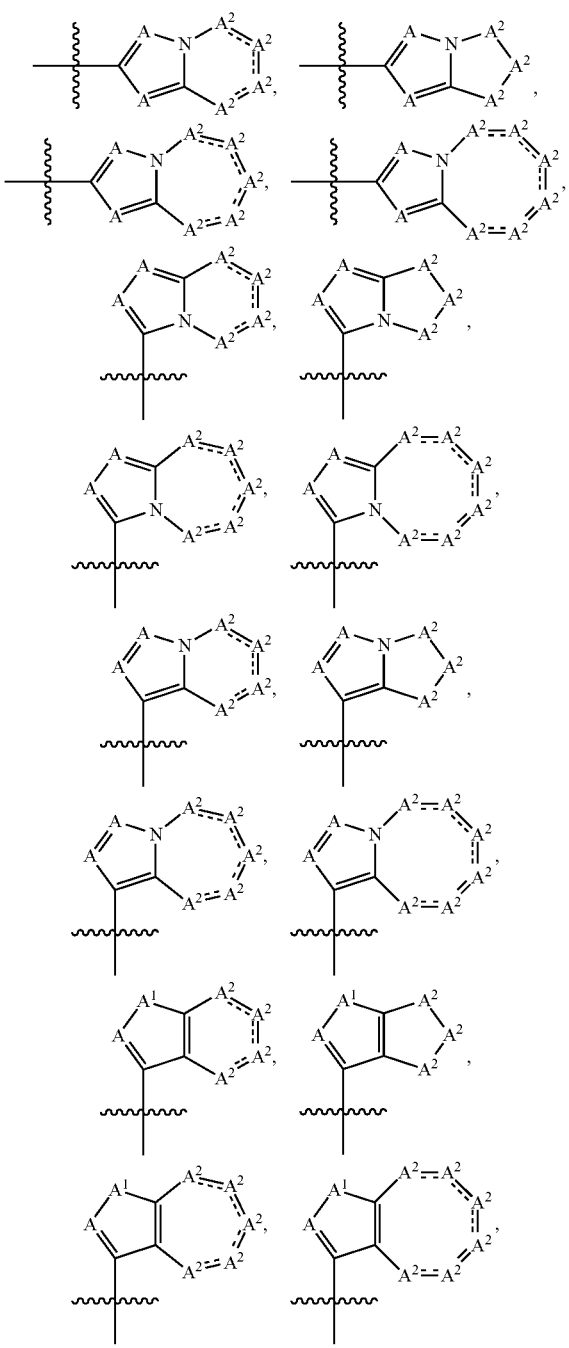

-continued

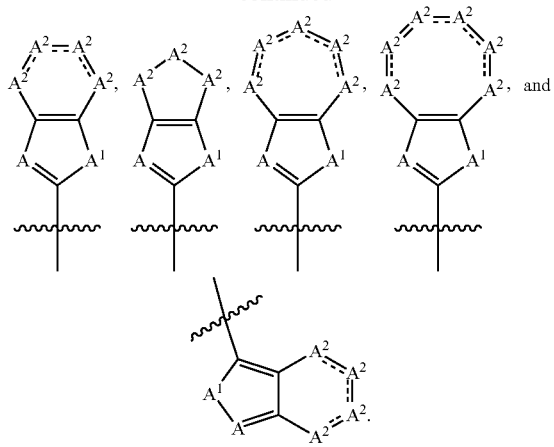

Embodiment II-6. The compound of any one of Embodiments II-1 to II-5, wherein $X^1$ is O.

Embodiment II-7. The compound of any one of Embodiments II-1 to II-5, wherein $X^1$ is S.

Embodiment II-8. The compound of any one of Embodiments II-1 to II-3 and II-5 to II-7, wherein $R^2$ is

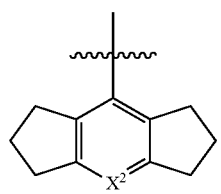

Embodiment II-9. The compound of any one of Embodiments II-1 to II-3 and II-5 to II-7, wherein $R^2$ is

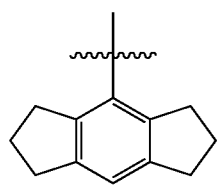

Embodiment II-10. The compound of any one of Embodiments II-1 to II-9, wherein the ═ are single bonds in the ring comprising $A^2$, thereby forming a saturated ring.

Embodiment II-11. The compound of any one of Embodiments II-1 to II-10, wherein $R^1$ is

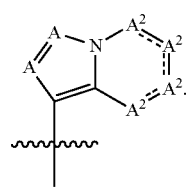

Embodiment II-12. The compound of Embodiment II-11, wherein each $A^2$ is independently $CH_2$ or O.

Embodiment II-13. The compound of any one of Embodiments II-1 to II-10, wherein $R^1$ is.

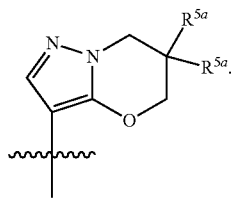

Embodiment II-14. The compound of any one of Embodiments II-1 to II-10, wherein $R^1$ is

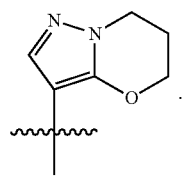 [SMILES: *c1cnn2c1OCCC2]

Embodiment II-15. The compound of any one of Embodiments II-1 to II-10, wherein $R^1$ is

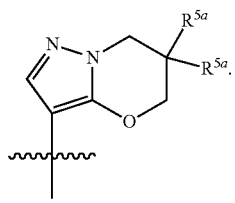

Embodiment II-16. The compound of any one of Embodiments II-1 to II-15, wherein $R^1$ is methyl.

Embodiment II-17. The compound of any one of Embodiments II-1 to II-3 and II-5 to II-16, wherein the compound is of formula:

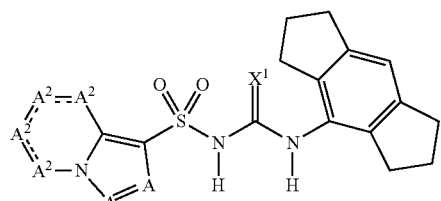

Embodiment II-18. The compound of Embodiment II-1, which is

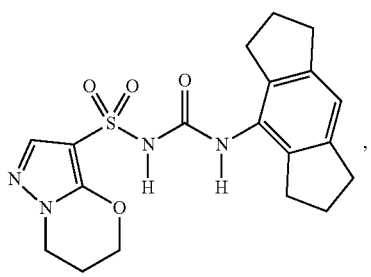 [SMILES: O=C(Nc1c2c(cc3c1CCC3)CCC2)NS(=O)(=O)c1cnn2c1OCCC2]

N-((1,2,3,5,6,7-hexahydro-s-indacen-4-yl)carbamoyl)-6,7-dihydro-5H-pyrazolo[5,1-b][1,3]oxazine-3-sulfonamide, or a pharmaceutically acceptable salt thereof.

Embodiment II-19. The compound of Embodiment II-1, which is

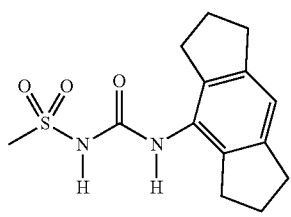

N-((1,2,3,5,6,7-hexahydro-s-indacen-4-yl)carbamoyl)methanesulfonamide, or a pharmaceutically acceptable salt thereof.

Embodiment II-20. The compound of Embodiment II-1, which is

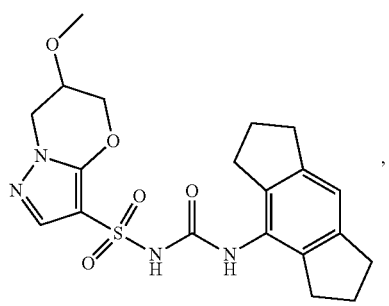 [SMILES: COC1COc2c(S(=O)(=O)NC(=O)Nc3c4c(cc5c3CCC5)CCC4)cnn2C1]

or a pharmaceutically acceptable salt thereof.

Embodiment II-21. The compound of Embodiment II-1, which is

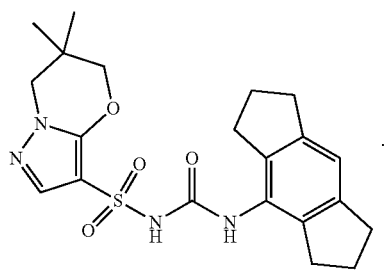 [SMILES: CC1(C)COc2c(S(=O)(=O)NC(=O)Nc3c4c(cc5c3CCC5)CCC4)cnn2C1]

or a pharmaceutically acceptable salt thereof.

Embodiment II-22. The compound of Embodiment II-1, which is selected from the group consisting of

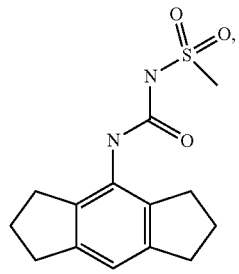

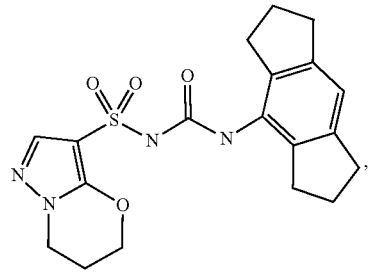

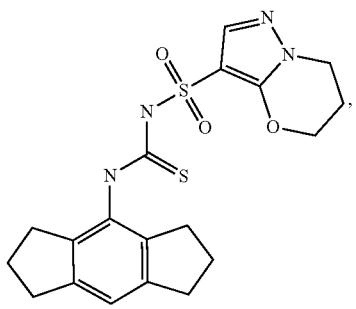

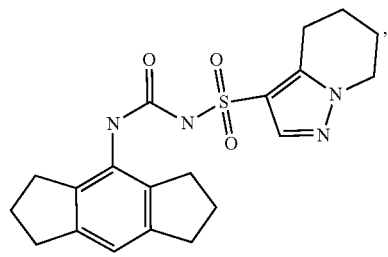

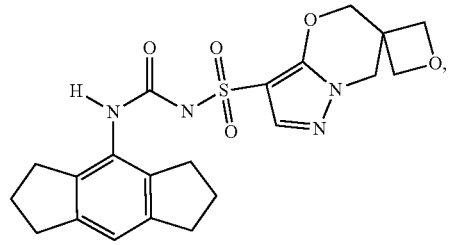

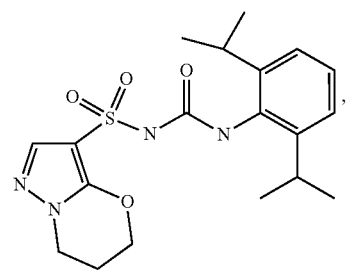

189
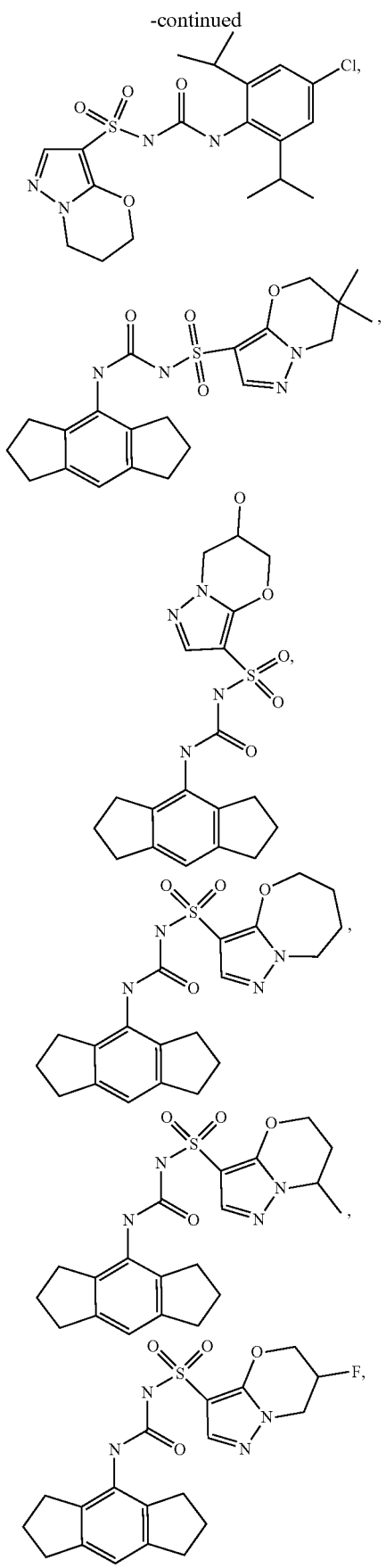
190
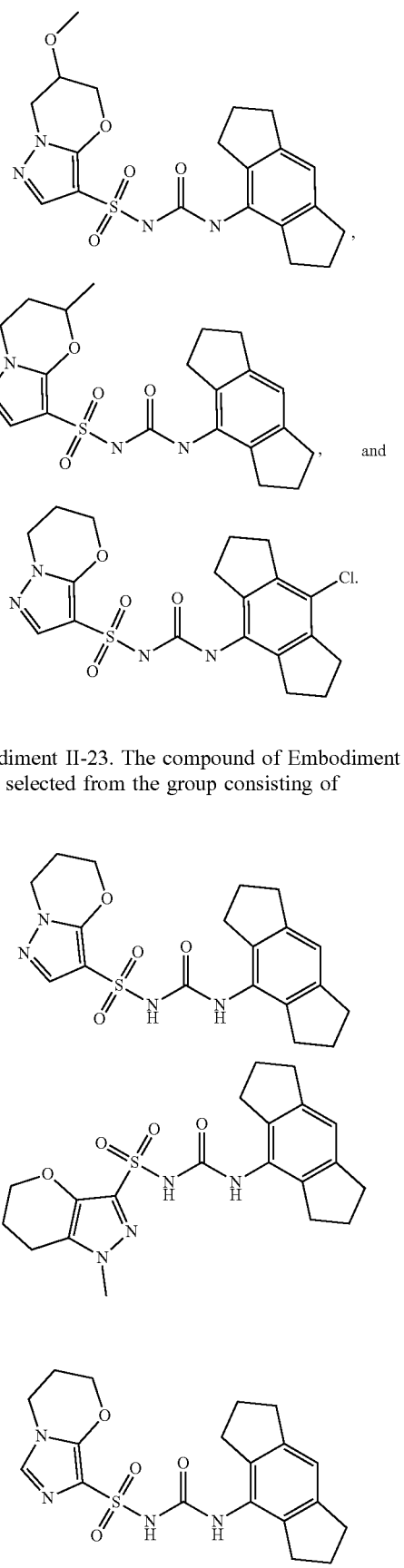
Embodiment II-23. The compound of Embodiment II-1, which is selected from the group consisting of 191
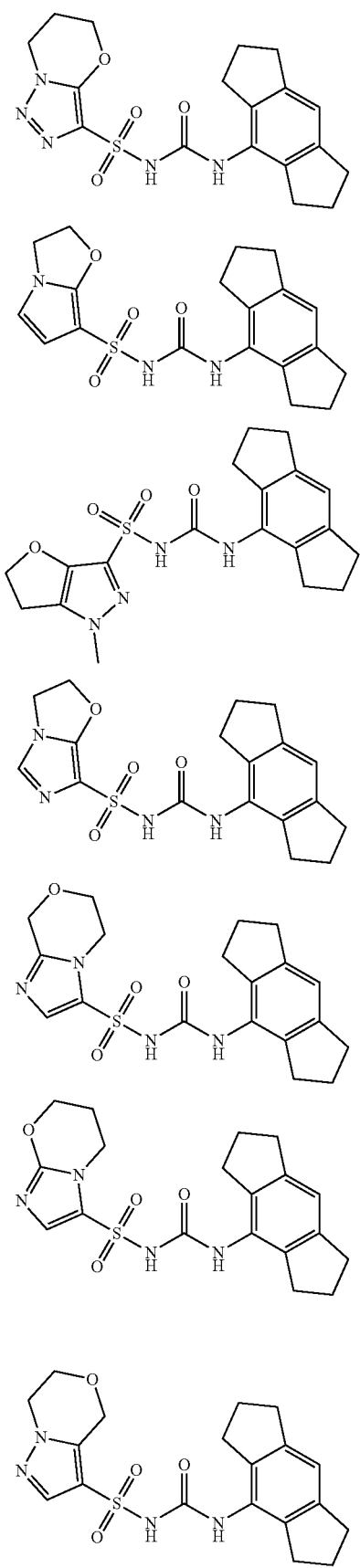
192
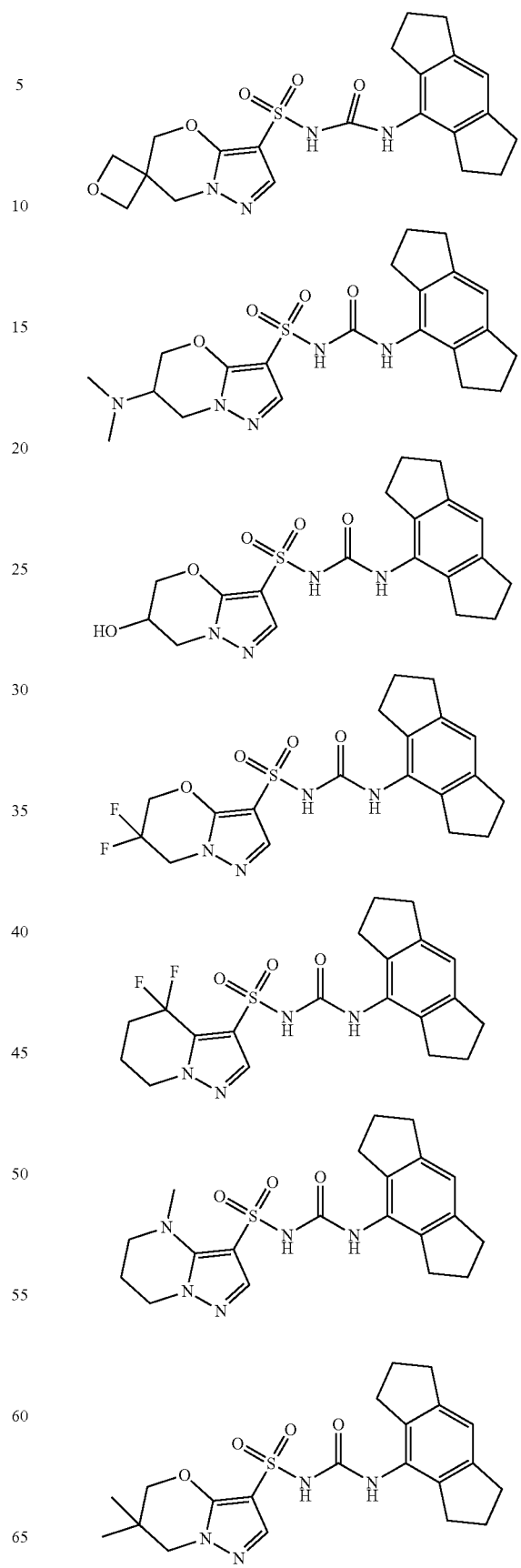

193
-continued
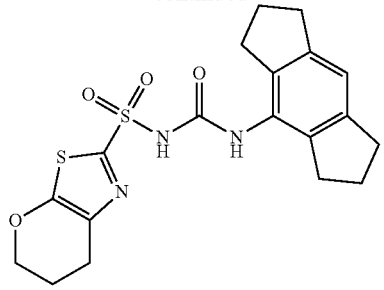
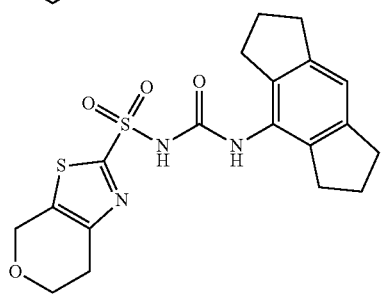
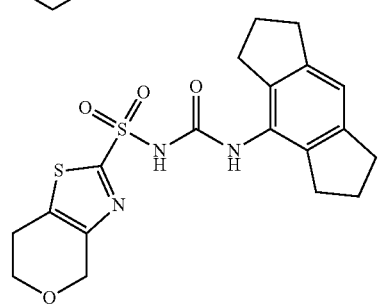
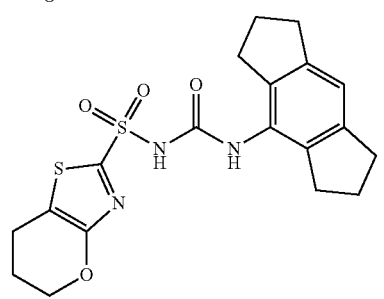
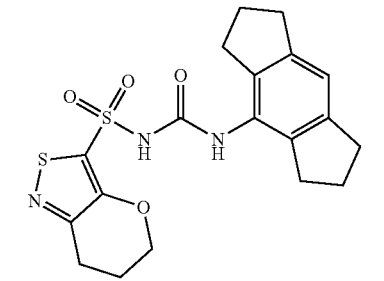
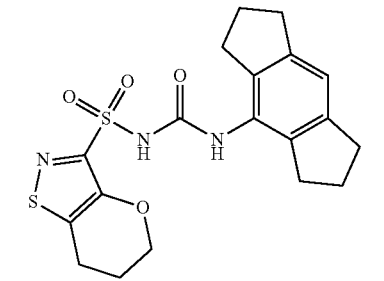
194
-continued
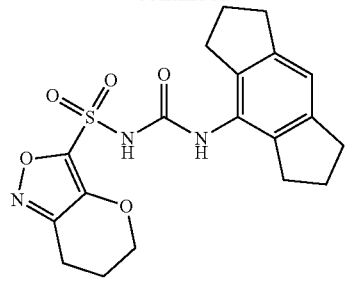
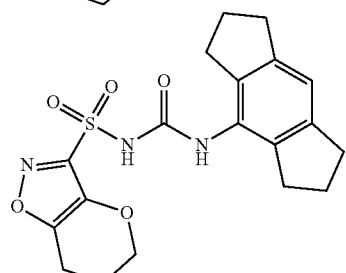
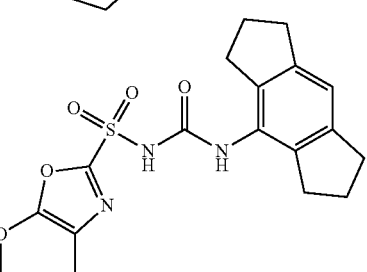
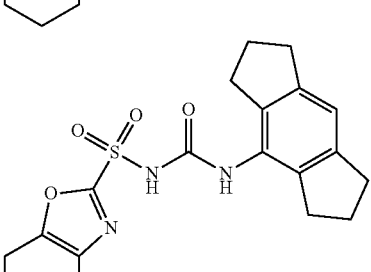
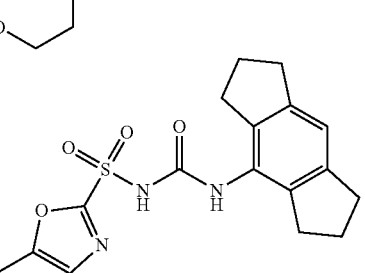
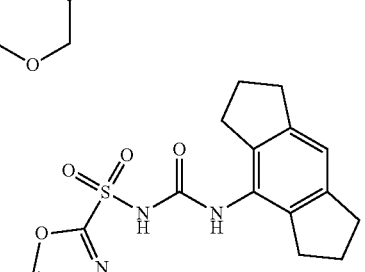

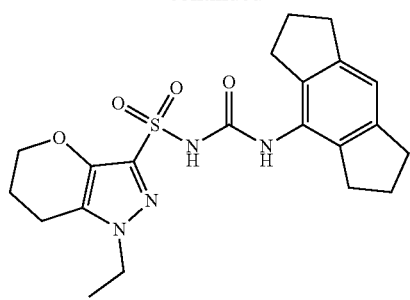
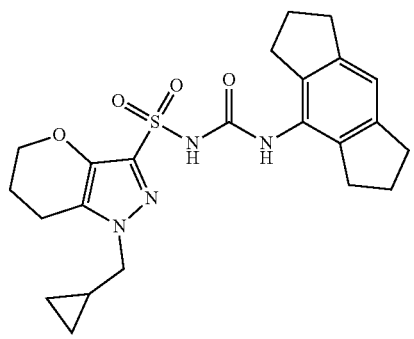
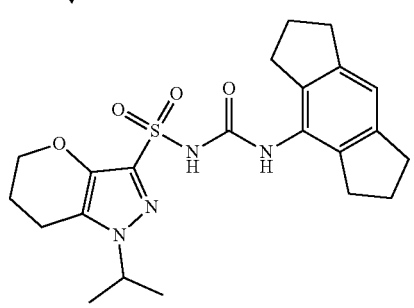
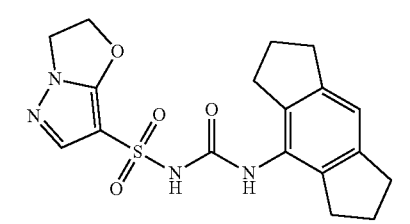
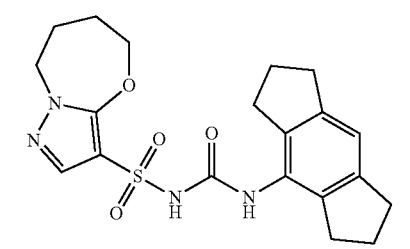
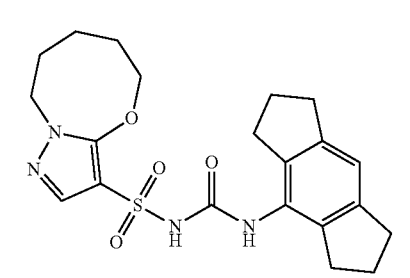
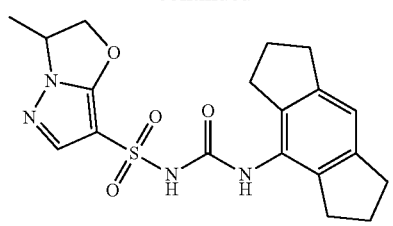
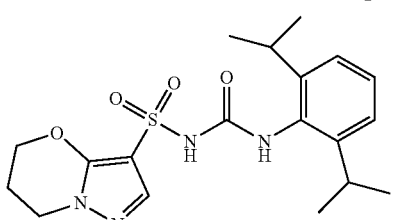
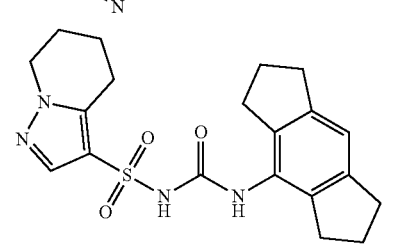
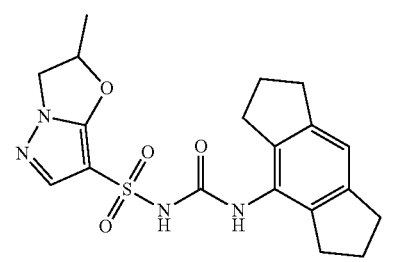
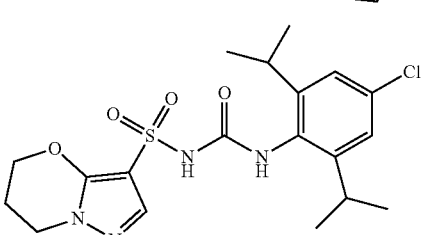
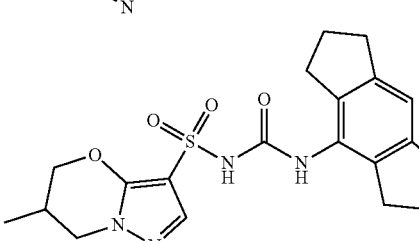
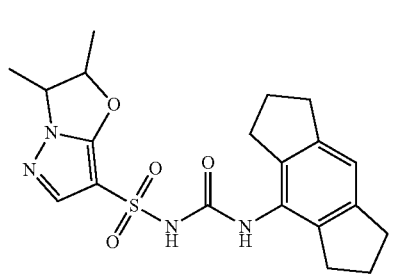

-continued
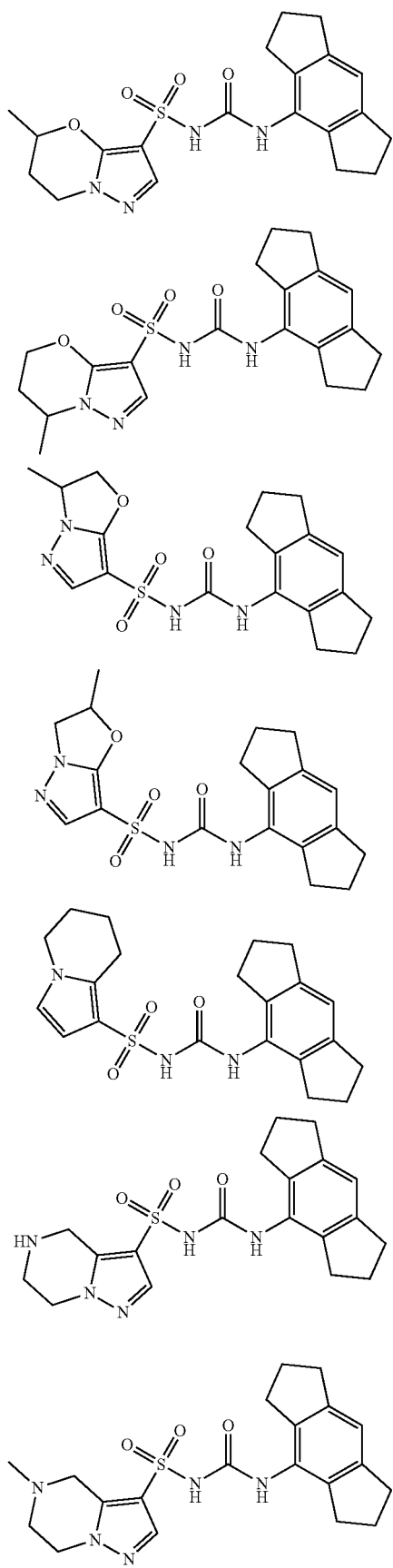
-continued
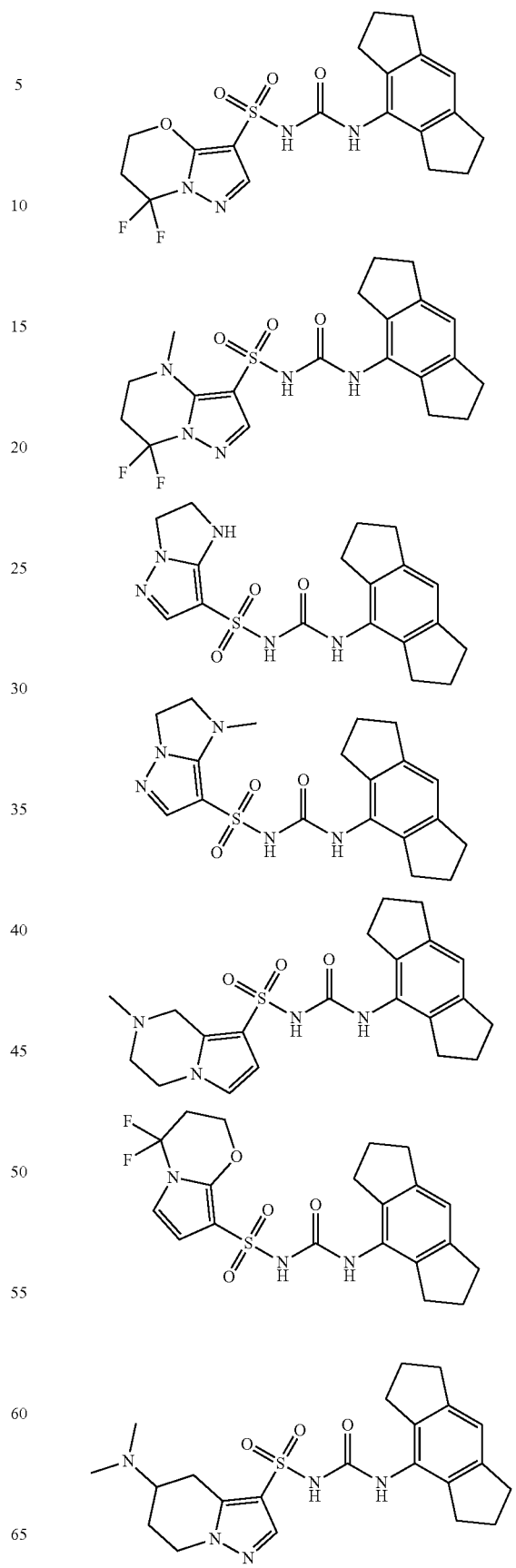

199
-continued
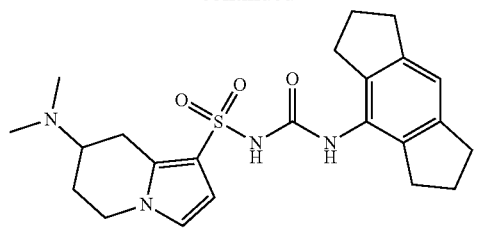
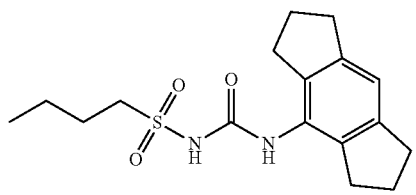
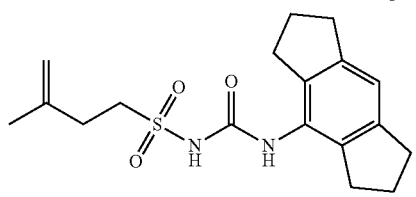
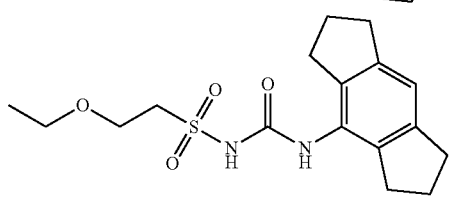
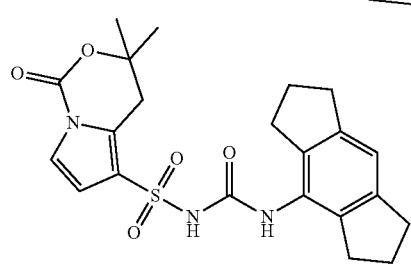
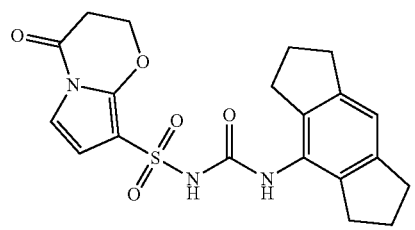
200
-continued
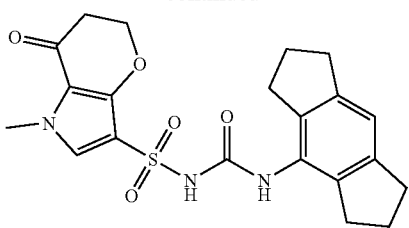
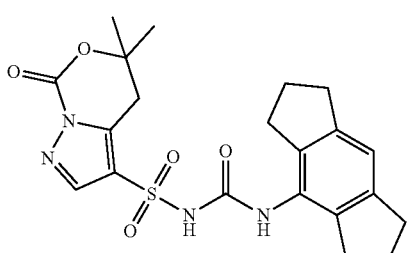
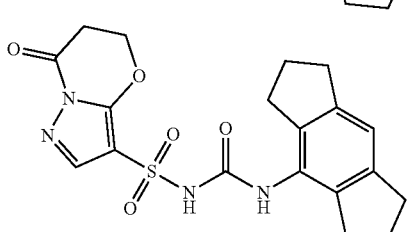
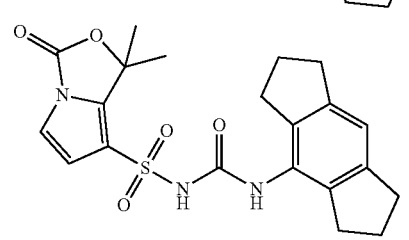
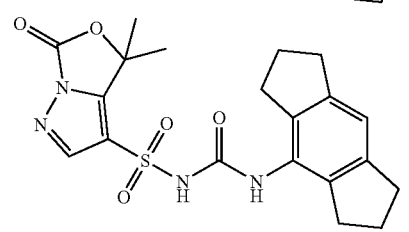
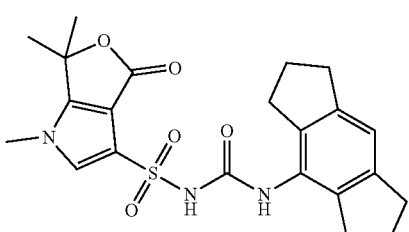
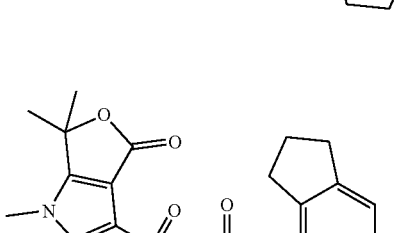

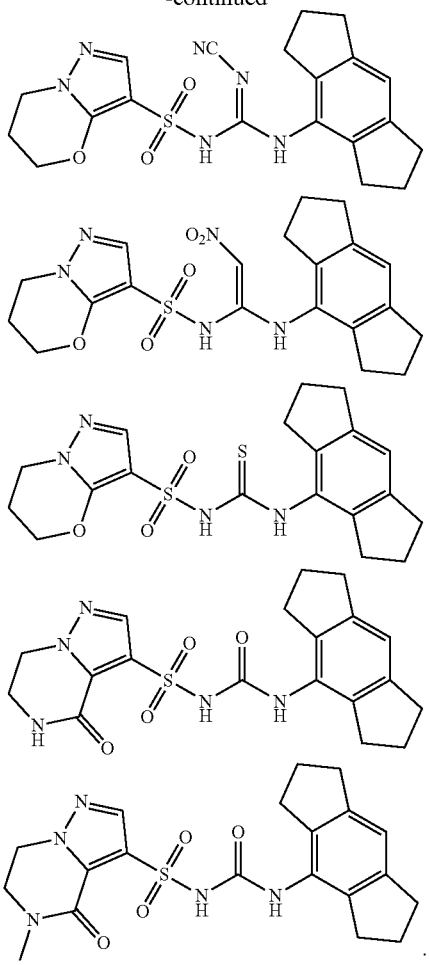
Embodiment II-24. The compound of any one of Embodiments II-1 to II-4, which is selected from the group consisting of
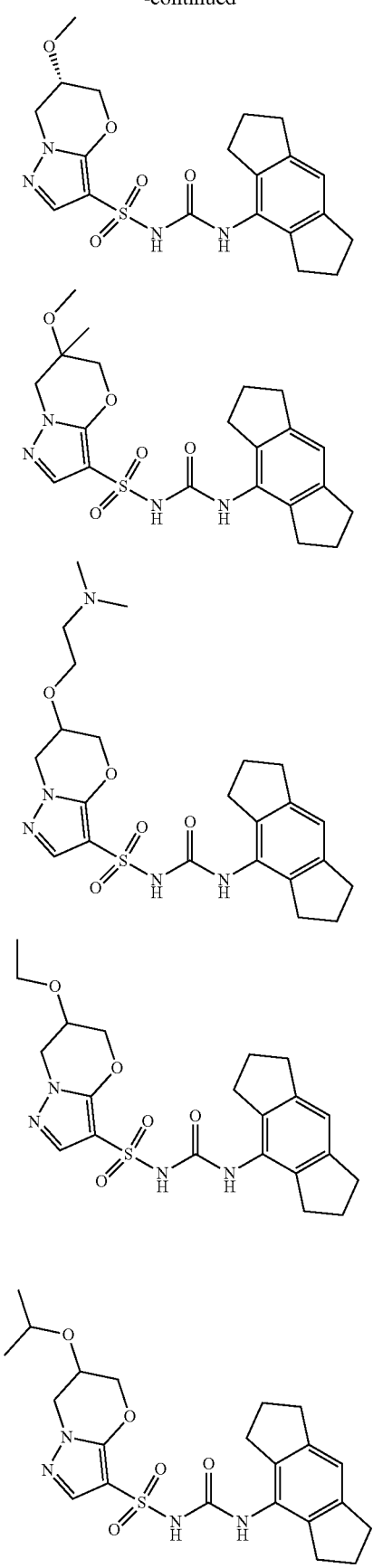

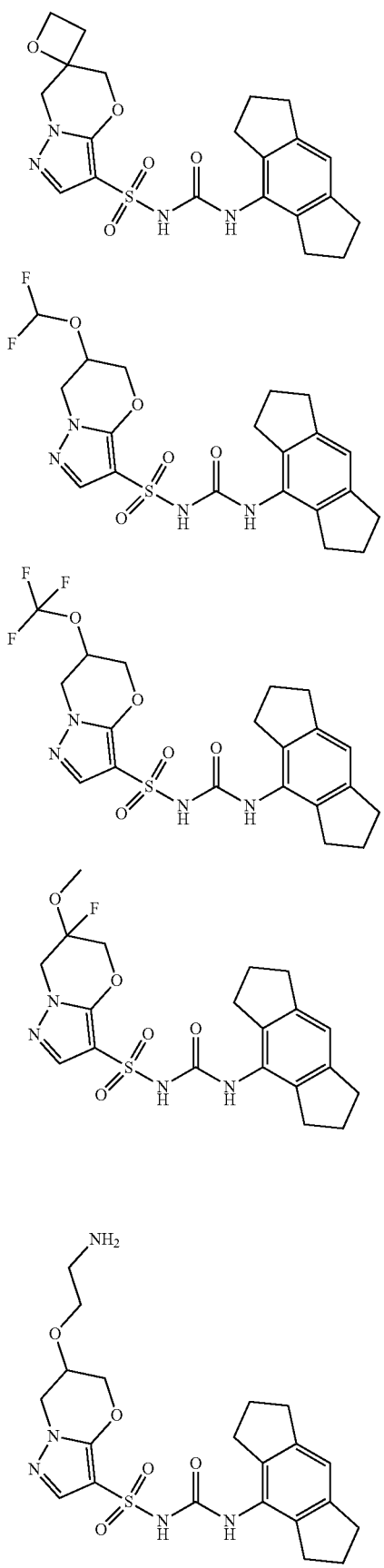
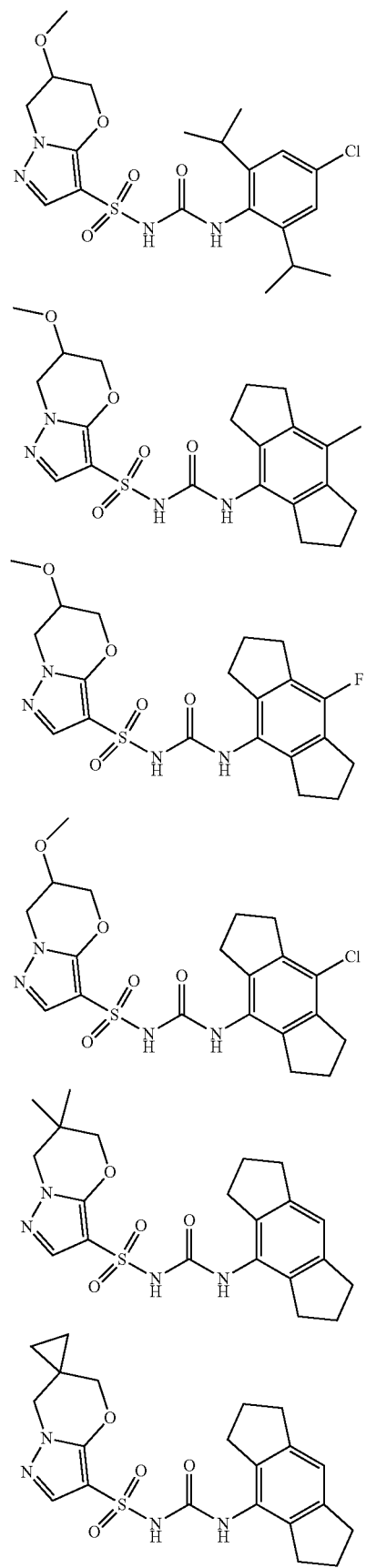

205
-continued
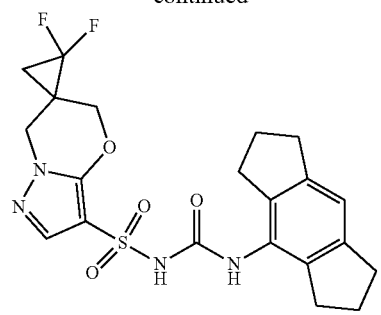
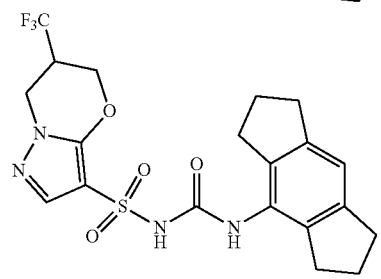
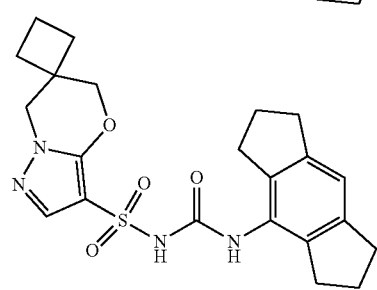
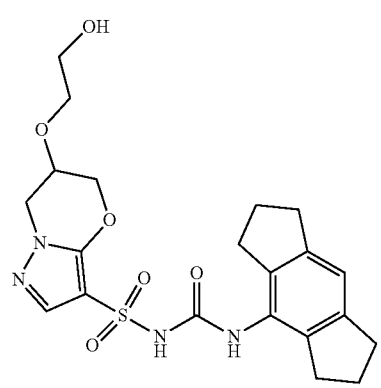
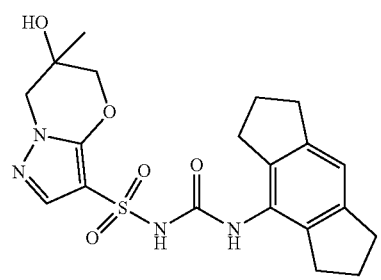
206
-continued
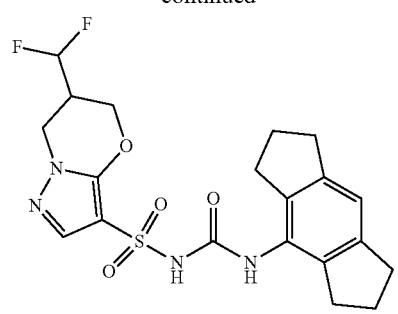
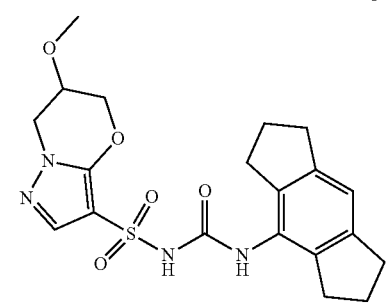
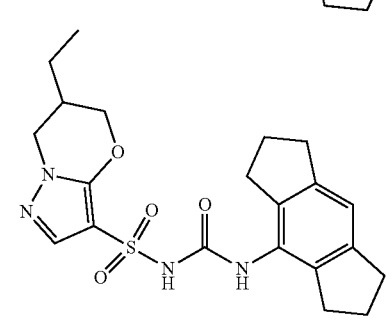
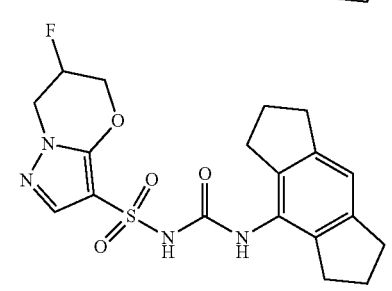
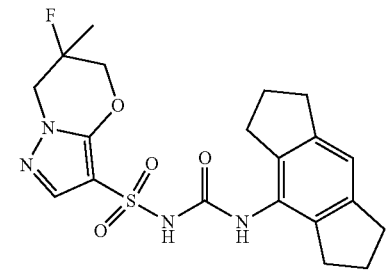
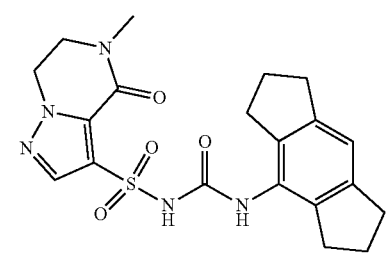

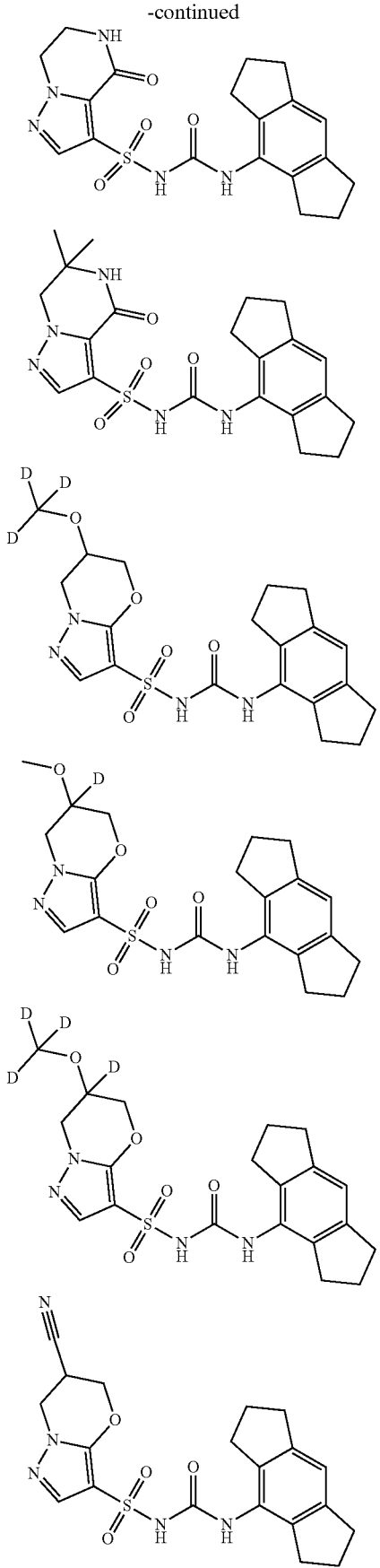
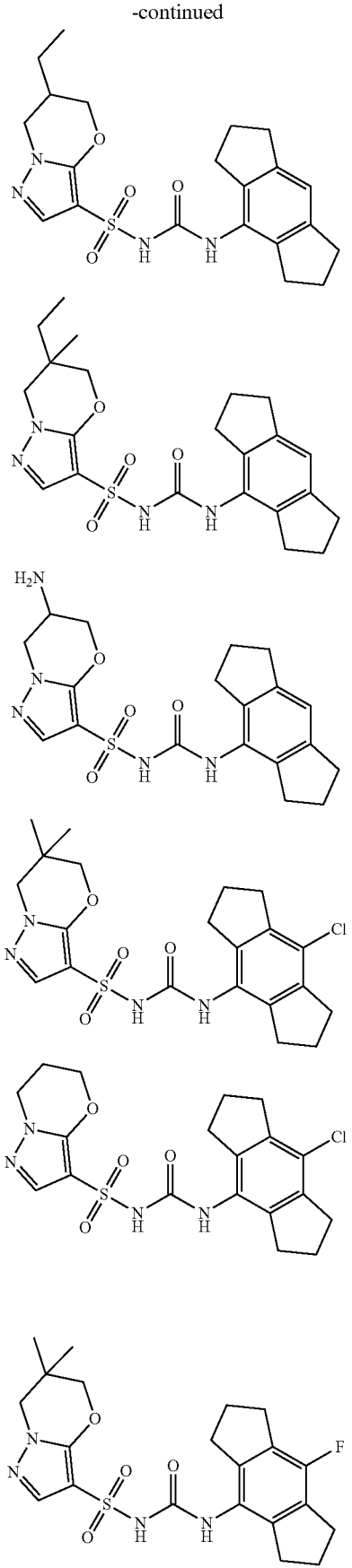

209
-continued
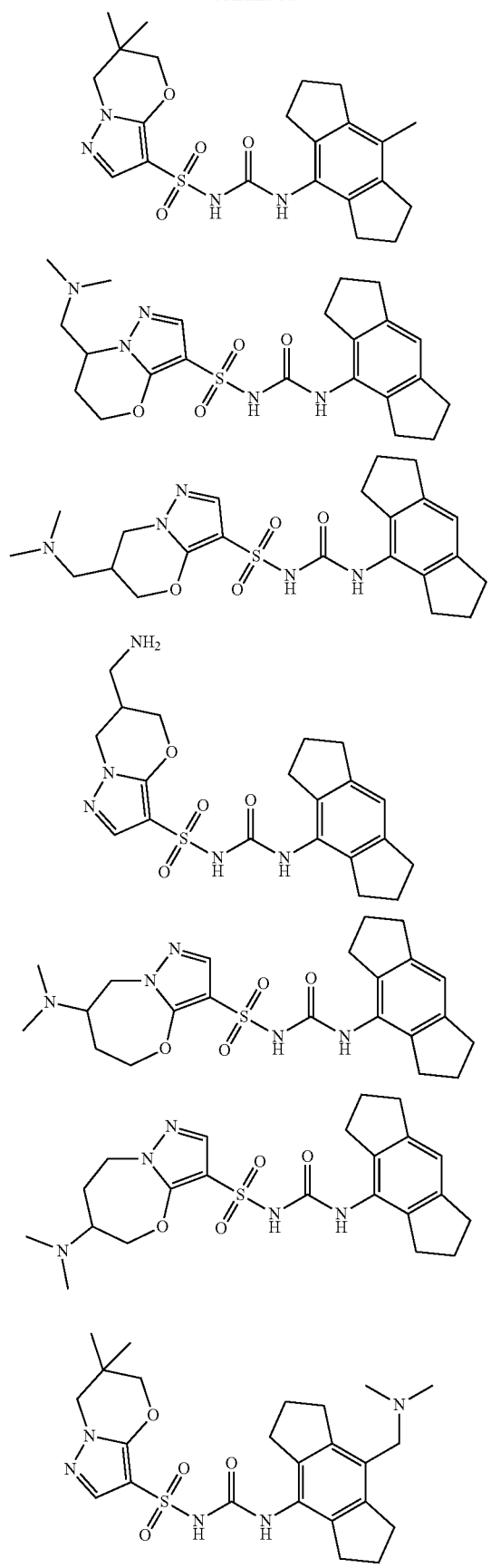
210
-continued
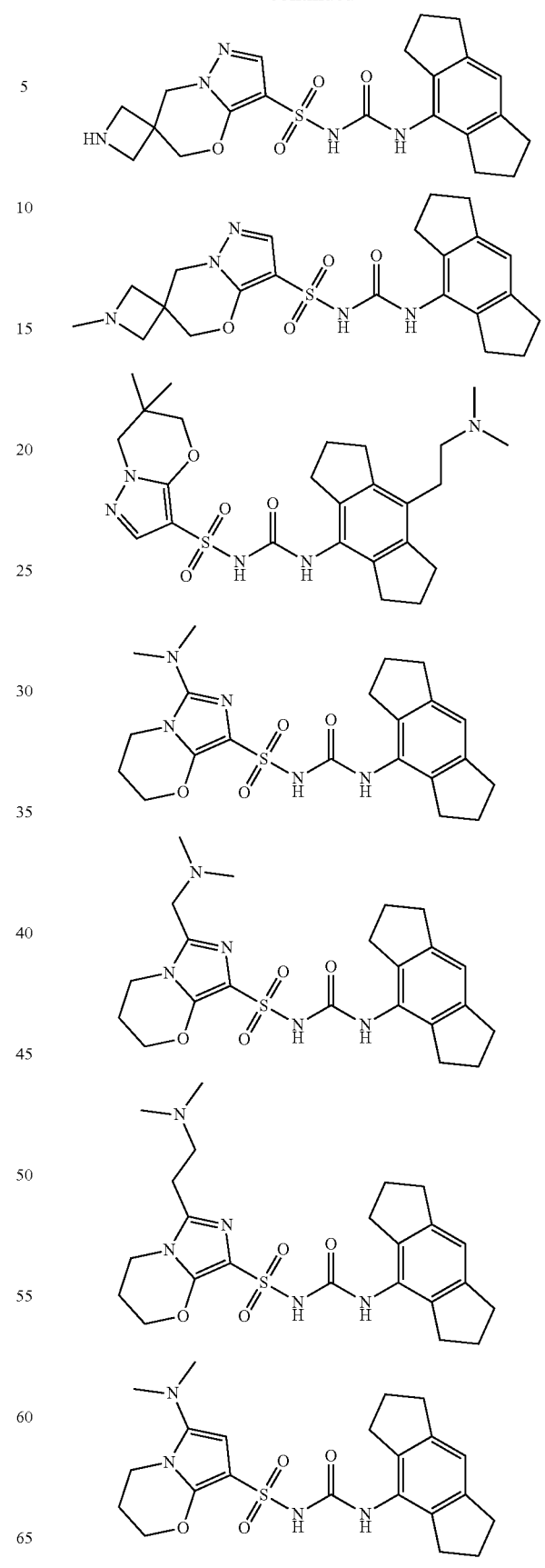

211
-continued
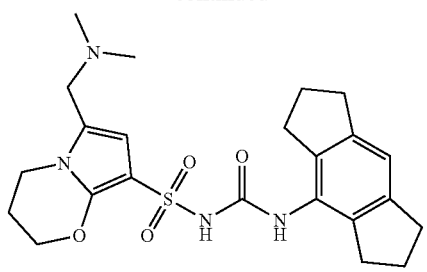
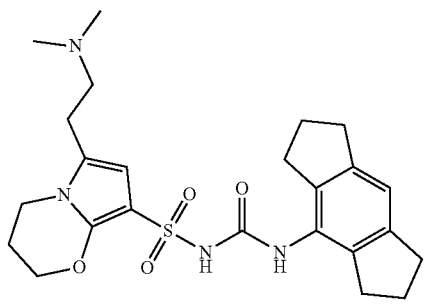
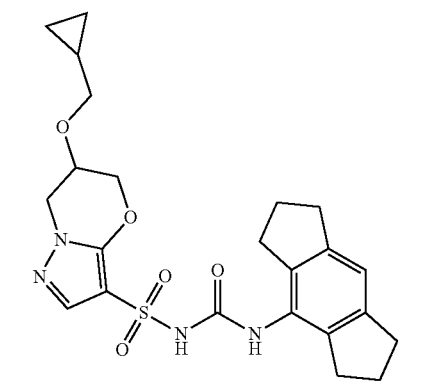
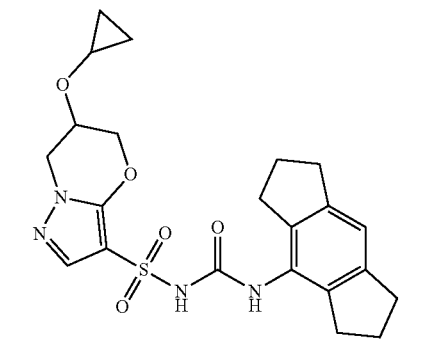
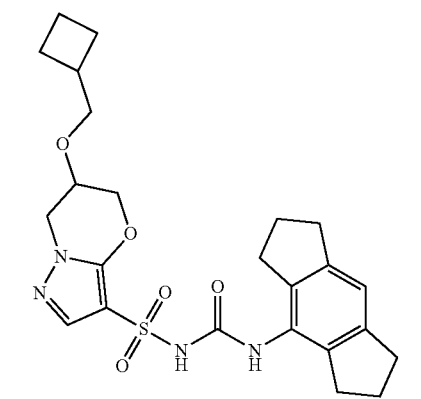
212
-continued
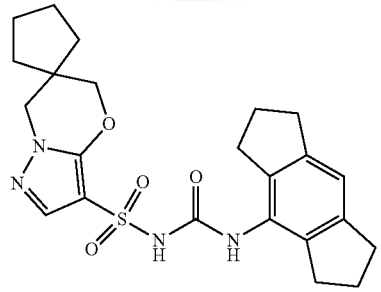
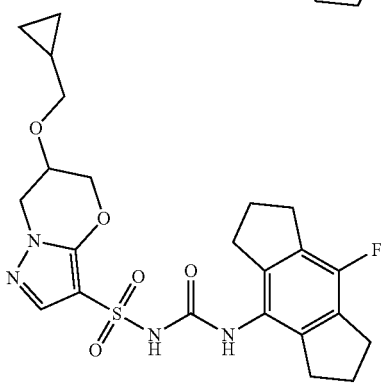
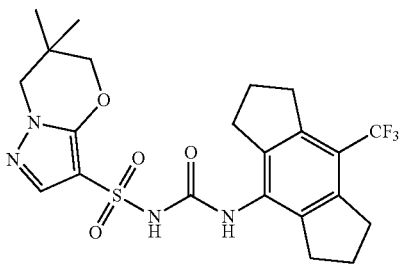
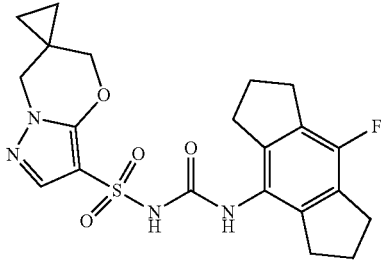
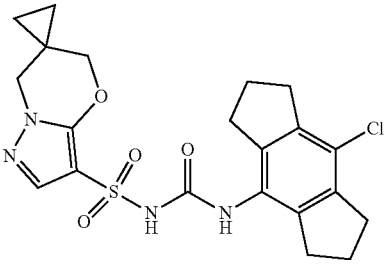
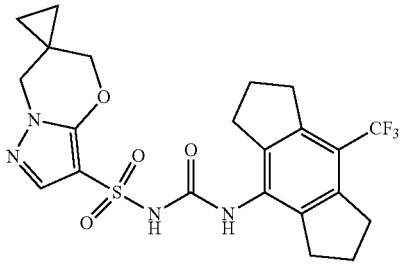

213
-continued
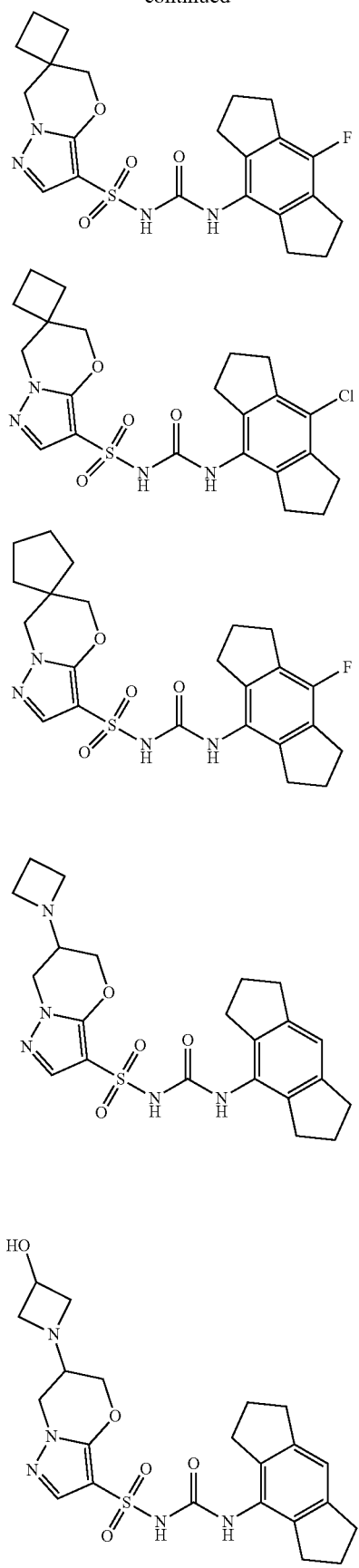
214
-continued
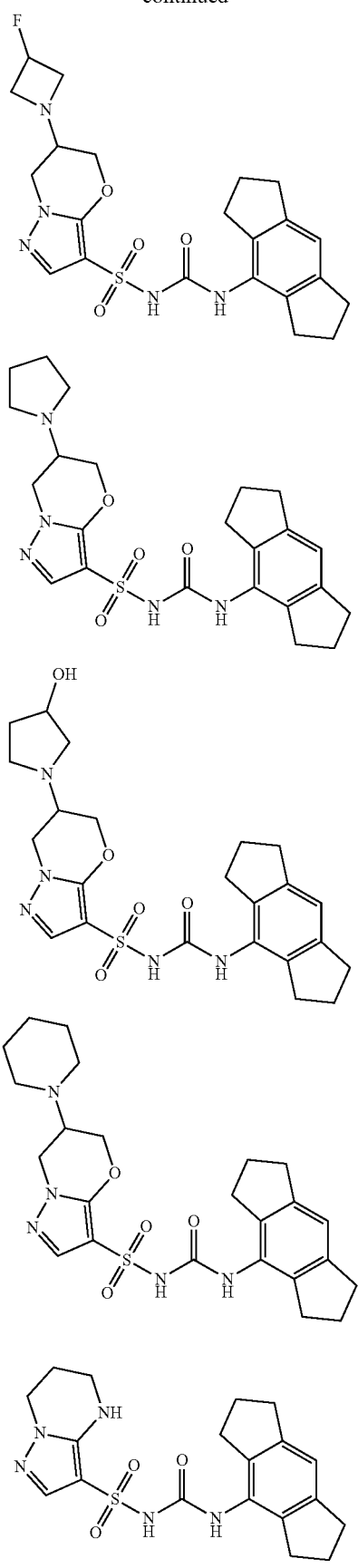

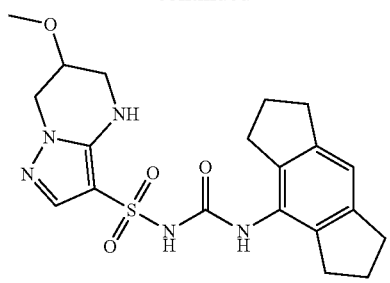
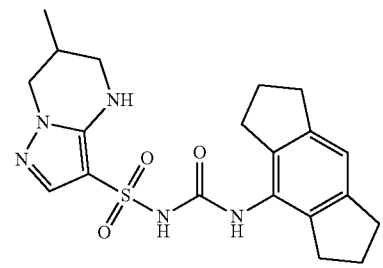
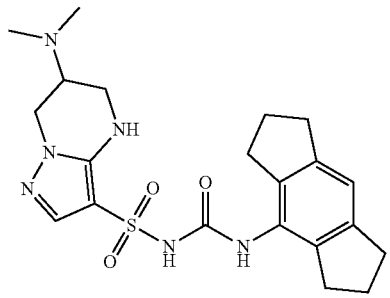
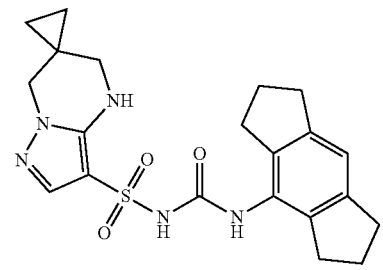
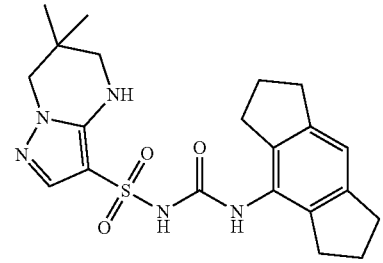
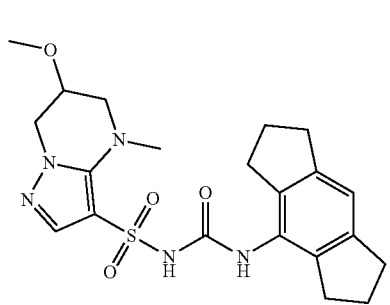
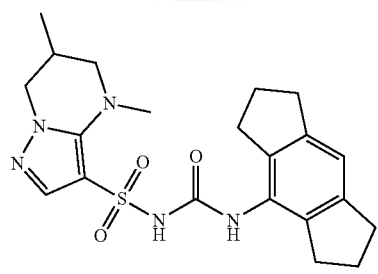
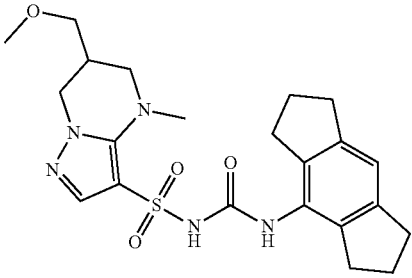
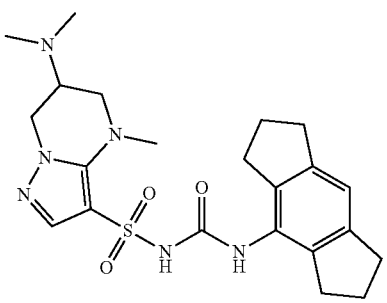
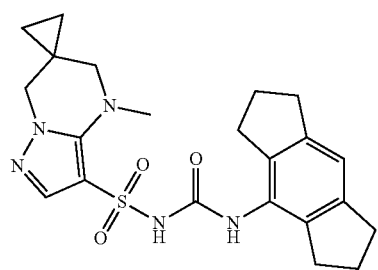
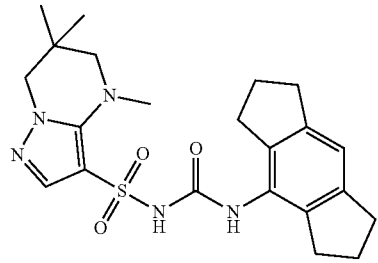
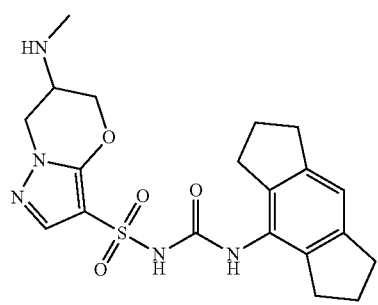

-continued

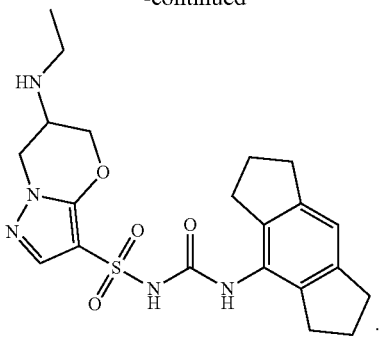

Embodiment II-25. A pharmaceutical composition comprising a compound of any one of Embodiments II-1 to II-24 and a pharmaceutically acceptable carrier.

Embodiment II-26. A method of treatment or prevention of a disease, disorder or condition including the step of administering an effective amount of a compound of any one of Embodiments II-1 to II-24, or a pharmaceutically acceptable salt, prodrug, solvate, hydrate, isomer, or tautomer thereof, to thereby treat or prevent the disease disorder or condition.

Embodiment II-27. The method of Embodiment II-25, wherein the disease, disorder or condition is responsive to inhibition of inflammasome.

Embodiment II-28. The method of Embodiment II-26 or II-27, wherein the disease, disorder or condition is one which is responsive to inhibition of activation of the NLRP3 inflammasome.

Embodiment II-29. The method of Embodiment II-26 or II-27, wherein the disease, disorder or condition is responsive to modulation of one or more of IL-6, IL-1β, IL-17, IL-18, IL-1α, IL-37, IL-22, IL-33 and Th17 cells.

Embodiment II-30. The method of any one of Embodiments II-26 to II-29, wherein the disease, disorder or condition is a disease, disorder or condition of the immune system.

Embodiment II-31. The method of any one of Embodiments II-26 to II-29, wherein the disease, disorder or condition is an inflammatory disease disorder or condition or an autoimmune disease disorder or condition.

Embodiment II-32. The method of any one of Embodiments II-26 to II-29, wherein the disease, disorder or condition is a disease, disorder or condition of the liver.

Embodiment II-33. The method of any one of Embodiments II-26 to II-29, wherein the disease, disorder or condition is a disease, disorder or condition of the lung.

Embodiment II-34. The method of any one of Embodiments II-26 to II-29, wherein the disease, disorder or condition is a disease, disorder or condition of the skin.

Embodiment II-35. The method of any one of Embodiments II-26 to II-29, wherein the disease, disorder or condition is a disease, disorder or condition of the cardiovascular system.

Embodiment II-36. The method of any one of Embodiments II-26 to II-29, wherein the disease, disorder or condition is a cancer, tumor or other malignancy.

Embodiment II-37. The method of any one of Embodiments II-26 to II-29, wherein the disease, disorder or condition is a disease, disorder or condition is of the renal system.

Embodiment II-38. The method of any one of Embodiments II-26 to II-29, wherein the disease, disorder or condition is a disease, disorder or condition is of the gastrointestinal tract.

Embodiment II-39. The method of any one of Embodiments II-26 to II-29, wherein the disease, disorder or condition is a disease, disorder or condition is of the respiratory system.

Embodiment II-40. The method of any one of Embodiments II-26 to II-29, wherein the disease, disorder or condition is a disease, disorder or condition is of the endocrine system.

Embodiment II-41. The method of any one of Embodiments II-26 to II-29, wherein the disease, disorder or condition is a disease, disorder or condition is of the central nervous system (CNS).

Embodiment II-42. The method of any one of Embodiments II-26 to II-29, wherein the disease, disorder or condition is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), corneal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

Embodiment II-43. The method of Embodiment II-26, wherein the disorder is selected from the group consisting of a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), and non-alcoholic steatohepatitis (NASH).

Embodiment II-44. The method of Embodiment II-43, wherein the disorder is non-alcoholic steatohepatitis (NASH).

Embodiment II-45. The method of any one of Embodiments II-26 to II-44, wherein the treatment or prevention of the disease, disorder or condition is performed on a mammal.

Embodiment II-46. The method of Embodiment II-45, wherein the mammal is a human subject.

Embodiment II-47. A method of modulating the activity of a biological target comprising the step of exposing the biological target to a compound of any one of Embodiments II-1 to II-24, or a pharmaceutically effective salt, solvate or prodrug thereof.

Embodiment II-48. The method of Embodiment II-47, wherein the biological target may be selected from the group consisting of the NLRP3 inflammasome, IL-6, IL-1β, IL-17, IL-18, IL-1α, IL-37, IL-22, IL-33 and Th17 cells.

Embodiment II-49. Use of a compound of any one of Embodiments II-1 to II-24 in the treatment of a disease, disorder or condition that is responsive to inhibition of inflammasome.

Embodiment II-50. A compound of any one of Embodiments II-1 to II-24 for use in the manufacture of a medicament for treating a disease, disorder or condition that is responsive to inhibition of inflammasome.

Embodiment III-1. A compound of formula If:

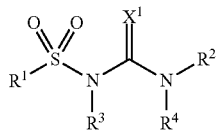

(If)

or a pharmaceutically acceptable salt, prodrug, solvate, hydrate, isomer, or tautomer thereof,
wherein:
$X^1$ is O or S;
$R^1$ is selected from the group consisting of

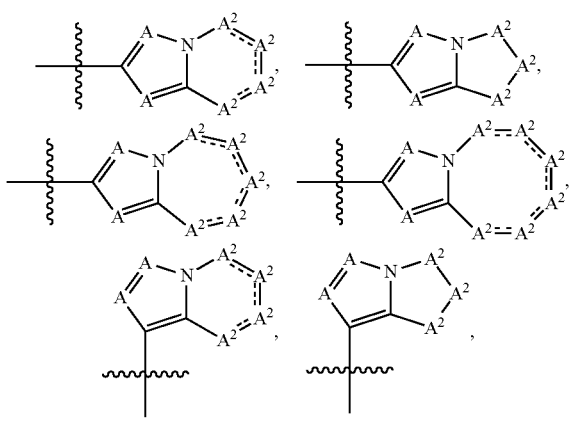

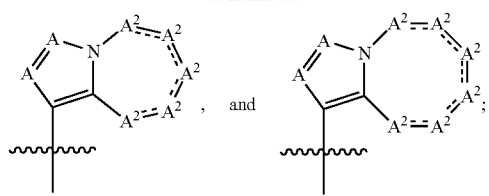

wherein ═ represents a single bond or a double bond provided that the ring comprising one or more $A^2$ is a non-aromatic ring;

each A is independently $CR^{5a1}$ or N;

each $A^2$ is independently $CR^{5a2}$, $C(R^{5a2})_2$, N, $NR^{5a2}$, O, S, or $S(O)_2$;

$R^2$ is

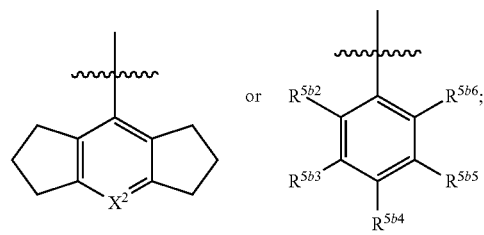

$X^2$ is N or $CR^{5b1}$;

$R^3$ and $R^4$ are H;

each $R^{5a1}$ is independently H, D, halogen, OH, CN, —$NO_2$, —$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, or —$NR^6C(O)R^6$;

each $R^{5a2}$ is independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)_2$, —$NR^6C(O)OR^6$, —$NR^6C(O)R^6$, —$NR^6C(O)NR^6$, —$NR^6C(O)R^6$, or —$NR^6S(O)_2R^6$; or two $R^{5a2}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)_2$, —$S(O)_2$—$R^6$, —$COR^6$, —NR⁶C(O)OR⁶, —NR⁶C(O)R⁶, —NR⁶C(O)NR⁶, or —NR⁶S(O)₂R⁶; or two geminal R⁵ᵃ² can form an oxo group;

R⁵ᵇ¹ is H, D, halogen, —CN —OR⁶, or C₁-C₆alkyl, C₃-C₈cycloalkyl, —C(O)NR⁶, —C(O)OR⁶; wherein the C₁-C₆alkyl, and C₃-C₈cycloalkyl, are optionally substituted with D, halogen, —CN, —OR⁶, —NH₂, —NH(C₁-C₆alkyl), or —N(C₁-C₆alkyl)₂;

each R⁵ᵇ², R⁵ᵇ³, R⁵ᵇ⁴, R⁵ᵇ⁵, and R⁵ᵇ⁶ is independently H, D, halogen, OH, —CN, —NO₂, —SR⁶, —OR⁶, —NHR⁶, —NR⁶R⁷, C₁-C₆alkyl, C₂-C₆alkenyl, C₄-C₈cycloalkenyl, C₃-C₈cycloalkyl, or C₂-C₆alkynyl; wherein the C₁-C₆alkyl, C₂-C₆alkenyl, C₄-C₈cycloalkenyl, C₃-C₈cycloalkyl, and C₂-C₆alkynyl are optionally substituted with D, halogen, —CN, —OR⁶, —NH₂, —NH(C₁-C₆alkyl), or —N(C₁-C₆alkyl)₂; or two adjacent R⁵ᵇ², R⁵ᵇ³, R⁵ᵇ⁴, R⁵ᵇ⁵, and R⁵ᵇ⁶ together with the atoms to which they are attached can form C₃-C₈cycloalkyl, heterocyclyl, aryl, or heteroaryl, wherein C₃-C₈cycloalkyl, heterocyclyl, aryl, or heteroaryl are optionally substituted with halogen, —CN, C₁-C₆alkyl, —OR⁶, —NH₂, —NH(C₁-C₆alkyl), or —N(C₁-C₆alkyl)₂; and R⁶ and R⁷ are independently, at each occurrence, H, D, C₁-C₈alkyl, C₂-C₈alkenyl, C₂-C₈alkynyl, C₃-C₈cycloalkyl, C₄-C₈cycloalkenyl, heterocyclyl, aryl, or heteroaryl; wherein the heterocyclyl and heteroaryl contain 1-5 heteroatoms selected from the group consisting of N, S, P and O; wherein the C₁-C₈alkyl, C₂-C₈alkenyl, C₂-C₈alkynyl, C₃-C₈cycloalkyl, C₄-C₈cycloalkenyl, heterocyclyl, aryl, and heteroaryl are optionally substituted with D, —CN, halogen, C₁-C₆alkyl, —OH, —O—C₁-C₆alkyl, —NH₂, —NH(C₁-C₆alkyl), or —N(C₁-C₆alkyl)₂; or R⁶ and R⁷ together with the atom to which they are attached can form heterocyclyl or heteroaryl containing 1-3 heteroatoms selected from the group consisting of N, S, P and O;

provided that when the ring comprising A and/or A¹ is an imidazole, then at least one A² is N, NR⁵ᵃ², O, S, or S(O)₂.

Embodiment III-2. The compound of claim 1, or a pharmaceutically acceptable salt, prodrug, solvate, hydrate, isomer, or tautomer thereof, wherein:

X¹ is O;

R¹ is selected from the group consisting of

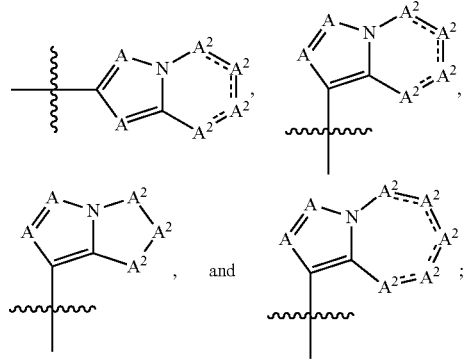

wherein ⟵ represents a single bond;
each A² is independently C(R⁵ᵃ²)₂ or O;
X² is CR⁵ᵇ¹;
each R⁵ᵃ¹ is independently H or C₁-C₆alkyl; wherein the C₁-C₆alkyl is optionally substituted with D, halogen, —OR⁶, —NH₂, —NH(C₁-C₆alkyl), —N(C₁-C₆alkyl)₂, —NR⁶C(O)OR⁶, or —NR⁶C(O)R⁶;

each R⁵ᵃ² is independently H, halogen, OH, —OR⁶, —NHR⁶, —NR⁶R⁷, C₁-C₆alkyl, or heterocyclyl; wherein the C₁-C₆alkyl and heterocyclyl are optionally substituted with D, halogen, —OR⁶, —NH₂, NH(C₁-C₆alkyl), N(C₁-C₆alkyl)₂, —NR⁶C(O)OR⁶, or —NR⁶C(O)R⁶; or two R⁵ᵃ² together with the atoms to which they are attached can form C₃-C₈cycloalkyl or heterocyclyl; wherein the heterocyclyl contains 1-3 heteroatoms selected from the group consisting of N, S, P and O; wherein the C₃-C₈cycloalkyl and heterocyclyl are optionally substituted with D, halogen, C₁-C₆alkyl, —OR⁶, —NH₂, —NH(C₁-C₆alkyl), —N(C₁-C₆alkyl)₂, or —S(O)₂—R⁶; or two geminal R⁵ᵃ² can form an oxo group;

R⁵ᵇ¹ is H, D, halogen, or C₁-C₆alkyl;

each R⁵ᵇ², R⁵ᵇ³, R⁵ᵇ⁴, R⁵ᵇ⁵, and R⁵ᵇ⁶ is independently H, D, halogen, —CN, —OR⁶, C₁-C₆alkyl, or C₃-C₈cycloalkyl; wherein the C₁-C₆alkyl, and C₃-C₈cycloalkyl, are optionally substituted with D, halogen, —OR⁶, —NH₂, —NH(C₁-C₆alkyl), or —N(C₁-C₆alkyl)₂; or two R⁵ᵇ², R⁵ᵇ³, R⁵ᵇ⁴, R⁵ᵇ⁵, and R⁵ᵇ⁶ together with the atoms to which they are attached can form C₃-C₈cycloalkyl, heterocyclyl, or heteroaryl, wherein C₃-C₈cycloalkyl, heterocyclyl, or heteroaryl are optionally substituted with halogen or C₁-C₆alkyl; and R⁶ and R⁷ are independently, at each occurrence, H, D, C₁-C₈alkyl, C₂-C₈alkynyl, or aryl; wherein the C₁-C₈alkyl, C₂-C₈alkynyl, and aryl, are optionally substituted with D, halogen or C₁-C₆alkyl.

Embodiment III-3. A compound of formula Ig:

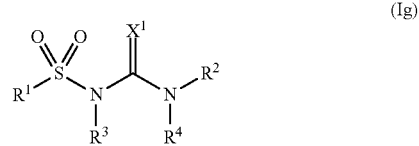

(Ig)

or a pharmaceutically acceptable salt, prodrug, solvate, hydrate, isomer, or a tautomer thereof, wherein:

X¹ is O or S;

R¹ is selected from the group consisting of

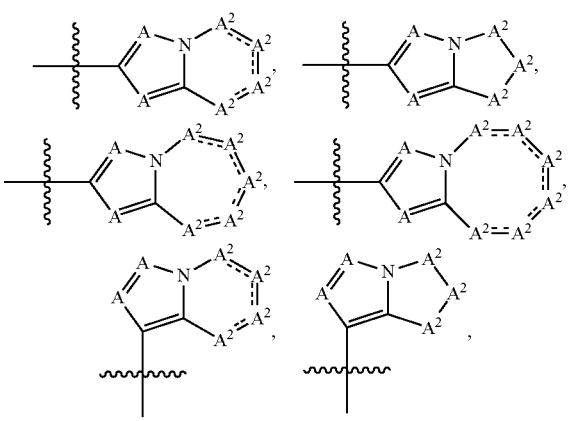

-continued

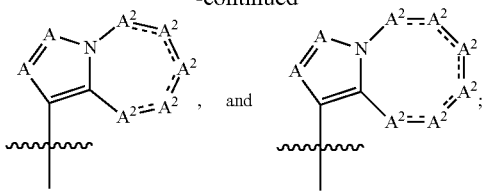

wherein ═ represents a single bond or a double bond provided that the ring comprising one or more $A^2$ is a non-aromatic ring;

each A is independently $CR^{5a1}$ or N;

each $A^2$ is independently $CR^{5a2}$, $C(R^{5a2})_2$, N, $NR^{5a2}$, O, S, or $S(O)_2$;

$R^2$ is

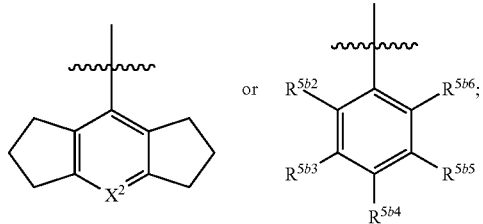

$X^2$ is N or $CR^{5b1}$;

$R^3$ and $R^4$ are H;

each $R^{5a1}$ is independently H, D, halogen, OH, CN, —$NO_2$, —$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), $N(C_1$-$C_6$alkyl$)_2$, —$NR^6C(O)OR^6$, or —$NR^6C(O)R^6$;

each $R^{5a2}$ is independently H, D, halogen, OH, CN, —$NO_2$, —$SR^6$, —$OR^6$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NR^6C(O)OR^6$, —$NR^6C(O)R^6$, —$NR^6C(O)NR^6$, —$NR^6C(O)R^6$, or —$NR^6S(O)_2R^6$; or two $R^{5a2}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$S(O)_2$—$R^6$; —$COR^6$, $NR^6C(O)OR^6$, —$NR^6C(O)R^6$, —$NR^6C(O)NR^6$, or —$NR^6S(O)_2R^6$; or two geminal $R^{5a2}$ can form an oxo group;

$R^{5b1}$ is H, D, halogen, —CN—$OR^6$, or $C_1$-$C_6$alkyl, $C_3$-$C_8$cycloalkyl, —$C(O)NR^6$, —$C(O)OR^6$; wherein the $C_1$-$C_6$alkyl, and $C_3$-$C_8$cycloalkyl, are optionally substituted with D, halogen, —CN, —$OR^6$, —$NH_2$, —$NH(C_1$-$C_6$alkyl), or —$N(C_1$-$C_6$alkyl$)_2$;

each $R^{5b2}$, $R^{5b3}$, $R^{5b4}$, $R^{5b5}$, and $R^{5b6}$ is independently H, D, halogen, OH, —CN, —$NO_2$, —$SR^6$, —$OR^6$, —$NHR^6$, —$NR^6R^7$, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, —CN, —$OR^6$, —$NH_2$, —$NH(C_1$-$C_6$alkyl), or —$N(C_1$-$C_6$alkyl$)_2$; or two adjacent $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, —CN, $C_1$-$C_6$alkyl, —$OR^6$, —$NH_2$, —$NH(C_1$-$C_6$alkyl), or —$N(C_1$-$C_6$alkyl$)_2$; and $R^6$ and $R^7$ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, and heteroaryl are optionally substituted with D, —CN, halogen, $C_1$-$C_6$alkyl, —OH, —O—$C_1$-$C_6$alkyl, —$NH_2$, —$NH(C_1$-$C_6$alkyl), or —$N(C_1$-$C_6$alkyl$)_2$; or $R^6$ and $R^7$ together with the atom to which they are attached can form heterocyclyl or heteroaryl containing 1-3 heteroatoms selected from the group consisting of N, S, P and O;

provided that when the ring comprising A and/or $A^1$ is an imidazole, then at least one $A^2$ is N, $NR^{5a2}$, O, S, or $S(O)_2$.

Embodiment III-4. A compound of formula Ih:

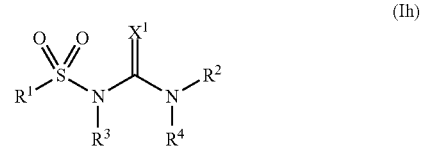

(Ih)

or a pharmaceutically acceptable salt, prodrug, solvate, hydrate, isomer, or a tautomer thereof, wherein:

$X^1$ is O or S;

$R^1$ is selected from the group consisting of

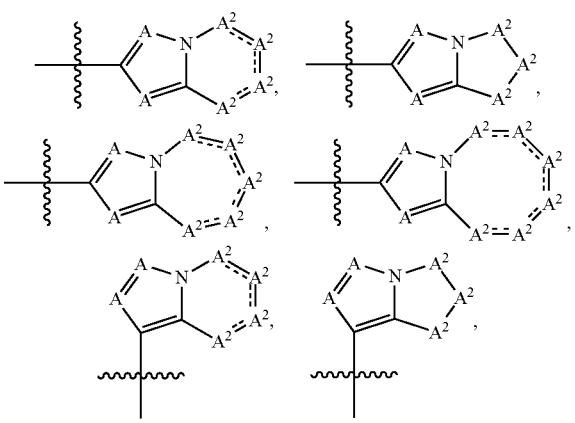

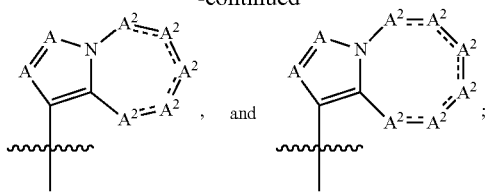

wherein ═ represents a single bond or a double bond provided that the ring comprising one or more A² is a non-aromatic ring;

each A is independently CR^{5a1} or N;

each A² is independently CR^{5a2}, C(R^{5a2})_2, N, NR^{5a2}, O, S, or S(O)_2;

R² is

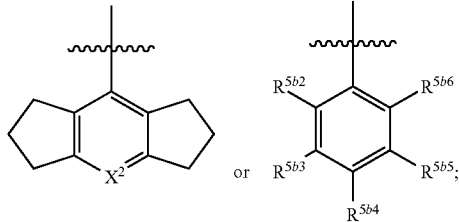

X² is N or CR^{5b1};

R³ and R⁴ are H;

each R^{5a1} is independently H, D, halogen, —OH, —CN, —NO_2, —SR⁶, —OR⁶, —NHR⁶, —NR⁶R⁷, —NR⁶C(O)R⁶, —NR⁶C(O)OR⁶, —NR⁶C(O)NR⁶, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —CH_2—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —CH_2—$C_3$-$C_8$cycloalkyl are optionally substituted with D, —CN, halogen, $C_1$-$C_6$alkyl, —OR⁶, —NH_2, —NH($C_1$-$C_6$alkyl), —N($C_1$-$C_6$alkyl)_2, —NR⁶C(O)OR⁶, or —NR⁶C(O)R⁶;

each R^{5a2} is independently H, D, halogen, OH, —CN, —NO_2, —SR⁶, —OR⁶, —NHR⁶, —NR⁶R⁷, —C(O)R⁶, —S(O)_2R⁶, —C(O)OR⁶, —C(O)NR⁶, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —CH_2—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —CH_2—$C_3$-$C_8$cycloalkyl are optionally substituted with D, —CN, halogen, $C_1$-$C_6$alkyl, —OR⁶, —NH_2, —NH($C_1$-$C_6$alkyl), —N($C_1$-$C_6$alkyl)_2, —NR⁶C(O)OR⁶, or —NR⁶C(O)R⁶, —NR⁶C(O)NR⁶, —NR⁶C(O)R⁶, or —NR⁶S(O)_2R⁶; or wherein at least one R^{5a2} is —NHR⁶, —NR⁶R⁷, $C_1$-$C_6$alkyl, or heterocyclyl containing N, wherein the $C_1$-$C_6$alkyl is substituted with —NH_2, —NH($C_1$-$C_6$alkyl), or —N($C_1$-$C_6$alkyl)_2, and wherein the heterocyclyl is optionally substituted with D, —CN, halogen, $C_1$-$C_6$alkyl, —OR⁶, —NH_2, —NH($C_1$-$C_6$alkyl), —N($C_1$-$C_6$alkyl)_2, —NR⁶C(O)OR⁶, or —NR⁶C(O)R⁶, —NR⁶C(O)NR⁶, —NR⁶C(O)R⁶, or —NR⁶S(O)_2R⁶;

R^{5b1} is H, D, halogen, —CN—OR⁶, or $C_1$-$C_6$alkyl, $C_3$-$C_8$cycloalkyl, —C(O)NR⁶, —C(O)OR⁶; wherein the $C_1$-$C_6$alkyl, and $C_3$-$C_8$cycloalkyl, are optionally substituted with D, halogen, —CN, —OR⁶, —NH_2, —NH($C_1$-$C_6$alkyl), or —N($C_1$-$C_6$alkyl)_2;

each R^{5b2}, R^{5b3}, R^{5b4}, R^{5b5}, and R^{5b6} is independently H, D, halogen, OH, —CN, —NO_2, —SR⁶, —OR⁶, —NHR⁶, —NR⁶R⁷, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, —CN, —OR⁶, —NH_2, —NH($C_1$-$C_6$alkyl), or —N($C_1$-$C_6$alkyl)_2; or two adjacent R^{5b2}, R^{5b3}, R^{5b4}, R^{5b5}, and R^{5b6} together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, —CN, $C_1$-$C_6$alkyl, —OR⁶, —NH_2, —NH($C_1$-$C_6$alkyl), or —N($C_1$-$C_6$alkyl)_2; and R⁶ and R⁷ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, and heteroaryl are optionally substituted with D, —CN, halogen, $C_1$-$C_6$alkyl, —OH, —O—$C_1$-$C_6$alkyl, —NH_2, —NH($C_1$-$C_6$alkyl), or —N($C_1$-$C_6$alkyl)_2; or R⁶ and R⁷ together with the atom to which they are attached can form heterocyclyl or heteroaryl containing 1-3 heteroatoms selected from the group consisting of N, S, P and O;

provided that when the ring comprising A and/or A¹ is an imidazole, then at least one A² is N, NR^{5a2}, O, S, or S(O)_2.

Embodiment III-5. A compound of formula Ie:

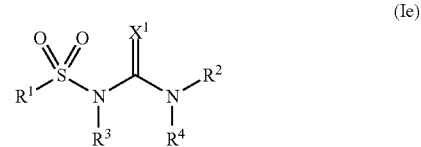

(Ie)

or a pharmaceutically acceptable salt, prodrug, solvate, hydrate, isomer, or a tautomer thereof, wherein:

X¹ is O or S;

R¹ is selected from the group consisting of

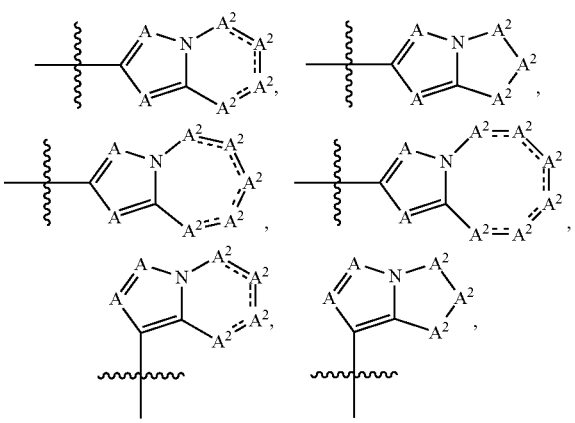

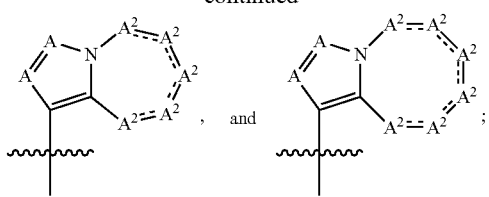

wherein ═ represents a single bond or a double bond provided that the ring comprising one or more $A^2$ is a non-aromatic ring;

each A is independently $CR^{5a1}$ or N;

each $A^2$ is independently $CR^{5a2}$, $C(R^{5a2})_2$, N, $NR^{5a2}$, O, S, or $S(O)_2$;

$R^2$ is

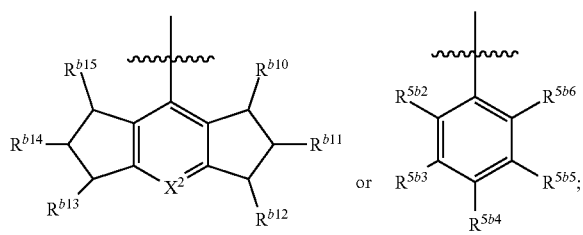

$X^2$ is N or $CR^{5b1}$;

each $R^{b10}$, $R^{b11}$, $R^{b12}$, $R^{b13}$, $R^{b14}$, and $R^{b15}$ is independently H, —OH, or oxo;

$R^3$ and $R^4$ are H;

each $R^{5a1}$ is independently H, D, halogen, OH, CN, —$NO_2$, —$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$;

each $R^{5a2}$ is independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S(O)_2R^6$; or two $R^{5a2}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or two geminal $R^{5a2}$ can form an oxo group;

$R^{5b1}$ is H, D, halogen, —CN—$OR^6$, or $C_1$-$C_6$alkyl, $C_3$-$C_8$cycloalkyl, —$C(O)NR^6$, —$C(O)OR^6$; wherein the $C_1$-$C_6$alkyl, and $C_3$-$C_8$cycloalkyl, are optionally substituted with D, halogen, —CN, —$OR^6$, —$NH_2$, —$NH(C_1$-$C_6$alkyl), or —$N(C_1$-$C_6$alkyl)$_2$;

each $R^{5b2}$, $R^{5b3}$, $R^{5b4}$, $R^{5b5}$, and $R^{5b6}$ is independently H, D, halogen, OH, —CN, —$NO_2$, —$SR^6$, —$OR^6$, —$NHR^6$, —$NR^6R^7$, $C_1$-$C_6$alkyl, $C_2$-$C_6$alkenyl, $C_4$-$C_8$cycloalkenyl, $C_3$-$C_8$cycloalkyl, or $C_2$-$C_6$alkynyl; wherein the $C_1$-$C_6$alkyl, $C_2$-$C_6$alkenyl, $C_4$-$C_8$cycloalkenyl, $C_3$-$C_8$cycloalkyl, and $C_2$-$C_6$alkynyl are optionally substituted with D, halogen, —CN, —$OR^6$, —$NH_2$, —$NH(C_1$-$C_6$alkyl), or —$N(C_1$-$C_6$alkyl)$_2$; or two adjacent $R^{5b2}$, $R^{5b3}$, $R^{5b4}$, $R^{5b5}$, and $R^{5b6}$ together with the atoms to which they are attached can form $C_3$-$C_8$cycloalkyl, heterocyclyl, aryl, or heteroaryl, wherein $C_3$-$C_8$cycloalkyl, heterocyclyl, aryl, or heteroaryl are optionally substituted with halogen, —CN, $C_1$-$C_6$alkyl, —$OR^6$, —$NH_2$, —$NH(C_1$-$C_6$alkyl), or —$N(C_1$-$C_6$alkyl)$_2$; and $R^6$ and $R^7$ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, and heteroaryl are optionally substituted with D, —CN, halogen, $C_1$-$C_6$alkyl, —OH, —O—$C_1$-$C_6$alkyl, —$NH_2$, —$NH(C_1$-$C_6$alkyl), or —$N(C_1$-$C_6$alkyl)$_2$; or $R^6$ and $R^7$ together with the atom to which they are attached can form heterocyclyl or heteroaryl containing 1-3 heteroatoms selected from the group consisting of N, S, P and O;

provided that when the ring comprising A and/or $A^1$ is an imidazole, then at least one $A^2$ is N, $NR^{5a2}$, O, S, or $S(O)_2$.

Embodiment III-6. The compound of any one of Embodiments III-1 and III-3 to III-5, or a pharmaceutically acceptable salt, prodrug, solvate, hydrate, isomer, or tautomer thereof, wherein $X^1$ is O.

Embodiment III-7. The compound of any one of Embodiments III-1 to III-6, or a pharmaceutically acceptable salt, prodrug, solvate, hydrate, isomer, or tautomer thereof, wherein $R^2$ is

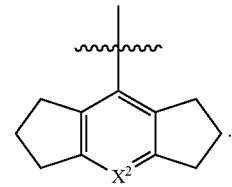

Embodiment III-8. The compound of Embodiment III-7, or a pharmaceutically acceptable salt, prodrug, solvate, hydrate, isomer, or tautomer thereof, wherein $X^2$ is $CR^{5b1}$.

Embodiment III-9. The compound of Embodiment III-8, or a pharmaceutically acceptable salt, prodrug, solvate, hydrate, isomer, or tautomer thereof, wherein $R^{5b1}$ is H, halogen, or $C_1$-$C_6$alkyl.

Embodiment III-10. The compound of Embodiment III-8, or a pharmaceutically acceptable salt, prodrug, solvate, hydrate, isomer, or tautomer thereof, wherein $R^{5b1}$ is H, fluoro, chloro, or methyl.

Embodiment III-11. The compound of any one of Embodiments III-1 to III-10, or a pharmaceutically acceptable salt, prodrug, solvate, hydrate, isomer, or tautomer thereof, wherein $R^2$ is

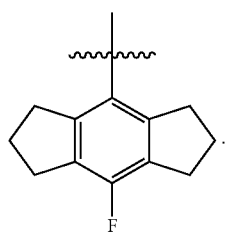 [SMILES: *c1c2c(c(F)c3c1CCC3)CCC2]

Embodiment III-12. The compound of any one of Embodiments III-1 to III-10, or a pharmaceutically acceptable salt, prodrug, solvate, hydrate, isomer, or tautomer thereof, wherein $R^2$ is

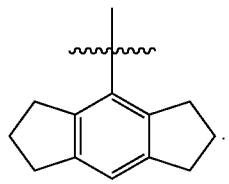 [SMILES: *c1c2c(cc3c1CCC3)CCC2]

Embodiment III-13. The compound of any one of Embodiments III-1 to III-6, or a pharmaceutically acceptable salt, prodrug, solvate, hydrate, isomer, or tautomer thereof, wherein $R^2$ is

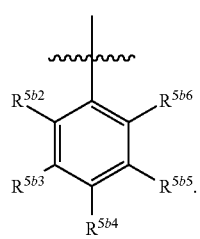

Embodiment III-14. The compound of Embodiment III-13, or a pharmaceutically acceptable salt, prodrug, solvate, hydrate, isomer, or tautomer thereof, wherein each $R^{5b2}$, $R^{5b3}$, $R^{5b4}$, $R^{5b5}$, and $R^{5b6}$ is independently H, D, halogen, OH, CN, —NO$_2$, —OR$^6$, $C_1$-$C_6$alkyl, $C_2$-$C_6$alkenyl, $C_4$-$C_8$cycloalkenyl, or $C_3$-$C_8$cycloalkyl.

Embodiment III-15. The compound of any one of Embodiments III-1 to III-13, or a pharmaceutically acceptable salt, prodrug, solvate, hydrate, isomer, or tautomer thereof, wherein $R^2$ is

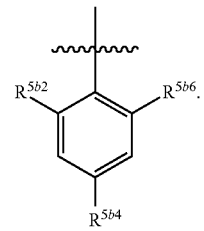

Embodiment III-16. The compound of Embodiment III-15, or a pharmaceutically acceptable salt, prodrug, solvate, hydrate, isomer, or tautomer thereof, wherein each $R^{5b2}$, $R^{5b3}$, $R^{5b4}$, $R^{5b5}$, and $R^{5b6}$ is independently selected from the group consisting of H, D, halogen, $C_1$-$C_6$alkyl, $C_3$-$C_8$cycloalkyl, and —CN.

Embodiment III-17. The compound of any one of Embodiments III-1 to III-16, or a pharmaceutically acceptable salt, prodrug, solvate, hydrate, isomer, or tautomer thereof, wherein $R^2$ is selected from the group consisting of

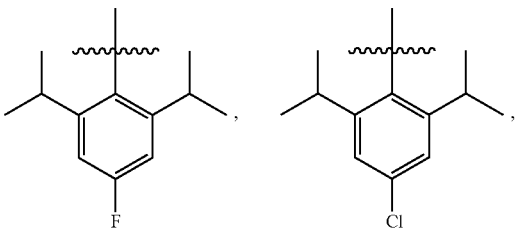

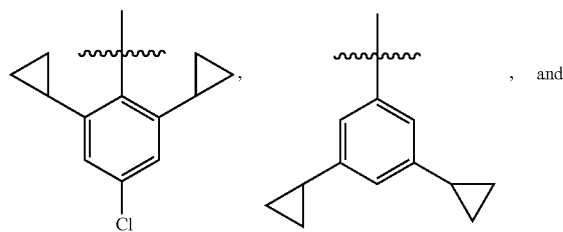

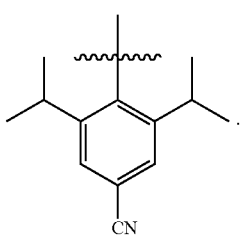

Embodiment III-18. The compound of any one of Embodiments III-1 to III-17, or a pharmaceutically acceptable salt, prodrug, solvate, hydrate, isomer, or tautomer thereof, wherein $R^2$ is selected from the group consisting of

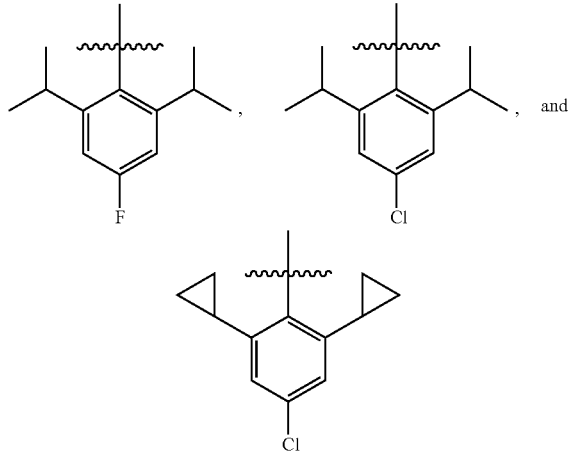

Embodiment III-19. The compound of any one of Embodiments III-1 to III-18, or a pharmaceutically acceptable salt, prodrug, solvate, hydrate, isomer, or tautomer thereof, wherein $R^2$ is

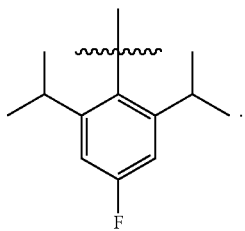 [SMILES: *c1c(C(C)C)cc(F)cc1C(C)C]

Embodiment III-20. The compound of any one of Embodiments III-1 to III-13, or a pharmaceutically acceptable salt, prodrug, solvate, hydrate, isomer, or tautomer thereof, wherein
$R^2$ is

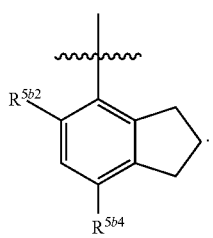

Embodiment III-21. The compound of Embodiment III-20, or a pharmaceutically acceptable salt, prodrug, solvate, hydrate, isomer, or tautomer thereof, wherein each $R^{5b2}$ and $R^{5b4}$ is selected from the group consisting of H, D, halogen, $C_1$-$C_6$alkyl, $C_3$-$C_8$cycloalkyl, and —CN.

Embodiment III-22. The compound of any one of Embodiments III-20 and III-21, or a pharmaceutically acceptable salt, prodrug, solvate, hydrate, isomer, or tautomer thereof, wherein $R^2$ is

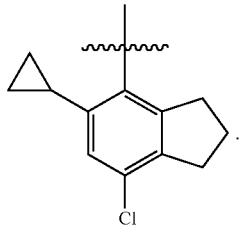 [SMILES: *c1c(C2CC2)cc(Cl)c2c1CCC2]

Embodiment III-23. The compound of any one of Embodiments III-1 to III-22, or a pharmaceutically acceptable salt, prodrug, solvate, hydrate, isomer, or tautomer thereof, wherein $R^1$ is

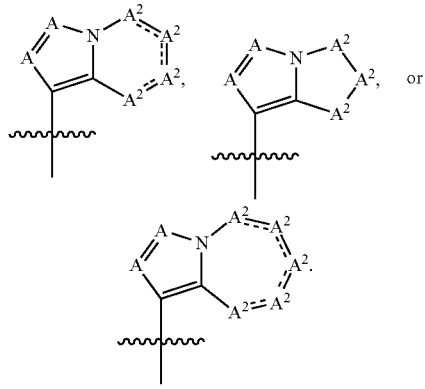

Embodiment III-24. The compound of any one of Embodiments III-1 to III-22, or a pharmaceutically acceptable salt, prodrug, solvate, hydrate, isomer, or tautomer thereof, wherein $R^1$ is

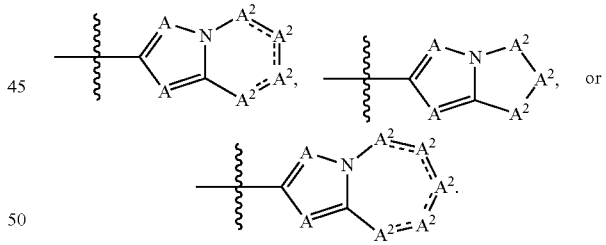

Embodiment III-25. The compound of any one of Embodiments III-1 to III-24, or a pharmaceutically acceptable salt, prodrug, solvate, hydrate, isomer, or tautomer thereof, wherein one A is $CR^{5a1}$ and the other A is N.

Embodiment III-26. The compound of any one of Embodiments III-1 to III-25, or a pharmaceutically acceptable salt, prodrug, solvate, hydrate, isomer, or tautomer thereof, wherein each $A^2$ is independently $C(R^{5a2})_2$, $NR^{5a2}$, or O.

Embodiment III-27. The compound of Embodiment III-26, wherein each $R^{5a2}$ is independently H, —$NHR^6$, —$NR^6R^7$, $C_1$-$C_6$alkyl, or heterocyclyl containing N, wherein the $C_1$-$C_6$alkyl is substituted with —$NH_2$, —NH($C_1$-$C_6$alkyl), or —N($C_1$-$C_6$alkyl)$_2$, and wherein the heterocyclyl is optionally substituted with with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$, —$NR^6C(O)$ $NR^6$, —$NR^6C(O)R^6$, or —$NR^6S(O)_2R^6$.

Embodiment III-28. The compound of Embodiment III-27, wherein $R^1$ is selected from the group consisting of

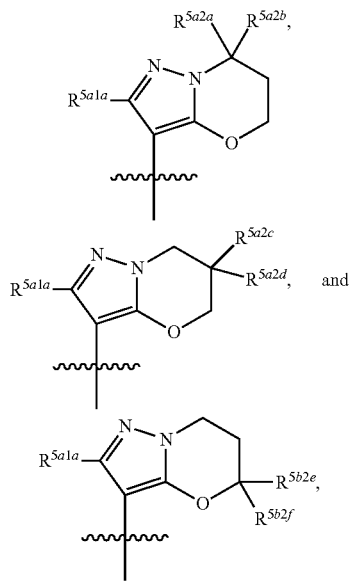

wherein $R^{5a1a}$ is H, D, halogen, OH, CN, —$NO_2$, —$SR^6$, —$OR^6$, —$NHR^6$, —$NR^6R^7$, —$NR^6C(O)R^6$, —$NR^6C(O)$ $OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$; and $R^{5a2a}$, $R^{5a2b}$, $R^{5a2c}$, $R^{5a2d}$, $R^{5a2e}$, and $R^{5a2f}$ are selected from independently H, —$NHR^6$, —$NR^6R^7$, $C_1$-$C_6$alkyl, or heterocyclyl containing N, wherein the $C_1$-$C_6$alkyl is substituted with —$NH_2$, —$NH(C_1$-$C_6$alkyl), or —$N(C_1$-$C_6$alkyl)$_2$, and wherein the heterocyclyl is optionally substituted with with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)$ $OR^6$, or —$NR^6C(O)R^6$, —$NR^6C(O)NR^6$, —$NR^6C(O)R^6$, or —$NR^6S(O)_2R^6$.

Embodiment III-29. The compound of any one of Embodiments III-1 to III-23, or a pharmaceutically acceptable salt, prodrug, solvate, hydrate, isomer, or tautomer thereof, wherein $R^1$ is

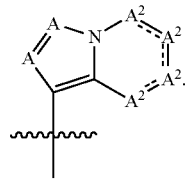

Embodiment III-30. The compound of Embodiment III-29, or a pharmaceutically acceptable salt, prodrug, solvate, hydrate, isomer, or tautomer thereof, wherein one A is $CR^{5a1}$ and the other A is N.

Embodiment III-31. The compound of any one of Embodiments III-29 to III-30, or a pharmaceutically acceptable salt, prodrug, solvate, hydrate, isomer, or tautomer thereof, wherein each $A^2$ is independently $C(R^{5a2})_2$, $NR^{5a2}$, or O.

Embodiment III-32. The compound of any one of Embodiments III-29 to III-30, or a pharmaceutically acceptable salt, prodrug, solvate, hydrate, isomer, or tautomer thereof, wherein each $R^{5a2}$ is independently H, halogen, OH, —$OR^6$, —$NHR^6$, —$NR^6R^7$, $C_1$-$C_6$alkyl, $C_3$-$C_8$cycloalkyl, heterocyclyl, aryl, heteroaryl, or —$CH_2$—$C_3$-$C_8$cycloalkyl.

Embodiment III-33. The compound of any one of Embodiments III-20 to III-32, or a pharmaceutically acceptable salt, prodrug, solvate, hydrate, isomer, or tautomer thereof, wherein two $R^{5a2}$ together with the atoms to which they are attached can form $C_3$-$C_8$cycloalkyl or heterocyclyl.

Embodiment III-34. The compound of any one of Embodiments III-1 to III-22, or a pharmaceutically acceptable salt, prodrug, solvate, hydrate, isomer, or tautomer thereof, wherein $R^1$ is

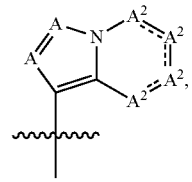

which is a formula of

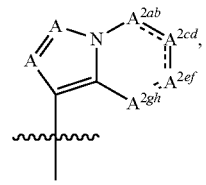

wherein $A^{2ab}$ is selected from $CR^{5a2}$, $C(R^{5a2a})(R^{5a2b})$, N, $NR^{5a2}$, O, S, or $S(O)_2$;

$A^{2cd}$ is selected from $CR^{5a2}$, $C(R^{5a2c})(R^{5a2d})$, N, $NR^{5a2}$, O, S, or $S(O)_2$;

$A^{2ef}$ is selected from $CR^{5a2}$, $C(R^{5a2e})(R^{5a2f})$, N, $NR^{5a2}$, O, S, or $S(O)_2$; and $A^{2gh}$ is selected from $CR^{5a2}$, $C(R^{5a2g})(R^{5a2h})$, N, $NR^{5a2}$, O, S, or $S(O)_2$;

each $R^{5a2a}$, $R^{5a2b}$, $R^{5a2c}$, $R^{5a2d}$, $R^{5a2e}$, $R^{5a2f}$, $R^{5a2g}$, and $R^{5a2h}$ are independently H, D, halogen, OH, CN, —$NO_2$— $SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_5$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S$ $(O)_2R^6$; or two $R^{5a2a}$, $R^{5a2b}$, $R^{5a2c}$, $R^{5a2d}$, $R^{5a2e}$, $R^{5a2f}$, $R^{5a2g}$, and $R^{5a2h}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or two geminal $R^{5a2a}$, $R^{5a2b}$, $R^{5a2c}$, $R^{5a2d}$, $R^{5a2e}$, $R^{5a2f}$, $R^{5a2g}$, and $R^{5a2h}$ can form an oxo group.

Embodiment III-35. The compound of Embodiment III-34, or a pharmaceutically acceptable salt, prodrug, solvate, hydrate, isomer, or tautomer thereof, wherein $R^1$ is.

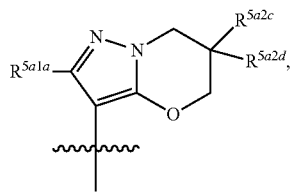

wherein wherein $R^{5a1a}$ is H, D, halogen, OH, CN, —$NO_2$, —$SR^6$, —$OR^6$, —$NHR^6$, —$NR^6R^7$, —$NR^6C(O)R^6$, —$NR^6C(O)OR^6$, —$NR^6C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, or —$NR^6C(O)R^6$;

$R^{5a2c}$ and $R^{5a2d}$ are each independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S(O)_2R^6$; or $R^{5a2c}$ and $R^{5a2d}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or $R^{5a2c}$ and $R^{5a2d}$ can form an oxo group.

Embodiment III-36. The compound of Embodiment III-35, or a pharmaceutically acceptable salt, prodrug, solvate, hydrate, isomer, or tautomer thereof, wherein each $R^{5a2c}$ and $R^{5a2d}$ is independently H, halogen, OH, —$OR^6$, —$NHR^6$, —$NR^6R^7$, $C_1$-$C_6$alkyl, $C_3$-$C_8$cycloalkyl, heterocyclyl, aryl, heteroaryl, or —$CH_2$—$C_3$-$C_8$cycloalkyl.

Embodiment III-37. The compound of any one of Embodiments III-35 to III-36, or a pharmaceutically acceptable salt, prodrug, solvate, hydrate, isomer, or tautomer thereof, wherein $R^{5a2c}$ and $R^{5a2d}$ together with the atoms to which they are attached can form $C_3$-$C_8$cycloalkyl or heterocyclyl.

Embodiment III-38. The compound of Embodiment III-34, or a pharmaceutically acceptable salt, prodrug, solvate, hydrate, isomer, or tautomer thereof, wherein $R^1$ is.

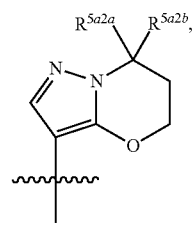

wherein $R^{5a2a}$ and $R^{5a2b}$ are each independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S(O)_2R^6$; or $R^{5a2a}$ and together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or $R^{5a2a}$ and $R^{5a2b}$ can form an oxo group.

Embodiment III-39. The compound of Embodiment III-38, or a pharmaceutically acceptable salt, prodrug, solvate, hydrate, isomer, or tautomer thereof, wherein each $R^{5a2a}$ and $R^{5a2b}$ is independently H, halogen, OH, —$OR^6$, —$NHR^6$, —$NR^6R^7$, $C_1$-$C_6$alkyl, $C_3$-$C_8$cycloalkyl, heterocyclyl, aryl, heteroaryl, or —$CH_2$—$C_3$-$C_8$cycloalkyl.

Embodiment III-40. The compound of any one of Embodiments III-38 to III-39, or a pharmaceutically acceptable salt, prodrug, solvate, hydrate, isomer, or tautomer thereof, wherein $R^{5a2a}$ and $R^{5a2b}$ together with the atoms to which they are attached can form $C_3$-$C_8$cycloalkyl or heterocyclyl.

Embodiment III-41. The compound of Embodiment III-33, or a pharmaceutically acceptable salt, prodrug, solvate, hydrate, isomer, or tautomer thereof, wherein $R^1$ is.

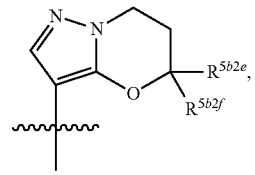

wherein $R^{5a2e}$ and $R^{5a2f}$ are each independently independently H, D, halogen, OH, CN, —NO$_2$, —SR$^6$, —OR$^6$, —NHR$^6$, —NR$^6$R$^7$, —C(O)R$^6$, —S(O)$_2$R$^6$, —C(O)OR$^6$, —C(O)NR$^6$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, —NR$^6$C(O)R$^6$, NR$^6$C(O)NR$^6$, —NR$^6$C(O)R$^6$, or —NR$^6$S(O)$_2$R$^6$; or $R^{5a2e}$ and $R^{5a2f}$ together with the atoms to which they are attached can form C$_3$-C$_8$cycloalkyl or heterocyclyl; wherein the heterocyclyl contains 1-3 heteroatoms selected from the group consisting of N, S, P and O; wherein the C$_3$-C$_8$cycloalkyl and heterocyclyl are optionally substituted with D, halogen, C$_1$-C$_6$alkyl, —OR$^6$, —NH$_2$, —NH(C$_1$-C$_6$alkyl), —N(C$_1$-C$_6$alkyl)$_2$, —S(O)$_2$—R$^6$, —COR$^6$, NR$^6$C(O)OR$^6$, —NR$^6$C(O)R$^6$, —NR$^6$C(O)NR$^6$, or —NR$^6$S(O)$_2$R$^6$; or $R^{5a2e}$ and $R^{5a2f}$ can form an oxo group.

Embodiment III-42. The compound of Embodiment III-41, or a pharmaceutically acceptable salt, prodrug, solvate, hydrate, isomer, or tautomer thereof, wherein each $R^{5a2e}$ and $R^{5a2f}$ is independently H, halogen, OH, —OR$^6$, —NHR$^6$, —NR$^6$R$^7$, C$_1$-C$_6$alkyl, C$_3$-C$_8$cycloalkyl, heterocyclyl, aryl, heteroaryl, or —CH$_2$—C$_3$-C$_8$cycloalkyl.

Embodiment III-43. The compound of any one of Embodiments III-41 to III-42, or a pharmaceutically acceptable salt, prodrug, solvate, hydrate, isomer, or tautomer thereof, wherein $R^{5a2e}$ and $R^{5a2f}$ together with the atoms to which they are attached can form C$_3$-C$_8$cycloalkyl or heterocyclyl.

Embodiment III-44. The compound of Embodiments III-34, or a pharmaceutically acceptable salt, prodrug, solvate, hydrate, isomer, or tautomer thereof, wherein R$^1$ is.

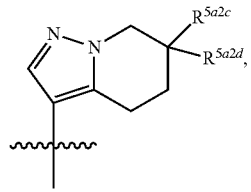

wherein $R^{5a2c}$ and $R^{5a2d}$ are each independently H, D, halogen, OH, CN, —NO$_2$, —SR$^6$, —OR$^6$, —NHR$^6$, —NR$^6$R$^7$, —C(O)R$^6$, —S(O)$_2$R$^6$, —C(O)OR$^6$, —C(O)NR$^6$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, —CN, halogen, C$_1$-C$_6$alkyl, —OR$^6$, —NH$_2$, —NH(C$_1$-C$_6$alkyl), —N(C$_1$-C$_6$alkyl)$_2$, —NR$^6$C(O)OR$^6$, —NR$^6$C(O)R$^6$, NR$^6$C(O)NR$^6$, —NR$^6$C(O)R$^6$, or —NR$^6$S(O)$_2$R$^6$; or $R^{5a2c}$ and $R^{5a2d}$ together with the atoms to which they are attached can form C$_3$-C$_8$cycloalkyl or heterocyclyl; wherein the heterocyclyl contains 1-3 heteroatoms selected from the group consisting of N, S, P and O; wherein the C$_3$-C$_8$cycloalkyl and heterocyclyl are optionally substituted with D, halogen, C$_1$-C$_6$alkyl, —OR$^6$, —NH$_2$, —NH(C$_1$-C$_6$alkyl), —N(C$_1$-C$_6$alkyl)$_2$, —S(O)$_2$—R$^6$, —COR$^6$, NR$^6$C(O)OR$^6$, —NR$^6$C(O)R$^6$, —NR$^6$C(O)NR$^6$, or —NR$^6$S(O)$_2$R$^6$; or $R^{5a2c}$ and $R^{5a2d}$ can form an oxo group.

Embodiment III-45. The compound of Embodiment III-44, or a pharmaceutically acceptable salt, prodrug, solvate, hydrate, isomer, or tautomer thereof, wherein each $R^{5a2c}$ and $R^{5a2d}$ is independently H, halogen, OH, —OR$^6$, —NHR$^6$, —NR$^6$R$^7$, C$_1$-C$_6$alkyl, C$_3$-C$_8$cycloalkyl, heterocyclyl, aryl, heteroaryl, or —CH$_2$—C$_3$-C$_8$cycloalkyl.

Embodiment III-46. The compound of any one of Embodiments III-44 to III-45, or a pharmaceutically acceptable salt, prodrug, solvate, hydrate, isomer, or tautomer thereof, wherein $R^{5a2c}$ and $R^{5a2d}$ together with the atoms to which they are attached can form C$_3$-C$_8$cycloalkyl or heterocyclyl.

Embodiment III-47. The compound of Embodiment III-29, or a pharmaceutically acceptable salt, prodrug, solvate, hydrate, isomer, or tautomer thereof, wherein R$^1$ is selected from the group consisting of

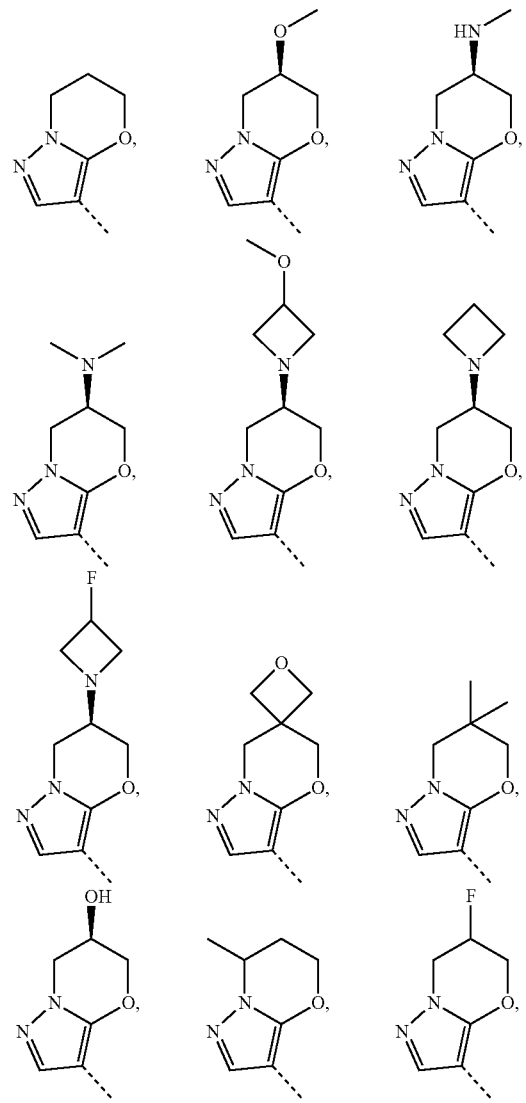

-continued

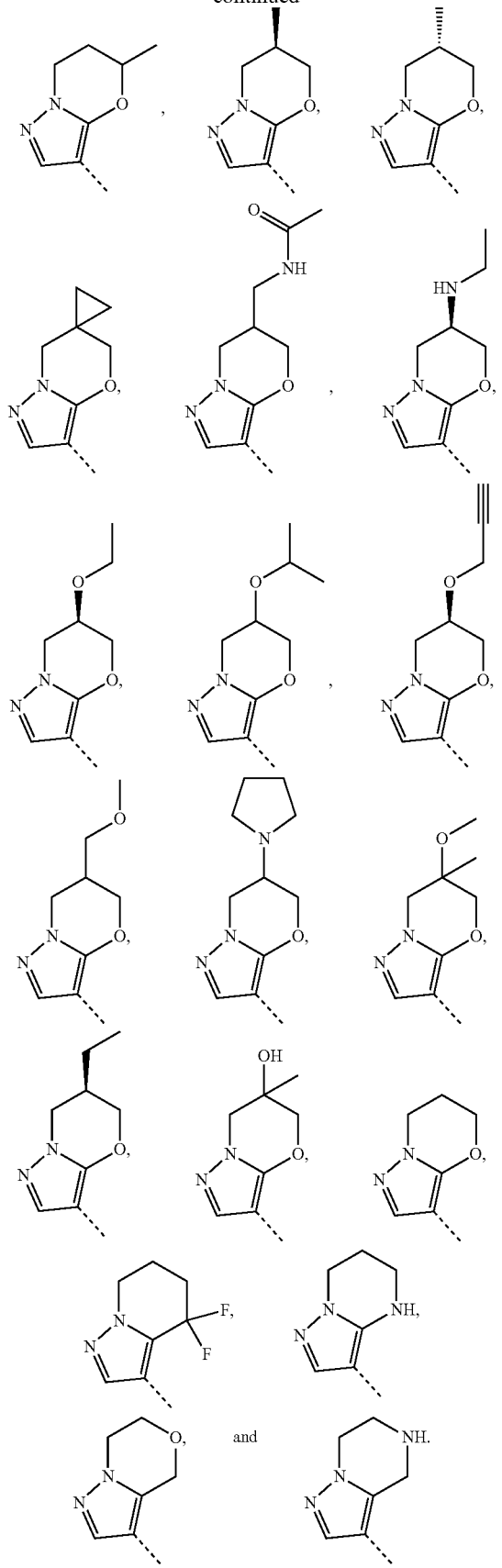

Embodiment III-48. The compound of Embodiment III-29, or a pharmaceutically acceptable salt, prodrug, solvate, hydrate, isomer, or tautomer thereof, wherein $R^1$ is selected from the group consisting of

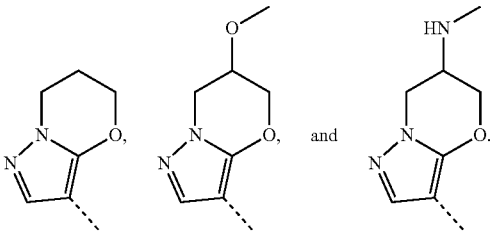

Embodiment III-49. The compound of Embodiment III-29, or a pharmaceutically acceptable salt, prodrug, solvate, hydrate, isomer, or tautomer thereof, wherein $R^1$ is selected from the group consisting of

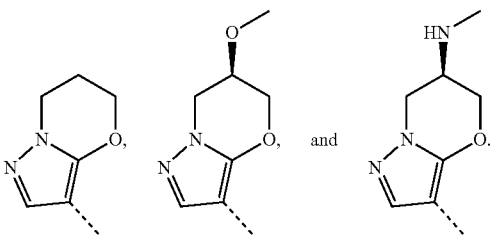

Embodiment III-50. The compound of any one of Embodiments III-1 to III-22, or a pharmaceutically acceptable salt, prodrug, solvate, hydrate, isomer, or tautomer thereof, wherein $R^1$ is

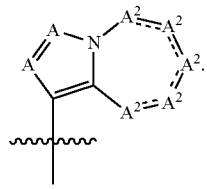

Embodiment III-51. The compound of Embodiment III-50, or a pharmaceutically acceptable salt, prodrug, solvate, hydrate, isomer, or tautomer thereof, wherein one A is $CR^{5a1}$ and the other A is N.

Embodiment III-52. The compound of any one of Embodiments III-50 to III-51, or a pharmaceutically acceptable salt, prodrug, solvate, hydrate, isomer, or tautomer thereof, wherein each $A^2$ is independently $C(R^{5a2})_2$, $NR^{5a2}$, or O.

Embodiment III-53. The compound of any one of Embodiments III-1 to III-22, or a pharmaceutically acceptable salt, prodrug, solvate, hydrate, isomer, or tautomer thereof, wherein $R^1$ is

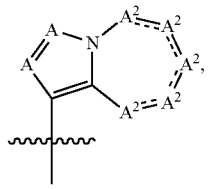

which is a formula of

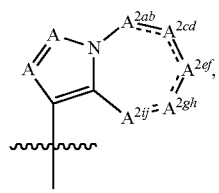

wherein.

$A^{2ab}$ is selected from $CR^{5a2}$, $C(R^{5a2a})(R^{5a2b})$, N, $NR^{5a2}$, O, S, or $S(O)_2$;

$A^{2cd}$ is selected from $CR^{5a2}$, $C(R^{5a2c})(R^{5a2d})$, N, $NR^{5a2}$, O, S, or $S(O)_2$;

$A^{2ef}$ is selected from $CR^{5a2}$, $C(R^{5a2e})(R^{5a2f})$, N, $NR^{5a2}$, O, S, or $S(O)_2$; and $A^{2gh}$ is selected from $CR^{5a2}$, $C(R^{5a2g})(R^{5a2h})$, N, $NR^{5a2}$, O, S, or $S(O)_2$;

$A^{2ij}$ is selected from $CR^{5a2}$, $C(R^{5a2i})(R^{5a2j})$, N, $NR^{5a2}$, O, S, or $S(O)_2$;

each $R^{5a2a}$, $R^{5a2b}$, $R^{5a2c}$, $R^{5a2d}$, $R^{5a2e}$, $R^{5a2f}$, $R^{5a2g}$, $R^{5a2h}$, $R^{5a2i}$, and $R^{5a2j}$ are independently H, D, halogen, OH, CN, $-NO_2$ $-SR^6$, $-OR^6$, $-NHR^6$, $-NR^6R^7$, $-C(O)R^6$, $-S(O)_2R^6$, $-C(O)OR^6$, $-C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or $-CH_2-C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and $-CH_2-C_3$-$C_8$cycloalkyl are optionally substituted with D, $-CN$, halogen, $C_1$-$C_6$alkyl, $-OR^6$, $-NH_2$, $-NH(C_1$-$C_6$alkyl), $-N(C_1$-$C_6$alkyl)$_2$, $-NR^6C(O)OR^6$, $-NR^6C(O)R^6$, $NR^6C(O)NR^6$, $-NR^6C(O)R^6$, or $-NR^6S(O)_2R^6$; or two $R^{5a2a}$, $R^{5a2b}$, $R^{5a2c}$, $R^{5a2d}$, $R^{5a2e}$, $R^{5a2f}$, $R^{5a2g}$, $R^{5a2h}$, $R^{5a2i}$, and $R^{5a2j}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, $-OR^6$, $-NH_2$, $-NH(C_1$-$C_6$alkyl), $-N(C_1$-$C_6$alkyl)$_2$, $-S(O)_2-R^6$, $-COR^6$, $NR^6C(O)OR^6$, $-NR^6C(O)R^6$, $-NR^6C(O)NR^6$, or $-NR^6S(O)_2R^6$; or two geminal $R^{5a2a}$, $R^{5a2b}$, $R^{5a2c}$, $R^{5a2d}$, $R^{5a2e}$, $R^{5a2f}$, $R^{5a2g}$, $R^{5a2h}$, $R^{5a2i}$, and $R^{5a2j}$ can form an oxo group.

Embodiment III-54. The compound of Embodiment III-50, or a pharmaceutically acceptable salt, prodrug, solvate, hydrate, isomer, or tautomer thereof, wherein $R^1$ is

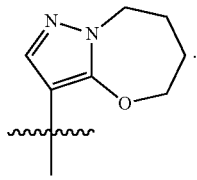 [SMILES: *c1cnn2c1OCCCC2]

Embodiment III-55. The compound of any one of Embodiments III-1 to III-22, or a pharmaceutically acceptable salt, prodrug, solvate, hydrate, isomer, or tautomer thereof, wherein $R^1$ is

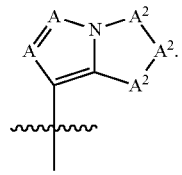

Embodiment III-56. The compound of Embodiment III-55, or a pharmaceutically acceptable salt, prodrug, solvate, hydrate, isomer, or tautomer thereof, wherein one A is $CR^{5a1}$ and the other A is N.

Embodiment III-57. The compound of any one of Embodiments III-55 to III-56, or a pharmaceutically acceptable salt, prodrug, solvate, hydrate, isomer, or tautomer thereof, wherein each $A^2$ is independently $C(R^{5a2})_2$, $NR^{5a2}$, or O.

Embodiment III-58. The compound of any one of Embodiments III-1 to III-22, or a pharmaceutically acceptable salt, prodrug, solvate, hydrate, isomer, or tautomer thereof, wherein $R^1$ is

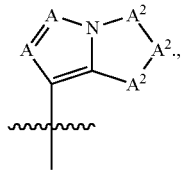

which is a formula of

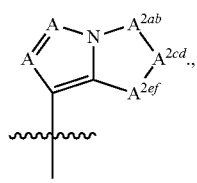

wherein.

$A^{2ab}$ is selected from $C(R^{5a2a})(R^{5a2b})$, $NR^{5a2}$, O, S, or $S(O)_2$;

$A^{2cd}$ is selected from $C(R^{5a2c})(R^{5a2d})$, $NR^{5a2}$, O, S, or $S(O)_2$;

$A^{2ef}$ is selected from $C(R^{5a2e})(R^{5a2f})$, $NR^{5a2}$, O, S, or $S(O)_2$; and each $R^{5a2a}$, $R^{5a2b}$, $R^{5a2c}$, $R^{5a2d}$, $R^{5a2e}$, and $R^{5a2f}$ are independently H, D, halogen, OH, CN, —$NO_2$, —$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S(O)_2R^6$; or two $R^{5a2a}$, $R^{5a2b}$, $R^{5a2c}$, $R^{5a2d}$, $R^{5a2e}$, and $R^{5a2f}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$; or two geminal $R^{5a2a}$, $R^{5a2b}$, $R^{5a2c}$, $R^{5a2d}$, $R^{5a2e}$, and $R^{5a2f}$ can form an oxo group.

Embodiment III-59. The compound of Embodiment III-55, or a pharmaceutically acceptable salt, prodrug, solvate, hydrate, isomer, or tautomer thereof, wherein $R^1$ is

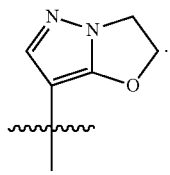 [SMILES: *c1cnn2c1OCC2]

Embodiment III-60. The compound of any one of Embodiments III-1 to III-22, or a pharmaceutically acceptable salt, prodrug, solvate, hydrate, isomer, or tautomer thereof, wherein $R^1$ is

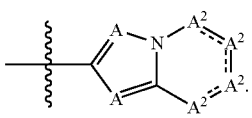

Embodiment III-61. The compound of Embodiment III-60, or a pharmaceutically acceptable salt, prodrug, solvate, hydrate, isomer, or tautomer thereof, wherein one A is $CR^{5a1}$ and the other A is N.

Embodiment III-62. The compound of any one of Embodiments III-60 to III-61, or a pharmaceutically acceptable salt, prodrug, solvate, hydrate, isomer, or tautomer thereof, wherein each $A^2$ is independently $C(R^{5a2})_2$, $NR^{5a2}$, or O.

Embodiment III-63. The compound of any one of Embodiments III-1 to III-22, or a pharmaceutically acceptable salt, prodrug, solvate, hydrate, isomer, or tautomer thereof, wherein $R^1$ is

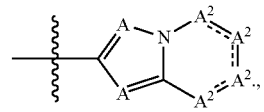

which is a formula of

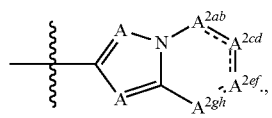

wherein.

$A^{2ab}$ is selected from $CR^{5a2}$, $C(R^{5a2a})(R^{5a2b})$, N, $NR^{5a2}$, O, S, or $S(O)_2$;

$A^{2cd}$ is selected from $CR^{5a2}$, $C(R^{5a2c})(R^{5a2d})$, N, $NR^{5a2}$, O, S, or $S(O)_2$;

$A^{2ef}$ is selected from $CR^{5a2}$, $C(R^{5a2e})(R^{5a2f})$, N, $NR^{5a2}$, O, S, or $S(O)_2$; and $A^{2gh}$ is selected from $CR^{5a2}$, $C(R^{5a2g})(R^{5a2h})$, N, $NR^{5a2}$, O, S, or $S(O)_2$;

each $R^{5a2a}$, $R^{5a2b}$, $R^{5a2c}$, $R^{5a2d}$, $R^{5a2e}$, $R^{5a2f}$, $R^{5a2g}$, and $R^{5a2h}$ are independently H, D, halogen, OH, CN, —$NO_2$—$SR^6$, —$OR^6$, —$NHR^6$, —$NR^6R^7$, —$C(O)R^6$, —$S(O)_2R^6$, —$C(O)OR^6$, —$C(O)NR^6$, $C_1$-$C_6$alkyl, $C_2$-$C_6$alkenyl, $C_2$-$C_6$cycloalkenyl, $C_2$-$C_6$alkynyl, $C_3$-$C_5$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, —CN, halogen, $C_1$-$C_6$alkyl, —$OR^6$, —$NH_2$, —$NH(C_1$-$C_6$alkyl), —$N(C_1$-$C_6$alkyl)$_2$, —$NR^6C(O)OR^6$, —$NR^6C(O)R^6$, $NR^6C(O)NR^6$, —$NR^6C(O)R^6$, or —$NR^6S(O)_2R^6$ or two $R^{5a2a}$, $R^{5a2b}$, $R^{5a2c}$, $R^{5a2d}$, $R^{5a2e}$, $R^{5a2f}$, $R^{5a2g}$, and $R^{5a2h}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —$NH(C_1$-$C_6$alkyl), —$N(C_1$-$C_6$alkyl)$_2$, —$S(O)_2$—$R^6$, —$COR^6$, $NR^6C(O)OR^6$, —$NR^6C(O)R^6$, —$NR^6C(O)NR^6$, or —$NR^6S(O)_2R^6$ or two geminal $R^{5a2a}$, $R^{5a2b}$, $R^{5a2c}$, $R^{5a2d}$, $R^{5a2e}$, $R^{5a2f}$, $R^{5a2g}$, and $R^{5a2h}$ can form an oxo group.

Embodiment III-64. The compound of any one of Embodiments III-1 to III-63, or a pharmaceutically acceptable salt, prodrug, solvate, hydrate, isomer, or tautomer thereof, wherein the === are single bonds in the ring comprising $A^2$, thereby forming a saturated ring.

Embodiment III-65. A compound, or a pharmaceutically acceptable salt, prodrug, solvate, hydrate, isomer, or tautomer thereof, selected from the group consisting of
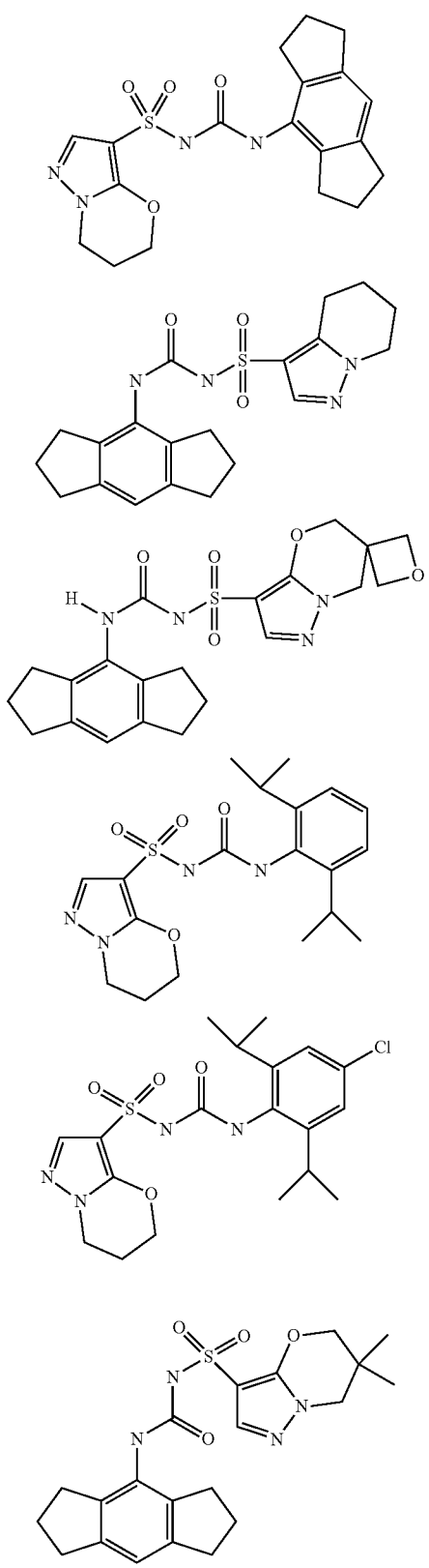
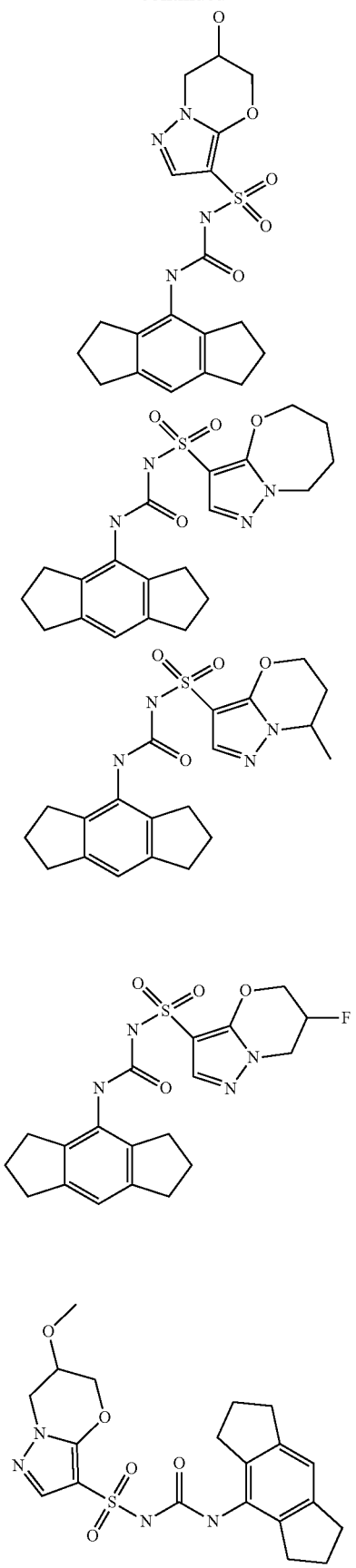

247
-continued
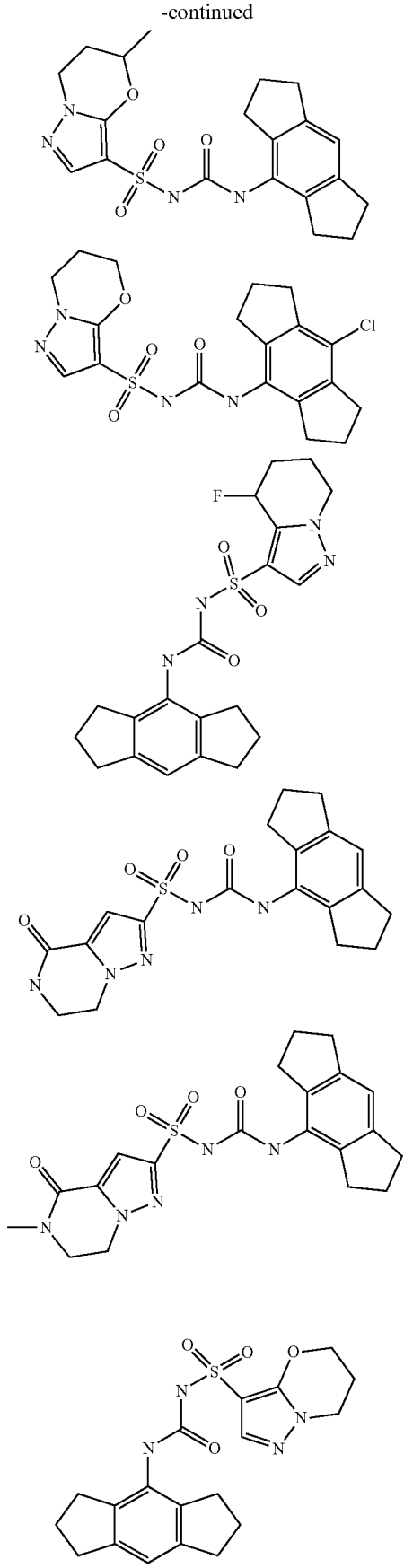
248
-continued
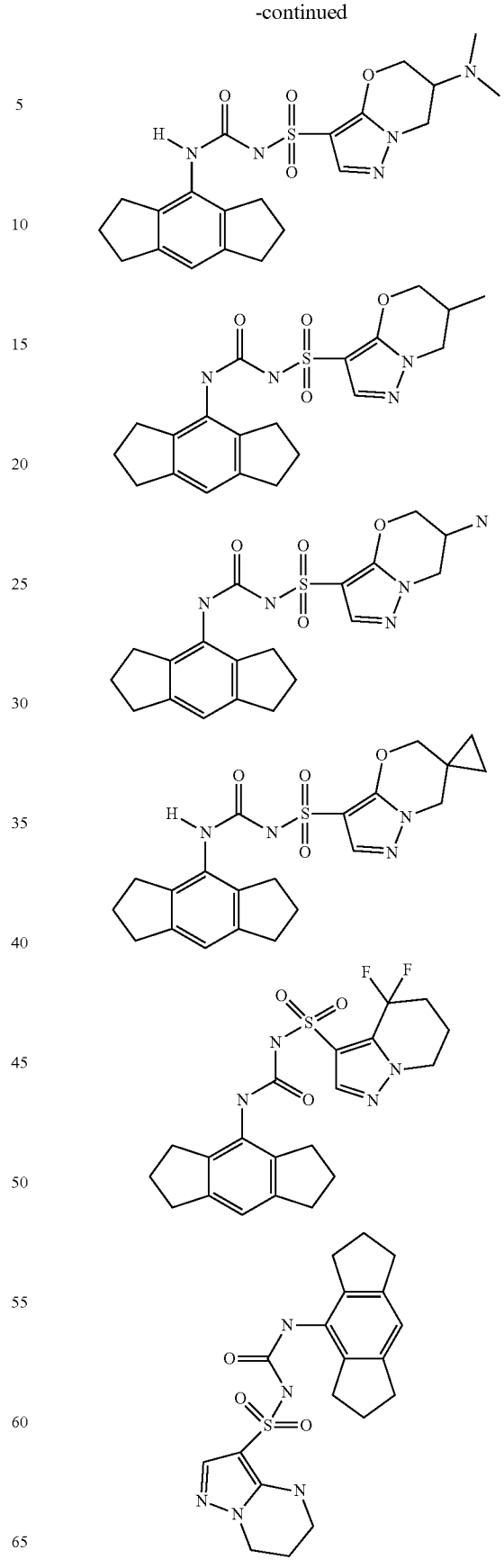

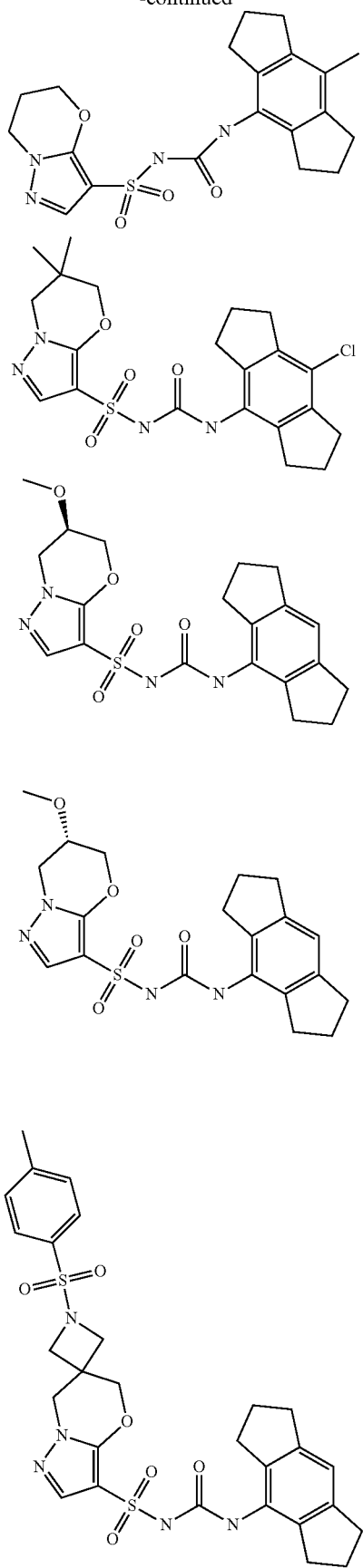
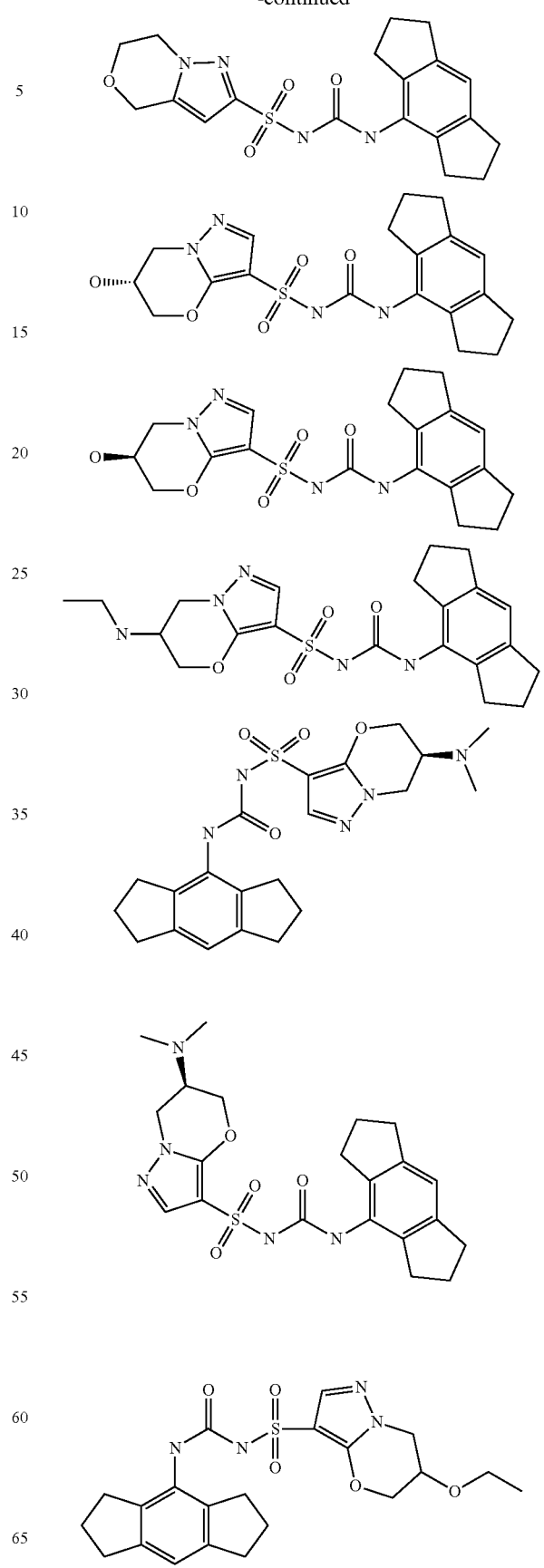

251
-continued
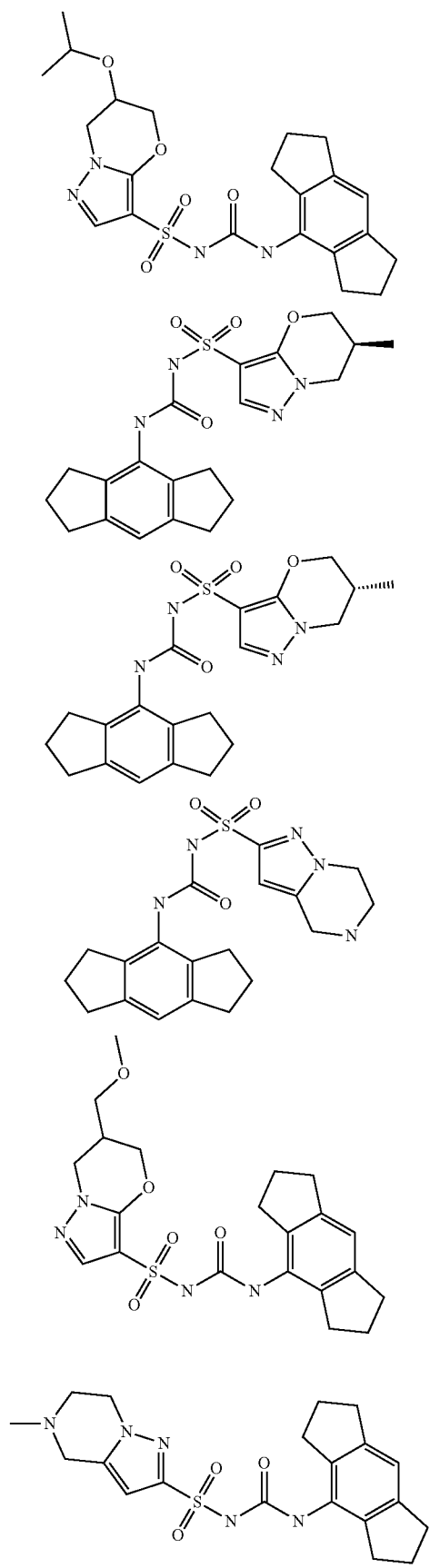
252
-continued
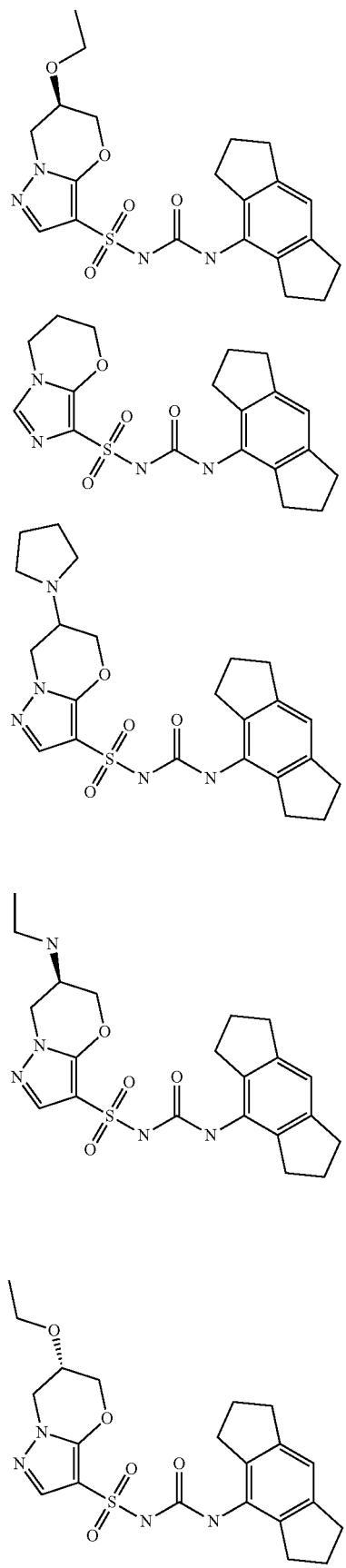

253
-continued
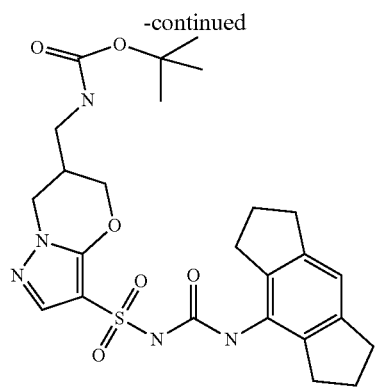
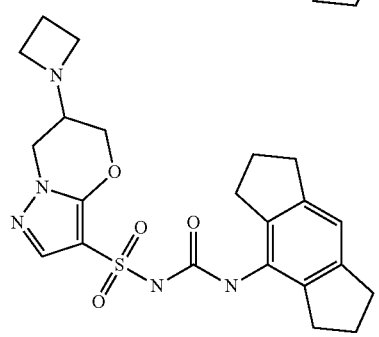
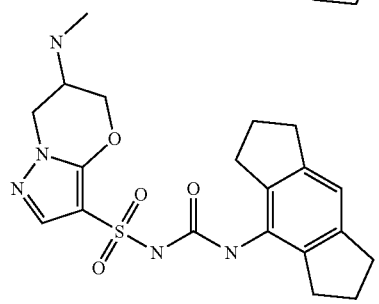
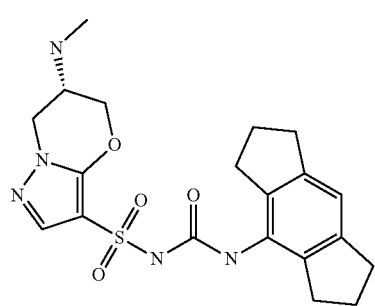
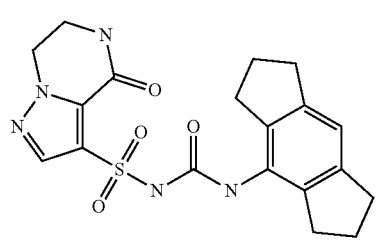
254
-continued
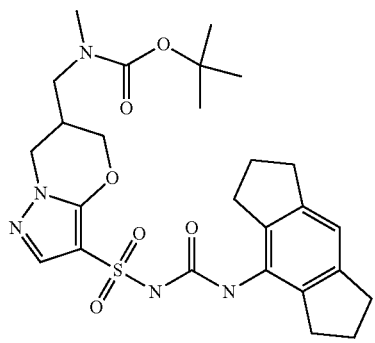
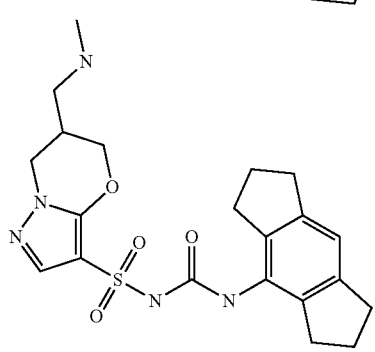
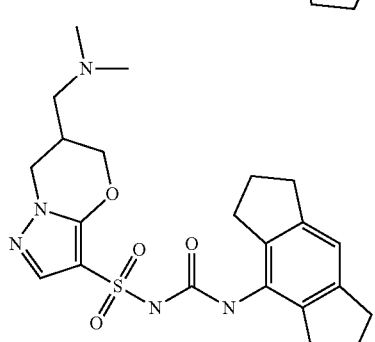
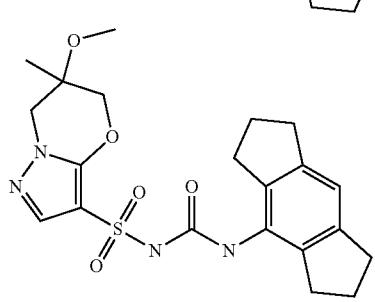
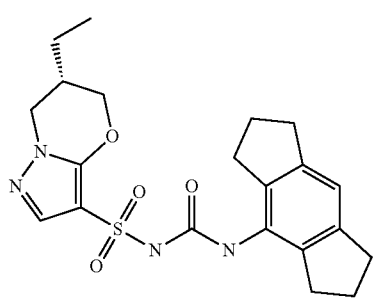

255
-continued
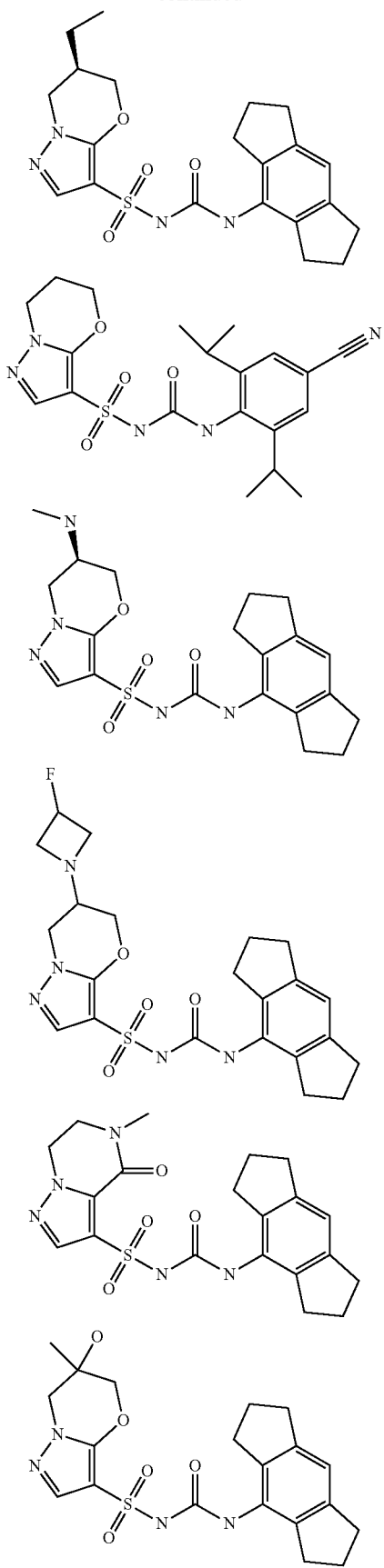 [SMILES: CC[C@H]1COc2c(S(=O)(=O)NC(=O)Nc3c4c(cc5c3CCC5)CCC4)cnn2C1 ; CC(C)c1cc(C#N)cc(C(C)C)c1NC(=O)NS(=O)(=O)c1cnn2c1OCCC2 ; CN[C@H]1COc2c(S(=O)(=O)NC(=O)Nc3c4c(cc5c3CCC5)CCC4)cnn2C1 ; O=C(Nc1c2c(cc3c1CCC3)CCC2)NS(=O)(=O)c1cnn2c1OCC(N1CC(F)C1)C2 ; CN1CCn2ncc(S(=O)(=O)NC(=O)Nc3c4c(cc5c3CCC5)CCC4)c2C1=O ; CC1(O)COc2c(S(=O)(=O)NC(=O)Nc3c4c(cc5c3CCC5)CCC4)cnn2C1]
256
-continued
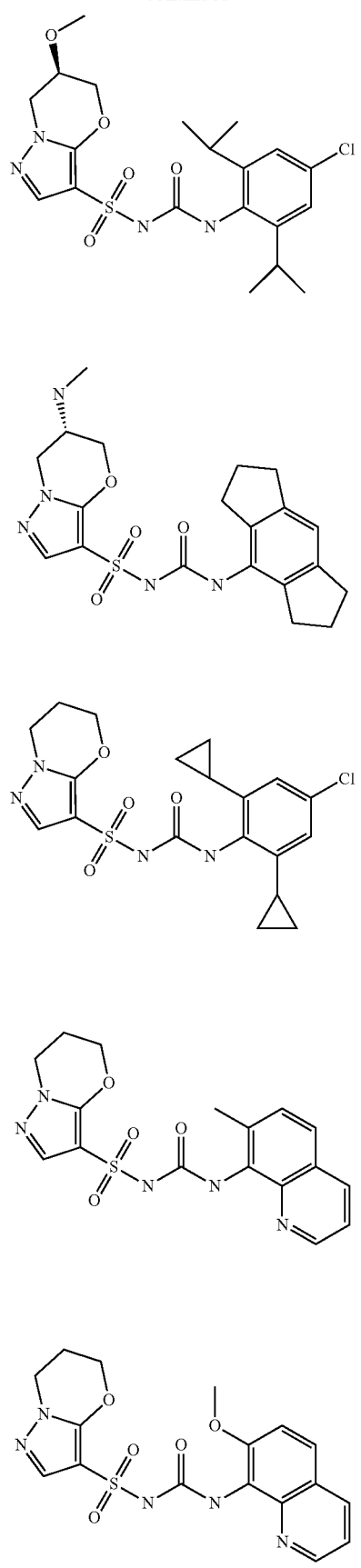

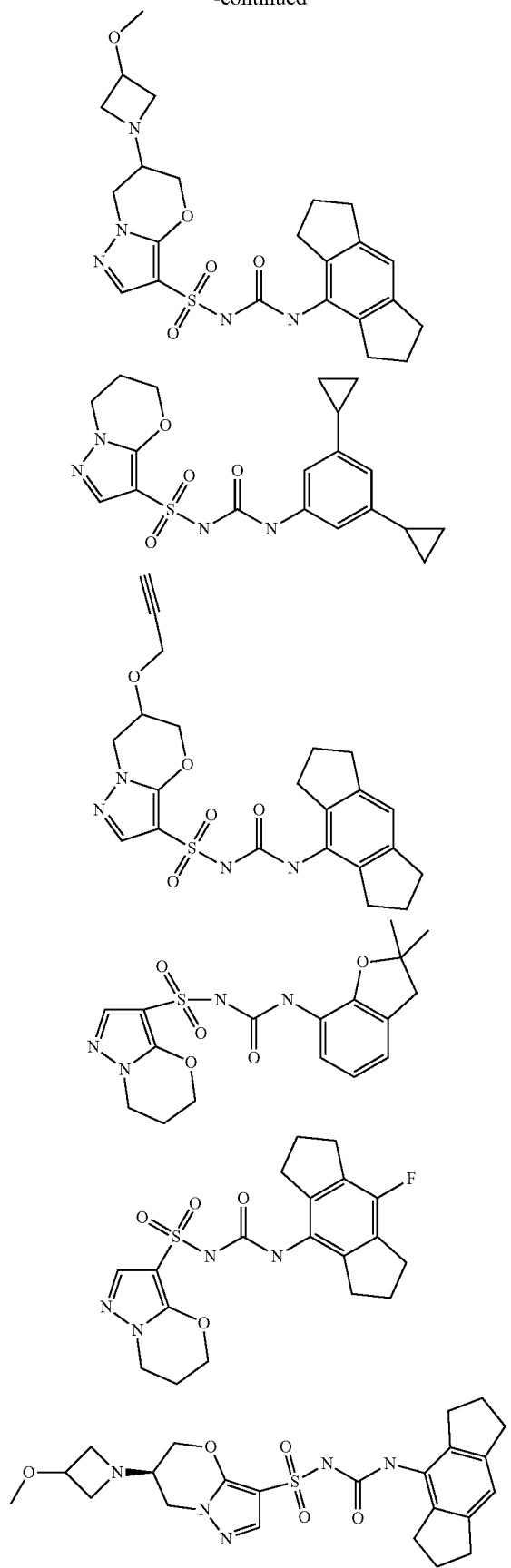
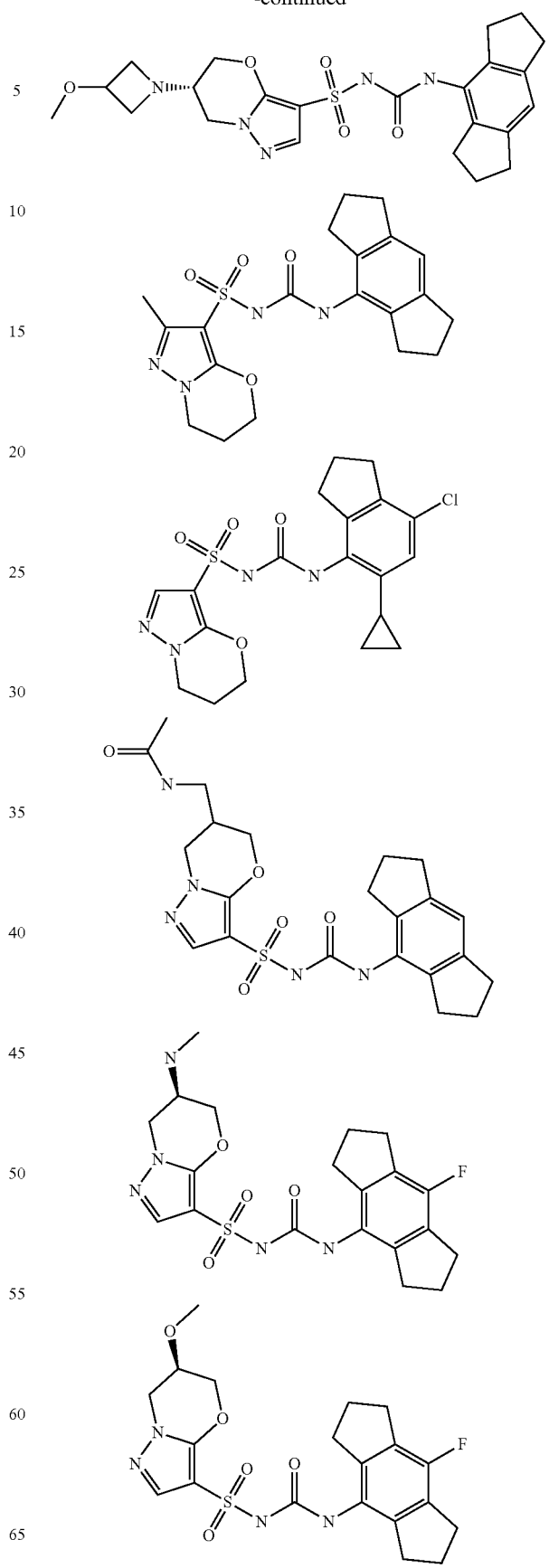

259
-continued
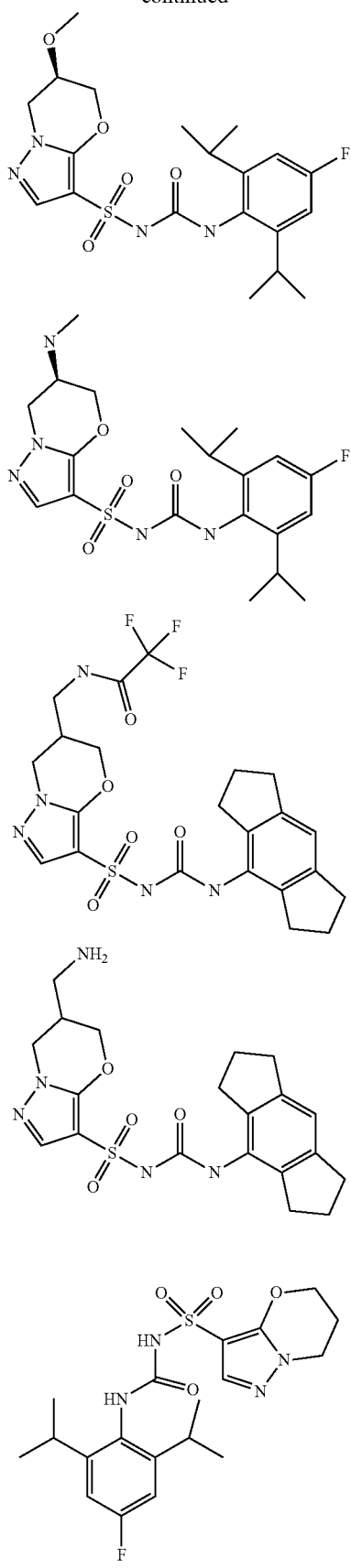
260
Embodiment III-66. A compound, or a pharmaceutically acceptable salt, prodrug, solvate, hydrate, isomer, or tautomer thereof, selected from the group consisting of
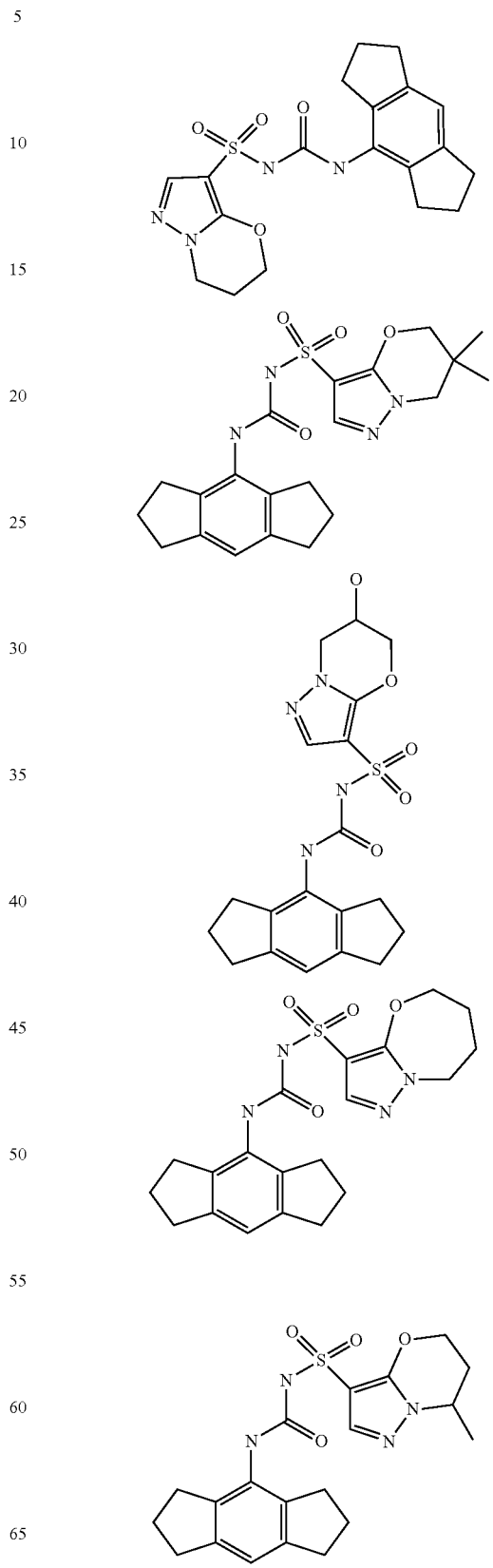

261
-continued
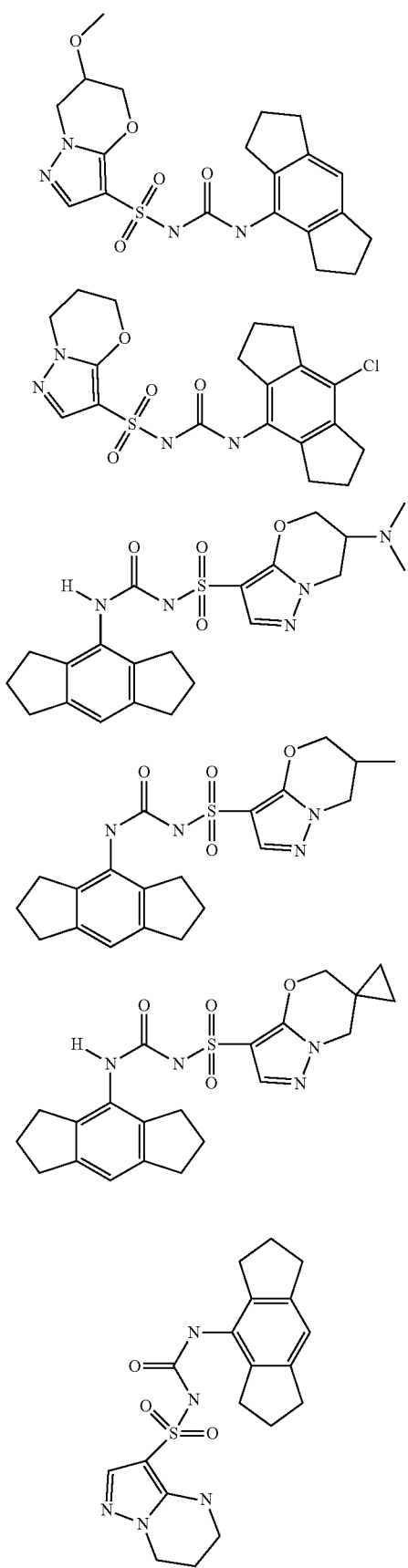
262
-continued
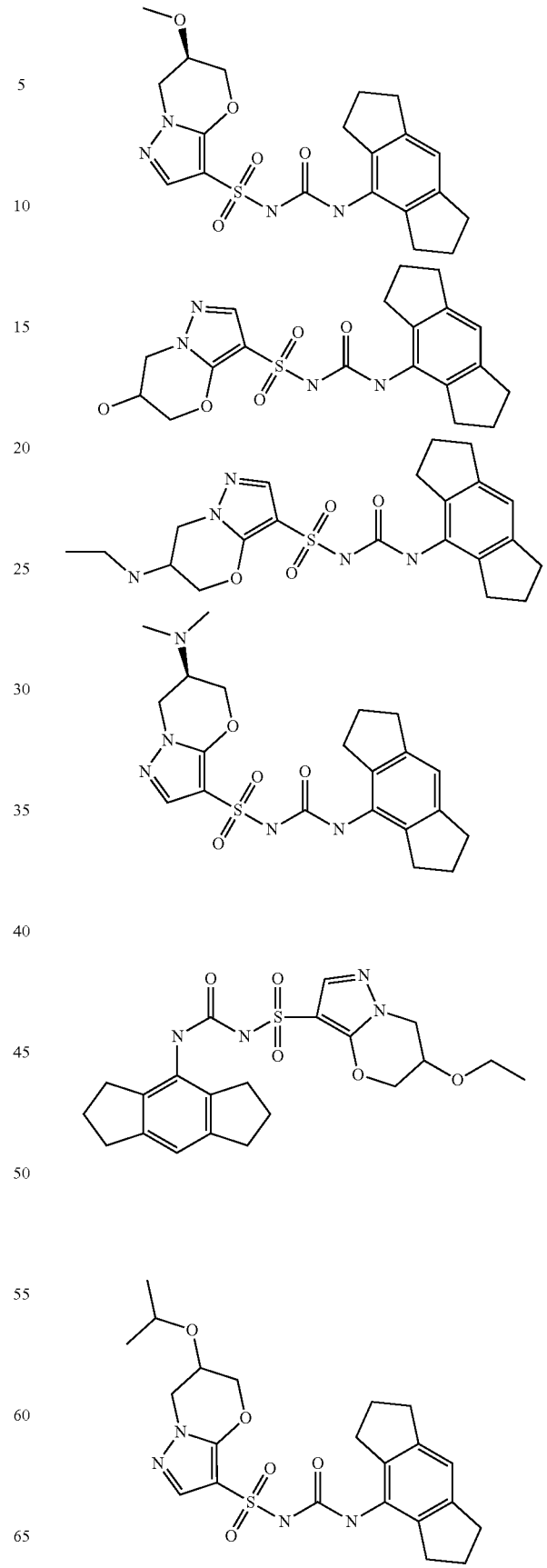

263
-continued
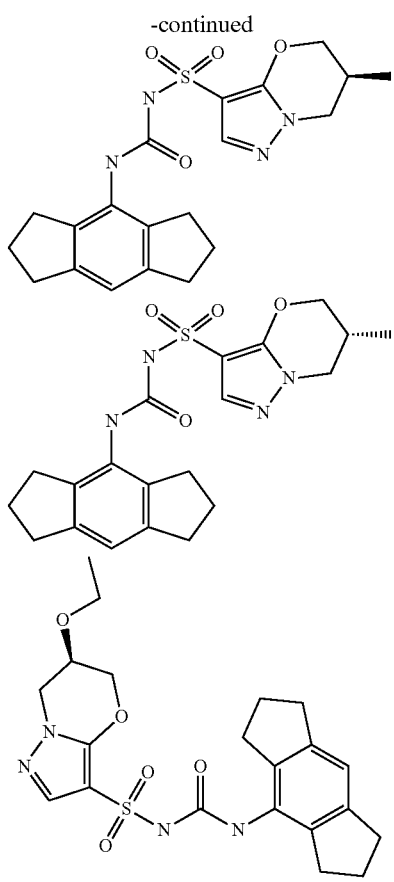
264
-continued
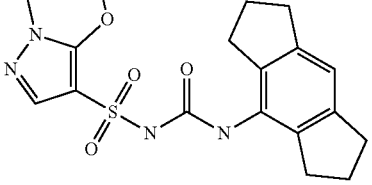
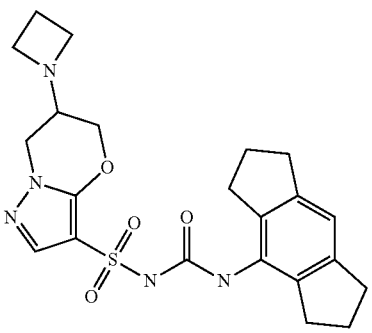
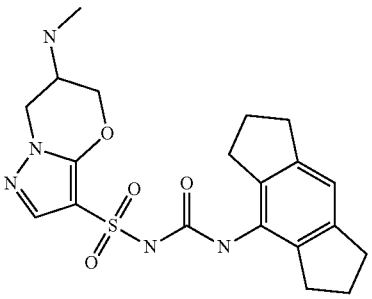
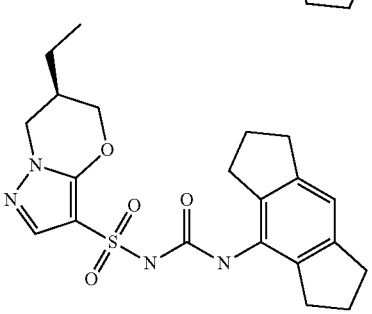
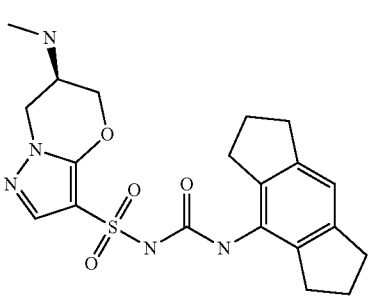

265
-continued
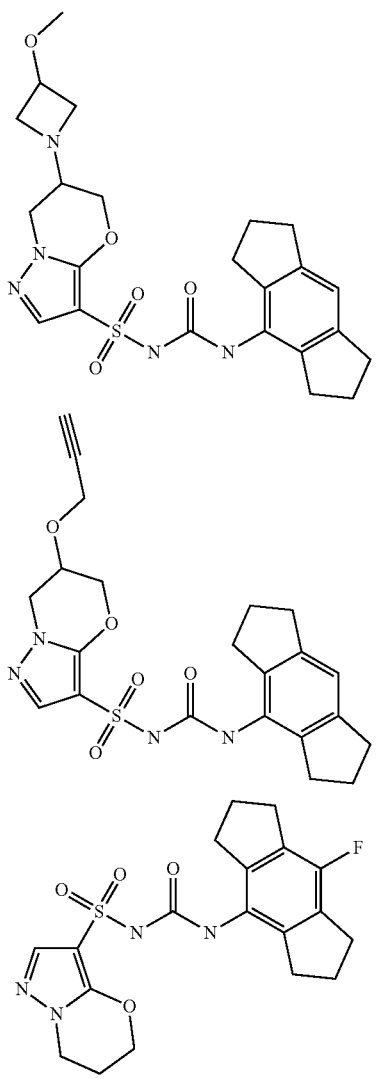
266
-continued
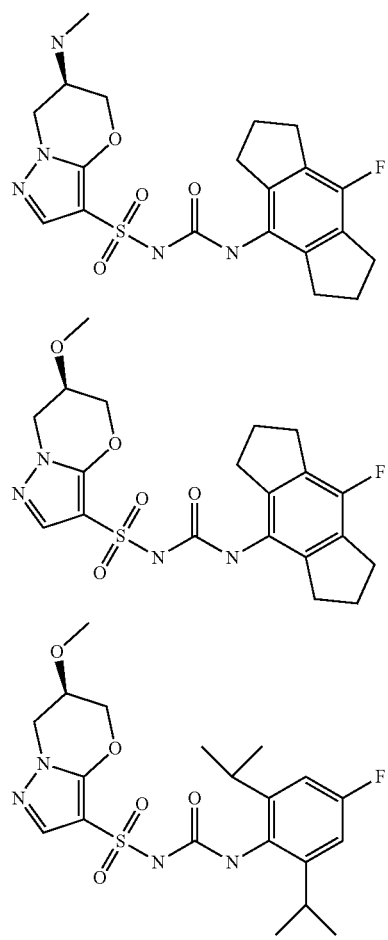
Embodiment III-67. A compound, or a pharmaceutically acceptable salt, prodrug, solvate, hydrate, isomer, or tautomer thereof, selected from the group consisting of
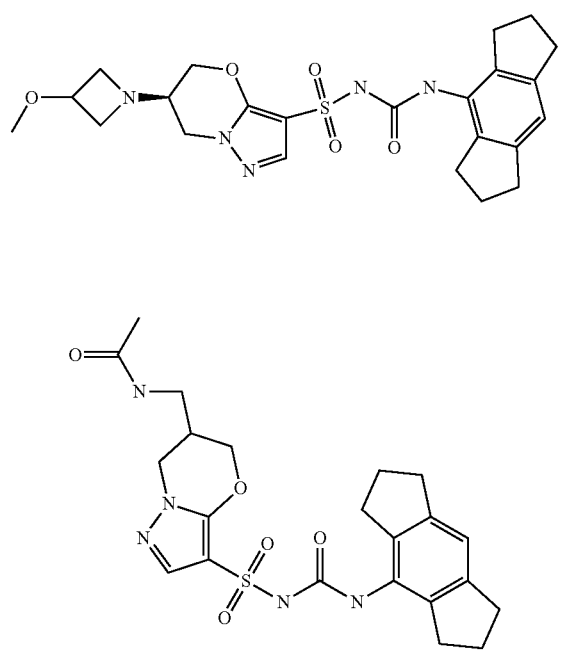
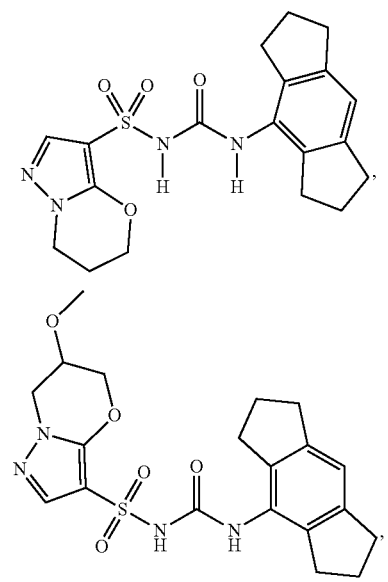

267
-continued
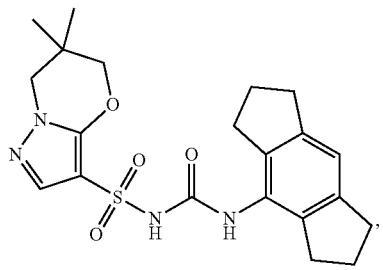
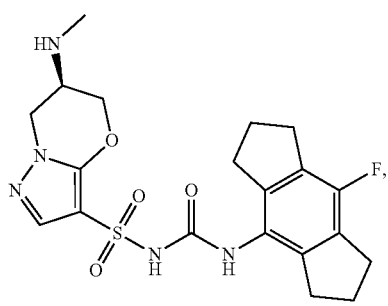
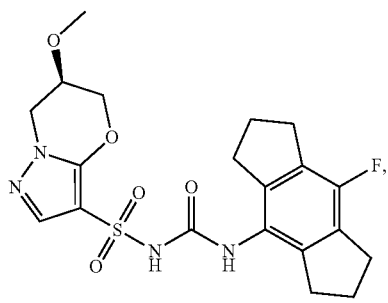
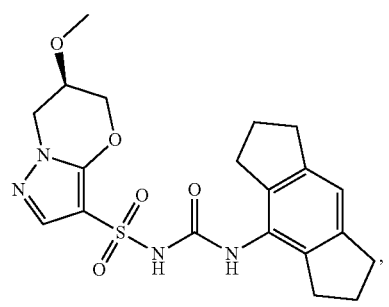
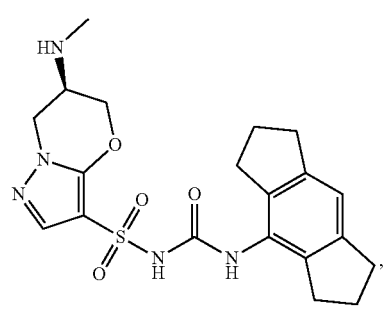
268
-continued
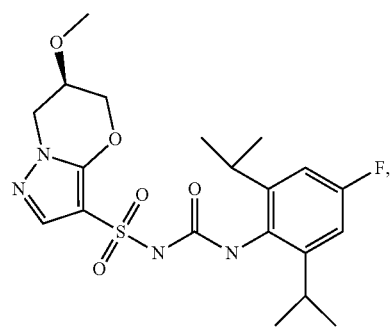
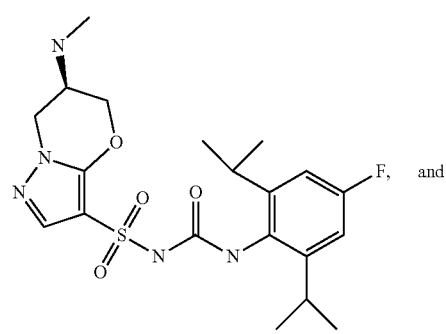
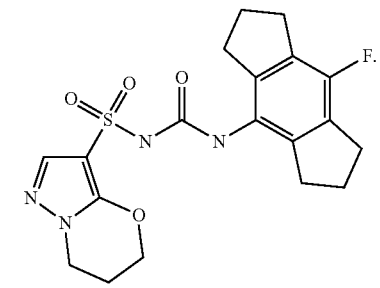
Embodiment III-68. A compound, or a pharmaceutically acceptable salt, prodrug, solvate, hydrate, isomer, or tautomer thereof, selected from the group consisting of
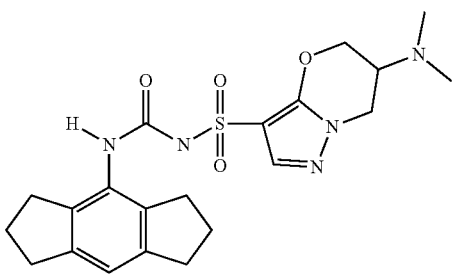
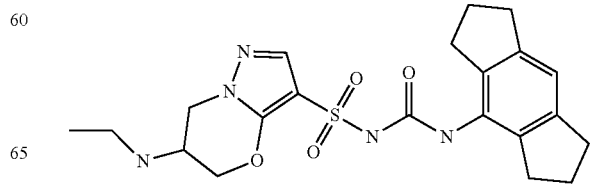

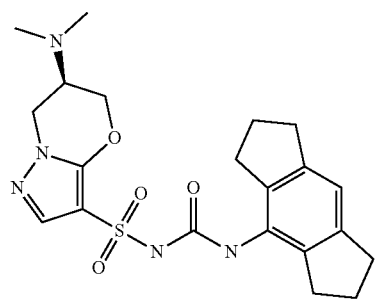
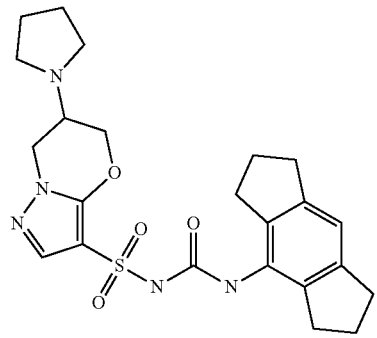
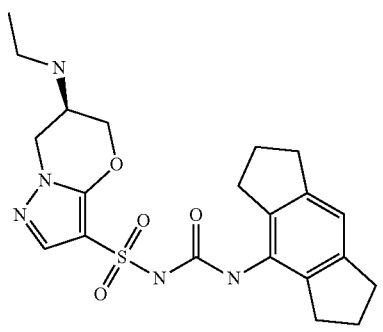
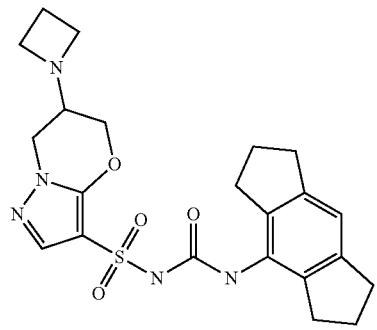
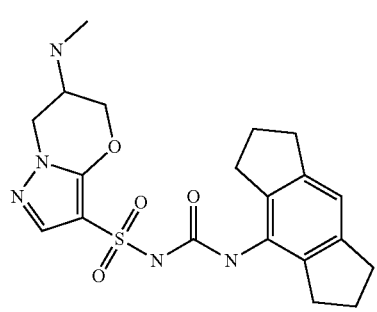
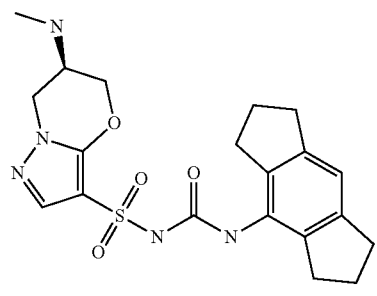
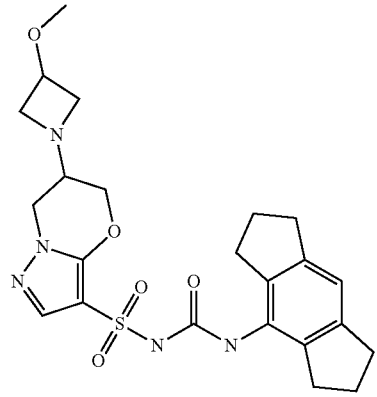
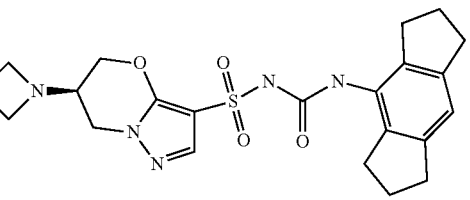
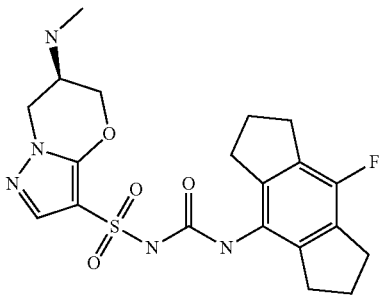
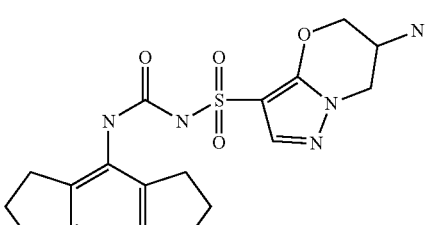

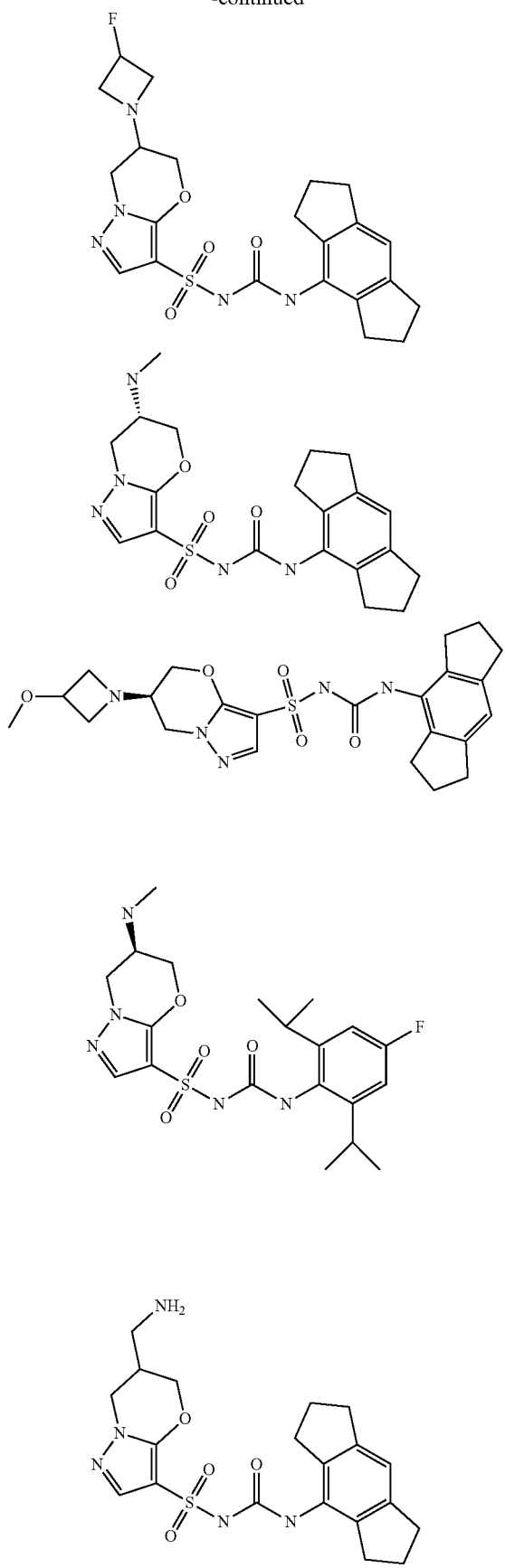
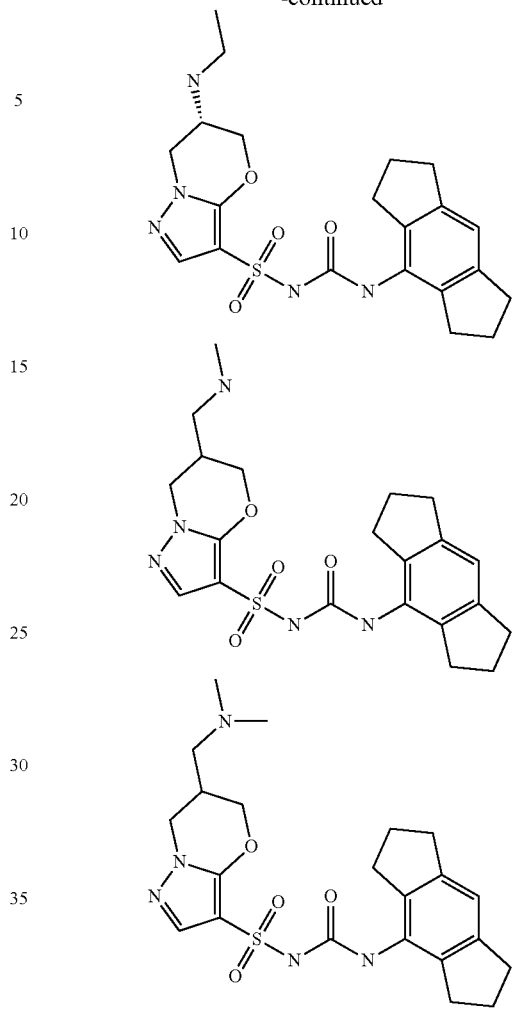

Embodiment III-69. A pharmaceutical composition comprising a compound of any one of Embodiments III-1 to III-68, or a pharmaceutically acceptable salt, prodrug, solvate, hydrate, isomer, or tautomer thereof, and a pharmaceutically acceptable carrier.

Embodiment III-70. A method of treatment or prevention of a disease, disorder, or condition that is is responsive to inhibition of inflammasome, comprising administering an effective amount of a compound of any one of Embodiments III-1 to III-68, or a pharmaceutically acceptable salt, prodrug, solvate, hydrate, isomer, or tautomer thereof, to thereby treat or prevent the disease disorder or condition in a subject in need thereof.

Embodiment III-71. The method of Embodiment III-70, wherein the disease, disorder or condition is one which is responsive to inhibition of activation of the NLRP3 inflammasome.

Embodiment III-72. The method of Embodiment III-70 or III-71, wherein the disease, disorder or condition is responsive to modulation of one or more of IL-6, IL-1β, IL-17, IL-18, IL-1α, IL-37, IL-22, IL-33 and Th17 cells.

Embodiment III-73. The method of Embodiment III-70 or III-71, wherein the disease, disorder or condition is responsive to modulation of one or more of IL-1β and IL-18.

Embodiment III-74. The method of any one of Embodiments III-70 to III-73, wherein the disease, disorder or condition is a disease, disorder or condition of the immune system.

Embodiment III-75. The method of any one of Embodiments III-70 to III-73, wherein the disease, disorder or condition is an inflammatory disease disorder or condition or an autoimmune disease disorder or condition.

Embodiment III-76. The method of any one of Embodiments III-70 to III-73, wherein the disease, disorder or condition is a disease, disorder or condition of the liver.

Embodiment III-77. The method of any one of Embodiments III-70 to III-73, wherein the disease, disorder or condition is a disease, disorder or condition of the lung.

Embodiment III-78. The method of any one of Embodiments III-70 to III-73, wherein the disease, disorder or condition is a disease, disorder or condition of the skin.

Embodiment III-79. The method of any one of Embodiments III-70 to III-73, wherein the disease, disorder or condition is a disease, disorder or condition of the cardiovascular system.

Embodiment III-80. The method of any one of Embodiments III-70 to III-73, wherein the disease, disorder or condition is a cancer, tumor or other malignancy.

Embodiment III-81. The method of any one of Embodiments III-70 to III-73, wherein the disease, disorder or condition is a disease, disorder or condition is of the renal system.

Embodiment III-82. The method of any one of Embodiments III-70 to III-73, wherein the disease, disorder or condition is a disease, disorder or condition is of the gastro-intestinal tract.

Embodiment III-83. The method of any one of Embodiments III-70 to III-73, wherein the disease, disorder or condition is a disease, disorder or condition is of the respiratory system.

Embodiment III-84. The method of any one of Embodiments III-70 to III-73, wherein the disease, disorder or condition is a disease, disorder or condition is of the endocrine system.

Embodiment III-85. The method of any one of Embodiments III-70 to III-73, wherein the disease, disorder or condition is a disease, disorder or condition is of the central nervous system (CNS).

Embodiment III-86. The method of any one of Embodiments III-70 to III-73, wherein the disease, disorder or condition is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), corneal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

Embodiment III-87. The method of Embodiment III-86, wherein the disorder is selected from the group consisting of a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), and non-alcoholic steatohepatitis (NASH).

Embodiment III-88. The method of Embodiment III-87, wherein the disorder is non-alcoholic steatohepatitis (NASH).

Embodiment III-89. The method of any one of Embodiments III-70 to III-88, wherein the treatment or prevention of the disease, disorder or condition is performed on a mammal.

Embodiment III-90. The method of Embodiment III-89, wherein the mammal is a human subject.

Embodiment III-91. A method of modulating the activity of a biological target comprising the step of exposing the biological target to a compound of any one of Embodiments III-1 to III-68, or a pharmaceutically acceptable salt, prodrug, solvate, hydrate, isomer, or tautomer thereof.

Embodiment III-92. The method of Embodiment III-91, wherein the biological target may be selected from the group consisting of the NLRP3 inflammasome, IL-6, IL-1β, IL-17, IL-18, IL-1α, IL-37, IL-22, IL-33 and Th17 cells.

Embodiment III-93. The method of Embodiment III-91, wherein the biological target may be selected from the group consisting of IL-1β and IL-18.

Embodiment III-94. A method of inhibiting activation of an inflammasome comprising the step of exposing the biological target to a compound of any one of Embodiments III-1 to III-68, or a pharmaceutically acceptable salt, prodrug, solvate, hydrate, isomer, or tautomer thereof.

Embodiment III-95. The method of Embodiment III-94, wherein the inflammasome is NLRP3 inflammasome.

Embodiment III-96. The method of Embodiment III-94 or III-95, wherein inhibition of inflammasome is associated with one or more of IL-6, IL-1β, IL-17, IL-18, IL-1α, IL-37, IL-22, IL-33 and Th17 cells.

Embodiment III-97. The method of Embodiment III-96, wherein inhibition of inflammasome is associated with one or more of IL-1β and IL-18.

Embodiment III-98. Use of a compound of any one of Embodiments III-1 to III-68, or a pharmaceutically acceptable salt, prodrug, solvate, hydrate, isomer, or tautomer thereof, in the treatment of a disease, disorder or condition that is responsive to inhibition of inflammasome.

Embodiment III-99. A compound of any one of Embodiment III-1 to III-68, or a pharmaceutically acceptable salt, prodrug, solvate, hydrate, isomer, or tautomer thereof, for use in the manufacture of a medicament for treating a disease, disorder or condition that is responsive to inhibition of inflammasome.

EXAMPLES

The following examples are provided to illustrate the present disclosure, and should not be construed as limiting thereof. In these examples, all parts and percentages are by weight, unless otherwise noted. Abbreviations in the examples are noted below.

Abbreviations aq. aqueous
EtOAc ethyl acetate
h hour
HPLC high performance liquid chromatography
min minutes
mL milliliter
mmol millimole
MeOH methanol
NMR nuclear magnetic resonance
sat. saturated
THF tetrahydrofuran
TLC thin layer chromatography Example 1: Synthesis of Compound 1. (N-((1,2,3,5,6,7-hexahydro-s-indacen-4-yl)carbamoyl)-6,7-dihydro-5H-pyrazolo[5,1-b][1,3]oxazine-3-sulfonamide)

Method A:

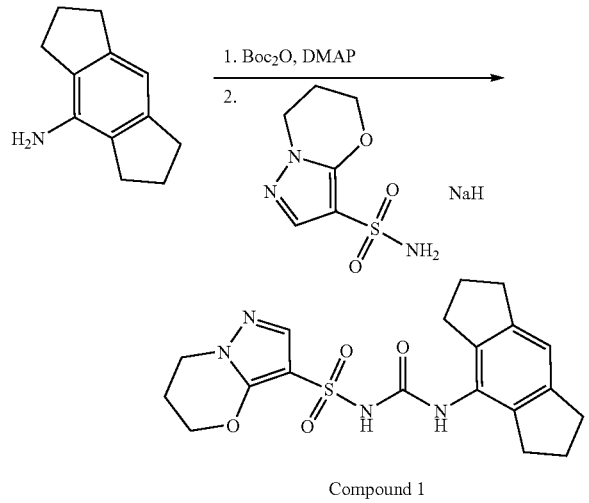

Compound 1

N,N-dimethylpyridin-4-amine (0.517 mmol, 0.063 g) was dissolved in THF (1.5 mL) and then a solution of di-tert-butyl dicarbonate (0.492 mmol, 0.113 mL) in THF (1.5 mL) was added slowly. After stirring for a few minutes, a solution of 1,2,3,5,6,7-hexahydro-s-indacen-4-amine (0.492 mmol, 0.085 g) in THF (1 mL) was added and the mixture was left to stir for 30 min. At the same time, 6,7-dihydro-5H-pyrazolo[5,1-b][1,3]oxazine-3-sulfonamide (0.492 mmol, 100 mg) in THF (1 mL) was treated with sodium hydride (0.492 mmol, 0.018 g) and left to stir for 30 min. At this time the two solutions were mixed and left to stir for 18 h.

The reaction was then quenched with sat. NH$_4$Cl (10 mL) and diluted with EtOAc (10 mL). The layers were separated and the aq. layer extracted with EtOAc (10 mL). The combined organic extracts were then washed with water (10 mL) and concentrated. The resulting solid was suspended in MeOH (5 mL), filtered off, and the filtrate purified by prep HPLC (10-40% MeCN: 10 mM aq. NH$_3$). The purified fractions were combined and concentrated to yield N-((1,2,3,5,6,7-hexahydro-s-indacen-4-yl)carbamoyl)-6,7-dihydro-5H-pyrazolo[5,1-b][1,3]oxazine-3-sulfonamide (Compound 1) (3.5 mg, 1.768%) as a white solid. [M+H]$^+$ found 403.

$^1$H-NMR (400 MHz; MeOD): δ 7.67 (s, 1H), 6.93 (d, J=0.9 Hz, 1H), 6.93 (d, J=0.9 Hz, 1H), 4.42 (t, J=5.3 Hz, 2H), 4.42 (t, J=5.3 Hz, 2H), 4.16 (t, J=6.2 Hz, 2H), 4.16 (t, J=6.2 Hz, 2H), 2.86 (t, J=7.4 Hz, 4H), 2.86 (t, J=7.4 Hz, 4H), 2.74-2.71 (m, 4H), 2.74-2.71 (m, 4H), 2.31-2.25 (m, 3H), 2.31-2.25 (m, 3H), 2.08-2.00 (m, 6H), 2.08-2.00 (m, 6H).

Method B:

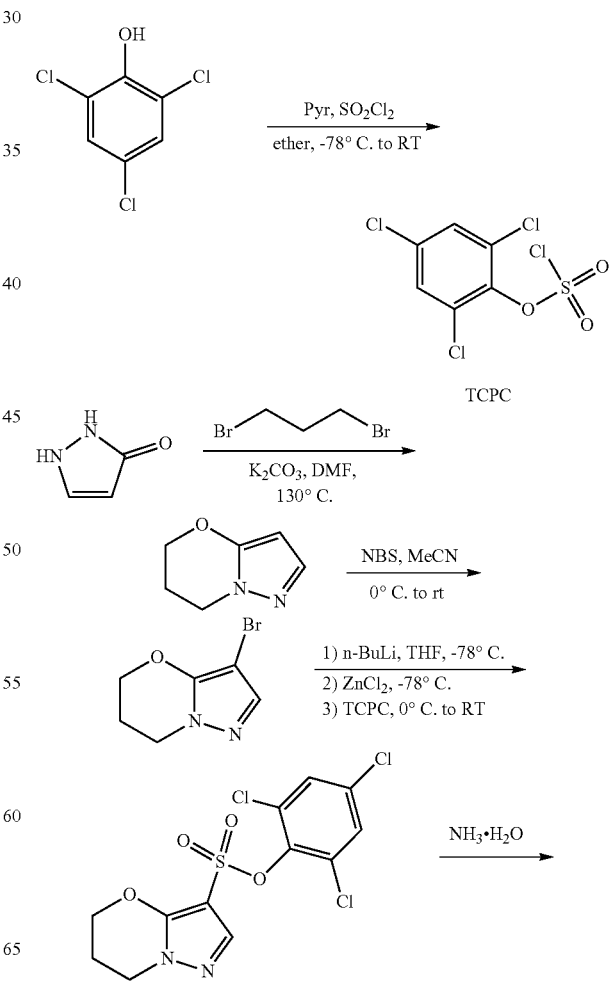

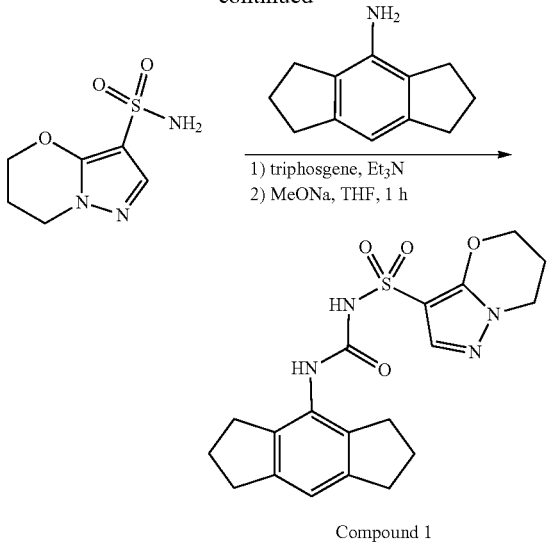

Compound 1

Preparation of TCPC

A solution of 2,4,6-trichloro-phenol (50 g, 250 mmol) and pyridine (20.5 mL, 250 mmol) in ether (800 mL) was cooled to −78° C. under N₂. Upon cooling, solids formed in the mixture. To the mixture was added SO₂Cl₂ (21 mL, 250 mmol) slowly. The reaction was then stirred at r.t. overnight. The reaction mixture was filtered through a celite-pad and rinsed with ether (300 mL). The ether solution was concentrated below 40° C. The residue was purified by silica gel column (hexane~PE) to give TCPC (55 g, yield 75%) as a colorless oil.

¹H NMR (400 MHz, CDCl₃): δ=7.45 (s, 2H).

Step 1

1,2-Dihydro-pyrazol-3-one (4.0 g, 47.6 mmol) and K₂CO₃ (23.0 g, 166.7 mmol) were heated to 130° C. in DMF (80 mL). 1,3-Dibromopropane (11.6 g, 57.1 mmol) was added and the mixture was heated for 3 hrs and then concentrated. The residue was partitioned between ethyl acetate (100 mL) and water (100 mL) and the layers were separated. The aqueous layer was extracted with EA (50 mL) and the combined organic layer was washed with brine (50 mL), dried over Na₂SO₄, filtered and concentrated in vacuo. The residue was purified by silica gel column (PE/EA=1/2) to give 6,7-dihydro-5H-pyrazolo[5,1-b][1,3]oxazine (3.0 g, yield: 51%) as a yellow oil.

¹H NMR (400 MHz, CDCl₃): δ=7.31 (d, J=2.0 Hz, 1H), 5.48 (d, J=2.0 Hz, 1H), 4.28 (t, J=5.2 Hz, 2H), 4.18 (t, J=6.2 Hz, 2H), 2.29-2.22 (m, 2H).

Step 2

NBS (4.4 g, 24.7 mmol) was added portionwise to a solution of 6,7-dihydro-5H-pyrazolo[5,1-b][1,3]oxazine (3.0 g, 24.3 mmol) in MeCN (40 mL) at 0° C. and the reaction was stirred for 2 hrs at room temperature. The mixture was filtered and purified by reverse phase column (5%-95% MeCN in H₂O) to give 3-bromo-6,7-dihydro-5H-pyrazolo[5,1-b][1,3]oxazine (3.6 g, yield: 74%) as a yellow solid.

¹H NMR (400 MHz, CDCl₃): δ=7.30 (s, 1H), 4.36 (t, J=5.2 Hz, 2H), 4.17 (t, J=6.2 Hz, 2H), 2.30-2.24 (m, 2H).

Step 3

To a solution of 3-bromo-6,7-dihydro-5H-pyrazolo[5,1-b][1,3]oxazine (1.8 g, 8.9 mmol) in dry THF (15 mL) was added n-BuLi in hexane (2.5 M, 3.5 mL, 8.9 mmol) slowly at −78° C. under N₂. After stirred with cooling for 20 min, ZnCl₂ in ether (1 M, 8.9 mL, 8.9 mmol) was added slowly at this temperature. The cold bath was removed and the reaction was stirred at r.t. for 1 hr. TCPC (2.6 g, 8.9 mmol) was then added at 0° C. and stirred at r.t. for 1 hr. The reaction was quenched with saturated NH₄Cl solution (10 mL) and partitioned between water (80 mL) and EA (80 mL). The organic layer was washed with brine (80 mL), dried over Na₂SO₄ and concentrated to give crude 6,7-dihydro-5H-pyrazolo[5,1-b][1,3]oxazine-3-sulfonic acid 2,4,6-trichloro-phenyl ester as a yellow oil which was used for next step directly without any purification.

Step 4

A mixture of 6,7-dihydro-5H-pyrazolo[5,1-b][1,3]oxazine-3-sulfonic acid 2,4,6-trichloro-phenyl ester (crude, ~8.9 mmol), NH₄OH (10 mL) and THF (10 mL) was stirred at 60° C. overnight. The reaction was concentrated under reduced pressure until 10 mL of liquid remained. The remained solution was acidified with 1 N HCl to pH=5 and partitioned between EA (10 mL) and water (50 mL). The aqueous layer was purified by reverse phase column (MeCN/H₂O) to give 6,7-dihydro-5H-pyrazolo[5,1-b][1,3]oxazine-3-sulfonic acid amide (650 mg, yield: 36% over 2 steps) as a light yellow solid.

¹HNMR (400 MHz, DMSO-d6): δ=7.47 (s, 1H), 7.09 (brs, 2H), 4.40 (t, J=5.2 Hz, 2H), 4.25 (t, J=6.0 Hz, 2H), 2.22-2.14 (m, 2H). MS: m/z 203.9 (M+H⁺).

Step 5

To a solution of 6,7-dihydro-5H-pyrazolo[5,1-b][1,3]oxazine-3-sulfonic acid amide (120 mg, 0.6 mmol) in THF (10 mL) was added MeONa (40 mg, 0.7 mmol) and stirred at r.t. for 20 mins to give a sodium salt suspension.

In another flask, to a solution of 1,2,3,5,6,7-hexahydro-s-indacen-4-ylamine (110 mg, 0.6 mmol) and TEA (120 mg, 1.2 mmol) in THF (10 mL), was added triphosgene (120 mg, 0.4 mmol) in one portion and stirred at r.t. under N₂ for 20 mins. The reaction mixture was then filtered. The filtrate was added to the sodium salt suspension above and stirred at r.t. for 20 min. After that, the reaction solution was partitioned between EA (60 mL) and water (60 mL). The aqueous phase was acidified to pH=5 with conc. HCl and extracted with EA (60 mL). The organic layer was washed with water (50 mL) and brined (50 mL), dried over Na₂SO₄ and concentrated until white solid appeared. The solid formed was collected by filtration and dried to give N-((1,2,3,5,6,7-hexahydro-s-indacen-4-yl)carbamoyl)-6,7-dihydro-5H-pyrazolo[5,1-b][1,3]oxazine-3-sulfonamide (57 mg, yield: 22%) as a white solid.

¹HNMR (400 MHz, DMSO-d6): δ=10.46 (brs, 1H), 7.91 (s, 1H), 7.61 (s, 1H), 6.93 (s, 1H), 4.42 (t, J=5.2 Hz, 2H), 4.25 (t, J=5.8 Hz, 2H), 2.79 (t, J=7.6 Hz, 4H), 2.60 (t, J=7.6 Hz, 4H), 2.22-2.18 (m, 2H), 1.99-1.92 (m, 4H). MS: m/z 403.0 (M+H⁺).

Example 2: Synthesis of Compound 2. N-((1,2,3,5,6,7-hexahydro-s-indacen-4-yl)carbamoyl)methanesulfonamide

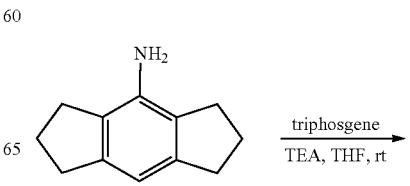

-continued

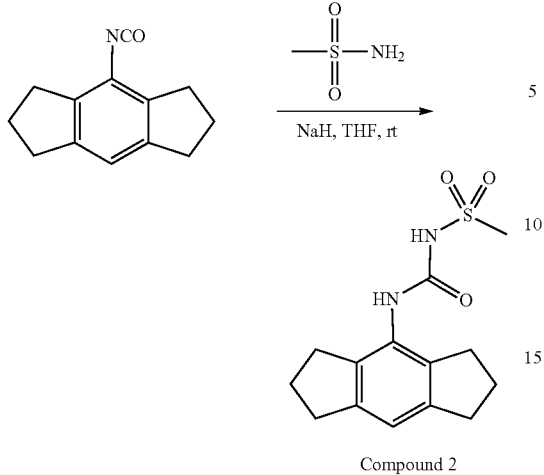

Compound 2

To a solution of methanesulfonamide (95 mg, 1.0 mmol) in THF (5 mL) was added NaH (60%, 45 mg, 1.1 mmol) and stirred at room temperature for 10 min to give a sodium salt suspension.

To a solution of 1,2,3,5,6,7-hexahydro-s-indacen-4-ylamine (173 mg, 1.0 mmol) and TEA (0.5 mL, 3.5 mmol) in THF (10 mL) was added triphosgene (120 mg, 0.4 mmol) in one portion and the mixture was stirred at room temperature under $N_2$ for 20 min. The reaction mixture was then filtered. The filtrate was added to the sodium salt suspension above and stirred at room temperature for 30 min. After that, the reaction solution was partitioned between ethyl acetate (50 mL) and water (100 mL). The aqueous phase was filtered and acidified to pH=5 with aq.HCl (1N). The solid formed was collected by filtration and dried to give N-((1,2,3,5,6,7-hexahydro-s-indacen-4-yl)carbamoyl)methanesulfonamide (130 mg, yield: 44%) as a white solid.

$^1$H NMR (400 MHz, DMSO-$d_6$): δ=10.19 (brs, 1H), 8.13 (s, 1H), 6.96 (s, 1H), 3.26 (s, 3H), 2.82 (t, J=7.2 Hz, 4H), 2.71 (t, J=7.2 Hz, 4H), 2.03-1.94 (m, 4H). MS: m/z 295.0 (M+H$^+$).

Example 3: Synthesis of N-((1,2,3,5,6,7-hexahydro-s-indacen-4-yl)carbamothioyl)-6,7-dihydro-5H-pyrazolo[5,1-b][1,3]oxazine-3-sulfonamide Synthesis of N-((1,2,3,5,6,7-hexahydro-s-indacen-4-yl)carbamothioyl)-6,7-dihydro-5H-pyrazolo[5,1-b][1,3]oxazine-3-sulfonamide is shown below.

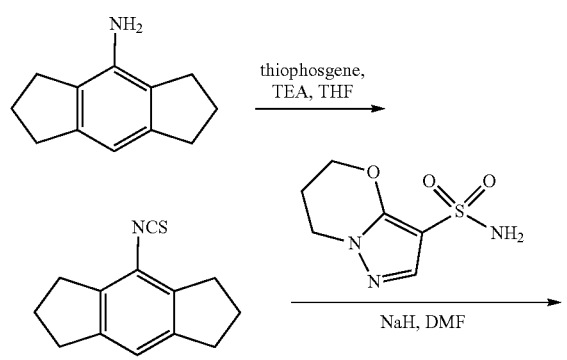

-continued

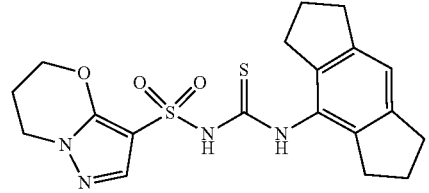

Step 1

To a solution of 1,2,3,5,6,7-hexahydro-s-indacen-4-ylamine (350 mg, 2 mmol) in THF (20 mL) was added thiophosgene (233 mg, 2 mmol) and TEA (612 mg, 6 mmol). The reaction mixture was stirred at room temperature overnight and then evaporated in vacuo. The residue was diluted in saturated NaHCO$_3$ (50 mL) and the aqueous phase was extracted with EA (50 mL×3). Organic extracts was combined, dried over anhydrous Na$_2$SO$_4$ and concentrated in vacuo to give 4-isothiocyanato-1,2,3,5,6,7-hexahydro-s-indacene as a crude product which was used for the next step without further purification.

Step 2

To a solution of 6,7-dihydro-5H-pyrazolo[5,1-b][1,3]oxazine-3-sulfonic acid amide (60 mg, 0.3 mmol) in DMF (5 mL) was added 4-isothiocyanato-1,2,3,5,6,7-hexahydro-s-indacene (64.5 mg, 0.3 mmol) and NaH (60% in mineral oil, 24 mg, 0.6 mmol). The reaction was stirred at room temperature for 2 hrs (monitored by LC-MS) and was quenched by H$_2$O (20 mL). The mixture was acidified by 1 M HCl to pH=3 and extracted with EA (20 mL×3). Organic phase was combined, dried over anhydrous Na$_2$SO$_4$ and evaporated in vacuo. The residue was purified by pre-HPLC to give N-((1,2,3,5,6,7-hexahydro-s-indacen-4-yl)carbamothioyl)-6,7-dihydro-5H-pyrazolo[5,1-b][1,3]oxazine-3-sulfonamide (30 mg, yield: 24.2%) as a white solid.

$^1$H NMR (400 MHz, DMSO-d6): δ=7.62 (s, 1H), 7.21-6.96 (m, 2H), 4.40-4.35 (m, 2H), 4.11-4.08 (m, 2H), 2.80 (t, J=7.2 Hz, 4H), 2.63-2.58 (m, 4H), 2.19-2.16 (m, 2H), 1.98-1.91 (m, 4H). MS: m/z 417.0 (M−H$^+$).

Example 4: Synthesis of N-((1,2,3,5,6,7-hexahydro-s-indacen-4-yl)carbamoyl)-4,5,6,7-tetrahydropyrazolo[1,5-a]pyridine-3-sulfonamide Synthesis of N-((1,2,3,5,6,7-hexahydro-s-indacen-4-yl)carbamoyl)-4,5,6,7-tetrahydropyrazolo[1,5-a]pyridine-3-sulfonamide is shown below.

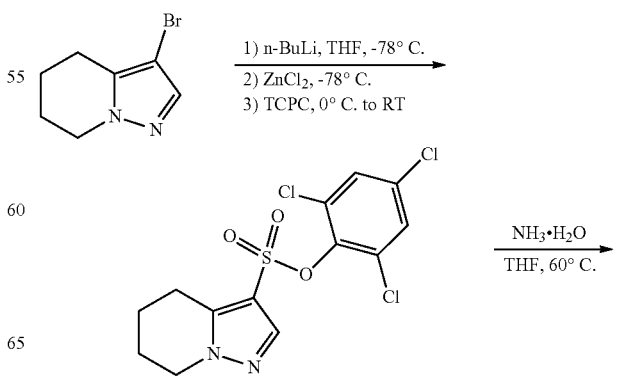

-continued

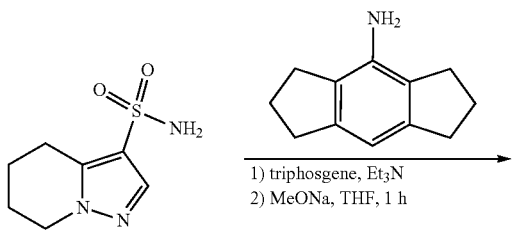

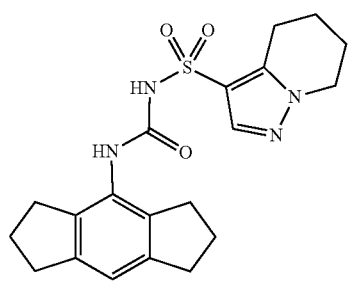

Step 1

To a solution of 3-bromo-4,5,6,7-tetrahydro-pyrazolo[1,5-a]pyridine (1 g, 5 mmol) in dry THF (10 mL) was added n-BuLi in hexane (2.5 M, 2 mL, 5 mmol) slowly at −78° C. under $N_2$. After stirring with cooling for 20 min, $ZnCl_2$ in ether (1 M, 5 mL, 5 mmol) was added slowly at this temperature. The cold bath was removed and the reaction was stirred at room temperature for 1 hr. TCPC (1.8 g, 5 mmol) was then added and the reaction solution was stirred at room temperature for 1 hr. The reactant was partitioned between water (80 mL) and EA (80 mL). The organic layer was washed with brine (80 mL), dried over $Na_2SO_4$ and concentrated to give crude 4,5,6,7-tetrahydro-pyrazolo[1,5-a]pyridine-3-sulfonic acid 2,4,6-trichloro-phenyl ester as a yellow gel which was used for next step directly without any purification.

Step 2

A mixture of 4,5,6,7-tetrahydro-pyrazolo[1,5-a]pyridine-3-sulfonic acid 2,4,6-trichloro-phenyl ester (crude, ~5 mmol), $NH_3 \cdot H_2O$ (15 mL) and THF (15 mL) was stirred at 60° C. overnight. The reaction was concentrated under reduced pressure. The remaining solution was acidified with 1 N HCl to pH=5 and partitioned between EA (15 mL) and water (70 ml). The aqueous phase was purified by reverse phase column to give 4,5,6,7-Tetrahydro-pyrazolo[1,5-a]pyridine-3-sulfonic acid amide (270 mg, yield: 27% over 2 steps) as a yellow solid.

$^1$H NMR (400 MHz, DMSO-d6): δ=7.62 (s, 1H), 7.15 (brs, 2H), 4.08 (t, J=6.0 Hz, 2H), 2.90 (t, J=6.4 Hz, 2H), 1.98-1.92 (m, 2H), 1.83-1.77 (m, 2H). MS: m/z 201.9 (M+H$^+$).

Step 3

This step is similar to general procedure for N-((1,2,3,5,6,7-hexahydro-s-indacen-4-yl)carbamoyl)-6,7-dihydro-5H-pyrazolo[5,1-b][1,3]oxazine-3-sulfonamide (Example 1).

HNMR (400 MHz, DMSO-d6): δ=10.54 (s, 1H), 7.99 (s, 1H), 7.79 (s, 1H), 6.94 (s, 1H), 4.09 (t, J=5.6 Hz, 2H), 2.97 (t, J=6.4 Hz, 2H), 2.78 (t, J=7.6 Hz, 4H), 2.57 (t, J=7.6 Hz, 4H), 1.98-1.90 (m, 6H), 1.82-1.78 (m, 2H). MS: m/z 401.0 (M+H$^+$).

Example 5: Synthesis of N-((1,2,3,5,6,7-hexahydro-s-indacen-4-yl)carbamoyl)-5',7'-dihydrospiro[oxetane-3,6'-pyrazolo[5,1-b][1,3]oxazine]-3'-sulfonamide Synthesis of N-((1,2,3,5,6,7-hexahydro-s-indacen-4-yl)carbamoyl)-5',7'-dihydrospiro[oxetane-3,6'-pyrazolo[5,1-b][1,3]oxazine]-3'-sulfonamide is shown below.

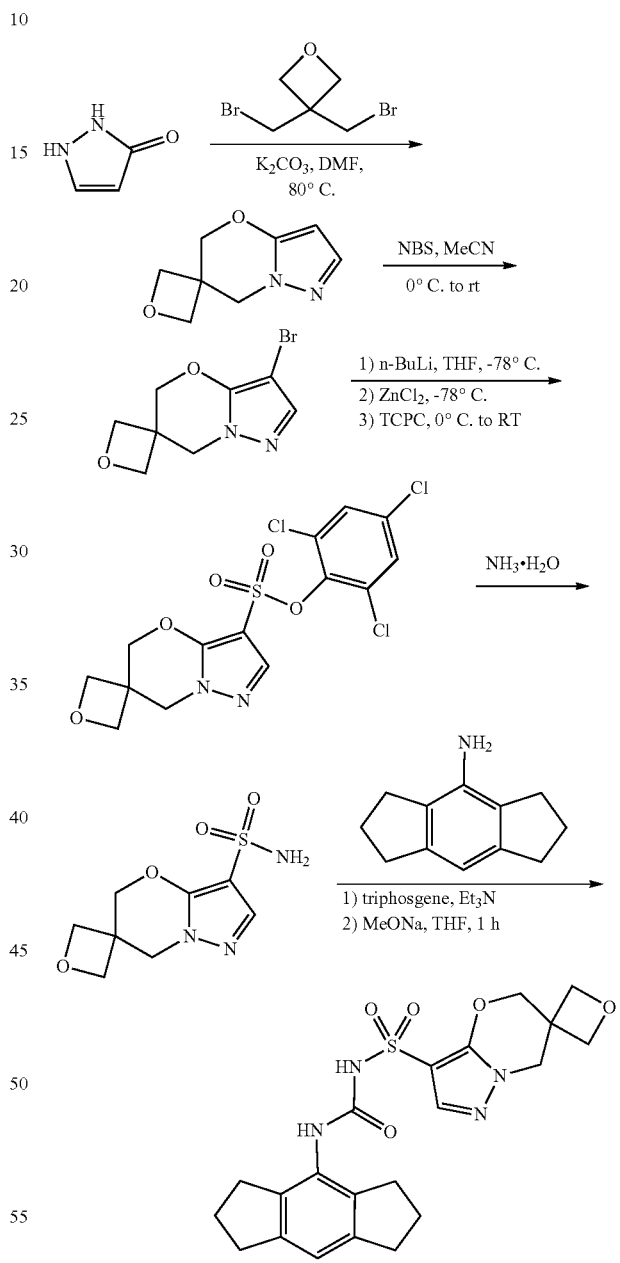

The title compound was prepared using general procedure of N-((1,2,3,5,6,7-hexahydro-s-indacen-4-yl)carbamoyl)-6,7-dihydro-5H-pyrazolo[5,1-b][1,3]oxazine-3-sulfonamide (Example 1).

$^1$H NMR (400 MHz, DMSO-d6): δ=7.77 (s, 1H), 7.51 (s, 1H), 6.85 (s, 1H), 4.59 (s, 2H), 4.50 (d, J=6.0 Hz, 2H), 4.43 (d, J=6.4 Hz, 2H), 4.38 (s, 2H), 2.76 (t, J=7.2 Hz, 4H), 2.60 (t, J=6.4 Hz, 4H), 1.94-1.90 (m, 4H). MS: m/z 445.0 (M+H$^+$).

Example 6: Synthesis of N-((2,6-diisopropylphenyl)carbamoyl)-6,7-dihydro-5H-pyrazolo[5,1-b][1,3]oxazine-3-sulfonamide Synthesis of N-((2,6-diisopropylphenyl)carbamoyl)-6,7-dihydro-5H-pyrazolo[5,1-b][1,3]oxazine-3-sulfonamide is shown below.

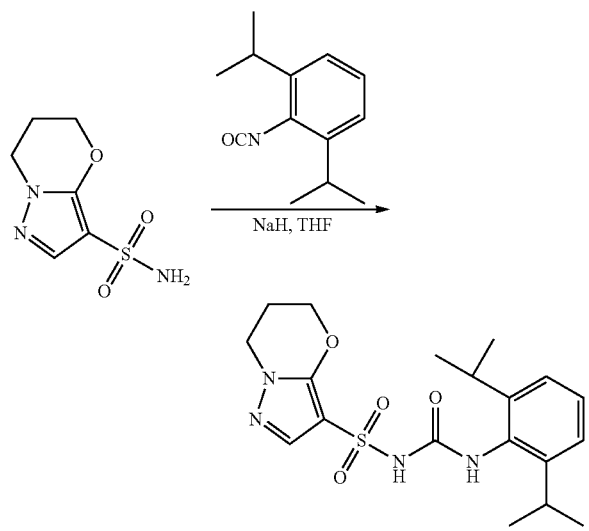

6,7-Dihydro-5H-pyrazolo[5,1-b][1,3]oxazine-3-sulfonamide (0.123 mmol, 0.025 g) was suspended in THF (1 mL) and cooled to 0 C. NaH (0.123 mmol, 2.95 mg) was added and the mixture left to stir for 5 min. 2-Isocyanato-1,3-diisopropylbenzene (0.123 mmol, 0.026 mL) was then added and the mixture left to stir at room temperature for 2 h. At this time the reaction was quenched with water and the organic solvent evaporated. The reaction was then acidified with HCl and a white precipitate filtered off, washed with water and dried to yield N-((2,6-diisopropylphenyl)carbamoyl)-6,7-dihydro-5H-pyrazolo[5,1-b][1,3]oxazine-3-sulfonamide (38 mg, 76%). $^1$H-NMR (400 MHz; DMSO-$d_6$): δ 10.60 (s, 1H), 7.69 (s, 1H), 7.59 (s, 1H), 7.24 (t, J=7.7 Hz, 1H), 7.12 (d, J=7.7 Hz, 2H), 4.46-4.44 (m, 2H), 4.11 (dd, J=7.5, 4.7 Hz, 2H), 2.91 (t, J=6.9 Hz, 2H), 2.23-2.20 (m, 2H), 1.13-1.01 (m, 12H). MS: m/z 407 (M+H$^+$).

Example 7: Synthesis of N-((4-chloro-2,6-diisopropylphenyl)carbamoyl)-6,7-dihydro-5H-pyrazolo[5,1-b][1,3]oxazine-3-sulfonamide Synthesis of N-((4-chloro-2,6-diisopropylphenyl)carbamoyl)-6,7-dihydro-5H-pyrazolo[5,1-b][1,3]oxazine-3-sulfonamide is shown below.

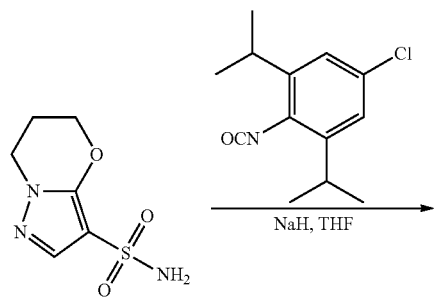

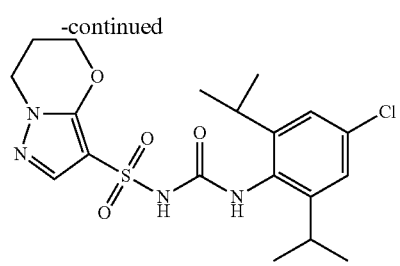

6,7-Dihydro-5H-pyrazolo[5,1-b][1,3]oxazine-3-sulfonamide (0.105 mmol, 0.021 g) was dissolved in THF (2 mL) and treated with NaH (0.105 mmol, 4.21 mg) at 0 C. After a few minutes 5-chloro-2-isocyanato-1,3-diisopropylbenzene (0.105 mmol, 25 mg) was added and the mixture was left to stir over the weekend. The reaction was then quenched with water and the solvent reduced to ~⅓ of the original volume. The reaction was then acidified with 1M HCl and a fine white precipitate filtered off, washed with water and dried to yield N-((4-chloro-2,6-diisopropylphenyl)carbamoyl)-6,7-dihydro-5H-pyrazolo[5,1-b][1,3]oxazine-3-sulfonamide (23.7 mg, 51.1%). $^1$H-NMR (400 MHz; DMSO-$d_6$): δ 10.70 (s, 1H), 7.76 (s, 1H), 7.59 (s, 1H), 7.15 (s, 2H), 4.45 (dd, J=5.4, 4.8 Hz, 2H), 4.11 (t, J=6.1 Hz, 2H), 3.62-3.59 (m, 3H), 2.93-2.86 (m, 2H), 2.24-2.20 (m, 2H), 1.78-1.75 (m, 3H), 1.11-1.01 (m, 13H). MS: m/z 442 (M+H$^+$).

Example 8: Synthesis of N-((1,2,3,5,6,7-hexahydro-s-indacen-4-yl)carbamoyl)-6,6-dimethyl-6,7-dihydro-5H-pyrazolo[5,1-b][1,3]oxazine-3-sulfonamide Synthesis of N-((1,2,3,5,6,7-hexahydro-s-indacen-4-yl)carbamoyl)-6,6-dimethyl-6,7-dihydro-5H-pyrazolo[5,1-b][1,3]oxazine-3-sulfonamide is shown below.

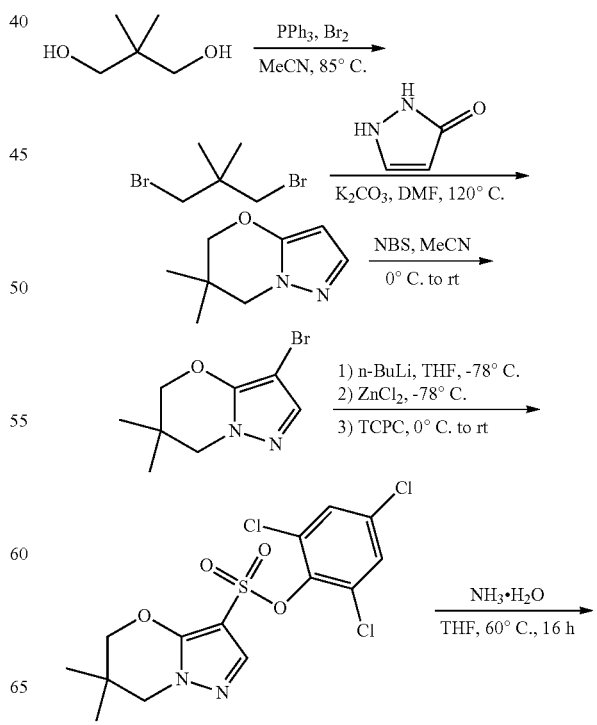

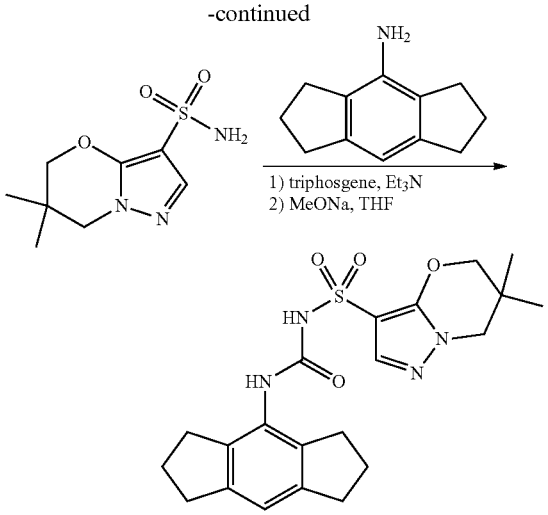

Step 1

To a suspension of PPh$_3$ (252.0 g, 961.5 mmol) in acetonitrile (600 mL) was added dropwise a solution of Br$_2$ (49.3 mL, 961.5 mmol) in acetonitrile (200 mL) at 0° C., then 2,2-dimethyl-propane-1,3-diol (50.0 g, 480.8 mmol) was added. The reaction mixture was heated to 85° C., and refluxed for 16 hrs. The solvent was removed in vacuo. The residual solid was washed with (PE/EA=3/1, 300 mL) and filtered. The filtrate was concentrated and distilled to give 1,3-dibromo-2,2-dimethyl-propane (45.0 g, yield: 41%) as a colorless oil.

$^1$HNMR (300 MHz, CDCl$_3$): δ=3.42 (s, 4H), 1.18 (s, 6H).

Step 2

1,2-Dihydro-pyrazol-3-one (25.0 g, 297.6 mmol) and K$_2$CO$_3$ (144.0 g, 1041.7 mmol) were heated to 120° C. in DMF (700 mL). 1,3-Dibromo-2,2-dimethyl-propane (82.0 g, 357.1 mmol) was added and the mixture was heated for 24 hrs. The solvent was removed in vacuo. The residue was partitioned between EA/H$_2$O (200 mL/500 mL) and the layers were separated. The aqueous layer was extracted with EA (200 mL) and the combined organic layer was washed with brine (100 mL), dried over Na$_2$SO$_4$ and concentrated. The residue was cooled to 5° C. and washed with PE (100 mL) to give 6,6-dimethyl-6,7-dihydro-5H-pyrazolo[5,1-b][1,3]oxazine (14.0 g, yield: 31%) as a yellow solid.

$^1$HNMR (300 MHz, CDCl$_3$): δ=7.32 (s, 1H), 5.48 (s, 1H), 3.87 (s, 2H), 3.84 (s, 2H), 1.13 (s, 6H).

Step 3-5

These three steps are similar to general procedure of N-((1,2,3,5,6,7-hexahydro-s-indacen-4-yl)carbamoyl)-6,7-dihydro-5H-pyrazolo[5,1-b][1,3]oxazine-3-sulfonamide (Example 1).

Step 6

To a suspension of 6,6-dimethyl-6,7-dihydro-5H-pyrazolo[5,1-b][1,3]oxazine-3-sulfonic acid amide (400 mg, 1.7 mmol) in THF (10 mL) was added MeONa (190 mg, 3.5 mmol) and the mixture was stirred at room temperature for 20 mins to give a sodium salt suspension.

In another flask, to a solution of 1,2,3,5,6,7-hexahydro-s-indacen-4-ylamine (300 mg, 1.7 mmol) and TEA (530 mg, 5.2 mmol) in THF (15 mL) was added triphosgene (210 mg, 0.7 mmol) in one portion and the mixture was stirred at room temperature under N$_2$ for 20 mins. The reaction mixture was then filtered. The filtrate was added to the sodium salt suspension above and stirred at room temperature for 16 hrs. After that, the reaction solution was partitioned between EA (50 mL) and water (150 mL). The aqueous phase was filtered and bubbled by N$_2$ for 5 mins, then acidified to pH=5 with conc. HCl. The solid formed was dissolved after MeCN (50 mL) was added. And the mixture was concentrated to remove MeCN at 40° C. The solid formed was collected by filtration and dried to give N-((1,2,3,5,6,7-hexahydro-s-indacen-4-yl)carbamoyl)-6,6-dimethyl-6,7-dihydro-5H-pyrazolo[5,1-b][1,3]oxazine-3-sulfonamide (320 mg, yield: 43%) as a white solid.

$^1$HNMR (400 MHz, DMSO-d$_6$): δ=10.49 (s, 1H), 7.90 (s, 1H), 7.64 (s, 1H), 6.93 (s, 1H), 4.14 (s, 2H), 3.88 (s, 2H), 2.78 (t, J=7.2 Hz, 4H), 2.58 (t, J=7.2 Hz, 4H), 1.98-1.90 (m, 4H), 1.02 (s, 6H). MS: m/z 431.0 (M+H$^+$).

Example 9: Synthesis of 6,6-dimethyl-6,7-dihydro-5H-pyrazolo[5,1-b][1,3]oxazine-3-sulfonic acid amide Another method to synthesize 6,6-dimethyl-6,7-dihydro-5H-pyrazolo[5,1-b][1,3]oxazine-3-sulfonic acid amide is shown below.

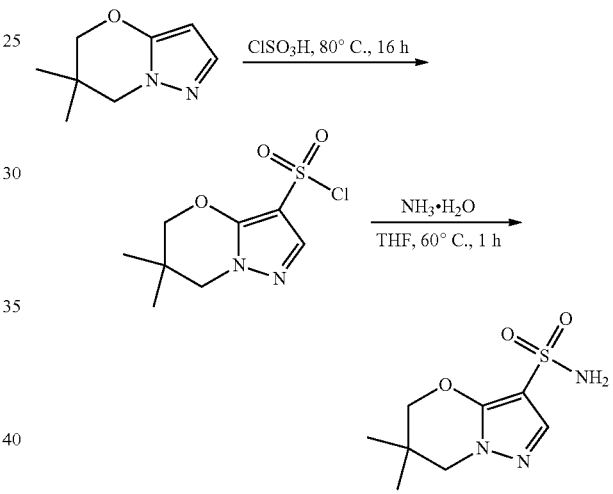

Step 1

6,6-Dimethyl-6,7-dihydro-5H-pyrazolo[5,1-b][1,3]oxazine (3.0 g, 19.7 mmol) was added portion wise to ClSO$_3$H (25 mL) at 0° C. After stirred at 80° C. for 16 hrs, the reaction mixture was added dropwise to ice-water (250 mL) and extracted with EA (100 mL×3). The combined organic layer were washed with brine (50 mL), dried over Na$_2$SO$_4$ and concentrated. The residue was cooled to 5° C. and washed with PE/EA (5/1, 30 mL) to give 6,6-dimethyl-6,7-dihydro-5H-pyrazolo[5,1-b][1,3]oxazine-3-sulfonyl chloride (2.4 g, yield: 49%) as a yellow solid.

$^1$HNMR (300 MHz, CDCl$_3$): δ=7.79 (s, 1H), 4.16 (s, 2H), 3.90 (s, 2H), 1.20 (s, 6H).

Step 2

To a solution of 6,6-dimethyl-6,7-dihydro-5H-pyrazolo[5,1-b][1,3]oxazine-3-sulfonyl chloride (2.2 g, 8.8 mmol) in THF (18 mL) was added NH$_3$.H$_2$O (10 mL). After stirred at 60° C. for 1 hr, the reaction mixture was concentrated to dryness. The residue was diluted with MeOH (20 mL) and acidified by aq.HCl (2 N) to pH=5. The resulting solution was purified by reverse phase column (0%-60% MeCN in H$_2$O) to give 6,6-dimethyl-6,7-dihydro-5H-pyrazolo[5,1-b][1,3]oxazine-3-sulfonic acid amide (1.6 g, yield: 79%) as a yellow solid.

Example 10: Synthesis of N-((1,2,3,5,6,7-hexahydro-s-indacen-4-yl)carbamoyl)-6-hydroxy-6,7-dihydro-5H-pyrazolo[5,1-b][1,3]oxazine-3-sulfonamide Synthesis of N-((1,2,3,5,6,7-hexahydro-s-indacen-4-yl)carbamoyl)-6-hydroxy-6,7-dihydro-5H-pyrazolo[5,1-b][1,3]oxazine-3-sulfonamide is shown below.

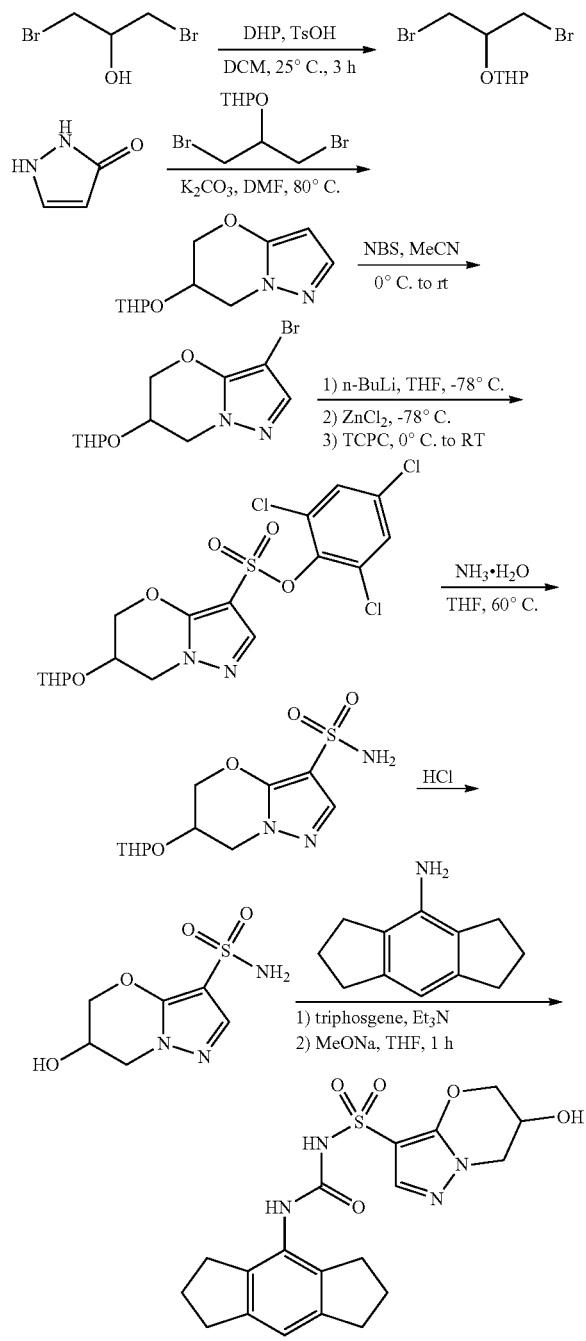

Step 1

To as solution of 1,3-dibromo-propan-2-ol (42.5 g, 0.19 mol) and DHP (33 g, 0.38 mol) in DCM (300 mL), was added TsOH (3.6 g, 0.019 mol) in portions and the mixture was stirred at room temperature for 2 hrs. The reaction solution was concentrated and the residue was purified by silica gel column (PE/EA=50/1) to give 2-(2-bromo-1-bromomethyl-ethoxy)-tetrahydro-pyran (34 g, yield: 60%) as a colorless oil.

$^1$H NMR (300 MHz, DMSO-d6): δ=4.80-4.79 (m, 1H), 4.04-3.90 (m, 2H), 3.72-3.52 (m, 5H), 1.87-1.55 (m, 6H).

Step 2

A mixture of 2-(2-bromo-1-bromomethyl-ethoxy)-tetrahydro-pyran (17 g, 56.3 mmol), 1,2-dihydro-pyrazol-3-one (4 g, 47 mmol) and $K_2CO_3$ (23 g, 165 mmol) in DMF (250 mL) was stirred at 100° C. overnight. The solvent was removed under reduced pressure. The residue was partitioned between EA (200 mL) and water (200 ml). The aqueous phase was extracted with EA (200 ml). The organic layers were combined, washed with water (100 mL) and brine (100 mL), dried over $Na_2SO_4$ and concentrated. The residue was purified by silica gel column (EA) to give 6-(tetrahydro-pyran-2-yloxy)-6,7-dihydro-5H-pyrazolo[5,1-b][1,3]oxazine (4.9 g, yield: 46%) as a yellow oil.

$^1$H NMR (300 MHz, DMSO-d6): δ=7.34 (s, 1H), 5.51 (s, 1H), 4.89-4.83 (m, 1H), 4.36-4.24 (m, 4H), 3.93-3.88 (m, 1H), 3.59-3.54 (m, 1H), 1.79-1.69 (m, 3H), 1.65-1.51 (m, 4H). MS: m/z 224.9 (M+H$^+$).

Step 3

To a solution of 6-(tetrahydro-pyran-2-yloxy)-6,7-dihydro-5H-pyrazolo[5,1-b][1,3]oxazine (5.1 g, 22.8 mmol) in MeCN, was added NBS at 0° C. under $N_2$ in two portions. The reaction was then stirred at room temperature for 1 hr. The reaction was partitioned between EA (100 mL) and water (200 mL). The organic layer was washed with water (100 mL) and brine (100 mL), dried over $Na_2SO_4$ and concentrated. The residue was purified by silica gel column (PE/EA=1/1) to give 3-bromo-6-(tetrahydro-pyran-2-yloxy)-6,7-dihydro-5H-pyrazolo[5,1-b][1,3]oxazine (5.6 g, yield: 81%) as a yellow solid.

$^1$H NMR (300 MHz, DMSO-d6): δ=7.33 (s, 1H), 4.88-4.82 (m, 1H), 4.48-4.18 (m, 5H), 3.88-3.75 (m, 1H), 3.58-3.53 (m, 1H), 1.84-1.51 (m, 7H). MS: m/z 303.0 (M+H$^+$).

Step 4

To a solution of 3-bromo-6-(tetrahydro-pyran-2-yloxy)-6,7-dihydro-5H-pyrazolo[5,1-b][1,3]oxazine (2 g, 6.6 mmol) in dry THF (20 mL) was added n-BuLi in hexane (2.5 M, 2.6 mL, 6.6 mmol) slowly at −78° C. under $N_2$. After stirred with cooling for 20 min, $ZnCl_2$ in ether (1 M, 6.6 mL, 6.6 mmol) was added slowly at this temperature. The cold bath was removed and the reaction was stirred at room temperature for 1 hr. TCPC (2 g, 6.6 mmol) was then added and the mixture was stirred at room temperature for 1 hr. The reaction was partitioned between water (100 mL) and EA (100 mL). The organic layer was washed with brine (100 mL), dried over $Na_2SO_4$ and concentrated to give crude 6-(tetrahydro-pyran-2-yloxy)-6,7-dihydro-5H-pyrazolo[5,1-b][1,3]oxazine-3-sulfonic acid 2,4,6-trichloro-phenyl ester as a yellow gel which was used for next step directly without any purification.

Step 5

A mixture of 6-(tetrahydro-pyran-2-yloxy)-6,7-dihydro-5H-pyrazolo[5,1-b][1,3]oxazine-3-sulfonic acid 2,4,6-trichloro-phenyl ester (crude, ~6.6 mmol), $NH_4OH$ (20 mL) and THF (20 mL) was stirred at 60° C. overnight. The reaction was concentrated under reduced pressure until 10 mL of liquid remained. The remained solution was acidified with 1 N HCl to pH=5 and extracted with EA (100 mL×5). The organic layers were combined, dried over $Na_2SO_4$ and concentrated to give crude 6-(tetrahydro-pyran-2-yloxy)-6,7-dihydro-5H-pyrazolo[5,1-b][1,3]oxazine-3-sulfonic acid amide as a yellow gel which was used for next step directly without any purification. MS: m/z 304.1 (M+H⁺).

Step 6

To a solution of 6-(tetrahydro-pyran-2-yloxy)-6,7-dihydro-5H-pyrazolo[5,1-b][1,3]oxazine-3-sulfonic acid amide (crude, 6.6 mmol) in THF/H₂O/EtOH (50 mL/10 mL/50 mL) was added conc. HCl (10 mL) and stirred at room temperature overnight. The reaction was concentrated under reduced pressure. The residue was purified by reverse phase column (MeCN/H₂O) to give 6-hydroxy-6,7-dihydro-5H-pyrazolo[5,1-b][1,3]oxazine-3-sulfonic acid amide (290 mg, yield: 21% over 3 steps) as a white solid.

¹H NMR (300 MHz, DMSO-d6): δ=7.48 (s, 1H), 7.11 (brs, 2H), 5.65 (brs, 1H), 4.30-4.20 (m, 4H), 3.96-3.92 (m, 1H). MS: m/z 220.1 (M+H⁺).

Step 7

To a solution of 1,2,3,5,6,7-hexahydro-s-indacen-4-ylamine (63.1 mg, 0.365 mmoL) and TEA (0.203 ml, 1.1 mmoL) in THF (5 ml), was added triphosgene (43.7 mg, 0.146 mmoL), and the mixture was stirred for 10 min at room temperature. In another round-bottomed flask, to a solution of 6-hydroxy-6,7-dihydro-5H-pyrazolo[5,1-b][1,3]oxazine-3-sulfonic acid amide (80 mg, 0.365 mmoL) in THF (5 ml) was added MeONa (21.7 mg, 0.401 mmoL) and the mixture was stirred for 20 mins at room temperature. The prepared 4-isocyanato-1,2,3,5,6,7-hexahydro-s-indacene was filtered to remove the resulting precipitate and the filtrate was added to another flask containing sulfonamide salt. The reaction was check by TLC and quenched with the addition of water (30 mL) after 20 mins. The aqueous phase was washed with EA (20 mL) and filtered later. The filtrate was acidified to pH=3~4. The resulting solid was collected by filtration to give N-((1,2,3,5,6,7-hexahydro-s-indacen-4-yl)carbamoyl)-6-hydroxy-6,7-dihydro-5H-pyrazolo[5,1-b][1,3]oxazine-3-sulfonamide (15 mg, yield: 10%) as a white solid.

¹H NMR (400 MHz, DMSO-d6): δ=10.45 (s, 1H), 7.90 (s, 1H), 7.62 (s, 1H), 6.93 (s, 1H), 5.67 (s, 1H), 4.34 (s, 3H), 4.24 (dd, J=4.0, 3.2 Hz, 1H), 3.96 (d, J=12.4 Hz, 1H), 2.78 (t, J=7.2 Hz, 4H), 2.60 (t, J=7.6 Hz, 4H), 1.98-1.93 (m, 4H). MS: m/z 419.1 (M+H⁺).

Example 11: Synthesis of N-((1,2,3,5,6,7-hexahydro-s-indacen-4-yl)carbamoyl)-5,6,7,8-tetrahydro-pyrazolo[5,1-b][1,3]oxazepine-3-sulfonamide Synthesis of N-((1,2,3,5,6,7-hexahydro-s-indacen-4-yl)carbamoyl)-5,6,7,8-tetrahydropyrazolo[5,1-b][1,3]oxazepine-3-sulfonamide is shown below

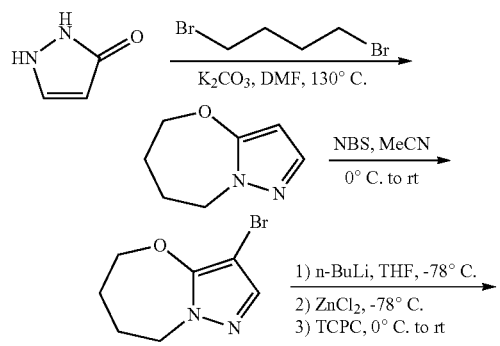

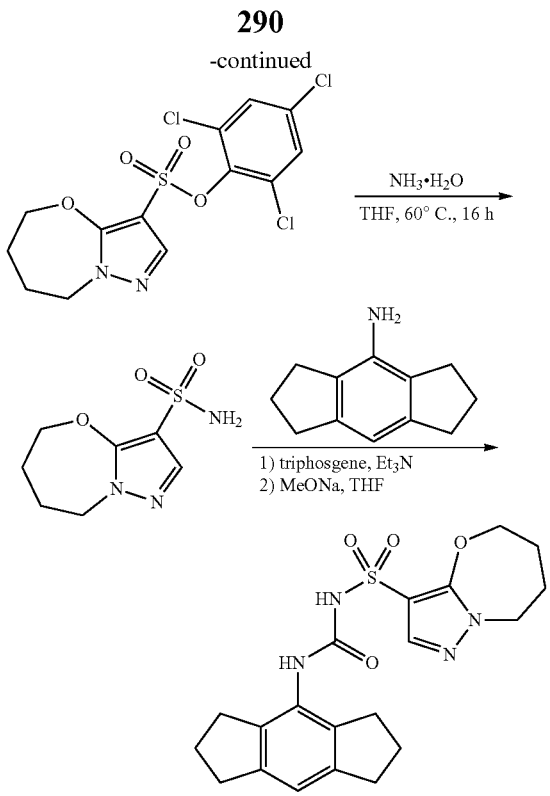

Step 1

1,2-Dihydro-pyrazol-3-one (3.0 g, 35.7 mmol) and K₂CO₃ (17.0 g, 125.0 mmol) were heated to 130° C. in DMF (100 mL). 1,4-Dibromo-butane (9.3 g, 42.9 mmol) was added and the mixture was heated for 16 hrs. The solvent was removed in vacuo. The residue was partitioned between EA/H₂O (50 mL/80 mL) and the layers were separated. The aqueous layer was extracted with EA (50 mL) and the combined organic layers were washed with brine (50 mL), dried over Na₂SO₄ and concentrated. The residue was purified by silica gel column (PE/EA=1/1) to give 5,6,7,8-tetrahydro-4-oxa-1,8a-diaza-azulene (1.3 g, yield: 27%) as a colorless oil.

¹H NMR (300 MHz, CDCl₃): δ=7.24 (d, J=1.5 Hz, 1H), 5.69 (d, J=1.5 Hz, 1H), 4.25-4.20 (m, 2H), 4.06 (t, J=5.1 Hz, 2H), 2.07-2.03 (m, 2H), 1.91-1.84 (m, 2H).

Step 2-5

These four steps are similar to general procedure of N-((1,2,3,5,6,7-hexahydro-s-indacen-4-yl)carbamoyl)-6,7-dihydro-5H-pyrazolo[5,1-b][1,3]oxazine-3-sulfonamide (Example 3).

¹HNMR (400 MHz, DMSO-d₆): δ=10.60 (s, 1H), 7.94 (s, 1H), 7.60 (s, 1H), 6.94 (s, 1H), 4.22-4.16 (m, 4H), 2.79 (t, J=7.6 Hz, 4H), 2.58 (t, J=7.2 Hz, 4H), 2.03-1.90 (m, 6H), 1.80-1.70 (m, 2H). MS: m/z 417.0 (M+H⁺).

Example 12: Synthesis of N-((1,2,3,5,6,7-hexahydro-s-indacen-4-yl)carbamoyl)-6,7-dihydro-5H-pyrazolo[5,1-b][1,3]oxazine-3-sulfonamide Synthesis of N-((1,2,3,5,6,7-hexahydro-s-indacen-4-yl)carbamoyl)-6,7-dihydro-5H-pyrazolo[5,1-b][1,3]oxazine-3-sulfonamide is shown below. 3

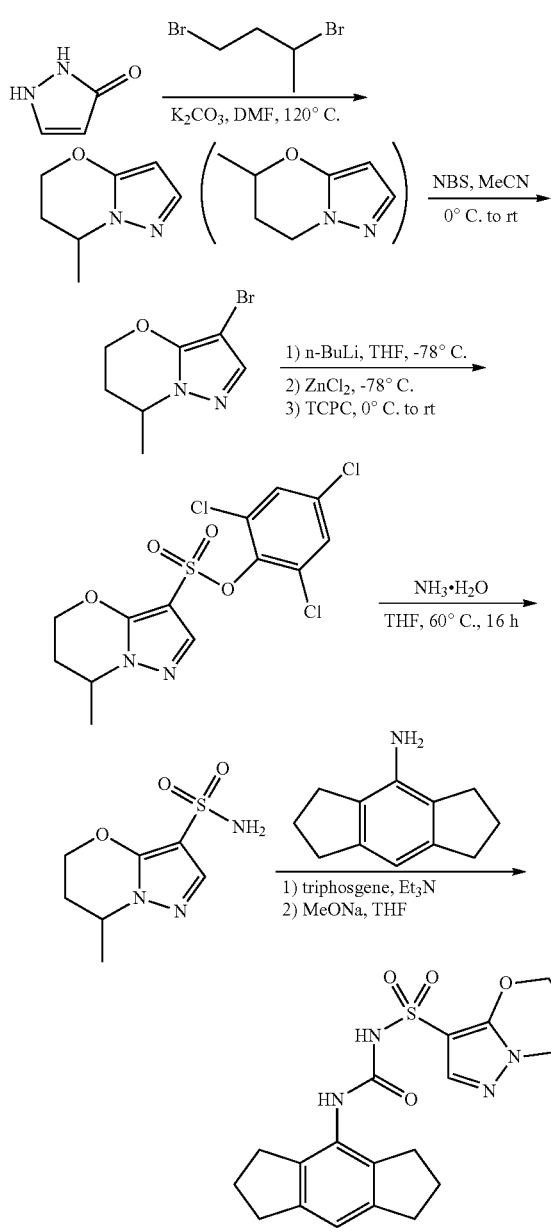

(d, J=1.6 Hz, 1H), 4.36-4.31 (m, 2H), 4.24-4.18 (m, 1H), 2.34-2.27 (m, 1H), 2.02-1.94 (m, 1H), 1.59 (d, J=6.0 Hz, 3H).

5-methyl-6,7-dihydro-5H-pyrazolo[5,1-b][1,3]oxazine:
¹HNMR (400 MHz, CDCl₃): δ=7.30 (d, 7=1.6 Hz, 1H), 5.45 (d, 7=2.0 Hz, 1H), 4.38-4.30 (m, 1H), 4.25-4.20 (m, 1H), 4.15-4.08 (m, 1H), 2.19-2.03 (m, 2H), 1.46 (d, J=6.4 Hz, 3H).

Step 2-5

These four steps are similar to general procedure of N-((1,2,3,5,6,7-hexahydro-s-indacen-4-yl)carbamoyl)-6,7-dihydro-5H-pyrazolo[5,1-b][1,3]oxazine-3-sulfonamide (Example 1).

¹HNMR (400 MHz, DMSO-d₆): δ=10.47 (s, 1H), 7.91 (s, 1H), 7.64 (s, 1H), 6.94 (s, 1H), 4.53-4.32 (m, 3H), 2.79 (t, J=7.2 Hz, 4H), 2.58 (t, J=7.2 Hz, 4H), 2.38-2.31 (m, 1H), 1.99-1.91 (m, 5H), 1.45 (d, J=6.0 Hz, 3H). MS: m/z 417.0 (M+H⁺).

Example 13: Synthesis of 6-fluoro-N-((1,2,3,5,6,7-hexahydro-s-indacen-4-yl)carbamoyl)-6,7-dihydro-5H-pyrazolo[5,1-b][1,3]oxazine-3-sulfonamide Synthesis of 6-fluoro-N-((1,2,3,5,6,7-hexahydro-s-indacen-4-yl)carbamoyl)-6,7-dihydro-5H-pyrazolo[5,1-b][1,3]oxazine-3-sulfonamide is shown below.

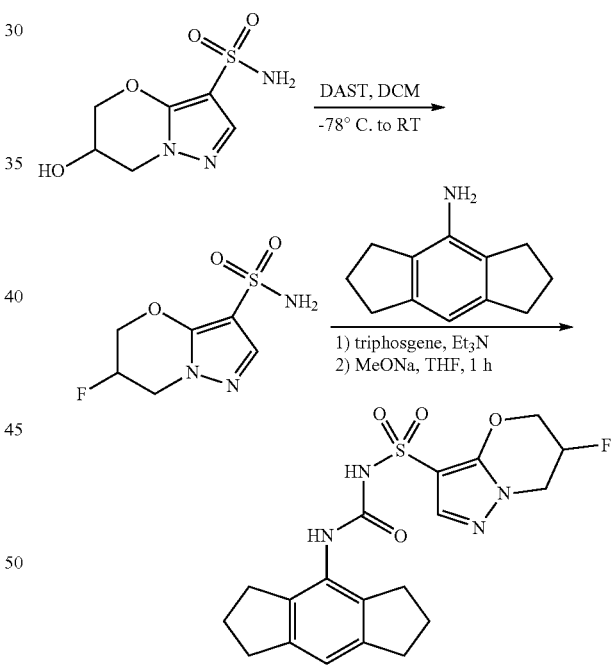

Step 1

To a solution of 6-hydroxy-6,7-dihydro-5H-pyrazolo[5,1-b][1,3]oxazine-3-sulfonic acid amide (100 mg, 0.46 mmol) in DCM (5 mL) was added DAST (148 mg, 0.92 mmol) at −78° C. under N₂. The reaction was then stirred at room temperature overnight. The reaction was quenched with H₂O (20 mL) and partitioned between DCM (40 mL) and water (20 mL). The organic layer was dried over Na₂SO₄ and concentrated. The residue was purified by reverse phase column (MeCN/H2O) to give 6-fluoro-6,7-dihydro-5H-pyrazolo[5,1-b][1,3]oxazine-3-sulfonic acid amide (18 mg, yield: 18%) as a white solid. MS: m/z 222.1 (M+H⁺).

Step 1

1,2-Dihydro-pyrazol-3-one (2.0 g, 23.8 mmol) and K₂CO₃ (11.5 g, 83.3 mmol) were heated to 120° C. in DMF (60 mL). 1,3-Dibromo-butane (6.2 g, 28.6 mmol) was added and the mixture was heated for 16 hrs. The solvent was removed in vacuo. The residue was partitioned between EA/H₂O (50 mL/80 mL) and the layers were separated. The aqueous layer was extracted with EA (50 mL) and the combined organic layers were washed with brine (50 mL), dried over Na₂SO₄ and concentrated. The residue was purified by silica gel column (PE/EA=5/1 to 1/1) to give 7-methyl-6,7-dihydro-5H-pyrazolo[5,1-b][1,3]oxazine (1.3 g, yield: 40%) as a yellow oil and 5-methyl-6,7-dihydro-5H-pyrazolo[5,1-b][1,3]oxazine (500 mg, yield: 15%) as a yellow solid.

7-methyl-6,7-dihydro-5H-pyrazolo[5,1-b][1,3]oxazine:
¹HNMR (400 MHz, CDCl₃): δ=7.32 (d, J=2.0 Hz, 1H), 5.45

Step 2

This step is similar to general procedure for N-((1,2,3,5,6,7-hexahydro-s-indacen-4-yl)carbamoyl)-6,7-dihydro-5H-pyrazolo[5,1-b][1,3]oxazine-3-sulfonamide (Example 1).

$^1$H NMR (400 MHz, DMSO-d6): δ=10.58 (s, 1H), 8.00 (s, 1H), 7.69 (s, 1H), 6.93 (s, 1H), 5.58 (d, J=44.0 Hz, 1H), 4.75 (t, J=12.0 Hz, 1H), 4.59-4.37 (m, 3H), 2.78 (t, J=7.2 Hz, 4H), 2.60 (t, J=7.2 Hz, 4H), 1.97-1.90 (m, 4H). MS: m/z 421.0 (M+H$^+$).

Example 14: Synthesis of N-((1,2,3,5,6,7-hexahydro-s-indacen-4-yl)carbamoyl)-6-methoxy-6,7-dihydro-5H-pyrazolo[5,1-b][1,3]oxazine-3-sulfonamide Synthesis of N-((1,2,3,5,6,7-hexahydro-s-indacen-4-yl)carbamoyl)-6-methoxy-6,7-dihydro-5H-pyrazolo[5,1-b][1,3]oxazine-3-sulfonamide is shown below.

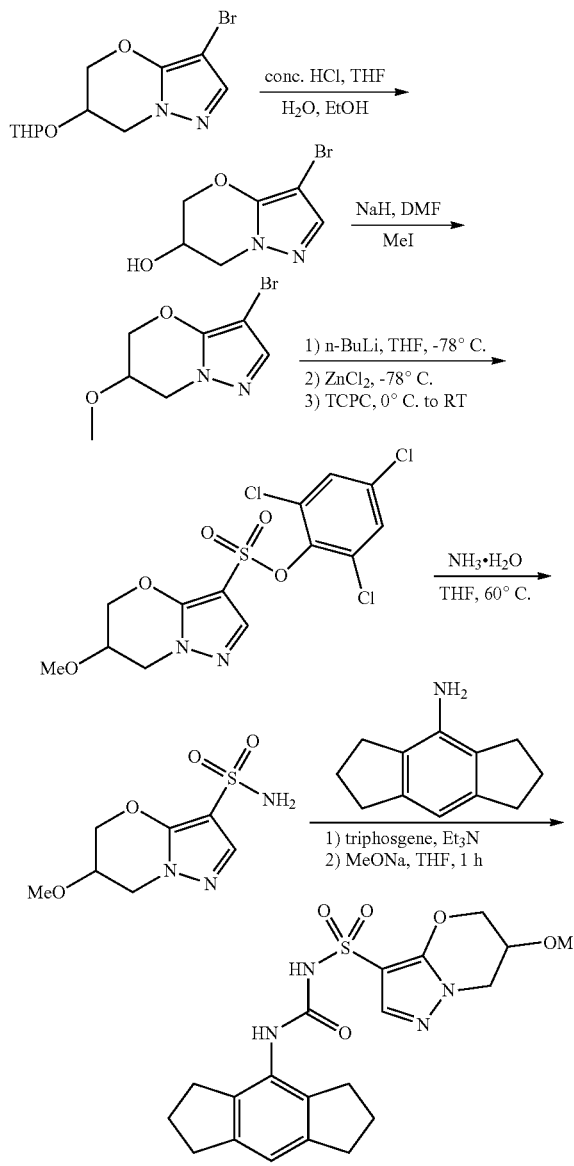

Step 1

To a solution of 3-bomo-6-(tetrahydro-pyran-2-yloxy)-6,7-dihydro-5H-pyrazolo[5,1-b][1,3]oxazine (4.6 g, 15.2 mmol) in THF/H$_2$O/EtOH (50 mL/10 mL/50 mL) was added conc.HCl. The reaction was stirred at room temperature for 2 hrs. The reaction solution was concentrated. The residue was treated with saturated NaHCO$_3$ solution. The solid formed was collected by filtration to give 3-bromo-6,7-dihydro-5H-pyrazolo[5,1-b][1,3]oxazin-6-ol (2.76 g, yield: 84%) as a white solid.

$^1$H NMR (300 MHz, DMSO-d6): δ=7.36 (s, 1H), 5.59 (brs, 1H), 4.28-4.18 (m, 4H), 3.95-3.90 (m, 1H).

Step 2

To a solution of 3-bromo-6,7-dihydro-5H-pyrazolo[5,1-b][1,3]oxazin-6-ol (1.2 g, 5.5 mmol) in DMF (12 mL) was added NaH (60% in mineral oil, 263 mg, 6.6 mmol). The reaction was stirred at room temperature for 1 hr under N$_2$. Then MeI (940 mg, 6.6 mmol) was added and the mixture was stirred at room temperature for 2 hrs. The reaction mixture was poured into water (60 mL) and extracted with EA (50 mL). The organic layer was washed with water (50 mL) and brine (50 mL), dried over Na$_2$SO$_4$ and concentrated. The residue was purified by reverse phase column (MeCN/H$_2$O) to give 3-bromo-6-methoxy-6,7-dihydro-5H-pyrazolo[5,1-b][1,3]oxazine (1 g, yield: 78%) as a white solid.

$^1$H NMR (300 MHz, CDCl$_3$): δ=7.34 (s, 1H), 4.53-4.48 (m, 1H), 4.27-4.18 (m, 3H), 3.94-3.93 (m, 1H), 3.49 (s, 3H). MS: m/z 232.9 (M+H$^+$).

Step 3~5

These steps are similar to general procedure for N-((1,2,3,5,6,7-hexahydro-s-indacen-4-yl)carbamoyl)-6,7-dihydro-5H-pyrazolo[5,1-b][1,3]oxazine-3-sulfonamide (Example 1).

$^1$H NMR (400 MHz, DMSO-d6): δ=10.47 (s, 1H), 7.91 (s, 1H), 7.62 (s, 1H), 6.93 (s, 1H), 4.65 (d, J=11.6 Hz, 1H), 4.37 (d, J=11.2 Hz, 1H), 4.24-4.22 (m, 2H), 4.06 (s, 1H), 3.34 (overlap, 3H), 2.78 (t, J=7.6 Hz, 4H), 2.60 (t, J=7.2 Hz, 4H), 1.98-1.91 (m, 4H). MS: m/z 433.0 (M+H$^+$).

Example 15: Synthesis of N-((1,2,3,5,6,7-hexahydro-s-indacen-4-yl)carbamoyl)-5-methyl-6,7-dihydro-5H-pyrazolo[5,1-b][1,3]oxazine-3-sulfonamide Synthesis of N-((1,2,3,5,6,7-hexahydro-s-indacen-4-yl)carbamoyl)-5-methyl-6,7-dihydro-5H-pyrazolo[5,1-b][1,3]oxazine-3-sulfonamide is shown below.

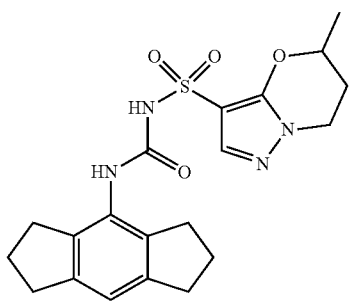 [SMILES: CC1CCn2ncc(S(=O)(=O)NC(=O)Nc3c4c(cc5c3CCC5)CCC4)c2O1]

The title compound was prepared using general procedure for N-((1,2,3,5,6,7-hexahydro-s-indacen-4-yl)carbamoyl)-6,7-dihydro-5H-pyrazolo[5,1-b][1,3]oxazine-3-sulfonamide (Example 1).

$^1$HNMR (400 MHz, DMSO-d$_6$): δ=10.51 (s, 1H), 7.90 (s, 1H), 7.61 (s, 1H), 6.94 (s, 1H), 4.60-4.56 (m, 1H), 4.13-4.08 (m, 2H), 2.79 (t, J=7.2 Hz, 4H), 2.59 (t, J=6.8 Hz, 4H), 2.28-2.24 (m, 1H), 1.98-1.93 (m, 5H), 1.38 (d, J=6.0 Hz, 3H). MS: m/z 417.0 (M+H⁺).

Example 16: Synthesis of N-((8-chloro-1,2,3,5,6,7-hexahydro-s-indacen-4-yl)carbamoyl)-6,7-dihydro-5H-pyrazolo[5,1-b][1,3]oxazine-3-sulfonamide Synthesis of N-((8-chloro-1,2,3,5,6,7-hexahydro-s-indacen-4-yl)carbamoyl)-6,7-dihydro-5H-pyrazolo[5,1-b][1,3]oxazine-3-sulfonamide is shown below.

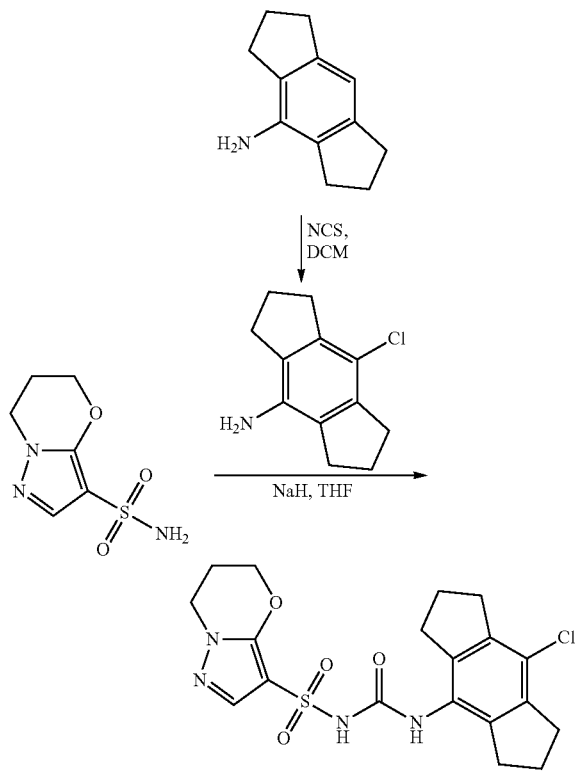 [SMILES: Nc1c2c(cc3c1CCC3)CCC2 ; NS(=O)(=O)c1cnn2c1OCCC2 ; Nc1c2c(c(Cl)c3c1CCC3)CCC2 ; O=C(Nc1c2c(c(Cl)c3c1CCC3)CCC2)NS(=O)(=O)c1cnn2c1OCCC2]

Step 1
1,2,3,5,6,7-hexahydro-s-indacen-4-amine (2.332 mmol, 404 mg) and NCS (2.332 mmol, 0.311 g) were mixed in DCM (5 mL) and left to stir overnight. The mixture was then partitioned between water (20 mL) and DCM (20 mL). The layers were separated and the aq. layer extracted with DCM (20 mL). The combined organic layers were then dried over Na2SO4, filtered and concentrated to yield 1,2,3,5,6,7-hexahydro-s-indacen-4-amine (2.332 mmol, 404 mg) as a brown solid which was used without purification. MS: m/z 209 (M+H⁺).

Step 2
N,N-dimethylpyridin-4-amine (0.481 mmol, 0.059 g) was dissolved in THF (1.5 mL) and then a solution of di-tert-butyl dicarbonate (0.481 mmol, 0.111 mL) in THF (1.5 mL) was added slowly. After stirring for a few minutes, a solution of 8-chloro-1,2,3,5,6,7-hexahydro-s-indacen-4-amine (0.481 mmol, 100 mg) in THF (1 mL) was added and the mixture was left to stir for 30 min. At the same time, 6,7-dihydro-5H-pyrazolo[5,1-b][1,3]oxazine-3-sulfonamide (0.481 mmol, 0.098 g) in THF (1 mL) was treated with sodium hydride (0.481 mmol, 0.012 g) and left to stir for 30 min. At this time the two solutions were mixed and left to stir for 18 h.

The reaction was then quenched with sat NH4Cl (10 mL) and diluted with EtOAc (40 mL). The layers were separated and the aq. layer extracted with EtOAc (30 mL). The combined organic extracts were then washed with water (20 mL) and concentrated. The resulting solid was suspended in MeOH:water (10:1, 10 mL), a reddish solid filtered off and discarded. The filtrate was concentrated and purified by prep HPLC (10-40% MeCN: 10 mM aq. NH3). The purified fractions were combined and concentrated to yield N-((8-chloro-1,2,3,5,6,7-hexahydro-s-indacen-4-yl)carbamoyl)-6,7-dihydro-5H-pyrazolo[5,1-b][1,3]oxazine-3-sulfonamide (5.8 mg, 2.76%) as a white solid.
¹H-NMR (400 MHz; DMSO-d₆): δ 7.88-7.85 (m, 1H), 7.55 (s, 1H), 4.42-4.39 (m, 2H), 4.11-4.08 (m, 2H), 2.85-2.82 (m, 4H), 2.71 (t, J=7.4 Hz, 4H), 2.22-2.16 (m, 2H), 2.04-1.97 (m, 4H). MS: m/z 437 (M+H⁺).

Example 17: Synthesis of 4-fluoro-N-((1,2,3,5,6,7-hexahydro-s-indacen-4-yl)carbamoyl)-4,5,6,7-tetrahydropyrazolo[1,5-a]pyridine-3-sulfonamide Synthesis of 4-fluoro-N-((1,2,3,5,6,7-hexahydro-s-indacen-4-yl)carbamoyl)-4,5,6,7-tetrahydropyrazolo[1,5-a]pyridine-3-sulfonamide is shown below.

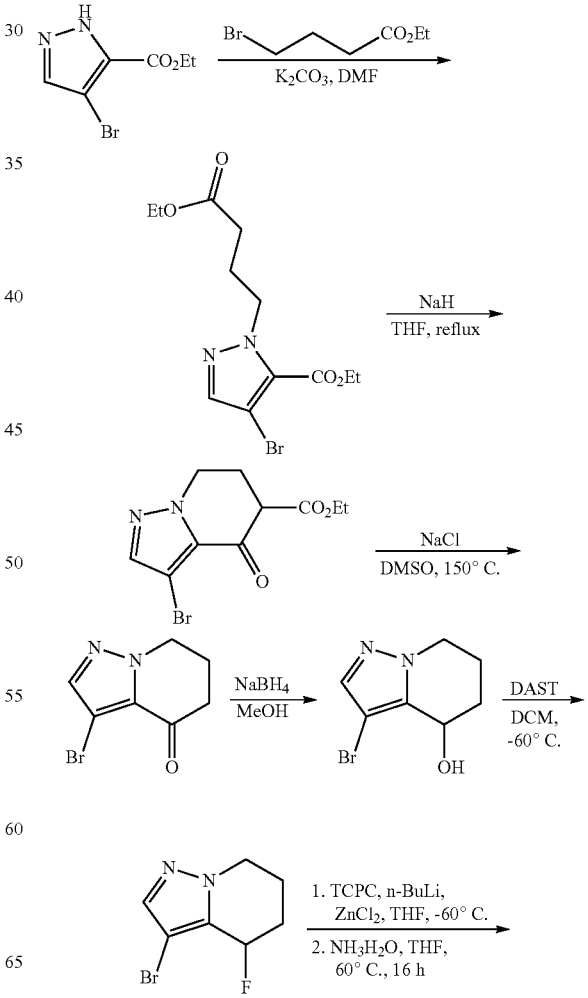

-continued

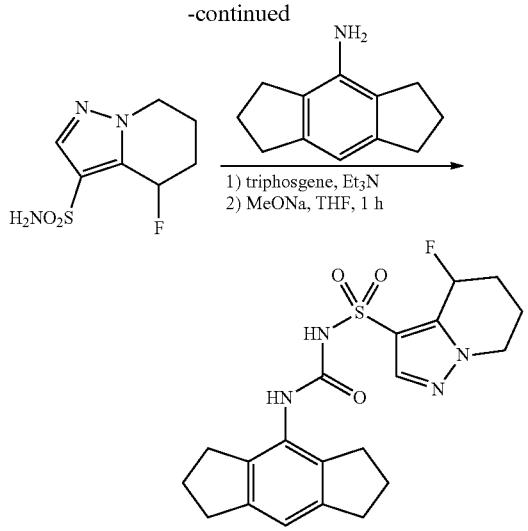

Step 1

To a solution of 4-bromo-2H-pyrazole-3-carboxylic acid ethyl ester (8.0 g, 36.4 mmol) in DMF (80 mL) was added $K_2CO_3$ (10 g, 72.8 mmol) and 4-bromo-butyric acid ethyl ester (10 g, 54.8 mmol), then the suspension was stirred overnight. The reaction was quenched with the addition of EA (200 mL) and water (200 mL). The organic layer was separated. The aqueous layer was extracted with EA (200 mL). The organic layers were combined and washed with water (300 mL×3), brine (300 mL), and dried over $Na_2SO_4$. The solution was concentrated in vacuo. The residue was purified by silica gel column (PE/EA=10/1) to give 4-bromo-2-(3-ethoxycarbonyl-propyl)-2H-pyrazole-3-carboxylic acid ethyl ester (6.7 g, yield: 55.4%) as a colorless oil. MS: m/z 332.8 (M+H$^+$).

Step 2

To a solution of 4-bromo-2-(3-ethoxycarbonyl-propyl)-2H-pyrazole-3-carboxylic acid ethyl ester (6.7 g, 20.2 mmol) in THF (120 mL) was added NaH (1.2 g, 30.3 mmol) at 0° C. and then the mixture was heated to reflux overnight. When the reaction was finished, the reaction was quenched with saturated aqueous solution of $NH_4Cl$ (20 mL). The aqueous phase was extracted with EA (100 mL×2). The extracts were washed with brine (100 mL), dried over $Na_2SO_4$, and concentrated to give 3-bromo-4-oxo-4,5,6,7-tetrahydro-pyrazolo[1,5-a]pyridine-5-carboxylic acid ethyl ester (5.2 g, yield: 90%) as a white solid. MS: m/z 286.9 (M+H$^+$).

Step 3

To a solution of 3-bromo-4-oxo-4,5,6,7-tetrahydro-pyrazolo[1,5-a]pyridine-5-carboxylic acid ethyl ester (5.2 g, 15.7 mmol) in DMSO (200 mL) and water (5 mL) was added NaCl (5.5 g, 94 mmol), and the mixture was heated to 150° C. for 2 hrs. After cooled to room temperature, the reactant was diluted with EA (200 mL) and water (200 mL). The organic layer was separated. The aqueous layer was extracted with EA (200 mL). The combined organic layers were washed with water (300 mL×3), brine (300 mL), and dried over $Na_2SO_4$. The solution was concentrated in vacuo. The residue was purified by silica gel column (PE/EA=5/1) to give 3-bromo-6,7-dihydro-5H-pyrazolo[1,5-a]pyridin-4-one (2.6 g, yield: 66%) as a white solid.

$^1$H NMR (400 MHz, DMSO-d6): δ=7.55 (s, 1H), 4.40 (t, J=6.0 Hz, 2H), 2.72 (t, J=6.4 Hz, 2H), 2.36-2.40 (m, 2H).

Step 4

To a solution of 3-bromo-6,7-dihydro-5H-pyrazolo[1,5-a]pyridin-4-one (1.6 g, 7.36 mmol) in MeOH (20 mL) was added $NaBH_4$ (1.4 g, 12.8 mmol) at 0° C., and the mixture was stirred at room temperature for 2 hrs. When the reaction was finished, the reactant was evaporated to remove MeOH. The residue was portioned between EA (50 mL) and water (50 mL). The organic layer was separated. The aqueous layer was extracted with EA (50 mL). The combined organic layers were washed with brine (30 mL), and dried over $Na_2SO_4$. The solution was concentrated to give 3-bromo-4,5,6,7-tetrahydro-pyrazolo[1,5-a]pyridin-4-ol (1.4 g, yield: 88%) as a white solid. MS: m/z 216.9 (M+H$^+$).

Step 5

To a solution of 3-bromo-4,5,6,7-tetrahydro-pyrazolo[1,5-a]pyridin-4-ol (1.4 g, 6.5 mmol) in DCM (30 mL) was added DAST (2.1 g, 13 mmol) at −60° C. The solution was allowed to warm slowly to room temperature, and stirred at room temperature for 2 hrs. When the reaction was finished, DCM (50 mL) and water (50 mL) was added to the mixture. The organic layer was separated. The aqueous layer was extracted with DCM (50 mL). The combined organic layers were washed with brine (50 mL), dried over $Na_2SO_4$, and concentrated in vacuo. The residue was purified by silica gel column (PE/EA=5/1) to give 3-bromo-4-fluoro-4,5,6,7-tetrahydro-pyrazolo[1,5-a]pyridine (830 mg, yield: 59%) as a yellow oil.

$^1$H NMR (400 MHz, DMSO-d6): δ=7.50 (s, 1H), 5.60 (dt, J=51.2, 2.8 Hz, 1H), 4.28-4.32 (m, 1H), 3.87-3.94 (m, 1H), 2.26-2.40 (m, 2H), 1.92-2.00 (m, 2H).

Step 6

To a solution of 3-bromo-4-fluoro-4,5,6,7-tetrahydro-pyrazolo[1,5-a]pyridine (0.5 g, 2.3 mmol) in dry THF (5 mL) was added n-BuLi in hexane (0.92 mL, 2.3 mmol, 2.5 M) slowly at −78° C. under $N_2$ protection, After stirred at this temperature for 20 min, $ZnCl_2$ in ether (2.3 mL, 2.3 mmol, 1 M) was added slowly at this temperature. The cold bath was removed and the reaction was stirred at room temperature for 1 hr. TCPC (0.68 g, 2.3 mmol) was added to the mixture at 0° C. and the mixture was allowed to stir at room temperature for 1 hr. The reaction was quenched with saturated $NH_4Cl$ solution (2 mL) and partitioned between water (20 mL) and EA (20 mL). The organic layer was washed with brine (80 mL), dried over $Na_2SO_4$ and concentrated to give crude 6,7-dihydro-5H-pyrazolo[5,1-b][1,3]oxazine-3-sulfonic acid 2,4,6-trichloro-phenyl ester as a yellow oil. The crude was dissolved in THF (5 mL), and $NH_3 \cdot H_2O$ (5 mL) was added, then heated to 60° C. overnight. When the reaction was finished, the reaction solution was concentrated to remove the solvent. The residue was acidified with 1 N HCl to pH=5 and partitioned between EA (20 mL) and water (20 mL). The organic layer was separated. The aqueous layer was extracted with EA (20 mL). The combined organic layers were washed with brine (30 mL), dried over $Na_2SO_4$, and concentrated in vacuum. The residue was purified by silica gel column (PE/EA=2/1) to give 4-fluoro-4,5,6,7-tetrahydro-pyrazolo[1,5-a]pyridine-3-sulfonic acid amide (0.17 g, yield: 34%) as a yellow solid. MS: m/z 220.0 (M+H$^+$).

Step 7

To a solution of 4-Fluoro-4,5,6,7-tetrahydro-pyrazolo[1,5-a]pyridine-3-sulfonic acid amide (75 mg, 0.34 mmol) in THF (2 mL) was added MeONa (22 mg, 0.41 mmol) and the mixture was stirred at room temperature for 20 mins to give a sodium salt suspension.

In another flask, to a solution of 1,2,3,5,6,7-Hexahydro-s-indacen-4-ylamine (59 mg, 0.34 mmol) and TEA (69 mg, 0.68 mmol) in THF (3 mL), was added triphosgene (141 mg, 0.14 mmol) in one portion and the mixture was stirred at room temperature under N₂ for 20 mins. The reaction mixture was then filtered. The filtrate was added to the sodium salt suspension above and stirred at room temperature for 1 hr. After that, the reaction solution was partitioned between EA (15 mL) and water (15 mL). The aqueous phase was separated and acidified to pH=5 with 1M HCl. The resulting solid was collected by filtration and air dried to give 4-fluoro-N-((1,2,3,5,6,7-hexahydro-s-indacen-4-yl) carbamoyl)-4,5,6,7-tetrahydropyrazolo[1,5-a]pyridine-3-sulfonamide (45 mg, yield: 31.4%) as a white solid.

¹H NMR (400 MHz, DMSO-d6): δ=10.67 (s, 1H), 8.03 (s, 1H), 7.94 (s, 1H), 6.93 (s, 1H), 6.08 (d, J=49.2 Hz, 1H), 4.35-4.37 (m, 1H), 4.05-4.08 (m, 1H), 2.78 (t, J=6.8 Hz, 4H), 2.55 (t, J=6.8 Hz, 4H), 1.92-2.29 (m, 8H). MS: m/z 419.0 (M+H⁺).

Example 18

Synthesis of sodium ((6,7-dihydro-5H-pyrazolo[5,1-b][1,3]oxazin-3-yl)sulfonyl)((1,2,3,5,6,7-hexahydro-s-indacen-4-yl)carbamoyl)amide is shown below.

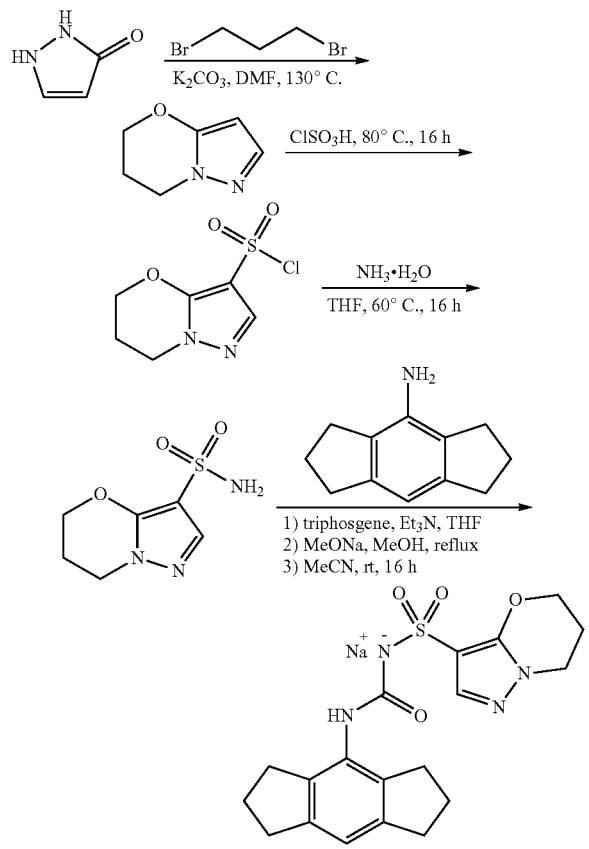

Step 1:

1,2-Dihydro-pyrazol-3-one (53.0 g, 630.9 mmol) and K₂CO₃ (305.0 g, 2210.1 mmol) were heated to 130° C. in DMF (1 L). 1,3-Dibromopropane (140.0 g, 693.1 mmol) was added and the mixture was heated for 8 hrs and then concentrated. The residue was partitioned between EA (200 mL) and water (500 mL) and the layers were separated. The aqueous layer was extracted with EA (150 mL×8) and the combined organic layer was washed with brine (300 mL), dried over Na₂SO₄, filtered and concentrated in vacuo. The residue was purified by silica gel column (PE/EA=3/1) to give 6,7-dihydro-5H-pyrazolo[5,1-b][1,3]oxazine (32.0 g, yield: 41%) as a yellow oil.

¹H NMR (400 MHz, CDCl₃): δ=7.31 (d, J=2.0 Hz, 1H), 5.48 (d, J=2.0 Hz, 1H), 4.28 (t, J=5.2 Hz, 2H), 4.18 (t, J=6.2 Hz, 2H), 2.29-2.22 (m, 2H).

Step 2:

6,7-Dihydro-5H-pyrazolo[5,1-b][1,3]oxazine (64.0 g, 516.1 mmol) was added dropwise to ClSO₃H (380 mL) at 0° C. After being stirred at 80° C. for 16 hrs, the reaction mixture was added dropwise to a mixture of ice-water/EA (4 L/1 0.5 L). The layers were separated and the aqueous layer was extracted with EA (300 mL×2). The combined organic layers were washed with brine (500 mL), dried over Na₂SO₄ and concentrated. The residue was washed with PE (200 mL) to give 6,7-dihydro-5H-pyrazolo[5,1-b][1,3]oxazine-3-sulfonyl chloride (73.0 g, yield: 63%) as a yellow solid.

Step 3:

To a solution of 6,7-dihydro-5H-pyrazolo[5,1-b][1,3] oxazine-3-sulfonyl chloride (73.0 g, 328.8 mmol) in THF (430 mL) was added NH₃·H₂O (180 mL). After being stirred at 60° C. for 16 hrs, the reaction mixture was concentrated to dryness. The residue was washed with aq.HCl (0.2 M, 110 mL), H₂O (40 mL), and dried to give 6,7-dihydro-5H-pyrazolo[5,1-b][1,3]oxazine-3-sulfonic acid amide (52.0 g, yield: 78%) as a yellow solid.

¹HNMR (300 MHz, DMSO-d₆): δ=7.47 (s, 1H), 7.08 (s, 2H), 4.40 (t, J=5.1 Hz, 2H), 4.10 (t, J=6.0 Hz, 2H), 2.23-2.15 (m, 2H).

Step 4:

To a solution of 1,2,3,5,6,7-hexahydro-s-indacen-4-ylamine (15.0 g, 87 mmol) and TEA (13.3 mL, 95.4 mmol) in THF (300 mL) was added triphosgene (8.5 g, 28.6 mmol) in one portion at 0~5° C. and the mixture was stirred at 70° C. under N₂ for 1 hour. The reaction mixture was then filtered through diatomite. Then filter cake was washed with 30 mL PE. The filtrate was concentrated to dryness and dissolved in 100 mL n-hexane. The mixture was filtered through a silica gel pad. The filtrate was concentrated to dryness to give the 4-isocyanato-1,2,3,5,6,7-hexahydro-s-indacene (14.6 g, yield: 84%) as a pink oil.

The suspension of 6,7-dihydro-5H-pyrazolo[5,1-b][1,3] oxazine-3-sulfonic acid amide (14.3 g, 70.4 mmol) in MeOH (500 mL) was stirred at 80° C. until getting a clear solution, then MeONa (3.8 g, 70.4 mmol) was added and the mixture was stirred for 5 mins. The solution was concentrated to dryness and the residue was co-evaporated with MeCN (100 mL). The residual solid was suspended in MeCN (320 mL) and 4-isocyanato-1,2,3,5,6,7-hexahydro-s-indacene (14.6 g, 73.3 mmol) was added. The mixture was stirred for 16 hours at room temperature and filtered. The filter cake was triturated with EtOH (250 mL), PE/EA (5/1, 250 mL) to give the product. The product was dissolved in H₂O (200 mL) and concentrated to dryness to give sodium ((6,7-dihydro-5H-pyrazolo[5,1-b][1,3]oxazin-3-yl)sulfonyl) ((1,2,3,5,6,7-hexahydro-s-indacen-4-yl)carbamoyl)amide (24.5 g, yield: 82%) as a white solid.

¹HNMR (400 MHz, D₂O): δ=7.64 (s, 1H), 7.02 (s, 1H), 4.40 (t, J=5.2 Hz, 2H), 4.11 (t, J=6.0 Hz, 2H), 2.83 (t, J=7.2 Hz, 4H), 2.66 (t, J=7.2 Hz, 4H), 2.28-2.22 (m, 2H), 2.04-1.96 (m, 4H). MS: m/z 403.1 (M+H⁺).

Example 19

Synthesis of 1-((1,2,3,5,6,7-Hexahydro-s-indacen-4-yl))-3-(2,3-dihydro-pyrazolo[5,1-b]oxazole-7-sulfonyl)-urea is shown below.

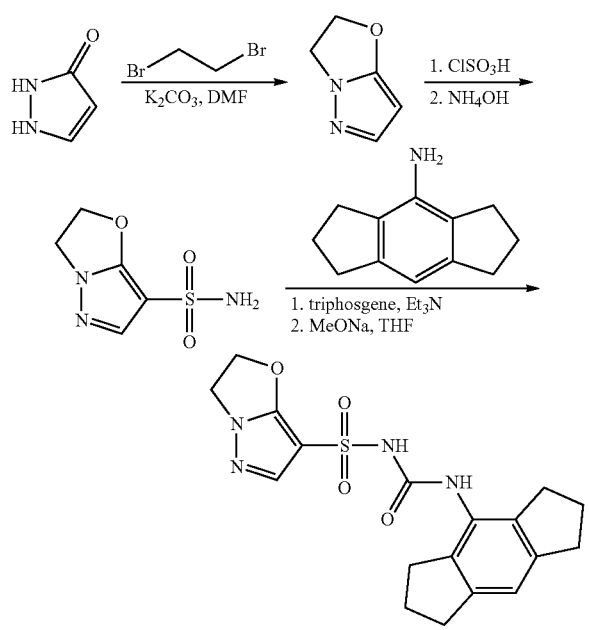

Step 1

To a solution of 1,2-dihydro-pyrazol-3-one (500 mg, 5.9 mmol) in MeCN (50 mL) was added 1,2-dibromo-ethane (3.3 g, 17.6 mmol) and $K_2CO_3$ (2.4 g, 17.6 mmol). After being stirred at reflux overnight, the reaction mixture was filtered and the filtrate was concentrated in vacuo. The residue was purified by reverse phase HPLC (MeCN in $H_2O$, 5% to 95%) to give 2,3-dihydro-pyrazolo[5,1-b]oxazole (260 mg, 40%) as a yellow solid.

$^1$H NMR (400 MHz, DMSO-$d_6$): δ=7.27 (s, 1H), 5.37 (d, J=1.6 Hz, 1H), 5.06 (t, J=8.0 Hz, 2H), 4.23 (t, J=8.0 Hz, 2H).

Step 2

2,3-Dihydro-pyrazolo[5,1-b]oxazole (1 g, 9.1 mmol) was dissolved in $ClSO_3H$ (20 mL). After being heated at 80° C. overnight, the reaction mixture was added dropwise to a mixture of EA (150 mL), $NH_3H_2O$ (20 mL), and $H_2O$ (150 mL). After being stirred at room temperature, the reaction mixture was concentrated in vacuo. The residue was suspended in MeOH (30 mL), stirred for 0.5 h, and the mixture was filtered. The filtrate was evaporated in vacuo and the residue was purified by reverse phase HPLC (MeCN in water, 0% to 60%) to give 2,3-dihydro-pyrazolo[5,1-b]oxazole-7-sulfonic acid amide (60 mg, 4%) as a yellow solid.

Step 3—Preparation E

To a solution of 1,2,3,5,6,7-hexahydro-s-indacen-4-ylamine (55 mg, 0.32 mmol) in THF (10 mL) was added triphosgene (30 mg, 0.1 mmol) and TEA (48 mg, 0.48 mmol). After being stirred at room temperature for 2 hrs, the reaction mixture was filtered. The filtrate was evaporated in vacuo. The residue was then dissolved in THF (5 mL). Then to the mixture was added 2,3-dihydro-pyrazolo[5,1-b]oxazole-7-sulfonic acid amide (60 mg, 0.32 mmol) and NaOMe (35 mg, 0.64 mmol). After being stirred at room temperature for 3 hrs, the reaction was quenched by $H_2O$ (10 mL), acidified by 3 N HCl to pH=3, and extracted with EA (10 mL×3). Organic phase was combined, dried over anhydrous $Na_2SO_4$, and evaporated in vacuo. The residue was purified by prep-HPLC to give 1-((1,2,3,5,6,7-hexahydro-s-indacen-4-yl))-3-(2,3-dihydro-pyrazolo[5,1-b]oxazole-7-sulfonyl)-urea (6 mg, 5%) as a white solid.

$^1$H NMR (400 MHz, DMSO-$d_6$): δ=10.52 (brs, 1H), 7.86 (s, 1H), 7.58 (s, 1H), 6.91 (s, 1H), 5.21 (t, J=8.0 Hz, 2H), 4.32 (t, J=8.0 Hz, 2H), 2.78 (t, J=7.2 Hz, 4H), 2.62 (t, J=7.2 Hz, 4H), 1.98-1.91 (m, 4H). MS: m/z 389.0 (M+H$^+$).

Example 20

Synthesis of (R)—N-((1,2,3,5,6,7-Hexahydro-s-indacen-4-yl)carbamoyl)-6-hydroxy-6,7-dihydro-5H-pyrazolo[5,1-b][1,3]oxazine-3-sulfonamide and (S)—N-((1,2,3,5,6,7-hexahydro-s-indacen-4-yl)carbamoyl)-6-hydroxy-6,7-dihydro-5H-pyrazolo[5,1-b][1,3]oxazine-3-sulfonamide is shown below.

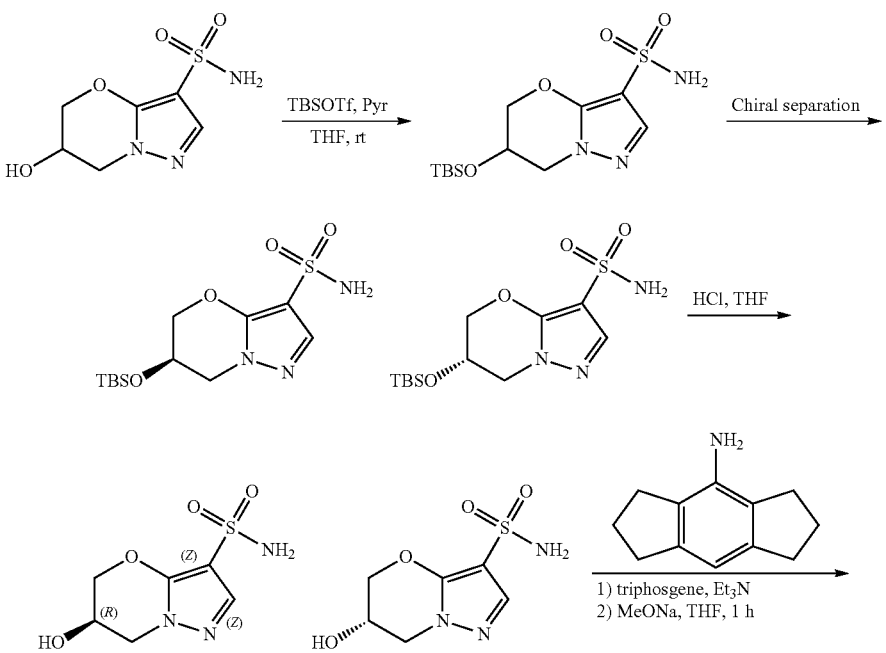

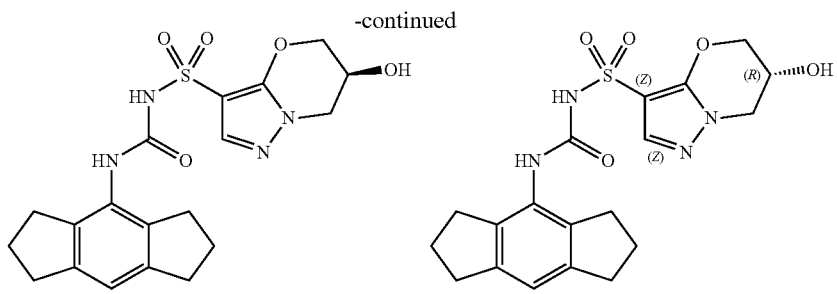
-continued

Step 1

To a solution of rac-6-hydroxy-6,7-dihydro-5H-pyrazolo[5,1-b][1,3]oxazine-3-sulfonamide (530 mg, 2.4 mmol) and pyridine (382 mg, 4.8 mmol) in THF (10 mL) was added TBSOTf (702 mg, 2.7 mmol) at 0° C. The reaction was stirred at room temperature for 2 hrs. The reaction was quenched by H₂O (20 mL) and acidified to pH=5 by 1 N HCl. The residue was purified by reverse phase HPLC (MeCN/H₂O) to give 6-((tert-butyldimethylsilyl)oxy)-6,7-dihydro-5H-pyrazolo[5,1-b][1,3]oxazine-3-sulfonamide (330 mg, yield: 41%) as a white solid. MS: m/z 334.1 (M+H⁺).

Step 2

Rac-6-((tert-Butyldimethylsilyl)oxy)-6,7-dihydro-5H-pyrazolo[5,1-b][1,3]oxazine-3-sulfonamide (420 mg, 1.3 mmol) was resolved by chiral prep-HPLC to give two isomers (S)-6-((tert-butyldimethylsilyl)oxy)-6,7-dihydro-5H-pyrazolo[5,1-b][1,3]oxazine-3-sulfonamide (180 mg, yield: 42%) as a white solid; (R)-6-((tert-butyldimethylsilyl)oxy)-6,7-dihydro-5H-pyrazolo[5,1-b][1,3]oxazine-3-sulfonamide (200 mg, yield: 46%) as a white solid.

Step 3

To a solution of (S)-6-((tert-butyldimethylsilyl)oxy)-6,7-dihydro-5H-pyrazolo[5,1-b][1,3]oxazine-3-sulfonamide (180 mg, 0.5 mmol) in THF (4 mL) was added conc. HCl (4 mL). After being stirred at room temperature overnight, the reaction was concentrated under reduced pressure. The residue was purified by reverse phase HPLC (MeCN/H₂O) to give (S)-6-hydroxy-6,7-dihydro-5H-pyrazolo[5,1-b][1,3]oxazine-3-sulfonamide (115 mg, yield: 97%) as a white solid. MS: m/z 220.1 (M+H⁺).

(R)-6-Hydroxy-6,7-dihydro-5H-pyrazolo[5,1-b][1,3]oxazine-3-sulfonamide was prepared using the same procedure.

Step 4

(S)—N-((1,2,3,5,6,7-hexahydro-s-indacen-4-yl)carbamoyl)-6-hydroxy-6,7-dihydro-5H-pyrazolo[5,1-b][1,3]oxazine-3-sulfonamide was synthesized as in Preparation A herein to yield the desired product (50 mg, yield: 23%) as a white solid.

¹H NMR (400 MHz, DMSO-d₆): δ=10.45 (s, 1H), 7.90 (s, 1H), 7.62 (s, 1H), 6.93 (s, 1H), 5.66 (d, J=2.4 Hz, 1H), 4.34 (s, 3H), 4.24 (dd, J=4.0, 3.2 Hz, 1H), 3.96 (d, J=12.4 Hz, 1H), 2.78 (t, J=7.2 Hz, 4H), 2.60 (t, J=7.2 Hz, 4H), 1.98-1.91 (m, 4H). MS: m/z 419.0 (M+H⁺).

(R)—N-((1,2,3,5,6,7-hexahydro-s-indacen-4-yl)carbamoyl)-6-hydroxy-6,7-dihydro-5H-pyrazolo[5,1-b][1,3]oxazine-3-sulfonamide was prepared using the same procedure.

¹H NMR (400 MHz, DMSO-d₆): δ=10.45 (s, 1H), 7.90 (s, 1H), 7.62 (s, 1H), 6.93 (s, 1H), 5.66 (d, J=3.2 Hz, 1H), 4.34 (s, 3H), 4.27-4.23 (m, 1H), 3.96 (d, J=13.6 Hz, 1H), 2.78 (t, J=7.2 Hz, 4H), 2.61 (t, J=7.2 Hz, 4H), 1.98-1.91 (m, 4H). MS: m/z 419.0 (M+H⁺).

Example 21

Synthesis of rac-6-(Dimethylamino)-N-((1,2,3,5,6,7-hexahydro-s-indacen-4-yl)carbamoyl)-6,7-dihydro-5H-pyrazolo[5,1-b][1,3]oxazine-3-sulfonamide is shown below.

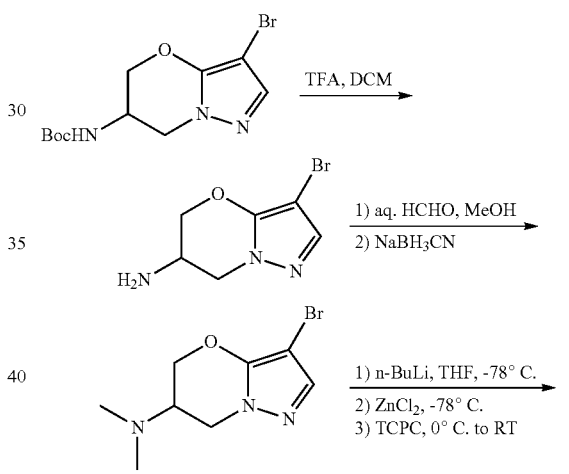

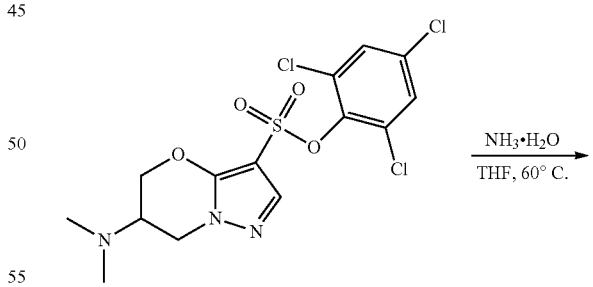

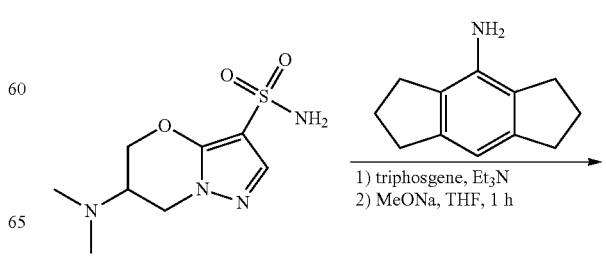

-continued

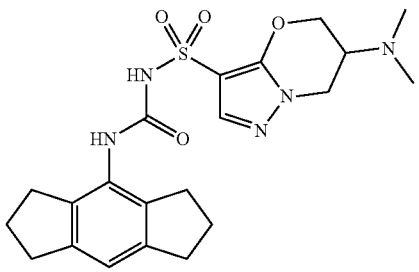

Step 1

To a solution of rac-tert-butyl (3-bromo-6,7-dihydro-5H-pyrazolo[5,1-b][1,3]oxazin-6-yl)carbamate (1.0 g, 3.2 mmol) in DCM (5 mL) was added TFA (5 mL) and the mixture was stirred at room temperature for 20 mins. The reaction was concentrated to dryness to give crude rac-3-bromo-6,7-dihydro-5H-pyrazolo[5,1-b][1,3]oxazin-6-amine as a yellow solid, which was used for next step directly without any purification. MS: m/z 218.0 (M+H$^+$).

Step 2

To a solution of rac-3-bromo-6,7-dihydro-5H-pyrazolo[5,1-b][1,3]oxazin-6-amine (crude, ~3.2 mmol) in MeOH (10 mL) was added HCHO (30%, 3.2 g, 31.5 mmol). The mixture was stirred for 2 hrs at room temperature, NaBH$_3$CN (2.0 g, 31.5 mmol) was then added. The reaction was then stirred at room temperature for 16 hrs. The reaction was purified by reverse phase HPLC (0%-95% MeCN in H$_2$O) to give rac-3-bromo-N,N-dimethyl-6,7-dihydro-5H-pyrazolo[5,1-b][1,3]oxazin-6-amine (410 mg, yield: 53%) as a white solid.

$^1$H NMR (300 MHz, CDCl$_3$): δ=7.33 (s, 1H), 4.45-4.44 (m, 1H), 4.30-4.24 (m, 2H), 4.18-4.11 (m, 1H), 3.00-2.97 (m, 1H), 2.40 (s, 6H). MS: m/z 245.9 (M+H$^+$).

Step 3—Preparation B

To a solution of rac-3-bromo-N,N-dimethyl-6,7-dihydro-5H-pyrazolo[5,1-b][1,3]oxazin-6-amine (400 mg, 1.6 mmol) in dry THF (5 mL) was added n-BuLi (2.5 M in hexane, 0.7 mL, 1.6 mmol) slowly at −78° C. under N$_2$ atmosphere. After stirring with cooling for 20 mins, ZnCl$_2$ (1 M in ether, 1.6 mL, 1.6 mmol) was added slowly at this temperature. The cooling bath was removed and the reaction was stirred at room temperature for 1 hr. TCPC (479 mg, 1.6 mmol) was then added and the mixture was stirred at room temperature for 1 hr. The reaction was partitioned between water (30 mL) and EA (30 mL). The organic layer was washed with brine (30 mL), dried over Na$_2$SO$_4$ and concentrated to give crude rac-2,4,6-trichlorophenyl 6-(dimethylamino)-6,7-dihydro-5H-pyrazolo[5,1-b][1,3]oxazine-3-sulfonate as a yellow gel which was used for next step without purification.

Step 4—Preparation C

A mixture of rac-2,4,6-trichlorophenyl 6-(dimethylamino)-6,7-dihydro-5H-pyrazolo[5,1-b][1,3]oxazine-3-sulfonate (crude, ~1.6 mmol), NH$_4$OH (10 mL) and THF (10 mL) was stirred at 60° C. overnight. The reaction was concentrated under reduced pressure until 10 mL of liquid remained. The remained solution was acidified with 1 N HCl to pH=5. The residue was purified by reverse phase HPLC (0%-95% MeCN in H$_2$O) to give rac-2,4,6-trichlorophenyl 6-(dimethylamino)-6,7-dihydro-5H-pyrazolo[5,1-b][1,3]oxazine-3-sulfonate (66 mg, yield: 16% over two steps) as a white solid. Alternatively, the solution may be concentrated to dryness and purified by flash chromatography.

$^1$H NMR (400 MHz, DMSO-d$_6$): δ=7.47 (s, 1H), 7.13 (brs, 2H), 4.95-4.41 (m, 2H), 4.23-4.13 (m, 2H), 2.89-2.86 (m, 1H), 2.26 (s, 6H).

Step 5—Preparation A

To a solution of rac-2,4,6-trichlorophenyl 6-(dimethylamino)-6,7-dihydro-5H-pyrazolo[5,1-b][1,3]oxazine-3-sulfonate (66 mg, 0.3 mmol) in THF (5 mL) was added MeONa (18 mg, 0.3 mmol) and the mixture was stirred at room temperature for 20 mins to give a sodium salt suspension.

In another flask, to a solution of 1,2,3,5,6,7-hexahydro-s-indacen-4-ylamine (47 mg, 0.3 mmol) and TEA (55 mg, 0.5 mmol) in THF (5 mL) was added triphosgene (33 mg, 0.1 mmol) in one portion and the mixture was stirred at room temperature under N$_2$ for 20 mins. The reaction mixture was then filtered. The filtrate was added to the above sodium salt suspension and stirred at room temperature for 20 mins. After that, the reaction solution was partitioned between EA (20 mL) and water (20 mL). The aqueous phase was acidified to pH=5 with 1 N HCl. The solid formed was collected by filtration and dried to give rac-6-(dimethylamino)-N-((1,2,3,5,6,7-hexahydro-s-indacen-4-yl)carbamoyl)-6,7-dihydro-5H-pyrazolo[5,1-b][1,3]oxazine-3-sulfonamide (27 mg, yield: 22%) as a white solid.

$^1$H NMR (400 MHz, DMSO-d$_6$): δ=7.41 (s, 1H), 7.33 (s, 1H), 6.76 (s, 1H), 4.37-4.22 (m, 2H), 4.11-4.09 (m, 1H), 4.03-4.01 (m, 1H), 2.83-2.82 (m, 1H), 2.74 (t, J=7.2 Hz, 4H), 2.64 (t, J=7.6 Hz, 4H), 2.25 (s, 6H), 1.93-1.86 (m, 4H). MS: m/z 446.0 (M+H$^+$).

Example 22

Synthesis of (S)-6-(Dimethylamino)-N-((1,2,3,5,6,7-hexahydro-s-indacen-4-yl)carbamoyl)-6,7-dihydro-5H-pyrazolo[5,1-b][1,3]oxazine-3-sulfonamide and (R)-6-(dimethylamino)-N-((1,2,3,5,6,7-hexahydro-s-indacen-4-yl)carbamoyl)-6,7-dihydro-5H-pyrazolo[5,1-b][1,3]oxazine-3-sulfonamide is shown below.

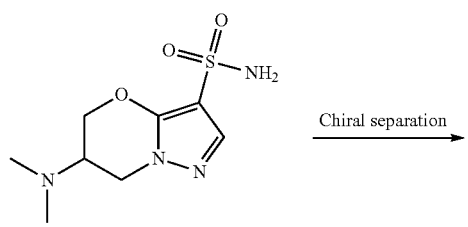

Chiral separation →

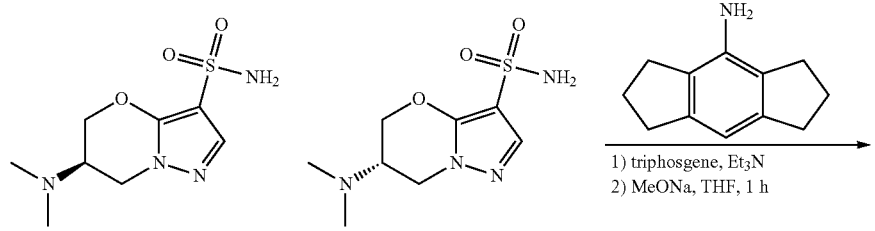

Step 1 rac-6-(Dimethylamino)-6,7-dihydro-5H-pyrazolo[5,1-b][1,3]oxazine-3-sulfonamide (110 mg, 0.4 mmol) was resolved by chiral prep-HPLC to afford (S)-6-(dimethylamino)-6,7-dihydro-5H-pyrazolo[5,1-b][1,3]oxazine-3-sulfonamide (41 mg, yield: 42%) as a white solid and (R)-6-(dimethylamino)-6,7-dihydro-5H-pyrazolo[5,1-b][1,3]oxazine-3-sulfonamide (36 mg, yield: 37%) as a white solid.

Step 2

(S)-6-(dimethylamino)-N-((1,2,3,5,6,7-hexahydro-s-indacen-4-yl)carbamoyl)-6,7-dihydro-5H-pyrazolo[5,1-b][1,3]oxazine-3-sulfonamide was synthesized as in Preparation A to yield the desired product (14 mg, yield: 18%) as a white solid.

$^1$H NMR (400 MHz, DMSO-d$_6$): δ=10.47 (brs, 1H), 7.84 (s, 1H), 7.57 (s, 1H), 6.90 (s, 1H), 4.46-4.43 (m, 2H), 4.24-4.12 (m, 2H), 2.92-2.91 (m, 1H), 2.80 (t, J=7.2 Hz, 4H), 2.64 (t, J=7.2 Hz, 4H), 2.25 (s, 6H), 1.93-1.90 (m, 4H). MS: m/z 446.0 (M+H$^+$).

(R)-6-(dimethylamino)-N-((1,2,3,5,6,7-hexahydro-s-indacen-4-yl)carbamoyl)-6,7-dihydro-5H-pyrazolo[5,1-b][1,3]oxazine-3-sulfonamide was synthesized in the same manner to yield the product as a white solid (15 mg, yield: 22%).

$^1$H NMR (400 MHz, DMSO-d$_6$): δ=7.91 (s, 1H), 7.61 (s, 1H), 6.93 (s, 1H), 4.54-4.45 (m, 2H), 4.25-4.15 (m, 2H), 2.93-2.91 (m, 1H), 2.79 (t, J=7.2 Hz, 4H), 2.62-2.54 (m, 4H), 2.27 (s, 6H), 1.99-1.92 (m, 4H). MS: m/z 446.0 (M+H$^+$).

Example 23

Synthesis of (R)—N-((1,2,3,5,6,7-Hexahydro-s-indacen-4-yl)carbamoyl)-6-methoxy-6,7-dihydro-5H-pyrazolo[5,1-b][1,3]oxazine-3-sulfonamide and (S)—N-((1,2,3,5,6,7-hexahydro-s-indacen-4-yl)carbamoyl)-6-methoxy-6,7-dihydro-5H-pyrazolo[5,1-b][1,3]oxazine-3-sulfonamide is shown below.

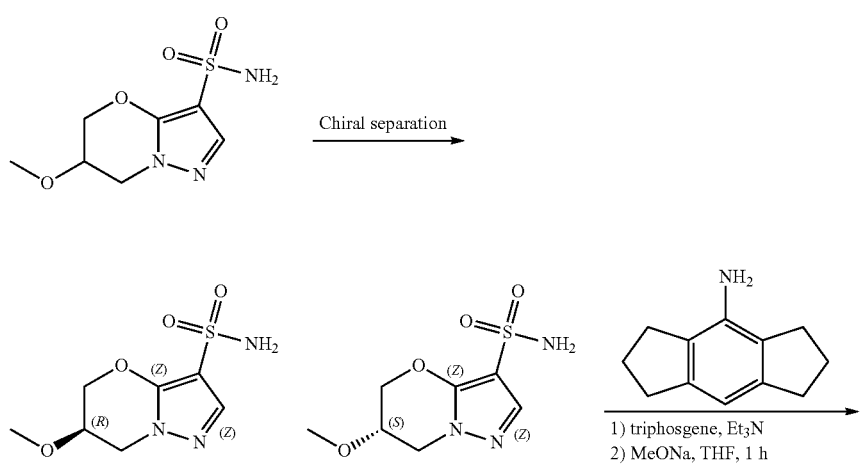

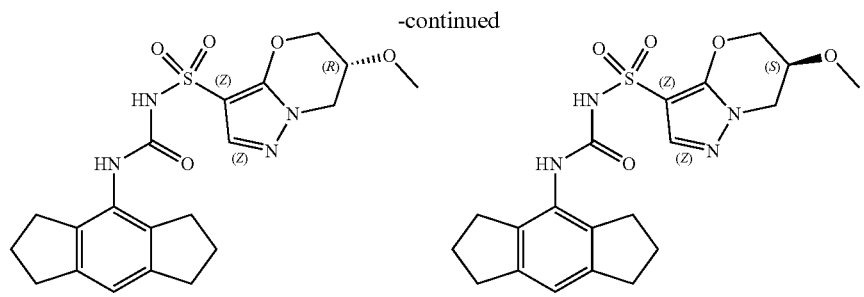

Step 1 rac-6-Methoxy-6,7-dihydro-5H-pyrazolo[5,1-b][1,3]oxazine-3-sulfonamide (460 mg) was resolved by chiral column to give two isomers:

(R)-6-methoxy-6,7-dihydro-5H-pyrazolo[5,1-b][1,3]oxazine-3-sulfonamide (peak 1, 91 mg) and (S)-6-methoxy-6,7-dihydro-5H-pyrazolo[5,1-b][1,3]oxazine-3-sulfonamide (peak 2, 116 mg).

Step 2

(R)—N-((1,2,3,5,6,7-hexahydro-s-indacen-4-yl)carbamoyl)-6-methoxy-6,7-dihydro-5H-pyrazolo[5,1-b][1,3]oxazine-3-sulfonamide was synthesized using Preparation A to deliver the desired product (44 mg, yield: 31%) as a white solid.

$^1$H NMR (400 MHz, DMSO-D$_6$): δ=10.48 (brs, 1H), 7.92 (brs, 1H), 7.62 (s, 1H), 6.93 (s, 1H), 4.63 (d, J=11.6 Hz, 1H), 4.36 (d, J=11.6 Hz, 1H), 4.27-4.19 (m, 2H), 4.06 (s, 1H), 3.34 (overlap, 3H), 2.78 (t, J=12 Hz, 4H), 2.60 (t, J=12 Hz, 4H), 1.99-1.93 (m, 4H). MS: m/z 433.0 (M+H$^+$).

(S)—N-((1,2,3,5,6,7-hexahydro-s-indacen-4-yl)carbamoyl)-6-methoxy-6,7-dihydro-5H-pyrazolo[5,1-b][1,3]oxazine-3-sulfonamide was prepared using the same procedure.

$^1$H NMR (400 MHz, DMSO-d$_6$): δ=10.51 (s, 1H), 7.98 (s, 1H), 7.62 (s, 1H), 6.93 (s, 1H), 4.64 (d, J=11.6 Hz, 1H), 4.37 (d, J=12.0 Hz, 1H), 4.24-4.22 (m, 2H), 4.05 (s, 1H), 3.34 (overlap, 3H), 2.78 (t, J=7.6 Hz, 4H), 2.60 (t, J=12 Hz, 4H), 1.98-1.91 (m, 4H). MS: m/z 433.0 (M+H$^+$).

Example 24

Synthesis of (R)-((1,2,3,5,6,7-Hexahydro-s-indacen-4-yl)carbamoyl)((6-methoxy-6,7-dihydro-5H-pyrazolo[5,1-b][1,3]oxazin-3-yl)sulfonyl)amide and sodium (S)-((1,2,3,5,6,7-hexahydro-s-indacen-4-yl)carbamoyl)((6-methoxy-6,7-dihydro-5H-pyrazolo[5,1-b][1,3]oxazin-3-yl)sulfonyl)amide is shown below.

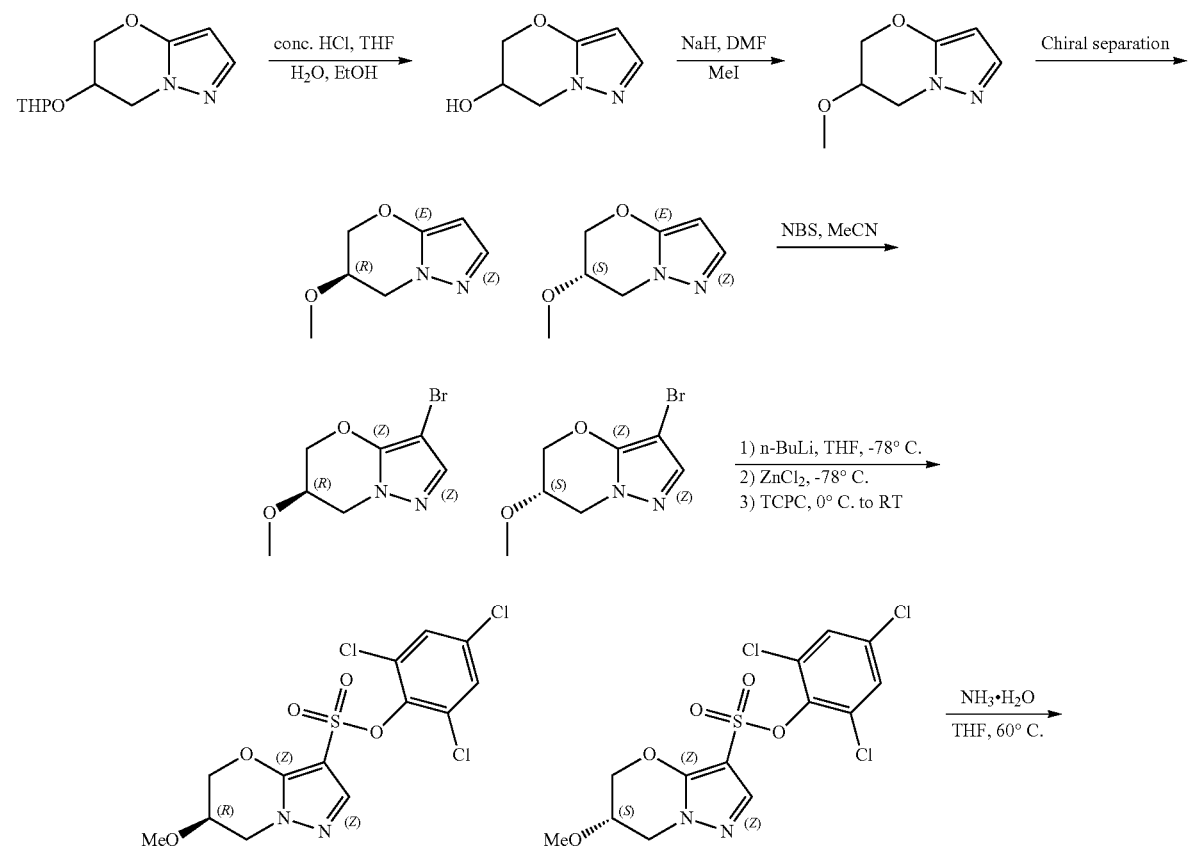

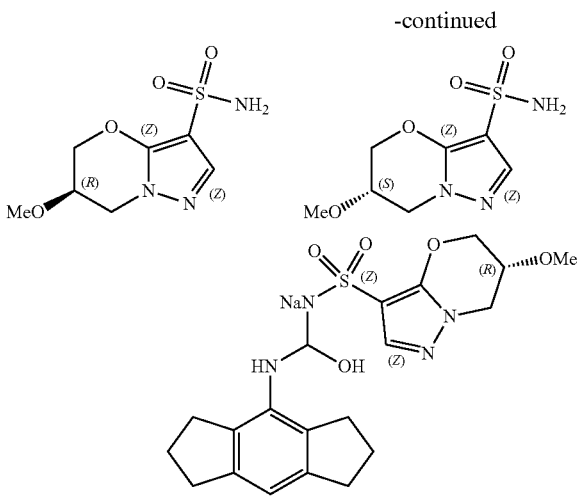
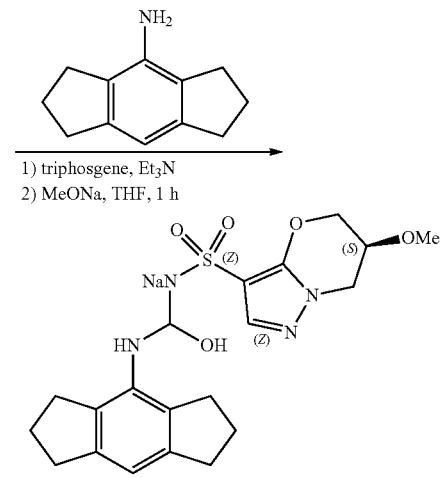

Step 1

To a solution of rac-6-((tetrahydro-2H-pyran-2-yl)oxy)-6,7-dihydro-5H-pyrazolo[5,1-b][1,3]oxazine (36 g, 0.161 mol) in MeOH (200 mL) and H$_2$O (50 mL) was added conc. HCl (50 mL). After being stirred at room temperature for 1 hr, the reaction solution was concentrated under reduced pressure. The residue was treated with saturated NaHCO$_3$ solution (pH=8) and purified by reverse phase HPLC (0%-50% MeCN in H$_2$O) to give rac-6,7-dihydro-5H-pyrazolo[5,1-b][1,3]oxazin-6-ol (27 g, crude yield: quantitative) as a yellow solid.

$^1$H NMR (300 MHz, DMSO-d$_6$): δ=7.21 (s, 1H), 5.56 (s, 1H), 5.43 (s, 1H), 4.23-4.15 (m, 4H), 3.94-3.89 (m, 1H).

Step 2

To a solution of rac-6,7-dihydro-5H-pyrazolo[5,1-b][1,3]oxazin-6-ol (10 g, 71.4 mmol) in dry DMF (150 mL) was added NaH (60%, 4.3 g, 107 mmol) at 0° C. under N$_2$. After stirring at room temperature for 1 hr, MeI (15.2 g, 107 mml) was added to the reaction. The reaction was stirred at room temperature overnight, poured into water (100 mL) and filtered. The filter cake was dried to give rac-6-methoxy-6,7-dihydro-5H-pyrazolo[5,1-b][1,3]oxazine (5.5 g, yield: 50%) as a yellow solid.

$^1$H NMR (300 MHz, DMSO-d$_6$): δ=7.21 (s, 1H), 5.44 (s, 1H), 4.44-4.40 (m, 1H), 4.23-4.10 (m, 3H), 3.96 (s, 1H), 3.34 (overlap, 3H).

Step 3

Rac-6-Methoxy-6,7-dihydro-5H-pyrazolo[5,1-b][1,3]oxazine (5.5 g) was resolved by chiral column to give two isomers:

(S)-6-methoxy-6,7-dihydro-5H-pyrazolo[5,1-b][1,3]oxazine (peak 1, 2.4 g) as a white solid and (S)-6-methoxy-6,7-dihydro-5H-pyrazolo[5,1-b][1,3]oxazine (peak 2, 2.5 g) as a white solid.

Step 4

To a solution of (R)-6-methoxy-6,7-dihydro-5H-pyrazolo[5,1-b][1,3]oxazine (2.4 g, 15.6 mmol) in MeCN was added NBS (2.78 g, 15.6 mmol) in portions with ice-cooling. After stirring at room temperature for 1 hr, the reaction solution was purified by reverse phase HPLC (MeCN/H$_2$O) to give (R)-3-bromo-6-methoxy-6,7-dihydro-5H-pyrazolo[5,1-b][1,3]oxazine (2.6 g, yield: 72%).

$^1$H NMR (300 MHz, CDCl$_3$): δ=7.33 (s, 1H), 4.52-4.48 (m, 1H), 4.32-4.20 (m, 3H), 3.93-3.92 (m, 1H), 3.49 (s, 3H).

(S)-3-bromo-6-methoxy-6,7-dihydro-5H-pyrazolo[5,1-b][1,3]oxazine was prepared using the same procedure.

Step 5

(R)-2,4,6-trichlorophenyl 6-methoxy-6,7-dihydro-5H-pyrazolo[5,1-b][1,3]oxazine-3-sulfonate was synthesized using Preparation B to yield the product as a yellow oil which was used for next step without any purification.

(S)-2,4,6-trichlorophenyl 6-methoxy-6,7-dihydro-5H-pyrazolo[5,1-b][1,3]oxazine-3-sulfonate was prepared using the same procedure.

Step 6

(R)-6-methoxy-6,7-dihydro-5H-pyrazolo[5,1-b][1,3]oxazine-3-sulfonamide was synthesized as in Preparation C to yield the desired product (800 mg, yield: 32% over 2 steps) as a yellow solid. MS: m/z 234.0 (M+H$^+$).

(S)-6-Methoxy-6,7-dihydro-5H-pyrazolo[5,1-b][1,3]oxazine-3-sulfonamide was prepared using the same procedure.

Step 7—Preparation D

To a solution of (R)-6-methoxy-6,7-dihydro-5H-pyrazolo[5,1-b][1,3]oxazine-3-sulfonamide (800 mg, 3.43 mol) in THF (10 mL) was added MeONa (370 mg, 6.86 mmol). The mixture was stirred at room temperature for 30 mins to give a sodium salt suspension.

In another flask, to a solution of 1,2,3,5,6,7-hexahydro-s-indacen-4-amine (891 mg, 5.1 mol) and TEA (1.5 g, 15.3 mmol) in THF (20 mL), was added triphosgene (611 mg, 2.1 mmol) in one portion. After stirring at room temperature under N$_2$ for 30 mins, the reaction mixture was filtered. The filtrate was added to the sodium salt suspension above and the reaction was stirred at room temperature overnight. After that, the reaction solution was partitioned between EA (50 mL) and water (80 mL). The aqueous phase was purified by reverse phase HPLC (MeCN/H$_2$O) to give sodium (R)-((1,2,3,5,6,7-hexahydro-s-indacen-4-yl)carbamoyl)((6-methoxy-6,7-dihydro-5H-pyrazolo[5,1-b][1,3]oxazin-3-yl)sulfonyl)amide (250 mg, yield: 16%) as a yellow solid.

$^1$H NMR (400 MHz, D$_2$O): δ=7.52 (s, 1H), 6.88 (s, 1H), 4.51 (d, J=12.0 Hz, 1H), 4.16-4.11 (m, 3H), 4.02-4.00 (m, 1H), 3.30 (s, 3H), 2.68 (t, J=7.2 Hz, 4H), 2.51 (t, J=7.6 Hz, 4H), 1.90-1.81 (m, 4H). MS: m/z 433.1 (M+H$^+$).

Sodium (S)-((1,2,3,5,6,7-hexahydro-s-indacen-4-yl)carbamoyl)((6-methoxy-6,7-dihydro-5H-pyrazolo[5,1-b][1,3]oxazin-3-yl)sulfonyl)amide was prepared using the same procedure.

¹H NMR (400 MHz, DMSO-d₆): δ=7.47 (brs, 1H), δ=7.39 (s, 1H), 6.78 (s, 1H), 4.49 (dt, J=8.0 Hz, 2.0 Hz, 1H), 4.23-4.15 (m, 2H), 4.14-4.08 (m, 1H), 3.99-3.95 (m, 1H), 3.34 (s, 3H), 2.75 (t, J=7.2 Hz, 4H), 2.65 (t, J=7.2 Hz, 4H), 1.96-1.86 (m, 4H). MS: m/z 433.1 (M+H⁺).

Example 25

Synthesis of Sodium (R)-((1,2,3,5,6,7-Hexahydro-s-indacen-4-yl)carbamoyl)((6-methoxy-6,7-dihydro-5H-pyrazolo[5,1-b][1,3]oxazin-3-yl)sulfonyl)amide is shown below.

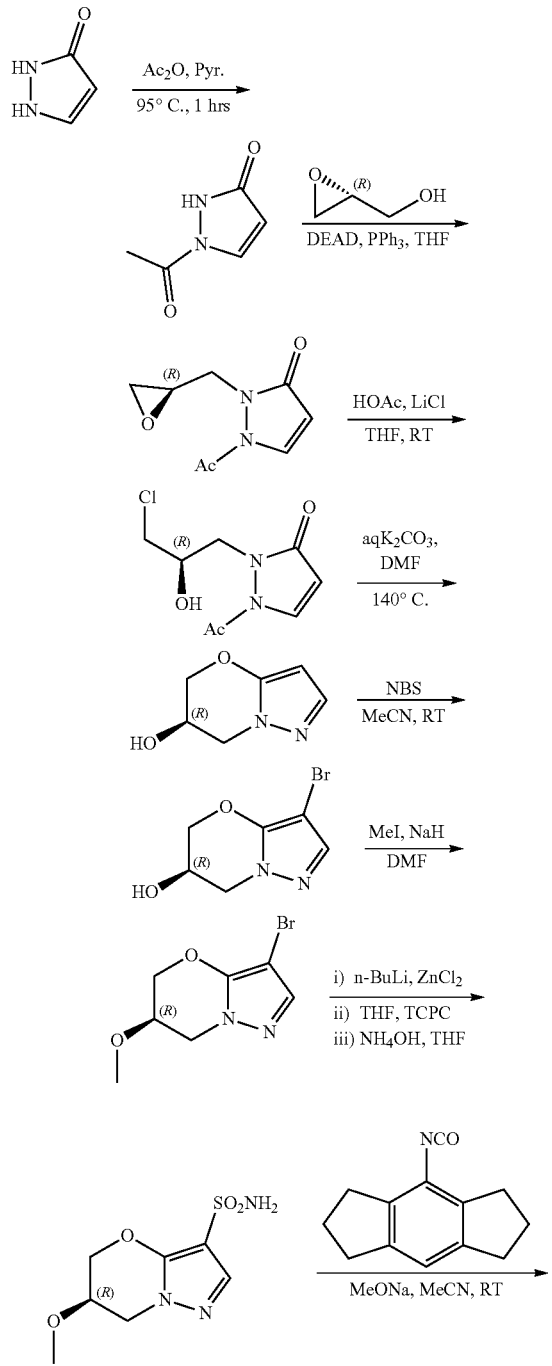

-continued

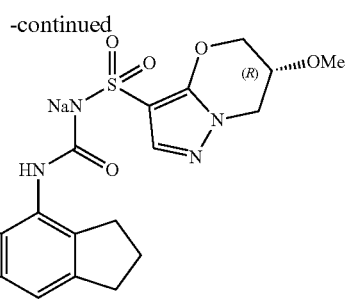

Step 1

A solution of 1,2-dihydro-pyrazol-3-one (50.0 g, 600 mmol) in pyridine (300 mL) was heated to 95° C. To the solution, a solution of acetic anhydride (61.2 g, 600 mmol) in pyridine (100 mL) was added slowly over 0.5 hour. The reaction was heated for additional 1 hr at 95° C. The reaction mixture was concentrated in vacuo resulting a dark red oil which was triturated with MeOH (150 mL) and filtered to give the 1-acetyl-1,2-dihydro-pyrazol-3-one (54.0 g, yield: 71%) as a white solid. ¹H NMR (300 MHz, DMSO-d₆): δ=10.92 (s, 1H), 8.08 (s, 1H), 5.96 (s, 1H), 2.45 (overlap, 3H).

Step 2

A mixture of 1-acetyl-1,2-dihydro-pyrazol-3-one (34.7 g, 280 mol) and PPh₃ (24.9 g, 420 mol) in THF (400 mL) was cooled to 0° C. under N₂. To the mixture was added DIAD (84.8 g, 420 mmol) slowly. The reaction was stirred for additional 1 hour at 0° C., then (R)-oxiran-2-ylmethanol (25.2 g, 340 mmol) was added slowly. The reaction was then stirred at room temperature overnight. The reaction mixture was concentrated in vacuo and the residue was purified by silica gel column (PE/EA=10/1) to give (R)-1-acetyl-2-(oxiran-2-ylmethyl)-1H-pyrazol-3(2H)-one (34.8 g, yield: 68%) as a white solid.

¹H NMR (400 MHz, CDCl₃): δ=8.06 (d, J=2.8 Hz, 1H), 6.00 (d, J=3.2 Hz, 1H), 4.55 (dd, J=12.0, 3.2 Hz, 1H), 4.20 (dd, J=12.0, 3.2 Hz, 1H), 3.39 (q, J=3.2 Hz, 1H), 2.92 (t, J=4.4 Hz, 1H), 2.76 (dd, J=4.4, 2.4 Hz, 1H), 2.57 (s, 3H).

Step 3

To a solution of (R)-1-acetyl-2-(oxiran-2-yl methyl)-1H-pyrazol-3(2H)-one (34.8 g, 190 mmol) in AcOH (34.2 g, 570 mmol) and THF (200 mL), was added LiCl (13.1 g, 310 mmol) at room temperature. The reaction was then stirred at room temperature overnight. The reaction was partitioned between EA (200 mL) and water (200 mL). The organic layer was washed with sat.NaHCO₃ (100 mL) and brine (100 mL), dried over Na₂SO₄ and concentrated in vacuo to give crude (R)-1-acetyl-2-(3-chloro-2-hydroxypropyl)-1H-pyrazol-3(2H)-one as a colorless oil which was used for next step directly without any purification.

¹H NMR (300 MHz, DMSO-d₆): δ=8.25 (d, J=2.7 Hz, 1H), 6.23 (d, J=3.0 Hz, 1H), 5.59 (brs, 1H), 4.24-4.19 (m, 2H), 4.07-4.04 (m, 1H), 3.75-3.62 (m, 2H), 2.50 (overlap, 3H). MS: m/z 219.4 (M+H⁺).

Step 4

A mixture of (R)-1-acetyl-2-(3-chloro-2-hydroxypropyl)-1H-pyrazol-3(2H)-one (crude, 190 mmol) and K₂CO₃ (78.7 g, 570 mmol) in DMF (400 mL) was stirred at 135° C. overnight. The solvent was removed under reduced pressure. The residue was purified by silica gel column (EA) to give (R)-6,7-dihydro-5H-pyrazolo[5,1-b][1,3]oxazin-6-ol (12.8 g, yield: 48%) as a white solid.

¹H NMR (400 MHz, DMSO-d₆): δ=7.21 (d, J=1.6 Hz, 1H), 5.51 (d, J=3.2 Hz, 1H), 5.44 (d, J=1.6 Hz, 1H), 4.24-4.13 (m, 4H), 3.92 (d, J=12.4 Hz, 1H).

Step 5

To a solution of (R)-6,7-dihydro-5H-pyrazolo[5,1-b][1,3]oxazin-6-ol (12.8 g, 91.4 mmol) in MeCN (200 mL) was added NBS (17.9 g, 100.6 mmol) at 0° C. under N₂ in two portions. The reaction was then stirred at room temperature for 1 hr. The reaction was partitioned between EA (200 mL) and water (200 mL). The organic layer was washed with sat.NaHCO₃ (100 mL) and brine (100 mL), dried over Na₂SO₄ and concentrated in vacuo. The residue was triturated with EA (50 mL) and filtered to give the (R)-3-bromo-6,7-dihydro-5H-pyrazolo[5,1-b][1,3]oxazin-6-ol (11.3 g, yield: 57%) as a white solid. MS: m/z 219.3 (M+H⁺).

Step 6

To a solution of (R)-3-bromo-6,7-dihydro-5H-pyrazolo[5,1-b][1,3]oxazin-6-ol (12.2 g, 55.7 mmol) in DMF (60 mL) was added NaH (60% in mineral oil, 2.7 g, 66.8 mmol). The reaction was stirred at room temperature for 1 hr under N₂. Then MeI (9.5 g, 66.8 mmol) was added. After being stirred at room temperature for 2 hrs, the reaction was poured into water (200 mL) and extracted with EA (100 mL×2). The organic layer was washed with water (100 mL) and brine (100 mL), dried over Na₂SO₄ and concentrated. The residue was triturated with MeOH/H₂O (2/1, 100 mL) and filtered to give (R)-3-bromo-6-m ethoxy-6,7-dihydro-5H-pyrazolo[5,1-b][1,3]oxazine (9.5 g, yield: 73%) as a white solid. MS: m/z 233.3 (M+H⁺).

Step 7

(R)-2,4,6-trichlorophenyl 6-methoxy-6,7-dihydro-5H-pyrazolo[5,1-b][1,3]oxazine-3-sulfonate was synthesized using Preparation B to yield the product as a yellow oil which was used for next step directly without any purification.

(R)-6-methoxy-6,7-dihydro-5H-pyrazolo[5,1-b][1,3]oxazine-3-sulfonamide was synthesized as in Preparation C to yield the desired product (2.6 g, yield: 27% over 2 steps) as a white solid.

¹H NMR (300 MHz, DMSO-d₆): δ=7.47 (s, 1H), 7.08 (s, 2H), 4.58-4.54 (m, 1H), 4.32-4.18 (m, 3H), 4.01 (d, J=1.2 Hz, 1H), 3.35 (overlap, 3H).

Step 8

To a solution of 1,2,3,5,6,7-hexahydro-s-indacen-4-ylamine (15.0 g, 87 mmol) and TEA (13.3 mL, 95.4 mmol) in THF (30 mL), was added triphosgene (8.5 g, 28.6 mmol) in one portion at 0° C. and the mixture was stirred at 70° C. under N₂ for 1 hr. The reaction mixture was then filtered through diatomite. The filter cake was washed with 30 mL PE. The filtrate was concentrated to dryness and dissolved in 100 mL n-hexane. The mixture was filtered through a silica gel pad. The filtrate was concentrated to dryness to give the 4-isocyanato-1,2,3,5,6,7-hexahydro-s-indacene (14.1 g, yield: 81%) as a pink oil.

The suspension of (R)-6-methoxy-6,7-dihydro-5H-pyrazolo[5,1-b][1,3]oxazine-3-sulfonamide (1.6 g, 6.9 mmol) in MeOH (30 mL) was stirred at 80° C. until getting a clear solution, then MeONa (372.6 mg, 6.9 mmol) was added and the mixture was stirred for 30 mins. The solution was concentrated to dryness and the residue was co-evaporated with MeCN (30 mL). The residual solid was suspended in MeCN (30 mL) and 4-isocyanato-1,2,3,5,6,7-hexahydro-s-indacene (1.4 g, 7.2 mmol) was added. The mixture solution was stirred for 16 hrs at room temperature and filtered. The filter cake was triturated with PE/EA (5/1, 40 mL) to give sodium (R)-((1,2,3,5,6,7-hexahydro-s-indacen-4-yl)carbamoyl)((6-methoxy-6,7-dihydro-5H-pyrazolo[5,1-b][1,3]oxazin-3-yl)sulfonyl)amide (2.4 g, yield: 80%) as a white solid.

¹H NMR (400 MHz, DMSO-d₆): δ=7.42 (s, 1H), 7.36 (s, 1H), 6.76 (s, 1H), 4.50 (d, J=12.0 Hz, 1H), 4.21-4.08 (m, 3H), 3.95 (s, 1H), 3.34 (overlap, 3H), 2.76 (t, J=6.8 Hz, 4H), 2.67 (t, J=6.8 Hz, 4H), 1.94-1.88 (m, 4H). MS: m/z 433.1 (M+H⁺).

Example 26

Synthesis of sodium (R)-((1,2,3,5,6,7-Hexahydro-s-indacen-4-yl)carbamoyl)((6-methoxy-6,7-dihydro-5H-pyrazolo[5,1-b][1,3]oxazin-3-yl)sulfonyl)amide is shown below.

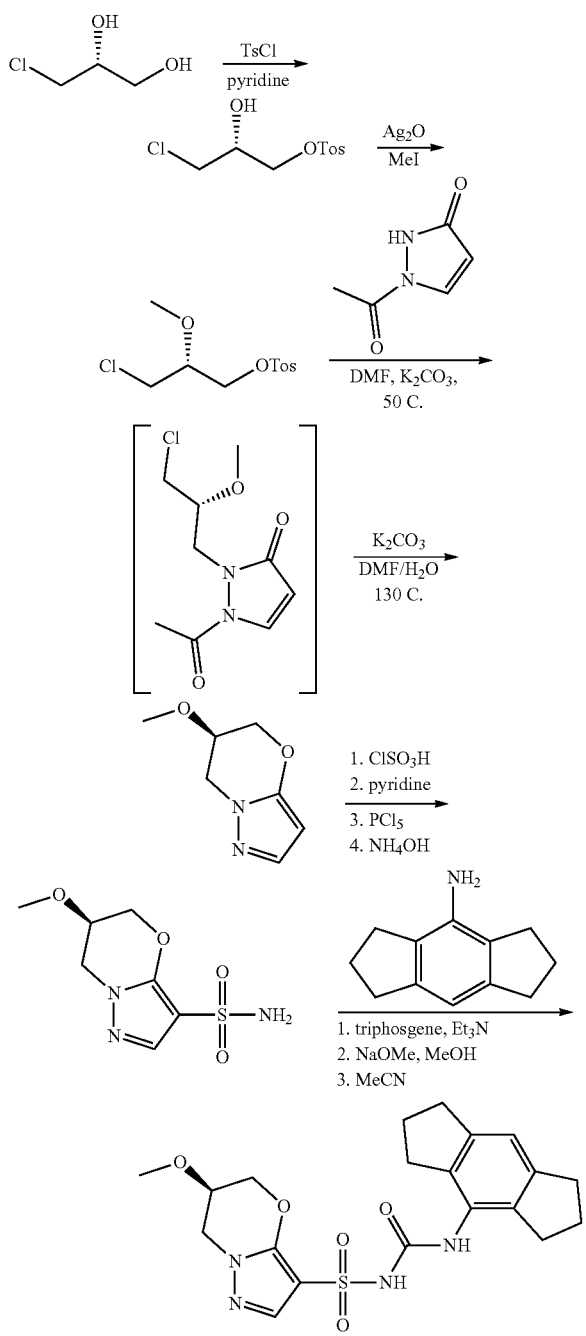

Step 1

To a solution of (R)-3-chloropropane-1,2-diol (61.0 g, 552.0 mmol) in pyridine (450 mL) was added TsCl (105.2 g, 552.0 mmol) in portions at 0° C. After being stirred at room temperature for 1 hr, the reaction was quenched with $H_2O$ (10 mL) and concentrated. The residue was poured to aq.HCl (2 N, 200 mL) and extracted with DCM (300 mL×3). The combined organic layer was washed with sat.$NaHCO_3$ (300 mL), dried over $Na_2SO_4$ and concentrated to give (R)-3-chloro-2-hydroxypropyl 4-methylbenzenesulfonate (121.8 g, crude, yield: 76%) as a yellow oil.

Step 2

A mixture of (R)-3-chloro-2-hydroxypropyl 4-methylbenzenesulfonate (121.8 g, 461.4 mmol), $CH_3I$ (43 mL, 690.4 mmol) and $Ag_2O$ (128.0 g, 551.7 mmol) in DCM (1 L) was refluxed at 45° C. for 24 hrs. Another portion $CH_3I$ (28.7 mL, 460.8 mmol) was added and the reaction was refluxed for another 24 hrs. $Ag_2O$ was removed by filtration and the filtrate was concentrated, purified by silica gel column (PE/EA=8/1) to give (R)-3-chloro-2-methoxypropyl 4-methylbenzenesulfonate (77.0 g, yield: 60%) as a yellow oil.

$^1$H NMR (300 MHz, $CDCl_3$): δ=7.79 (d, J=8.1 Hz, 2H), 7.35 (d, J=8.1 Hz, 2H), 4.15-4.08 (m, 2H), 3.64-3.50 (m, 3H), 3.38 (s, 3H), 2.44 (s, 3H).

Step 3~4

A mixture of (R)-3-chloro-2-methoxypropyl 4-methyl-benzenesulfonate (26.2 g, 94.2 mmol), 1-acetyl-1,2-dihydro-pyrazol-3-one (11.9 g, 94.2 mmol) and $K_2CO_3$ (39.0 g, 282.6 mmol) in DMF (350 mL) was stirred at 50° C. for 16 hrs. $H_2O$ (35 mL) was added and the reaction was stirred at 130° C. for another 3 hrs. $K_2CO_3$ was removed by filtration and the filtrate was concentrated. The residue was purified by silica gel column (PE/EA=2/1) to give (R)-6-methoxy-6,7-dihydro-5H-pyrazolo[5,1-b][1,3]oxazine (13.8 g, contain some DMF and an unknown byproduct, yield: 95%) as a white solid.

$^1$H NMR (400 MHz, $CDCl_3$): δ=7.33 (d, J=2.0 Hz, 1H), 5.50 (d, J=2.4 Hz, 1H), 4.40-4.34 (m, 1H), 4.32-4.23 (m, 2H), 4.17 (dd, J=11.6, 1.6 Hz, 1H), 3.92-3.89 (m, 1H), 3.48 (s, 3H).

Step 5

To a solution of (R)-6-methoxy-6,7-dihydro-5H-pyrazolo[5,1-b][1,3]oxazine (13.8 g, 89.6 mmol) in DCM (150 mL) was added $ClSO_3H$ (13.1 mL, 197.1 mmol) dropwise at 0° C. After being stirred at room temperature for 16 hrs, pyridine (15.8 mL, 197.1 mmol) was added dropwise at 0° C. and then $PCl_5$ (41.0 g, 197.1 mmol) was added portion wise at 0° C. The reaction mixture was stirred at room temperature for 1 hr, poured onto ice-water (200 mL) and extracted with EA (100 mL×3). The combined organic layer was washed with brine (100 mL), dried over $Na_2SO_4$ and concentrated to give (R)-6-methoxy-6,7-dihydro-5H-pyrazolo[5,1-b][1,3]oxazine-3-sulfonyl chloride (16.7 g, crude, yield: 74%) as a yellow solid.

Step 6

To a solution of (R)-6-methoxy-6,7-dihydro-5H-pyrazolo[5,1-b][1,3]oxazine-3-sulfonyl chloride (16.7 g, 66.3 mmol) in THF (100 mL) was added $NH_3.H_2O$ (42 mL). After being stirred at 60° C. for 2 hrs, the reaction mixture was concentrated to about 20 mL. The residual suspension was acidified with aq.HCl (1 N) to pH=3 and filtered. The filter cake was washed with $H_2O$ (50 mL) and triturated with MeOH (20 mL) to give (R)-6-methoxy-6,7-dihydro-5H-pyrazolo[5,1-b][1,3]oxazine-3-sulfonamide (10.7 g, yield: 69%) as a white solid.

$^1$H NMR (400 MHz, DMSO-$d_6$): δ=7.49 (s, 1H), 7.12 (s, 2H), 4.59 (td, 7=11.6, 2.4 Hz, 1H), 4.32 (d, J=12.0 Hz, 1H), 4.27-4.17 (m, 2H), 4.04-4.02 (m, 1H), 3.35 (s, 3H).

Step 7

(R)-((1,2,3,5,6,7-hexahydro-s-indacen-4-yl)carbamoyl)((6-methoxy-6,7-dihydro-5H-pyrazolo[5,1-b][1,3]oxazin-3-yl)sulfonyl)amide was synthesized as described in Step 8 in the previous example to produce the desired product (2.4 g, yield: 80%) as a white solid.

Example 27

An alternative synthesis of (R)-6-methoxy-6,7-dihydro-5H-pyrazolo[5,1-b][1,3]oxazine-3-sulfonamide is shown below.

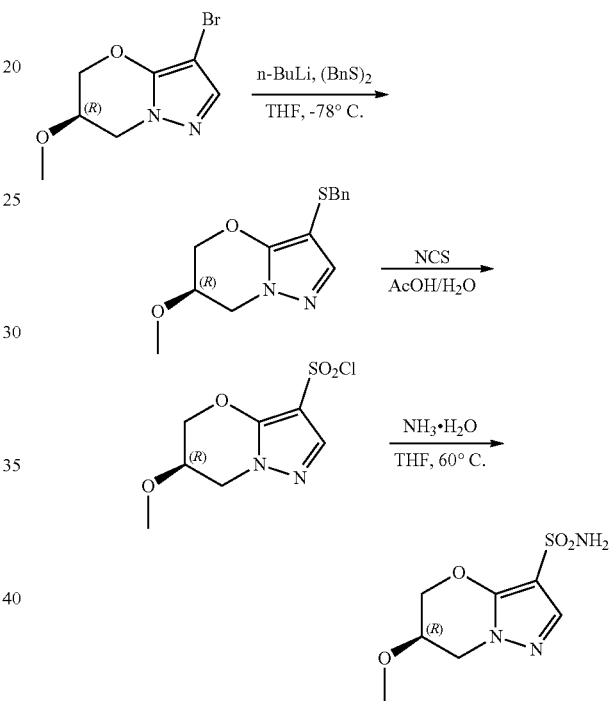

Step 1

To a solution of (R)-3-bromo-6-methoxy-6,7-dihydro-5H-pyrazolo[5,1-b][1,3]oxazine (1.0 g, 4.3 mmol) in dry THF (10 mL) was added n-BuLi in hexane (2.5 M, 2.1 mL, 5.2 mmol) slowly at −78° C. under $N_2$. After being stirred with cooling for 1 hr, $(BnS)_2$ (1.6 g, 6.5 mmol) was added slowly at this temperature. The cooling bath was removed and the reaction was stirred at room temperature overnight. The reaction was quenched with saturated $NH_4Cl$ solution (5 mL) and partitioned between water (20 mL) and EA (20 mL). The organic layer was washed with brine (20 mL), dried over $Na_2SO_4$ and concentrated. The residue was purified by silica gel column (PE/EA=1/1) to give (R)-3-(benzylthio)-6-m ethoxy-6,7-dihydro-5H-pyrazolo[5,1-b][1,3]oxazine (760 mg, yield: 63%) as a yellow oil. MS: m/z 277.4 $(M+H^+)$.

Step 2

To a solution of (R)-3-(benzylthio)-6-methoxy-6,7-dihydro-5H-pyrazolo[5,1-b][1,3]oxazine (750 mg, 2.7 mmol) in $AcOH/H_2O$ (3 mL/1 mL) was added NCS (1.5 g, 10.9 mmol) at 0° C. under $N_2$ in two portions. The reaction was then stirred at room temperature for 1 hr. The reaction was partitioned between EA (20 mL) and water (20 mL). The organic layer was washed with sat.NaHCO$_3$ (20 mL) and brine (20 mL), dried over Na$_2$SO$_4$ and concentrated in vacuo to give the crude (R)-6-methoxy-6,7-dihydro-5H-pyrazolo[5,1-b][1,3]oxazine-3-sulfonyl chloride as a yellow oil which was used for next step directly without any purification.

Step 3

(R)-6-methoxy-6,7-dihydro-5H-pyrazolo[5,1-b][1,3]oxazine-3-sulfonamide was synthesized as in Preparation C to yield the desired product (280 mg, yield: 44% over 2 steps) as a white solid.

$^1$H NMR (400 MHz, DMSO-d$_6$): δ=7.48 (s, 1H), 7.11 (s, 2H), 4.61-4.56 (m, 1H), 4.34 (d, $J$=11.6 Hz, 1H), 4.26-4.16 (m, 2H), 4.03 (d, $J$=1.2 Hz, 1H), 3.35 (s, 3H). MS: m/z 233.8 (M+H$^+$).

Example 28

Synthesis of rac-N-((1,2,3,5,6,7-Hexahydro-s-indacen-4-yl)carbamoyl)-6-methyl-6,7-dihydro-5H-pyrazolo[5,1-b][1,3]oxazine-3-sulfonamide is shown below.

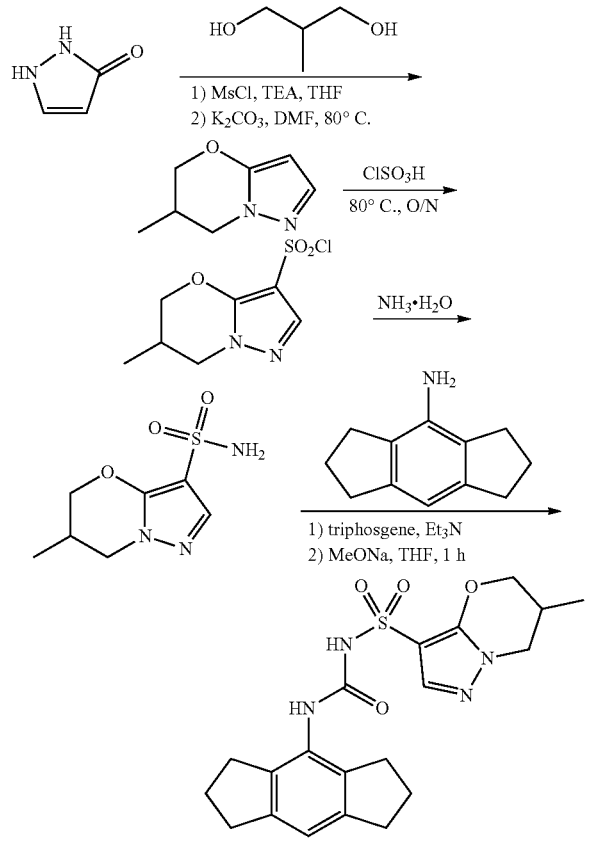

Step 1

To a solution of 2-methyl-propane-1,3-diol (1 g, 11.1 mmol) and TEA (4.5 g, 44.4 mmol) in THF (30 mL), was added MsCl (2.8 g, 24.4 mmol) slowly with ice-cooling under N$_2$. The reaction was stirred at room temperature for 1 hr and filtered. The filtrate was concentrated to give a colorless oil. A mixture of this oil, 1,2-dihydro-pyrazol-3-one (993 mg, 11.1 mmol) and K$_2$CO$_3$ (6.1 g, 44.4 mmol) in DMF (40 mL) was heated to 80° C. for 12 hrs. The reaction was cooled and partitioned between EA (100 mL) and water (200 mL) and the layers were separated. The organic layer was washed with water (80 mL) and brine (50 mL), dried over Na$_2$SO$_4$ and concentrated. The residue was purified by silica gel column (PE/EA=2/1) to give rac-6-methyl-6,7-dihydro-5H-pyrazolo[5,1-b][1,3]oxazine (500 mg, yield: 33%) as a white solid.

$^1$H NMR (300 MHz, CDCl$_3$): δ=7.31 (s, 1H), 5.47 (s, 1H), 4.27-4.23 (m, 2H), 3.87-3.68 (m, 2H), 2.47-2.45 (m, 1H), 1.23-1.09 (m, 3H). MS: m/z 139.0 (M+H$^+$).

Step 2~3

A solution of rac-6-methyl-6,7-dihydro-5H-pyrazolo[5,1-b][1,3]oxazine (500 mg, 3.6 mmol) in chlorosulfonic acid (5 mL) was stirred at 80° C. overnight. The reaction was dissolved in EA (60 mL) and added slowly to water (100 mL). The organic layer was washed with brine (60 mL), dried over Na$_2$SO$_4$ and concentrated. The residue was dissolved in THF (15 mL) and ammonia (5 mL) was added. The mixture was stirred at 60° C. for 1 hr. The reaction was concentrated, acidified with 1 N HCl and purified by reverse phase HPLC (MeCN/H$_2$O) to give rac-6-methyl-6,7-dihydro-5H-pyrazolo[5,1-b][1,3]oxazine-3-sulfonic acid amide (450 mg, yield: 58% over 2 steps) as a white solid.

$^1$H NMR (300 MHz, DMSO-d$_6$): δ=7.46 (s, 1H), 7.11 (brs, 2H), 4.43-4.38 (m, 1H), 4.21-4.15 (m, 1H), 4.06-3.99 (m, 1H), 3.76-3.69 (m, 1H), 2.42-2.34 (m, 1H), 1.02-1.00 (m, 3H).

Step 4 rac-N-((1,2,3,5,6,7-hexahydro-s-indacen-4-yl)carbamoyl)-6-methyl-6,7-dihydro-5H-pyrazolo[5,1-b][1,3]oxazine-3-sulfonamide was synthesized using Preparation A to deliver the desired product (29.7 mg, yield: 18%) as a white solid.

$^1$H NMR (400 MHz, DMSO-d$_6$): δ=10.49 (s, 1H), 7.92 (s, 1H), 7.62 (s, 1H), 6.93 (s, 1H), 4.48-4.45 (m, 1H), 4.44-4.18 (m, 1H), 4.08 (t, $J$=11.4 Hz, 1H), 3.77-3.72 (m, 1H), 2.78 (t, $J$=7.6 Hz, 4H), 2.60 (t, $J$=7.2 Hz, 4H), 2.40 (overlap, 1H), 1.98-1.91 (m, 4H), 1.01 (d, $J$=6.4 Hz, 3H). MS: m/z 417.0 (M+H$^+$).

Example 29

Synthesis of (S)—N-((1,2,3,5,6,7-Hexahydro-s-indacen-4-yl)carbamoyl)-6-methyl-6,7-dihydro-5H-pyrazolo[5,1-b][1,3]oxazine-3-sulfonamide and (R)—N-((1,2,3,5,6,7-hexahydro-s-indacen-4-yl)carbamoyl)-6-methyl-6,7-dihydro-5H-pyrazolo[5,1-b][1,3]oxazine-3-sulfonamide is shown below.

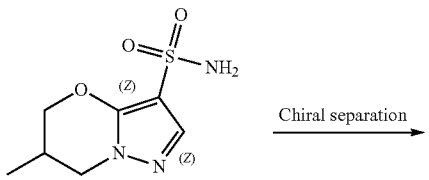

Chiral separation

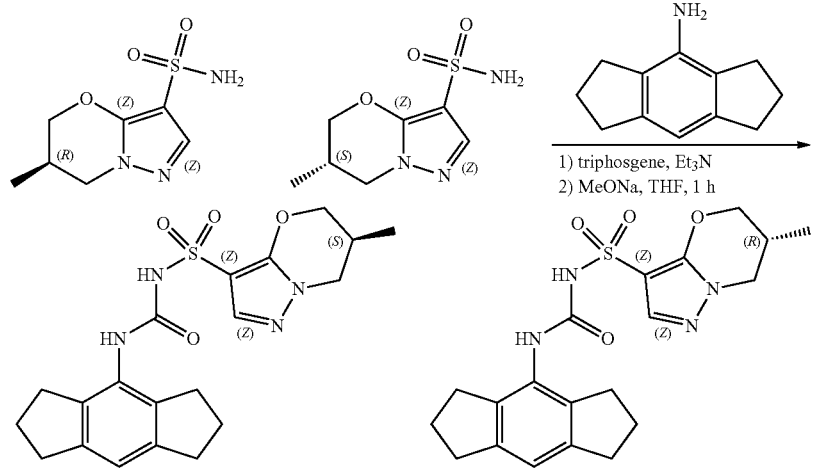

Step 1 rac-6-Methyl-6,7-dihydro-5H-pyrazolo[5,1-b][1,3]oxazine-3-sulfonamide (350 mg) was resolved by chiral prep-HPLC to give (S)-6-methyl-6,7-dihydro-5H-pyrazolo[5,1-b][1,3]oxazine-3-sulfonamide (242 mg as diethylamine salt) and (R)-6-methyl-6,7-dihydro-5H-pyrazolo[5,1-b][1,3]oxazine-3-sulfonamide (240 mg as diethylamine salt)

Step 2

(R)—N-((1,2,3,5,6,7-hexahydro-s-indacen-4-yl)carbamoyl)-6-methyl-6,7-dihydro-5H-pyrazolo[5,1-b][1,3]oxazine-3-sulfonamide was synthesized as in Preparation A to yield the desired product (112 mg, yield: 37%) as a white solid.

$^1$H NMR (400 MHz, DMSO-d$_6$): δ=10.45 (brs, 1H), 7.90 (s, 1H), 7.61 (s, 1H), 6.93 (s, 1H), 4.48-4.45 (m, 1H), 4.44-4.18 (m, 1H), 4.08 (t, J=11.4 Hz, 1H), 3.77-3.72 (m, 1H), 2.78 (t, J=7.6 Hz, 4H), 2.60 (t, J=7.2 Hz, 4H), 2.40 (overlap, 1H), 1.98-1.91 (m, 4H), 1.00 (d, J=6.4 Hz, 3H). MS: m/z 417.1 (M+H$^+$).

(S)—N-((1,2,3,5,6,7-Hexahydro-s-indacen-4-yl)carbamoyl)-6-methyl-6,7-dihydro-5H-pyrazolo[5,1-b][1,3]oxazine-3-sulfonamide was prepared using the same procedure.

$^1$H NMR (400 MHz, DMSO-d$_6$): δ=10.45 (s, 1H), 7.90 (s, 1H), 7.61 (s, 1H), 6.93 (s, 1H), 4.48-4.44 (m, 1H), 4.22-4.18 (m, 1H), 4.11-4.06 (m, 1H), 3.77-3.72 (m, 1H), 2.78 (t, J=7.2 Hz, 4H), 2.60 (t, J=6.8 Hz, 4H), 2.42-2.38 (m, 1H), 1.98-1.92 (m, 4H), 1.00 (d, J=6.8 Hz, 3H). MS: m/z 417.1 (M+H$^+$).

Example 30

Synthesis of N-((1,2,3,5,6,7-Hexahydro-s-indacen-4-yl)carbamoyl)-5',7'-dihydrospiro[cyclopropane-1,6'-pyrazolo[5,1-b][1,3]oxazine]-3'-sulfonamide is shown below.

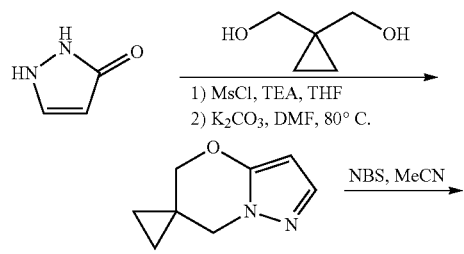

Step 1

To a solution of (1-hydroxymethyl-cyclopropyl)-methanol (1.53 g, 15 mmol) and TEA (6.1 g, 60 mmol) in THF (45 mL), was added MsCl (3.8 g, 33 mmol) slowly with ice-cooling under N$_2$. After being stirred at room temperature for 1 hr, the reaction was partitioned between EA (500 mL) and water (100 mL). The organic layer was washed with brine (100 mL), dried over Na$_2$SO$_4$ and concentrated to give a colorless oil. A mixture of this oil, 1,2-dihydro-pyrazol-3-one (1.3 g, 15 mmol) and K$_2$CO$_3$ (8.3 g, 60 mmol) in DMF (60 mL) was heated to 80° C. overnight. The reaction was cooled and partitioned between EA (120 mL) and water (300 mL). The organic layer was washed with water (100 mL) and brine (80 mL), dried over $Na_2SO_4$ and concentrated. The residue was purified by reverse phase HPLC (MeCN/$H_2O$) to give 5',7'-dihydrospiro[cyclopropane-1,6'-pyrazolo[5,1-b][1,3]oxazine] (380 mg, yield: 17%) as a white solid.

$^1$H NMR (300 MHz, CDCl$_3$): δ=7.33 (d, J=1.8 Hz, 1H), 5.52 (d, J=1.8 Hz, 1H), 3.99 (s, 4H), 0.81-0.49 (m, 4H). MS: m/z 151.0 (M+H$^+$).

Step 2

NBS (960 mg, 5 mmol) was added portionwise to a solution of 5',7'-dihydrospiro[cyclopropane-1,6'-pyrazolo[5,1-b][1,3]oxazine] (380 mg, 5.3 mmol) in MeCN (15 mL). After being stirred at room temperature for 1 hr, the reaction was partitioned between EA (60 mL) and water (60 mL). The organic layer was washed with brine (60 mL), dried over $Na_2SO_4$ and concentrated. The residue was purified by silica gel column (PE/EA=2/1) to 3'-bromo-5',7'-dihydrospiro[cyclopropane-1,6'-pyrazolo[5,1-b][1,3]oxazine] (380 mg, yield: 66%) as a yellow solid.

$^1$H NMR (300 MHz, CDCl$_3$): δ=7.33 (s, 1H), 4.07 (s, 2H), 3.98 (s, 2H), 0.86-0.81 (m, 4H). MS: m/z 230.9 (M+H$^+$).

Step 3

2,4,6-trichlorophenyl 5',7'-dihydrospiro[cyclopropane-1,6'-pyrazolo[5,1-b][1,3]oxazine]-3'-sulfonate was synthesized using Preparation B to yield the product as a yellow oil which was used for next step without any purification.

Step 4

5',7'-dihydrospiro[cyclopropane-1,6'-pyrazolo[5,1-b][1,3]oxazine]-3'-sulfonamide was synthesized as in Preparation C to yield the desired product (105 mg, yield: 27% over 2 steps) as a white solid.

$^1$H NMR (400 MHz, DMSO-d$_6$): δ=7.49 (s, 1H), 7.12 (brs, 2H), 4.20 (s, 2H), 4.00 (s, 2H), 0.78 (s, 4H).

Step 5

N-((1,2,3,5,6,7-hexahydro-s-indacen-4-yl)carbamoyl)-5',7'-dihydrospiro[cyclopropane-1,6'-pyrazolo[5,1-b][1,3]oxazine]-3'-sulfonamide was synthesized using Preparation A to deliver the desired product (54 mg, yield: 34%) as a white solid.

$^1$H NMR (400 MHz, DMSO-d$_6$): δ=10.53 (s, 1H), 8.01 (s, 1H), 7.62 (s, 1H), 6.94 (s, 1H), 4.25 (s, 2H), 4.01 (s, 2H), 2.79 (t, J=7.2 Hz, 4H), 2.60 (t, J=7.2 Hz, 4H), 1.99-1.93 (m, 4H), 0.78 (s, 4H). MS: m/z 429.0 (M+H$^+$).

Example 31

Synthesis of N-((1,2,3,5,6,7-Hexahydro-s-indacen-4-yl)carbamoyl)-1-tosyl-5',7'-dihydrospiro[azetidine-3,6'-pyrazolo[5,1-b][1,3]oxazine]-3'-sulfonamide is shown below.

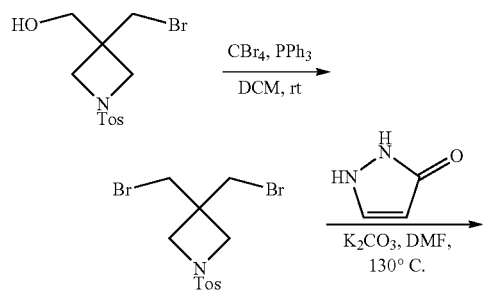

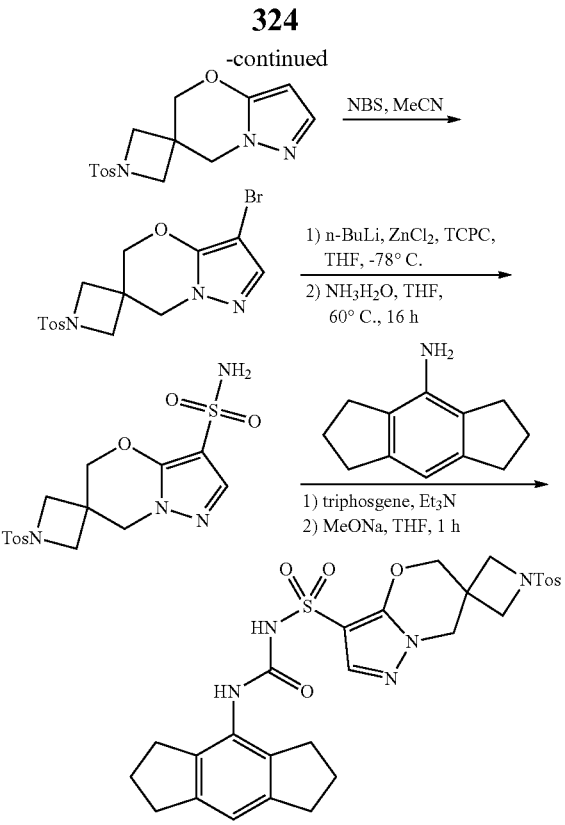

Step 1

To a solution of [3-bromomethyl-1-(toluene-4-sulfonyl)-azetidin-3-yl]-methanol (4 g, 12 mmol) in DCM (60 mL) was added CBr$_4$ (6.4 g, 19.2 mmol) and PPh$_3$ (5.2 g, 19.2 mmol) at 0° C. After being stirred at room temperature for 16 hrs, the reaction was partitioned between DCM (200 mL) and $H_2O$ (200 mL). The aqueous layer was extracted with DCM (200 mL). The combined organic layer was washed with brine (100 mL), dried over $Na_2SO_4$ and concentrated. The residue was purified by silica gel column (PE/EA=5/1) to give 3,3-bis-bromomethyl-1-(toluene-4-sulfonyl)-azetidine (3.8 g, yield: 79%) as a yellow solid. MS: m/z 395.9 (M+H$^+$).

Step 2

To a solution of 3,3-bis-bromomethyl-1-(toluene-4-sulfonyl)-azetidine (4.2 g, 10.6 mmol) and 1,2-dihydro-pyrazol-3-one (0.89 g, 10.6 mmol) in DMF (50 mL) was added K$_2$CO$_3$ (3.7 g, 26.5 mmol). After being stirred at 130° C. for 16 hrs, the reaction was cooled down and quenched with the addition of EA (100 mL) and water (100 mL). The organic layer was separated. The aqueous layer was extracted with EA (100 mL). The organic layers were combined, washed with brine (80 mL), dried over $Na_2SO_4$ and concentrated in vacuo. The residue was purified by silica gel column (PE/EA=1/1) to give 1-tosyl-5',7'-dihydrospiro[azetidine-3,6'-pyrazolo[5,1-b][1,3]oxazine] (1.4 g, yield: 42%) as a white solid. MS: m/z 320 (M+H$^+$).

Step 3

NBS (0.64 g, 3.6 mmol) was added portionwise to a solution of 1-tosyl-5',7'-dihydrospiro[azetidine-3,6'-pyrazolo[5,1-b][1,3]oxazine] (1 g, 0.33 mmol) in MeCN (10 mL) at 0° C. and the reaction was stirred for 2 hrs at room temperature. The mixture was filtered and the filtrate was purified by reverse phase HPLC (5%-95% MeCN in H$_2$O) to give 3'-bromo-1-tosyl-5',7'-dihydrospiro[azetidine-3,6'- pyrazolo[5,1-b][1,3]oxazine] (1.16 g, yield: 83%) as a yellow solid. MS: m/z 398 (M+H⁺).

Step 4

2,4,6-trichlorophenyl 1-tosyl-5',7'-dihydrospiro[azetidine-3,6'-pyrazolo[5,1-b][1,3]oxazine]-3'-sulfonate was synthesized using Preparation B to yield the product as a yellow oil.

1-tosyl-5',7'-dihydrospiro[azetidine-3,6'-pyrazolo[5,1-b][1,3]oxazine]-3'-sulfonamide was synthesized as in Preparation C to yield the desired product (140 mg, yield: 32%) as a light yellow solid. MS: m/z 399.1 (M+H⁺).

Step 5

N-((1,2,3,5,6,7-hexahydro-s-indacen-4-yl)carbamoyl)-1-tosyl-5',7'-dihydrospiro[azetidine-3,6'-pyrazolo[5,1-b][1,3]oxazine]-3'-sulfonamide was synthesized using Preparation A and further purified by prep HPLC to deliver the desired product (24 mg, yield: 22%) as a white solid.

$^1$H NMR (400 MHz, DMSO-d$_6$): δ=10.52 (s, 1H), 7.90 (s, 1H), 7.74 (d, J=8.0 Hz, 2H), 7.62 (s, 1H), 7.53 (d, J=8.0 Hz, 2H), 6.94 (s, 1H), 4.24 (s, 2H), 4.00 (s, 2H), 3.68 (s, 4H), 2.80 (t, J=7.2 Hz, 4H), 2.55 (t, J=6.8 Hz, 4H), 2.46 (s, 3H), 1.91-1.98 (m, 4H). MS: m/z 598.2 (M+H⁺).

Example 32

Synthesis of 6-Amino-N-((1,2,3,5,6,7-hexahydro-s-indacen-4-yl)carbamoyl)-6,7-dihydro-5H-pyrazolo[5,1-b][1,3]oxazine-3-sulfonamide is shown below.

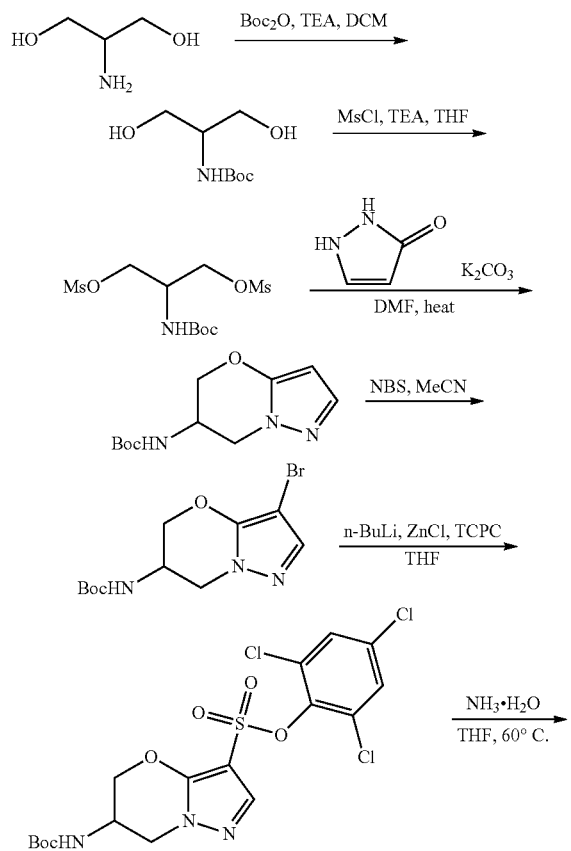

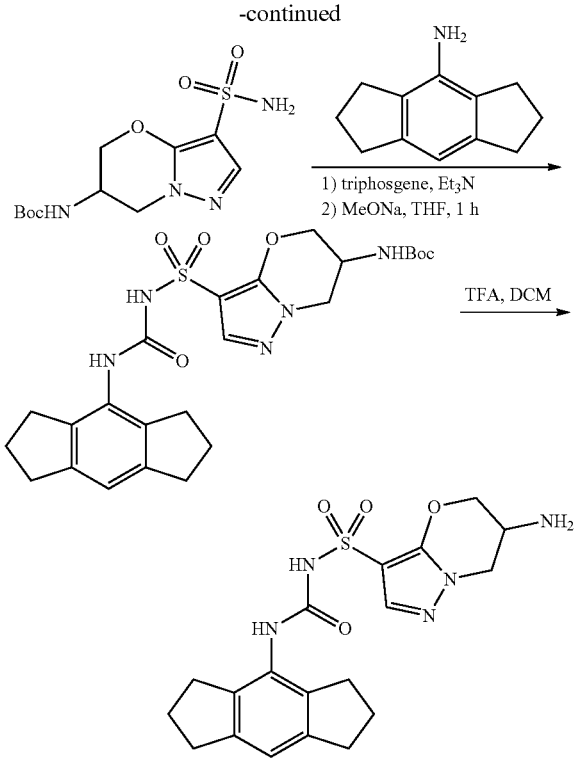

Step 1

To a solution of 2-aminopropane-1,3-diol (5.0 g, 54.9 mmol) and TEA (11.1 g, 109.9 mmol) in DCM (40 mL) was added Boc$_2$O (14.4 g, 65.9 mmol) and the reaction was stirred at room temperature for 2 hrs. The reaction was partitioned between water (80 mL) and EA (80 mL). The organic layer was washed with brine (80 mL), dried over Na$_2$SO$_4$ and concentrated to give crude tert-butyl (1,3-dihydroxypropan-2-yl)carbamate as a white solid which was used for next step directly without any purification.

Step 2

To a solution of tert-butyl (1,3-dihydroxypropan-2-yl)carbamate (crude, ~21.0 mmol) and TEA (8.5 g, 84.0 mmol) in dry THF (30 mL) was added MsCl (5.3 g, 46.0 mmol) and at 0° C. After stirring at room temperature for 2 hrs, the reaction was filtered. The filtrate was concentrated to dryness. The residue was purified by silica gel column (PE/EA=1/1) to give 2-((tert-butoxycarbonyl)amino)propane-1,3-diyl dimethanesulfonate (3.9 g, yield: 53%) as a white solid.

$^1$H NMR (300 MHz, CDCl$_3$): δ=5.11 (d, J=7.5 Hz, 1H), 4.36-4.22 (m, 5H), 3.07 (s, 6H), 1.44 (s, 9H).

Step 3

A mixture of 2-((tert-butoxycarbonyl)amino)propane-1,3-diyl dimethanesulfonate (3.9 g, 11.2 mmol), 1,2-dihydropyrazol-3-one (945 mg, 11.2 mmol) and K$_2$CO$_3$ (5.4 g, 39.3 mmol) in DMF (30 mL) was heated to 80° C. for 12 hrs. The reaction was cooled and partitioned between EA (150 mL) and water (200 mL). The organic layer was washed with water (80 mL) and brine (50 mL), dried over Na$_2$SO$_4$ and concentrated. The residue was purified by silica gel column (PE/EA=1/1) to give tert-butyl (6,7-dihydro-5H-pyrazolo[5,1-b][1,3]oxazin-6-yl)carbamate (975 mg, yield: 13%) as a white solid.

$^1$H NMR (300 MHz, CDCl$_3$): δ=7.37 (d, J=1.2 Hz, 1H), 5.55 (d, J=1.5 Hz, 1H), 5.14-5.04 (m, 1H), 4.43-4.12 (m, 5H), 1.46 (s, 9H). MS: m/z 240.1 (M+H⁺).

Step 4

To a solution of tert-butyl (6,7-dihydro-5H-pyrazolo[5,1-b][1,3]oxazin-6-yl)carbamate (610 mg, 2.6 mmol) in MeCN, was added NBS (454 mg, 2.6 mmol) at 0° C. under N₂ in two portions. The reaction was then stirred at room temperature for 1 hr. The reaction was partitioned between EA (20 mL) and water (20 mL). The organic layer was washed with water (20 mL) and brine (20 mL), dried over Na₂SO₄ and concentrated. The residue was purified by silica gel column (PE/EA=1/1) to give tert-butyl (3-bromo-6,7-dihydro-5H-pyrazolo[5,1-b][1,3]oxazin-6-yl)carbamate (640 mg, yield: 79%) as a white solid. MS: m/z 318.0 (M+H⁺).

Step 5

2,4,6-trichlorophenyl 6-((tert-butoxycarbonyl)amino)-6,7-dihydro-5H-pyrazolo[5,1-b][1,3]oxazine-3-sulfonate was synthesized using Preparation B to yield the product as a yellow gel which was used for next step directly without any purification.

Step 6

A mixture of 2,4,6-trichlorophenyl 6-((tert-butoxycarbonyl)amino)-6,7-dihydro-5H-pyrazolo[5,1-b][1,3]oxazine-3-sulfonate (crude, ~1.9 mmol), NH₄OH (20 mL) and THF (20 mL) was stirred at 60° C. overnight. The reaction was concentrated under reduced pressure until 10 mL of liquid remained. The remained solution was acidified with 1 N HCl to pH=5 and extracted with EA (20 mL×2). The organic layers were combined, dried over Na₂SO₄ and concentrated. The residue was purified by silica gel column (DCM/MeOH=40/1) to give tert-butyl (3-sulfamoyl-6,7-dihydro-5H-pyrazolo[5,1-b][1,3]oxazin-6-yl)carbamate (80 mg, yield: 13% over 2 steps) as a yellow semi-solid. MS: m/z 317.0 (M−H⁺).

Step 7 tert-Butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)carbamate was synthesized using Preparation A to deliver the desired product (28 mg, yield: 22%) as a white solid.

Step 8

To a solution of tert-butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)carbamate (28 mg, 0.05 mmol) in DCM (5 mL) was added TFA (5 mL) and the mixture was stirred at room temperature for 20 mins. The reaction was concentrated to dryness and the residue was triturated with EA to give TFA salt of 6-amino-N-((1,2,3,5,6,7-hexahydro-s-indacen-4-yl)carbamoyl)-6,7-dihydro-5H-pyrazolo[5,1-b][1,3]oxazine-3-sulfonamide (5.4 mg, yield: 23%) as a white solid.

¹H NMR (400 MHz, DMSO-d₆): δ=8.15 (brs, 1H), 7.54 (s, 1H), 6.88 (s, 1H), 4.32-4.30 (m, 1H), 4.21-4.16 (m, 1H), 4.11-4.01 (m, 1H), 3.81-3.75 (m, 1H), 3.47 (overlap, 1H), 2.77 (t, J=7.2 Hz, 4H), 2.67-2.62 (m, 4H), 1.97-1.92 (m, 4H). MS: m/z 418.2 (M+H⁺).

Example 33

Synthesis of Sodium ((6-(((tert-butoxycarbonyl)amino)methyl)-6,7-dihydro-5H-pyrazolo[5,1-b][1,3]oxazin-3-yl)sulfonyl)((1,2,3,5,6,7-hexahydro-s-indacen-4-yl)carbamoyl)amide is shown below.

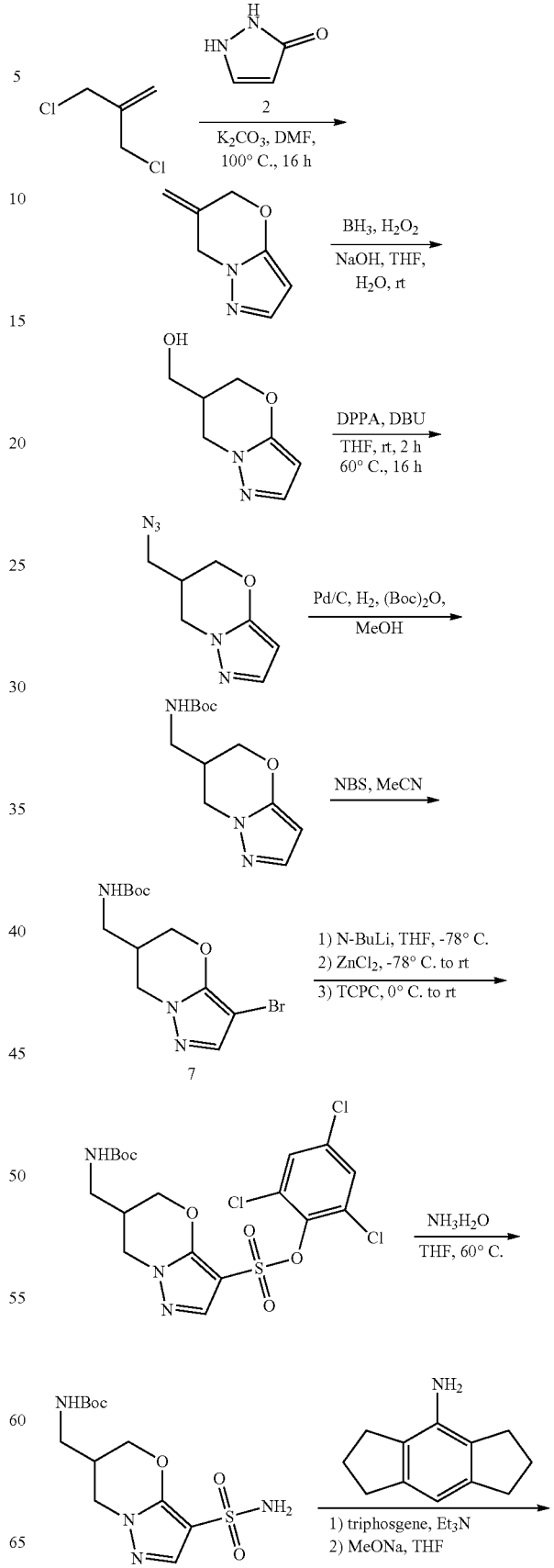

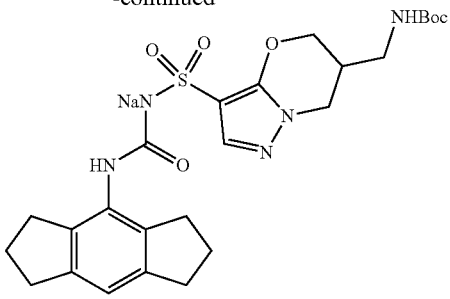

Step 1

A mixture of 1,2-dihydro-pyrazol-3-one (10.42 g, 0.124 mol) and K₂CO₃ (42.8 g, 0.31 mol) in DMF (700 mL) was heated to 100° C. 3-Chloro-2-chloromethyl-propene (15.5 g, 0.124 mol) was added and the mixture was stirred at 100° C. for 16 hrs. The solvent was removed in vacuo. The residue was partitioned between EA (200 mL) and H₂O (500 mL). The aqueous layer was extracted with EA (200 mL). The combined organic layer was washed with brine (100 mL), dried over Na₂SO₄ and concentrated. The residue was purified by silica gel column (PE/EA=1/1) to give 6-methylene-6,7-dihydro-5H-pyrazolo[5,1-b][1,3]oxazine (1.7 g, yield: 10%) as a yellow oil.

¹H NMR (300 MHz, CDCl₃): δ=7.34 (s, 1H), 5.51 (s, 1H), 5.39 (s, 2H), 4.80 (s, 2H), 4.63 (s, 2H). MS: m/z 137.1 (M+H⁺).

Step 2

To a solution of 6-methylene-6,7-dihydro-5H-pyrazolo[5,1-b][1,3]oxazine (1.7 g, 12.5 mmol) in THF (20 mL) was added BH₃/Me₂S (10 M, 5 mL, 50 mmol) at 0° C. After stirring at room temperature for 16 hrs, NaOH solution (3 M, 50 mL, 150 mmol) and H₂O₂ (30%, 5.7 g, 50 mmol) were added to the reaction slowly. After stirring at 80° C. for 2 hrs, the reaction was cooled down. Saturated aqueous solution of Na₂SO₃ (50 mL) was added to the reaction. After stirring at room temperature for 0.5 hr, the resulting mixture was extracted with EA (100 mL×3). The combined organic layer was washed with brine (100 mL), dried over Na₂SO₄ and concentrated to give (6,7-dihydro-5H-pyrazolo[5,1-b][1,3]oxazin-6-yl)-methanol (1.3 g, yield: 68%) as a yellow oil.

¹H NMR (300 MHz, CDCl₃): δ=7.31 (d, J=1.8 Hz, 1H), 5.49 (d, J=1.8 Hz, 1H), 4.37 (dd, 7=11.4, 3 Hz, 1H), 4.28-4.12 (m, 2H), 4.07-4.00 (m, 1H), 3.77 (d, J=6.6 Hz, 2H), 2.58-2.50 (m, 1H).

Step 3

To a solution of (6,7-dihydro-5H-pyrazolo[5,1-b][1,3]oxazin-6-yl)-methanol (2.05 g, 13.3 mmol) in THF (30 mL) was added DPPA (7.3 g, 26.6 mmol) and DBU (6.1 g, 39.9 mmol) at room temperature. The suspension was stirred at 60° C. for 16 hrs. The reaction was quenched by the addition of EA (100 mL) and water (100 mL). The organic layer was separated. The aqueous layer was extracted with EA (100 mL). The organic layer was washed with brine (100 mL), dried over Na₂SO₄ and concentrated in vacuo. The residue was purified by silica gel column (PE/EA=2/1) to give 6-azidomethyl-6,7-dihydro-5H-pyrazolo[5,1-b][1,3]oxazine (1.24 g, yield: 62%) as a yellow oil. MS: m/z 180.3 (M+H⁺).

Step 4

To a solution of 6-azidomethyl-6,7-dihydro-5H-pyrazolo[5,1-b][1,3]oxazine (1.24 g, 16.9 mmol) in MeOH (20 mL) was added Boc₂O (3 g, 13.8 mmol) and Pd/C (5%, 0.2 g). The mixture was stirred under H₂ (balloon atmosphere) at room temperature for 16 hrs. The reaction was filtered and the filtrate was concentrated to give a crude product, which was used for next step directly without further purification. MS: m/z 254.0 (M+H⁺).

Step 5

NBS (1.3 g, 24.7 mmol) was added portionwise to a solution of tert-butyl ((6,7-dihydro-5H-pyrazolo[5,1-b][1,3]oxazin-6-yl)methyl)carbamate (crude, 6.9 mmol) in MeCN (20 mL) at 0° C. and the reaction was stirred for 2 hrs at room temperature. The mixture was filtered and purified by reverse phase HPLC (5%-95% MeCN in H₂O) to give tert-butyl ((3-bromo-6,7-dihydro-5H-pyrazolo[5,1-b][1,3]oxazin-6-yl)methyl)carbamate (1.62 g, yield: 71%) as a yellow solid. MS: m/z 331.9 (M+H⁺).

Step 6

2,4,6-trichlorophenyl 6-(((tert-butoxycarbonyl)amino)methyl)-6,7-dihydro-5H-pyrazolo[5,1-b][1,3]oxazine-3-sulfonate was synthesized using Preparation B to yield the product as a yellow oil which was used for next step directly without any purification.

Step 7 tert-butyl ((3-sulfamoyl-6,7-dihydro-5H-pyrazolo[5,1-b][1,3]oxazin-6-yl)methyl)carbamate was synthesized as in Preparation C to yield the desired product (80 mg, yield: 33% over 2 steps) as a light yellow solid. MS: m/z 333.4 (M+H⁺).

Step 8

((6-(((tert-butoxycarbonyl)amino)methyl)-6,7-dihydro-5H-pyrazolo[5,1-b][1,3]oxazin-3-yl)sulfonyl)((1,2,3,5,6,7-hexahydro-s-indacen-4-yl)carbamoyl)amide was synthesized as in Preparation D to yield the desired product (27 mg, yield: 21%) as a white solid.

¹H NMR (400 MHz, DMSO-d₆): δ=7.35 (s, 1H), 7.31 (s, 1H), 7.11 (s, 1H), 6.75 (s, 1H), 4.31 (d, J=5.6 Hz, 1H), 4.10-3.98 (m, 2H), 3.78 (dd, J=10.0, 2.0 Hz, 1H), 3.07-3.04 (m, 2H), 2.74 (t, J=7.2 Hz, 4H), 2.64 (t, J=7.2 Hz, 4H), 2.40-2.3 (m, 1H), 1.93-1.86 (m, 4H), 1.39 (s, 9H). MS: m/z 532.2 (M+H⁺).

Example 34

Synthesis of rac-N-((3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)methyl)acetamide is shown below.

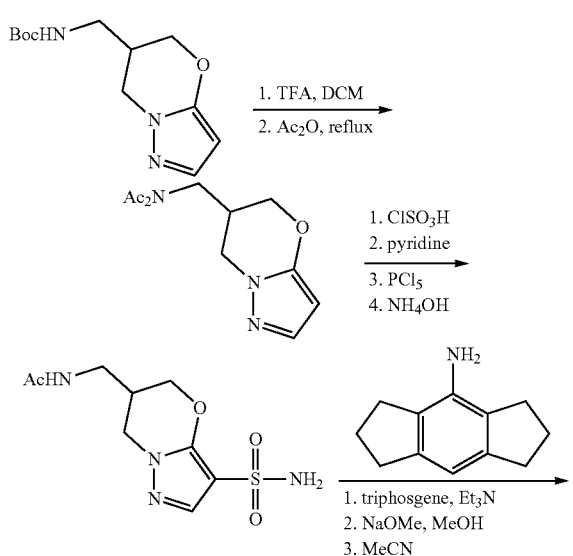

-continued

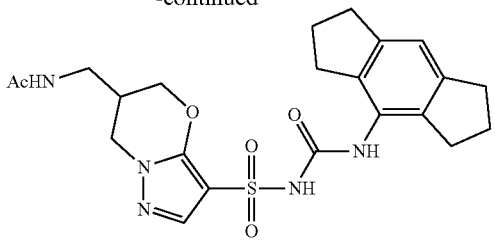

Step 1

To a solution of rac-tert-butyl ((6,7-dihydro-5H-pyrazolo[5,1-b][1,3]oxazin-6-yl)methyl)carbamate (crude, ~1.05 mmol) in DCM (3 mL) was added TFA (1 mL). After the solution was stirred at room temperature for 2 hrs, the solution was concentrated and dissolved with Ac$_2$O (3 mL). After stirring at reflux for 3 hrs, the reaction solution was quenched with the addition of EA (20 mL) and water (10 mL). The organic layer was separated. The aqueous layer was extracted with EA (10 mL). The organic layers were combined and washed with brine (10 mL), and dried over Na$_2$SO$_4$. The solution was concentrated in vacuo. The residue was purified by silica gel column (PE/EA=1/1) to give rac-N-acetyl-N-((6,7-dihydro-5H-pyrazolo[5,1-b][1,3]oxazin-6-yl)methyl)acetamide (90 mg, yield: 31%) as a yellow oil. MS: m/z 238.4 (M+H$^+$).

Step 2

To a solution of rac-N-acetyl-N-((6,7-dihydro-5H-pyrazolo[5,1-b][1,3]oxazin-6-yl)methyl)acetamide (90 mg, 0.38 mmol) in DCM (2 mL) was added ClSO$_3$H (0.075 mL, 1.14 mmol) dropwise at 0° C. After stirring at room temperature for 16 hrs, pyridine (0.092 mL, 1.14 mmol) was added to the reaction dropwise at 0° C., followed by addition of PCl$_5$ (237 mg, 1.14 mmol) in portions. The reaction mixture was stirred at room temperature for 1 hr, poured to ice-water (2 mL) and extracted with EA (10 mL×3). The combined organic layer was washed with brine (10 mL), dried over Na$_2$SO$_4$ and concentrated to give a crude product, which was directly used for next step without further purification.

Step 3

To a solution of rac-6-((N-acetylacetamido)methyl)-6,7-dihydro-5H-pyrazolo[5,1-b][1,3]oxazine-3-sulfonyl chloride (crude, ~0.387 mmol) in THF (3 mL) was added NH$_3$.H$_2$O (3 mL). After stirring at 60° C. for 2 hrs, the reaction mixture was concentrated to about 1 mL. The residual suspension was acidified with aq.HCl (1 N) to pH=3 and filtered. The filtrate was purified by reverse phase HPLC (MeCN/H$_2$O) to give rac-N-((3-sulfamoyl-6,7-dihydro-5H-pyrazolo[5,1-b][1,3]oxazin-6-yl)methyl)acetamide (67 mg, yield: 64%) as a white solid.

$^1$H NMR (400 MHz, DMSO-d$_6$): δ=8.02 (brs, 1H), 7.37 (s, 1H), 6.65 (brs, 2H), 4.40-4.30 (m, 1H), 4.17-4.04 (m, 2H), 3.85-3.73 (m, 1H), 3.10-3.00 (m, 2H), 2.50 (overlap, 1H), 1.76 (s, 3H).

Step 4 rac-N-(3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)methyl)acetamide was synthesized as in Preparation D to yield the desired product (34 mg, yield: 48%) as a white solid.

$^1$H NMR (400 MHz, DMSO-d$_6$): δ=10.47 (s, 1H), 8.07 (t, J=6 Hz, 1H), 7.90 (s, 1H), 7.63 (s, 1H), 6.93 (s, 1H), 4.48 (d, J=8.8 Hz, 1H), 4.26-4.14 (m, 2H), 3.93-3.85 (m, 1H), 3.23-3.08 (m, 2H), 2.79 (t, J=7.2 Hz, 4H), 2.59 (t, J=6.8 Hz, 4H), 2.50 (overlap, 1H), 2.10-1.90 (m, 4H), 1.83 (s, 3H). MS: m/z 474.2 (M+H$^+$).

Example 35

Synthesis of rac-6-((Dimethylamino)methyl)-N-((1,2,3,5,6,7-hexahydro-s-indacen-4-yl)carbamoyl)-6,7-dihydro-5H-pyrazolo[5,1-b][1,3]oxazine-3-sulfonamide is shown below.

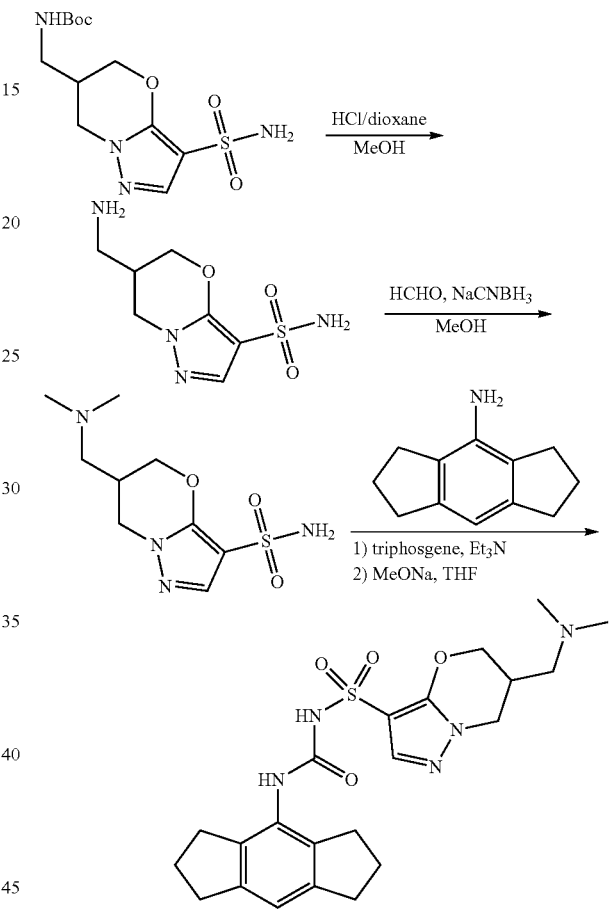

Step 1

To a solution of rac-tert-butyl ((3-sulfamoyl-6,7-dihydro-5H-pyrazolo[5,1-b][1,3]oxazin-6-yl)methyl)carbamate (110 mg, 0.33 mmol) in MeOH (2 mL) was added HCl/dioxane (4 M, 1 mL, 4 mmol) at 0° C. After stirring at room temperature for 2 hrs, the solution was concentrated to give the crude of rac-6-(aminomethyl)-6,7-dihydro-5H-pyrazolo[5,1-b][1,3]oxazine-3-sulfonamide hydrochloride, which was directly used for next step without further purification.

Step 2

To a solution of rac-6-(aminomethyl)-6,7-dihydro-5H-pyrazolo[5,1-b][1,3]oxazine-3-sulfonamide hydrochloride (crude, 0.33 mmol) in MeOH (2 mL) was added HCHO (1.5 mL) and NaCNBH$_3$ (20.8 mg, 0.33 mmol). After stirring at room temperature for 3 hrs, the reaction was filtered and the filtrate was purified by reverse phase HPLC (MeCN/H$_2$O) to give rac-6-((dimethylamino)methyl)-6,7-dihydro-5H-pyrazolo[5,1-b][1,3]oxazine-3-sulfonamide (50 mg, yield: 59%) as a white solid. MS: m/z 261.1 (M+H$^+$).

Step 3 rac-6-((dimethylamino)methyl)-N-((1,2,3,5,6,7-hexahydro-s-indacen-4-yl)carbamoyl)-6,7-dihydro-5H-pyrazolo[5,1-b][1,3]oxazine-3-sulfonamide was synthesized as in Preparation D to yield the desired product (27 mg, yield: 21%) as a white solid.

$^1$H NMR (400 MHz, DMSO-d$_6$+CD$_3$OD): δ=7.37 (s, 1H), 7.32 (s, 1H), 6.75 (s, 1H), 4.37 (dd, J=6.8, 2.8 Hz, 1H), 4.10-4.00 (m, 2H), 3.80-3.75 (m, 1H), 2.74 (t, J=7.2 Hz, 4H), 2.64 (t, J=7.2 Hz, 4H), 2.47-2.43 (m, 1H), 2.23 (d, J=7.2 Hz, 2H), 2.14 (s, 6H), 1.95-1.85 (m, 4H). MS: m/z 460.1 (M+H$^+$).

Example 36

Synthesis of rac-N-((1,2,3,5,6,7-Hexahydro-s-indacen-4-yl)carbamoyl)-6-(methoxymethyl)-6,7-dihydro-5H-pyrazolo[5,1-b][1,3]oxazine-3-sulfonamide is shown below.

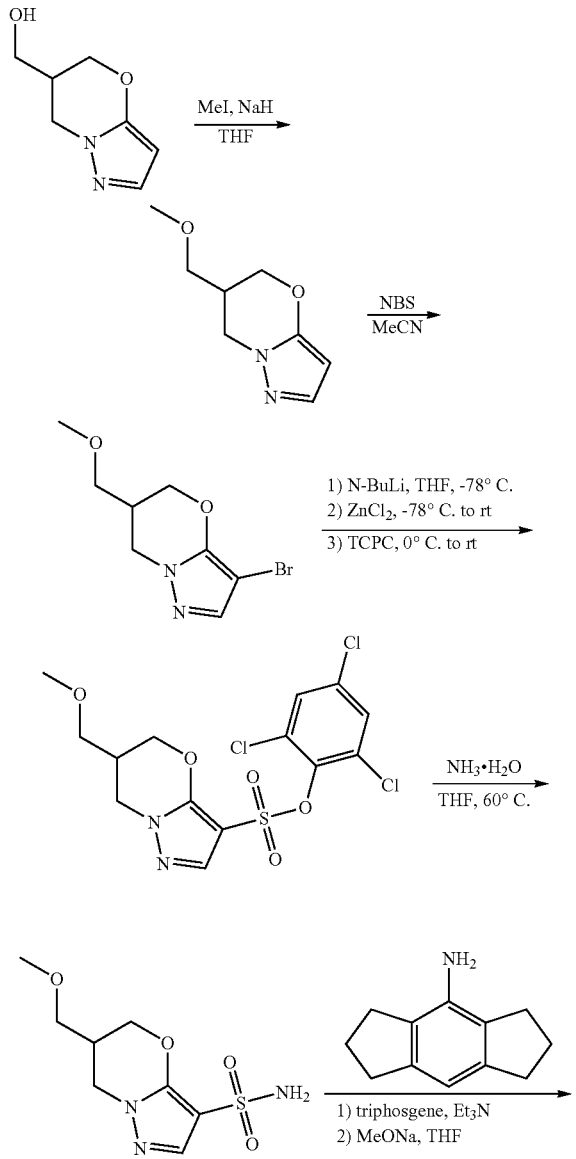

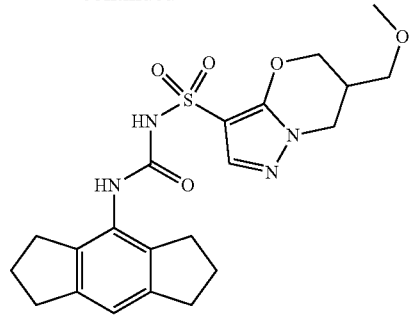

Step 1

To a solution of rac-(6,7-dihydro-5H-pyrazolo[5,1-b][1,3]oxazin-6-yl)-methanol (0.6 g, 3.9 mmol) in THF (10 mL) was added NaH (187 mg, 4.7 mmol) followed by MeI (667 mg, 4.7 mmol) at 0° C. After being stirred at overnight, the reaction was quenched with the addition of EA (20 mL) and water (20 mL). The organic layer was separated. The aqueous layer was extracted with EA (20 mL). The organic layers were combined, washed with brine (30 mL), dried over Na$_2$SO$_4$ and concentrated in vacuo. The residue was purified by silica gel column (PE/EA=1/1) to give rac-6-methoxymethyl-6,7-dihydro-5H-pyrazolo[5,1-b][1,3]oxazine (270 mg, yield: 41%) as a yellow solid. MS: m/z 169.3 (M+H$^+$).

Step 2

NBS (256 mg, 1.44 mmol) was added portionwise to a solution of 6-methoxymethyl-6,7-dihydro-5H-pyrazolo[5,1-b][1,3]oxazine (230 mg, 1.37 mmol) in MeCN (5 mL) at 0° C. and the reaction was stirred for 2 hrs at room temperature. The mixture was filtered and the filtrate was purified by reverse phase HPLC (5%-95% MeCN in H$_2$O) to give 3-bromo-6-(methoxymethyl)-6,7-dihydro-5H-pyrazolo[5,1-b][1,3]oxazine (220 mg, yield: 65%) as a yellow oil. MS: m/z 247.3 (M+H$^+$).

Step 3

2,4,6-trichlorophenyl 6-(methoxymethyl)-6,7-dihydro-5H-pyrazolo[5,1-b][1,3]oxazine-3-sulfonate was synthesized using Preparation B to yield the product as a yellow oil which was used for next step directly without any purification.

Step 4

6-(methoxymethyl)-6,7-dihydro-5H-pyrazolo[5,1-b][1,3]oxazine-3-sulfonamide was synthesized as in Preparation C to yield the desired product (25 mg, yield: 13% over 2 steps) as a light yellow solid.

Step 5

N-((1,2,3,5,6,7-hexahydro-s-indacen-4-yl)carbamoyl)-6-(methoxymethyl)-6,7-dihydro-5H-pyrazolo[5,1-b][1,3]oxazine-3-sulfonamide was synthesized as in Preparation D to yield the desired product (9 mg, yield: 20%) as a white solid.

$^1$H NMR (400 MHz, DMSO-d$_6$): δ=10.46 (s, 1H), 7.90 (s, 1H), 7.63 (s, 1H), 6.93 (s, 1H), 4.51 (dd, J=10.8, 2.8 Hz, 1H), 4.29 (dd, J=11.2, 7.2 Hz, 1H), 4.51 (dd, J=12.4, 5.2 Hz, 1H), 4.51 (dd, J=12.4, 7.2 Hz, 1H), 3.43 (d, J=3.6 Hz, 2H), 3.25 (s, 3H), 2.79 (t, J=7.2 Hz, 4H), 2.61-2.58 (m, 5H), 1.99-1.92 (m, 4H). MS: m/z 446.8 (M+H$^+$).

Example 37

Synthesis of rac-6-Ethoxy-N-((1,2,3,5,6,7-hexahydro-s-indacen-4-yl)carbamoyl)-6,7-dihydro-5H-pyrazolo[5,1-b][1,3]oxazine-3-sulfonamide is shown below.

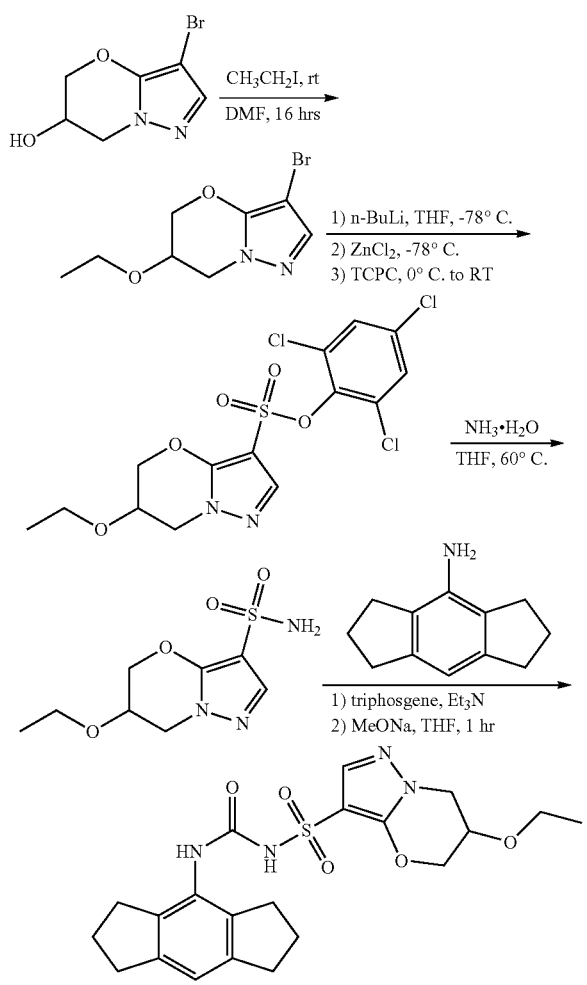

Step 1

To a solution of rac-3-bromo-6,7-dihydro-5H-pyrazolo[5,1-b][1,3]oxazin-6-ol (700 mg, 3.2 mmol) in DMF (10 mL) was added NaH (60% in mineral oil, 192 mg, 4.8 mmol). The reaction was stirred at room temperature for 1 hr under $N_2$. Then iodoethane (549 mg, 3.5 mmol) was added and the mixture was stirred at room temperature for 2 hrs. The reaction mixture was poured into water (60 mL) and extracted with EA (50 mL). The organic layer was washed with water (50 mL) and brine (50 mL), dried over $Na_2SO_4$ and concentrated. The residue was purified by reverse phase HPLC (MeCN/$H_2O$) to give rac-3-bromo-6-ethoxy-6,7-dihydro-5H-pyrazolo[5,1-b][1,3]oxazine (640 mg, yield: 81%) as a white solid.

MS: m/z 248.9 (M+H$^+$).

Step 2

2,4,6-trichlorophenyl 6-ethoxy-6,7-dihydro-5H-pyrazolo[5,1-b][1,3]oxazine-3-sulfonate was synthesized using Preparation B to yield the product as a yellow oil which was used for next step directly without any purification.

Step 3

A solution of rac-2,4,6-trichlorophenyl 6-ethoxy-6,7-dihydro-5H-pyrazolo[5,1-b][1,3]oxazine-3-sulfonate (crude) and $NH_3 \cdot H_2O$ (8.4 mL) in THF (8.4 mL) was stirred at 60° C. for 16 hrs. The mixture was concentrated in vacuo. The residue was purified by reverse phase HPLC (MeCN/$H_2O$) to give rac-6-ethoxy-6,7-dihydro-5H-pyrazolo[5,1-b][1,3]oxazine-3-sulfonamide (222.0 mg, yield: 35%) as a white solid.

MS: m/z 247.9 (M+H$^+$).

Step 4—Preparation F

To a solution of rac-6-ethoxy-6,7-dihydro-5H-pyrazolo[5,1-b][1,3]oxazine-3-sulfonamide (116 mg, 0.47 mmol) in THF (8.0 mL) was added MeONa (28 mg, 0.52 mmol) and the mixture was stirred at room temperature for 20 mins to give a sodium salt suspension.

In another flask, to a solution of 1,2,3,5,6,7-hexahydro-s-indacen-4-ylamine (81 mg, 0.47 mmol) and TEA (142 mg, 1.4 mmol) in THF (10 mL) was added triphosgene (56.0 mg, 0.19 mmol) in one portion and the mixture was stirred at room temperature under $N_2$ for 20 mins. The reaction mixture was then filtered. The filtrate was added to the sodium salt suspension above and the mixture was stirred at room temperature for 20 min. After that, the reaction solution was partitioned between EA (60 mL) and water (60 mL). The aqueous phase was acidified to pH=5 with conc.HCl and extracted with EA (60 mL). The organic layer was washed with water (50 mL) and brined (50 mL), dried over $Na_2SO_4$ and concentrated until white solid appeared. The solid formed was collected by filtration and dried to give rac-6-ethoxy-N-((1,2,3,5,6,7-hexahydro-s-indacen-4-yl)carbamoyl)-6,7-dihydro-5H-pyrazolo[5,1-b][1,3]oxazine-3-sulfonamide (68 mg, yield: 32%) as a white solid.

$^1$H NMR (400 MHz, DMSO-$d_6$): δ=10.48 (s, 1H), 7.91 (s, 1H), 7.63 (s, 1H), 6.93 (s, 1H), 4.58 (d, J=11.6 Hz, 1H), 4.36 (d, J=11.6 Hz, 1H), 4.27-4.24 (m, 1H), 4.18-4.15 (m, 2H), 3.61-3.56 (m, 2H), 2.79 (t, J=7.2 Hz, 4H), 2.60 (t, J=7.2 Hz, 4H), 1.99-1.91 (m, 4H), 1.09 (t, J=7.2 Hz, 3H). MS: m/z 447.0 (M+H$^+$).

Example 38

Synthesis of (R)-6-Ethoxy-N-((1,2,3,5,6,7-hexahydro-s-indacen-4-yl)carbamoyl)-6,7-dihydro-5H-pyrazolo[5,1-b][1,3]oxazine-3-sulfonamide and (S)-6-ethoxy-N-((1,2,3,5,6,7-hexahydro-s-indacen-4-yl)carbamoyl)-6,7-dihydro-5H-pyrazolo[5,1-b][1,3]oxazine-3-sulfonamide is shown below.

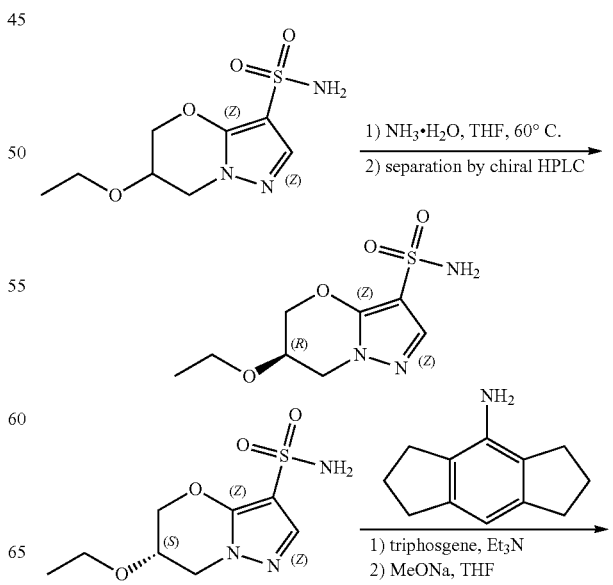

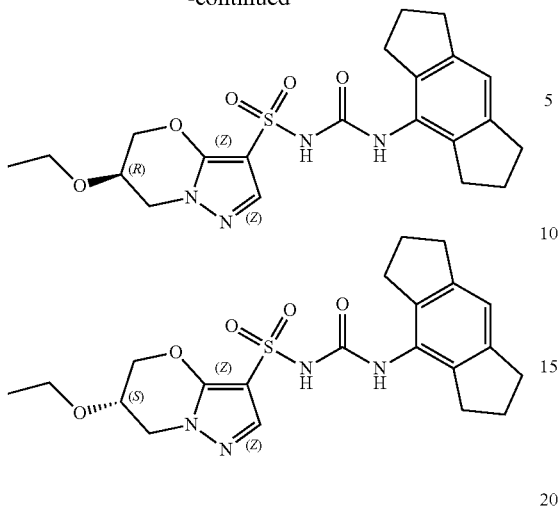

Step 1 rac-6-Ethoxy-N-((1,2,3,5,6,7-hexahydro-s-indacen-4-yl)carbamoyl)-6,7-dihydro-5H-pyrazolo[5,1-b][1,3]oxazine-3-sulfonamide (222 mg) was resolved by chiral prep-HPLC to give (R)-6-ethoxy-6,7-dihydro-5H-pyrazolo[5,1-b][1,3]oxazine-3-sulfonamide (20 mg) as a white solid and (S)-6-ethoxy-6,7-dihydro-5H-pyrazolo[5,1-b][1,3]oxazine-3-sulfonamide (20 mg) as a white solid.

Step 2

(R)-6-ethoxy-N-((1,2,3,5,6,7-hexahydro-s-indacen-4-yl)carbamoyl)-6,7-dihydro-5H-pyrazolo[5,1-b][1,3]oxazine-3-sulfonamide was synthesized as described in Preparation F to deliver the desired product (5.0 mg, yield: 14%) as a white solid.

$^1$H NMR (400 MHz, DMSO-$d_6$): δ=10.47 (s, 1H), 7.90 (s, 1H), 7.63 (s, 1H), 6.93 (s, 1H), 4.58 (d, J=10.0 Hz, 1H), 4.36 (d, 7=11.2 Hz, 1H), 4.27-4.24 (m, 1H), 4.18-4.15 (m, 2H), 3.59 (q, J=7.2 Hz, 2H), 2.79 (t, J=7.6 Hz, 4H), 2.60 (t, J=7.2 Hz, 4H), 1.99-1.91 (m, 4H), 1.09 (t, 7=6.8 Hz, 3H). MS: m/z 447.1 (M+H$^+$).

(S)-6-ethoxy-N-((1,2,3,5,6,7-hexahydro-s-indacen-4-yl)carbamoyl)-6,7-dihydro-5H-pyrazolo[5,1-b][1,3]oxazine-3-sulfonamide was prepared using the same procedure.

$^1$H NMR (400 MHz, DMSO-$d_6$): δ=10.47 (s, 1H), 7.94 (s, 1H), 7.62 (s, 1H), 6.93 (s, 1H), 4.59 (d, J=11.6 Hz, 1H), 4.37 (d, J=11.6 Hz, 1H), 4.27-4.23 (m, 1H), 4.17-4.15 (m, 2H), 3.53 (q, J=7.2 Hz, 2H), 2.78 (t, J=7.2 Hz, 4H), 2.60 (t, J=7.2 Hz, 4H), 1.98-1.91 (m, 4H), 1.08 (t, J=7.2 Hz, 3H). MS: m/z 447.1 (M+H$^+$).

Example 39

Synthesis of N-((1,2,3,5,6,7-Hexahydro-s-indacen-4-yl)carbamoyl)-6-isopropoxy-6,7-dihydro-5H-pyrazolo[5,1-b][1,3]oxazine-3-sulfonamide is shown below.

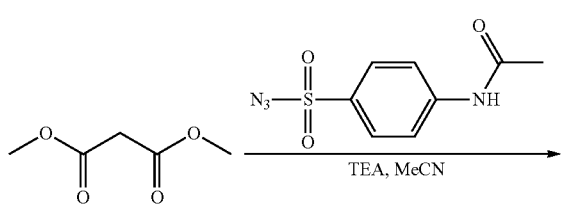

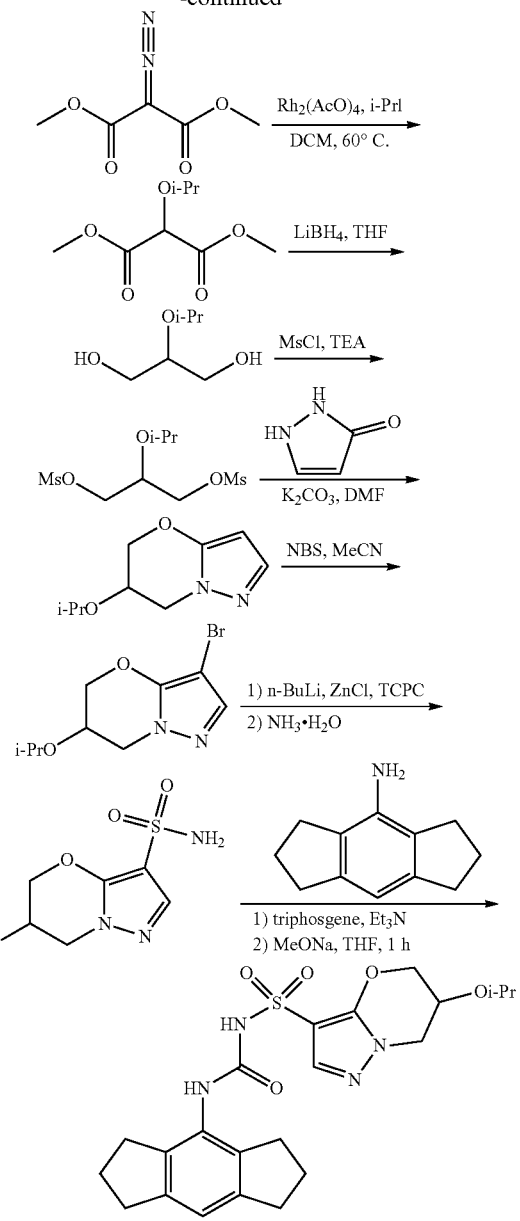

Step 1

To a solution of dimethyl malonate (5.0 g, 38.0 mmol) and TEA (7.7 g, 76.0 mmol) in MeCN (80 mL) was added 4-acetamidobenzenesulfonyl azide (9.1 g, 38.0 mmol) and the reaction was stirred at room temperature for 16 hrs. The reaction was filtered and the filtrate was partitioned between water (80 mL) and EA (80 mL). The organic layer was washed with brine (80 mL), dried over Na$_2$SO$_4$ and concentrated. The residue was purified by silica gel column (PE/EA=10/1) to give dimethyl 2-diazomalonate (3.9 g, yield: 53%) as a yellow oil.

Step 2

To a solution of dimethyl 2-diazomalonate (3.4 g, 21.5 mmol) and Rh$_2$(Ac)$_4$ (36 mg, 0.2 mmol) in DCM (10 mL) was added i-PrOH (132.0 g, 0.2 mol) and the reaction was stirred at 70° C. for 4 hrs. The reaction was concentrated to dryness. The residue was purified by silica gel column (PE/EA=10/1) to give dimethyl 2-isopropoxymalonate (3.7 g, yield: 90%) as a colorless oil.

¹H NMR (300 MHz, CDCl₃): δ=4.60 (s, 1H), 3.81-3.74 (m, 7H), 1.26 (d, J=6.0 Hz, 6H).

Step 3

To a solution of dimethyl 2-isopropoxymalonate (3.7 g, 19.4 mmol) in dry THF (30 mL) was added LiBH₄ (2 M in THF, 19.4 mL, 38.7 mol) at 0° C. and the reaction was stirred at room temperature for 2 hrs. The reaction was quenched by H₂O (20 mL) and the mixture was dried over MgSO₄. The reaction was filtered and the filtrate was concentrated to dryness to give 2-isopropoxypropane-1,3-diol (2.5 g, yield: 96%) as a colorless oil.

¹H NMR (300 MHz, CDCl₃): δ=3.72-3.50 (m, 6H), 1.26 (t, J=5.4 Hz, 2H), 1.22 (d, J=6.0 Hz, 6H).

Step 4

To a solution of 2-isopropoxypropane-1,3-diol (2.5 g, 18.7 mmol) and TEA (5.7 g, 56.0 mmol) in dry THF (30 mL) was added MsCl (4.7 g, 41.0 mmol) at 0° C. After stirring at room temperature for 2 hrs, the reaction was filtered. The filtrate was concentrated to dryness to give crude 2-isopropoxypropane-1,3-diyl dimethanesulfonate as a white solid which was used for next step directly without any purification.

Step 5

A mixture of 2-isopropoxypropane-1,3-diyl dimethanesulfonate (crude, ~18.7 mmol), 1,2-dihydro-pyrazol-3-one (1.6 g, 18.7 mmol) and K₂CO₃ (7.7 g, 56.0 mmol) in DMF (40 mL) was heated to 100° C. for 16 hrs. The reaction was cooled and partitioned between EA (150 mL) and water (200 mL) and the layers were separated. The organic layer was washed with water (80 mL) and brine (50 mL), dried over Na₂SO₄ and concentrated. The residue was purified by silica gel column (PE/EA=1/2) to give 6-isopropoxy-6,7-dihydro-5H-pyrazolo[5,1-b][1,3]oxazine (2.1 g, yield: 88%) as a white solid.

¹H NMR (300 MHz, CDCl₃): δ=7.33 (s, 1H), 5.49 (s, 1H), 4.31-3.84 (m, 5H), 3.84-3.80 (m, 1H), 1.22-118 (m, 6H). MS: m/z 183.3 (M+H⁺).

Step 6

To a solution of 6-isopropoxy-6,7-dihydro-5H-pyrazolo[5,1-b][1,3]oxazine (1.0 g, 7.8 mmol) in MeCN, was added NBS (1.5 g, 8.6 mmol) at 0° C. under N₂ in two portions. The reaction was then stirred at room temperature for 2 hrs. The reaction was partitioned between EA (40 mL) and water (40 mL). The organic layer was washed with water (40 mL) and brine (40 mL), dried over Na₂SO₄ and concentrated. The residue was purified by silica gel column (PE/EA=2/1) to give 3-bromo-6-isopropoxy-6,7-dihydro-5H-pyrazolo[5,1-b][1,3]oxazine (1.2 g, yield: 75%) as a yellow solid. MS: m/z 261.2 (M+H⁺).

Step 7

2,4,6-trichlorophenyl 6-isopropoxy-6,7-dihydro-5H-pyrazolo[5,1-b][1,3]oxazine-3-sulfonate was synthesized using Preparation B to yield the product as a yellow gel which was used for next step directly without any purification.

6-isopropoxy-6,7-dihydro-5H-pyrazolo[5,1-b][1,3]oxazine-3-sulfonamide was synthesized as in Preparation C to yield the desired product (110 mg, yield: 22% over 2 steps) as a yellow solid. MS: m/z 262.3 (M+H⁺).

Step 8

N-((1,2,3,5,6,7-hexahydro-s-indacen-4-yl)carbamoyl)-6-isopropoxy-6,7-dihydro-5H-pyrazolo[5,1-b][1,3]oxazine-3-sulfonamide was synthesized using Preparation A to deliver the desired product (18 mg, yield: 10%) as a white solid.

¹H NMR (400 MHz, DMSO-d₆): δ=10.47 (brs, 1H), 7.90 (s, 1H), 7.62 (s, 1H), 6.93 (s, 1H), 4.49-4.46 (m, 1H), 4.37 (d, J=12.0 Hz, 1H), 4.28-4.24 (m, 2H), 4.09-4.06 (m, 1H), 3.87-3.81 (m, 1H), 2.77 (t, J=8.0 Hz, 4H), 2.61 (overlap, 4H), 1.97-1.91 (m, 4H), 1.09-1.05 (m, 6H). MS: m/z 461.1 (M+H⁺).

Example 40

Synthesis of sodium rac-((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide is shown below.

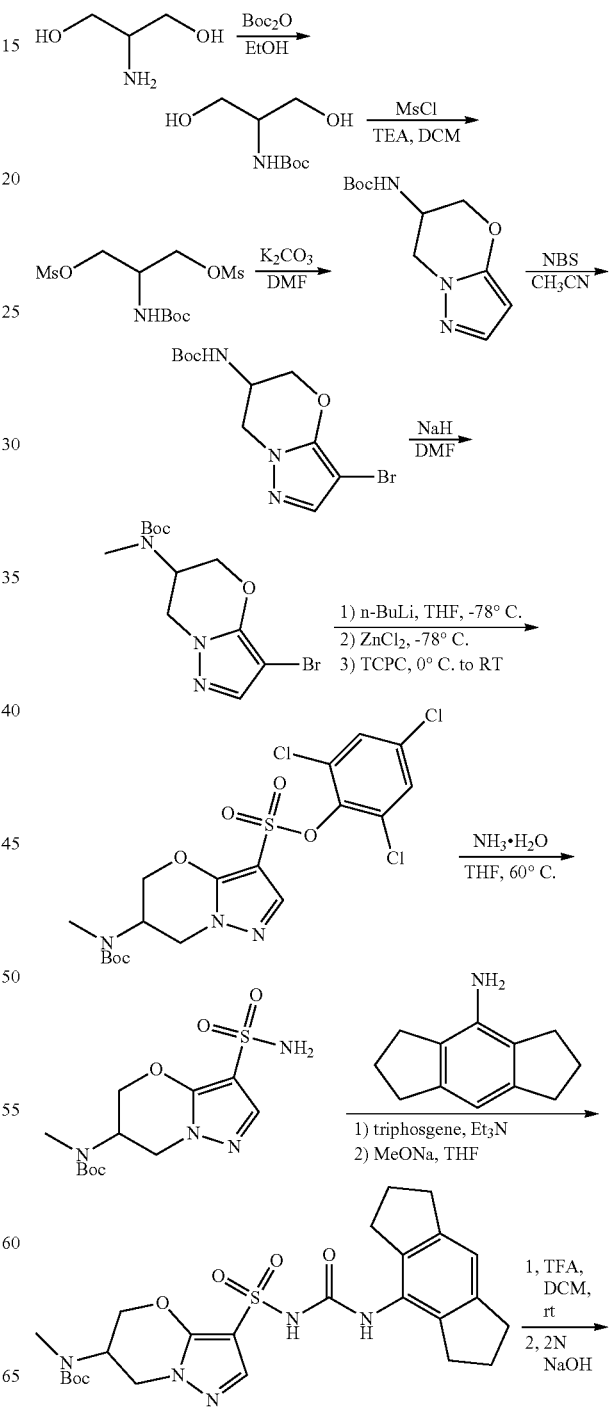

-continued

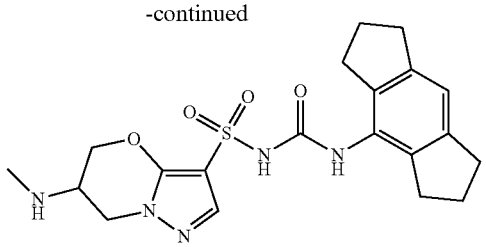

Step 1

To a solution of 2-aminopropane-1,3-diol (10.0 g, 0.1 mol) in EtOH (100 mL) was added di-tert-butyl dicarbonate (24.0 g, 0.1 mol). The reaction was stirred at room temperature for 16 hrs. The reaction solution was concentrated in vacuo to dryness to give tert-butyl (1,3-dihydroxypropan-2-yl)carbamate (21.0 g, yield: 100%) as a white solid.

Step 2

To a solution of tert-butyl (1,3-dihydroxypropan-2-yl)carbamate (21.0 g, 0.1 mol) and TEA (23.0 g, 0.2 mol) in dry $CH_2Cl_2$ (200 mL) was added MsCl (26.0 g, 0.2 mol) at 0° C. After the stirring at room temperature for 2 hrs, the reaction was filtered. The filtrate was concentrated to dryness to give crude 2-((tert-butoxycarbonyl)amino)propane-1,3-diyl dimethanesulfonate (37.0 g, yield: 97%) as a white solid which was used for next step directly without any purification.

Step 3

2-((tert-butoxycarbonyl)amino)propane-1,3-diyl dimethanesulfonate (37.3 g, 0.11 mol), 1H-pyrazol-3(2H)-one (9.0 g, 0.11 mol) and $K_2CO_3$ (30.0 g, 0.22 mol) in DMF (300 mL) were heated at 120° C. for 16 hrs. After concentration, the residue was partitioned between EA (300 mL) and water (500 mL). The aqueous layer was extracted with EA (300 mL). The combined organic layer was washed with brine (100 mL), dried over $Na_2SO_4$, filtered and concentrated in vacuo to dryness to give rac-tert-butyl (6,7-dihydro-5H-pyrazolo[5,1-b][1,3]oxazin-6-yl)carbamate (8.8 g, yield: 34%) as a yellow solid. MS: m/z 240.0 (M+H$^+$).

Step 4

NBS (6.5 g, 37.0 mmol) was added portionwise to a solution of rac-tert-butyl (6,7-dihydro-5H-pyrazolo[5,1-b][1,3]oxazin-6-yl)carbamate (8.8 g, 37.0 mmol) in MeCN (100 mL) at 0° C. and the reaction was stirred for 2 hrs at room temperature. The reaction mixture was concentrated. The residue was purified by silica gel column (PE/EA=5/1) to give rac-tert-butyl (3-bromo-6,7-dihydro-5H-pyrazolo[5,1-b][1,3]oxazin-6-yl)carbamate (2.5 g, yield: 21%) as a yellow solid. MS: m/z 319.9 (M+H$^+$).

Step 5

To a solution of rac-tert-butyl (3-bromo-6,7-dihydro-5H-pyrazolo[5,1-b][1,3]oxazin-6-yl)carbamate (900 mg, 2.8 mmol) in DMF (10 mL) was added NaH (60% in mineral oil, 226 mg, 5.7 mmol). The reaction was stirred at room temperature for 1 hr under $N_2$. Then iodomethane (2.0 g, 14.2 mmol) was added and the mixture was stirred at room temperature for 2 hrs. The reaction mixture was poured into water (60 mL) and extracted with EA (50 mL). The organic layer was washed with water (50 mL) and brine (50 mL), dried over $Na_2SO_4$ and concentrated. The residue was purified by reverse phase HPLC (MeCN/$H_2O$) to give rac-tert-butyl (3-bromo-6,7-dihydro-5H-pyrazolo[5,1-b][1,3]oxazin-6-yl)(methyl)carbamate (550 mg, yield: 59%) as a yellow solid.

$^1$H NMR (300 MHz, CDCl$_3$): δ=7.36 (s, 1H), 4.6 (br, 1H), 4.38-4.29 (m, 4H), 2.82 (d, J=3.6 Hz, 3H), 1.50 (s, 9H). MS: m/z 333.9 (M+H$^+$).

Step 6 rac-2,4,6-trichlorophenyl 6-((tert-butoxycarbonyl)(methyl)amino)-6,7-dihydro-5H-pyrazolo[5,1-b][1,3]oxazine-3-sulfonate was synthesized using Preparation B to yield the product as a yellow oil which was used for next step directly without any purification.

Step 7

A solution of rac-2,4,6-trichlorophenyl 6-((tert-butoxycarbonyl)(methyl)amino)-6,7-dihydro-5H-pyrazolo[5,1-b][1,3]oxazine-3-sulfonate (crude) and NH$_3$·H$_2$O (3.0 mL) in THF (5.0 mL) was stirred at 60° C. for 16 hrs. The mixture was concentrated in vacuo. The residue was purified by silica gel column (CH$_2$Cl$_2$/MeOH=25/1) to give tert-butyl methyl(3-sulfamoyl-6,7-dihydro-5H-pyrazolo[5,1-b][1,3]oxazin-6-yl)carbamate (26.0 mg, yield: 8%, 2 steps) as a colorless oil.

$^1$H NMR (400 MHz, CDCl$_3$): δ=7.64 (s, 1H), 5.14 (br, 2H), 4.68 (br, 1H), 4.53-4.44 (m, 2H), 4.38-4.26 (m, 2H), 2.84 (s, 3H), 1.48 (s, 9H). MS: m/z 276.9 (M−56+H$^+$).

Step 8 tert-Butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate was synthesized as in Preparation D to yield the desired product (40 mg, yield: 95%) as a white solid. MS: m/z 476.0 (M−55$^-$).

Step 9

To a solution of tert-butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate (40 mg, 0.08 mmol) in CH$_2$Cl$_2$ (2 mL) was added TFA (0.6 mL) and the mixture was stirred at room temperature for 30 mins. Then the mixture was concentrated in vacuo to remove off the solvent. The residue was treated with 2 M NaOH solution to pH>13. The resulting solution was purified by reverse phase HPLC (MeCN/H$_2$O) to give rac-sodium ((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide (25.0 mg, 78%) as a white solid.

$^1$H NMR (400 MHz, DMSO-d$_6$): δ=7.33 (s, 1H), 7.30 (s, 1H), 6.75 (s, 1H), 4.25-4.10 (m, 3H), 3.83-3.79 (m, 1H), 3.07 (m, 1H), 2.77-2.73 (m, 4H), 2.67-2.63 (m, 4H), 2.33 (s, 3H), 1.92-1.88 (m, 4H). MS: m/z 432.1 (M+H$^+$).

Example 41

Synthesis of sodium (R)-((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide and sodium (S)-((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide is shown below.

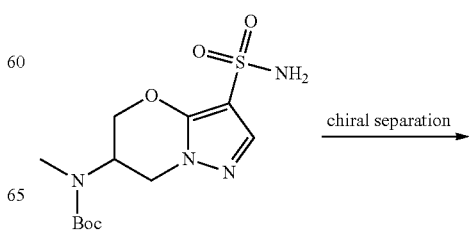

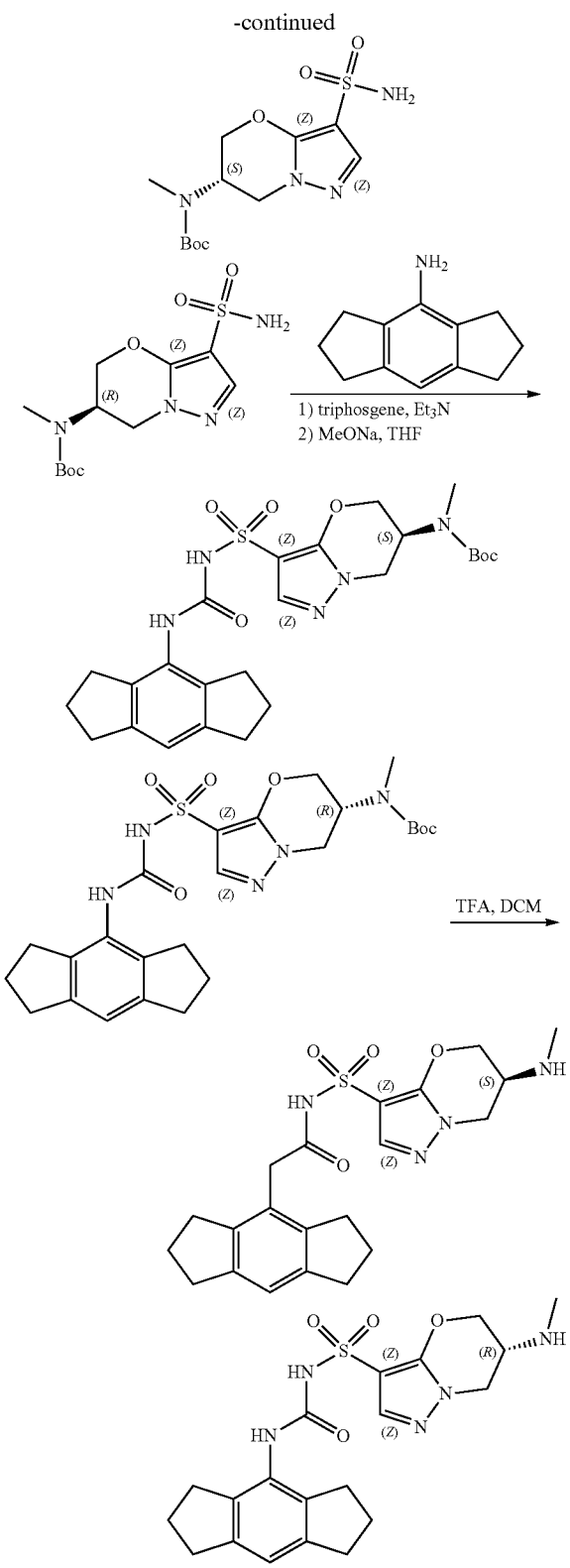

Step 1 rac-N-((1,2,3,5,6,7-hexahydro-s-indacen-4-yl)carbamoyl)-6-(methylamino)-6,7-dihydro-5H-pyrazolo[5,1-b][1,3]oxazine-3-sulfonamide (400 mg, 1.2 mmol) was resolved by chiral prep-HPLC to give (R)—N-((1,2,3,5,6,7-hexahydro-s-indacen-4-yl)carbamoyl)-6-(methylamino)-6,7-dihydro-5H-pyrazolo[5,1-b][1,3]oxazine-3-sulfonamide (240 mg, yield: 60%) as a white solid and (S)—N-((1,2,3,5,6,7-hexahydro-s-indacen-4-yl)carbamoyl)-6-(methylamino)-6,7-dihydro-5H-pyrazolo[5,1-b][1,3]oxazine-3-sulfonamide (150 mg, yield: 37%) as a white solid.

Step 2:

(R)-tert-butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate was synthesized as in Preparation D to yield the desired product (200 mg, yield: 52%) as a white solid.

(S)-tert-butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate was prepared using the same procedure.

Step 3

To a solution of (R)-tert-butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate (250 mg, 0.75 mmol) in $CH_2Cl_2$ (5 mL) was added TFA (2 mL) and the mixture was stirred at room temperature for 30 mins. Then the mixture was concentrated in vacuo to remove the solvent. The residue was treated with 2 M NaOH solution to pH>13. The resulting solution was purified by reverse phase HPLC ($MeCN/H_2O$) to give sodium (R)-((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide (130 mg, 30%) as a white solid.

$^1$H NMR (400 MHz, DMSO-d6): δ=7.50 (s, 1H), 7.38 (s, 1H), 6.8 (s, 1H), 4.28 (dd, J=10.8 Hz, 2.4 Hz, 1H), 4.20-4.10 (m, 2H), 3.85 (dd, J=11.6 Hz, 4.8 Hz, 1H), 3.14-3.06 (m, 1H), 2.76 (t, J=7.2 Hz, 4H), 2.64 (t, J=7.2 Hz, 4H), 2.33 (s, 3H), 1.97-1.86 (m, 4H). MS: m/z 432.1 (M+H$^+$).

Sodium (S)-((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide was prepared using the same procedure.

$^1$H NMR (400 MHz, DMSO-d6): δ=7.35 (s, 1H), 7.30 (s, 1H), 6.75 (s, 1H), 4.27-4.21 (m, 1H), 4.17-4.12 (m, 1H), 4.08-4.05 (m, 1H), 3.84-3.77 (m, 1H), 3.11-3.03 (m, 1H), 2.76 (t, J=8.0 Hz, 4H), 2.65 (t, J=7.6 Hz, 4H), 2.33-2.27 (m, 3H), 1.97-1.83 (m, 4H). MS: m/z 432.1 (M+H$^+$).

Example 42

Synthesis of (R)-((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide is shown below.

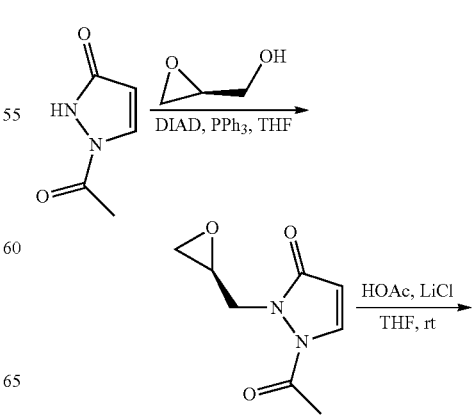

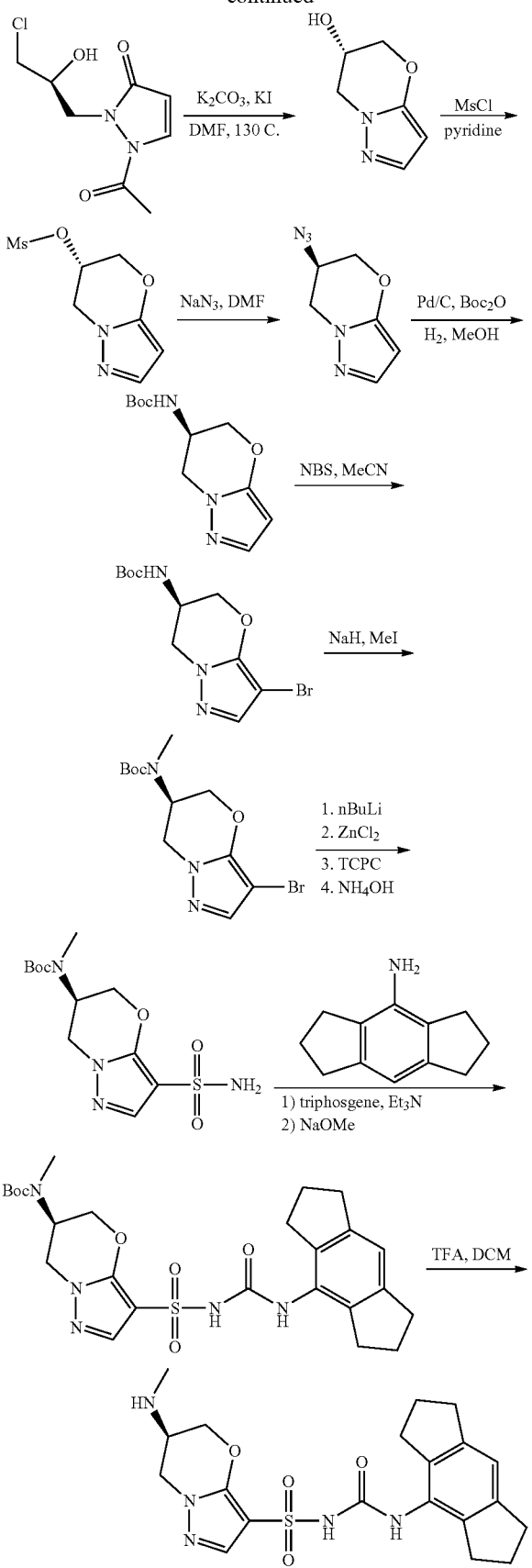

Step 1

A mixture of 1-acetyl-1,2-dihydro-pyrazol-3-one (10.0 g, 0.79 mmol), (S)-oxiran-2-ylmethanol (7.0 g, 95 mmol) and PPh$_3$ (31.0 g, 118.5 mmol) in THF (100 mL) was cooled to 0° C. under N$_2$. To the mixture was added DIAD (23.3 mL, 118.5 mmol) in THF (25 mL) slowly. The reaction was stirred for additional 1 hour at 0° C. The reaction was then stirred at room temperature overnight. The reaction mixture was concentrated in vacuo and the residue was purified by silica gel column (PE/EA=10/1) to give (S)-1-acetyl-2-(oxiran-2-ylmethyl)-1?7-pyrazol-3(2H)-one (10.1 g, yield: 70%) as a white solid.

$^1$H NMR (400 MHz, CDCl$_3$): δ=8.07 (d, J=2.8 Hz, 1H), 6.00 (d, J=2.8 Hz, 1H), 4.56-4.51 (m, 1H), 4.21-4.15 (m, 1H), 3.41-3.34 (m, 1H), 2.93-2.89 (m, 1H), 2.77-2.74 (m, 1H), 2.58 (s, 3H).

Step 2

To a solution of (S)-1-acetyl-2-(oxiran-2-ylmethyl)-1H-pyrazol-3(2H)-one (55.0 g, 300 mmol) in AcOH (52 mL, 900 mmol) and THF (250 mL), was added LiCl.H$_2$O (29.0 g, 480 mmol) at 0° C. in batches. The reaction was then stirred at room temperature overnight. After removal of AcOH and THF in vacuo, the residue was partitioned between EA (200 mL) and water (200 mL). The aqueous layer was extracted with EA (50 mL×4). The combined organic layer was washed with saturated NaHCO$_3$ solution and brine (100 mL), dried over Na$_2$SO$_4$ and concentrated in vacuo to give crude (S)-1-acetyl-2-(3-chloro-2-hydroxypropyl)-1H-pyrazol-3(2H)-one (59.0 g, 90%) as a colorless oil which was used for next step directly without any purification.

$^1$H NMR (400 MHz, CDCl$_3$): δ=8.07 (d, J=3.2 Hz, 1H), 6.00 (d, J=3.2 Hz, 1H), 4.41 (d, J=4.8 Hz, 2H), 4.28-4.20 (m, 1H), 3.78-3.64 (m, 2H), 2.58 (s, 3H).

Step 3

A mixture of (S)-1-acetyl-2-(3-chloro-2-hydroxypropyl)-1H-pyrazol-3(2H)-one (65.4 g, 0.3 mol), K$_2$CO$_3$ (82.8 g, 0.6 mol) and KI (9.96 g, 60 mmol) in DMF (500 mL) was stirred at 130° C. overnight. The solvent was removed under reduced pressure. The residue was purified by silica gel column (EA) to give (S)-6,7-dihydro-5/7-pyrazolo[5,1-b][1,3]oxazin-6-ol (27.6 g, yield: 66%) as a white solid.

$^1$H NMR (400 MHz, DMSO-d$_6$): δ=7.22 (d, J=2.0 Hz, 1H), 5.44 (d, J=2.0 Hz, 1H), 4.28-4.09 (m, 4H), 3.94-3.87 (m, 1H).

Step 4

To a solution of (S)-6,7-dihydro-5H-pyrazolo[5,1-b][1,3]oxazin-6-ol (28.0 g, 0.2 mol) in pyridine (200 mL) was added methanesulfonyl chloride (23.0 g, 0.2 mol). The reaction was stirred at room temperature for 30 mins. The reaction solution was concentrated in vacuo to dryness and the residue was partitioned between EA (300 mL) and water (500 mL). The aqueous layer was extracted with EA (300 mL). The combined organic layer was washed with brine (100 mL), dried over Na$_2$SO$_4$, filtered and concentrated in vacuo to dryness to give (S)-6,7-dihydro-5H-pyrazolo[5,1-b][1,3]oxazin-6-yl methanesulfonate (44.0 g, yield: 99%) as a white solid which was used for next step directly without any purification.

Step 5

A mixture of (S)-6,7-dihydro-5H-pyrazolo[5,1-b][1,3]oxazin-6-yl methanesulfonate (44.0 g, 0.2 mol) and NaN$_3$ (26.0 g, 0.4 mol) in dry DMF (300 mL) was stirred at 120° C. for 2 hrs. Then the mixture was used for next step directly without any purification.

Step 6

A solution of (R)-6-azido-6,7-dihydro-5H-pyrazolo[5,1-b][1,3]oxazine (crude solution in DMF), Boc$_2$O (44 g, 0.2 mol) and Pd/C (3.0 g) in MeOH (300 mL) was stirred at room temperature under a hydrogen atmosphere (50 Psi) for 16 hrs. The reaction mixture was filtered and concentrated to dryness in vacuo. The residue was purified by silica gel column (PE/EA=1/1) to give (R)-tert-butyl (6,7-dihydro-5H-pyrazolo[5,1-b][1,3]oxazin-6-yl)carbamate (30 g, 63%) as a white solid.

Step 7

NBS (10.7 g, 60.0 mmol) was added portionwise to a solution of (R)-tert-butyl (6,7-dihydro-5H-pyrazolo[5,1-b][1,3]oxazin-6-yl)carbamate (14.0 g, 60.0 mmol) in MeCN (200 mL) at 0° C. and the reaction was stirred for 2 hrs at room temperature. After filtration, the filtrate was concentrated. The residue was purified by silica gel column (PE/EA=1/2) to give (R)-tert-butyl (3-bromo-6,7-dihydro-5H-pyrazolo[5,1-b][1,3]oxazin-6-yl)carbamate (20.5 g, crude) as a yellow solid. MS: m/z 320.0 (M+H$^+$).

Step 8

To a solution of (R)-tert-butyl (3-bromo-6,7-dihydro-5H-pyrazolo[5,1-b][1,3]oxazin-6-yl)carbamate (20.5 g, 64.4 mmol) in DMF (150 mL) was added NaH (60% in mineral oil, 5.2 g, 130.0 mmol). The reaction was stirred at room temperature for 1 hr under N$_2$. Then iodomethane (46.0 g, 320.0 mmol) was added and the mixture was stirred at room temperature for 2 hrs. The reaction mixture was poured into water (300 mL) and extracted with EA (300 mL). The organic layer was washed with water (150 mL), brine (50 mL), dried over Na$_2$SO$_4$ and concentrated. The residue was purified by silica gel column (PE/EA=3/1) to give (R)-tert-butyl (3-bromo-6,7-dihydro-5H-pyrazolo[5,1-b][1,3]oxazin-6-yl)(methyl)carbamate (18 g, yield: 90%) as a white solid. MS: m/z 334.0 (M+H$^+$).

Step 9

(R)-2,4,6-trichlorophenyl 6-((tert-butoxycarbonyl)(methyl)amino)-6,7-dihydro-5H-pyrazolo[5,1-b][1,3]oxazine-3-sulfonate was synthesized using Preparation B to yield the product as a yellow oil which was used for next step without purification.

Step 10

A solution of (R)-2,4,6-trichlorophenyl 6-((tert-butoxycarbonyl)(methyl)amino)-6,7-dihydro-5H-pyrazolo[5,1-b][1,3]oxazine-3-sulfonate (crude) and NH$_3$.H$_2$O (12.0 mL) in THF (50.0 mL) was stirred at 60° C. for 16 hrs. The mixture was concentrated in vacuo. The residue was purified by silica gel column (DCM/MeOH=25/1) to give (R)-tert-butyl methyl(3-sulfamoyl-6,7-dihydro-5H-pyrazolo[5,1-b][1,3]oxazin-6-yl)carbamate (1.8 g, yield: 25%, 2 steps) as a yellow solid. MS: m/z 333.1 (M+H$^+$).

Step 11

(R)-tert-butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate was synthesized as in Preparation D to yield the desired product (230 mg, yield: 96%) as a yellow solid.

Step 12

To a solution of (R)-tert-butyl (3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate (230 mg, 0.43 mmol) in CH$_2$Cl$_2$ (2 mL) was added TFA (0.6 mL) and the mixture was stirred at room temperature for 30 mins. Then the mixture was concentrated in vacuo to remove the solvent. The residue was treated with 2 M NaOH solution to pH>13. The resulting solution was purified by reverse phase HPLC (0%-50% MeCN in H$_2$O) to give sodium (s)-((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide (150.0 mg, 80%) as a white solid.

$^1$H NMR (400 MHz, DMSO-d$_6$): δ=7.41 (s, 1H), 7.33 (s, 1H), 6.76 (s, 1H), 4.26 (d, J=9.2 Hz, 1H), 4.19-4.07 (m, 2H), 3.84-3.80 (m, 1H), 3.09 (br, 1H), 2.75 (t, J=7.2 Hz, 4H), 2.66 (t, J=7.2 Hz, 4H), 2.34 (s, 3H), 1.94-1.87 (m, 4H). MS: m/z 432.1 (M+H$^+$).

Example 43

Synthesis of rac-6-(Ethylamino)-N-((1,2,3,5,6,7-hexahydro-s-indacen-4-yl)carbamoyl)-6,7-dihydro-5H-pyrazolo[5,1-b][1,3]oxazine-3-sulfonamide is shown below.

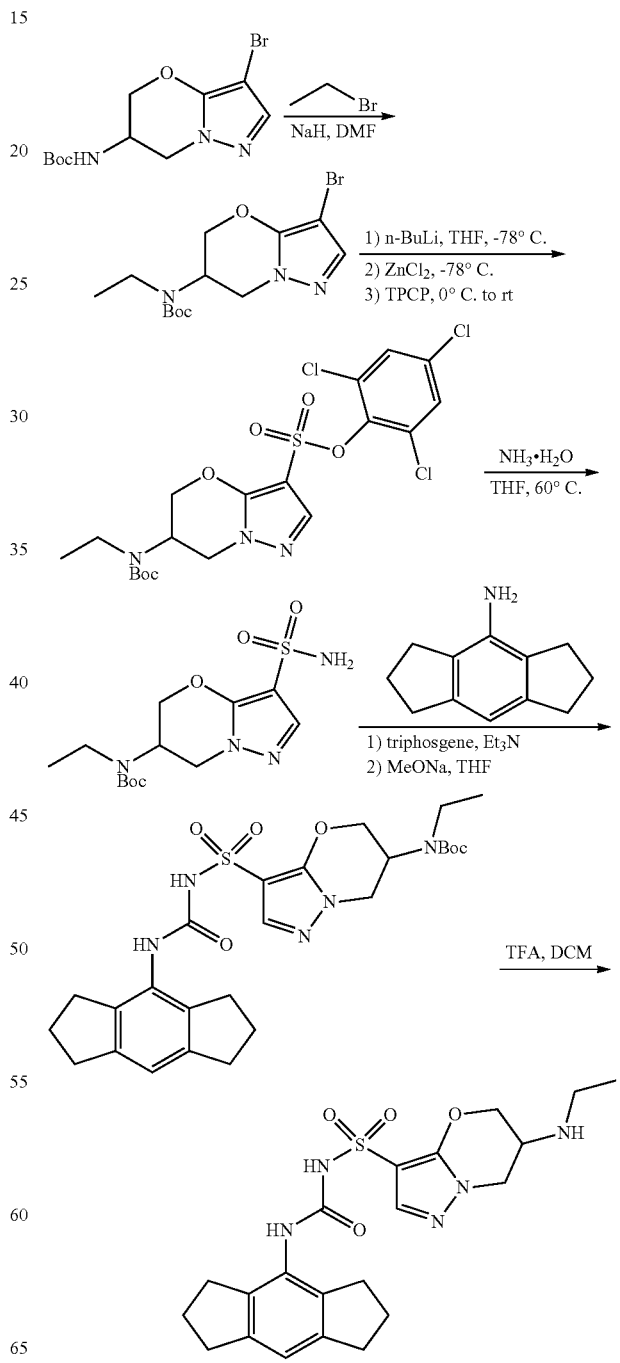

Step 1~3

These three steps are similar to general procedure of sodium ((1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide.

Step 4 rac-tert-Butyl ethyl(3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)carbamate was synthesized as described in Preparation F to deliver the desired product (100 mg, yield: 64%) as a white solid. MS: m/z 546.3 (M+H$^+$)

Step 5

To a solution of rac-tert-butyl ethyl(3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)carbamate (100 mg, 0.2 mmol) in CH$_2$Cl$_2$ (2 mL) was added TFA (1 mL) and the mixture was stirred at room temperature for 30 mins. Then the mixture was concentrated to remove the solvent. The residue was co-evaporated with CH$_2$Cl$_2$ (5 mL×3) and then purified by reverse phase HPLC [0%-95% MeCN in H$_2$O (0.1% NH$_3$.H$_2$O)] to give rac-6-(ethylamino)-N-((1,2,3,5,6,7-hexahydro-s-indacen-4-yl)carbamoyl)-6,7-dihydro-5H-pyrazolo[5,1-b][1,3]oxazine-3-sulfonamide (60 mg, 73%) as a white solid.

$^1$H NMR (400 MHz, DMSO-d$_6$): δ=7.91 (s, 1H), 7.62 (s, 1H), 6.93 (s, 1H), 4.41 (dd, J=11.2, 2.4 Hz, 1H), 4.31 (dd, J=10.8, 4.8 Hz, 1H), 4.24 (dd, J=12.8, 4.4 Hz, 1H), 3.95 (dd, J=12.8, 4.4 Hz, 1H), 3.33 (overlap, 1H), 2.79 (t, J=7.2 Hz, 4H), 2.68-2.58 (m, 6H), 2.00-1.91 (m, 4H), 1.01 (t, J=7.2 Hz, 3H). MS: m/z 446.1 (M+H$^+$).

Example 44

Synthesis of (R)-6-(Ethylamino)-N-((1,2,3,5,6,7-hexahydro-s-indacen-4-yl)carbamoyl)-6,7-dihydro-5H-pyrazolo[5,1-b][1,3]oxazine-3-sulfonamide hydrochloride and (S)-6-(ethylamino)-N-((1,2,3,5,6,7-hexahydro-s-indacen-4-yl)carbamoyl)-6,7-dihydro-5H-pyrazolo[5,1-b][1,3]oxazine-3-sulfonamide hydrochloride is shown below.

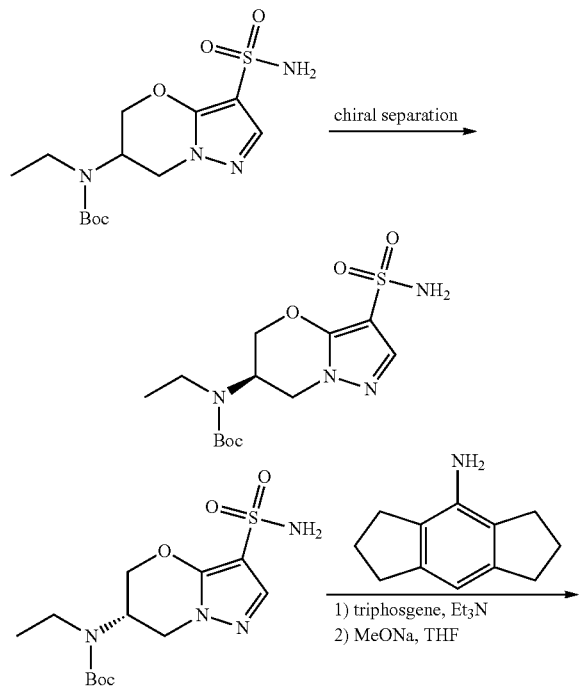

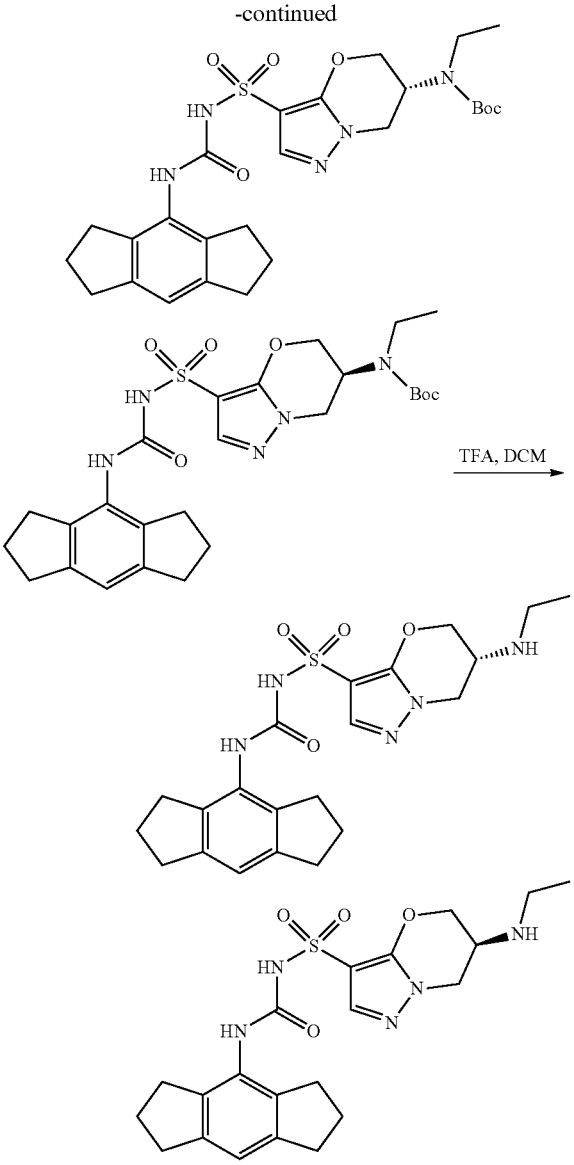

Step 1 rac-tert-Butyl ethyl(3-sulfamoyl-6,7-dihydro-5H-pyrazolo[5,1-b][1,3]oxazin-6-yl)carbamate (120 mg) was resolved by chiral prep-HPLC to give (R)-tert-butyl ethyl(3-sulfamoyl-6,7-dihydro-5H-pyrazolo[5,1-b][1,3]oxazin-6-yl)carbamate (peak 1, 52 mg) and (S)-tert-butyl ethyl(3-sulfamoyl-6,7-dihydro-5H-pyrazolo[5,1-b][1,3]oxazin-6-yl)carbamate (peak 2, 48 mg).

Step 2

This step is similar to general procedure of rac-6-(ethylamino)-N-((1,2,3,5,6,7-hexahydro-s-indacen-4-yl)carbamoyl)-6,7-dihydro-5H-pyrazolo[5,1-b][1,3]oxazine-3-sulfonamide.

Step 3

To a solution of (R)-tert-butyl ethyl(3-(N-((1,2,3,5,6,7-hexahydro-s-indacen-4-yl)carbamoyl)sulfamoyl)-6,7-dihydro-5H-pyrazolo[5,1-b][1,3]oxazin-6-yl)carbamate (40 mg, 0.1 mmol) in CH$_2$Cl$_2$ (2 mL) was added TFA (1 mL) and the mixture was stirred at room temperature for 30 mins. Then the mixture was concentrated to remove the solvent. The residue was co-evaporated with CH$_2$Cl$_2$ (5 mL×3) and then neutralized to pH=8 with sat.NaHCO₃. The resulting solution was acidified to pH=5 with aq.HCl (2 N) and then purified by reverse phase HPLC [0%-95% MeCN in H₂O] to give (R)-6-(ethylamino)-N-((1,2,3,5,6,7-hexahydro-s-indacen-4-yl)carbamoyl)-6,7-dihydro-5H-pyrazolo[5,1-b][1,3]oxazine-3-sulfonamide hydrochloride (15 mg, 22%) as a white solid.

¹H NMR (300 MHz, DMSO-d₆): δ=7.74 (s, 1H), 7.52 (s, 1H), 6.88 (s, 1H), 4.38-4.33 (m, 1H), 4.24-4.17 (m, 2H), 3.92-3.85 (m, 1H), 3.32 (overlap, 1H), 2.77 (t, J=7.2 Hz, 4H), 2.64-2.59 (m, 6H), 2.00-1.89 (m, 4H), 1.00 (t, J=7.2 Hz, 3H). MS: m/z 446.1 (M+H⁺).

(S)-6-(ethylamino)-N-((1,2,3,5,6,7-hexahydro-s-indacen-4-yl)carbamoyl)-6,7-dihydro-5H-pyrazolo[5,1-b][1,3]oxazine-3-sulfonamide hydrochloride was prepared using the same procedure.

¹H NMR (400 MHz, DMSO-d₆): δ=7.89 (s, 1H), 7.60 (s, 1H), 6.93 (s, 1H), 4.41 (dd, J=10.8, 2.4 Hz, 1H), 4.31 (dd, J=10.8, 5.2 Hz, 1H), 4.24 (dd, J=12.4, 4.4 Hz, 1H), 3.95 (dd, J=12.4, 4.4 Hz, 1H), 3.00 (overlap, 1H), 2.78 (t, J=7.6 Hz, 4H), 2.63-2.58 (m, 6H), 1.97-1.93 (m, 4H), 1.01 (t, J=7.2 Hz, 3H). MS: m/z 446.1 (M+H⁺).

Example 45

Synthesis of Sodium (R)-((8-fluoro-1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide is shown below.

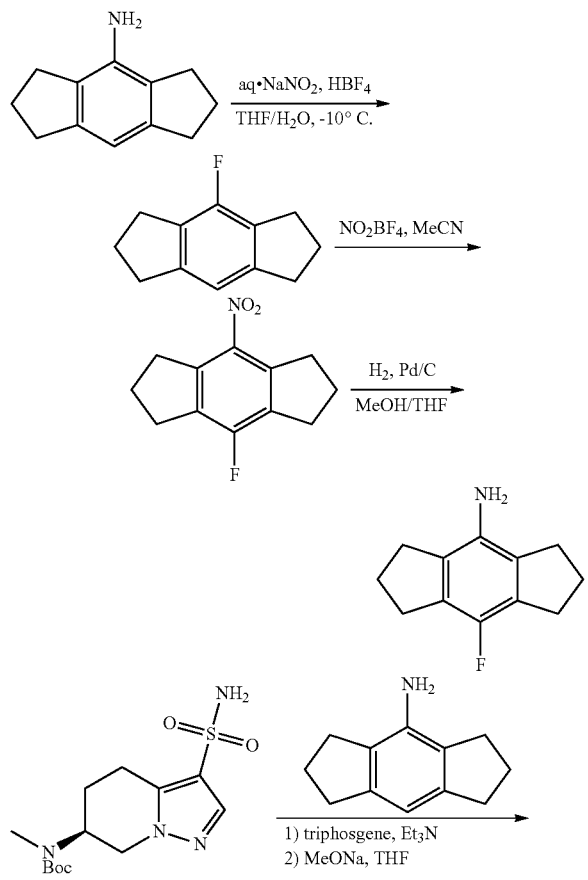

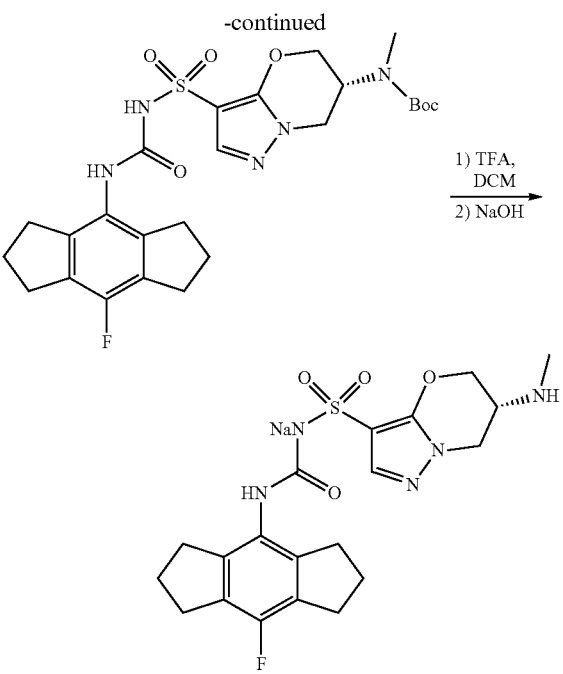

Step 1

To a solution of 1,2,3,5,6,7-hexahydro-s-indacen-4-amine (3.0 g, 17.3 mmol) in THF/H₂O/HBF₄ (45 mL/7 mL/22 mL) was added a solution of NaNO₂ (1.3 g, 18.2 mmol) in H₂O (3 mL) dropwise at −10° C. under N₂. After stirring with cooling for 2 hrs, the cold bath was removed and the reaction was partitioned between water (100 mL) and EA (100 mL). The organic layer was washed with sat.NaHCO₃ (50 mL), brine (50 mL), dried over Na₂SO₄ and concentrated. The residue was purified by silica gel column (PE) to give 4-fluoro-1,2,3,5,6,7-hexahydro-s-indacene (1.4 g, yield: 46%) as a white solid.

¹H NMR (300 MHz, CDCl₃): δ=6.88 (s, 1H), 2.92-2.87 (m, 8H), 2.17-2.07 (m, 4H).

Step 2

To a solution of 4-fluoro-1,2,3,5,6,7-hexahydro-s-indacene (1.4 g, 8.0 mmol) in MeCN (20 mL) was added NO₂BF₄ (1.3 g, 9.8 mmol) at 0° C. under N₂ in two portions. The reaction was then stirred at 0° C. for 1 hr. The reaction was partitioned between EA (100 mL) and water (100 mL). The organic layer was washed with water (20 mL) and brine (20 mL), dried over Na₂SO₄ and concentrated. The residue was purified by silica flash column (0%~45% EA in PE) to give 4-fluoro-8-nitro-1,2,3,5,6,7-hexahydro-s-indacene (1.4 g, yield: 80%) as a white solid.

¹H NMR (400 MHz, CDCl₃): δ=3.30 (t, J=6.8 Hz, 4H), 2.95 (t, J=7.6 Hz, 4H), 2.22-2.13 (m, 4H).

Step 3

To a solution of 4-fluoro-8-nitro-1,2,3,5,6,7-hexahydro-s-indacene (1.4 g, 6.3 mmol) in MeOH (20 mL) was added 10% Pd/C (200 mg). After stirring at room temperature under balloon hydrogen atmosphere overnight, the reaction mixture was filtered. The filtrate was evaporated in vacuo to dryness and the residue was purified by silica flash column (0%~45% EA in PE) to give 8-fluoro-1,2,3,5,6,7-hexahydro-s-indacen-4-amine (1.1 g, yield: 91%) as a white solid.

¹H NMR (400 MHz, DMSO-d₆): δ=4.42 (s, 2H), 2.75 (t, J=7.6 Hz, 4H), 2.62 (t, J=7.6 Hz, 4H), 2.05-1.97 (m, 4H). MS: m/z 192.4 (M+H⁺).

Step 4

(R)-tert-butyl (3-(N-((8-fluoro-1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate was synthesized as in Preparation D to yield the desired product (1.8 g, yield: 72%) as a yellow solid. MS: m/z 550.2 (M+H$^+$).

Step 5

To a solution of (R)-tert-butyl (3-(N-((8-fluoro-1,2,3,5,6,7-hexahydro-s-indacen-4-yl)carbamoyl)sulfamoyl)-6,7-dihydro-5H-pyrazolo[5,1-b][1,3]oxazin-6-yl)(methyl)carbamate (1.8 g, 3.3 mmol) in CH$_2$Cl$_2$ (8 mL) was added TFA (8 mL) and the mixture was stirred at room temperature for 30 mins. Then the mixture was concentrated in vacuo to remove the solvent. The residue was treated with 2 N aq.NaOH to PH>13. The resulting solution was purified by reverse phase HPLC (MeCN/H$_2$O) to give sodium (R)-((8-fluoro-1,2,3,5,6,7-hexahydro-s-indacen-4-yl)carbamoyl)((6-(methylamino)-6,7-dihydro-5H-pyrazolo[5,1-b][1,3]oxazin-3-yl)sulfonyl)amide (1.2 g, 80%) as a yellow solid.

$^1$H NMR (400 MHz, DMSO-d$_6$): δ=7.42 (s, 1H), 7.32 (s, 1H), 4.28-4.24 (m, 1H), 4.16 (q, J=4.8 Hz, 1H), 4.09 (q, J=6.0 Hz, 1H), 3.82 (q, J=5.2 Hz, 1H), 3.08 (br, 1H), 2.78 (t, J=7.6 Hz, 4H), 2.71 (t, J=7.6 Hz, 4H), 2.33 (s, 3H), 1.99-1.93 (m, 4H). MS: m/z 450.1 (M+H$^+$).

Example 46

Synthesis of (R)—N-((8-Fluoro-1,2,3,5,6,7-hexahydro-s-indacen-4-yl)carbamoyl)-6-methoxy-6,7-dihydro-5H-pyrazolo[5,1-b][1,3]oxazine-3-sulfonamide is shown below.

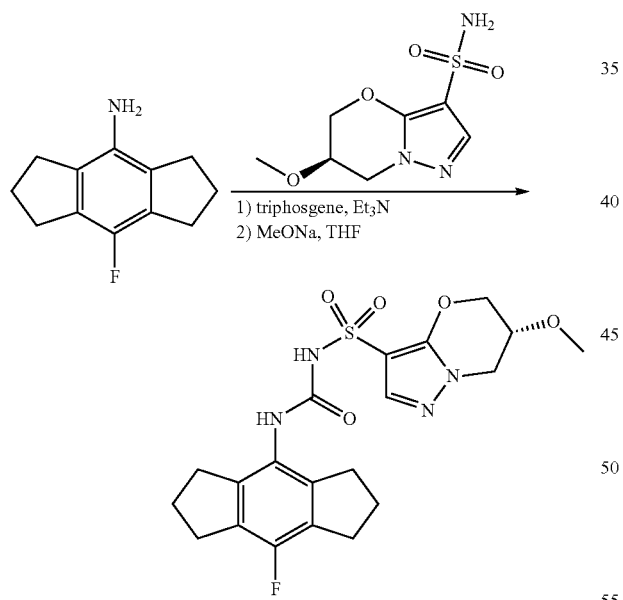

To a solution of (R)-6-methoxy-6,7-dihydro-5H-pyrazolo[5,1-b][1,3]oxazine-3-sulfonic acid amide (80 mg, 0.34 mmol) in THF (10 mL) was added MeONa (54 mg, 1.0 mmol) and the mixture was stirred at room temperature for 30 mins to give a sodium salt suspension.

In another flask, to a solution of 8-fluoro-1,2,3,5,6,7-hexahydro-s-indacen-4-amine (66 mg, 0.34 mmol) and TEA (102 mg, 1 mmol) in THF (10 mL), was added triphosgene (40 mg, 0.14 mmol) in one portion and the mixture was stirred at room temperature under N$_2$ for 30 mins. The reaction mixture was then filtered. The filtrate was added to the sodium salt suspension above and stirred at room temperature for overnight. After that, the reaction solution was partitioned between EA (10 mL) and water (5 mL). The aqueous phase was acidified to pH=5 with 1 N HCl. The solid formed was collected by filtration and dried to give (R)—N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonamide (27 mg, yield: 17.6%) as a white solid.

$^1$H NMR (400 MHz, DMSO-d$_6$): δ=10.55 (brs, 1H), 7.91 (brs, 1H), 7.61 (s, 1H), 4.62 (d, J=11.6 Hz, 1H), 4.35 (d, J=11.6 Hz, 1H), 4.18-4.27 (m, 2H), 4.06 (s, 1H), 3.35 (s, 3H), 2.82 (t, J=7.2 Hz, 4H), 2.64 (t, J=7.6 Hz, 4H), 1.98-2.05 (m, 4H) MS: m/z 450.8 (M+H$^+$).

Example 47

Synthesis of sodium (R)-((1,2,3,5,6,7-hexahydro-s-indacen-4-yl)carbamoyl)((6-(prop-2-yn-1-yloxy)-6,7-dihydro-5H-pyrazolo[5,1-b][1,3]oxazin-3-yl)sulfonyl)amide is shown below.

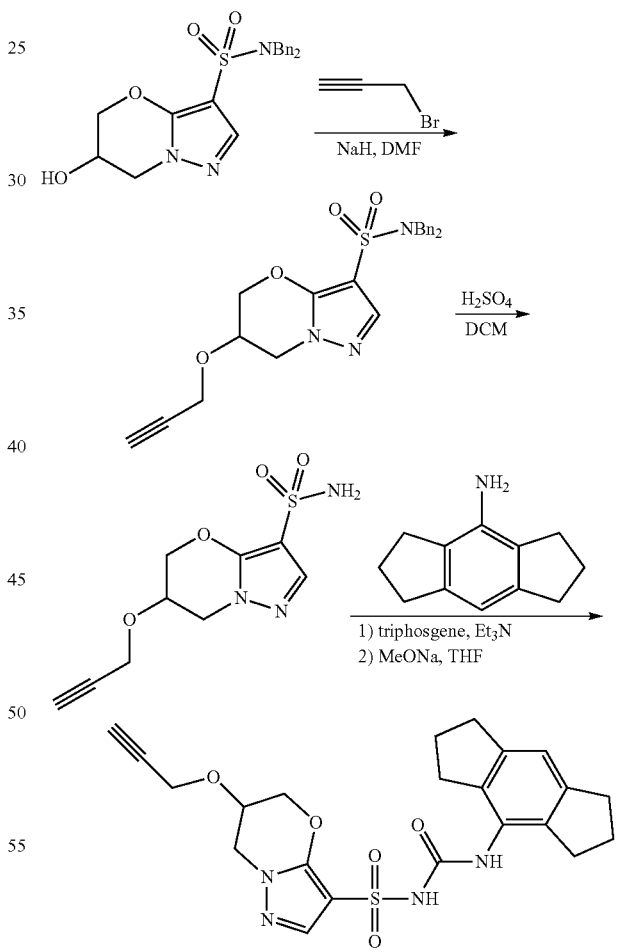

Step 1

To a solution of rac-N,N-dibenzyl-6-(3-hydroxyazetidin-1-yl)-6,7-dihydro-5H-pyrazolo[5,1-b][1,3]oxazine-3-sulfonamide (840 mg, 2.1 mmol) in DMF (10 mL) was added NaH (60% in mineral oil, 126.0 mg, 3.2 mmol). The reaction was stirred at room temperature for 1 hr under N$_2$. Then 3-bromoprop-1-yne (273.0 mg, 2.3 mmol) was added and the mixture was stirred at room temperature for 2 hrs. The reaction mixture was poured into water (20 mL) and extracted with EA (20 mL). The organic layer was washed with water (10 mL) and brine (10 mL), dried over $Na_2SO_4$ and concentrated to dryness to give rac-N,N-dibenzyl-6-(prop-2-yn-1-yloxy)-6,7-dihydro-5H-pyrazolo[5,1-b][1,3]oxazine-3-sulfonamide (580 mg, yield: 63%) as a yellow solid.

$^1$H NMR (300 MHz, CDCl$_3$): δ=7.63 (s, 1H), 7.25-7.16 (m, 1 OH), 4.52-4.17 (m, 11H), 2.55 (s, 1H). MS: m/z 438.1 (M+H$^+$).

Step 2

To a stirred solution of rac-N,N-dibenzyl-6-(prop-2-yn-1-yloxy)-6,7-dihydro-5H-pyrazolo[5,1-b][1,3]oxazine-3-sulfonamide (115 mg, 0.3 mmol) in CH$_2$Cl$_2$ (3.0 mL) was added conc.H$_2$SO$_4$ (16 drops, 0.32 mL) and stirred at 0° C. for 10 mins. The reaction solution was concentrated. The residue was neutralized with saturated NaHCO$_3$ solution. Then the mixture was filtered off the solid and the filtrate was purified by reverse phase HPLC (MeCN/H$_2$O) to give rac-6-(prop-2-yn-1-yloxy)-6,7-dihydro-5H-pyrazolo[5,1-b][1,3]oxazine-3-sulfonamide (23.0 mg, yield: 34%) as a yellow solid.

MS: m/z 258.0 (M+H$^+$).

Step 3 rac-((1,2,3,5,6,7-hexahydro-s-indacen-4-yl)carbamoyl)((6-(prop-2-yn-1-yloxy)-6,7-dihydro-5H-pyrazolo[5,1-b][1,3]oxazin-3-yl)sulfonyl)amide was synthesized as in Preparation D to yield the desired product (20.0 mg, yield: 49%) as a white solid.

$^1$H NMR (400 MHz, DMSO-d$_6$): δ=7.86 (brs, 1H), 7.85 (s, 1H), 6.92 (s, 1H), 4.63-4.59 (m, 1H), 4.40-4.25 (m, 6H), 3.52 (t, J=2.4 Hz, 1H), 2.79 (t, J=7.2 Hz, 4H), 2.62 (t, J=7.2 Hz, 4H), 1.99-1.92 (m, 4H). MS: m/z 457.1 (M+H$^+$).

Example 48

Synthesis of sodium rac-((6-(((tert-butoxycarbonyl)(methyl)amino)methyl)-6,7-dihydro-5H-pyrazolo[5,1-b][1,3]oxazin-3-yl)sulfonyl)((1,2,3,5,6,7-hexahydro-s-indacen-4-yl)carbamoyl)amide is shown below.

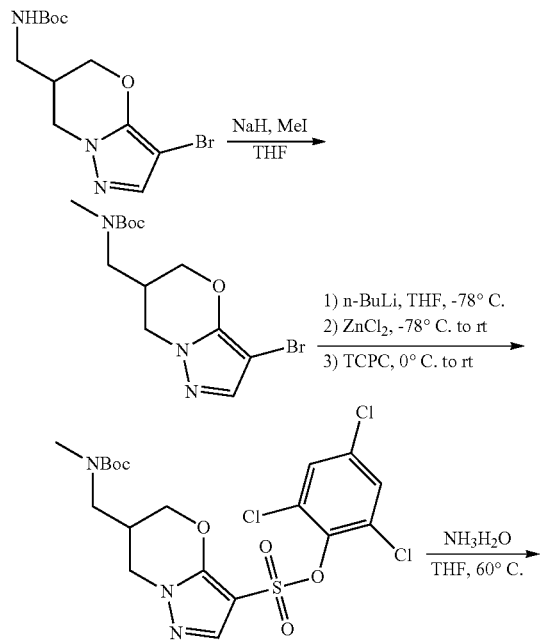

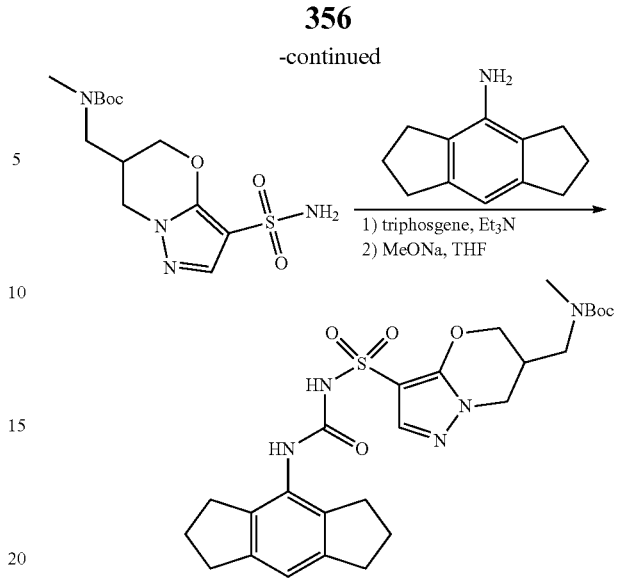

Step 1

To a solution of rac-tert-butyl ((3-bromo-6,7-dihydro-5H-pyrazolo[5,1-b][1,3]oxazin-6-yl)methyl)carbamate (0.3 g, 0.9 mmol) in THF (3 mL) was added NaH (60%, 108 mg, 2.7 mmol) followed by MeI (639 mg, 4.5 mmol) at 0° C. After stirring at room temperature for 16 hrs, the suspension was quenched with the addition of EA (20 mL) and water (10 mL). The organic layer was separated. The aqueous layer was extracted with EA (10 mL). The organic layers were combined, washed with brine (10 mL), dried over Na$_2$SO$_4$ and concentrated in vacuo. The residue was purified by silica gel column (PE/EA=2/1) to give rac-tert-butyl ((3-bromo-6,7-dihydro-5H-pyrazolo[5,1-b][1,3]oxazin-6-yl)methyl)(methyl)carbamate (290 mg, yield: 93%) as a yellow oil.

Step 2 rac-2,4,6-trichlorophenyl 6-(((tert-butoxycarbonyl)(methyl)amino)methyl)-6,7-dihydro-5H-pyrazolo[5,1-b][1,3]oxazine-3-sulfonate was synthesized using Preparation B to yield the product as a yellow oil which was used for next step without purification.

Step 3 rac-tert-Butyl methyl((3-sulfamoyl-6,7-dihydro-5H-pyrazolo[5,1-b][1,3]oxazin-6-yl)methyl)carbamate was synthesized as in Preparation C to yield the desired product (60 mg, yield: 16% over 2 steps) as a light yellow solid. MS: m/z 369.4 (M+Na$^+$).

Step 4

Sodium ((6-(((tert-butoxycarbonyl)(methyl)amino)methyl)-6,7-dihydro-5H-pyrazolo[5,1-b][1,3]oxazin-3-yl)sulfonyl)((1,2,3,5,6,7-hexahydro-s-indacen-4-yl)carbamoyl)amide was synthesized as in Preparation D to yield the desired product (28 mg, yield: 31%) as a white solid.

$^1$H NMR (400 MHz, DMSO-d$_6$): δ=7.33 (s, 1H), 7.31 (s, 1H), 6.75 (s, 1H), 4.28 (d, J=10.4 Hz, 1H), 4.10-4.0 (m, 2H), 3.80-3.73 (m, 1H), 3.25-3.15 (m, 2H), 2.80 (s, 3H), 2.74 (t, J=7.2 Hz, 4H), 2.64 (t, J=7.2 Hz, 4H), 2.50 (overlap, 1H), 1.95-1.85 (m, 4H), 1.41-1.31 (m, 9H). MS: m/z 546.2 (M+H$^+$).

Example 49

Synthesis of sodium ((1,2,3,5,6,7-hexahydro-s-indacen-4-yl)carbamoyl)((6-((methylamino)methyl)-6,7-dihydro-5H-pyrazolo[5,1-b][1,3]oxazin-3-yl)sulfonyl)amide is shown below.

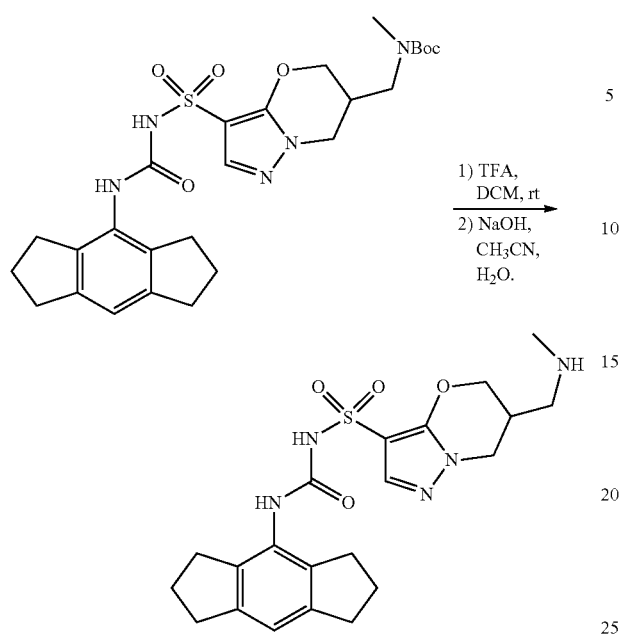

To a solution of sodium rac-((6-(((tert-butoxycarbonyl)(methyl)amino)methyl)-6,7-dihydro-5H-pyrazolo[5,1-b][1,3]oxazin-3-yl)sulfonyl)((1,2,3,5,6,7-hexahydro-s-indacen-4-yl)carbamoyl)amide (15 mg, 0.03 mmol) in $CH_2Cl_2$ (2 mL) was added TFA (0.6 mL) and the mixture was stirred at room temperature for 30 mins. Then the mixture was concentrated in vacuo to remove the solvent. The residue was added 2 N NaOH solution to pH>13. The resulting solution was purified by reverse phase HPLC ($MeCN/H_2O$) to give sodium rac-((1,2,3,5,6,7-hexahydro-s-indacen-4-yl)carbamoyl)((6-((methylamino)methyl)-6,7-dihydro-5H-pyrazolo[5,1-b][1,3]oxazin-3-yl)sulfonyl)amide (10 mg, 80%) as a white solid.

$^1$H NMR (400 MHz, DMSO-$d_6$): δ=7.36 (s, 1H), 6.77 (s, 1H), 4.39 (dd, J=11.2 Hz, 2.8 Hz, 1H), 4.20-4.1 (m, 2H), 3.83 (dd, J=12.4 Hz, 7.6 Hz, 1H), 3.42 (m, 5H), 3.16-3.11 (m, 1H), 2.75 (t, J=7.2 Hz, 4H), 2.66 (t, J=7.2 Hz, 4H), 1.96-1.86 (m, 4H). MS: m/z 446.1 (M+H$^+$).

Example 50

Synthesis of (R)-6-Ethyl-N-((1,2,3,5,6,7-hexahydro-s-indacen-4-yl)carbamoyl)-6,7-dihydro-5H-pyrazolo[5,1-b][1,3]oxazine-3-sulfonamide and (S)-6-ethyl-N-((1,2,3,5,6,7-hexahydro-s-indacen-4-yl)carbamoyl)-6,7-dihydro-5H-pyrazolo[5,1-b][1,3]oxazine-3-sulfonamide is shown below.

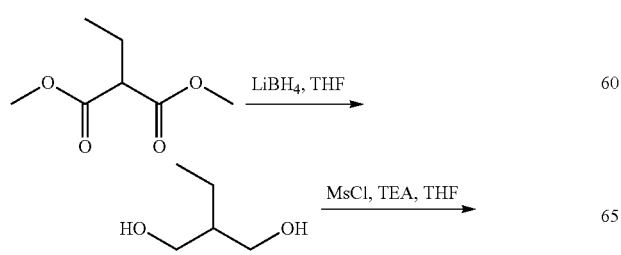

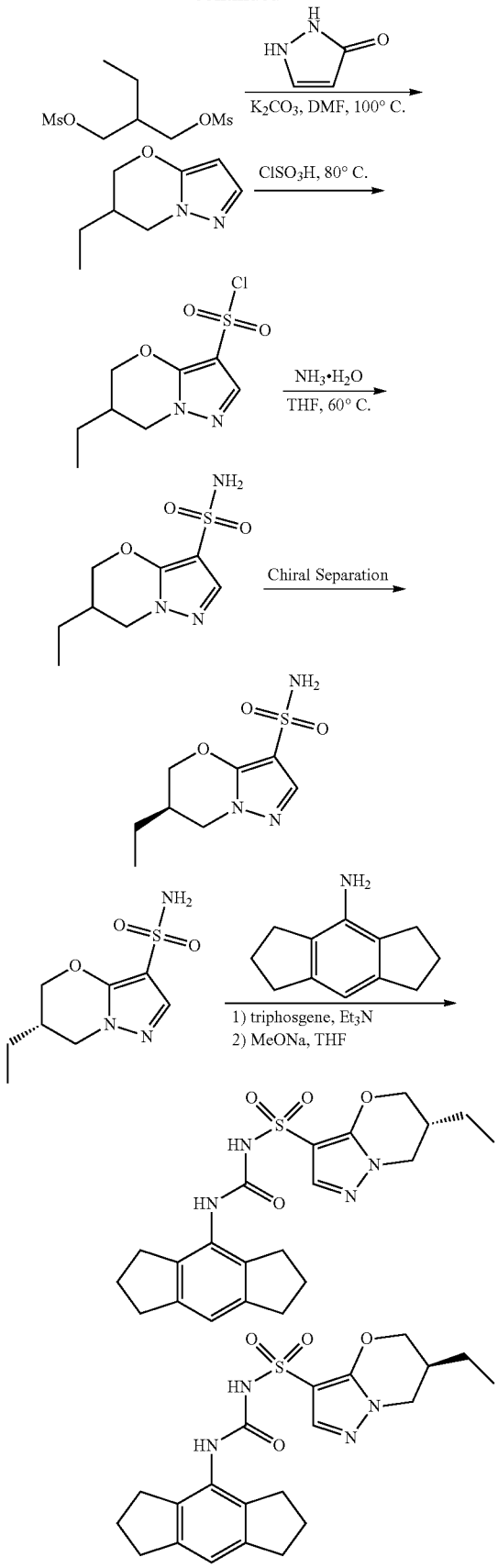

Step 1

To a solution of dimethyl 2-ethylmalonate (1.8 g, 9.6 mmol) in THF (10 mL) was added LiBH$_4$ (2 M in THF, 9.6 mL, 19.2 mmol) dropwise at 0° C. under N$_2$ atmosphere. The reaction mixture was stirred at room temperature for 16 hrs and then poured to water (40 mL). The resulting solution was concentrated to about 5 mL and mixed with EA (50 mL). The mixture was stirred vigorously for 5 mins, dried with MgSO$_4$ and concentrated to give 2-ethylpropane-1,3-diol (970 mg, yield: 97%) as a colorless oil.

Step 2

To a solution of 2-ethylpropane-1,3-diol (970 mg, 9.3 mol) and Et$_3$N (2.4 g, 23.8 mmol) in dry THF (20 mL) was added MsCl (2.2 g, 19.3 mmol) at 0° C. After being stirred at room temperature for 30 mins, the reaction mixture was filtered. The filtrate was concentrated to dryness to give crude 2-ethylpropane-1,3-diyl dimethanesulfonate as a yellow oil.

Step 3

A mixture of 2-ethylpropane-1,3-diyl dimethanesulfonate (crude), 1H-pyrazol-3(2H)-one (750 mg, 8.9 mmol) and K$_2$CO$_3$ (4.3 g, 31.2 mmol) in DMF (40 mL) was heated at 100° C. for 16 hrs. The reaction mixture was partitioned between EA/H$_2$O (80 mL/200 mL) and the layers were separated. The aqueous layer was extracted with EA (80 mL×3) and the combined organic layer was washed with brine (50 mL), dried over Na$_2$SO$_4$ and concentrated. The residue was purified by silica gel column (PE/EA=3/1) to give rac-6-ethyl-6,7-dihydro-5H-pyrazolo[5,1-b][1,3]oxazine (650 mg, yield: 48%) as a colorless oil.

$^1$H NMR (300 MHz, CDCl$_3$): δ=7.32 (d, J=1.5 Hz, 1H), 5.48 (d, J=1.5 Hz, 1H), 4.34-4.26 (m, 2H), 3.95-3.87 (m, 1H), 3.81-3.73 (m, 1H), 2.30-2.19 (m, 1H), 1.60-1.40 (m, 2H), 1.05 (t, 7=7.5 Hz, 3H).

Step 4 rac-6-Ethyl-6,7-dihydro-5H-pyrazolo[5,1-b][1,3]oxazine (650 mg, 4.3 mmol) was added dropwise to ClSO$_3$H (4 mL) at 0° C. After being stirred at 80° C. for 2 hrs, the reaction mixture was added dropwise to a mixture of ice-water/EA (30 mL/20 mL). The layers were separated and the aqueous layer was extracted with EA (10 mL×2). The combined organic layer was washed with brine (20 mL), dried over Na$_2$SO$_4$ and concentrated to give crude rac-6-ethyl-6,7-dihydro-5H-pyrazolo[5,1-b][1,3]oxazine-3-sulfonyl chloride as a yellow solid.

Step 5

To a solution of crude rac-6-ethyl-6,7-dihydro-5H-pyrazolo[5,1-b][1,3]oxazine-3-sulfonyl chloride in THF (3 mL) was added NH$_3$.H$_2$O (1 mL). After being stirred at 60° C. for 1 h, the reaction mixture was concentrated to dryness. The residue was dissolved in MeOH (3 mL) and acidified with aq.HCl (1 N) to pH=3. The residue was purified by reverse phase HPLC (0%-95% MeCN in H$_2$O) to give rac-6-ethyl-6,7-dihydro-5H-pyrazolo[5,1-b][1,3]oxazine-3-sulfonamide (200 mg, yield: 20%, two steps) as a yellow solid.

$^1$H NMR (400 MHz, DMSO-d$_6$): δ=7.48 (s, 1H), 7.08 (s, 2H), 4.48-4.44 (m, 1H), 4.21 (dd, J=12.4, 5.6 Hz, 1H), 4.12-4.07 (m, 1H), 3.81-3.75 (m, 1H), 2.24-2.17 (m, 1H), 1.47-1.32 (m, 2H), 0.96 (t, J=7.2 Hz, 3H).

Step 6 rac-6-Ethyl-6,7-dihydro-5H-pyrazolo[5,1-b][1,3]oxazine-3-sulfonamide (200 mg) was separated by chiral HPLC to give two isomers:

(R)-6-ethyl-6,7-dihydro-5H-pyrazolo[5,1-b][1,3]oxazine-3-sulfonamide (peak 1, 80 mg) and (S)-6-ethyl-6,7-dihydro-5H-pyrazolo[5,1-b][1,3]oxazine-3-sulfonamide (peak 2, 83 mg).

Step 7

(S)-6-ethyl-N-((1,2,3,5,6,7-hexahydro-s-indacen-4-yl)carbamoyl)-6,7-dihydro-5H-pyrazolo[5,1-b][1,3]oxazine-3-sulfonamide was synthesized using Preparation A to deliver the desired product (53 mg, yield: 34%) as a white solid.

$^1$H NMR (400 MHz, DMSO-d$_6$): δ=10.48 (brs, 1H), 7.90 (s, 1H), 7.61 (s, 1H), 6.93 (s, 1H), 4.51 (d, J=2.8 Hz, 1H), 4.48-4.15 (m, 2H), 3.82-3.77 (m, 1H), 2.78 (t, J=7.2 Hz, 4H), 2.60 (t, 7=6.8 Hz, 4H), 2.20-1.98 (m, 1H), 1.97-1.91 (m, 4H), 1.45-1.11 (m, 2H), 0.96 (t, 7=7.6 Hz, 3H). MS: m/z 431.1 (M+H$^+$).

(R)-6-Ethyl-N-((1,2,3,5,6,7-hexahydro-s-indacen-4-yl)carbamoyl)-6,7-dihydro-5H-pyrazolo[5,1-b][1,3]oxazine-3-sulfonamide was prepared using the same procedure.

$^1$H NMR (400 MHz, DMSO-d$_6$): δ=10.46 (s, 1H), 7.90 (s, 1H), 7.62 (s, 1H), 6.93 (s, 1H), 4.50 (dd, J=10.8, 3.2 Hz, 1H), 4.24-4.13 (m, 2H), 3.83-3.78 (m, 1H), 2.79 (t, J=7.2 Hz, 4H), 2.59 (t, J=7.2 Hz, 4H), 2.21-2.19 (m, 1H), 1.99-1.92 (m, 4H), 1.42-1.35 (m, 2H), 0.95 (t, J=7.2 Hz, 3H). MS: m/z 431.1 (M+H$^+$).

Example 51

Synthesis of 6-(3-Fluoroazetidin-1-yl)-N-((1,2,3,5,6,7-hexahydro-s-indacen-4-yl)carbamoyl)-6,7-dihydro-5H-pyrazolo[5,1-b][1,3]oxazine-3-sulfonamide is shown below.

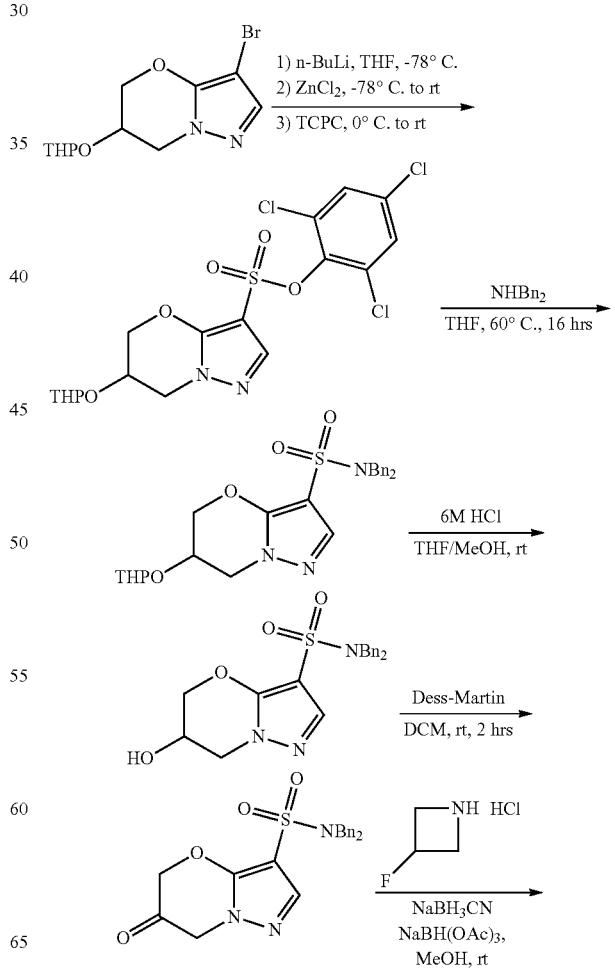

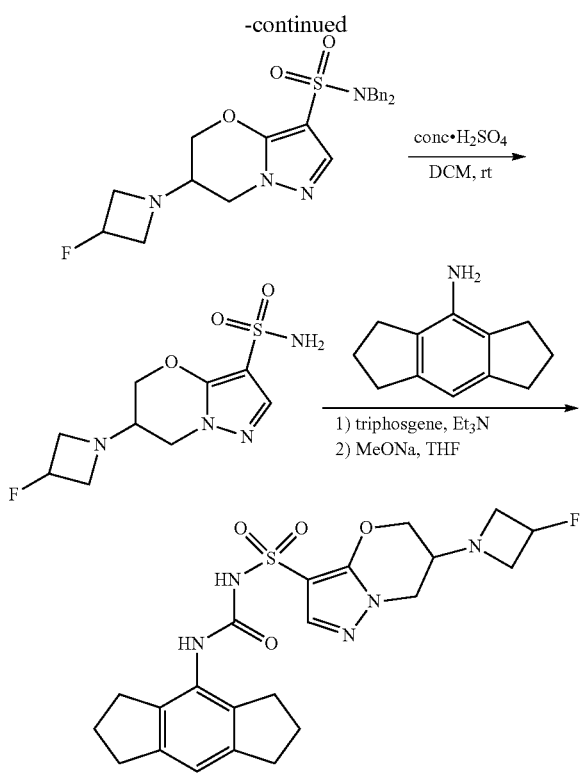

Step 1

6-(tetrahydro-pyran-2-yloxy)-6,7-dihydro-5H-pyrazolo[5,1-b][1,3]oxazine-3-sulfonic acid 2,4,6-trichloro-phenyl ester was synthesized using Preparation B to yield the product as a yellow gel which was used for next step without purification.

Step 2

A mixture of 6-(tetrahydro-pyran-2-yloxy)-6,7-dihydro-5H-pyrazolo[5,1-b][1,3]oxazine-3-sulfonic acid 2,4,6-trichloro-phenyl ester (crude, ~6.6 mmol), dibenzylamine (2.5 g, 12.0 mmol) and THF (20 mL) was stirred at 60° C. overnight. The reaction was concentrated under reduced pressure until 10 mL of liquid remained. The remained solution was acidified with aq.HCl (1 N) to pH=5 and extracted with EA (100 mL×5). The organic layers were combined, dried over $Na_2SO_4$ and concentrated to give N,N-dibenzyl-6-((tetrahydro-2H-pyran-2-yl)oxy)-6,7-dihydro-5H-pyrazolo[5,1-b][1,3]oxazine-3-sulfonamide (1.5 g, yield: 51%) as a yellow solid.

MS: m/z 484.2 (M+H$^+$).

Step 3

To a solution of N,N-dibenzyl-6-((tetrahydro-2H-pyran-2-yl)oxy)-6,7-dihydro-5H-pyrazolo[5,1-b][1,3]oxazine-3-sulfonamide (6.1 g, 12.6 mmol) in THF/H$_2$O/EtOH (50 mL/10 mL/50 mL) was added conc.HCl (10 mL) and the mixture was stirred at room temperature overnight. The reaction was concentrated under reduced pressure. The residue was purified by reverse phase HPLC (MeCN/H$_2$O) to give N,N-dibenzyl-6-hydroxy-6,7-dihydro-5H-pyrazolo[5,1-b][1,3]oxazine-3-sulfonamide (4.0 g, yield: 80%) as a white solid. MS: m/z 400.1 (M+H$^+$).

Step 4

A solution of N,N-dibenzyl-6-hydroxy-6,7-dihydro-5H-pyrazolo[5,1-b][1,3]oxazine-3-sulfonamide (3.4 g, 8.5 mmol) and Dess-Martin periodiane (7.2 g, 17.0 mmol) in CH$_2$Cl$_2$ (50.0 mL) was stirred at room temperature for 16 hrs. The mixture was concentrated in vacuo. The residue was purified by silica gel column chromatography (PE:EA=1:2) to give N,N-dibenzyl-6-oxo-6,7-dihydro-5H-pyrazolo[5,1-b][1,3]oxazine-3-sulfonamide (3.0 g, yield: 91%) as a yellow solid.

Step 5

To a stirred solution of N,N-dibenzyl-6-oxo-6,7-dihydro-5H-pyrazolo[5,1-b][1,3]oxazine-3-sulfonamide (397.0 mg, 1.0 mmol) and 3-fluoroazetidine hydrochloride (224.0 mg, 2.0 mmol) in MeOH (10.0 mL) was added sodium triacetoxyborohydride (424.0 mg, 2.0 mmol) at room temperature. After stirring at room temperature for 30 mins, sodium cyanotrihydroborate (126 mg, 2.0 mmol) was added to the mixture. The reaction was stirred at room temperature for 16 hrs and concentrated in vacuo. The residue was purified by silica gel column chromatography (CH$_2$Cl$_2$/MeOH=5/1) to give N,N-dibenzyl-6-(3-fluoroazetidin-1-yl)-6,7-dihydro-5H-pyrazolo[5,1-b][1,3]oxazine-3-sulfonamide (160 mg, yield: 35%) as a yellow solid.

Step 6

To a solution of N,N-dibenzyl-6-(3-fluoroazetidin-1-yl)-6,7-dihydro-5H-pyrazolo[5,1-b][1,3]oxazine-3-sulfonamide (140 mg, 0.3 mmol) in CH$_2$Cl$_2$ (3.0 mL) was added conc.H$_2$SO$_4$ (16 drops, 0.32 mL) and the mixture was stirred at room temperature for 30 mins. The reaction solution was concentrated. The residue was neutralized with saturated NaHCO$_3$ solution and filtered. The filtrate was purified by reverse phase HPLC (0%-95% MeCN in H$_2$O) to give 6-(3-fluoroazetidin-1-yl)-6,7-dihydro-5H-pyrazolo[5,1-b][1,3]oxazine-3-sulfonamide (60.0 mg, yield: 71%) as a yellow solid.

Step 7

6-(3-fluoroazetidin-1-yl)-N-((1,2,3,5,6,7-hexahydro-s-indacen-4-yl)carbamoyl)-6,7-dihydro-5H-pyrazolo[5,1-b][1,3]oxazine-3-sulfonamide was synthesized as described in Preparation F to deliver the desired product (11.0 mg, yield: 11%) as a white solid.

$^1$H NMR (400 MHz, DMSO-d$_6$): δ=10.48 (brs, 1H), 7.87 (s, 1H), 7.58 (s, 1H), 6.93 (s, 1H), 5.20-5.17 (m, 0.5H), 5.06-5.03 (m, 0.5H), 4.32 (q, J=6.0 Hz, 2H), 4.17 (dd, J=12.8, 4.0 Hz, 1H), 3.89 (d, 7=13.2 Hz, 1H), 3.65-3.60 (m, 2H), 3.28 (overlap, 2H), 3.09 (d, J=4.0 Hz, 1H), 2.79 (t, J=7.6 Hz, 4H), 2.61 (t, J=7.6 Hz, 4H), 1.99-1.94 (m, 4H). MS: m/z 476.1 (M+H$^+$).

Example 52

Synthesis of sodium ((1,2,3,5,6,7-Hexahydro-s-indacen-4-yl)carbamoyl)((6-(pyrrolidin-1-yl)-6,7-dihydro-5H-pyrazolo[5,1-b][1,3]oxazin-3-yl)sulfonyl)amide is shown below.

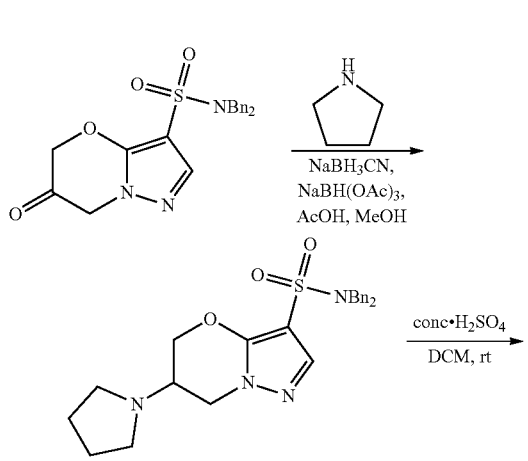

363

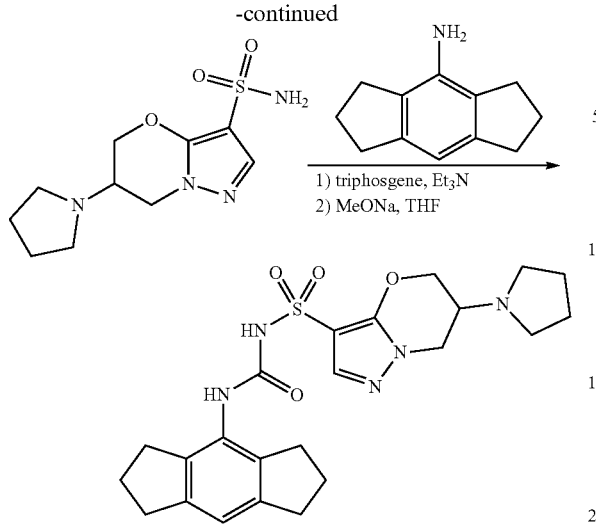

Step 1

To a solution of 6-oxo-6,7-dihydro-5H-pyrazolo[5,1-b][1,3]oxazine-3-sulfonic acid dibenzylamide (750 mg, 1.9 mmol) and pyrrolidine (270 mg, 3.8 mmol) in MeOH (18 mL) was added AcOH until pH=6. Then NaBH(OAc)$_3$ (810 mg, 3.8 mmol) was added and the reaction mixture was stirred at room temperature for 3 hrs. NaBH$_3$CN (240 mg, 3.8 mmol) was added and the reaction mixture was stirred at room temperature for another 16 hrs. The reaction solution was concentrated to about 6 mL and then purified by reverse phase HPLC (0%-95% MeCN in H$_2$O) to give 6-pyrrolidin-1-yl-6,7-dihydro-5H-pyrazolo[5,1-b][1,3]oxazine-3-sulfonic acid dibenzylamide (290 mg, yield: 34%) as a gummy yellow solid. MS: m/z 453.1 (M+H$^+$)

Step 2

This step is similar to general procedure of 6-(3-fluoro-azetidin-1-yl)-N-((1,2,3,5,6,7-hexahydro-s-indacen-4-yl)carbamoyl)-6,7-dihydro-5H-pyrazolo[5,1-b][1,3]oxazine-3-sulfonamide.

Step 3

To a suspension of 6-pyrrolidin-1-yl-6,7-dihydro-5H-pyrazolo[5,1-b][1,3]oxazine-3-sulfonic acid amide (50 mg, 0.2 mmol) in THF (2 mL) was added MeONa (35 mg, 0.6 mmol) and the mixture was stirred at room temperature for 20 mins to give a sodium salt suspension.

In another flask, to a solution of 1,2,3,5,6,7-hexahydro-s-indacen-4-ylamine (30 mg, 0.2 mmol) and TEA (50 mg, 0.5 mmol) in THF (3 mL) was added triphosgene (20 mg, 0.1 mmol) in one portion and the mixture was stirred at room temperature under N$_2$ for 20 mins. The reaction mixture was then filtered. The filtrate was added to the sodium salt suspension above. After stirring at room temperature for 16 hrs, the reaction solution was partitioned between EA (10 mL) and water (30 mL). The aqueous phase was bubbled by N$_2$ for 5 mins and then purified by reverse phase HPLC (0%-95% MeCN in H$_2$O) to give sodium ((1,2,3,5,6,7-hexahydro-s-indacen-4-yl)carbamoyl)((6-(pyrrolidin-1-yl)-6,7-dihydro-5H-pyrazolo[5,1-b][1,3]oxazin-3-yl)sulfonyl)amide (10 mg, yield: 12%) as a white solid.

$^1$H NMR (400 MHz, DMSO-d$_6$): δ=7.86 (s, 1H), 7.60 (s, 1H), 6.92 (s, 1H), 4.50-4.40 (m, 2H), 4.27 (dd, J=12.8, 4.0 Hz, 1H), 4.13 (dd, J=12.8, 4.0 Hz, 1H), 2.94-2.91 (m, 1H), 2.79 (t, J=7.2 Hz, 4H), 2.68-2.58 (m, 8H), 2.00-1.91 (m, 4H), 1.70-1.60 (m, 4H). MS: m/z 472.1 (M+H$^+$).

364

Example 53

Sodium ((6-(Azetidin-1-yl)-6,7-dihydro-5H-pyrazolo[5,1-b][1,3]oxazin-3-yl)sulfonyl)((1,2,3,5,6,7-hexahydro-s-indacen-4-yl)carbamoyl)amide

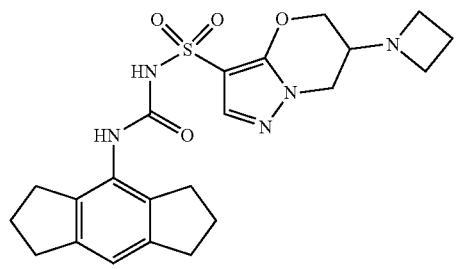 [SMILES: O=C(Nc1c2c(cc3c1CCC3)CCC2)NS(=O)(=O)c1cnn2c1OCC(N1CCC1)C2]

The title compound was prepared using general procedure of sodium ((1,2,3,5,6,7-hexahydro-s-indacen-4-yl)carbamoyl)((6-(pyrrolidin-1-yl)-6,7-dihydro-5H-pyrazolo[5,1-b][1,3]oxazin-3-yl)sulfonyl)amide.

$^1$H NMR (400 MHz, DMSO-d$_6$): δ=7.42 (s, 1H), 7.33 (s, 1H), 6.77 (s, 1H), 4.15-4.02 (m, 3H), 3.75 (dd, J=12.8, 1.6 Hz, 1H), 3.20 (t, J=6.8 Hz, 4H), 2.84-2.80 (m, 1H), 2.75 (t, J=7.2 Hz, 4H), 2.66 (t, J=7.2 Hz, 4H), 1.97-1.87 (m, 6H). MS: m/z 458.1 (M+H$^+$).

Example 54

Synthesis of N-((1,2,3,5,6,7-Hexahydro-s-indacen-4-yl)carbamoyl)-6-methoxy-6-methyl-6,7-dihydro-5H-pyrazolo[5,1-b][1,3]oxazine-3-sulfonamide is shown below.

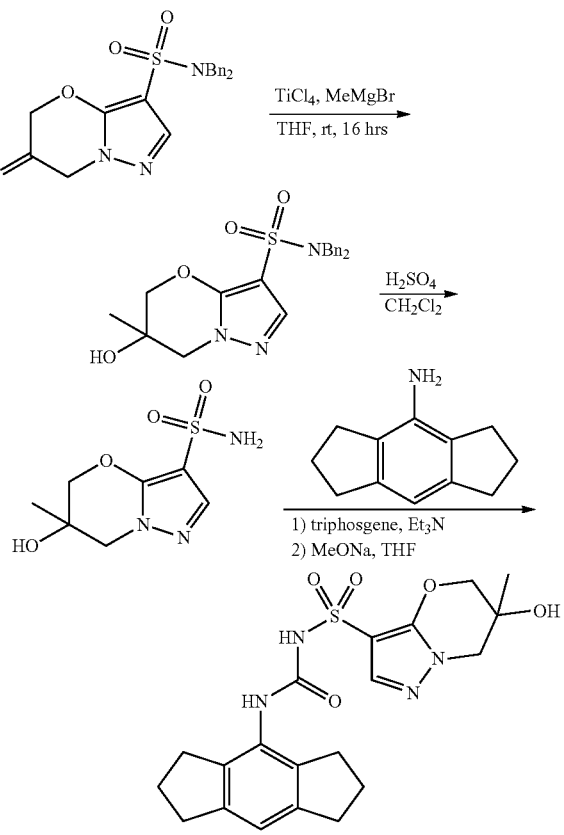

Step 1

To a stirred solution of TiCl$_4$ (0.5 mL, excess) and methylmagnesium bromide (1.0 mL, excess) in THF (5.0 mL) was added N,N-dibenzyl-6-oxo-6,7-dihydro-5H-pyrazolo[5,1-b][1,3]oxazine-3-sulfonamide (140.0 mg, 0.4 mmol) at −78° C. under N$_2$. Then the mixture was filtered and the filtrate was purified by silica gel column chromatography (CH$_2$Cl$_2$/MeOH=25/1) to give N,N-dibenzyl-6-hydroxy-6-methyl-6,7-dihydro-5H-pyrazolo[5,1-b][1,3]oxazine-3-sulfonamide (55 mg, yield: 38%) as a white solid.

Step 2

To a stirred solution of N,N-dibenzyl-6-hydroxy-6-methyl-6,7-dihydro-5H-pyrazolo[5,1-b][1,3]oxazine-3-sulfonamide (55 mg, 0.1 mmol) in CH$_2$Cl$_2$ (3.0 mL) was added conc.H$_2$SO$_4$ (8 drops, 0.16 mL) and stirred at room temperature for 30 mins. The reaction solution was concentrated. The residue was neutralized with saturated NaHCO$_3$ solution. Then the mixture was filtered and the filtrate was purified by reverse phase HPLC (MeCN/H$_2$O) to give 6-hydroxy-6-methyl-6,7-dihydro-5H-pyrazolo[5,1-b][1,3]oxazine-3-sulfonamide (26.0 mg, yield: 87%) as a white solid.

Step 3

N-((1,2,3,5,6,7-hexahydro-s-indacen-4-yl)carbamoyl)-6-hydroxy-6-methyl-6,7-dihydro-5H-pyrazolo[5,1-b][1,3]oxazine-3-sulfonamide was synthesized as described in Preparation F to deliver the desired product (7.0 mg, yield: 15%) as a white solid.

$^1$H NMR (400 MHz, DMSO-d$_6$): δ=10.4 (s, 1H), 7.89 (s, 1H), 7.62 (s, 1H), 6.93 (s, 1H), 5.45 (s, 1H), 4.18 (s, 2H), 4.04 (d, J=12.4 Hz, 1H), 3.91 (d, J=12.0 Hz, 1H), 2.79 (t, J=7.2 Hz, 4H), 2.61 (t, J=7.2 Hz, 4H), 1.99-1.92 (m, 4H), 1.25 (s, 3H). MS: m/z 433.1 (M+H$^+$).

Example 55

Synthesis of N-((1,2,3,5,6,7-Hexahydro-s-indacen-4-yl) carbamoyl)-6-methoxy-6-methyl-6,7-dihydro-5H-pyrazolo[5,1-b][1,3]oxazine-3-sulfonamide is shown below.

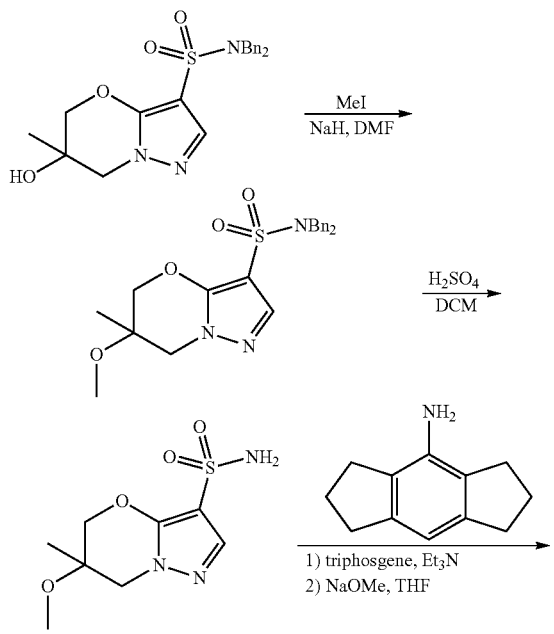

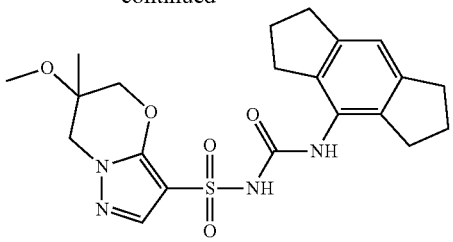

Step 1

To a solution of N,N-dibenzyl-6-hydroxy-6-methyl-6,7-dihydro-5H-pyrazolo[5,1-b][1,3]oxazine-3-sulfonamide (35 mg, 0.08 mmol) in DMF (3 mL) was added NaH (60% in mineral oil, 6.4 mg, 0.16 mmol). The reaction was stirred at room temperature for 1 hr under N$_2$. Then iodomethane (60 mg, 0.4 mmol) was added and the mixture was stirred at room temperature for 2 hrs. The reaction mixture was poured into water (20 mL) and extracted with EA (20 mL). The organic layer was washed with water (10 mL) and brine (10 mL), dried over Na$_2$SO$_4$ and concentrated. The residue was purified by reverse phase HPLC (MeCN/H$_2$O) to give N,N-dibenzyl-6-methoxy-6-methyl-6,7-dihydro-5H-pyrazolo[5,1-b][1,3]oxazine-3-sulfonamide (30 mg, yield: 83%) as a yellow oil.

$^1$H NMR (300 MHz, CDCl$_3$): δ=7.58 (s, 1H), 7.29-7.26 (m, 5H), 7.18-7.15 (m, 5H), 4.34 (s, 4H), 4.21 (s, 3H), 4.16 (s, 2H), 2.67 (s, 2H), 1.38 (s, 3H).

MS: m/z 428.0 (M+H$^+$).

Step 2

To a stirred solution of N,N-dibenzyl-6-methoxy-6-methyl-6,7-dihydro-5H-pyrazolo[5,1-b][1,3]oxazine-3-sulfonamide (25 mg, 0.06 mmol) in CH$_2$Cl$_2$ (3.0 mL) was added conc.H$_2$SO$_4$ (8 drops, 0.16 mL) and the mixture was stirred at room temperature for 30 mins. The reaction solution was concentrated. The residue was neutralized with saturated NaHCO$_3$ solution. Then the mixture was filtered and the filtrate was purified by reverse phase HPLC (MeCN/H$_2$O) to give 6-methoxy-6-methyl-6,7-dihydro-5H-pyrazolo[5,1-b][1,3]oxazine-3-sulfonamide (6.0 mg, yield: 35%) as a yellow solid.

$^1$H NMR (400 MHz, DMSO-d$_6$): δ=7.57 (s, 1H), 4.09 (s, 3H), 3.89 (q, J=10.4 Hz, 2H), 3.66 (q, J=10.0 Hz, 2H), 1.24 (s, 3H).

MS: m/z 247.9 (M+H$^+$).

Step 3

N-((1,2,3,5,6,7-hexahydro-s-indacen-4-yl)carbamoyl)-6-methoxy-6-methyl-6,7-dihydro-5H-pyrazolo[5,1-b][1,3]oxazine-3-sulfonamide was synthesized as in Preparation D to yield the desired product (7.0 mg, yield: 73%) as a white solid.

$^1$H NMR (400 MHz, DMSO-d$_6$): δ=7.42 (s, 1H), 6.80 (s, 1H), 4.15 (s, 3H), 4.01 (s, 2H), 2.75 (t, J=7.2 Hz, 4H), 2.60 (t, J=8.4 Hz, 4H), 2.58 (overlap, 2H), 1.92-1.88 (m, 4H), 1.20 (s, 3H). MS: m/z 447.1 (M+H$^+$).

Example 56

Synthesis of sodium rac-((1,2,3,5,6,7-Hexahydro-s-indacen-4-yl)carbamoyl)((6-(3-methoxyazetidin-1-yl)-6,7-dihydro-5H-pyrazolo[5,1-b][1,3]oxazin-3-yl)sulfonyl)amide is shown below.

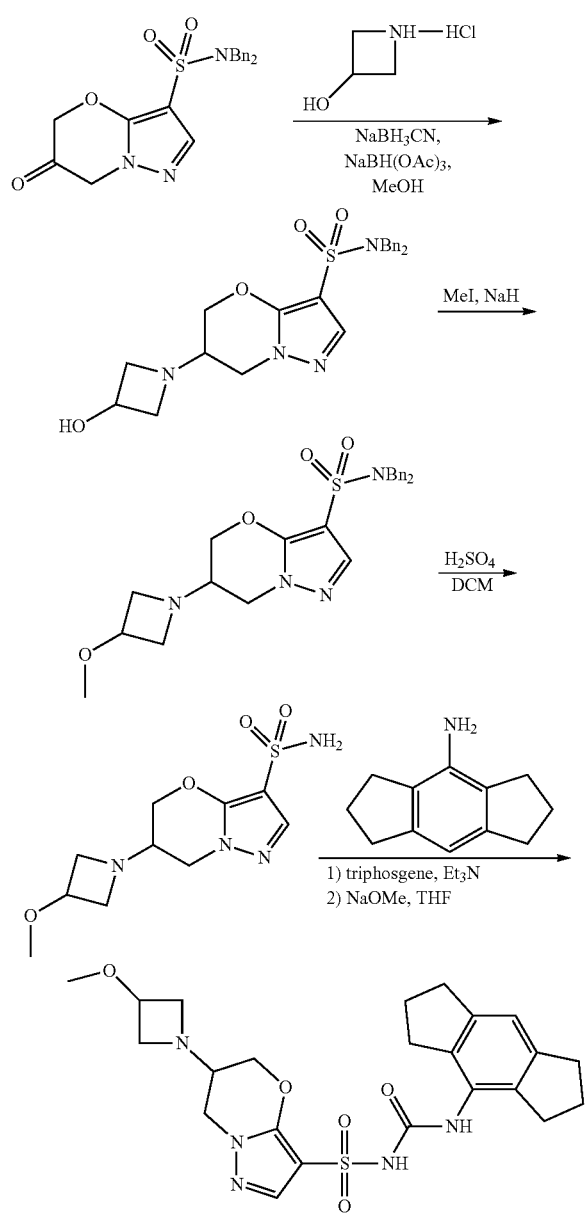

Step 1

To a stirred solution of N,N-dibenzyl-6-oxo-6,7-dihydro-5H-pyrazolo[5,1-b][1,3]oxazine-3-sulfonamide (794 mg, 2.0 mmol) and azetidin-3-ol hydrochloride (440.0 mg, 4.0 mmol) in MeOH (30.0 mL) was added sodium triacetoxyborohydride (848.0 mg, 4.0 mmol) at room temperature. Then the mixture was stirred at room temperature for 30 mins. Sodium cyanotrihydroborate (252.0 mg, 4.0 mmol) was added to the mixture and stirred at room temperature for 16 hrs. The mixture was concentrated in vacuo. The residue was purified by silica gel column chromatography ($CH_2Cl_2$/MeOH=5/1) to give rac-N,N-dibenzyl-6-(3-hydroxyazetidin-1-yl)-6,7-dihydro-5H-pyrazolo[5,1-b][1,3]oxazine-3-sulfonamide (340 mg, yield: 37%) as a yellow solid. MS: m/z 455.2 ($M+H^+$).

Step 2

To a solution of rac-N,N-dibenzyl-6-(3-hydroxyazetidin-1-yl)-6,7-dihydro-5H-pyrazolo[5,1-b][1,3]oxazine-3-sulfonamide (105 mg, 0.2 mmol) in DMF (3 mL) was added NaH (60% in mineral oil, 14.0 mg, 0.4 mmol). The reaction was stirred at room temperature for 1 hr under $N_2$. Then iodomethane (39.0 mg, 0.3 mmol) was added and the mixture was stirred at room temperature for 2 hrs. The reaction mixture was poured into water (20 mL) and extracted with EA (20 mL). The organic layer was washed with water (10 mL) and brine (10 mL), dried over $Na_2SO_4$ and concentrated to dryness to give rac-N,N-dibenzyl-6-(3-methoxyazetidin-1-yl)-6,7-dihydro-5H-pyrazolo[5,1-b][1,3]oxazine-3-sulfonamide (120 mg, crude) as a yellow oil. MS: m/z 469.1 ($M+H^+$).

Step 3

To a stirred solution of rac-N,N-dibenzyl-6-(3-methoxyazetidin-1-yl)-6,7-dihydro-5H-pyrazolo[5,1-b][1,3]oxazine-3-sulfonamide (120 mg, 0.3 mmol) in $CH_2Cl_2$ (3.0 mL) was added conc.$H_2SO_4$ (16 drops, 0.32 mL) and stirred at room temperature for 30 mins. The reaction solution was concentrated. The residue was neutralized with saturated $NaHCO_3$ solution. Then the mixture was filtered off the solid and the filtrate was purified by reverse phase HPLC (MeCN/$H_2O$) to give rac-6-(3-methoxyazetidin-1-yl)-6,7-dihydro-5H-pyrazolo[5,1-b][1,3]oxazine-3-sulfonamide (52.0 mg, yield: 70%) as a white solid. MS: m/z 289.1 ($M+H^+$).

Step 4

Sodium rac-((1,2,3,5,6,7-hexahydro-s-indacen-4-yl)carbamoyl)((6-(3-methoxyazetidin-1-yl)-6,7-dihydro-5H-pyrazolo[5,1-b][1,3]oxazin-3-yl)sulfonyl)amide was synthesized as in Preparation D to yield the desired product (10.0 mg, yield: 11%) as a white solid.

$^1$H NMR (400 MHz, DMSO-$d_6$): δ=7.85 (brs, 1H), 7.57 (s, 1H), 6.92 (s, 1H), 4.30-4.28 (m, 2H), 4.17-4.12 (m, 1H), 3.91-3.84 (m, 2H), 3.52 (t, J=7.2 Hz, 2H), 3.14 (s, 3H), 3.01-2.94 (m, 3H), 2.79 (t, J=7.2 Hz, 4H), 2.62 (t, J=7.2 Hz, 4H), 1.99-1.92 (m, 4H). MS: m/z 488.2 ($M+H^+$).

Example 57

Synthesis of sodium (R)-((1,2,3,5,6,7-Hexahydro-s-indacen-4-yl)carbamoyl)((6-(3-methoxyazetidin-1-yl)-6,7-dihydro-5H-pyrazolo[5,1-b][1,3]oxazin-3-yl)sulfonyl)amide and sodium (S)-((1,2,3,5,6,7-hexahydro-s-indacen-4-yl)carbamoyl)((6-(3-methoxyazetidin-1-yl)-6,7-dihydro-5H-pyrazolo[5,1-b][1,3]oxazin-3-yl)sulfonyl)amide is shown below.

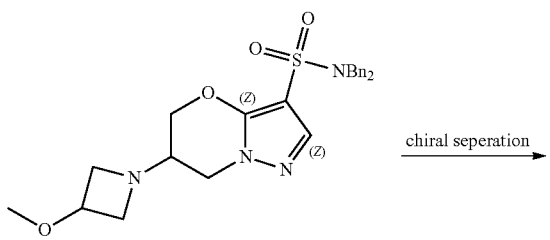

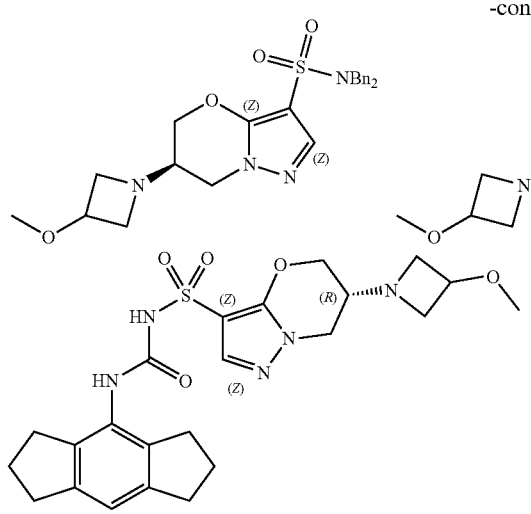
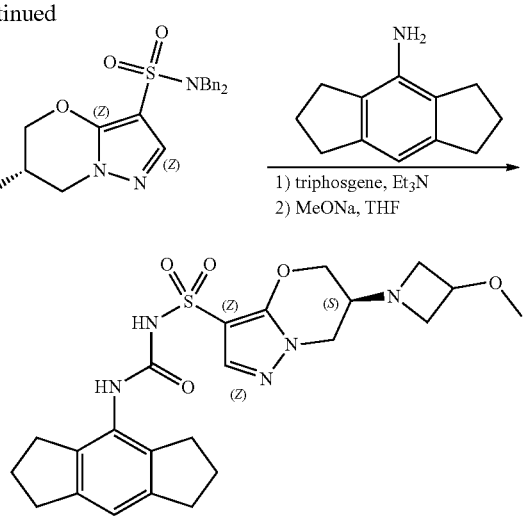

Step 1 rac-6-(3-Methoxyazetidin-1-yl)-6,7-dihydro-5H-pyrazolo[5,1-b][1,3]oxazine-3-sulfonamide (150 mg) was resolved by chiral prep-HPLC to give (R)-6-(3-methoxyazetidin-1-yl)-6,7-dihydro-5H-pyrazolo[5,1-b][1,3]oxazine-3-sulfonamide (65 mg) as a white solid (S)-6-(3-methoxyazetidin-1-yl)-6,7-dihydro-5H-pyrazolo[5,1-b][1,3]oxazine-3-sulfonamide (60 mg) as a white solid.

Step 2

Sodium (R)-((1,2,3,5,6,7-hexahydro-s-indacen-4-yl)carbamoyl)((6-(3-methoxyazetidin-1-yl)-6,7-dihydro-5H-pyrazolo[5,1-b][1,3]oxazin-3-yl)sulfonyl)amide was synthesized as in Preparation D to yield the desired product (54.0 mg, yield: 48%) as a white solid.

$^1$H NMR (400 MHz, DMSO-d$_6$): δ=7.37 (brs, 1H), 7.30 (s, 1H), 6.75 (s, 1H), 4.13-4.08 (m, 3H), 3.96-3.92 (m, 1H), 3.79-3.76 (m, 1H), 3.55-3.53 (m, 2H), 3.14 (s, 3H), 2.98-2.94 (m, 2H), 2.87 (br, 1H), 2.75 (t, J=6.8 Hz, 4H), 2.66 (t, J=6.8 Hz, 4H), 1.92-1.89 (m, 4H). MS: m/z 488.2 (M+H$^+$).

Sodium (S)-((1,2,3,5,6,7-hexahydro-s-indacen-4-yl)carbamoyl)((6-(3-methoxyazetidin-1-yl)-6,7-dihydro-5H-pyrazolo[5,1-b][1,3]oxazin-3-yl)sulfonyl)amide was prepared using the same procedure.

$^1$H NMR (400 MHz, DMSO-d$_6$): δ=7.39 (brs, 1H), 7.30 (s, 1H), 6.76 (s, 1H), 4.12-4.06 (m, 3H), 3.95-3.92 (m, 1H), 3.79-3.76 (m, 1H), 3.55-3.52 (m, 2H), 3.14 (s, 3H), 2.98-2.92 (m, 2H), 2.88 (br, 1H), 2.75 (t, J=7.2 Hz, 4H), 2.66 (t, J=7.2 Hz, 4H), 1.95-1.87 (m, 4H). MS: m/z 488.2 (M+H$^+$).

Example 58

Synthesis of N-((1,2,3,5,6,7-Hexahydro-s-indacen-4-yl)carbamoyl)-6,7-dihydro-4H-pyrazolo[5,1-c][1,4]oxazine-2-sulfonamide is shown below.

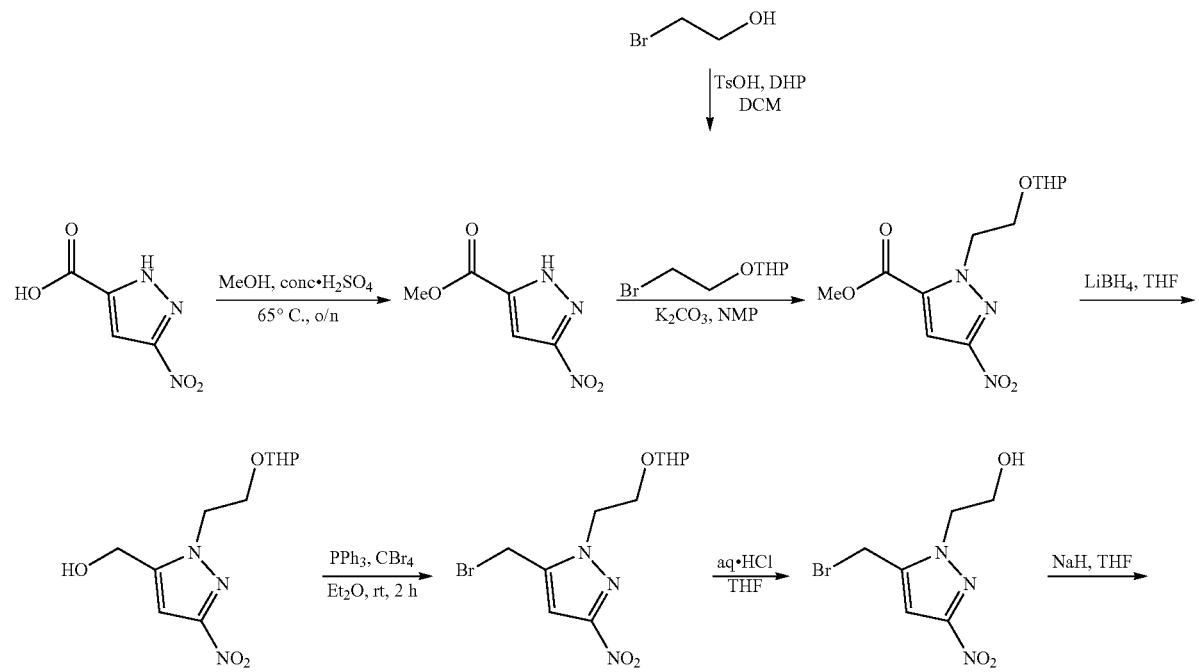

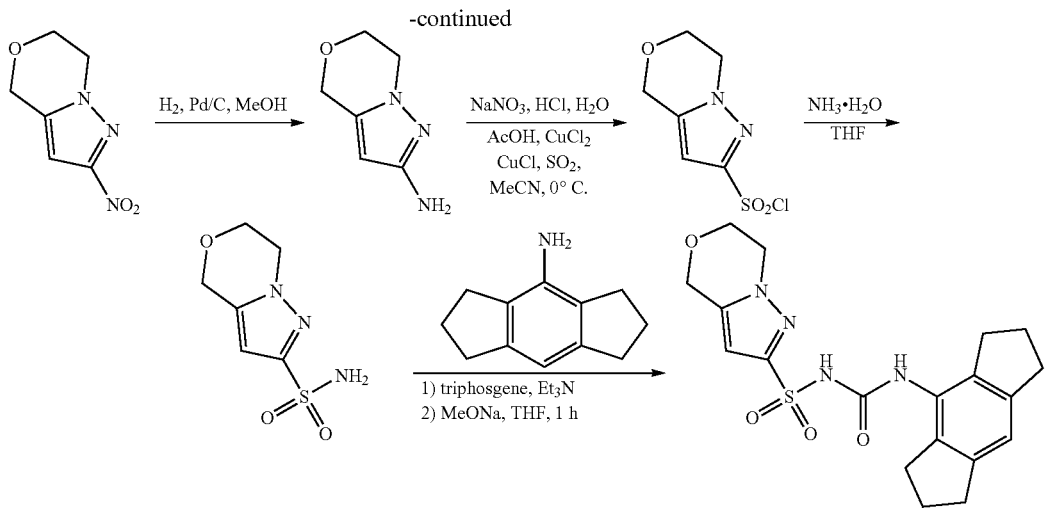

Step 1

To as solution of 2-bromoethanol (3.8 g, 30.0 mmol) and DHP (2.5 g, 30.0 mmol) in DCM (50 mL), was added TsOH (380.0 mg, 2.2 mmol) in portions and the mixture was stirred at room temperature for 2 hrs. The reaction was concentrated and purified by silica gel column (PE/EA=50/1) to give 2-(2-bromoethoxy)tetrahydro-2H-pyran (5.6 g, yield: 89%) as a colorless oil.

$^1$H NMR (400 MHz, CDCl$_3$): δ=4.68 (t, J=3.2 Hz, 1H), 4.05-3.99 (m, 1H), 3.92-3.86 (m, 1H), 3.80-3.74 (m, 1H), 3.54-3.49 (m, 3H), 1.85-1.71 (m, 3H), 1.65-1.53 (m, 3H).

Step 2

To a solution of 3-nitro-1H-pyrazole-5-carboxylic acid (1.57 g, 10.0 mmol) in MeOH (20 mL) was added conc.H$_2$SO$_4$ (2.0 mL). The resulting mixture was stirred at 65° C. overnight. Then the mixture was concentrated in vacuo to give a residue, which was purified by silica gel column (DCM/MeOH=50/1) to afford methyl 3-nitro-1H-pyrazole-5-carboxylate (1.42 g, yield: 83%) as yellow solid.

$^1$H NMR (400 MHz, DMSO-d$_6$): δ=15.24 (brs, 1H), 7.54 (s, 1H), 3.90 (s, 3H).

Step 3

To a solution of methyl 3-nitro-1H-pyrazole-5-carboxylate (1.7 g, 10.0 mmol) in NMP (20 mL) was added 2-(2-bromoethoxy)tetrahydro-2H-pyran (2.6 g, 13.0 mmol), followed by K$_2$CO$_3$ (1.7 g, 13.0 mmol). The resulting mixture was stirred at 80° C. for 16 hrs. Then K$_2$CO$_3$ was filtered off. The filtrate was concentrated in vacuo to give a residue, which was purified by silica gel column (PE/EA=2/1) to afford methyl 3-nitro-1-(2-((tetrahydro-2H-pyran-2-yl)oxy)ethyl)-1H-pyrazole-5-carboxylate (2.8 g, yield: 94%) as yellow oil.

$^1$H NMR (400 MHz, CDCl$_3$): δ=7.39 (s, 1H), 4.92 (t, J=7.2 Hz, 2H), 4.57 (s, 1H), 4.11-4.07 (m, 1H), 3.98 (overlap, 1H), 3.96 (s, 3H), 3.84-3.80 (m, 1H), 3.64-3.60 (m, 1H), 3.49-3.46 (m, 1H), 1.67-1.46 (m, 6H).

Step 4

To a solution of methyl 3-nitro-1-(2-((tetrahydro-2H-pyran-2-yl)oxy)ethyl)-1H-pyrazole-5-carboxylate (2.5 g, 8.4 mmol) in dry THF (50 mL) was added LiBH$_4$ (6.3 mL, 2.0 M in THF) at 0° C. The resulting mixture was stirred from 0° C. to room temperature for 3 hrs. Then the reaction was quenched by addition of MeOH (4 mL). The mixture was concentrated in vacuo to give a residue, which was purified by silica gel column (PE/EA=1/1) to afford (3-nitro-1-(2-((tetrahydro-2H-pyran-2-yl)oxy)ethyl)-1H-pyrazol-5-yl)methanol (2.2 g, yield: 96%) as yellow oil.

$^1$H NMR (300 MHz, CDCl$_3$): δ=6.88 (s, 1H), 4.69 (t, J=6.3 Hz, 2H), 4.57-4.49 (m, 3H), 4.21-4.16 (m, 1H), 3.92-3.85 (m, 1H), 3.77-3.65 (m, 2H), 3.51-3.42 (m, 2H), 1.72-1.48 (m, 6H).

Step 5

To a stirred solution of (3-nitro-1-(2-((tetrahydro-2H-pyran-2-yl)oxy)ethyl)-1H-pyrazol-5-yl)methanol (2.0 g, 7.5 mmol), pyridine (593 mg, 7.5 mmol) and perbromomethane (5.0 g, 15.0 mmol) in dry Et$_2$O (30 mL) was added triphenylphosphine (3.9 g, 15.0 mmol) at 0° C. The resulting mixture was stirred from 0° C. to room temperature for 3 hrs. The reaction was stirred at room temperature for 16 hrs. Then the reaction was filtered off the solid and the solvent was concentrated in vacuo to dryness to give a yellow gum, which was purified by silica gel column (PE/EA=1/1) to afford 5-(bromomethyl)-3-nitro-1-(2-((tetrahydro-2H-pyran-2-yl)oxy)ethyl)-1H-pyrazole (1.5 g, yield: 60%) as yellow oil.

$^1$H NMR (400 MHz, CDCl$_3$): δ=6.89 (s, 1H), 4.69 (t, J=16.0 Hz, 2H), 4.57-4.48 (m, 3H), 4.16-4.10 (m, 1H), 3.84-3.77 (m, 1H), 3.64-3.57 (m, 1H), 3.48-3.43 (m, 1H), 1.72-1.45 (m, 6H).

Step 6:

To a solution of 5-(bromomethyl)-3-nitro-1-(2-((tetrahydro-2H-pyran-2-yl)oxy)ethyl)-1H-pyrazole (1.5 g, 4.5 mmol) in THF (5 mL) was added cone. HCl (1.0 mL) and the mixture was stirred at room temperature 16 hrs. The reaction was concentrated under reduced pressure. The residue was neutralized with saturated NaHCO$_3$ solution and extracted with EA (60 mL). The organic layer was washed with water (50 mL) and brined (50 mL), dried over Na$_2$SO$_4$ and concentrated in vacuo to dryness to give a yellow gum, which was purified by silica gel column (PE/EA=1/1) to give 2-(5-(bromomethyl)-3-nitro-1H-pyrazol-1-yl)ethanol (1.0 g, yield: 91%) as a yellow oil.

Step 7

To a solution of 2-(5-(bromomethyl)-3-nitro-1H-pyrazol-1-yl)ethanol (1.4 g, 4.47 mmol) in dry THF was added NaH (60%, 197 mg, 4.92 mmol). After stirring at room temperature under N$_2$ for 4 hrs, the reaction was partitioned between water (50 mL) and EA (50 mL). The organic layer was washed with brine (50 mL), dried over Na$_2$SO$_4$ and concentrated. The residue was purified by silica gel column (PE/EA=4/1) to give 2-nitro-6,7-dihydro-4H-pyrazolo[5,1-c][1,4]oxazine (300 mg, yield: 40%) as a white solid.

$^1$H NMR (300 MHz, DMSO-d$_6$): δ=6.88 (s, 1H), 4.82 (s, 2H), 4.23 (t, J=4.8 Hz, 2H), 4.12 (t, 7=4.8 Hz, 2H).

Step 8

To a solution of 2-nitro-6,7-dihydro-4H-pyrazolo[5,1-c][1,4]oxazine (300 mg, 1.78 mmol) in MeOH (10 mL) was added Pd/C (10% wet, 100 mg). The reaction was stirred at room temperature under H$_2$ (1 atm) for 3 hrs and filtered. The filtrate was concentrated to give 6,7-dihydro-4H-pyrazolo[5,1-c][1,4]oxazin-2-amine (250 mg, yield: quantitative) as a yellow gum. MS: m/z 277.0 (M−56+H$^+$).

$^1$H NMR (300 MHz, DMSO-d$_6$): δ=5.20 (s, 1H), 4.63-4.55 (m, 4H), 3.98-3.94 (m, 2H), 3.79-3.75 (m, 2H).

Step 9

To a solution of 6,7-dihydro-4H-pyrazolo[5,1-c][1,4]oxazin-2-amine (250 mg, 1.8 mmol) in MeCN/H$_2$O (12 mL/1 mL) was added conc. HCl (2.7 mL) and AcOH (1.1 mL). The mixture was then cooled to 0° C. and a solution of NaNO$_2$ (149 mg, 2.2 mmol) in H$_2$O (1 mL) was added slowly. After stirring at 0° C. for 30 mins, CuCl$_2$ (121 mg, 0.9 mmol) and CuCl (9 mg, 0.09 mmol) were added. SO$_2$ was then bubbled through the reaction solution for 10 mins. The reaction was partitioned between water (50 mL) and EA (50 mL). The organic layer was washed with brine (40 mL), dried over Na$_2$SO$_4$ and concentrated to give crude 6,7-dihydro-4H-pyrazolo[5,1-c][1,4]oxazine-2-sulfonyl chloride which was used for next step directly.

Step 10

To a solution of crude 6,7-dihydro-4H-pyrazolo[5,1-c][1,4]oxazine-2-sulfonyl chloride (crude, ~1.8 mmol) in THF (15 mL) was added ammonia (5 mL). The mixture was stirred at 60° C. for 1 hr. The reaction was concentrated, acidified with 2 N HCl to pH=5 and purified by reverse phase HPLC (MeCN/H$_2$O) to give 6,7-dihydro-4H-pyrazolo[5,1-c][1,4]oxazine-2-sulfonamide (100 mg, yield: 27% over 2 steps) as a white solid.

$^1$H NMR (300 MHz, DMSO-d$_6$): δ=7.42 (s, 2H), 6.39 (s, 1H), 4.80 (s, 2H), 4.17-4.14 (m, 2H), 4.08 (t, J=4.8 Hz, 2H).

Step 11

N-((1,2,3,5,6,7-hexahydro-s-indacen-4-yl)carbamoyl)-6,7-dihydro-4H-pyrazolo[5,1-c][1,4]oxazine-2-sulfonamide was synthesized using Preparation A to deliver the desired product (60 mg, yield: 30%) as a white solid.

$^1$H NMR (400 MHz, DMSO-d$_6$): δ=10.86 (brs, 1H), 8.05 (s, 1H), 6.95 (s, 1H), 6.59 (s, 1H), 4.81 (s, 2H), 4.19 (t, J=4.8 Hz, 2H), 4.10 (t, J=4.8 Hz, 2H), 2.79 (t, J=7.2 Hz, 4H), 2.60 (t, J=7.2 Hz, 4H), 1.97-1.94 (m, 4H). MS: m/z 403.0 (M+H$^+$).

Example 59

Synthesis of N-((1,2,3,5,6,7-hexahydro-s-indacen-4-yl)carbamoyl)-3,4-dihydro-2H-imidazo[5,1-b][1,3]oxazine-8-sulfonamide is shown below.

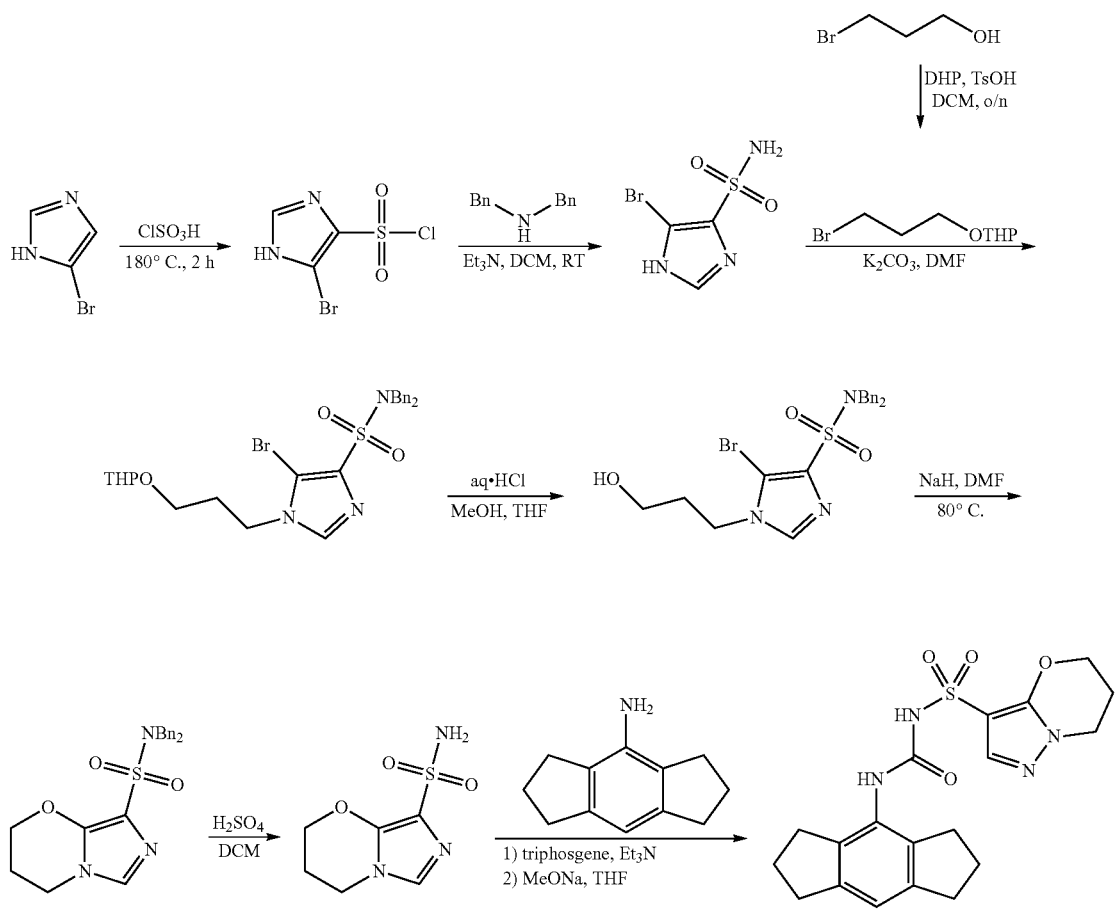

JCT-053-1

Step 1

To a solution of 3-bromo-1-propanol (4 g, 28.8 mmol) in DCM (50 mL) was added TsOH (496 mg, 2.88 mmol) and 3,4-2H-dihydropyran (7.2 g, 86.2 mmol) at 0° C. The mixture was stirred at room temperature overnight. The reaction mixture was poured into H₂O (100 mL). The mixture was extracted with DCM (70 mL×2). The combined extracts was washed with brine (100 mL), dried over Na₂SO₄ and concentrated to dryness. The residue was purified by silica gel column (PE) to give 2-(3-bromo-propoxy)-tetrahydro-pyran (838 mg, yield: 57%) as a red solid.

¹H NMR (300 MHz, DMSO-d₆): δ=4.60-4.56 (m, 1H), 3.77-3.72 (m, 2H), 3.61-3.56 (m, 2H), 3.47-3.42 (m, 2H), 2.07-2.03 (m, 2H), 1.70-1.61 (m, 2H), 1.51-1.45 (m, 4H).

Step 2

A solution of 5-bromo-1H-imidazole (6.6 g, 44.9 mmol) in ClSO₃H (30 mL) was stirred at 180° C. under N₂ atmosphere for 2 hrs. The reaction mixture was poured into ice-water (70 mL) and filtered. The filter cake was washed with H₂O (30 mL) and dried to give 5-bromo-1H-imidazole-4-sulfonyl chloride (7 g, yield: 63%) as a yellow solid.

Step 3

To a solution of 5-bromo-1H-imidazole-4-sulfonyl chloride (4 g, 16.3 mmol) in THF (50 mL) was added TEA (4.5 mL, 32.6 mmol) and dibenzylamine (3.2 g, 16.3 mmol) at room temperature. After being stirred at room temperature overnight, the reaction mixture was poured into H₂O (100 mL) and extracted with EA (50 mL×2). The combined EA was washed with brine (50 mL), dried over Na₂SO₄ and concentrated. The residue was purified by silica gel column (PE/EA=1/1) to give 5-bromo-1H-imidazole-4-sulfonic acid dibenzylamide (1.4 g, yield: 21%) as a red solid.

¹H NMR (300 MHz, DMSO-d₆): δ=7.96 (s, 1H), 7.25-7.19 (m, 6H), 7.12-7.05 (m, 4H), 4.36 (s, 4H).

Step 4

To a solution of 5-bromo-1H-imidazole-4-sulfonic acid dibenzylamide (1.4 g, 3.2 mmol) in DMF (20 mL) was added K₂CO₃ (883 mg, 6.4 mmol), 2-(3-bromo-propoxy)-tetrahydro-pyran (856 mg, 3.8 mmol) at room temperature and the mixture was stirred at 80° C. with N₂ overnight. The reaction mixture was added silica gel and concentrated to dryness. The residue was purified by silica gel column (PE/EA=3/1 to 1/1) to give 5-bromo-1-[3-(tetrahydro-pyran-2-yloxy)-propyl]-1H-imidazole-4-sulfonic acid dibenzylamide (1.6 g, yield: 69%) as a red oil.

¹H NMR (300 MHz, DMSO-d₆): δ=8.08 (s, 1H), 7.23-7.20 (m, 6H), 7.13-7.10 (m, 4H), 4.55-4.52 (m, 1H), 4.36 (s, 4H), 4.12 (t, J=6.9 Hz, 2H), 3.72-3.64 (m, 2H), 3.40-3.30 (m, 2H), 2.02-1.95 (m, 2H), 1.80-1.59 (m, 2H), 1.50-1.40 (m, 4H).

Step 5

To a solution of 5-bromo-1-[3-(tetrahydro-pyran-2-yloxy)-propyl]-1H-imidazole-4-sulfonic acid dibenzylamide (1.6 g, 3.0 mmol) in THF (10 mL) was added MeOH (5 mL), aq.HCl (6 mL, 6 N) at room temperature and it was stirred at room temperature for 1 hr. The reaction mixture was poured into H₂O (50 mL) and neutralized to pH=7 with sat.NaHCO₃. The resulting mixture was extracted with EA (30 mL×2). The combined EA was washed with brine (50 mL), dried over Na₂SO₄ and concentrated to give 5-bromo-1-(3-hydroxy-propyl)-1H-imidazole-4-sulfonic acid dibenzylamide (1.4 g, crude) as a red oil.

Step 6

To a solution of 5-bromo-1-(3-hydroxy-propyl)-1H-imidazole-4-sulfonic acid dibenzylamide (1.4 g, 3.0 mmol) in DMF (20 mL) was added NaH (60%, 145 mg, 3.6 mmol) and the mixture was stirred at 80° C. under N₂ for 4 hrs. The reaction mixture was poured into H₂O (100 mL) and extracted with EA (50 mL×3). The combined EA layer was washed with H₂O (60 mL×2), dried over Na₂SO₄ and concentrated to dryness. The residue was purified by prep-HPLC (NH₄HCO₃) to give 3,4-dihydro-2H-imidazo[5,1-b][1,3]oxazine-8-sulfonic acid dibenzylamide (176 mg, yield: 16%) as a colorless oil.

¹H NMR (300 MHz, DMSO-d₆): δ=7.42 (s, 1H), 7.23-7.18 (m, 6H), 7.15-7.12 (m, 4H), 4.34 (t, J=5.1 Hz, 2H), 4.26 (s, 4H), 4.08 (t, J=6.3 Hz, 2H), 2.10-2.06 (m, 2H).

Step 7

To a solution of 3,4-dihydro-2H-imidazo[5,1-b][1,3]oxazine-8-sulfonic acid dibenzylamide (170 mg, 0.44 mmol) in DCM (3 mL) was added conc. H₂SO₄ (12 drops) at 0° C. and the mixture was stirred at room temperature for 30 minutes. The reaction mixture was poured into sat..NaHCO₃ (20 mL) and then concentrated to remove DCM. The resulting solution was neutralized to pH=7 and filtered. The filtrate was purified by reverse phase HPLC (20% MeCN in H₂O) to give 3,4-dihydro-2H-imidazo[5,1-b][1,3]oxazine-8-sulfonic acid amide (60 mg, yield: 62%) as a white solid.

¹H NMR (300 MHz, DMSO-d₆): δ=7.32 (s, 1H), 6.87 (s, 2H), 4.33 (t, J=5.7 Hz, 2H), 4.07 (t, J=6.3 Hz, 2H), 2.09-2.05 (m, 2H).

Step 8

N-((1,2,3,5,6,7-hexahydro-s-indacen-4-yl)carbamoyl)-3,4-dihydro-2H-imidazo[5,1-b][1,3]oxazine-8-sulfonamide was synthesized as described in Preparation E to deliver the desired product (8 mg, yield: 8%) as a white solid.

¹H NMR (300 MHz, DMSO-d₆): δ=7.98 (s, 1H), 7.40 (s, 1H), 6.91 (s, 1H), 4.33 (t, J=2.4 Hz, 2H), 4.06 (t, J=2.4 Hz, 2H), 2.80 (t, J=3.0 Hz, 4H), 2.60 (t, J=2.4 Hz, 4H), 2.07-2.05 (m, 2H), 1.98-1.92 (m, 4H). MS: m/z 403.1 (M+H⁺).

Example 60

Synthesis of N-((1,2,3,5,6,7-hexahydro-s-indacen-4-yl)carbamoyl)-4-oxo-4,5,6,7-tetrahydropyrazolo[1,5-a]pyrazine-2-sulfonamide is shown below.

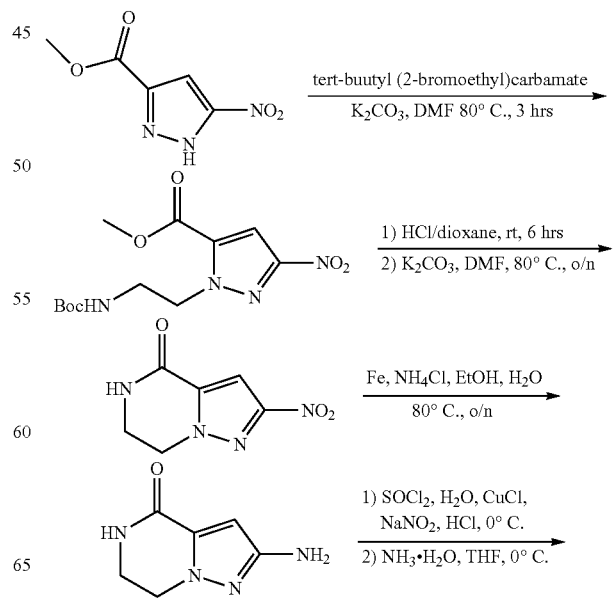

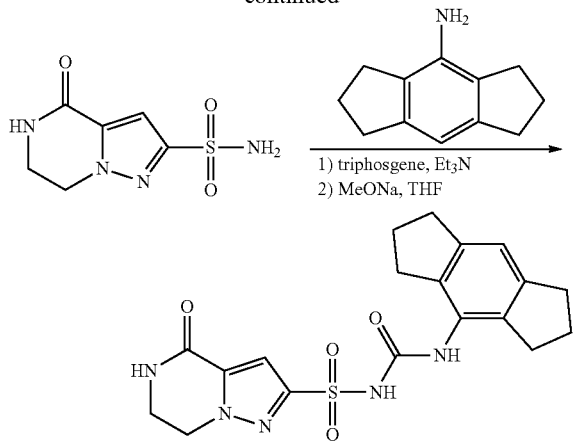

Step 1

To a solution of methyl 5-nitro-1H-pyrazole-3-carboxylate (100 mg, 0.58 mmol) in DMF (10 mL) was added tert-butyl (2-bromoethyl)carbamate (197 mg, 0.88 mmol) and $K_2CO_3$ (240 mg, 1.74 mmol). Then the reaction mixture was stirred at 80° C. for 3 hrs. The reaction mixture was filtered, and filtrate was concentrated in vacuo. The residue was purified by silica gel column chromatography (PE/EA=3/1) to give methyl 1-(2-((tert-butoxycarbonyl)amino)ethyl)-3-nitro-1H-pyrazole-5-carboxylate (166 mg, 80%) as a yellow solid.

$^1$H NMR (400 MHz, DMSO-$d_6$): δ=7.57 (s, 1H), 6.96 (t, J=6.0 Hz, 1H), 4.60 (d, J=5.6 Hz, 2H), 3.90 (s, 3H), 3.41-3.36 (m, 2H), 1.26 (s, 9H).

Step 2

To a solution of methyl 1-(2-((tert-butoxycarbonyl)amino)ethyl)-3-nitro-1H-pyrazole-5-carboxylate (166 mg, 0.46 mmol) in dioxane (5 mL) was added HCl (1.15 mL, 4.6 mmol, 4 M in dioxane). Then the reaction mixture was stirred at room temperature for 6 hrs. The reaction mixture was concentrated in vacuo. The residue was added into the suspension of DMF (10 mL) and $K_2CO_3$ (127 mg, 0.92 mmol). The reaction mixture was stirred at 80° C. overnight and was monitored by LCMS. The reaction mixture was filtered, and filtrate was concentrated in vacuo. The residue was purified by silica gel column chromatography (DCM/MeOH=50/1~10/1) to give 2-nitro-6,7-dihydropyrazolo[1,5-a]pyrazin-4(5H)-one (65 mg, 68%) as a yellow solid.

$^1$H NMR (400 MHz, DMSO-$d_6$): δ=8.61 (s, 1H), 7.43 (s, 1H), 4.46 (t, J=6.0 Hz, 2H), 3.72-3.65 (m, 2H).

Step 3

To a solution of 2-nitro-6,7-dihydropyrazolo[1,5-a]pyrazin-4(5H)-one (1.2 g, 6.6 mmol) in EtOH (30 mL) was added iron powder (1.8 g, 33.0 mmol), $NH_4Cl$ (1.76 g, 33.0 mmol) and $H_2O$ (10 mL). The reaction mixture was stirred at 80° C. in $N_2$ overnight and was monitored by LCMS. The reaction mixture was filtered, and filtrate was concentrated in vacuo. The crude product was purified by silica gel column chromatography (DCM/MeOH=10/1) to give 2-amino-6,7-dihydropyrazolo[1,5-a]pyrazin-4(5H)-one (0.76 g, 76%) as a yellow solid.

$^1$H NMR (400 MHz, DMSO-$d_6$): δ=8.01 (s, 1H), 5.80 (s, 1H), 4.88 (s, 2H), 3.98 (t, J=5.6 Hz, 2H), 3.54-3.45 (m, 2H).

Step 4

To a suspension of CuCl (0.204 g, 2.1 mmol) in $H_2O$ (265 mL) was added dropwise $SOCl_2$ (44.85 mL, 0.618 mol) at 0° C. with vigorous stirring. The solution was stirred at room temperature overnight to give a light yellow solution. Separately, to a solution of 2-amino-6,7-dihydropyrazolo[1,5-a]pyrazin-4(5H)-one (0.62 g, 4.1 mmol) in conc. HCl (4 mL) was added dropwise a solution of $NaNO_2$ (0.33 g, 4.8 mmol) in $H_2O$ (2 mL) at −10° C. The resulting dark orange solution was stirred at −10° C. for 30 minutes, and then added to the solution (10.6 mL) of copper (I) chloride from the first step at −5° C. over 5 minutes. The reaction was stirred at −5° C. for 1 hr and extracted with EA (10 mL×3). The organic layer was concentrated in vacuo to give a yellow solid. This solid was dissolved in THF (20 mL), followed by the dropwise addition of $NH_3$ (10 mL, 28% wt) at 0° C. The reaction was stirred for 2 hrs at 0° C. and then concentrated in vacuo. The resulting solid was purified by silica gel column chromatography (DCM/MeOH=10/1) to give 4-oxo-4,5,6,7-tetrahydropyrazolo[1,5-a]pyrazine-2-sulfonamide (0.2 g, 23%) as a white solid.

$^1$H NMR (400 MHz, DMSO-$d_6$): δ=8.46 (s, 1H), 7.59 (s, 2H), 6.94 (s, 1H), 4.39 (t, J=5.2 Hz, 2H), 3.70-3.63 (m, 2H).

Step 5

N-((1,2,3,5,6,7-hexahydro-s-indacen-4-yl)carbamoyl)-4-oxo-4,5,6,7-tetrahydropyrazolo[1,5-a]pyrazine-2-sulfonamide was synthesized as described in Preparation F to deliver the desired product (8.3 mg, 4.3%) as a white solid.

$^1$H NMR (400 MHz, DMSO-$d_6$): δ=8.37 (s, 1H), 7.81 (s, 1H), 7.11 (s, 1H), 6.92 (s, 1H), 6.85 (s, 1H), 4.33 (t, J=6.0 Hz, 2H), 3.65-3.61 (m, 2H), 2.76 (t, J=7.2 Hz, 4H), 2.63 (t, J=6.8 Hz, 4H), 1.96-1.88 (m, 4H). MS: m/z 414.1 (M−H$^+$).

Example 61

Synthesis of N-((1,2,3,5,6,7-hexahydro-s-indacen-4-yl)carbamoyl)-5-methyl-4-oxo-4,5,6,7-tetrahydropyrazolo[1,5-a]pyrazine-2-sulfonamide is shown below.

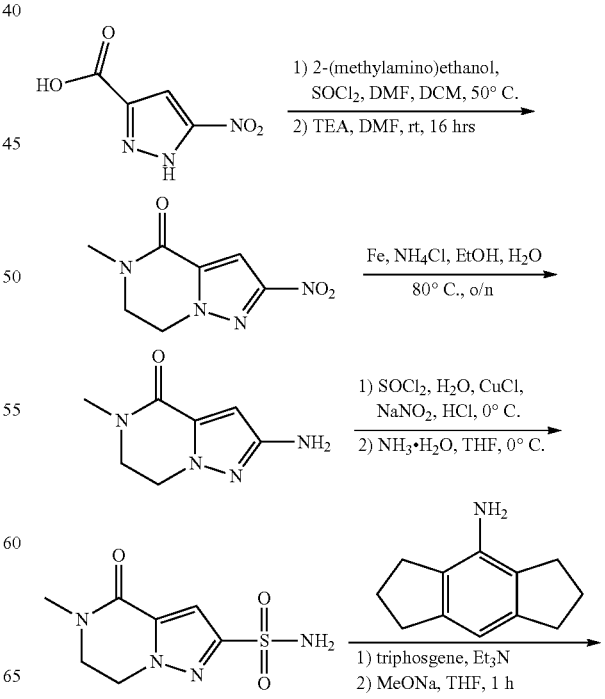

-continued

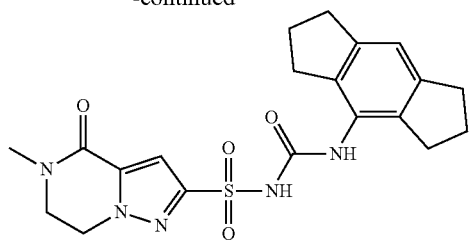

Step 1

To a solution of 5-nitro-1H-pyrazole-3-carboxylic acid (5.0 g, 31.8 mmol) and 2-(methylamino)ethanol (3.58 g, 47.7 mmol) in DCM (50 mL) was added dropwise SOCl₂ (11.5 mL, 159 mmmol) and DMF (4 drops) at −5° C. for 10 min. Then the reaction mixture was stirred at 50° C. overnight. The reaction mixture was concentrated in vacuo. The residue was added into DMF (50 mL) and TEA (13.3 mL, 95.4 mmol). The reaction was then stirred at 60° C. overnight. After removal of solvent in vacuo, the residue was purified by silica gel column chromatography (DCM/MeOH=50/1~10/1) to give 5-methyl-2-nitro-6,7-dihydropyrazolo[1,5-a]pyrazin-4(5H)-one (4.66 g, 75%) as a yellow solid.

$^1$H NMR (400 MHz, DMSO-d₆): δ=7.42 (s, 1H), 4.53 (t, J=6.0 Hz, 2H), 3.87 (t, J=6.8 Hz, 2H), 3.03 (s, 3H).

Step 2

To a solution of 5-methyl-2-nitro-6,7-dihydropyrazolo[1,5-a]pyrazin-4(5H)-one (700 mg, 3.6 mmol) in EtOH (20 mL) was added iron powder (1.0 g, 17.9 mmol), NH₄Cl (0.96 g, 17.9 mmol) and H₂O (7 mL). The reaction mixture was stirred at 80° C. under N₂ atmosphere overnight and was monitored by LCMS. The reaction mixture was filtered, and filtrate was concentrated in vacuo. The crude product was purified by silica gel column chromatography (DCM/MeOH=50/1~10/1) to give 2-amino-5-methyl-6,7-dihydropyrazolo[1,5-a]pyrazin-4(5H)-one (0.44 g, 73%) as a yellow solid.

$^1$H NMR (400 MHz, DMSO-d₆): δ=5.80 (s, 1H), 4.85 (brs, 2H), 4.08 (t, J=6.0 Hz, 2H), 3.87 (t, J=6.4 Hz, 2H), 2.95 (s, 3H).

Step 3

To a suspension of CuCl (0.204 g, 2.1 mmol) in H₂O (265 mL) was added dropwise SOCl₂ (44.85 mL, 0.618 mol) at −5° C. with vigorous stirring. The solution was stirred at room temperature overnight to give a light yellow solution. Separately, to a solution of 2-amino-5-methyl-6,7-dihydropyrazolo[1,5-a]pyrazin-4(5H)-one (100 mg, 0.6 mmol) in conc. HCl (0.97 mL) was added dropwise a solution of NaNO₂ (50 mg, 0.72 mmol) in H₂O (2 mL) at −10° C. The resulting dark orange solution was stirred at −10° C. for 30 minutes and then added to the above solution (1.6 mL) of copper (I) chloride at −5° C. over 5 minutes. The reaction was stirred at −5° C. for 1 hr and extracted with EA (10 mL×3). The organic layer was concentrated in vacuo to give a yellow solid. This solid was added THF (5 mL), followed added dropwise NH₃ (3 mL, 28% wt) at −5° C. The reaction was stirred for 2 hrs at 0° C. then concentrated in vacuo. The resulting solid was purified by silica gel column chromatography (DCM/MeOH=10/1) to give 5-methyl-4-oxo-4,5, 6,7-tetrahydropyrazolo[1,5-a]pyrazine-2-sulfonamide (42 mg, 30%) as a yellow solid.

$^1$H NMR (400 MHz, DMSO-d₆): δ=7.60 (s, 2H), 6.93 (s, 1H), 4.46 (t, J=6.0 Hz, 2H), 3.87 (t, J=6.4 Hz, 2H), 3.01 (s, 3H).

Step 4

N-((1,2,3,5,6,7-hexahydro-s-indacen-4-yl)carbamoyl)-5-methyl-4-oxo-4,5,6,7-tetrahydropyrazolo[1,5-a]pyrazine-2-sulfonamide was synthesized as described in Preparation E to deliver the desired product (21.8 mg, 12%) as a white solid.

$^1$H NMR (400 MHz, DMSO-d₆): δ=7.70 (s, 1H), 7.13 (s, 1H), 6.86 (s, 1H), 6.82 (s, 1H), 4.39 (t, J=6.0 Hz, 2H), 3.78 (t, J=6.4 Hz, 2H), 3.34 (s, 3H), 2.76 (t, J=7.2 Hz, 4H), 2.64 (t, 7=7.2 Hz, 4H), 1.96-1.86 (m, 4H). MS: m/z 430.0 (M+H⁺).

Example 62

Synthesis of N-((1,2,3,5,6,7-hexahydro-s-indacen-4-yl)carbamoyl)-4-oxo-4,5,6,7-tetrahydropyrazolo[1,5-a]pyrazine-3-sulfonamide is shown below.

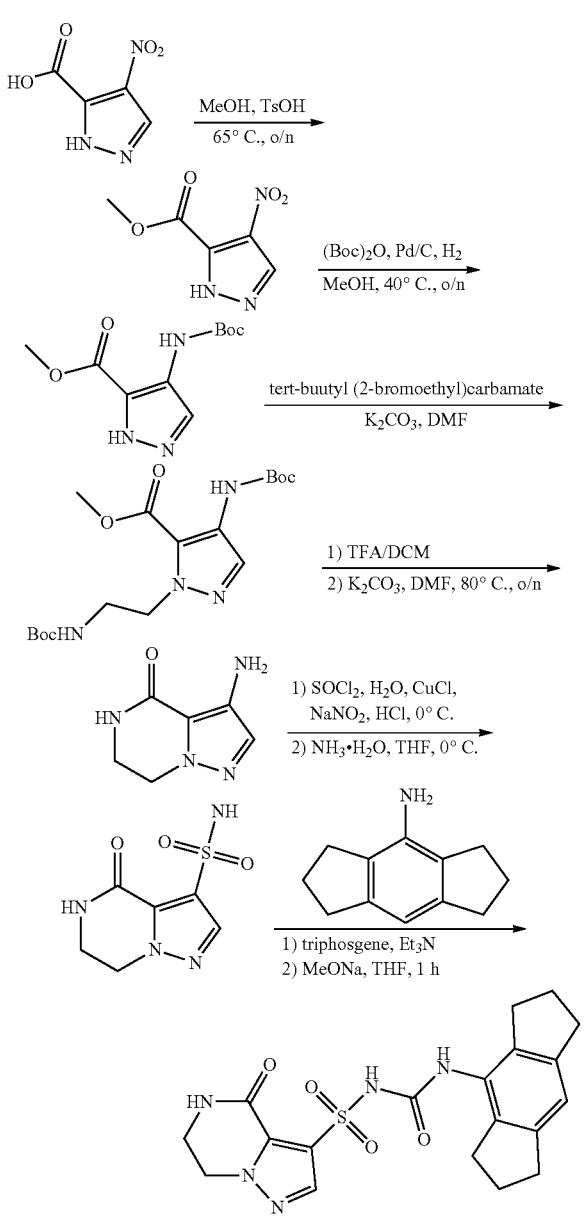

Step 1

To a solution of 4-nitro-1H-pyrazole-5-carboxylic acid (1.0 g, 6.4 mmol) in MeOH (30 mL) was added TsOH (52 mg, 0.3 mmol). Then the reaction mixture was stirred at 65° C. overnight. The reaction mixture was concentrated in vacuo. The residue was purified by silica gel column chromatography (DCM/MeOH=40/1~10/1) to give methyl 4-nitro-1H-pyrazole-5-carboxylate (1.0 g, 91%) as a white solid.

$^{1}$H NMR (400 MHz, DMSO-d$_{6}$): δ=8.90 (s, 1H), 3.88 (s, 3H).

Step 2

To a solution of 4-nitro-1H-pyrazole-5-carboxylate (3.0 g, 17.5 mmol) in MeOH (100 mL) was added (Boc)$_2$O (4.2 g, 19.25 mmol) and Pd/C (300 mg, 10% wt). Then the reaction mixture was stirred at 40° C. overnight under H$_2$ atmosphere and was monitored by LCMS. The reaction mixture was filtered and the filtrate was concentrated in vacuo. The residue was purified by silica gel column chromatography (PE/EA=2/1~1/1) to give methyl 4-((tert-butoxycarbonyl)amino)-1H-pyrazole-5-carboxylate (2.52 g, 60%) as a white solid.

Step 3

To a solution of methyl 4-((tert-butoxycarbonyl)amino)-1H-pyrazole-5-carboxylate (4.2 g, 17.4 mmol) in DMF (50 mL) was added tert-butyl (2-bromoethyl)carbamate (5.8 g, 26.1 mmol) and K$_2$CO$_3$ (7.2 g, 52.2 mmol). Then the reaction mixture was stirred at 80° C. for overnight and was monitored by LCMS. The reaction mixture was filtered, and the filtrate was concentrated in vacuo. The residue was purified by silica gel column chromatography (PE/EA=3/1) to give methyl 4-((tert-butoxycarbonyl)amino)-1-(2-((tert-butoxycarbonyl)amino)ethyl)-1H-pyrazole-5-carboxylate (1.26 g, 19%) as a yellow oil.

$^{1}$H NMR (400 MHz, DMSO-d$_{6}$): δ=8.16 (s, 1H), 7.80 (s, 1H), 6.81 (t, J=6.8 Hz, 1H), 4.40 (t, J=6.4 Hz, 2H), 3.86 (s, 3H), 3.29-3.22 (m, 2H), 1.46 (s, 9H), 1.33 (s, 9H).

Step 4

To a solution of methyl 4-((tert-butoxycarbonyl)amino)-1-(2-((tert-butoxycarbonyl)amino)ethyl)-1H-pyrazole-5-carboxylate (1.26 g, 3.3 mmol) in DCM (20 mL) was added CF$_3$CO$_2$H (2.4 mL, 33 mmol). Then the reaction mixture was stirred at room temperature overnight and was monitored by LCMS. The reaction mixture was concentrated in vacuo. The residue was added to the suspension of DMF (20 mL) and K$_2$CO$_3$ (1.36 mg, 9.9 mmol). The reaction mixture was stirred at 80° C. overnight and was monitored by LCMS. The reaction mixture was filtered, and filtrate was concentrated in vacuo. The residue was purified by silica gel column chromatography (DCM/MeOH=20/1~10/1) to give 3-amino-6,7-dihydropyrazolo[1,5-a]pyrazin-4(5H)-one (354 mg, 71%) as a white solid.

$^{1}$H NMR (400 MHz, DMSO-d$_{6}$): δ=7.75 (brs, 1H), 7.00 (s, 1H), 4.68 (brs, 2H), 4.08 (d, J=5.6 Hz, 2H), 3.55-3.47 (m, 2H).

Step 5

To a suspension of CuCl (0.204 g, 2.1 mmol) in H$_2$O (265 mL) was added dropwise SOCl$_2$ (44.85 mL, 0.618 mol) at 0° C. with vigorous stirring. The solution was stirred at room temperature overnight to give a light yellow solution. Separately, to a solution of 3-amino-6,7-dihydropyrazolo[1,5-a]pyrazin-4(5H)-one (155 mg, 1.02 mmol) in conc. HCl (1 mL) was added dropwise a solution of NaNO$_2$ (84.4 mg, 1.23 mmol) in H$_2$O (2 mL) at −10° C. The resulting dark orange solution was stirred at −10° C. for 30 minutes and then added to the above solution (2.65 mL) of copper (I) chloride at −5° C. over 5 minutes. The reaction was stirred at −5° C. for 1 hr and then extracted with EA (10 mL×3). The organic layer was concentrated in vacuo to give a yellow solid. This solid was dissolved in THF (5 mL), followed by dropwise addition of NH$_3$ (4 mL, 28% wt) at 0° C. The reaction was stirred for 2 hrs at 0° C. and then concentrated in vacuo. The resulting solid was purified by prep-TLC (DCM/MeOH=10/1) to give 4-oxo-4,5,6,7-tetrahydropyrazolo[1,5-a]pyrazine-3-sulfonamide (5 mg, 2.2%) as a yellow solid.

Step 6

N-((1,2,3,5,6,7-hexahydro-s-indacen-4-yl)carbamoyl)-4-oxo-4,5,6,7-tetrahydropyrazolo[1,5-a]pyrazine-3-sulfonamide was synthesized as described in Preparation E to deliver the desired product (1.1 mg, 5.8%) as a yellow solid.

$^{1}$H NMR (400 MHz, DMSO-d$_{6}$): δ=8.64 (s, 1H), 8.15 (s, 1H), 7.85 (s, 1H), 6.87 (s, 1H), 4.38 (d, J=5.6 Hz, 2H), 3.65-3.59 (m, 2H), 2.77 (t, J=6.8 Hz, 4H), 2.57 (t, J=7.2 Hz, 4H), 1.97-1.87 (m, 4H). MS: m/z 416.1 (M+H$^{+}$).

Example 63

Synthesis of N-((1,2,3,5,6,7-hexahydro-s-indacen-4-yl)carbamoyl)-5-methyl-4-oxo-4,5,6,7-tetrahydropyrazolo[1,5-a]pyrazine-3-sulfonamide is shown below.

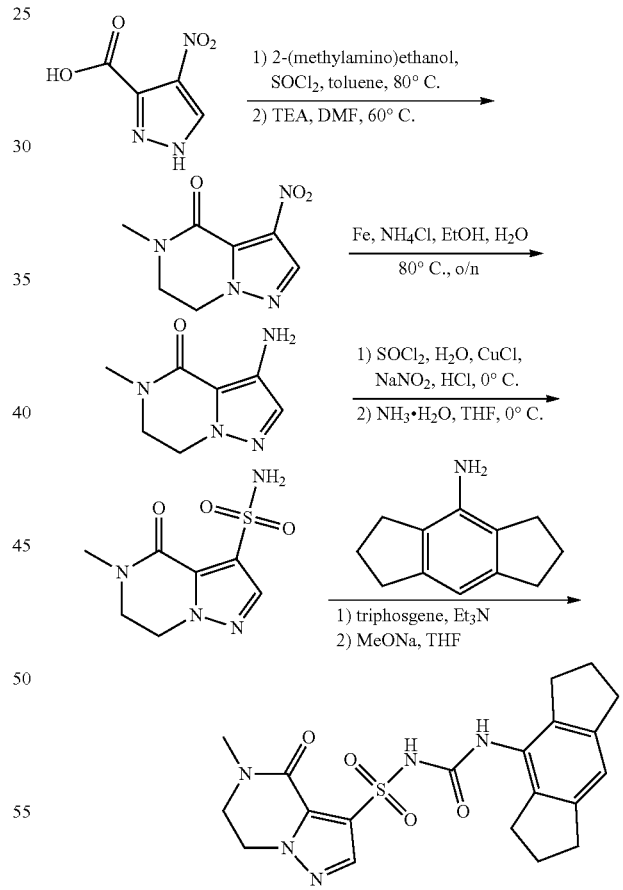

Step 1

To a solution of 4-nitro-1H-pyrazole-5-carboxylic acid (1.0 g, 6.4 mmol) and 2-(methylamino)ethanol (0.55 g, 7.3 mmol) in toluene (5 mL) was added dropwise SOCl$_2$ (20 mL) and DMF (3 drops) at −5° C. for 10 min. Then the reaction mixture was stirred at 80° C. overnight. The reaction mixture was concentrated in vacuo. The residue was dissolved in DMF (20 mL) and TEA (2.7 mL, 19.3 mmol).

The reaction was then stirred at 60° C. overnight and was monitored by LCMS. After removal of solvent in vacuo, the residue was purified by silica gel column chromatography (PE/EA=3/1~1/1) to give 5-methyl-3-nitro-6,7-dihydropyrazolo[1,5-a]pyrazin-4(5H)-one (0.7 g, 56%) as a yellow solid.

$^1$H NMR (400 MHz, DMSO-d$_6$): δ=8.34 (s, 1H), 4.47 (t, J=5.6 Hz, 2H), 3.85 (t, J=6.4 Hz, 2H), 3.05 (s, 3H).

Step 2

To a solution of 5-methyl-3-nitro-6,7-dihydropyrazolo[1,5-a]pyrazin-4(5H)-one (3.52 g, 18 mmol) in EtOH (75 mL) was added iron powder (5.04 g, 90 mmol), NH$_4$Cl (4.82 g, 90 mmol) and H$_2$O (25 mL). The reaction mixture was stirred at 80° C. under N$_2$ atmosphere overnight and was monitored by LCMS. The reaction mixture was filtered, and filtrate was concentrated in vacuo. The crude product was purified by silica gel column chromatography (DCM/MeOH=10/1) to give 3-amino-5-methyl-6,7-dihydropyrazolo[1,5-a]pyrazin-4(5H)-one (2.58 g, 86%) as a yellow solid.

$^1$H NMR (400 MHz, DMSO-d$_6$): δ=7.01 (s, 1H), 4.76 (s, 2H), 4.16 (t, J=6.0 Hz, 2H), 3.66 (t, J=6.4 Hz, 2H), 2.94 (s, 3H).

Step 3

SOCl$_2$ (20 mL) was added dropwise to water (70 mL) at −5° C. The solution was stirred at 5° C. for 1 hr and at room temperature for 1 hr. CuCl (0.16 g) was added to give a yellow solution. It was stirred at room temperature for 5 min then cooled to −10° C. Separately, to a solution of 3-amino-5-methyl-6,7-dihydropyrazolo[1,5-a]pyrazin-4(5H)-one (358 mg, 2.2 mmol) in conc. HCl (2.0 mL) was added dropwise a solution of NaNO$_2$ (180 mg, 2.62 mmol) in H$_2$O (1.6 mL) at −10° C. The resulting dark orange solution was stirred at −10° C. for 30 minutes and then added to the above solution (5.7 mL) of copper (I) chloride at −5° C. over 5 minutes. The reaction was stirred at −5° C. for 1 hr and then extracted with EA (5 mL×3). The organic layer was concentrated in vacuo to give a yellow solid. This solid was dissolved in THF (5 mL), followed by the dropwise addition of NH$_3$ (3 mL, 28% wt) at −5° C. The reaction was stirred for 2 hrs at 0° C. and then concentrated in vacuo. The resulting solid was purified by prep-TLC (DCM/MeOH=10/1) to give 5-methyl-4-oxo-4,5,6,7-tetrahydropyrazolo[1,5-a]pyrazine-3-sulfonamide (30 mg, 6%) as a yellow solid.

$^1$H NMR (400 MHz, DMSO-d$_6$): δ=7.86 (s, 1H), 7.18 (s, 2H), 4.48 (t, J=6.0 Hz, 2H), 3.87 (t, J=6.4 Hz, 2H), 3.06 (s, 3H).

Step 4

NaH (6.24 mg, 0.156 mmol, 60% dispersion in paraffin liquid) in DMSO (2 mL) was stirred at 70° C. for 30 min. Then 5-methyl-4-oxo-4,5,6,7-tetrahydropyrazolo[1,5-a]pyrazine-3-sulfonamide (30 mg, 0.13 mmol) was added to the solution of NaH in DMSO (2 mL) at −5° C. and was stirred at −5° C. for 30 min. Separately, to a solution of 1,2,3,5,6,7-hexahydro-5-indacen-4-amine (24.8 mg, 0.14 mmol) in THF (5 mL) was added triphosgene (15.4 mg, 0.052 mmol) and TEA (0.1 mL) at −5° C. Then the reaction mixture was stirred at −5° C. for 30 min and was monitored by TCL. This reactant was filtered and the filtrate was added to the above suspension of sodium ((5-methyl-4-oxo-4,5,6,7-tetrahydropyrazolo[1,5-a]pyrazin-3-yl)sulfonyl)amide at −5° C. The reaction was stirred at room temperature overnight and was monitored by LC-MS. The reaction was then washed with saturated aqueous NH$_4$Cl (5 mL×3). The organic layer was dried over anhydrous Na$_2$SO$_4$, and concentrated in vacuo. The residue was purified by prep-HPLC to give N-((1,2,3,5,6,7-hexahydro-s-indacen-4-yl)carbamoyl)-5-methyl-4-oxo-4,5,6,7-tetrahydropyrazolo[1,5-a]pyrazine-3-sulfonamide (12.8 mg, 25%) as a white solid.

$^1$H NMR (400 MHz, DMSO-d$_6$): δ=8.27 (brs, 1H), 7.91 (s, 1H), 6.90 (s, 1H), 4.47 (t, J=5.6 Hz, 2H), 3.83 (t, J=6.0 Hz, 2H), 3.06 (s, 3H), 2.77 (t, J=6.8 Hz, 4H), 2.55 (t, J=7.6 Hz, 4H), 1.99-1.88 (m, 4H). MS: m/z 430.1 (M+H$^+$).

Example 64

Synthesis of N-((1,2,3,5,6,7-Hexahydro-s-indacen-4-yl)carbamoyl)-4,5,6,7-tetrahydropyrazolo[1,5-a]pyrimidine-3-sulfonamide is shown below.

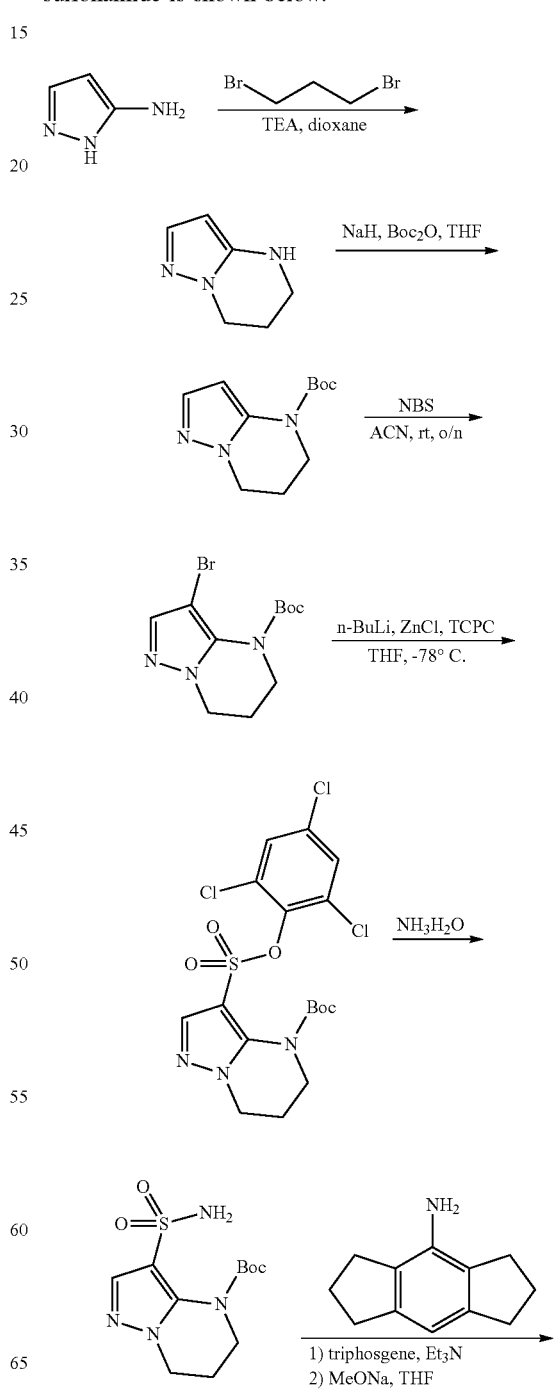

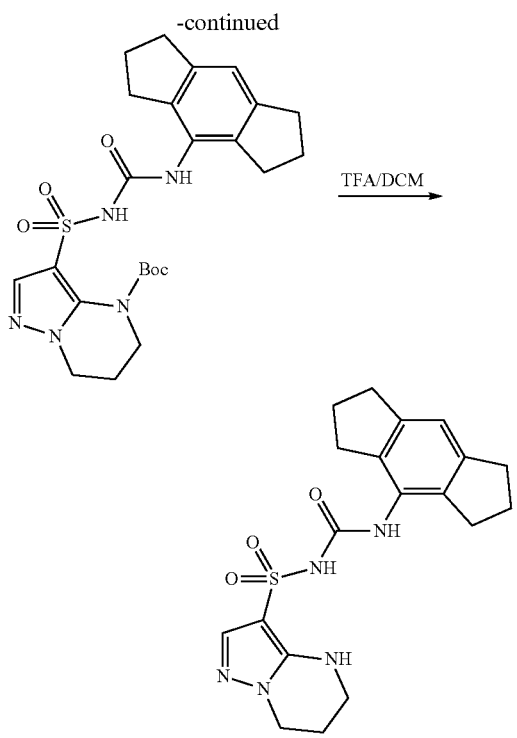

Step 1

To a solution of 1H-pyrazol-5-amine (9.8 g, 0.1 mol) and TEA (36.0 g, 0.3 mmol) in 1,4-dioxane (200 mL) was added 1,3-dibromopropane (26.3 g, 0.1 mmol). After stirring at 110° C. for 5 hrs, the reaction mixture was filtered. The filtration was concentrated to dryness. The residue was purified by silica gel column (DCM/MeOH=100/1) to give 4,5,6,7-tetrahydropyrazolo[1,5-a]pyrimidine (5.3 g, yield: 36%) as a white solid.

$^1$H NMR (300 MHz, CDCl$_3$): δ=7.18 (s, 1H), 5.26 (s, 1H), 4.22-4.00 (m, 3H), 3.26-3.22 (m, 2H), 2.11-2.03 (m, 2H).

Step 2

To a solution of 4,5,6,7-tetrahydropyrazolo[1,5-a]pyrimidine (3.0 g, 24.4 mmol) in THF (20 mL) was added NaH (60% in mineral oil, 1.5 g, 36.6 mmol). The reaction was stirred at room temperature for 1 hr under N$_2$. Then Boc$_2$O (8.0 g, 36.6 mmol) was added and the mixture was stirred at room temperature for 16 hrs. The reaction mixture was poured into water (60 mL) and extracted with EA (50 mL×2). The organic layer was washed with water (50 mL) and brine (50 mL), dried over Na$_2$SO$_4$ and concentrated. The residue was purified by silica gel column (DCM/MeOH=100/1) to give tert-butyl 6,7-dihydropyrazolo[1,5-a]pyrimidine-4(5H)-carboxylate (4.4 g, yield: 81%) as a white solid.

$^1$H NMR (300 MHz, CDCl$_3$): δ=7.37 (s, 1H), 6.28 (s, 1H), 4.21-4.16 (m, 2H), 3.86-3.80 (m, 2H), 2.20-2.15 (m, 2H), 1.57 (s, 9H). MS: m/z 224.4 (M+H$^+$).

Step 3

NBS (4.2 g, 23.5 mmol) was added in portions to a solution of tert-butyl 6,7-dihydropyrazolo[1,5-a]pyrimidine-4(5H)-carboxylate (4.4 g, 19.6 mmol) in MeCN (20 mL) at 0° C. and the reaction was stirred at room temperature for 16 hrs. The reaction mixture was poured into water (40 mL) and extracted with EA (40 mL×2). The organic layer was washed with water (40 mL) and brine (40 mL), dried over Na$_2$SO$_4$ and concentrated. The residue was purified by silica gel column (PE/EA=1/1) to give tert-butyl 3-bromo-6,7-dihydropyrazolo[1,5-a]pyrimidine-4(5H)-carboxylate (4.1 g, yield: 69%) as a yellow solid. MS: m/z 304.3 (M+H$^+$).

Step 4 tert-Butyl 3-((2,4,6-trichlorophenoxy)sulfonyl)-6,7-dihydropyrazolo[1,5-a]pyrimidine-4(5H)-carboxylate was synthesized using Preparation B to yield the product as a yellow oil which was used for next step without purification.

Step 5

A mixture of tert-butyl 3-((2,4,6-trichlorophenoxy)sulfonyl)-6,7-dihydropyrazolo[1,5-a]pyrimidine-4(5H)-carboxylate (crude, ~1.85 mmol), NH$_4$OH (5 mL) and THF (20 mL) was stirred at 60° C. for 12 hrs. The reaction was concentrated under reduced pressure. The remained solution was acidified with aq.HCl (1 N) to pH=5 and partitioned between EA (60 mL) and water (60 mL). The organic layer was washed with water (60 mL), brine (60 mL), dried over Na$_2$SO$_4$ and concentrated. The residue was purified by silica gel column (PE/EA=1/1) to give tert-butyl 3-sulfamoyl-6,7-dihydropyrazolo[1,5-a]pyrimidine-4(5H)-carboxylate (100 mg, yield: 18% over 2 steps) as a white solid.

$^1$H NMR (300 MHz, CDCl$_3$): δ=7.80 (s, 1H), 5.54 (brs, 2H), 4.23 (t, J=6.3 Hz, 2H), 3.96 (t, J=6.0 Hz, 2H), 2.23-2.19 (m, 2H), 1.57 (s, 9H). MS: m/z 303.1 (M+H$^+$).

Step 6

To a solution of 1,2,3,5,6,7-hexahydro-s-indacen-4-ylamine (68.7 mg, 0.397 mmol) and TEA (0.16 mL, 1.2 mmol) in THF (5 mL) was added triphosgene (47.2 mg, 0.16 mmol). The mixture was stirred for 20 minutes at room temperature. In another round-bottomed flask, to a solution of tert-butyl 3-sulfamoyl-6,7-dihydropyrazolo[1,5-a]pyrimidine-4(5H)-carboxylate (120 mg, 0.397 mmol) in THF (5 ml) was added MeONa (23.6 mg, 0.436 mmol) and the mixture was stirred for 20 minutes at room temperature. The prepared 4-isocyanato-1,2,3,5,6,7-hexahydro-s-indacene was filtered to remove the resulting precipitate and the filtrate was added to another flask containing sulfonamide salt. The reaction was quenched with the addition of water (30 mL) after 30 minutes. The aqueous phase was extracted with EA (20 mL) and filtered. The filtrate was acidified to pH=3~4, and it was extracted with EA (20 mL×2) to give tert-butyl 3-(N-((1,2,3,5,6,7-hexahydro-s-indacen-4-yl)carbamoyl)sulfamoyl)-6,7-dihydropyrazolo[1,5-a]pyrimidine-4(5H)-carboxylate (32 mg, yield: 16%) as a white solid.

Step 7

To a solution of tert-butyl 3-(N-((1,2,3,5,6,7-hexahydro-s-indacen-4-yl)carbamoyl)sulfamoyl)-6,7-dihydropyrazolo[1,5-a]pyrimidine-4(5H)-carboxylate (32 mg, 0.064 mmol) in DCM (2 mL) was added TFA (1 mL) and the mixture solution was stirred for 30 minutes at room temperature. The reaction was monitored by LC-MS, and the reaction mixture was concentrated to dryness in vacuo. The residue was purified by prep-HPLC (NH3H2O) to give N-((1,2,3,5,6,7-hexahydro-s-indacen-4-yl)carbamoyl)-4,5,6,7-tetrahydropyrazolo[1,5-a]pyrimidine-3-sulfonamide (11.6 mg, yield: 45%) as a white solid.

$^1$H NMR (300 MHz, DMSO-d$_6$): δ=8.01 (s, 1H), 7.39 (s, 1H), 6.92 (s, 1H), 6.42 (s, 1H), 3.96 (t, J=5.6 Hz, 2H), 3.25-3.23 (m, 2H), 2.79 (t, J=7.6 Hz, 4H), 2.60 (t, J=7.2 Hz, 4H), 1.97-1.91 (m, 6H). MS: m/z 402.0 (M+H$^+$).

Example 65

Synthesis of N-((1,2,3,5,6,7-hexahydro-s-indacen-4-yl)carbamoyl)-4,5,6,7-tetrahydropyrazolo[1,5-a]pyrazine-2-sulfonamide trifluoroacetic acid is shown below.

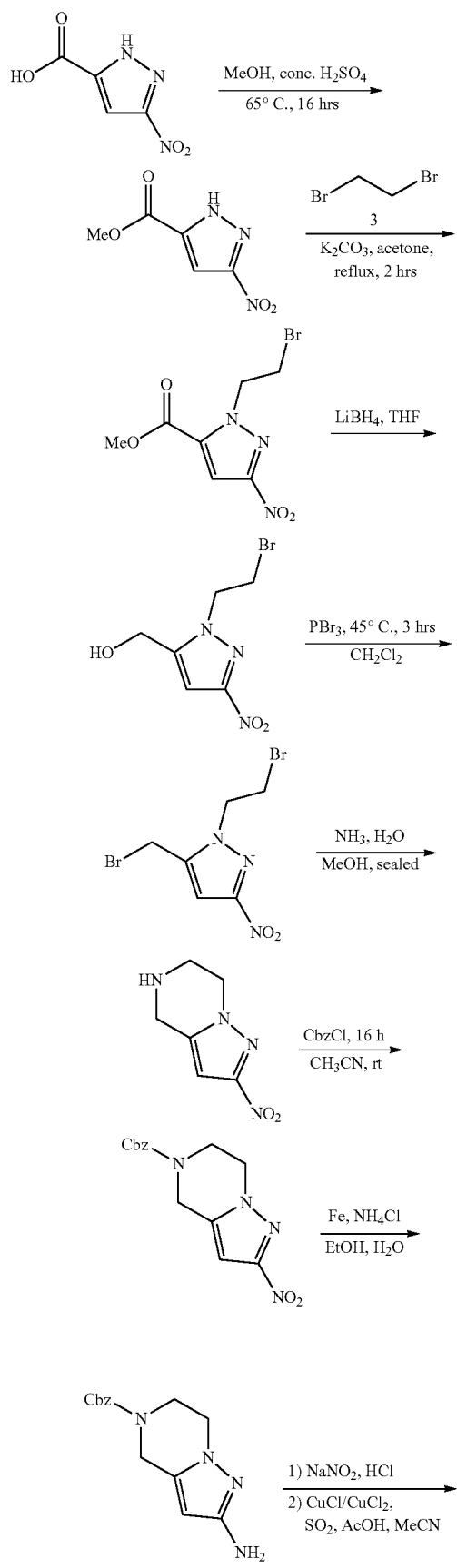

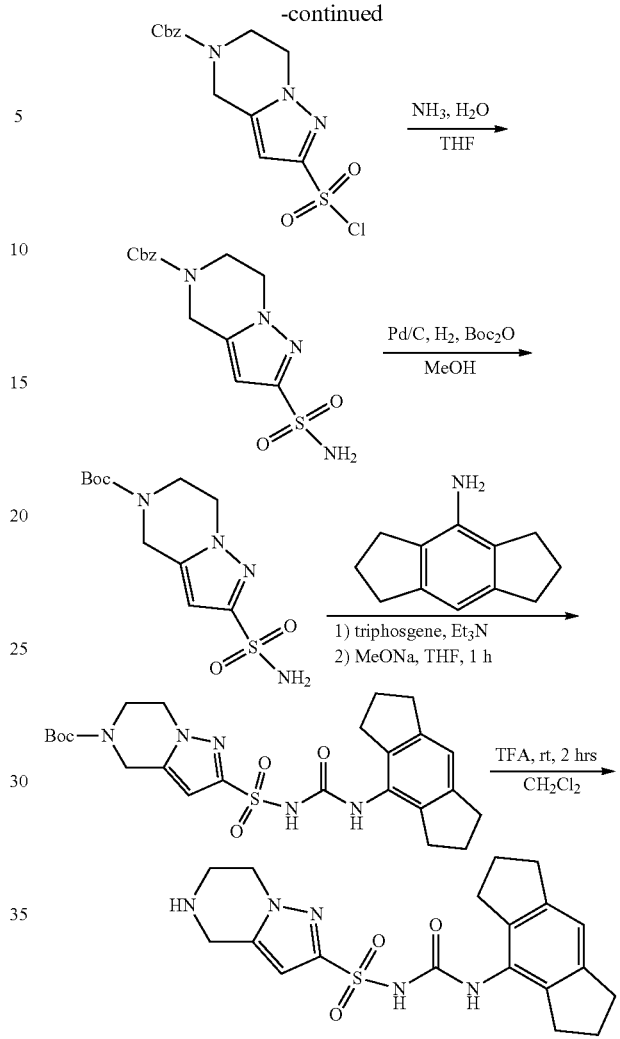

Step 1

To a solution of 3-nitro-1H-pyrazole-5-carboxylic acid (1.57 g, 10.0 mmol) in MeOH (20 mL) was added conc.H$_2$SO$_4$ (2.0 mL). The resulting mixture was stirred at 65° C. overnight. Then the mixture was concentrated in vacuo to give a residue, which was purified by silica gel column (DCM/MeOH=50/1) to afford methyl 3-nitro-1H-pyrazole-5-carboxylate (1.42 g, yield: 83%) as yellow solid.

$^1$H NMR (400 MHz, DMSO-d$_6$): δ=15.24 (brs, 1H), 7.54 (s, 1H), 3.90 (s, 3H).

Step 2

To a solution of methyl 3-nitro-1H-pyrazole-5-carboxylate (342 mg, 2.0 mmol) in acetone (40 mL) was added 1,2-dibromoethane (412 mg, 2.2 mmol), followed by K$_2$CO$_3$ (828 mg, 6.0 mmol). The resulting mixture was stirred to reflux for 2 hrs. Then K$_2$CO$_3$ was filtered off. The filtrate was concentrated in vacuo to give a residue, which was purified by silica gel column (DCM/MeOH=50/1) to afford methyl 1-(2-bromoethyl)-3-nitro-1H-pyrazole-5-carboxylate (430 mg, yield: 77%) as yellow solid.

$^1$H NMR (400 MHz, CDCl$_3$): δ=7.42 (s, 1H), 5.08 (t, J=6.4 Hz, 2H), 3.97 (s, 3H), 3.78 (t, 7=6.4 Hz, 2H).

Step 3

To a solution of 1-(2-bromoethyl)-3-nitro-1H-pyrazole-5-carboxylate (278 mg, 1.0 mmol) in dry THF (20 mL) was added LiBH$_4$ (2 mL, 2.0 M in THF) at 0° C. The resulting mixture was stirred from 0° C. to room temperature for 3 hrs. Then the reaction was quenched by addition of MeOH (4 mL). The mixture was concentrated in vacuo to give a residue, which was purified by silica gel column (DCM/MeOH=100/1) to afford (1-(2-bromoethyl)-3-nitro-1H-pyrazol-5-yl)methanol (122 mg, yield: 49%) as white solid.

$^1$H NMR (400 MHz, DMSO-d$_6$): δ=6.99 (s, 1H), 5.69 (t, J=5.6 Hz, 1H), 4.66 (t, J=6.0 Hz, 2H), 4.61 (d, 7=5.6 Hz, 2H), 3.91 (t, J=6.4 Hz, 2H).

Step 4

A mixture of [2-(2-Bromo-ethyl)-5-nitro-2H-pyrazol-3-yl]-methanol (3.0 g, 12.0 mmol), PBr$_3$ (4.9 g, 18.0 mmol) and CH$_2$Cl$_2$ (50 mL) was stirred at 45° C. for 3 hrs. The reaction was neutralized with sat. NaHCO$_3$ and extracted with CH$_2$Cl$_2$ (60 mL) and the combined organic layer was washed with brine (50 mL), dried over Na$_2$SO$_4$, filtered and concentrated in vacuo to dryness to give 1-(2-bromo-ethyl)-5-bromomethyl-3-nitro-1H-pyrazole (2.2 g, yield: 58%) as a light yellow solid.

$^1$H NMR (300 MHz, CDCl$_3$): δ=6.93 (s, 1H), 4.63 (t, J=3.8 Hz, 2H), 4.53 (s, 2H), 3.86 (t, 7=4.2 Hz, 2H).

Step 5

A mixture of 1-(2-bromo-ethyl)-5-bromomethyl-3-nitro-1H-pyrazole (1.5 g, 4.8 mmol), NH$_3$H$_2$O (8 mL) and MeOH (10 mL) was stirred at 50° C. for 16 hrs in sealed tube. The reaction mixture was concentrated in vacuo to dryness to give 2-nitro-4,5,6,7-tetrahydro-pyrazolo[1,5-a]pyrazine (700 mg, yield: 87%) as a white solid.

MS: m/z 169.0 (M+H$^+$).

Step 6

A mixture of 2-nitro-4,5,6,7-tetrahydro-pyrazolo[1,5-a]pyrazine (700 mg, 4.2 mmol), CbzCl (700 mg, 4.2 mmol), K$_2$CO$_3$ (1.2 g, 8.4 mmol) and CH$_3$CN (20 mL) was stirred at room temperature for 16 hrs. The reaction mixture was concentrated in vacuo to dryness. The residue was purified by silica gel column (PE/EA=5/1 to 1/1) to give 2-nitro-6,7-dihydro-4H-pyrazolo[1,5-a]pyrazine-5-carboxylic acid benzyl ester (900 mg, yield: 69%) as a yellow solid.

Step 7

A mixture of 2-nitro-6,7-dihydro-4H-pyrazolo[1,5-a]pyrazine-5-carboxylic acid benzyl ester (710 mg, 2.4 mmol), Fe (658 mg, 11.8 mmol), NH$_4$Cl (637 mg, 11.8 mmol), H$_2$O (10 mL) and EtOH (20 mL) was stirred at 80° C. for 16 hrs. The reaction mixture was filtered through a celite-pad and rinsed with CH$_2$Cl$_2$ (30 mL). The filtrate solution was concentrated to dryness to give 2-amino-6,7-dihydro-4H-pyrazolo[1,5-a]pyrazine-5-carboxylic acid benzyl ester (639 mg, yield: 98%) as a yellow oil.

Step 8

A solution of benzyl 2-amino-6,7-dihydropyrazolo[1,5-a]pyrazine-5(4H)-carboxylate (639 mg, 2.4 mmol) in MeCN (8 mL) at 0° C. was treated with conc.HCl (3.0 mL) in H$_2$O (1.2 mL) followed by aqueous solution of NaNO$_2$ (198 mg, 2.9 mmol) dissolved in H$_2$O (0.9 mL). The resulting solution was stirred at 0° C. for 45 mins. AcOH (1.2 mL), CuCl$_2$ (162 mg, 1.2 mmol) and CuCl (12 mg, 0.12 mmol) were sequentially added to the above mixture and purged with SO$_2$ gas for 25 mins at 0° C. After being stirred for 1 hr at 0° C., the reaction mixture was poured to ice-water (100 mL) and extracted with EA (40 mL×3). The combined organic layer was dried over Na$_2$SO$_4$, filtered and evaporated in vacuo to give benzyl 2-(chlorosulfonyl)-6,7-dihydropyrazolo[1,5-a]pyrazine-5(4H)-carboxylate (crude) as a yellow oil. This material was used for next step without further purification.

Step 9

To a solution of benzyl 2-(chlorosulfonyl)-6,7-dihydropyrazolo[1,5-a]pyrazine-5(4H)-carboxylate (crude) in THF (6 mL) was added NH$_3$H$_2$O (3 mL). After being stirred at room temperature for 20 mins, the reaction mixture was concentrated, diluted with MeOH (5 mL) and acidified by aq.HCl (1 N) to pH=5. The resulting solution was purified by reverse phase HPLC (0%-50% MeCN in H$_2$O) to give benzyl 2-sulfamoyl-6,7-dihydropyrazolo[1,5-a]pyrazine-5(4H)-carboxylate (122 mg, yield: 15%, two steps) as a white solid.

MS: m/z 337.0 (M+H$^+$).

Step 10

A solution of benzyl 2-sulfamoyl-6,7-dihydropyrazolo[1,5-a]pyrazine-5(4H)-carboxylate (102 mg, 0.3 mmol), Boc$_2$O (73 mg, 0.33 mmol) and Pd/C (20 mg) in MeOH (10 mL) was stirred at room temperature under a hydrogen atmosphere (50 psi) for 16 hrs. The reaction mixture was filtered and concentrated to dryness in vacuo. The residue was purified by silica gel column (CH$_2$Cl$_2$/MeOH=40/1) to give tert-butyl 2-sulfamoyl-6,7-dihydropyrazolo[1,5-a]pyrazine-5(4H)-carboxylate (106 mg, yield: 96%) as a yellow solid.

MS: m/z 303.0 (M+H$^+$).

Step 11 tert-Butyl 2-(N-((1,2,3,5,6,7-hexahydro-s-indacen-4-yl)carbamoyl)sulfamoyl)-6,7-dihydropyrazolo[1,5-a]pyrazine-5(4H)-carboxylate was synthesized as described in Preparation F to deliver the desired product (108 mg, crude) as a yellow solid.

MS: m/z 502.1 (M+H$^+$).

Step 12:

To a solution of tert-butyl 2-(N-((1,2,3,5,6,7-hexahydro-s-indacen-4-yl)carbamoyl)sulfamoyl)-6,7-dihydropyrazolo[1,5-a]pyrazine-5(4H)-carboxylate (68 mg, crude) in CH$_2$Cl$_2$ (1 mL) was added TFA (0.5 mL) and the mixture was stirred at room temperature for 30 mins. The resulting solution was purified by reverse phase HPLC (0%-50% MeCN in H$_2$O) to give N-((1,2,3,5,6,7-hexahydro-s-indacen-4-yl)carbamoyl)-4,5,6,7-tetrahydropyrazolo[1,5-a]pyrazine-2-sulfonamide TFA salt (7.9 mg, 15%) as a white solid.

$^1$H NMR (400 MHz, DMSO-d$_6$): δ=8.01 (s, 1H), 6.93 (s, 1H), 6.50 (s, 1H), 4.05 (t, J=4.8 Hz, 2H), 3.93 (s, 2H), 3.17 (t, J=5.2 Hz, 2H), 2.79 (t, J=7.2 Hz, 4H), 2.61 (t, J=7.6 Hz, 4H), 1.99-1.94 (m, 4H). MS: m/z 401.9 (M+H$^+$).

Example 66

Synthesis of N-((1,2,3,5,6,7-Hexahydro-s-indacen-4-yl)carbamoyl)-5-methyl-4,5,6,7-tetrahydropyrazolo[1,5-a]pyrazine-2-sulfonamide is shown below.

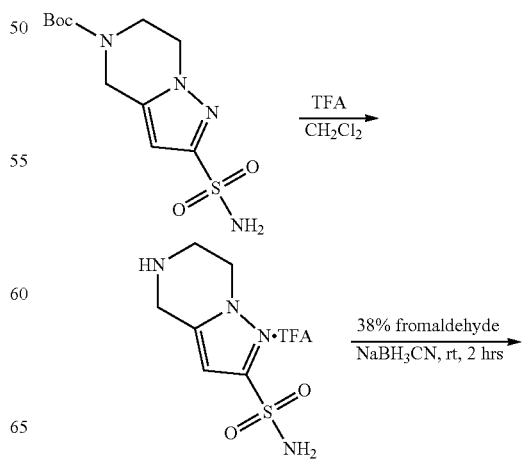

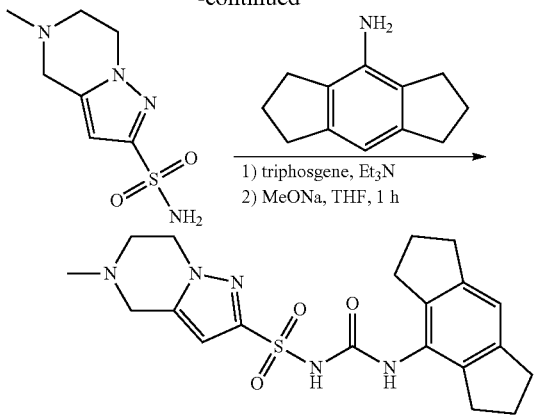

Step 1

To a solution of tert-butyl 2-sulfamoyl-6,7-dihydropyrazolo[1,5-a]pyrazine-5(4H)-carboxylate (60 mg, 0.2 mmol) in $CH_2Cl_2$ (1 mL) was added TFA (2 mL) and the mixture was stirred at room temperature for 30 mins. The resulting solution was purified by reverse phase HPLC (0%-50% MeCN in $H_2O$) to give 4,5,6,7-tetrahydropyrazolo[1,5-a]pyrazine-2-sulfonamide TFA salt (50 mg, crude) as a brown solid. MS: m/z 202.9 (M+H$^+$).

Step 2

To a stirred solution of 4,5,6,7-tetrahydropyrazolo[1,5-a]pyrazine-2-sulfonamide TFA salt (45 mg, crude) in MeOH (10 mL) was added formaldehyde (40 mg, 1.3 mmol) and sodium cyanoborohydride (14 mg, 0.2 mmol). After being stirred at room temperature for 2 hrs. The reaction mixture was concentrated and purified by reverse phase column (0%-50% MeCN in $H_2O$) to give 5-methyl-4,5,6,7-tetrahydropyrazolo[1,5-a]pyrazine-2-sulfonamide (17 mg, yield: 32% as a white solid.

MS: m/z 217.0 (M+H$^+$).

Step 3:

N-((1,2,3,5,6,7-hexahydro-s-indacen-4-yl)carbamoyl)-5-methyl-4,5,6,7-tetrahydropyrazolo[1,5-a]pyrazine-2-sulfonamide was synthesized using Preparation A to deliver the desired product (9.6 mg, yield: 29%) as a white solid.

$^1$H NMR (400 MHz, DMSO-d$_6$): δ=10.80 (s, 1H), 8.02 (s, 1H), 6.94 (s, 1H), 6.55 (s, 1H), 4.16 (t, J=5.6 Hz, 2H), 3.62 (s, 2H), 2.89 (t, J=5.8 Hz, 2H), 2.79 (t, J=7.2 Hz, 4H), 2.60 (t, J=6.8 Hz, 4H), 2.40 (s, 3H), 1.99-1.93 (m, 4H). MS: m/z 416.1 (M+H$^+$).

Example 67

Synthesis of 4,4-Difluoro-N-((1,2,3,5,6,7-hexahydro-s-indacen-4-yl)carbamoyl)-4,5,6,7-tetrahydropyrazolo[1,5-a]pyridine-3-sulfonamide is shown below.

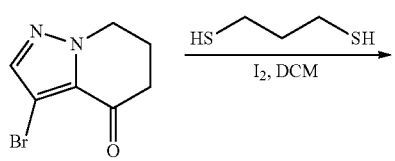

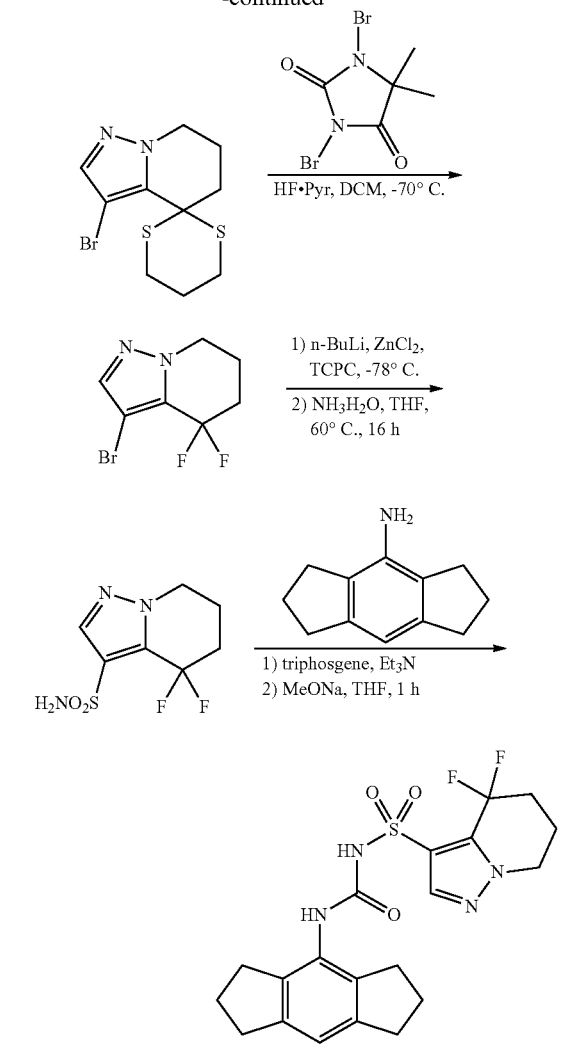

Step 1

To a solution of 3-bromo-6,7-dihydropyrazolo[1,5-a]pyridin-4(5H)-one (500 mg, 2.34 mmol) in DCM (5 mL) was added $I_2$ (58 mg, 0.23 mmol) and propane-1,3-dithiol (276 mg, 2.57 mmol), then the mixture was stirred at room temperature overnight. The reaction was then partitioned between DCM (20 mL) and water (20 mL). The organic layer was separated and the aqueous layer was extracted with DCM (20 mL). The combined organic layers were washed with brine (20 mL), dried over $Na_2SO_4$, filtered and concentrated in vacuo. The residue was purified by silica gel column (PE/EA=2/1) to give 3'-bromo-6',7'-dihydro-5'H-spiro[[1,3]dithiane-2,4'-pyrazolo[1,5-a]pyridine] (530 mg, yield: 75%) as a white solid.

Step 2

To a solution of 1,3-dibromo-5,5-dimethyl-imidazolidine-2,4-dione (1.61 g, 5.6 mmol) in DCM (5 mL) was added HF.pyridine (55%, 3.4 mL, 18.6 mmol) and 3'-bromo-6',7'-dihydro-5'H-spiro[[1,3]dithiane-2,4'-pyrazolo[1,5-a]pyridine] (430 mg, 1.4 mmol) at −70° C. After stirring at room temperature for 1 hour, the reaction was partitioned between DCM (20 mL) and water (20 mL). The organic layer was separated and the aqueous layer was extracted with DCM (20 mL). The organic layers were combined, washed with brine (20 mL), dried over Na₂SO₄, filtered and concentrated in vacuo. The residue was purified by silica gel column (PE/EA=5/1) to give 3-bromo-4,4-difluoro-4,5,6,7-tetrahydropyrazolo[1,5-a]pyridine (260 mg, yield: 57%) as a yellow oil. MS: m/z 236.9 (M+H⁺).

Step 3

To a solution of 3-bromo-4,4-difluoro-4,5,6,7-tetrahydropyrazolo[1,5-a]pyridine (0.26 g, 1.1 mmol) in dry THF (5 mL) was added n-BuLi in hexane (0.44 mL, 1.1 mmol, 2.5 M) slowly at −78° C. under N₂. After stirring at this temperature for 20 mins, ZnCl₂ in ether (1.1 mL, 1.1 mmol, 1 M) was added slowly at this temperature. The cold bath was removed and the reaction was stirred at r.t. for 1 hr. TCPC (0.33 g, 1.1 mmol) was added to the mixture at 0° C. and the mixture was stirred at r.t. for 1 hr. The reaction was quenched with saturated NH₄Cl solution (2 mL) and partitioned between water (20 mL) and EA (20 mL). The organic layer was washed with brine (80 mL), dried over Na₂SO₄ and concentrated to give crude 2,4,6-trichlorophenyl 4,4-difluoro-4,5,6,7-tetrahydropyrazolo[1,5-a]pyridine-3-sulfonate as a yellow oil. The crude was dissolved in THF (5 mL), and NH₃·H₂O (5 mL) was added to the solution. After stirring at 60° C. overnight, the reaction was concentrated to remove the solvent. The residue was acidified with 1 N HCl to pH=5 and partitioned between EA (20 mL) and water (20 mL). The organic layer was separated and the aqueous layer was extracted with EA (20 mL). The organic layers were combined, washed withe brine (30 mL), dried over Na₂SO₄, filtered and concentrated in vacuo. The residue was purified by silica gel column (PE/EA=2/1) to give 4,4-difluoro-4,5,6,7-tetrahydropyrazolo[1,5-a]pyridine-3-sulfonamide (50 mg, yield: 19% over 2 steps) as a yellow solid. MS: m/z 238 (M+H⁺).

Step 4

4,4-Difluoro-N-((1,2,3,5,6,7-hexahydro-s-indacen-4-yl)carbamoyl)-4,5,6,7-tetrahydropyrazolo[1,5-a]pyridine-3-sulfonamide was synthesized using Preparation A to deliver the desired product (26 mg, yield: 28%) as a white solid.

¹H NMR (400 MHz, DMSO-d₆): δ=10.65 (brs, 1H), 7.97 (s, 1H), 7.94 (s, 1H), 6.93 (s, 1H), 4.28 (t, J=5.6 Hz, 2H), 2.78 (t, J=6.8 Hz, 4H), 2.60 (t, J=6.8 Hz, 4H), 2.50 (overlap, 2H), 2.20-2.11 (m, 2H), 1.99-1.91 (m, 4H). MS: m/z 437.0 (M+H⁺).

Example 68

Synthesis of N-((8-Fluoro-1,2,3,5,6,7-hexahydro-s-indacen-4-yl)carbamoyl)-6,7-dihydro-5H-pyrazolo[5,1-b][1,3]oxazine-3-sulfonamide is shown below.

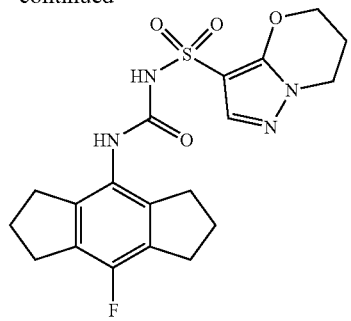

N-((8-fluoro-1,2,3,5,6,7-hexahydro-s-indacen-4-yl)carbamoyl)-6,7-dihydro-5H-pyrazolo[5,1-b][1,3]oxazine-3-sulfonamide was synthesized using Preparation A to deliver the desired product (210 mg, yield: 61%) as a white solid.

¹H NMR (400 MHz, DMSO-d₆): δ=10.51 (brs, 1H), 7.91 (s, 1H), 7.60 (s, 1H), 4.45 (t, J=5.2 Hz, 2H), 4.11 (t, J=6.4 Hz, 2H), 2.82 (t, J=7.6 Hz, 4H), 2.64 (t, J=6.8 Hz, 4H), 2.22-2.17 (m, 2H), 2.05-1.98 (m, 4H). MS: m/z 421.1 (M+H⁺).

Example 69

Synthesis of N-((8-Methyl-1,2,3,5,6,7-hexahydro-s-indacen-4-yl)carbamoyl)-6,7-dihydro-5H-pyrazolo[5,1-b][1,3]oxazine-3-sulfonamide is shown below.

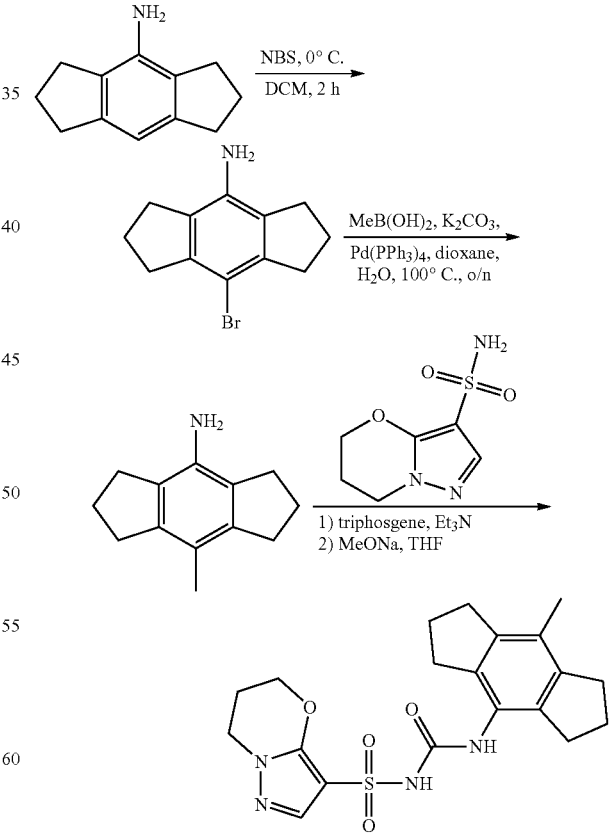

Step 1

To a solution of 1,2,3,5,6,7-hexahydro-s-indacen-4-ylamine (1 g, 5.78 mmol) in DCM (20 mL) was added NBS (1.03 g, 5.78 mmol) at 0° C. and the mixture was stirred at 0° C. for 2 hrs. The reaction mixture was poured into H₂O (30 mL) and extracted with EA (50 mL×2). The combined EA was washed with brine (100 mL), dried over Na₂SO₄ and concentrated to dryness. The residue was purified by silica gel column (PE/EA=50/1) to give 8-bromo-1,2,3,5,6,7-hexahydro-s-indacen-4-amine (838 mg, yield: 57%) as a red solid.

$^1$H NMR (300 MHz, CDCl₃): δ=3.48 (brs, 2H), 2.91 (t, J=7.5 Hz, 4H), 2.81 (t, J=6.9 Hz, 4H), 2.19-2.06 (m, 4H).

Step 2

To a solution of 8-bromo-1,2,3,5,6,7-hexahydro-s-indacen-4-amine (200 mg, 0.79 mmol) in dioxane (8 mL) and H₂O (2 mL) was added methylboronic acid (52 mg, 0.87 mmol), K₂CO₃ (327 mg, 2.37 mmol) and Pd(PPh₃)₄ (45 mg, 0.039 mmol) at room temperature and it was stirred at 100° C. under N₂ overnight. The reaction mixture was filtered over silica, and then it was purified by prep-HPLC (NH₃—H₂O) to give 8-methyl-1,2,3,5,6,7-hexahydro-s-indacen-4-amine (26 mg, yield: 18%) as a white solid.

Step 3

N-((8-methyl-1,2,3,5,6,7-hexahydro-s-indacen-4-yl)carbamoyl)-6,7-dihydro-5H-pyrazolo[5,1-b][1,3]oxazine-3-sulfonamide was synthesized as described in Preparation E to deliver the desired product (14 mg, yield: 24%) as a white solid.

$^1$H NMR (400 MHz, DMSO-d₆): δ=10.41 (s, 1H), 7.81 (s, 1H), 7.60 (s, 1H), 4.44 (t, J=4.8 Hz, 2H), 4.11 (t, J=5.6 Hz, 2H), 2.74 (t, J=6.8 Hz, 4H), 2.69-2.58 (m, 4H), 2.21-2.17 (m, 2H), 2.08 (s, 3H), 2.00-1.92 (m, 4H). MS: m/z 417.0 (M+H⁺).

Example 70

Synthesis of Sodium (R)-((4-chloro-2,6-diisopropylphenyl)carbamoyl)((6-methoxy-6,7-dihydro-5H-pyrazolo[5,1-b][1,3]oxazin-3-yl)sulfonyl)amide is shown below.

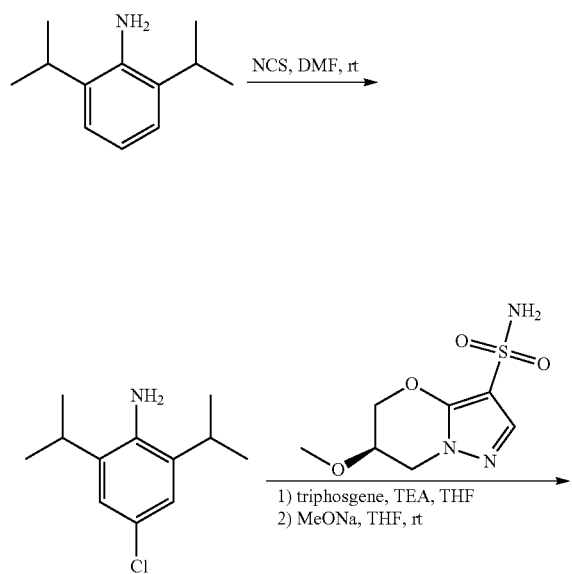

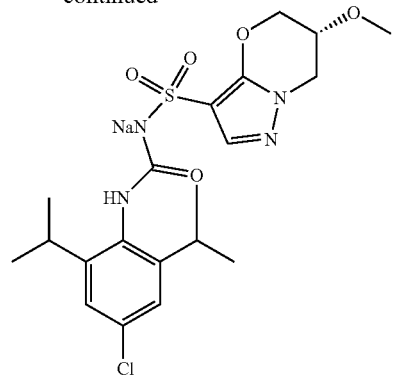

Step 1

To a solution of 2,6-diisopropyl-phenylamine (2.4 g, 13.5 mmol) in DMF (20 mL) was added NCS (1.9 g, 14.2 mmol) at one portion. After being stirred at room temperature for 16 hrs, the reaction mixture was poured to water (100 mL) and extracted with EA (50 mL×2). The combined organic layer was washed with brine (50 mL×2), dried over Na₂SO₄ and concentrated. The residue was purified by silica gel column (PE/EA=50/1) to give 4-chloro-2,6-diisopropyl-phenylamine (2.0 g, yield: 70%) as a red oil.

Step 2

(R)-((4-chloro-2,6-diisopropylphenyl)carbamoyl)((6-methoxy-6,7-dihydro-5H-pyrazolo[5,1-b][1,3]oxazin-3-yl)sulfonyl)amide was synthesized as described in Preparation E to deliver the desired product (50 mg, yield: 51%) as a white solid.

$^1$H NMR (400 MHz, DMSO-d₆): δ=7.38 (s, 1H), 7.33 (s, 1H), 7.00 (s, 2H), 4.49-4.45 (m, 1H), 4.18-4.08 (m, 3H), 4.00-3.90 (m, 1H), 3.34 (s, 3H), 3.20-3.05 (m, 2H), 1.05-1.03 (m, 12H). MS: m/z 471.0 (M+H⁺).

Example 71

Synthesis of N-((8-chloro-1,2,3,5,6,7-hexahydro-s-indacen-4-yl)carbamoyl)-6,6-dimethyl-6,7-dihydro-5H-pyrazolo[5,1-b][1,3]oxazine-3-sulfonamide is shown below.

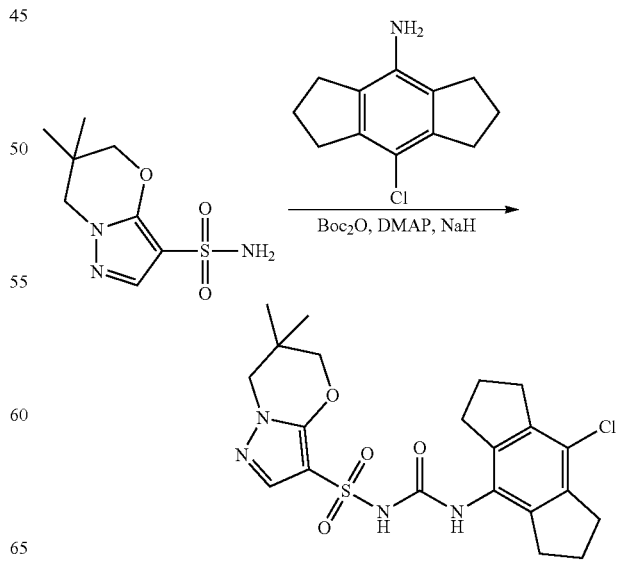

N,N-dimethylpyridin-4-amine (0.657 mmol, 0.080 g) was dissolved in THF (1.5 mL) and then a solution of di-tert-butyl dicarbonate (0.626 mmol, 0.144 mL) in THF (1.5 mL) was added slowly. After stirring for a few minutes, a solution of 8-chloro-1,2,3,5,6,7-hexahydro-s-indacen-4-amine (0.626 mmol, 130 mg) in THF (1 mL) was added and the mixture was left to stir for 30 min. At the same time, 6,6-dimethyl-6,7-dihydro-5H-pyrazolo[5,1-b][1,3]oxazine-3-sulfonamide (0.626 mmol, 0.145 g) in THF (1 mL) was treated with sodium hydride (0.626 mmol, 0.023 g) and left to stir for 30 min. At this time, the two solutions were mixed and left to stir for 18 h.

The reaction was then quenched with sat $NH_4Cl$ (10 mL) and diluted with EtOAc (10 mL). The layers were separated and the aq. layer extracted with EtOAc (10 mL). The combined organic extracts were then washed with water (10 mL) and concentrated. The resulting solid was suspended in MeOH (5 mL), filtered and purified by prep HPLC (10-40% MeCN: 10 mM aq. $NH_4OH$). The purified fractions were combined and concentrated to yield N-((8-chloro-1,2,3,5,6,7-hexahydro-s-indacen-4-yl)carbamoyl)-6,6-dimethyl-6,7-dihydro-5H-pyrazolo[5,1-b][1,3]oxazine-3-sulfonamide (4 mg, 1.374%) as a white solid.

$^1$H-NMR (400 MHz; MeOD): δ 7.68 (s, 1H), 4.08 (s, 2H), 3.86 (s, 3H), 2.90-2.87 (m, 4H), 2.80-2.76 (m, 4H), 2.09-2.02 (m, 5H), 1.11 (s, 6H). MS: m/z 465.0 (M+H$^+$).

Example 72

Synthesis of N-((2,2-dimethyl-2,3-dihydrobenzofuran-7-yl)carbamoyl)-6,7-dihydro-5H-pyrazolo[5,1-b][1,3]oxazine-3-sulfonamide is shown below.

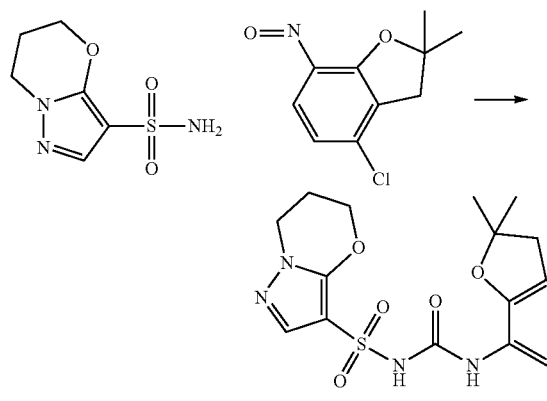

6,7-dihydro-5H-pyrazolo[5,1-b][1,3]oxazine-3-sulfonamide (100 mg, 0.492 mmol) was dissolved in MeOH (4 mL) at 80° C. sodium methoxide (0.106 g, 0.492 mmol) was then added and the mixture was stirred for 30 min. The solvent was then evaporated and 7-isocyanato-2,2-dimethyl-2,3-dihydrobenzofuran (0.093 g, 0.492 mmol) in MeCN (4 mL) was added and the mixture was left to stir overnight. At this time the reaction was filtered and the filter and washed with EtOAc and dried to yield N-((2,2-dimethyl-2,3-dihydrobenzofuran-7-yl)carbamoyl)-6,7-dihydro-5H-pyrazolo[5,1-b][1,3]oxazine-3-sulfonamide (108.5 mg, 56.19%) as a cream solid. MS: m/z 393 (M+H$^+$).

Example 73

Synthesis of N-((1,2,3,5,6,7-hexahydro-s-indacen-4-yl)carbamoyl)-2-methyl-6,7-dihydro-5H-pyrazolo[5,1-b][1,3]oxazine-3-sulfonamide is shown below.

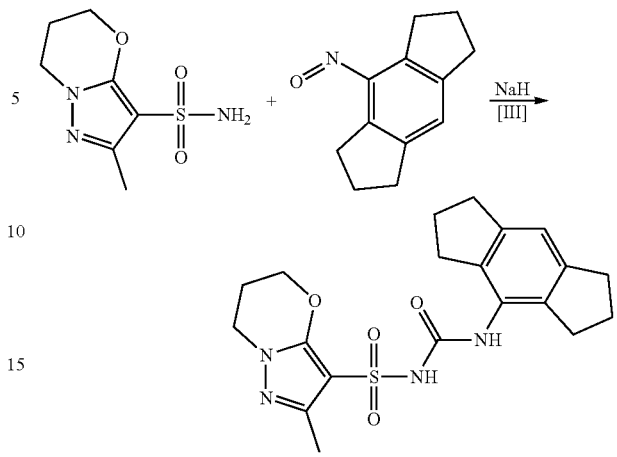

2-methyl-6,7-dihydro-5H-pyrazolo[5,1-b][1,3]oxazine-3-sulfonamide was prepared in the same manner as 6,7-dihydro-5H-pyrazolo[5,1-b][1,3]oxazine-3-sulfonamide except the using the appropriate 3-methyl-3-pyrazolin-5-one starting material.

2-methyl-6,7-dihydro-5H-pyrazolo[5,1-b][1,3]oxazine-3-sulfonamide (80 mg, 0.368 mmol), 4-isocyanato-1,2,3,5,6,7-hexahydro-sindacene (0.073 g, 0.368 mmol), and sodium hydride (13.595 mg, 0.368 mmol) were mixed in DMF (5 mL) and left to stir overnight. The reaction was then quenched with water and a white solid filtered off. The filtrate was concentrated and the residue suspended in acetone (10 mL), filtered and washed with acetone before drying to yield N-((1,2,3,5,6,7-hexahydro-s-indacen-4-yl)carbamoyl)-2-methyl-6,7-dihydro-5H-pyrazolo[5,1-b][1,3]oxazine-3-sulfonamide (51.4 mg, 33.51%) as a light tan solid. MS: m/z 417 (M+H$^+$).

Example 74

Synthesis of N-((4-cyano-2,6-diisopropylphenyl)carbamoyl)-6,7-dihydro-5H-pyrazolo[5,1-b][1,3]oxazine-3-sulfonamide is shown below.

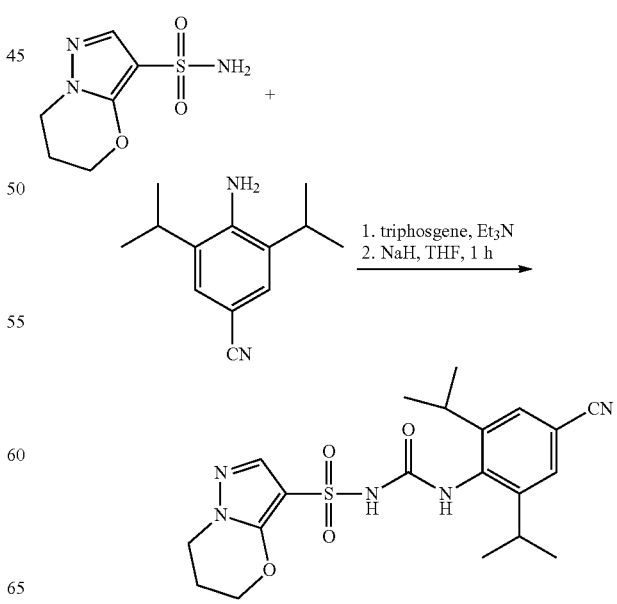

To a solution of 4-amino-3,5-diisopropylbenzonitrile (300 mg, 1.48 mmol) in anhydrous THF (10 mL) was added Et$_3$N (0.41 mL, 2.97 mmol) followed by triphosgene (220 mg, 0.74 mmol) at r.t. The reaction mixture was heated at 60° C. for 1 hr before cooled to r.t., and partitioned between EtOAc (30 mL) and water (20 mL). The aqueous phase was extracted with EtOAc (2×10 mL). The combined organic extracts were washed with water (20 mL), brine (20 mL), dried over Na$_2$SO$_4$ and concentrated under reduced pressure to yield a yellow solid (210 mg, 62%).

The solid (100 mg, 0.44 mmol) was dissolved in anhydrous DMF (1 mL). To this solution was added 6,7-dihydro-5H-pyrazolo[5,1-b][1,3]oxazine-3-sulfonamide (90 mg, 0.44 mmol) followed by NaH (60% in mineral oil, 17 mg, 0.44 mmol) at r.t. The reaction was stirred for 1 hr before MeOH (3 mL) was added. The solvent was removed under reduced pressure and the resulting residue was purified by silica gel chromatography (MeOH/DCM 0 to 5%) to afford N-((4-cyano-2,6-diisopropylphenyl)carbamoyl)-6,7-dihydro-5H-pyrazolo[5,1-b][1,3]oxazine-3-sulfonamide (36.3 mg, 19%) as white solids. MS: m/z 432 (M+H$^+$).

Example 75

Synthesis of N-((4-chloro-2,6-dicyclopropylphenyl)carbamoyl)-6,7-dihydro-5H-pyrazolo[5,1-b][1,3]oxazine-3-sulfonamide is shown below.

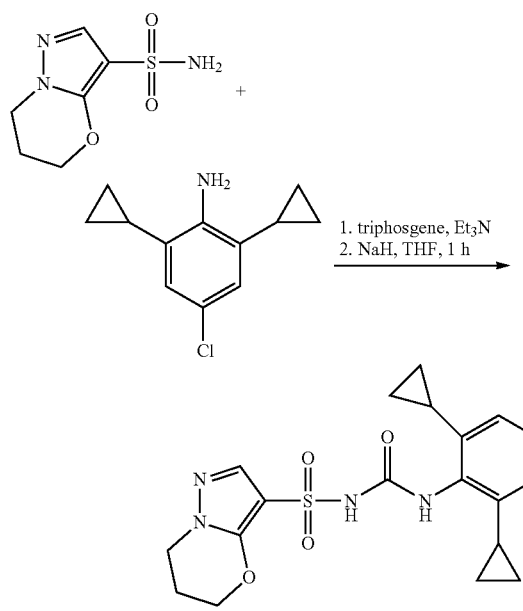

To a solution of 4-chloro-2,6-dicyclopropylaniline (180 mg, 0.87 mmol) in anhydrous THF (10 mL) was added Et$_3$N (0.24 mL, 1.73 mmol) followed by triphosgene (130 mg, 0.43 mmol) at r.t. The reaction mixture was heated at 60° C. for 1 hr before cooled to r.t., and partitioned between EtOAc (30 mL) and water (20 mL). The aqueous phase was extracted with EtOAc (2×10 mL). The combined organic extracts were washed with water (20 mL), brine (20 mL), dried over Na$_2$SO$_4$ and concentrated under reduced pressure to yield light yellow solids (170 mg, 84%).

The solids (100 mg, 0.49 mmol) were dissolved in anhydrous DMF (1 mL). To this solution was added 6,7-dihydro-5H-pyrazolo[5,1-b][1,3]oxazine-3-sulfonamide (115 mg, 0.49 mmol) followed by NaH (60% in mineral oil, 20 mg, 0.49 mmol) at r.t. The reaction mixture was stirred at RT for 1 hr before MeOH (3 mL) was added. The solvent was removed under reduced pressure and the resulting residue was purified by silica gel chromatography (MeOH/DCM 0 to 5%) to afford N-((4-chloro-2,6-dicyclopropylphenyl)carbamoyl)-6,7-dihydro-5H-pyrazolo[5,1-b][1,3]oxazine-3-sulfonamide (37.7 mg, 17%) as white solids. MS: m/z 437 (M+H$^+$).

Example 76

Synthesis of N-((3,5-dicyclopropylphenyl)carbamoyl)-6,7-dihydro-5H-pyrazolo[5,1-b][1,3]oxazine-3-sulfonamide

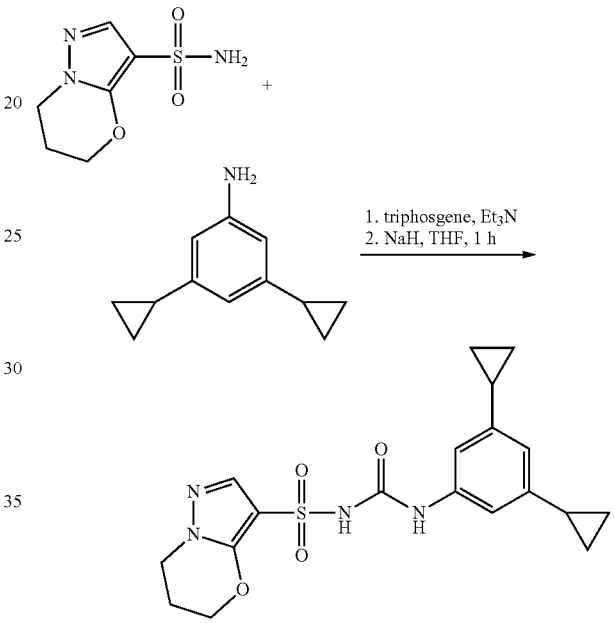

To a solution of 3,5-dicyclopropylaniline (200 mg, 1.15 mmol) in anhydrous THF (10 mL) was added Et$_3$N (0.27 mL, 2.0 mmol) followed by triphosgene (120 mg, 0.39 mmol) at r.t. The reaction was stirred for 2 hrs before THF was removed. The resulting residue was suspended in hexanes (50 mL), the insoluble white solids were removed by vacuum filtration and hexanes were removed under reduced pressure to yield a clear oil.

The oil obtained was then dissolved in anhydrous DMF (2 mL). To this solution was added 6,7-dihydro-5H-pyrazolo[5,1-b][1,3]oxazine-3-sulfonamide (80 mg, 0.39 mmol) followed by NaH (60% in mineral oil, 20 mg, 0.49 mmol) at r.t. The reaction mixture was stirred for 1 hr before MeOH (5 mL) was added. The solvent was removed under reduced pressure and the resulting residue was purified by silica gel chromatography (MeOH/DCM 0 to 10%) to afford N-((3,5-dicyclopropylphenyl)carbamoyl)-6,7-dihydro-5H-pyrazolo[5,1-b][1,3]oxazine-3-sulfonamide (90 mg, 57%) as white solids. MS: m/z 403 (M+H$^+$).

Example 77

Synthesis of N-((7-chloro-5-cyclopropyl-2,3-dihydro-1H-inden-4-yl)carbamoyl)-6,7-dihydro-5H-pyrazolo[5,1-b][1,3]oxazine-3-sulfonamide is shown below.

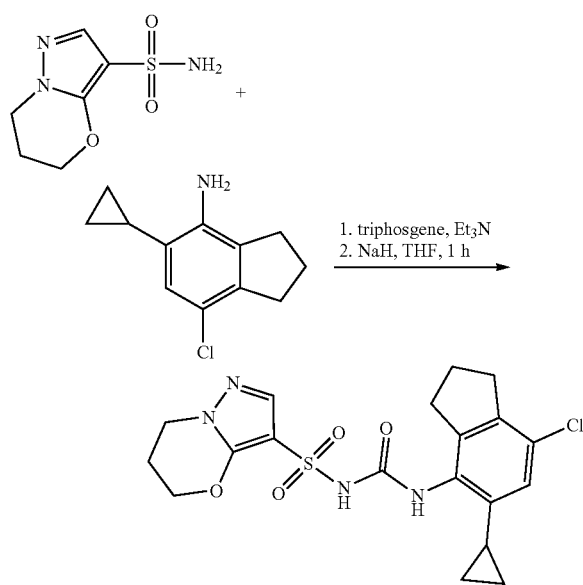

To a solution of 7-chloro-5-cyclopropyl-2,3-dihydro-1H-inden-4-amine (85 mg, 0.41 mmol) in anhydrous THF (10 mL) was added Et₃N (0.17 mL, 1.2 mmol) followed by triphosgene (60 mg, 0.20 mmol) at r.t. The reaction mixture was heated at 60° C. for 1 hr before cooled to r.t., and partitioned between EtOAc (30 mL) and water (20 mL). The aqueous phase was extracted with EtOAc (2×10 mL). The combined organic extracts were washed with water (20 mL), brine (20 mL), dried over Na₂SO₄ and concentrated under reduced pressure to yield a yellow oil.

The oil obtained was then dissolved in anhydrous DMF (1 mL). To this solution was added 6,7-dihydro-5H-pyrazolo[5,1-b][1,3]oxazine-3-sulfonamide (50 mg, 0.25 mmol) followed by NaH (60% in mineral oil, 16 mg, 0.41 mmol) at r.t. The reaction mixture was stirred for 1 hr before MeOH (5 mL) was added. The solvent was removed under reduced pressure and the resulting residue was purified by silica gel chromatography (MeOH/DCM 0 to 10%) to afford N-((7-chloro-5-cyclopropyl-2,3-dihydro-1H-inden-4-yl)carbamoyl)-6,7-dihydro-5H-pyrazolo[5,1-b][1,3]oxazine-3-sulfonamide (60 mg, 57%) as light yellow solids. MS: m/z 437 (M+H⁺).

Example 78

Synthesis of N-((1,2,3,4-tetrahydroacridin-9-yl)carbamoyl)-6,7-dihydro-5H-pyrazolo[5,1-b][1,3]oxazine-3-sulfonamide is shown below.

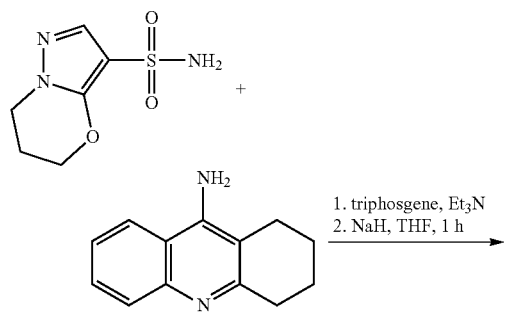

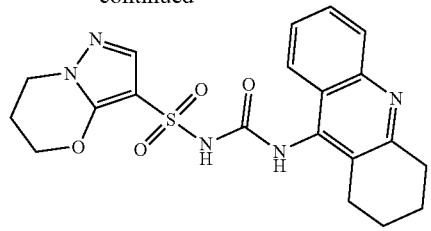

To a solution of 1,2,3,4-tetrahydroacridin-9-amine (200 mg, 1.01 mmol) in anhydrous THF (10 mL) was added Et₃N (0.17 mL, 1.2 mmol) followed by triphosgene (150 mg, 0.49 mmol) at r.t. The reaction mixture was heated at 60° C. for 2 hrs before cooled to RT. THF was removed and the resulting residue was suspended in hexanes (50 mL), the insoluble white solids were removed by vacuum filtration and hexanes were removed under reduced pressure to yield a yellow oil.

The oil obtained was then dissolved in anhydrous DMF (1 mL). To this solution was added 6,7-dihydro-5H-pyrazolo[5,1-b][1,3]oxazine-3-sulfonamide (50 mg, 0.25 mmol) followed by NaH (60% in mineral oil, 20 mg, 0.49 mmol) at r.t. The reaction mixture was stirred for 1 hr before MeOH (1 mL) was added. The residue was purified by pre-HPLC (MeCN/water/0.1% formic acid) to afford N-((1,2,3,4-tetrahydroacridin-9-yl)carbamoyl)-6,7-dihydro-5H-pyrazolo[5,1-b][1,3]oxazine-3-sulfonamide (1.8 mg, 2%) as white solids. MS: m/z 428 (M+H⁺).

Example 79

Synthesis of Sodium ((6-(aminomethyl)-6,7-dihydro-5H-pyrazolo[5,1-b][1,3]oxazin-3-yl)sulfonyl)((1,2,3,5,6,7-hexahydro-s-indacen-4-yl)carbamoyl)amide and sodium ((1,2,3,5,6,7-hexahydro-s-indacen-4-yl)carbamoyl)((6-((2,2,2-trifluoroacetamido)methyl)-6,7-dihydro-5H-pyrazolo[5,1-b][1,3]oxazin-3-yl)sulfonyl)amide are shown below.

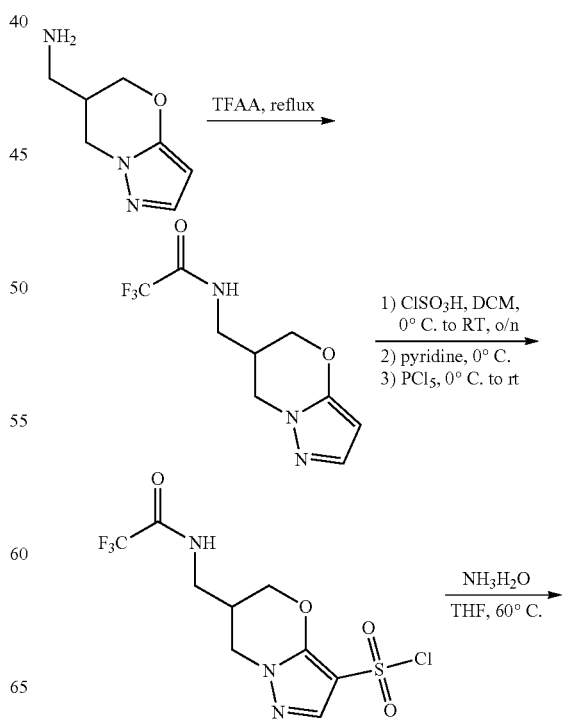

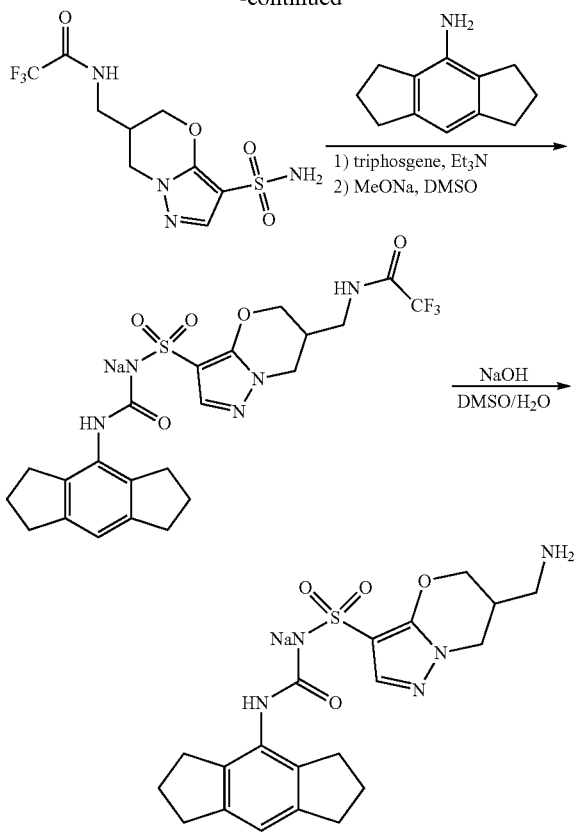

Step 1:

(6,7-Dihydro-5H-pyrazolo[5,1-b][1,3]oxazin-6-yl)methanamine (crude, ~1.2 mmol) was dissolved in TFAA (3 mL). After the solution was heated to reflux for 3 hrs, it was quenched with the addition of EA (20 mL) and water (10 mL). The organic layer was separated. The aqueous layer was extracted with EA (10 mL×3). The organic layers were combined and washed with brine (10 mL), and dried over anhydrous $Na_2SO_4$. The solution was concentrated in vacuo. The residue was purified by silica gel column (PE/EA=1/1) to give N-((6,7-dihydro-5??-pyrazolo[5,1-b][1,3]oxazin-6-yl)methyl)-2,2,2-trifluoroacetamide (140 mg, yield: 47%) as a yellow solid. MS: m/z 250.2 (M+H$^+$).

Step 2:

To a solution of N-((6,7-dihydro-5H-pyrazolo[5,1-b>][1,3]oxazin-6-yl)methyl)-2,2,2-trifluoroacetamide (140 mg, 0.56 mmol) in DCM (3 mL) was added $ClSO_3H$ (0.11 mL, 1.68 mmol) dropwise at 0° C. After being stirred at room temperature for 16 hrs, pyridine (0.14 mL, 1.68 mmol) was added dropwise at 0° C., and then $PCl_5$ (350 mg, 1.68 mmol) was added portionwise at 0° C. The reaction mixture was stirred at room temperature for 1 hr, poured into ice-water (2 mL) and extracted with EA (10 mL×3). The combined organic layers were washed with brine (10 mL), dried over anhydrous $Na_2SO_4$ and concentrated to give a crude product, which was directly used for next step without further purification.

Step 3:

To a solution of 6-((2,2,2-trifluoroacetamido)methyl)-6,7-dihydro-5H-pyrazolo[5,1-b][1,3]oxazine-3-sulfonyl chloride (crude, ~0.56 mmol) in THF (3 mL) was added $NH_3 \cdot H_2O$ (3 mL). After being stirred at 60° C. for 2 hrs, the reaction mixture was concentrated to about 1 mL. The residual suspension was acidified with 1 M aq. HCl to pH=3 and filtered. The filtrate was purified by reverse phase column (MeCN/$H_2O$) to give 2,2,2-trifluoro-N-((3-sulfamoyl-6,7-dihydro-5H-pyrazolo[5,1-b][1,3]oxazin-6-yl)methyl)acetamide (120 mg, yield: 65%) as a yellow solid.

$^1$H NMR (400 MHz, DMSO-d$_6$): δ=7.58 (s, 1H), 4.51 (dd, J=11.2, 2.8 Hz, 1H), 4.32-4.23 (m, 2H), 3.96 (dd, J=12.4, 3.2 Hz, 1H), 3.44 (d, J=7.2 Hz, 2H), 2.73-2.64 (m, 1H).

Step 4:

To a suspension of N-((3-sulfamoyl-6,7-dihydro-5H-pyrazolo[5,1-b][1,3]oxazin-6-yl)methyl)acetamide (60 mg, 0.18 mmol) in DMSO (2 mL) was added MeONa (10.7 mg, 0.2 mmol) and the mixture was stirred at room temperature for 20 min to give a sodium salt suspension. In another flask, to a solution of 1,2,3,5,6,7-hexahydro-s-indacen-4-ylamine (38 mg, 0.22 mmol) and TEA (54 mg, 0.54 mmol) in THF (2 mL) was added triphosgene (24 mg, 0.80 mmol) in one portion and the mixture was stirred at room temperature under $N_2$ for 20 min. The reaction mixture was then filtered. The filtrate was added to the above sodium salt suspension and stirred at room temperature for 16 hrs. After that, the above suspension was filtered, the filtrate was purified by reverse phase column (MeCN/$H_2O$) to give sodium ((1,2,3,5,6,7-hexahydro-s-indacen-4-yl)carbamoyl)((6-((2,2,2-trifiuoroacetamido)methyl)-6,7-dihydro-5H-pyrazolo[5,1-6][1,3]oxazin-3-yl)sulfonyl)amide (44 mg, yield: 44%) as a white solid.

$^1$H NMR (400 MHz, DMSO-d$_6$): δ=9.69 (t, J=5.6 Hz, 1H), 7.53 (brs, 1H), 7.41 (s, 1H), 6.80 (s, 1H), 4.37 (dd, J=10.8, 2.8 Hz, 1H), 4.19-4.11 (m, 2H), 3.88 (dd, J=12.0, 7.6 Hz, 1H), 3.30-3.25 (m, 2H), 2.75 (t, J=7.2 Hz, 4H), 2.66-2.59 (m, 5H), 1.95-1.85 (m, 4H). MS: m/z 528.1 (M+H$^+$).

Step 5:

To a solution of sodium ((1,2,3,5,6,7-hexahydro-s-indacen-4-yl)carbamoyl)((6-((2,2,2-trifluoroacetamido)methyl)-6,7-dihydro-5H-pyrazolo[5,1-b][1,3]oxazin-3-yl)sulfonyl)amide (7 mg, 0.01 mmol) in DMSO (1 mL) was added aqueous NaOH (0.5 mL, 1 mmol, 2 M) and the mixture was stirred at room temperature for 48 hrs. After that, the suspension was filtered and the filtrate was purified by reverse phase column (MeCN/$H_2O$) to give sodium ((6-(aminomethyl)-6,7-dihydro-5H-pyrazolo[5,1-b][1,3]oxazin-3-yl)sulfonyl)((1,2,3,5,6,7-hexahydro-s-indacen-4-yl)carbamoyl)amide (4.9 mg, yield: 84%) as a white solid.

$^1$H NMR (400 MHz, DMSO-d$_6$): δ=7.45 (brs, 1H), 7.34 (s, 1H), 6.76 (s, 1H), 4.37 (dd, J=10.8, 3.2 Hz, 1H), 4.13-4.02 (m, 2H), 3.82 (dd, J=12.4, 8.0 Hz, 1H), 2.74 (t, J=6.8 Hz, 4H), 2.68-2.57 (m, 6H), 2.30-2.12 (m, 1H), 1.94-1.85 (m, 4H). MS: m/z 432.1 (M+H$^+$).

Example 80

Synthesis of (R)-((4-fluoro-2,6-diisopropylphenyl)carbamoyl)((6-methoxy-6,7-dihydro-5H-pyrazolo[5,1-b][1,3]oxazin-3-yl)sulfonyl)amide is shown below.

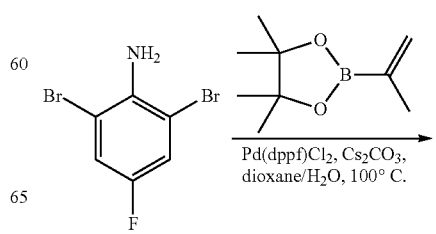

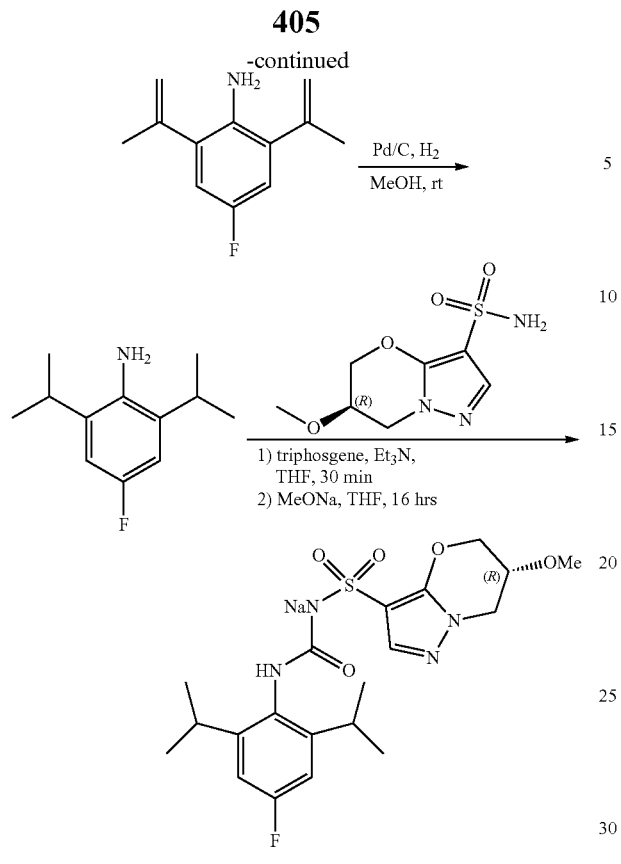

Step 1

To a solution of 2,6-dibromo-4-fluoroaniline (2.0 g, 7.4 mmol), 4,4,5,5-tetramethyl-2-(prop-1-en-2-yl)-1,3,2-dioxaborolane (3.37 g, 20.1 mmol), $Cs_2CO_3$ (7.23 g, 22.2 mmol) and $H_2O$ (4 mL) in dioxane (40 mL) was added $Pd(dppf)Cl_2$ (0.54 g, 0.74 mmol) in $N_2$. The reaction mixture was stirred at 100° C. overnight. The mixture was concentrated in vacuo. The residue was purified by silica gel column chromatography (PE/EA=10/1) to give 4-fluoro-2,6-di(prop-1-en-2-yl)aniline (1.10 g, 78%) as a brown oil.

$^1$H NMR (400 MHz, DMSO-$d_6$): δ=6.72 (d, J=9.6 Hz, 2H), 5.29 (t, J=1.6 Hz, 2H), 5.01 (d, J=1.2 Hz, 2H), 4.24 (s, 2H), 2.01 (s, 6H).

Step 2

To a solution of 4-fluoro-2,6-di(prop-1-en-2-yl)aniline (1.10 g, 5.7 mmol) in MeOH (30 mL) was added Pd/C (0.11 g, 10% wt). The reaction mixture was degassed and purged with $H_2$ for three times. It was stirred at room temperature overnight under $H_2$ balloon atmosphere and monitored by LCMS. The mixture was filtered. The filtrate was concentrated in vacuo to give 4-fluoro-2,6-diisopropylaniline (1.05 g, 94%) as a brown oil.

$^1$H NMR (400 MHz, DMSO-$d_6$): δ=6.67 (d, J=10.0 Hz, 2H), 4.44 (brs, 2H), 3.07-3.01 (m, 2H), 1.16-1.10 (m, 12H).

Step 3

To a solution of (R)-6-methoxy-6,7-dihydro-5H-pyrazolo[5,1-b][1,3]oxazine-3-sulfonamide (55 mg, 0.25 mmol) in THF (5 mL) was added MeONa (15 mg, 0.28 mmol) at −5° C. Then the reaction mixture was stirred at −5° C. for 30 min. Separately, to a solution of 4-fluoro-2,6-diisopropylaniline (45 mg, 0.23 mmol) in THF (5 mL) was added triphosgene (27 mg, 0.092 mmol) and TEA (47 mg, 0.46 mmol) at −5° C. Then the reaction mixture was stirred at −5° C. for 30 min. This reactant was filtered and the filtrate was added at −5° C. to the suspension of sodium (R)-((6-methoxy-6,7-dihydro-5H-pyrazolo[5,1-b][1,3]oxazin-3-yl)sulfonyl)amide from the first step. The reaction was stirred at room temperature overnight. After removal of solvent in vacuo, the residue was purified by prep-HPLC to give sodium (R)-((4-fluoro-2,6-diisopropylphenyl)carbamoyl)((6-m ethoxy-6,7-dihydro-5H-pyrazolo[5,1-b][1,3]oxazin-3-yl)sulfonyl)amide (28.2 mg, 27%) as a white solid.

$^1$H NMR (400 MHz, DMSO-$d_6$): δ=7.65 (s, 1H), 7.57 (s, 1H), 6.91 (d, J=9.6 Hz, 2H), 4.63 (d, J=11.6 Hz, 1H), 4.31 (d, J=11.6 Hz, 1H), 4.22 (d, J=1.6 Hz, 2H), 4.06 (s, 1H), 3.36 (s, 3H), 2.96-2.86 (m, 2H), 1.05 (s, 12H). MS: m/z 455.1 (M+H$^+$).

Example 81

Synthesis of sodium (R)-((4-fluoro-2,6-diisopropylphenyl)carbamoyl)((6-(methylamino)-6,7-dihydro-5H-pyrazolo[5,1-b][1,3]oxazin-3-yl)sulfonyl)amide

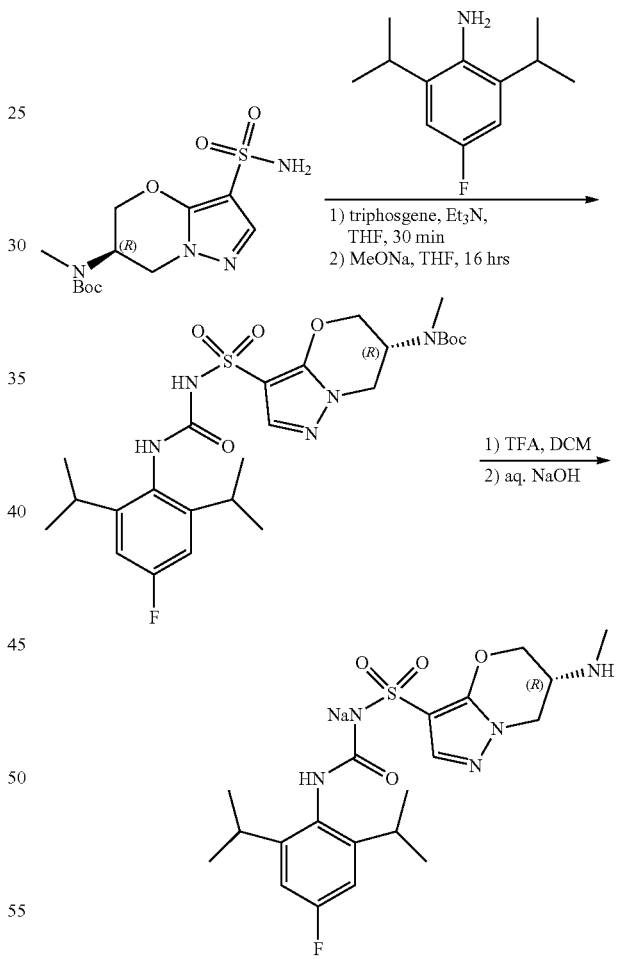

Step 1

To a solution of (R)-tert-butyl methyl(3-sulfamoyl-6,7-dihydro-5H-pyrazolo[5,1-b][1,3]oxazin-6-yl)carbamate (375 mg, 1.13 mmol) in THF (10 mL) was added MeONa (165 mg, 3.06 mmol) at −5° C. Then the reaction mixture was stirred at −5° C. for 30 min. Separately, to a solution of 4-fluoro-2,6-diisopropylaniline (200 mg, 1.02 mmol) in THF (5 mL) was added triphosgene (121 mg, 0.41 mmol) and TEA (0.28 mL, 2.04 mmol) at −5° C. Then the reaction mixture was stirred at −5° C. for 30 min and was monitored by TLC. This reactant was filtered and the filtrate was added at −5° C. to the suspension of sodium (R)-((6-((tert-butoxycarbonyl)(methyl)amino)-6,7-dihydro-5H-pyrazolo[5,1-b][1,3]oxazin-3-yl)sulfonyl)amide from the first step. The reaction was stirred at room temperature overnight. After removal of solvent in vacuum, the residue was purified by flash column chromatography to give (R)-tert-butyl (3-(N-((4-fluoro-2,6-diisopropylphenyl)carbamoyl)sulfamoyl)-6,7-dihydro-5H-pyrazolo[5,1-b][1,3]oxazin-6-yl)(methyl)carbamate (237 mg, 43%) as a yellow solid.

Step 2

To a solution of (R)-tert-butyl (3-(N-((4-fluoro-2,6-diisopropylphenyl)carbamoyl)sulfamoyl)-6,7-dihydro-5H-pyrazolo[5,1-b][1,3]oxazin-6-yl)(methyl)carbamate (100 mg, 0.18 mmol) in DCM (2 mL) was added $CF_3CO_2H$ (5 mL). Then the reaction mixture was stirred at room temperature for 20 min. The mixture was basified with 4 M aqueous NaOH to pH=12 at −5° C. The aqueous layer was concentrated in vacuo. The residue was purified by flash column chromatography to give sodium (R)-((4-fluoro-2,6-diisopropylphenyl)carbamoyl)((6-(methyl amino)-6,7-dihydro-5H-pyrazolo[5,1-b][1,3]oxazin-3-yl)sulfonyl)amide (23.6 mg, 23%) as a yellow solid.

$^1$H NMR (400 MHz, DMSO-$d_6$): δ=7.67 (s, 1H), 7.57 (s, 1H), 6.92 (d, J=10.0 Hz, 2H), 4.40-4.28 (m, 2H), 4.22 (dd, J=12.4, 4.4 Hz, 1H), 3.94 (dd, J=12.8, 4.4 Hz, 1H), 3.21-3.16 (m, 1H), 2.95-2.85 (m, 2H), 2.34 (s, 3H) 1.09-1.00 (m, 12H). MS: m/z 454.2 (M+H$^+$).

Example 82

Synthesis of N-((4-fluoro-2,6-diisopropylphenyl)carbamoyl)-6,7-dihydro-5H-pyrazolo[5,1-b][1,3]oxazine-3-sulfonamide is shown below.

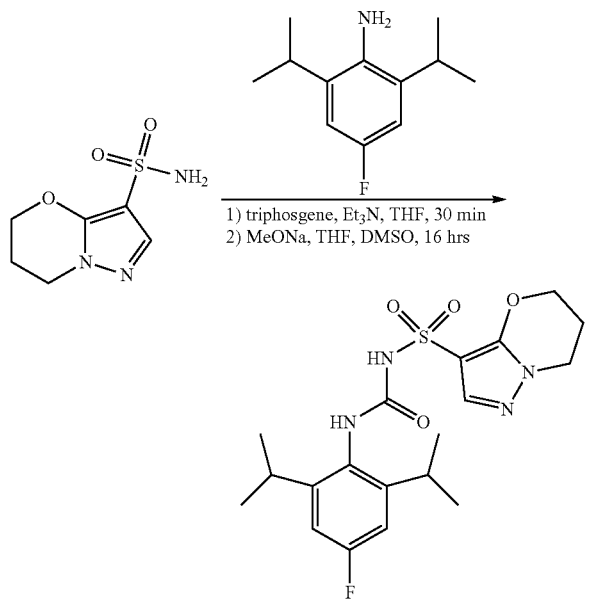

Step 1

To a solution of 6,7-dihydro-5H-pyrazolo[5,1-b][1,3]oxazine-3-sulfonamide (100 mg, 0.45 mmol) in THF (5 mL) was added MeONa (73 mg, 1.35 mmol) and DMSO (1 mL) at −5° C. Then the reaction mixture was stirred at −5° C. for 30 min. Separately, to a solution of 4-fluoro-2,6-diisopropylaniline (100 mg, 0.45 mmol) in THF (5 mL) was added triphosgene (53 mg, 0.18 mmol) and TEA (0.13 mL, 0.90 mmol) at −5° C. Then the reaction mixture was stirred at −5° C. for 30 min. This reactant was filtered and the filtrate was added at −5° C. to the suspension of sodium ((6,7-dihydro-5H-pyrazolo[5,1-b][1,3]oxazin-3-yl)sulfonyl)amide from the first step. The reaction was stirred at room temperature overnight. After removal of solvent in vacuo, the residue was purified by prep-HPLC to give N-((4-fluoro-2,6-diisopropylphenyl)carbamoyl)-6,7-dihydro-5H-pyrazolo[5,1-b][1,3]oxazine-3-sulfonamide (103.5 mg, 54%) as a white solid.

$^1$H NMR (400 MHz, DMSO-$d_6$): δ=8.52 (brs, 1H), 7.61 (s, 1H), 7.51 (s, 1H), 6.89 (d, J=10.0 Hz, 2H), 4.39 (t, J=4.8 Hz, 2H), 4.08 (t, J=6.4 Hz, 2H), 3.00-2.90 (m, 2H), 2.24-2.14 (m, 2H), 1.04 (s, 12H). MS: m/z 424.8 (M+H$^+$).

Biological Testing Methods

Abbreviations

PBMCs: peripheral blood mononuclear cells
KCs: Kupffer cells
FBS: fetal bovine serum
LPS: lipopolysaccharides
NLRP3 Activation and Inhibitory Assays Some of the following assays were used to determine the inhibitory activity of the compounds on the NLRP3 inflammasome using a common inflammasome activation stimuli—nigericin.

Biological Example 1: Cell Culture

Human peripheral blood mononuclear cells (PBMCs), consisting of lymphocytes (T, B and NK cells), monocytes and dendritic cells, were freshly isolated from human peripheral blood from healthy donors. Cells were obtained through an IRB approved donor program by iXCells Biotechnologies where all the donors were tested for bacterial and viral infections. Cells were purified from peripheral blood using ficoll gradient centrifugation.

Human Kupffer cells (KCs), specialized liver macrophages residing in the space of Disse, were obtained by gradient isolation from liver specimens harvested postmortem by Samsara Sciences. Cells were obtained through an IRB approved donor program by Samsara Sciences and all donors tested negative for bacterial and viral infections.

Biological Example 2: NLRP3 Inflammasome Activation Assays

Fresh or cryopreserved PMBCs were seeded in V-bottom 96-well plate at 0.5-1×10$^5$ cells per well and incubated overnight at 37° C. with 5% CO$_2$ in RPMI 1640 medium with GlutaMAX supplement, 4.5 g/L D-glucose, 10% Fetal Bovine Serum (FBS), 100 mM Sodium Pyruvate, 1% Penicillin/Streptomycin, 10 mM HEPES and 0.05 mM of β-mercaptoethanol. Freshly isolated or cryopreserved KCs cells were seeded in flat-bottom 96-well plates at 0.6-1.5×10$^5$ cells/well and incubated overnight at 37° C., 5% CO$_2$ in RPMI 1640 Medium with GlutaMAX supplement, FBS, 1% Penicillin/Streptomycin and 10 mM HEPES. The following day, the cells were primed with 100 ng/mL of lipopolysaccharides (LPS; Sigma Aldrich) in FBS-free RPMI 1640 for 3 h. After the priming step, the media was removed and PBMCs were pre-incubated with serial concentrations of test compounds (0.00017-10 uM) or vehicle (DMSO) for 30 min in FBS-free media prior to addition of the NLRP3 activator. Cells were then stimulated with 10 uM Nigericin (Sigma Aldrich; InvivoGen) for 1.5 h. Plates were centrifuged at 1,500 rpm for 3 minutes to pellet cells and supernatant was transferred into new plates for subsequent experiments. Measurement of Cytokines/Assessment of NLRP3 Inflammasome Activity For ELISA assays cells were seeded into 96-well plates. Post study, supernatants were removed and the levels of mature IL-1β, IL18 and TNFα (Quantikine ELISA, R&D systems) were measured in cell conditioned media by ELISA according to manufacturer's instructions.

Results

Results of certain compounds are shown below.

| Compound | IC$_{50}$ (μM) | Cell line | Assay Description |
|---|---|---|---|
| | C | PBMCs | IC$_{50}$ IL-1β |
| | A | PBMCs | IC$_{50}$ IL-1β |
| | A | KCs | IC$_{50}$ IL-1β |
| | C | PBMCs | IC$_{50}$ IL-1β |
| | B | PBMCs | IC$_{50}$ IL-1β |

-continued
| Compound | IC$_{50}$ (μM) | Cell line | Assay Description |
|---|---|---|---|
| 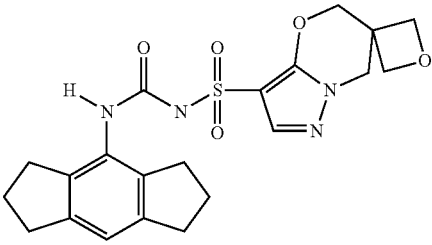 [SMILES: O=C(Nc1c2c(cc3c1CCC3)CCC2)NS(=O)(=O)c1cnn2c1OCC1(COC1)C2] | B | PBMCs | IC$_{50}$ IL-1β |
| 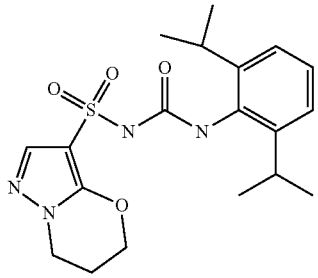 [SMILES: CC(C)c1cccc(C(C)C)c1NC(=O)NS(=O)(=O)c1cnn2c1OCCC2] | C | PBMCs | IC$_{50}$ IL-1β |
| 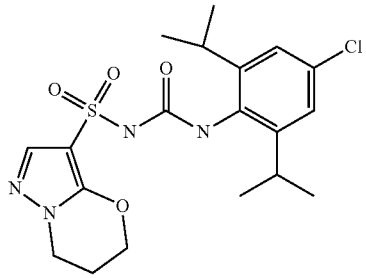 [SMILES: CC(C)c1cc(Cl)cc(C(C)C)c1NC(=O)NS(=O)(=O)c1cnn2c1OCCC2] | B | PBMCs | IC$_{50}$ IL-1β |
| 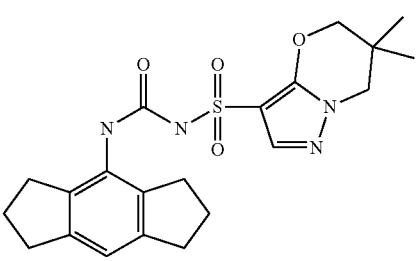 [SMILES: CC1(C)COc2c(S(=O)(=O)NC(=O)Nc3c4c(cc5c3CCC5)CCC4)cnn2C1] | A | PBMCs | IC$_{50}$ IL-1β |
| 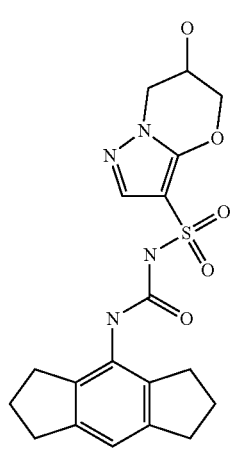 | A | PBMCs | IC$_{50}$ IL-1β |

| Compound | IC$_{50}$ (μM) | Cell line | Assay Description |
|---|---|---|---|
| 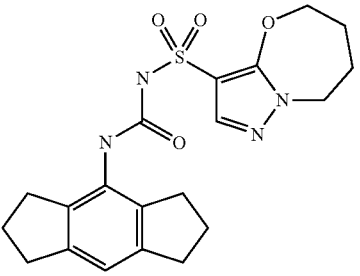 [SMILES: O=C(Nc1c2c(cc3c1CCC3)CCC2)NS(=O)(=O)c1cnn2c1OCCCC2] | B | PBMCs | IC$_{50}$ IL-1β |
| 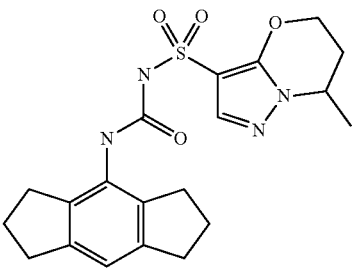 [SMILES: CC1CCOc2c(S(=O)(=O)NC(=O)Nc3c4c(cc5c3CCC5)CCC4)cnn21] | B | PBMCs | IC$_{50}$ IL-1β |
| 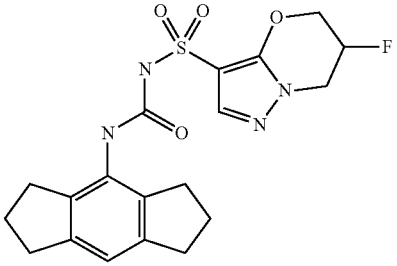 [SMILES: O=C(Nc1c2c(cc3c1CCC3)CCC2)NS(=O)(=O)c1cnn2c1OCC(F)C2] | B | PBMCs | IC$_{50}$ IL-1β |
| 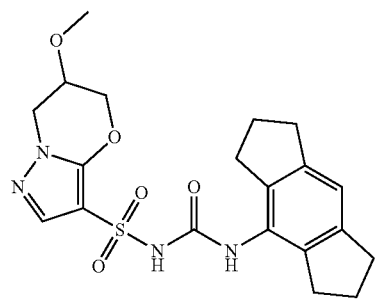 [SMILES: COC1COc2c(S(=O)(=O)NC(=O)Nc3c4c(cc5c3CCC5)CCC4)cnn2C1] | A | PBMCs | IC$_{50}$ IL-1β |
| 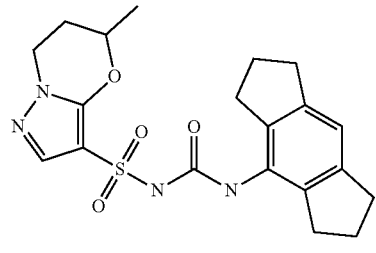 [SMILES: CC1CCn2ncc(S(=O)(=O)NC(=O)Nc3c4c(cc5c3CCC5)CCC4)c2O1] | A | PBMCs | IC$_{50}$ IL-1β |

| Compound | IC$_{50}$ (µM) | Cell line | Assay Description |
|---|---|---|---|
| 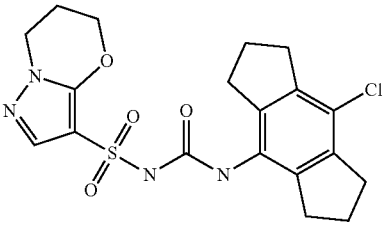 [SMILES: O=C(Nc1c2c(c(Cl)c3c1CCC3)CCC2)NS(=O)(=O)c1cnn2c1OCCC2] | A | PBMCs | IC$_{50}$ IL-1β |

A <100 nM
B 100 nM-1 µM
C 1-10 µM
D >10 µM

Biological Example 3: CTG (CellTitre-Glo) Assay

Viability of compound treated cells is measured using CellTiter-Glo® assay (Promega, Madison, Wis.) that measures the ATP content of cells which is proportional to the number of live cells within a well. This is a counter-screen to establish that the reduction of IL-1β levels in LPS and nigericin stimulated and compound treated cells is not due to cytotoxicity, but rather through the inhibition of the inflammasome pathway. Compounds inhibiting NRLP3 inflammasome activation ultimately increase the viability of LPS and nigericin stimulated cells by blocking NLRP3 mediated pyroptosis that would otherwise lead to cell lysis.

Biological Example 4: TNF-α

TNFα levels of LPS and nigericin stimulated cells is measured by HTRF assay (Cisbio, Bedford, Mass.). Inflammasome pathway selective compounds do not inhibit TNFα production that is solely dependent on LPS stimulation and proceeds through the TLR4/NFkB pathway. Measuring TNFalpha production also serves as a technical counter-screen to eliminate compounds that interfere with the HTRF reagents. Thus compounds that inhibit both IL-1β and TNFα levels are triaged for either being non-selective for inflammasome or interfering with the HTRF readout.
Additional Assays
Some of the following assays were used.

Biological Example 5: Human Microsomal Stability (Eh)

The stock solutions of test article and positive control were prepared at a concentration of 10 mM using DMSO as diluents. All stock solutions were then diluted to working concentrations at 0.25 mM with 70% acetonitrile. The cofactor used in this study was NADPH regenerating system, that was composed of 6.5 mM NADP, 16.5 mM G-6-P, 3 U/mL G-6-P D. The quench reagent was consisted of acetonitrile containing tolbutamide and propanolol (serve as internal standard). Incubation mixtures containing 0.5 mg/mL liver microsomal protein and 1 µM test article/positive control in 100 mM potassium phosphate buffer.
The 0-minute samples were prepared by addition of an 80 µL aliquot of each incubation mixture to 300 µL quench reagent to precipitate proteins. The samples were vortexed, and then a 20 µL aliquot of the NADPH regenerating system was added in. The reaction was initiated by addition of 80 µL of the NADPH regenerating system to 320 µL of each incubation mixture. The final incubation conditions achieved in 400 µL are: 0.5 mg/mL microsomal protein, 1 µM test article/positive control, 1.3 mM NADP, 3.3 mM glucose 6 phosphate, 0.6 U/mL glucose 6 phosphate dehydrogenase. The mixtures were incubated in a 37° C. water bath with gentle shaking. A 100 µL aliquot of each mixture was removed at 10, 30, 90 minutes to a clean 96-well plate which contains 300 µL quench reagent to precipitate proteins, and centrifuged (4000×g, 10 min). 80 µL of supernatant are taken into 96-well assay plates pre-added with 160 µL ultrapure water, and then analyzed by LC-MS/MS. Hepatic extraction ratio (Eh) values were calculated from measured in vitro clearance assuming a human liver blood flow of 20.7 mL/min/kg. Eh values of <0.3 are indicative of compounds with favorable metabolic stability.

Biological Example 6: Lipophilicity

Lipophilicity as represented by log D was calculated using Log D plugin from ChemAxon for certain compounds, as shown in the table below.
There have been multiple publications in recent years which associate the clinical success of drug candidates with their physical properties. For example, the degree of lipophilicity can be a factor to the success of drug candidates. In "Lipophilicity in Drug Discovery" (Waring, Expert Opinion on Drug Discovery Volume 5, 2010—Issue 3 Pages 235-248, which is herein incorporated by reference), the author's analysis of attrition indicated that the optimal lipophilicity for small molecule drugs, as measured by log D, is somewhere between 1 and 3. Design of compounds outside of this range can introduce unintended liabilities (i.e. ADMET, promiscuity). Care should be exercised when adding non-polar atoms during the course of lead optimization in drug discovery in order to identify quality molecules capable of successfully advancing through clinical trials.
For example, a pyrazolo-oxazine described herein can offer an advantageous position with respect to lipophilicity. As an example, when compared to an analog with a similar number of non-polar atoms, the cyclic saturated ring spares the rise of ~0.7 log units of clogD.

417

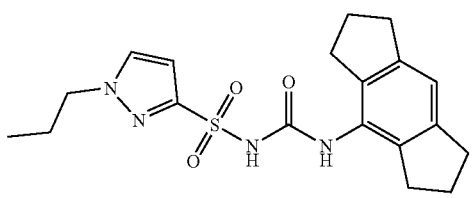

clogD 3.5

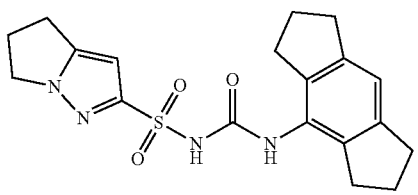

clogD 2.8

418

-continued

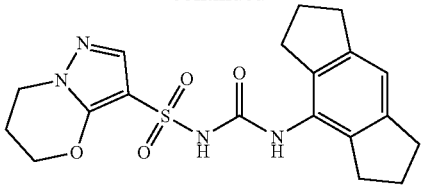

clogD 1.8

Additionally, an oxazine ring offers a scaffolding with a polar atom as well, resulting in a clogD of 1.8. This can allow for further elaboration with other substituents, such as non-polar substituents, without stepping outside of an ideal range described herein.

Results

Figure 2:
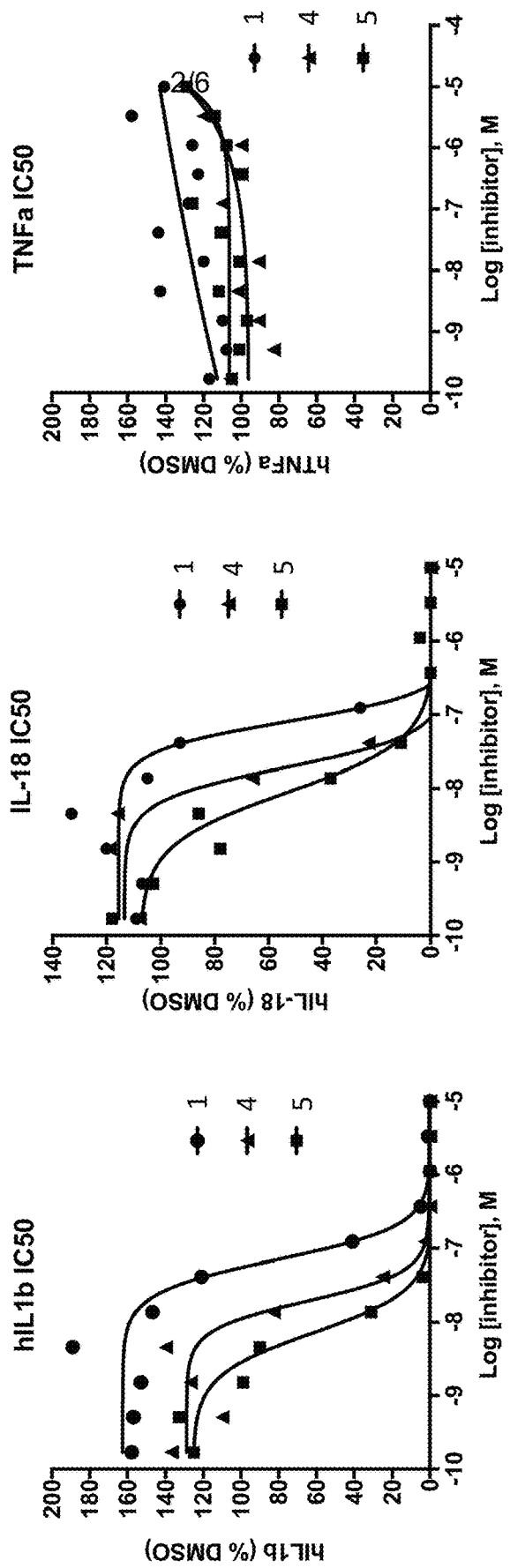
FIG. 2 shows inhibition of IL-1β and IL-18 production, but not TNFα production in Kupffer cells (KCs) as a result of treatment with Compound 1, Compound 4, or Compound 5.

Results of certain compounds are shown below and in FIGS. 1 and 2. PBMC IL-1β IC50 and KC IL-1β IC50 are described above. A<100 nM, B 100 nM-1 μM, C 1-10 μM, D>10 μM

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability ($E_h$) | clogD (pH 7.4) |
|---|---|---|---|---|---|---|
| 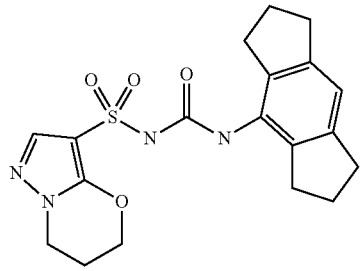 [SMILES: O=C(Nc1c2c(cc3c1CCC3)CCC2)NS(=O)(=O)c1cnn2c1OCCC2] | A | A | A | No Curve | 0.3 | 1.8 |
| 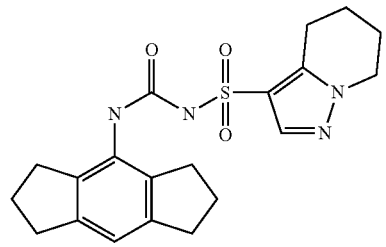 [SMILES: O=C(Nc1c2c(cc3c1CCC3)CCC2)NS(=O)(=O)c1cnn2c1CCCC2] | | | | B | | 2.7 |
| 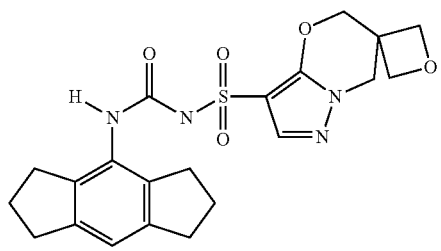 [SMILES: O=C(Nc1c2c(cc3c1CCC3)CCC2)NS(=O)(=O)c1cnn2c1OCC1(COC1)C2] | | | | B | | 1.4 |

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| 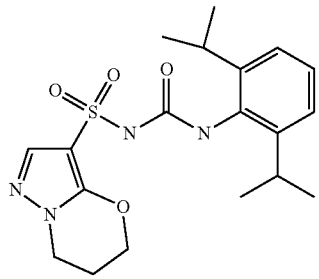 [SMILES: CC(C)c1cccc(C(C)C)c1NC(=O)NS(=O)(=O)c1cnn2c1OCCC2] | C | | | | | 2.3 |
| 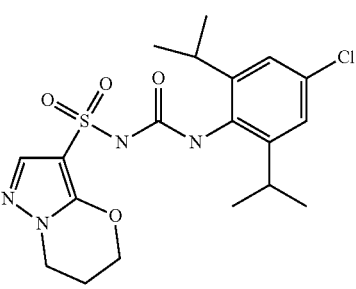 | B | | | | | 2.9 |
| 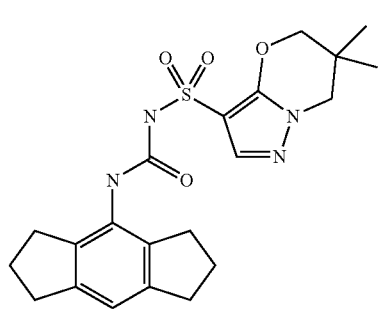 [SMILES: CC1(C)COc2c(S(=O)(=O)NC(=O)Nc3c4c(cc5c3CCC5)CCC4)cnn2C1] | A | A | A | No Curve | 0.5 | 2.8 |
| 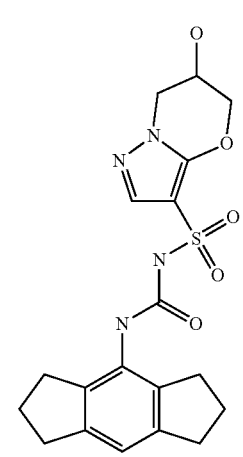 [SMILES: O=C(Nc1c2c(cc3c1CCC3)CCC2)NS(=O)(=O)c1cnn2c1OCC(O)C2] | A | A | A | No Curve | 0.1 | 1.1 |

-continued

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
| --- | --- | --- | --- | --- | --- | --- |
| (structure) | A | | | A | | 2.3 |
| (structure) | A | | | A | | 2.2 |
| (structure) | B | | | A | | 2.0 |
| (structure) | A | A | A | | No Curve | 1.8 |
| (structure) | B | A | | | No Curve | 2.2 |

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| | A | | | | | 2.4 |
| | B | | A | | | 2.5 |
| | B | | | | | 1.4 |
| | C | | | | | 1.6 |
| | B | | A | | | 1.8 |

-continued

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| | A | A | A | | 0.2 | 1.6 |
| | A | A | A | | 0.4 | 2.3 |
| | B | | A | | | 1.1 |
| | A | A | A | | 0.6 | 2.3 |
| | B | | D | | | 2.7 |

-continued
| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
| --- | --- | --- | --- | --- | --- | --- |
| 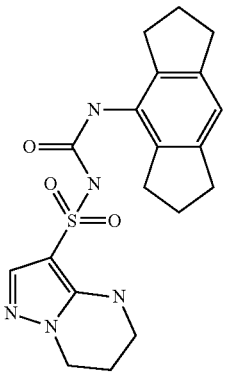 [SMILES: O=C(Nc1c2c(cc3c1CCC3)CCC2)NS(=O)(=O)c1cnn2c1NCCC2] | A | A | A | | 0.2 | 1.5 |
| 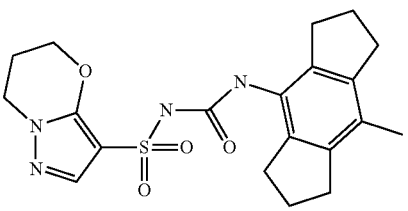 [SMILES: Cc1c2c(c(NC(=O)NS(=O)(=O)c3cnn4c3OCCC4)c3c1CCC3)CCC2] | B | | B | No Curve | | 2.3 |
| 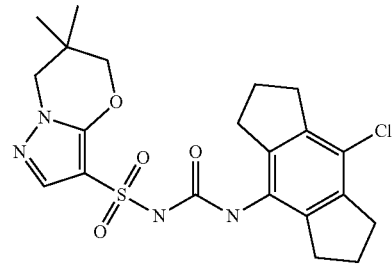 [SMILES: CC1(C)COc2c(S(=O)(=O)NC(=O)Nc3c4c(c(Cl)c5c3CCC5)CCC4)cnn2C1] | B | | | | | 3.4 |
| 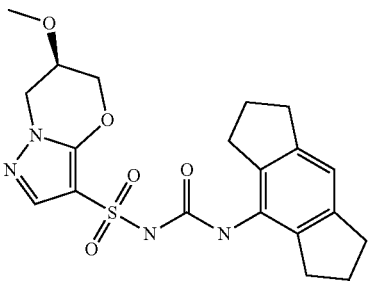 | A | A | A | No Curve | 0.3 | 1.8 |
| 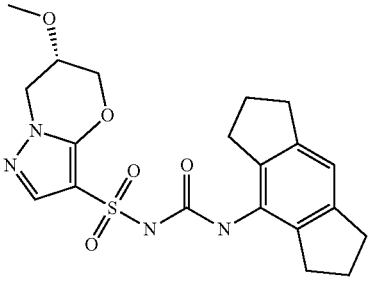 [SMILES: CO[C@@H]1COc2c(S(=O)(=O)NC(=O)Nc3c4c(cc5c3CCC5)CCC4)cnn2C1] | B | B | B | No Curve | 0.2 | 1.8 |

-continued

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| [structure] | | C | B | | | 2.8 |
| [structure] | B | B | | No Curve | | 2.2 |
| [structure] | A | A | A | No Curve | <0.1 | 1.1 |
| [structure] | B | A | | | | 1.1 |
| [structure] | A | A | | | | 1.7 |

-continued
| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| 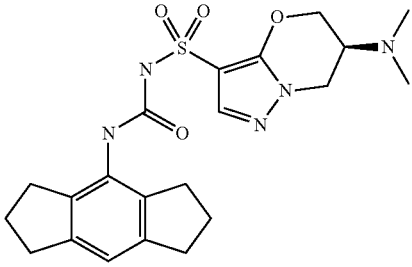 [SMILES: CN(C)[C@@H]1COc2c(S(=O)(=O)NC(=O)Nc3c4c(cc5c3CCC5)CCC4)cnn2C1] | B | | D | | | 1.6 |
| 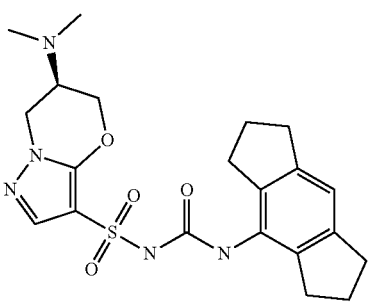 [SMILES: CN(C)[C@H]1COc2c(S(=O)(=O)NC(=O)Nc3c4c(cc5c3CCC5)CCC4)cnn2C1] | A | A | A | No Curve | 0.2 | 1.6 |
| 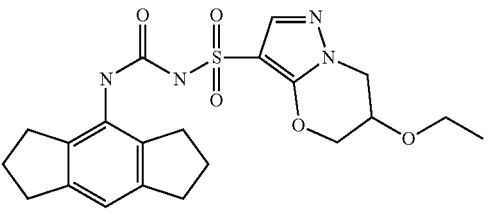 [SMILES: CCOC1COc2c(S(=O)(=O)NC(=O)Nc3c4c(cc5c3CCC5)CCC4)cnn2C1] | A | | A | | | 2.1 |
| 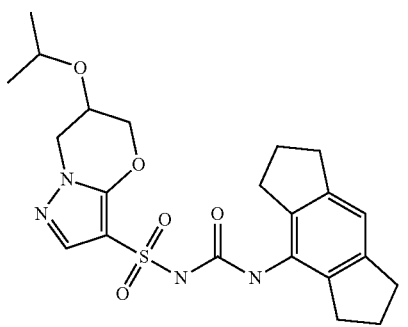 [SMILES: CC(C)OC1COc2c(S(=O)(=O)NC(=O)Nc3c4c(cc5c3CCC5)CCC4)cnn2C1] | B | | A | | | 2.5 |
| 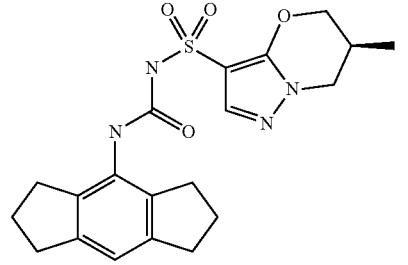 [SMILES: C[C@@H]1COc2c(S(=O)(=O)NC(=O)Nc3c4c(cc5c3CCC5)CCC4)cnn2C1] | A | | A | | | 2.3 |

-continued

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| *[structure]* | A | A | A | No Curve | | 2.3 |
| *[structure]* | B | | A | | | 1.8 |
| *[structure]* | B | | A | | | 1.8 |
| *[structure]* | C | | B | | | 2.3 |
| *[structure]* | A | A | A | No Curve | 0.4 | 2.1 |

-continued

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| (structure) | B | B | | | | 2.1 |
| (structure) | A | A | | | 0.6 | 2.1 |
| (structure) | A | A | | | 0.2 | 1.7 |
| (structure) | B | B | | | | 2.1 |

-continued
| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| 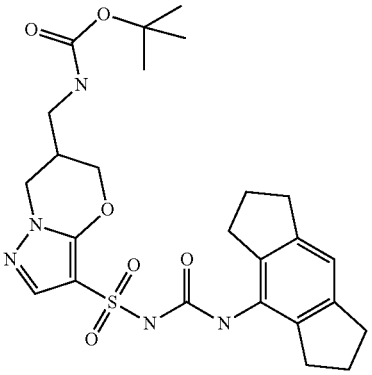 [SMILES: CC(C)(C)OC(=O)NCC1COc2c(S(=O)(=O)NC(=O)Nc3c4c(cc5c3CCC5)CCC4)cnn2C1] | A | A | | | | 2.5 |
| 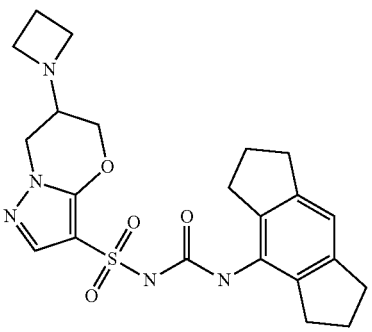 [SMILES: O=C(Nc1c2c(cc3c1CCC3)CCC2)NS(=O)(=O)c1cnn2c1OCC(N1CCC1)C2] | A | A | | | | 1.7 |
| 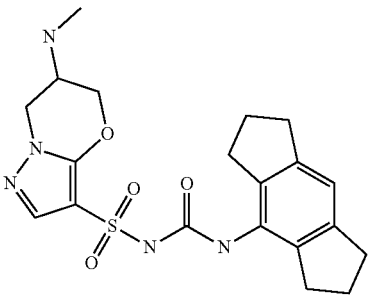 [SMILES: CNC1COc2c(S(=O)(=O)NC(=O)Nc3c4c(cc5c3CCC5)CCC4)cnn2C1] | A | A | | | 0.1 | 1.3 |
| 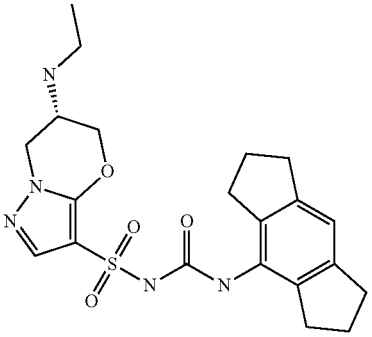 [SMILES: CCN[C@@H]1COc2c(S(=O)(=O)NC(=O)Nc3c4c(cc5c3CCC5)CCC4)cnn2C1] | C | C | | | | 1.7 |

-continued

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| (structure) | ND | ND | | | | 0.8 |
| (structure) | B | B | | | | 2.7 |
| (structure) | C | C | | | | 1.3 |
| (structure) | C | C | | | | 1.4 |

-continued

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| | B | B | | | | 2.1 |
| | B | B | | | | 2.7 |
| | A | A | | | | 2.7 |
| | B | A | | | | 2.2 |
| | A | A | A | No Curve | <0.1 | 1.3 |

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| | | B | | A | | 1.9 |
| | | C | | C | | 1.0 |
| | | B | | A | | 1.4 |
| | | B | | B | | 2.9 |
| | | C | | B | | 1.3 |

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
| --- | --- | --- | --- | --- | --- | --- |
| [structure] | B | | | B | | 2.0 |
| [structure] | No Curve | | | No Curve | | 0.5 |
| [structure] | No Curve | | | | | −0.2 |
| [structure] | A | | | A | | 1.7 |
| [structure] | B | | | A | | 1.4 |

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| 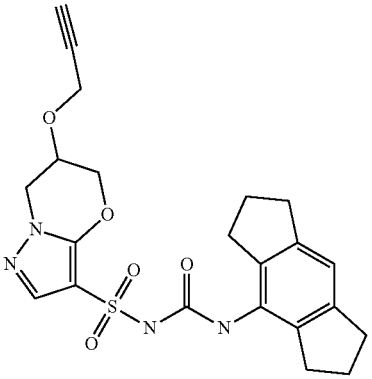 [SMILES: C#CCOC1COc2c(S(=O)(=O)NC(=O)Nc3c4c(cc5c3CCC5)CCC4)cnn2C1] | A | | | A | | 2 |
| 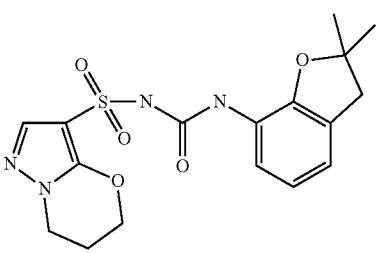 [SMILES: CC1(C)Cc2cccc(NC(=O)NS(=O)(=O)c3cnn4c3OCCC4)c2O1] | D | | | | | 0.4 |
| 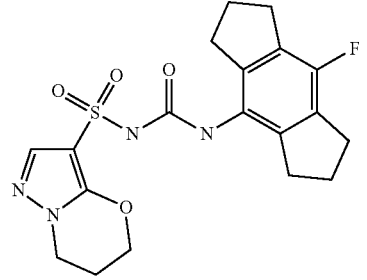 [SMILES: O=C(Nc1c2c(c(F)c3c1CCC3)CCC2)NS(=O)(=O)c1cnn2c1OCCC2] | A | | | A | | 2.0 |
| 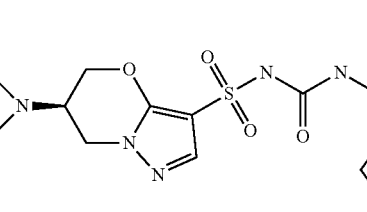 | A | | | A | | 1.7 |
| 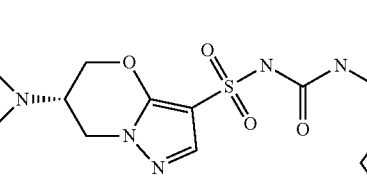 | B | | | A | | 1.7 |

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| | B | | A | | | 2.0 |
| | B | | C | | | 2.2 |
| | A | | A | | | 0.8 |
| | A | | A | | 0.2 | 1.4 |
| | A | | | | | 1.9 |

-continued
| Compound | PBMC IL-1β IC$_{50}$ | KC IL-1β IC$_{50}$ | CTG protective IC$_{50}$ | TNFα IC$_{50}$ (PBMC or KC) | Human Microsomal Stability (E$_h$) | clogD (pH 7.4) |
|---|---|---|---|---|---|---|
| 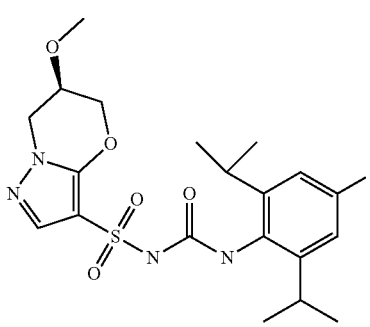 | A | | A | | | 2.4 |
| 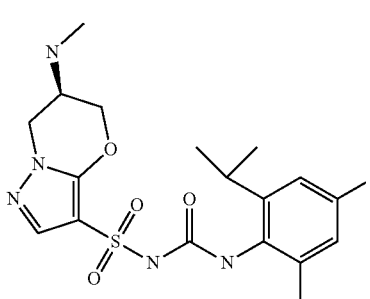 | A | | | | | 1.9 |
| 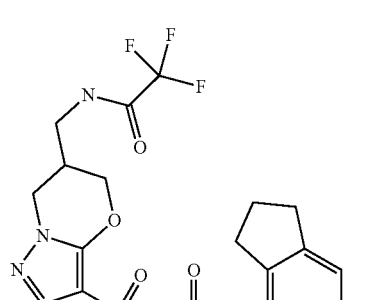 | A | | | | | 1.5 |
| 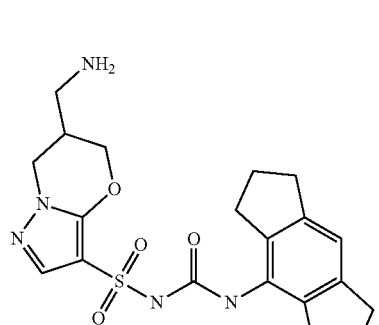 | B | | | | | 1.1 |

| Compound | PBMC IL-1β IC$_{50}$ | KC IL-1β IC$_{50}$ | CTG protective IC$_{50}$ | TNFα IC$_{50}$ (PBMC or KC) | Human Microsomal Stability ($E_h$) | clogD (pH 7.4) |
|---|---|---|---|---|---|---|
| (structure) | B | | | B | | 2.4 |

Biological Example 7: Effects of Treatment on Cytokine Production after LPS/ATP Injection in C57BL/6 Mice Summary:

The effect of Compounds 1 and 2 treatment on the NLRP3 dependent release of IL-1β and TNFα cytokines was explored in an acute in vivo LPS/ATP challenge model. Levels of IL-1β in peritoneal lavage from LPS plus ATP-challenged mice were reduced >98%, relative to vehicle treated animals, following single oral doses of Compound 1 at 1.5 and 5 mg/kg and Compound 2 at 1 and 2.5 mg/kg, at the 3.5 hour time point. IL-1β release was reduced >79% at 0.5 mg/kg Compound 1 and >57% at 0.25 mg/kg Compound 2 after a single oral dose at the 3.5 hour time point, relative to the vehicle treated animals. There were no significant changes in TNFα levels in any of the groups compared to vehicle treated animals.

Compound 1

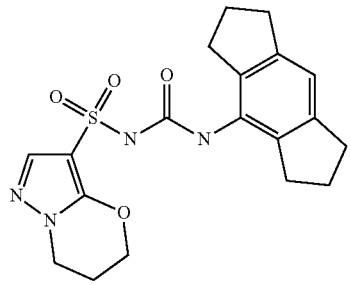

Compound 2

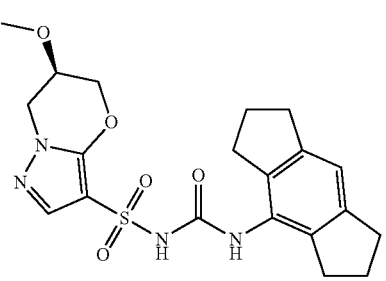

Compound 3

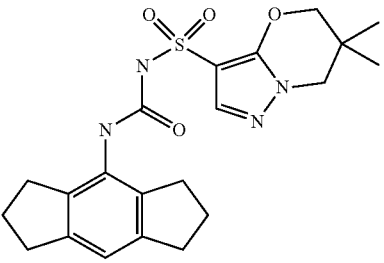

Compound 4

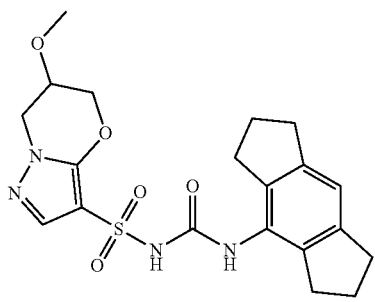

Compound 5

(structure)

Study Objectives:

The purpose of this study was to determine the effects of Compounds 1 and 2 treatment on cytokine production after LPS/ATP injection in female C57BL/6 mice.

Experimental Design and Procedures:
Key study parameters are shown in Table 1.

TABLE 1

| Description | Cytokine production after LPS/ATP injection in C57BL/6 mice |
|---|---|
| Animal strain(s) & gender(s) | C57BL/6 mice, females |
| Day 0 Hour 0 | Time of LPS administration |
| Study length | 1 day |
| ANIMALS & GROUPS | |
| Total number of animals | 56 |
| Source of animals | Taconic Biosciences (breeder) |
| Age at start of study (Day 0) | 8 12 weeks |
| Number of groups | 7 |
| Group size | 8 animals |
| Group assignment day(s) | Day −1 |
| TREATMENT | |
| Dosing starts | Day 0 |
| Dosing ends | Day 0 |
| READOUTS | |
| Tissue collection & analysis | Blood collected, plasma isolated, peritoneal lavage collected, cytokine analysis in peritoneal lavage |

Mice were acclimated to the facility for at least 7 days before the start of the study.

On Day −1 mice were weighed and assigned to groups per Table 2 (see below) in a balanced manner to achieve similar average weight across the groups at the start of the study.

TABLE 2

| Group | # mice | Treatment | Time of Treatment | Plasma Time Points | Dose (mg/kg) | Route | Volume (mL/kg) | Purpose |
|---|---|---|---|---|---|---|---|---|
| 1 | 8 | Vehicle | Hour 1 | | | p.o. | 5 | Negative control |
| 2 | 8 | Compound 1 | Hour 1 | 3.5 | 0.5* | p.o. | 5 | Test |
| 3 | 8 | Compound 1 | Hour 1 | 3.5 | 1.5* | p.o. | 5 | Test |
| 4 | 8 | Compound 1 | Hour 1 | 3.5 | 5.0* | p.o. | 5 | Test |
| 5 | 8 | Compound 2 | Hour 1 | 3.5 | 0.25 | p.o. | 5 | Test |
| 6 | 8 | Compound 2 | Hour 1 | 3.5 | 1.0 | p.o. | 5 | Test |
| 7 | 8 | Compound 2 | Hour 1 | 3.5 | 2.5 | p.o. | 5 | Test |

*corrected for salt content

All mice received a single dose of treatment or vehicle, at hour minus 1.

At hour 0, all mice received 1 μg of lipopolysaccharide, ultra pure (LPS, InvivoGen, San Diego, Calif.) in 0.5 ml PBS, intraperitoneally.

At hour 2 (two hours after LPS injection), all mice were injected intraperitoneally with 0.5 ml of 80 mM ATP disodium salt (Sigma, pH adjusted to 7.2 before injection).

At hour 2.5 (30 minutes after ATP injection and 3.5 hours after compound dosing), blood from all mice was collected via retro-orbital bleeding into K2 EDTA tubes and plasma was prepared and stored at 80 C. Samples were shipped to the customer or vendor of customers choosing within 7 days of completing the study.

Immediately after the collection of blood, each mouse was euthanized, the peritoneal cavity was lavaged with 3 ml of ice-cold PBS containing 25 U/ml heparin sodium salt, cocktail of protease inhibitors (Complete™ ULTRA Tablets, Sigma, Roche), and 10% FBS. Approximately 1 ml of the lavage was collected, spun down to remove cells and the supernatant stored at −80° C.

The vehicle for Compound 1 was PBS and for Compound 2 was 0.5% methylcellulose. Compound powders were stored at 4° C. All compounds were prepared fresh. Compounds were weighed out and first ground with a mortar and pestle, then ground with a small amount of vehicle. The mortar was then repeatedly rinsed with vehicle to remove all material and achieve the correct concentration. The final solution was vortexed to create a homogeneous mixture Cytokine Analysis:

Mouse IL-1β and TNFα concentrations in peritoneal lavage samples were determined using Becton Dickinson (Franklin Lakes, N.J.) CBA analysis kit, according to manufacturer's protocol. A single analysis was performed on each sample.

Statistical Analysis:

Concentrations of cytokines were compared using Student t-test.

Figure 3:
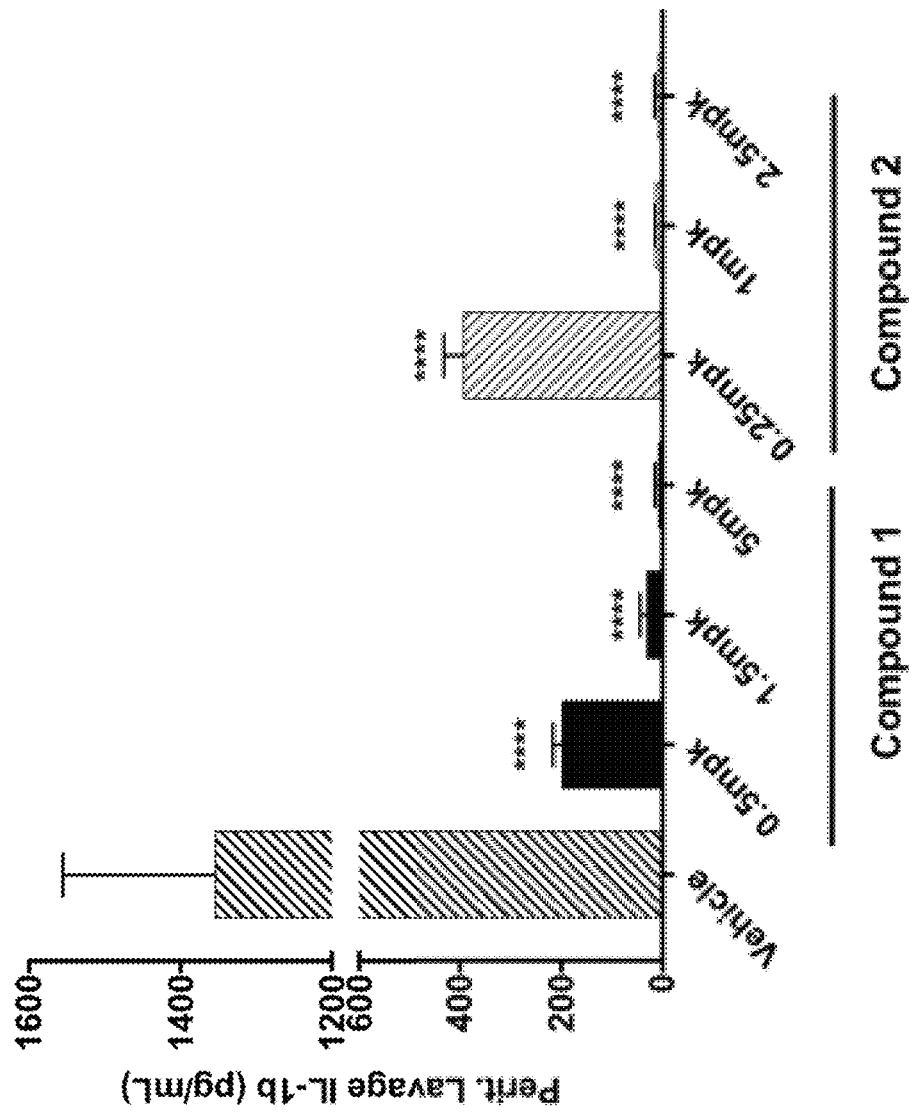
FIG. 3 shows modulation of IL-1β in an LPS and ATP challenge model of Compound 1 and Compound 2.

Results:

The effects of Compound 1 and Compound 2 treatment on IL-1β cytokine production was evaluated in the LPS/ATP injection model. Female C57BL/6 mice were dosed orally with either Compound 1 at 0.5, 1.5 and 5 mg/kg or Compound 2 at 0.25, 1 and 2.5 mg/kg and the relative amounts of IL-1β (pg/ml) were determined using Becton Dickinson CBA analysis kit. Levels of IL-1β in peritoneal lavage from LPS plus ATP-challenged mice were reduced >98%, relative to vehicle treated animals, following single oral doses of Compound 1 at 1.5 and 5 mg/kg, and Compound 2 at 1 and 2.5 mg/kg, at the 3.5 hour time point (Tables 3 and 4, FIG. 3).

Figure 4:
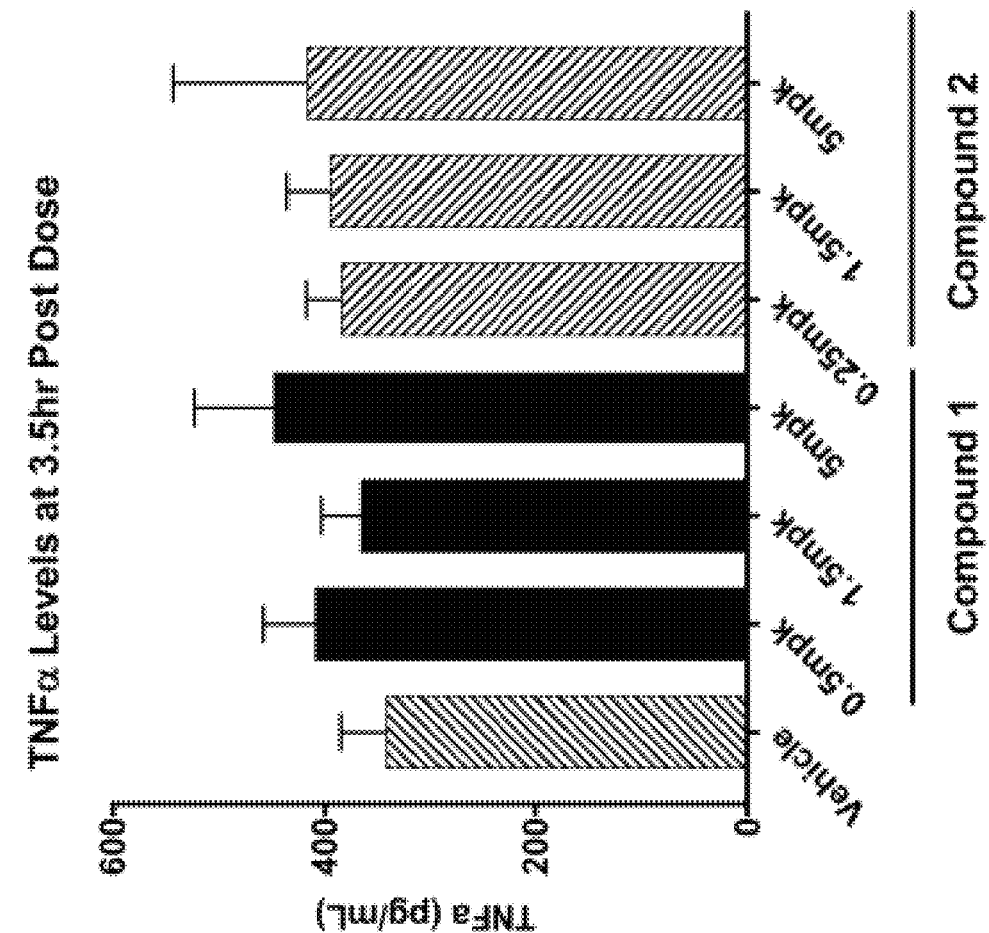
FIG. 4 shows modulation of TNFα in an LPS and ATP challenge model of Compound 1 and Compound 2.

IL-1β release was reduced >79% at 0.5 mg/kg Compound 1 and >57% at 0.25 mg/kg Compound 2 after a single oral dose at the 3.5 hour time point, relative to the vehicle treated animals. There were no significant changes in TNFα levels in any of the groups compared to vehicle treated animals (Tables 3 and 4, FIG. 4).

Figure 5:
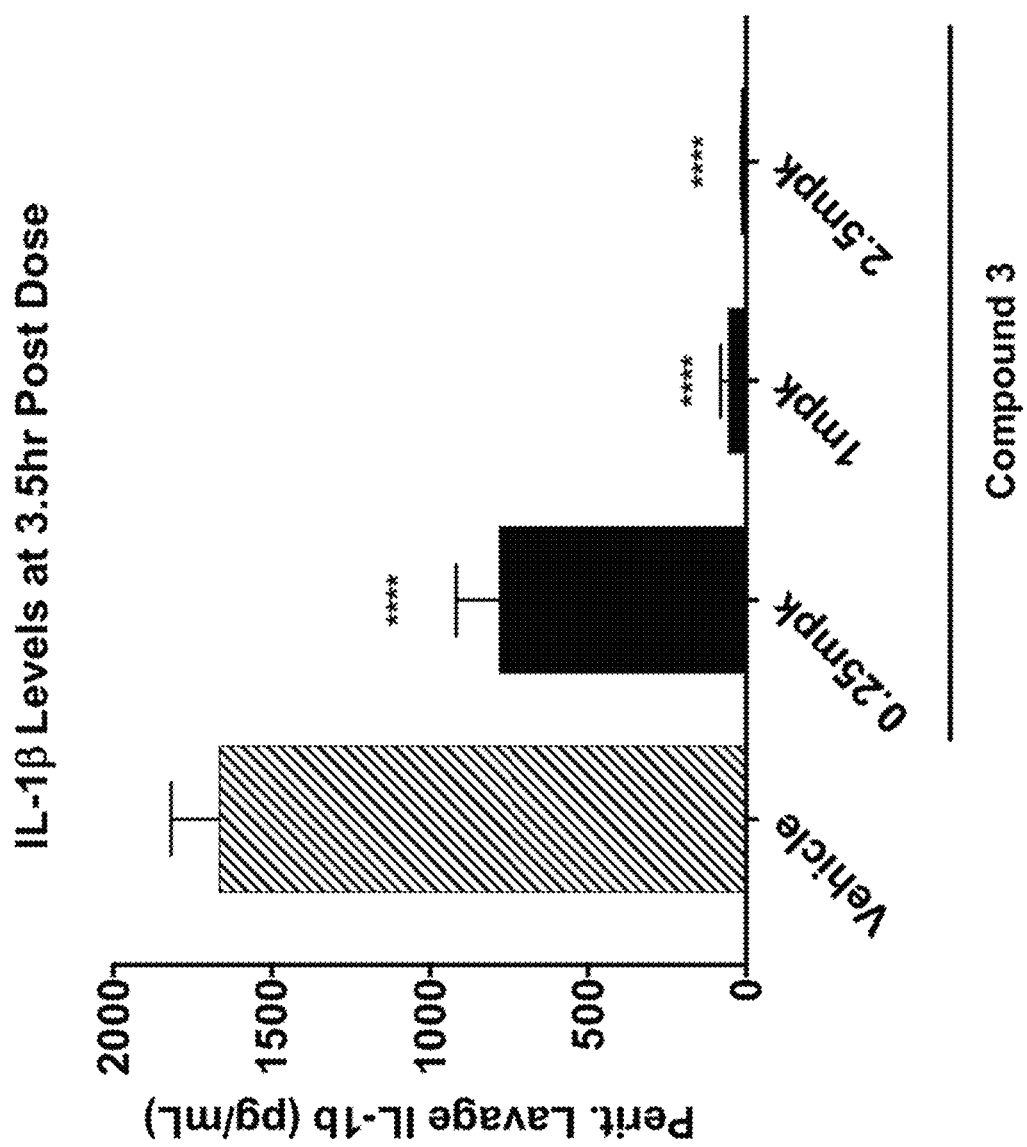
FIG. 5 shows modulation of IL-1β in an LPS and ATP challenge model of Compound 3.

The effect of Compound 3 treatment on IL-1β cytokine production was evaluated in the LPS/ATP injection model. Female C57BL/6 mice were dosed orally with Compound 3 at 0.25, 1 and 2.5 mg/kg and the relative amounts of IL-1β (pg/ml) were determined using Becton Dickinson CBA analysis kit. Levels of IL-1β in peritoneal lavage from LPS plus ATP-challenged mice were reduced >96%, relative to vehicle treated animals, following single oral doses of Compound 2 at 1 and 2.5 mg/kg, at the 3.5 hour time point (Tables 5, FIG. 5).

TABLE 3

Compound 1 at 3.5 hours post single oral dose

| Dose (mg/kg) | Mean (IL-1β) (pg/mL) | STD Dev | n | T-Test | % Decrease of IL-1β vs. Vehicle |
|---|---|---|---|---|---|
| Vehicle | 1354.2 | 569.2 | 8 | — | — |
| 0.5 | 198.4 | 50.0 | 8 | 0.0001 | 85.3 |
| 1.5 | 17.1 | 7.5 | 7 | 0.0000 | 98.7 |
| 5 | 10.2 | 4.5 | 8 | 0.0000 | 99.3 |

| Dose (mg/kg) | Mean (TNFα) (pg/mL) | STD Dev | n | T-Test | % Decrease of TNFα vs. Vehicle |
|---|---|---|---|---|---|
| Vehicle | 342.0 | 122.8 | 8 | — | . |
| 0.5 | 409.0 | 140.0 | 8 | 0.3260 | −19.6 |
| 1.5 | 339.9 | 84.4 | 7 | 0.9707 | 0.6 |
| 5 | 449.4 | 74.3 | 8 | 0.0526 | −31.4 |

TABLE 4

Compound 2 at 3.5 hours post single oral dose

| Dose (mg/kg) | Mean (pg/mL) | STD Dev | n | T-Test | % Decrease of IL-1β vs. Vehicle |
|---|---|---|---|---|---|
| Vehicle | 1354.2 | 569.2 | 8 | — | — |
| 0.25 | 392.7 | 110.5 | 8 | 0.0003 | 71.0 |
| 1 | 12.9 | 4.4 | 8 | 0.0000 | 99.0 |
| 2.5 | 10.7 | 4.8 | 8 | 0.0000 | 99.2 |

| Dose (mg/kg) | Mean (TNFα) (pg/mL) | STD Dev | n | T-Test | % Decrease of TNFα vs. Vehicle |
|---|---|---|---|---|---|
| Vehicle | 342.0 | 122.8 | 8 | | |
| 0.25 | 384.7 | 93.4 | 8 | 0.4459 | −12.5 |
| 1 | 394.9 | 116.2 | 8 | 0.3904 | −15.5 |
| 2.5 | 416.6 | 126.9 | 8 | 0.2516 | −21.8 |

TABLE 5

Compound 3 at 3.5 hours post single oral dose

| Dose (mg/kg) | Mean (pg/mL) | STD Dev | n | T-Test | % Decrease of IL-1β vs. Vehicle |
|---|---|---|---|---|---|
| Vehicle | 1664.7 | 432.4 | 8 | — | — |
| 0.25 | 781.8 | 384.7 | 8 | 0.0007 | 53.0 |
| 1 | 57.7 | 24.8 | 8 | 0.0000 | 96.5 |
| 2.5 | 14.6 | 7.1 | 8 | 0.0000 | 99.1 |

Conclusions:

The effect of Compound 1 and Compound 2 treatment on the NLRP3 dependent release of IL-1β cytokine was explored in an acute in vivo LPS/ATP challenge model. Levels of IL-1β in peritoneal lavage from LPS plus ATP-challenged mice were reduced >98%, relative to vehicle treated animals, following single oral doses of Compound 1 at 1,5 and 5 mg/kg, and Compound 2 at 1 and 2.5 mg/kg, at the 3.5 hour time point. IL-1β release was reduced >79% at 0.5 mg/kg Compound 1 and >57% at 0.25 mg/kg Compound 2 after a single oral dose at the 3.5 hour time point, relative to the vehicle treated animals. There were no significant changes in TNFα levels in any of the groups compared to vehicle treated animals.

Biological Example 8: Inhibition of Caspase1 Activation

Materials and Methods

Cell Culture

Bone marrow cells were collected from freshly harvested mouse bones of 16 Black 6 mice, from 4 bones each (2× tibia and 2× femur). Bones were delivered fresh in complete BMDM media: RPMI 1640 Medium, GlutaMAX™ Supplement, 1% Non-essential amino acids, 1% Penicillin/Streptomycin, 10 mM HEPES, 0.05 mM β-ME, 20 ng/ml GM-CSF and 10% FBS. Tops and bottoms were cut off with scissors and 25G needle had been used to wash out the cells carefully with complete BMDM media from each bone. Cells were run through a 100 μm cell strainer before centrifuging at 250 g. CD14+ cells were isolated through magnetic negative selection using EasySep Mouse Monocyte Isolation Kit (StemCell Technologies) according to manufacturer's instructions. Approximately 2 ml of cells were run through 3 independent purification procedures. Total number of cells was approximately 12.7 million. CD14+ cells were seeded at 25,000 cells/well into 96-well plates. Complete BMDM media was exchanged every 3 days. Experiments were performed at day 9 post-seeding.

Inflammasome Activation

Bone marrow derived macrophages (BMDMs) were pre-incubated with DMSO or compounds at indicated concentrations for 30 min before being stimulated with LPS at 100 ng/ml. Cells were incubated at 37° C. 5% $CO_2$ environment for 3 hours. Cells were then further stimulated with 10 μM nigericin and incubated at 37° C. 5% $CO_2$ for 90 minutes. At the end of the incubation period supernatants were collected and analyzed for cytokines. Cells were either harvested for Western Blot analysis or tested for viability using CellTiter-Glo (Promega).

Western Blots

Cell samples from 96-well plates were prepared by lysing cells in situ with 50 μl of 4× NuPAGE LDS sample buffer (Fisher)+5% β-mercaptoethanol. Plates were put on a plate shaker at 700 rpm for an hour and then sonicated for 10 minutes. Cell lysates were transferred to a PCR plate and heated to 95° C., for 5 min. Samples were run on NuPAGE Bis-Tris gels (Fisher) and transferred to PVDF membranes using the iBlot 2 system (Fisher). PVDF membranes were blocked in Azure Blot Washing Buffer (Azure Biosystems)+5% low-fat dry milk for at least 5 min. Membranes were probed with the following primary antibodies: pro-caspase-1+p10+p12 [EPR16883] (Abcam), β-actin (Sigma), NLRP3 [Cryo-2] (Adipogen) All antibody incubations were performed in Azure Blot Washing Buffer+5% low-fat dry milk. Secondary antibodies were purchased from Azure Biosystems. Membranes were washed for at least 3×5 minutes after each antibody incubations with Azure Blot Washing Buffer. Membranes were imaged with a Azure c300 imager (Azure Biosystems)

Results

Western Blots

Figure 6:
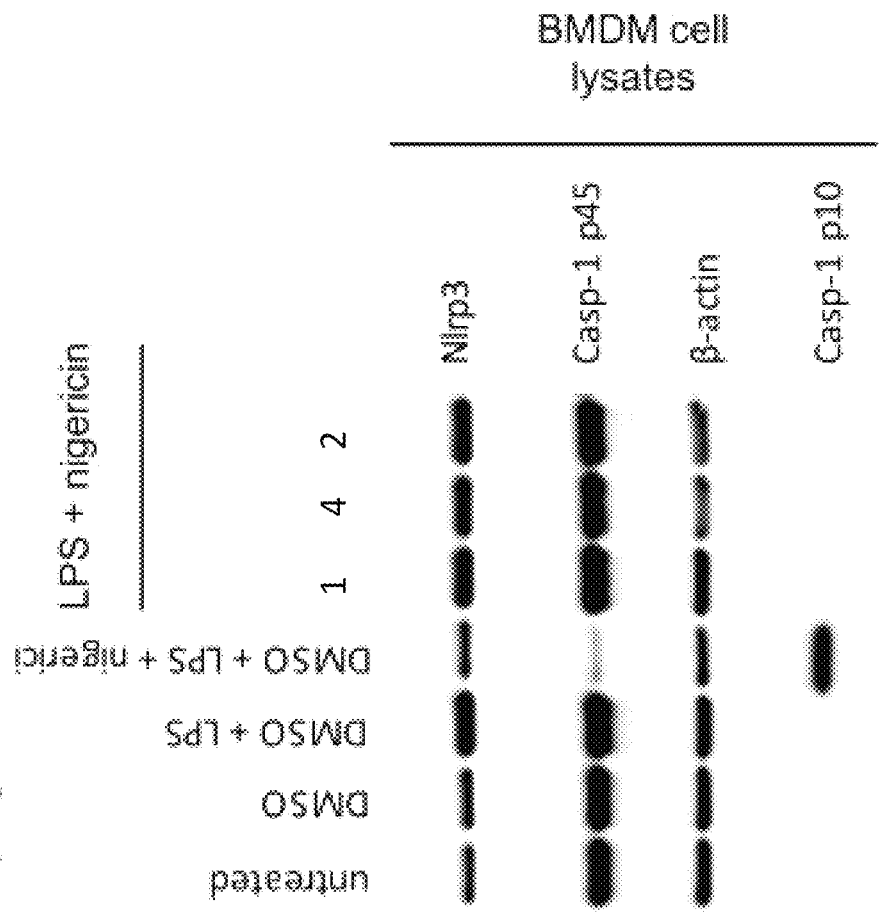
FIG. 6 shows inhibition of activation of Caspase1 (conversion of pro-Caspase1 to active Caspase1) as a result of treatment with Compound 1, Compound 4, or Compound 2.

Stimulation of BMDMs by LPS followed by nigericin results in the activation of the NLRP3 inflammasome which in turn initiates pro-caspase-1 activation. During autocatalytic cleavage, the p45 pro-caspase is cleaved in to a p10 and p20 fragment. The reduced intensity p45 band and the appearance of the p10 band on the attached Western Blots indicates successful pro-caspase-1 activation upon LPS and nigericin stimuli. In the presence of 10 μM Compounds 1, 4, and 2, the activation of pro-caspase-1 is blocked as indicated by intact p45 bands and lack of p10 bands (FIG. 6).

Biological Example 9: Pharmacokinetics in Mice

The intravenous dosing solutions were administered at 1 mg/kg and were made by dissolving the test article into the formulations shown below. The oral dosing suspensions or solutions were administered at 10 mg/kg and were made by dissolving the test article in the formulations shown below. Blood samples were collected into tubes containing either K2EDTA or sodium heparin and kept chilled on ice block or wet ice immediately following collection and during processing. After centrifugation, the resulting plasma samples were stored in a freezer at −80° C. until samples were analyzed. Pharmacokinetic parameters were determined following measurement of compound concentrations in plasma using standard bioanalytical methods at timepoints ranging from 0 to 24 hours.

Compound A

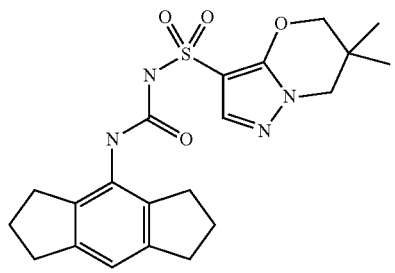 [SMILES: CC1(C)COc2c(S(=O)(=O)NC(=O)Nc3c4c(cc5c3CCC5)CCC4)cnn2C1]

Compound B

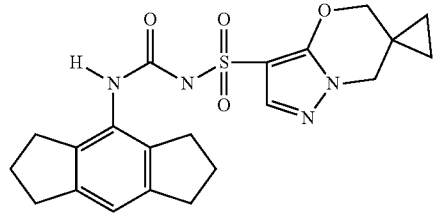 [SMILES: O=C(Nc1c2c(cc3c1CCC3)CCC2)NS(=O)(=O)c1cnn2c1OCC1(CC1)C2]

Compound C

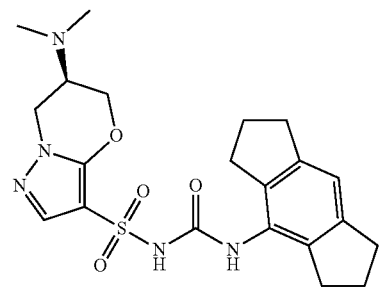 [SMILES: CN(C)[C@H]1COc2c(S(=O)(=O)NC(=O)Nc3c4c(cc5c3CCC5)CCC4)cnn2C1]

Compound D

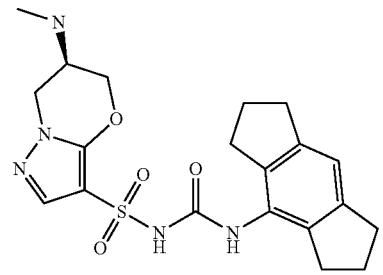 [SMILES: CN[C@H]1COc2c(S(=O)(=O)NC(=O)Nc3c4c(cc5c3CCC5)CCC4)cnn2C1]

-continued

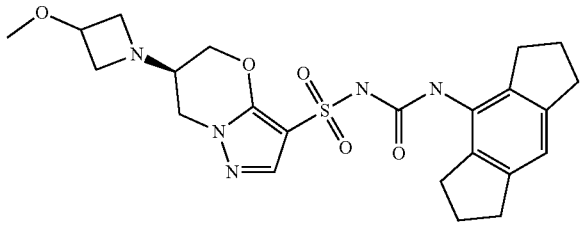 [SMILES: COC1CN([C@H]2COc3c(S(=O)(=O)NC(=O)Nc4c5c(cc6c4CCC6)CCC5)cnn3C2)C1]

Compound E

| Cmpd | Gender Species | Route | Formulation | Dose (mg/kg) | AUC 0-24 hr (hr*ng/mL) | Cmax (ng/mL) | $T_{1/2}$ (hr) | Cl (L/hr/kg) | Vz (L/kg) | Bio-availability (% F) |
|---|---|---|---|---|---|---|---|---|---|---|
| A | Male CD-1 Mice | IV | 5% DMSO + 10% Solutol HS 15 + 85% HP-beta-CD | 1 | 29234 | 9197 | 2.8 | 0.04 | 0.137 | |
| A | Male CD-1 Mice | PO | 0.5% MC | 10 | 186219 | 22684 | 3.4 | | | 64 |
| B | Male CD-1 Mice | IV | 5% DMSO + 10% Solutol HS 15 + 85% HP-beta-CD | 1 | 20174 | 11727 | 1.9 | 0.05 | 0.13 | |
| B | Male CD-1 Mice | PO | 0.5% MC | 10 | 255966 | 62977 | 1.9 | | | 100 |
| C | Male CD-1 Mice | IV | 5% DMSO + 10% Solutol HS 15 + 85% HP-beta-CD | 1 | 2991 | 5292 | 1.3 | 0.34 | 0.64 | |
| C | Male CD-1 Mice | PO | 0.5% MC | 10 | 9954 | 7528 | 1.0 | | | 33 |
| D | Female CD-1 Mice | IV | 10% Propylene Glycol; 5% Transcutol; 85% of 50 mM Na$_2$HPO$_4$ at pH 7.4 | 1 | 3400 | 3313 | 1.6 | 0.30 | 0.69 | |
| D | Female CD-1 Mice | PO | 0.5% MC; 0.25% Tween 80 in 50 mM Na$_2$HPO$_4$/NaH$_2$PO$_4$ at pH 8 | 10 | 23465 | 13700 | 1.7 | | | 69 |
| E | Female CD-1 Mice | IV | 5% Propylene Glycol; 5% Transcutol; 90% of 50 mM Na$_2$HPO$_4$ at pH 7.4 | 1 | 1570 | 2830 | 1.6 | 0.64 | 1.47 | |
| E | Female CD-1 Mice | PO | 0.5% MC; 0.25% Tween 80 in 50 mM Na$_2$HPO$_4$/NaH$_2$PO$_4$ at pH 7.4 | 10 | 8267 | 8620 | 1.9 | | | 53 |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A compound of formula (Ib):

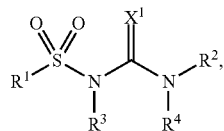

(Ib)

or a pharmaceutically acceptable salt, solvate, or tautomer thereof, wherein:

$X^1$ is O or S;

$R^1$ is selected from the group consisting of

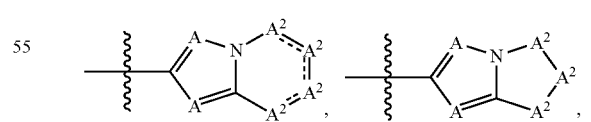

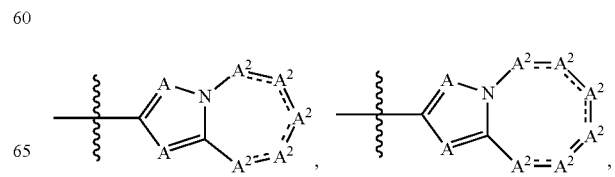

-continued

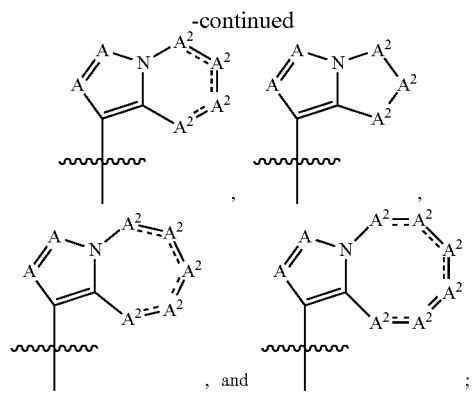
, and wherein ═ represents a single bond or a double bond provided that the ring comprising one or more $A^2$ is a non-aromatic ring;

each A is independently $CR^{5a}$ or N;

each $A^2$ is independently $CR^{5a}$, $C(R^{5a})_2$, N, $NR^{5a}$, O, S, or $S(O)_2$;

$R^2$ is

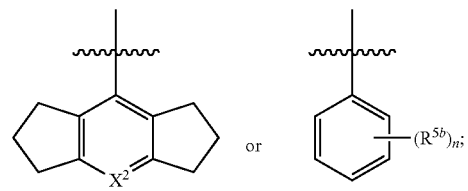

$X^2$ is N or $CR^{5b}$;

$R^3$ and $R^4$ are H;

each $R^{5a}$ is independently H, D, halogen, —OH, —CN, —$NO_2$, —$SR^6$, —$OR^6$, —$NHR^6$, —$NR^6R^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —$CH_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —$CH_2$—$C_3$-$C_8$cycloalkyl are optionally substituted with D, halogen, $C_1$-$C_6$alkyl, —$OR^6$, —$NH_2$, —NH($C_1$-$C_6$alkyl), or —N($C_1$-$C_6$alkyl); or two $R^{5a}$ together with the atoms to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —$OR^6$, —$NH_2$, —NH($C_1$-$C_6$alkyl), or —N($C_1$-$C_6$alkyl)$_2$; or two geminal $R^{5a}$ can form an oxo group;

each $R^{5b}$ is independently H, D, halogen, —OH, —CN, —$NO_2$, —$SR^6$, —$OR^6$, —$NHR^6$, —$NR^6R^7$, $C_1$-$C_6$alkyl, $C_2$-$C_6$alkenyl, $C_4$-$C_8$cycloalkenyl, or $C_2$-$C_6$alkynyl; wherein the $C_1$-$C_6$alkyl, $C_2$-$C_6$alkenyl, $C_4$-$C_8$cycloalkenyl, and $C_2$-$C_6$alkynyl are optionally substituted with D, halogen, —$OR^6$, —$NH_2$, —NH($C_1$-$C_6$alkyl), or —N($C_1$-$C_6$alkyl)$_2$;

$R^6$ and $R^7$ are independently, at each occurrence, H, D, $C_1$-$C_8$alkyl, $C_2$-$C_8$alkenyl, $C_2$-$C_8$alkynyl, $C_3$-$C_8$cycloalkyl, $C_4$-$C_8$cycloalkenyl, heterocyclyl, aryl, or heteroaryl; wherein the heterocyclyl and heteroaryl contain 1-5 heteroatoms selected from the group consisting of N, S, P and O; wherein the $C_1$-$C_6$alkyl, $C_2$-$C_8$alkenyl, $C_2$-$C_6$alkynyl, $C_3$-$C_8$cycloalkyl, $C_4$-$C_8$cycloalkenyl, heterocyclyl, aryl, and heteroaryl are optionally substituted with D, halogen, $C_1$-$C_6$alkyl, —OH, —O—$C_1$-$C_6$alkyl, —$NH_2$, —NH($C_1$-$C_6$alkyl), or —N($C_1$-$C_6$alkyl)$_2$; or $R^6$ and $R^7$ together with the atom to which they are attached can form heterocyclyl or heteroaryl containing 1-3 heteroatoms selected from the group consisting of N, S, P, and O; and n is an integer from 0 to 5;

provided that when the ring comprising A is an imidazole, then at least one $A^2$ is N, $NR^{5a}$, O, S, or $S(O)_2$.

2. The compound of claim 1, wherein the compound is of Formula (I):

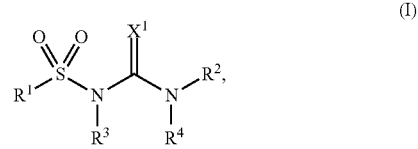

or a pharmaceutically acceptable salt, solvate, or tautomer thereof, wherein;

$X^1$ is O or S;

$R^1$ is selected from the group consisting of

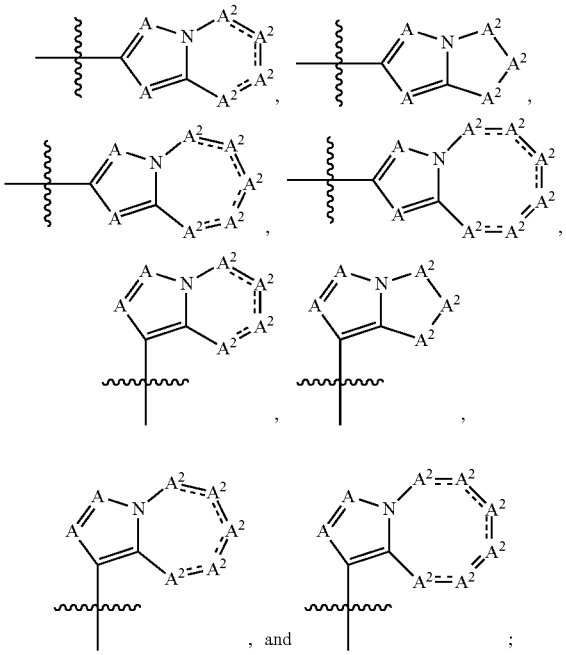
, and wherein ═ represents a single bond or a double bond provided that the ring comprising one or more $A^2$ is a non-aromatic ring;

each A is independently $CR^5$ or N;

each $A^2$ is independently $CR^5$, $C(R^5)_2$, N, $NR^5$, O, S, or $S(O)_2$;

$R^2$ is

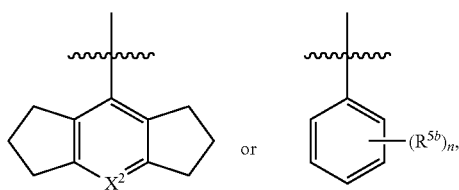

$X^2$ is N or $CR^5$;
$R^3$ and $R^4$ are H;
each $R^5$ is independently H, D, halogen, —OH, —CN, —NO$_2$, —SR$^6$, —OR$^6$, —NR$^6$R$^7$, C$_1$-C$_6$alkyl, C$_2$-C$_6$alkenyl, C$_4$-C$_8$cycloalkenyl, or C$_2$-C$_6$alkynyl;
$R^6$ and $R^7$ are independently, at each occurrence, H, D, C$_1$-C$_8$alkyl, C$_2$-C$_8$alkenyl, C$_4$-C$_8$cycloalkenyl, C$_2$-C$_8$alkynyl, C$_3$-C$_8$cycloalkyl, heterocyclyl, aryl, or heteroaryl; wherein the heterocyclyl and heteroaryl contain 1-5 heteroatoms selected from the group consisting of N, S, P and O; or
$R^6$ and $R^7$ together with the atom to which they are attached can form heterocyclyl or heteroaryl containing 1-3 heteroatoms selected from the group consisting of N, S, P, and O; and
n is an integer from 0 to 5;
provided that when the ring comprising A is an imidazole, then at least one A$^2$ is N, NR$^5$, O, S, or S(O)$_2$.

3. The compound of claim 1, or a pharmaceutically acceptable salt, solvate, or tautomer thereof, wherein $R^2$ is

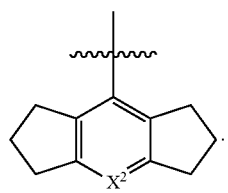

4. The compound of claim 3, or a pharmaceutically acceptable salt, solvate, or tautomer thereof, wherein $X^2$ is CR$^{5b}$ and R$^{5b}$ is H, fluoro, chloro, or methyl.

5. The compound of claim 1, or a pharmaceutically acceptable salt, solvate, or tautomer thereof, wherein $R^2$ is

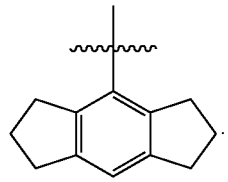 [SMILES: *c1c2c(cc3c1CCC3)CCC2]

6. The compound of claim 2, or a pharmaceutically acceptable salt, solvate, or tautomer thereof, wherein $R^2$ is

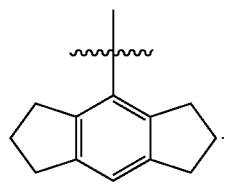 [SMILES: *c1c2c(cc3c1CCC3)CCC2]

7. The compound of claim 1, or a pharmaceutically acceptable salt, solvate, or tautomer thereof, wherein $R^2$ is

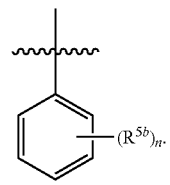

8. The compound of claim 7, or a pharmaceutically acceptable salt, solvate, or tautomer thereof, wherein each R$^{5b}$ is independently selected from the group consisting of H, D, halogen, —OH, —CN, NO$_2$, OR$^6$, C$_1$-C$_6$alkyl, C$_2$-C$_6$alkenyl, and C$_4$-C$_8$cycloalkenyl.

9. The compound of claim 7, or a pharmaceutically acceptable salt, solvate, or tautomer thereof, wherein $R^2$ is

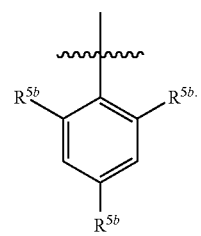

10. The compound of claim 9, or a pharmaceutically acceptable salt, solvate, or tautomer thereof, wherein each R$^{5b}$ is independently selected from the group consisting of H, D, halogen, C$_1$-C$_6$alkyl, and —CN.

11. The compound of claim 8, or a pharmaceutically acceptable salt, solvate, or tautomer thereof, wherein $R^2$ is selected from the group consisting of

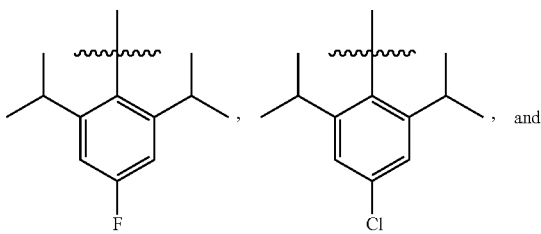

and

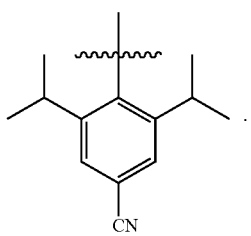

12. The compound of claim 1, or a pharmaceutically acceptable salt, solvate, or tautomer thereof, wherein $X^1$ is O;
$R^1$ is selected from the group consisting of

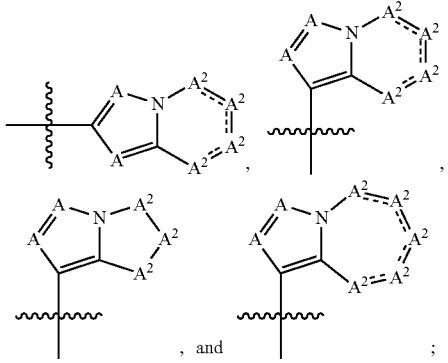
, and ;

wherein = represents a single bond;
each $A^2$ is independently $C(R^{5a})_2$ or O;
$X^2$ is $CR^{5b}$;
each $R^{5a}$ is independently H, halogen, —OH, —OR$^6$, —NR$^6$, —NR$^6$R$^7$, $C_1$-$C_6$alkyl, or heterocyclyl; wherein the $C_1$-$C_6$alkyl and heterocyclyl are optionally substituted with D, halogen, —OR$^6$, —NH$_2$, —NH($C_1$-$C_6$alkyl), or —N($C_1$-$C_6$alkyl)$_2$; or
two $R^{5a}$ together with the atoms to which they are attached can form $C_3$-$C_8$cycloalkyl or heterocyclyl; wherein the heterocyclyl contains 1-3 heteroatoms selected from the group consisting of N, S, P, and O; wherein the $C_3$-$C_8$cycloalkyl and heterocyclyl are optionally substituted with D, halogen, $C_1$-$C_6$alkyl, —OR$^6$, —NH$_2$, —NH($C_1$-$C_6$alkyl), or —N($C_1$-$C_6$alkyl)$_2$; or
two geminal $R^{5a}$ can form an oxo group;
each $R^{5b}$ is independently H, D, halogen, —CN, —OR$^6$, or $C_1$-$C_6$alkyl; wherein the $C_1$-$C_6$alkyl is optionally substituted with D, halogen, —OR$^6$, —NH$_2$, —NH($C_1$-$C_6$alkyl), or —N($C_1$-$C_6$alkyl)$_2$; and
$R^6$ and $R^7$ are independently, at each occurrence, H, D, $C_1$-$C_8$alkyl, $C_2$-$C_8$alkynyl, or aryl; wherein $C_1$-$C_6$alkyl, $C_2$-$C_6$alkynyl, and aryl are optionally substituted with D, halogen, or $C_1$-$C_6$alkyl.

13. The compound of claim 1, or a pharmaceutically acceptable salt, solvate, or tautomer thereof, wherein $R^1$ is

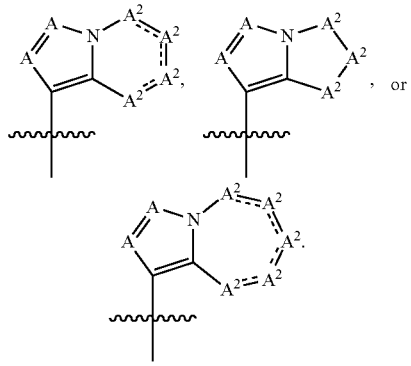

14. The compound of claim 1, or a pharmaceutically acceptable salt, solvate, or tautomer thereof, wherein $R^1$ is

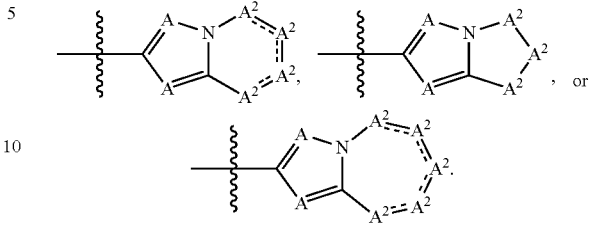

15. The compound of claim 1, or a pharmaceutically acceptable salt, solvate, or tautomer thereof, wherein each $A^2$ is independently $C(R^{5a})_2$, $NR^{5a}$, or O.

16. The compound of claim 15, or a pharmaceutically acceptable salt, solvate, or tautomer thereof, wherein each $R^{5a}$ is independently H, —NHR$^6$, —NR$^6$R$^7$, $C_1$-$C_6$alkyl, or heterocyclyl containing N, wherein the $C_1$-$C_6$alkyl is substituted with —NH$_2$, —NH($C_1$-$C_6$alkyl), or —N($C_1$-$C_6$alkyl)$_2$, and wherein the heterocyclyl is optionally substituted with D, halogen, $C_1$-$C_6$alkyl, —OR$^6$, —NH$_2$, —NH($C_1$-$C_6$alkyl), or —N($C_1$-$C_6$alkyl)$_2$.

17. The compound of claim 1, or a pharmaceutically acceptable salt, solvate, or tautomer thereof, wherein $R^1$ is

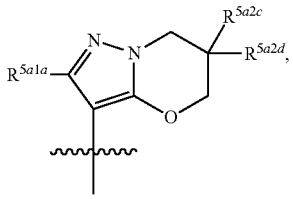

wherein:
$R^{5a1a}$ is H, D, halogen, —OH, —CN, —NO$_2$, —SR$^6$, —OR$^6$, —NR$^6$R$^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —CH$_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —CH$_2$—$C_3$-$C_8$cycloalkyl are optionally substituted with D, halogen, $C_1$-$C_6$alkyl, —OR$^6$, —NH$_2$, —NH($C_1$-$C_6$alkyl), or —N($C_1$-$C_6$alkyl)$_2$;
$R^{5a2c}$ and $R^{5a2d}$ are each independently H, D, halogen, —OH, —CN, —NO$_2$, —SR$^6$, —OR$^6$, —NHR$^6$, NR$^6$R$^7$, $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, or —CH$_2$—$C_3$-$C_8$cycloalkyl; wherein the $C_1$-$C_6$alkyl, $C_2$-$C_6$alkenyl, $C_4$-$C_8$cycloalkenyl, $C_2$-$C_6$alkynyl, $C_3$-$C_8$cycloalkyl, heterocyclyl, aryl, heteroaryl, and —CH$_2$—$C_3$-$C_8$cycloalkyl are optionally substituted with D, halogen, $C_1$-$C_6$alkyl, —OR$^6$, —NH$_2$, —NH($C_1$-$C_6$alkyl), or —N($C_1$-$C_6$alkyl)$_2$; or
$R^{5a2c}$ and $R^{5a2d}$ together with the atom to which they are attached can form $C_3$-$C_8$cycloalkyl or heterocyclyl; wherein the heterocyclyl contains 1-3 heteroatoms selected from the group consisting of N, S, P and O; wherein the $C_3$-$C_8$cycloalkyl and heterocyclyl are optionally substituted with D, halogen, $C_1$-$C_6$alkyl, —OR$^6$, —NH$_2$, —NH($C_1$-$C_6$alkyl), or —N($C_1$-$C_6$alkyl)$_2$; or
$R^{5a2c}$ and $R^{5a2d}$ can form an oxo group.

18. The compound of claim 17, or a pharmaceutically acceptable salt, solvate, or tautomer thereof, wherein each $R^{5a2c}$ and $R^{5a2d}$ is independently H, halogen, —OH, —OR$^6$, —NR$^6$R$^7$, C$_1$-C$_6$alkyl, C$_3$-C$_8$cycloalkyl, heterocyclyl, aryl, heteroaryl, or —CH$_2$—C$_3$-C$_8$cycloalkyl.

19. The compound of claim 17, or a pharmaceutically acceptable salt, solvate, or tautomer thereof, wherein $R^{5a2c}$ and $R^{5a2d}$ together with the atom to which they are attached form C$_3$-C$_8$cycloalkyl or heterocyclyl.

20. The compound of claim 1, or a pharmaceutically acceptable salt, solvate, or tautomer thereof, wherein R$^1$ is

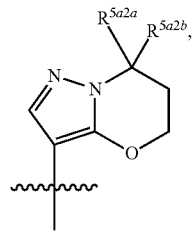

wherein:
$R^{5a2a}$ and $R^{5a2b}$ are each independently H, D, halogen, —OH, —CN, —NO$_2$, —SR$^6$, —OR$^6$, —NHR$^6$, —NR$^6$R$^7$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, halogen, C$_1$-C$_6$alkyl, —OR$^6$, —NH2, —NH(C$_1$-C$_6$alkyl), or —N(C$_1$-C$_6$alkyl)$_2$; or $R^{5a2a}$ and $R^{5a2b}$ together with the atom to which they are attached can form C$_3$-C$_8$cycloalkyl or heterocyclyl; wherein the heterocyclyl contains 1-3 heteroatoms selected from the group consisting of N, S, P and O; wherein the C$_3$-C$_8$cycloalkyl and heterocyclyl are optionally substituted with D, halogen, C$_1$-C$_6$alkyl, —OR$^6$, —NH2, —NH(C$_1$-C$_6$alkyl), or —N(C$_1$-C$_6$alkyl)$_2$; or $R^{5a2a}$ and $R^{5a2b}$ can form an oxo group.

21. The compound of claim 20, or a pharmaceutically acceptable salt, solvate, or tautomer thereof, wherein each $R^{5a2a}$ and $R^{5a2b}$ is independently H, halogen, —OH, —OR$^6$, —NR$^6$R$^7$, C$_1$-C$_6$alkyl, C$_3$-C$_8$cycloalkyl, heterocyclyl, aryl, heteroaryl, or —CH$_2$—C$_3$-C$_8$cycloalkyl.

22. The compound of claim 20, or a pharmaceutically acceptable salt, solvate, or tautomer thereof, wherein $R^{5a2a}$ and $R^{5a2b}$ together with the atom to which they are attached form C$_3$-C$_8$cycloalkyl or heterocyclyl.

23. The compound of claim 1, or a pharmaceutically acceptable salt, solvate, or tautomer thereof, wherein R$^1$ is

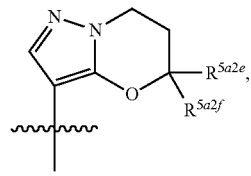

wherein
$R^{5a2e}$ and $R^{5a2f}$ are each independently H, D, halogen, —OH, —CN, —NO$_2$, —SR$^6$, —OR$^6$, —NHR$^6$, —NR$^6$R$^7$, C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, or —CH$_2$—C$_3$-C$_8$cycloalkyl; wherein the C$_1$-C$_6$alkyl, C$_2$-C$_6$alkenyl, C$_4$-C$_8$cycloalkenyl, C$_2$-C$_6$alkynyl, C$_3$-C$_8$cycloalkyl, heterocyclyl, aryl, heteroaryl, and —CH$_2$—C$_3$-C$_8$cycloalkyl are optionally substituted with D, halogen, C$_1$-C$_6$alkyl, —OR$^6$, —NH$_2$, —NH(C$_1$-C$_6$alkyl), or —N(C$_1$-C$_6$alkyl)$_2$; or $R^{5a2e}$ and $R^{5a2f}$ together with the atom to which they are attached can form C$_3$-C$_8$cycloalkyl or heterocyclyl; wherein the heterocyclyl contains 1-3 heteroatoms selected from the group consisting of N, S, P and O; wherein the C$_3$-C$_8$cycloalkyl and heterocyclyl are optionally substituted with D, halogen, C$_1$-C$_6$alkyl, —OR$^6$, —NH2, —NH(C$_1$-C$_6$alkyl), or —N(C$_1$-C$_6$alkyl)$_2$; or $R^{5a2e}$ and $R^{5a2f}$ can form an oxo group.

24. The compound of claim 23, or a pharmaceutically acceptable salt, solvate, or tautomer thereof, wherein each $R^{5a2e}$ and $R^{5a2f}$ is independently H, halogen, —OH, —OR$^6$, —NR$^6$R$^7$, C$_1$-C$_6$alkyl, C$_3$-C$_8$cycloalkyl, heterocyclyl, aryl, heteroaryl, or —CH$_2$—C$_3$-C$_8$cycloalkyl.

25. The compound of claim 23, or a pharmaceutically acceptable salt, solvate, or tautomer thereof, wherein $R^{5a2e}$ and $R^{5a2f}$ together with the atom to which they are attached form C$_3$-C$_8$cycloalkyl or heterocyclyl.

26. The compound of claim 1, or a pharmaceutically acceptable salt, solvate, or tautomer thereof, wherein R$^1$ is selected from the group consisting of:

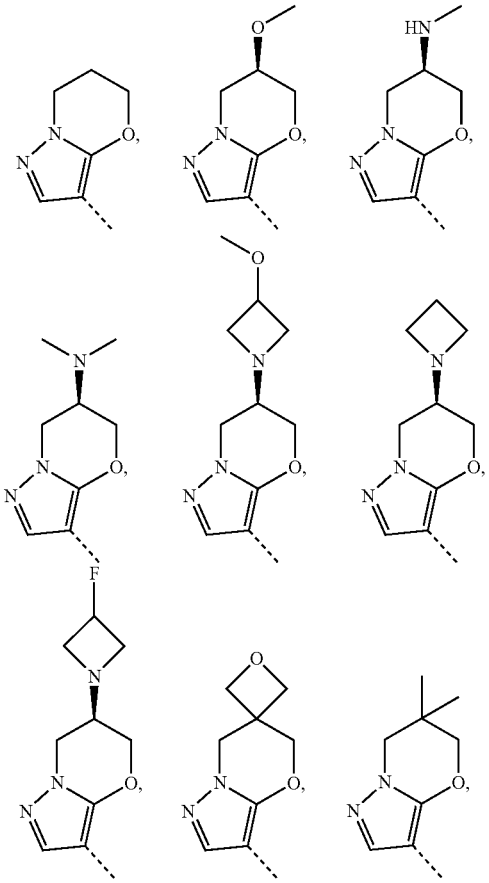

-continued

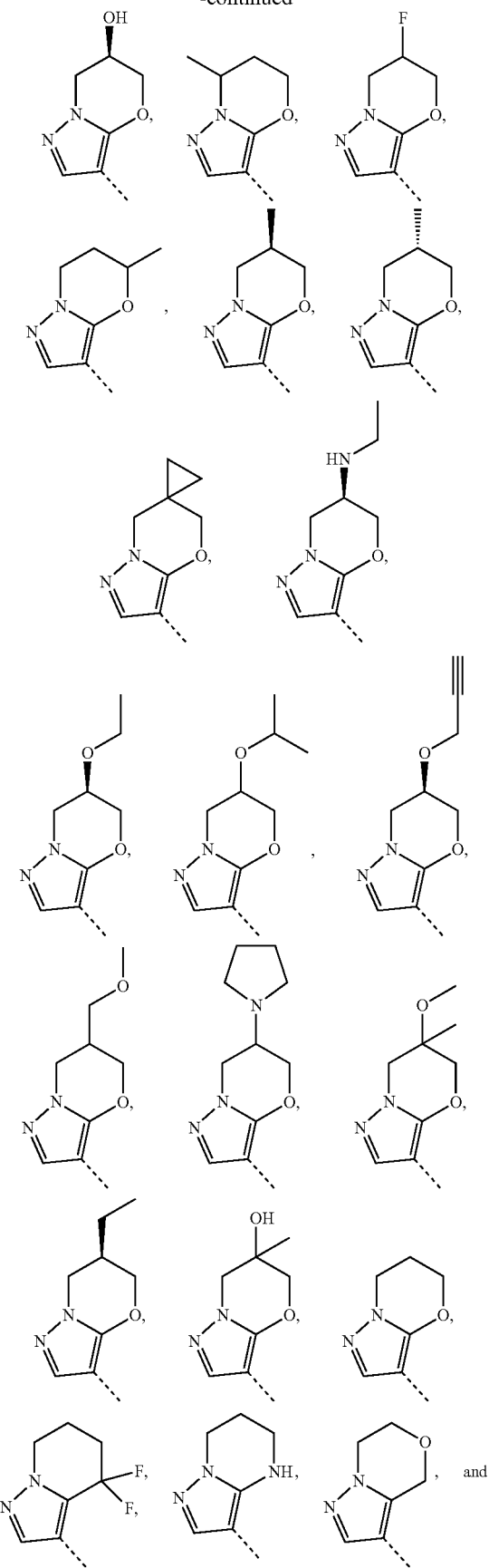

-continued

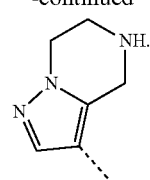

27. The compound of claim 1, or a pharmaceutically acceptable salt, solvate, or tautomer thereof, wherein R¹ is selected from the group consisting of

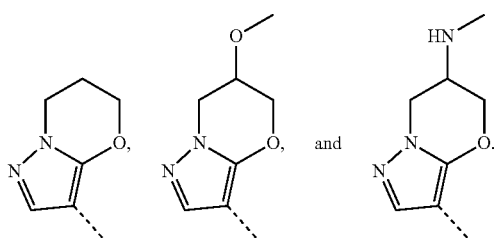

28. The compound of claim 1, or a pharmaceutically acceptable salt, solvate, or tautomer thereof, wherein X¹ is O.

29. A pharmaceutical composition comprising a compound of claim 1, or a pharmaceutically acceptable salt, solvate, or tautomer thereof, and a pharmaceutically acceptable carrier.

30. The compound of claim 1, wherein the compound is:

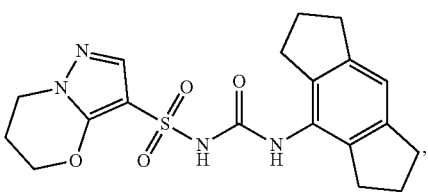

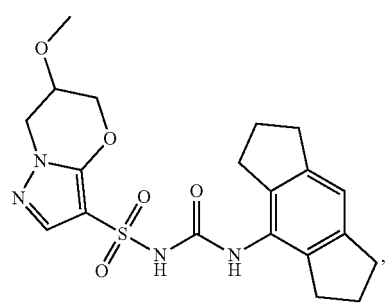

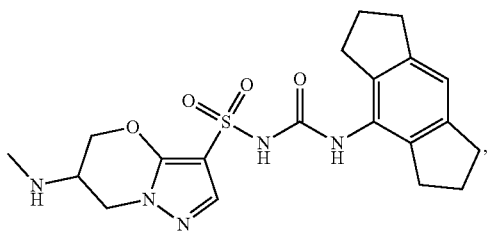

-continued

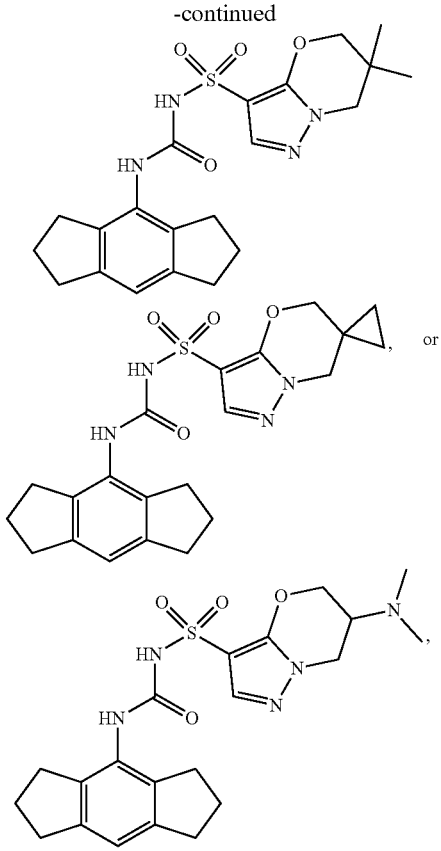

or a pharmaceutically acceptable salt, solvate, or tautomer thereof.

31. The compound of claim 1, wherein the compound is:

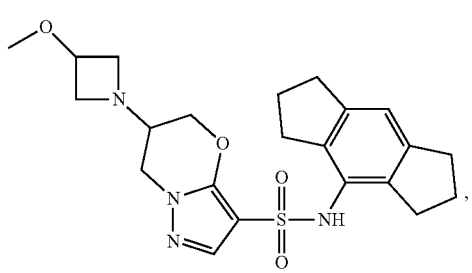 [SMILES: COC1CN(C2COc3c(S(=O)(=O)Nc4c5c(cc6c4CCC6)CCC5)cnn3C2)C1 ; ","]

or a pharmaceutically acceptable salt, solvate, or tautomer thereof.

32. The compound of claim 1, wherein the compound is

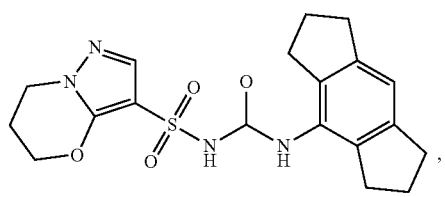 [SMILES: O=S(=O)(NC(O)Nc1c2c(cc3c1CCC3)CCC2)c1cnn2c1OCCC2]

or a pharmaceutically acceptable salt, solvate, or tautomer thereof.

33. The compound of claim 1, wherein the compound is

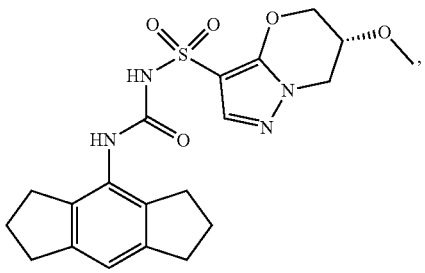 [SMILES: CO[C@H]1COc2c(S(=O)(=O)NC(=O)Nc3c4c(cc5c3CCC5)CCC4)cnn2C1]

or a pharmaceutically acceptable salt, solvate, or tautomer thereof.

34. The compound of claim 1, wherein the compound is

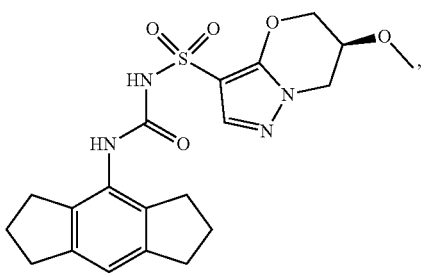 [SMILES: CO[C@@H]1COc2c(S(=O)(=O)NC(=O)Nc3c4c(cc5c3CCC5)CCC4)cnn2C1]

or a pharmaceutically acceptable salt, solvate, or tautomer thereof.

35. The compound of claim 1, wherein the compound is

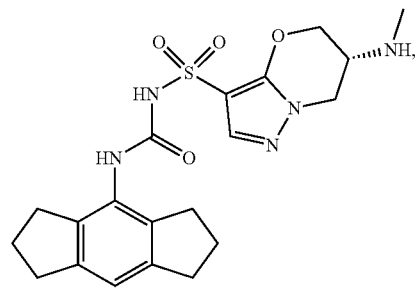 [SMILES: CN[C@H]1COc2c(S(=O)(=O)NC(=O)Nc3c4c(cc5c3CCC5)CCC4)cnn2C1]

or a pharmaceutically acceptable salt, solvate, or tautomer thereof.

36. The compound of claim 1, wherein the compound is

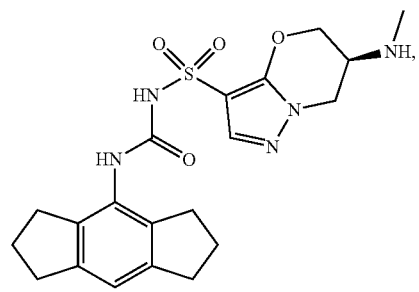 [SMILES: CN[C@@H]1COc2c(S(=O)(=O)NC(=O)Nc3c4c(cc5c3CCC5)CCC4)cnn2C1]

or a pharmaceutically acceptable salt, solvate, or tautomer thereof.

37. The compound of claim 1, wherein the compound is

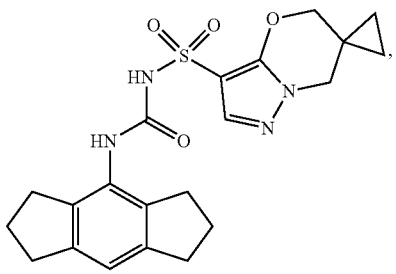 [SMILES: O=C(Nc1c2c(cc3c1CCC3)CCC2)NS(=O)(=O)c1cnn2c1OCC1(CC1)C2]

or a pharmaceutically acceptable salt, solvate, or tautomer thereof.

38. The compound of claim 1, wherein the compound is

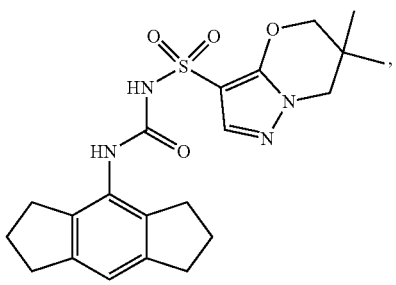 [SMILES: CC1(C)COc2c(S(=O)(=O)NC(=O)Nc3c4c(cc5c3CCC5)CCC4)cnn2C1]

or a pharmaceutically acceptable salt, solvate, or tautomer thereof.

39. The compound of claim 1, wherein the compound is

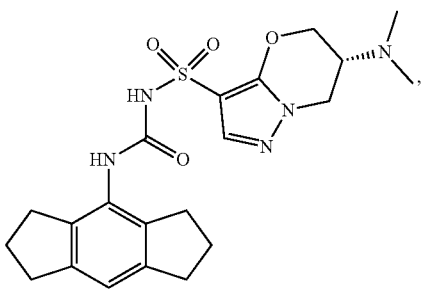 [SMILES: CN(C)[C@H]1COc2c(S(=O)(=O)NC(=O)Nc3c4c(cc5c3CCC5)CCC4)cnn2C1]

or a pharmaceutically acceptable salt, solvate, or tautomer thereof.

40. The compound of claim 1, wherein the compound is

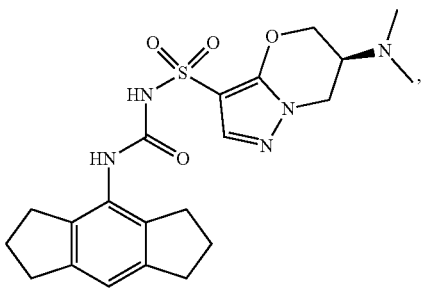 [SMILES: CN(C)[C@@H]1COc2c(S(=O)(=O)NC(=O)Nc3c4c(cc5c3CCC5)CCC4)cnn2C1]

or a pharmaceutically acceptable salt, solvate, or tautomer thereof.

41. The compound of claim 1, wherein the compound is

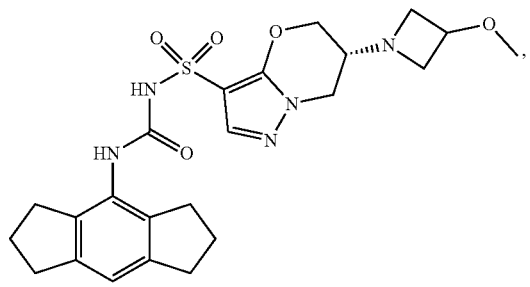 [SMILES: COC1CN([C@H]2COc3c(S(=O)(=O)NC(=O)Nc4c5c(cc6c4CCC6)CCC5)cnn3C2)C1]

or a pharmaceutically acceptable salt, solvate, or tautomer thereof.

42. The compound of claim 1, wherein the compound is

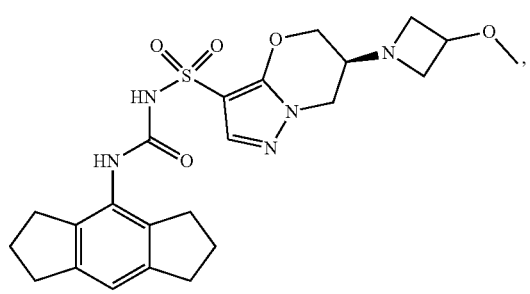 [SMILES: COC1CN([C@@H]2COc3c(S(=O)(=O)NC(=O)Nc4c5c(cc6c4CCC6)CCC5)cnn3C2)C1]

or a pharmaceutically acceptable salt, solvate, or tautomer thereof.

43. A pharmaceutical composition comprising a compound of claim 30, or a pharmaceutically acceptable salt, solvate, or tautomer thereof, and a pharmaceutically acceptable carrier.

44. A pharmaceutical composition comprising the compound of claim 31, or a pharmaceutically acceptable salt, solvate, or tautomer thereof, and a pharmaceutically acceptable carrier.

45. A pharmaceutical composition comprising the compound of claim 32, or a pharmaceutically acceptable salt, solvate, or tautomer thereof, and a pharmaceutically acceptable carrier.

46. A pharmaceutical composition comprising the compound of claim 33, or a pharmaceutically acceptable salt, solvate, or tautomer thereof, and a pharmaceutically acceptable carrier.

47. A pharmaceutical composition comprising the compound of claim 34, or a pharmaceutically acceptable salt, solvate, or tautomer thereof, and a pharmaceutically acceptable carrier.

48. A pharmaceutical composition comprising the compound of claim 35, or a pharmaceutically acceptable salt, solvate, or tautomer thereof, and a pharmaceutically acceptable carrier.

49. A pharmaceutical composition comprising the compound of claim 36, or a pharmaceutically acceptable salt, solvate, or tautomer thereof, and a pharmaceutically acceptable carrier.

50. A pharmaceutical composition comprising the compound of claim 37, or a pharmaceutically acceptable salt, solvate, or tautomer thereof, and a pharmaceutically acceptable carrier.

51. A pharmaceutical composition comprising the compound of claim 38, or a pharmaceutically acceptable salt, solvate, or tautomer thereof, and a pharmaceutically acceptable carrier.

52. A pharmaceutical composition comprising the compound of claim 39, or a pharmaceutically acceptable salt, solvate, or tautomer thereof, and a pharmaceutically acceptable carrier.

53. A pharmaceutical composition comprising the compound of claim 40, or a pharmaceutically acceptable salt, solvate, or tautomer thereof, and a pharmaceutically acceptable carrier.

54. A pharmaceutical composition comprising the compound of claim 41, or a pharmaceutically acceptable salt, solvate, or tautomer thereof, and a pharmaceutically acceptable carrier.

55. A pharmaceutical composition comprising the compound of claim 42, or a pharmaceutically acceptable salt, solvate, or tautomer thereof, and a pharmaceutically acceptable carrier.

56. The compound of claim 5, or a pharmaceutically acceptable salt, solvate, or tautomer thereof, wherein X is O and R¹ is

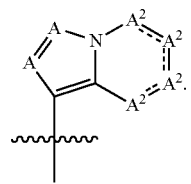

57. The compound of claim 6, or a pharmaceutically acceptable salt, solvate, or tautomer thereof, wherein X is O and R¹ is

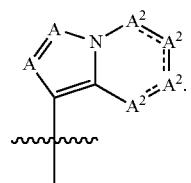

58. The compound of claim 1, wherein the compound is:

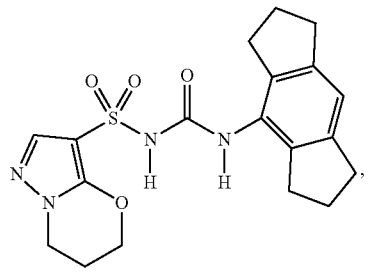

-continued

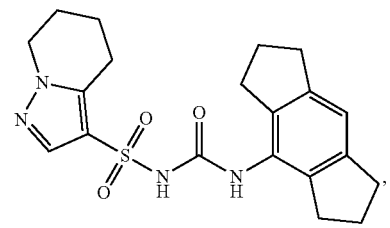

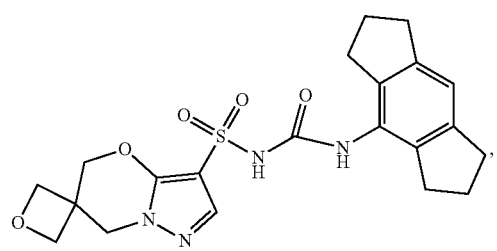

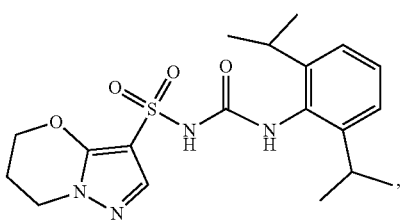

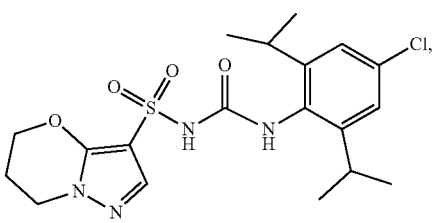

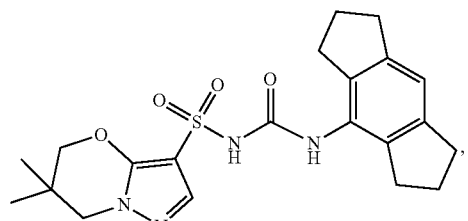

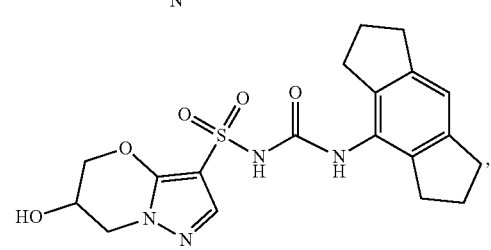

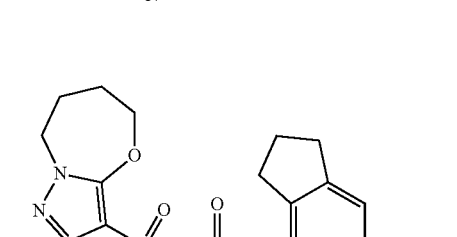

479
-continued
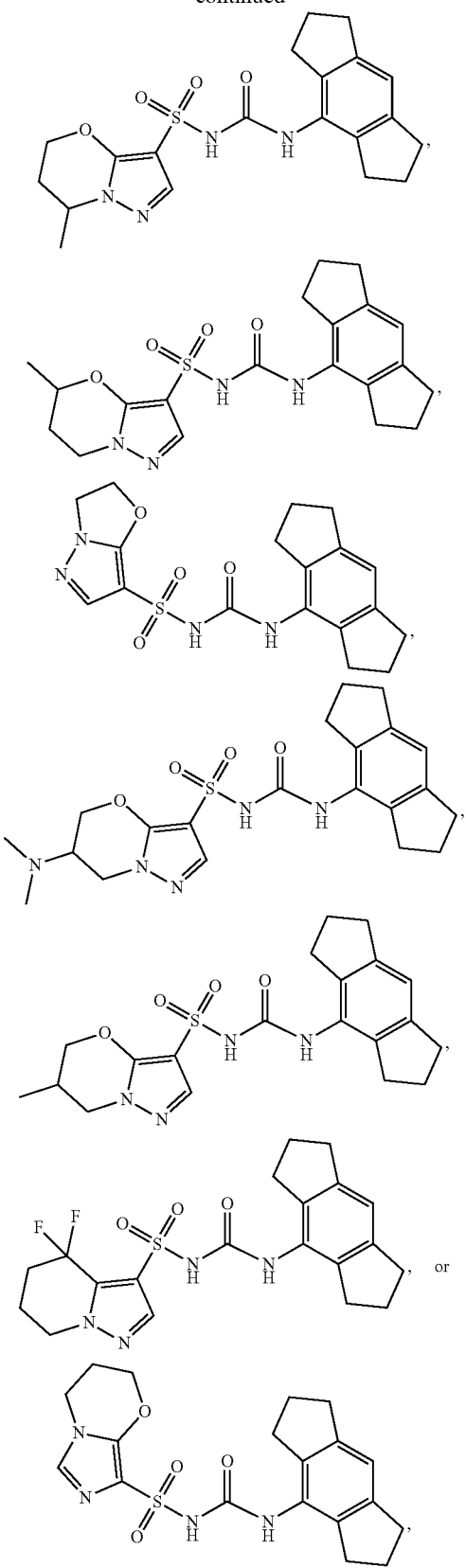
or a pharmaceutically acceptable salt, solvate, or tautomer thereof.
480
59. The compound of claim 1, wherein the compound is:
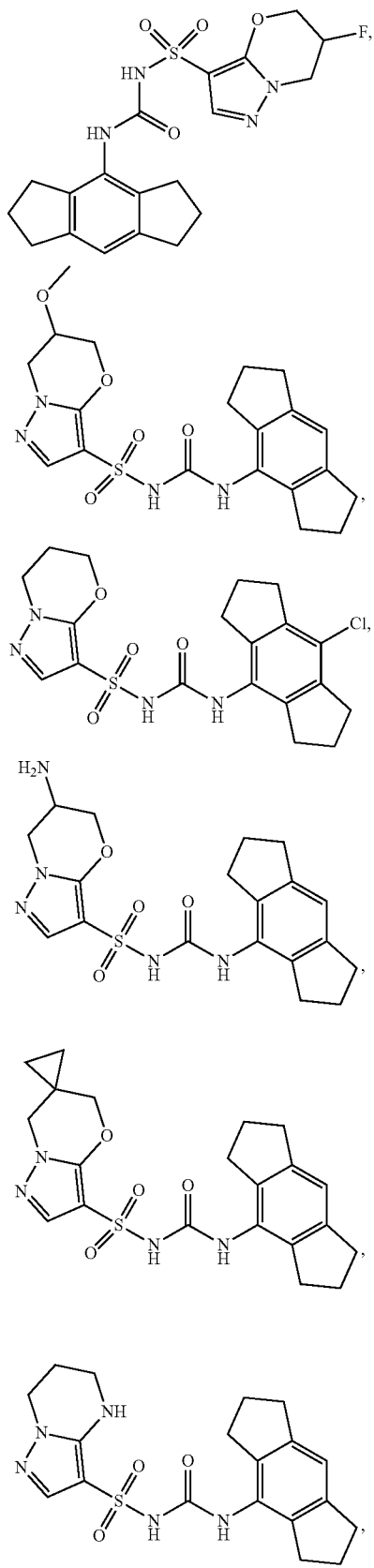

481
-continued
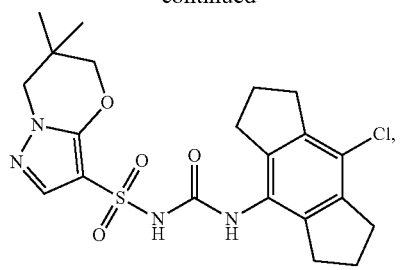
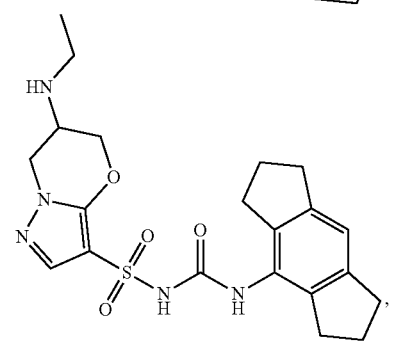
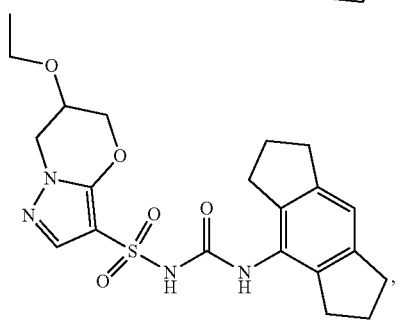
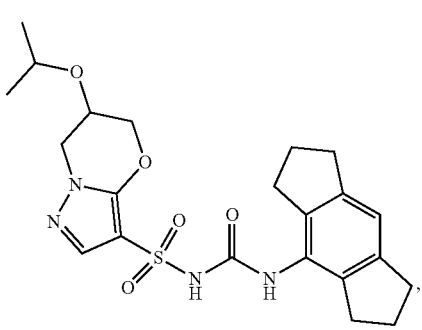
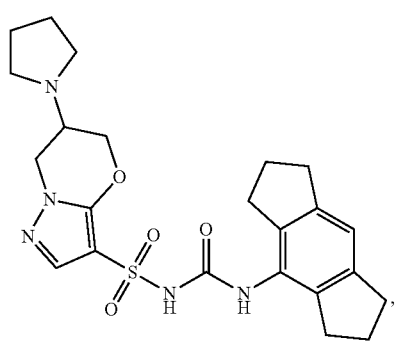
482
-continued
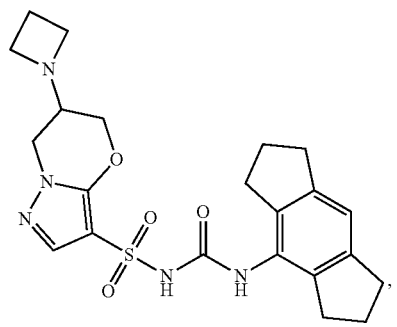
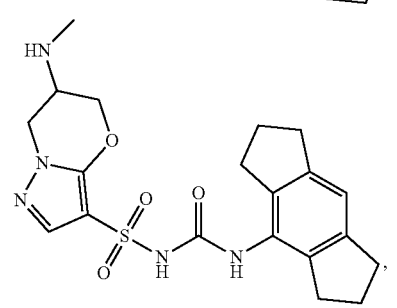
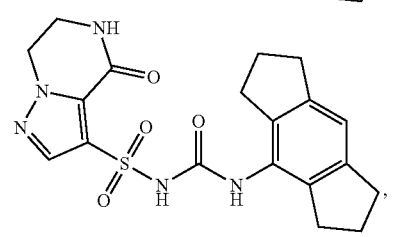
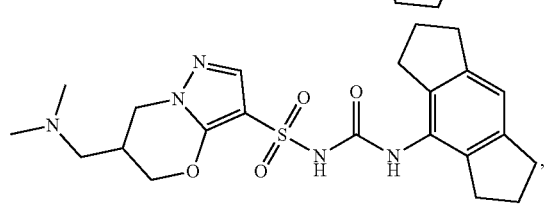
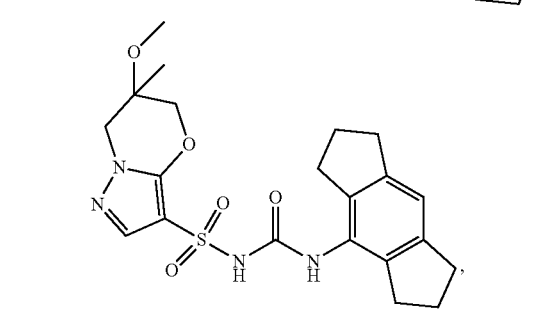
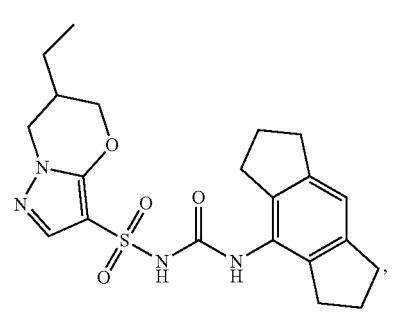

483
-continued
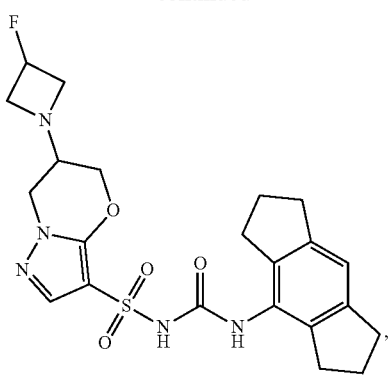
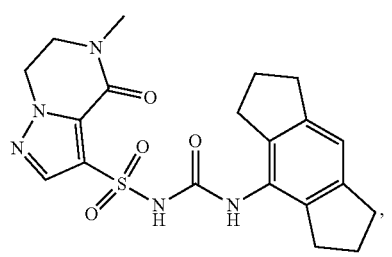
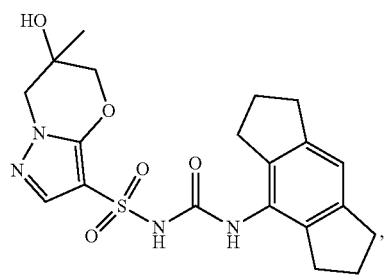
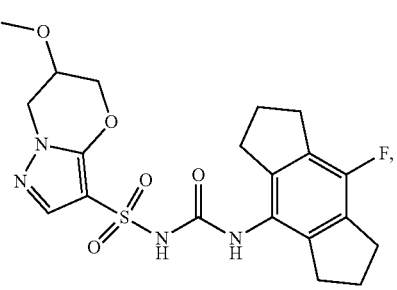
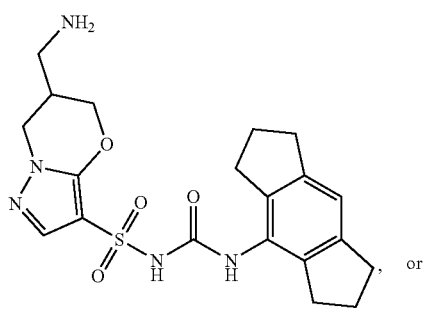, or
484
-continued
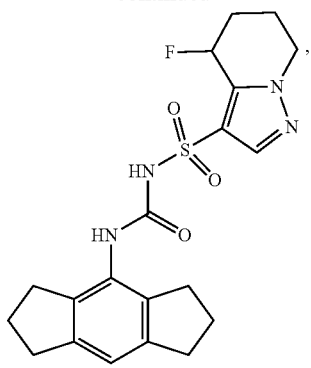
or a pharmaceutically acceptable salt, solvate, or tautomer thereof.
60. The compound of claim 1, wherein the compound is:
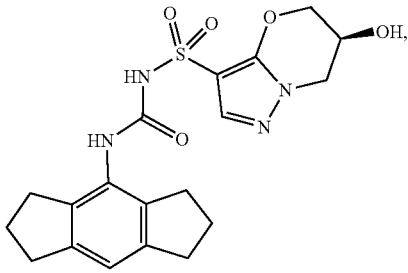
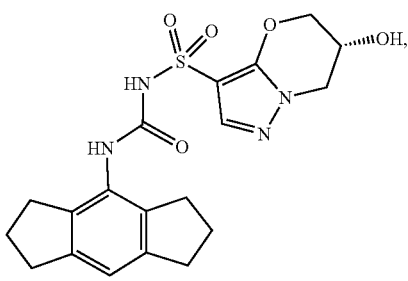
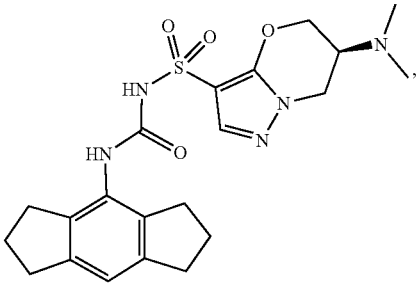
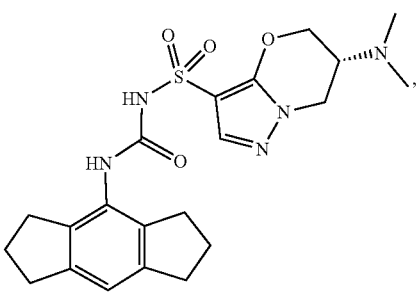

485
-continued
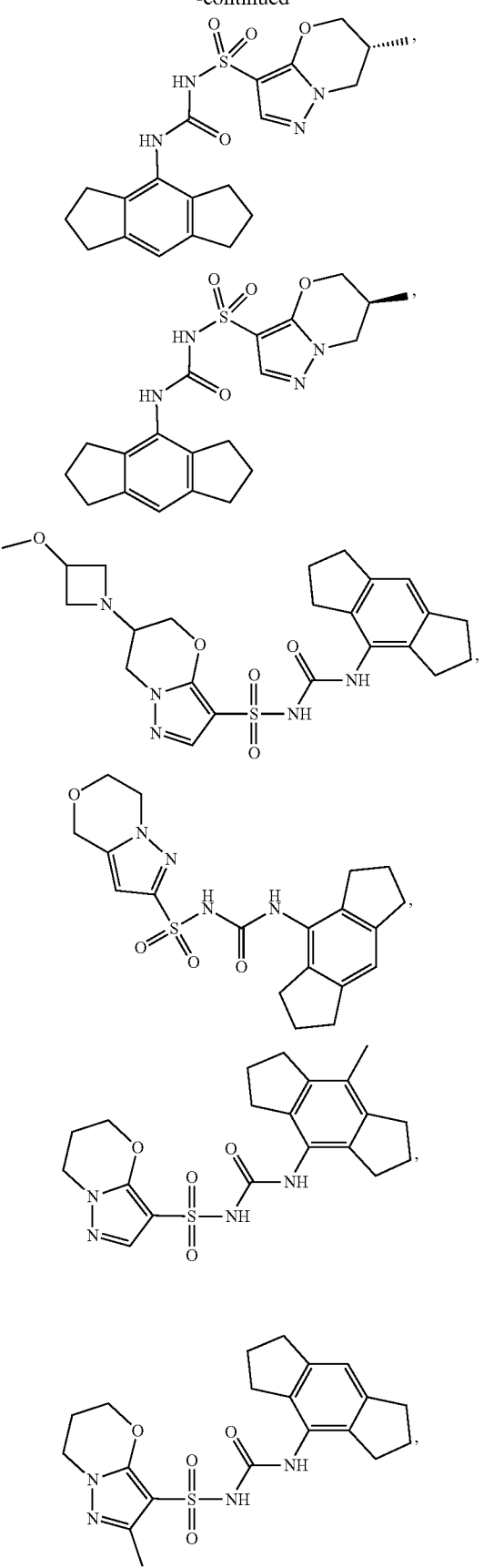
486
-continued
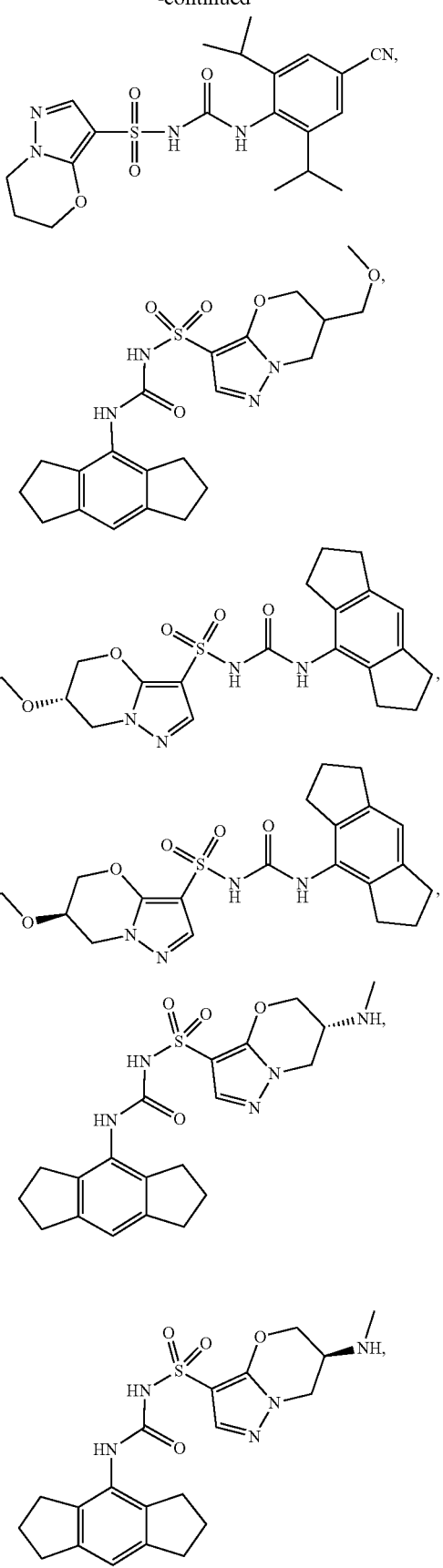

487
-continued
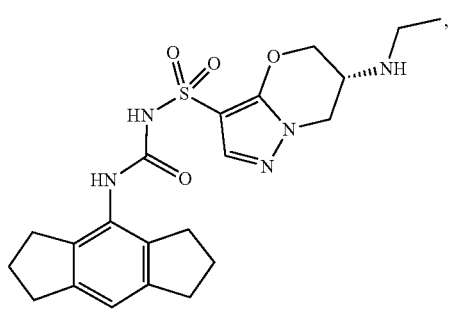
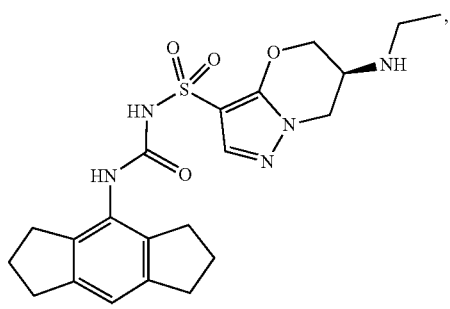
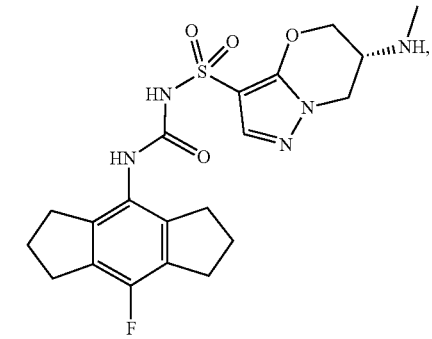
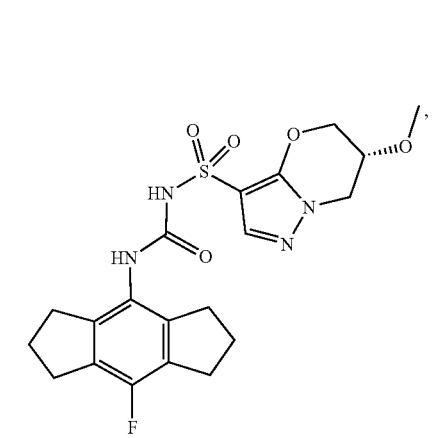
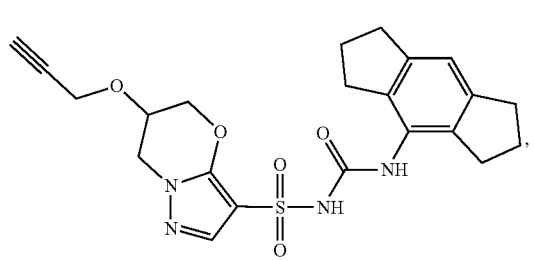
488
-continued
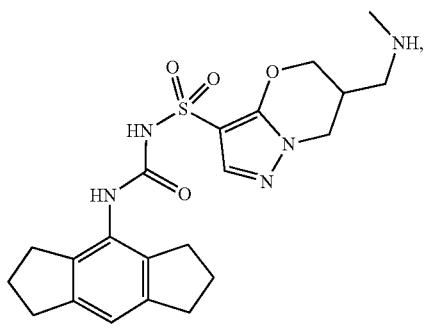
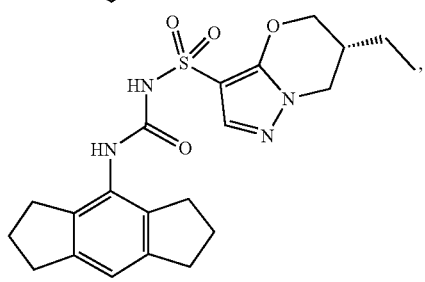
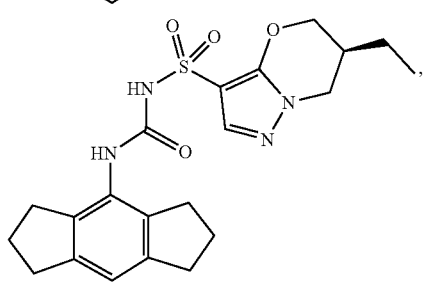
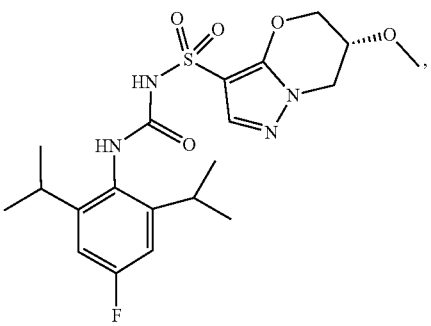
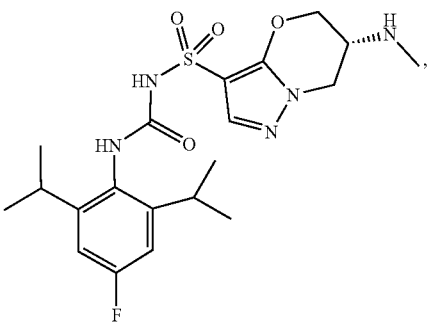

-continued

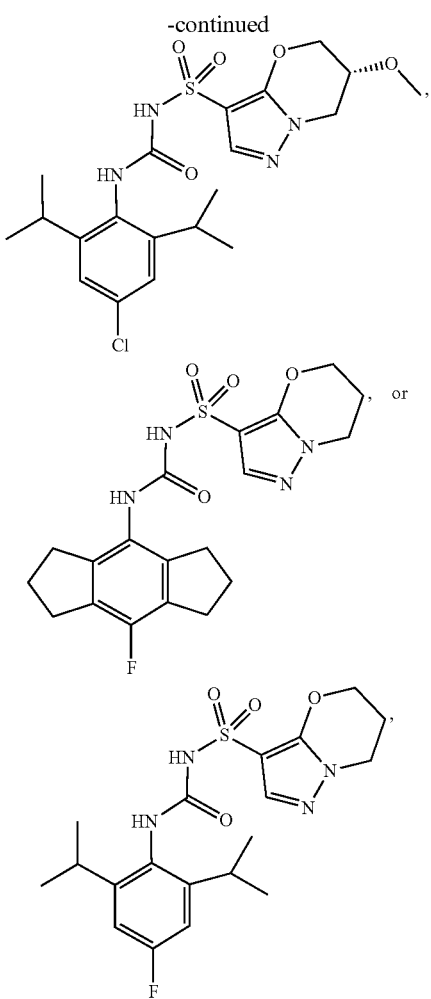

or a pharmaceutically acceptable salt, solvate, or tautomer thereof.

61. A pharmaceutical composition comprising a compound of claim 58, or a pharmaceutically acceptable salt, solvate, or tautomer thereof, and a pharmaceutically acceptable carrier.

62. A pharmaceutical composition comprising a compound of claim 59, or a pharmaceutically acceptable salt, solvate, or tautomer thereof, and a pharmaceutically acceptable carrier.

63. A pharmaceutical composition comprising a compound of claim 60, or a pharmaceutically acceptable salt, solvate, or tautomer thereof, and a pharmaceutically acceptable carrier.

64. The compound of claim 1, wherein the compound is

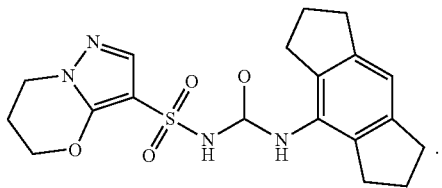 [SMILES: O=S(=O)(NC(O)Nc1c2c(cc3c1CCC3)CCC2)c1cnn2c1OCCC2]

65. The compound of claim 1, wherein the compound is

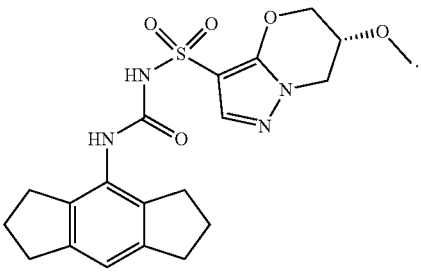 [SMILES: CO[C@H]1COc2c(S(=O)(=O)NC(=O)Nc3c4c(cc5c3CCC5)CCC4)cnn2C1]

66. The compound of claim 1, wherein the compound is

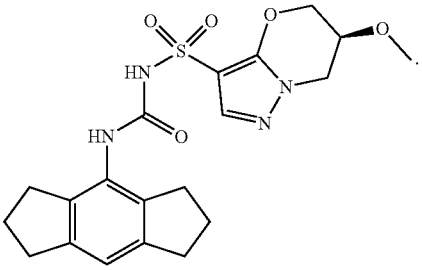 [SMILES: CO[C@@H]1COc2c(S(=O)(=O)NC(=O)Nc3c4c(cc5c3CCC5)CCC4)cnn2C1]

67. The compound of claim 1, wherein the compound is

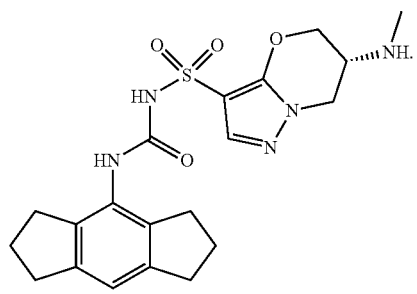 [SMILES: CN[C@H]1COc2c(S(=O)(=O)NC(=O)Nc3c4c(cc5c3CCC5)CCC4)cnn2C1]

68. The compound of claim 1, wherein the compound is

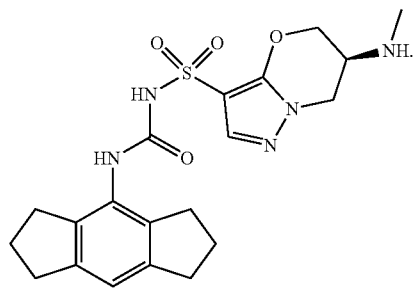 [SMILES: CN[C@@H]1COc2c(S(=O)(=O)NC(=O)Nc3c4c(cc5c3CCC5)CCC4)cnn2C1]

69. The compound of claim 1, wherein the compound is
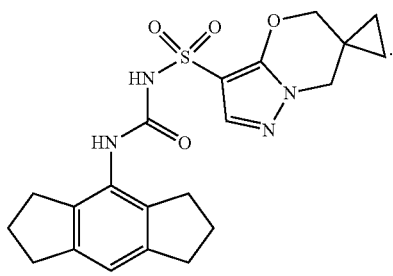 [SMILES: O=C(Nc1c2c(cc3c1CCC3)CCC2)NS(=O)(=O)c1cnn2c1OCC1(CC1)C2]
70. The compound of claim 1, wherein the compound is
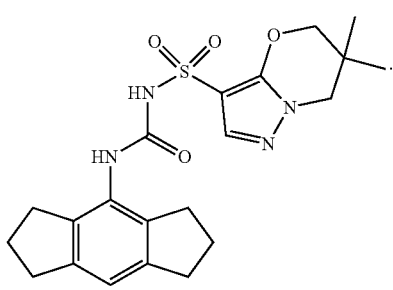 [SMILES: CC1(C)COc2c(S(=O)(=O)NC(=O)Nc3c4c(cc5c3CCC5)CCC4)cnn2C1]
71. The compound of claim 1, wherein the compound is
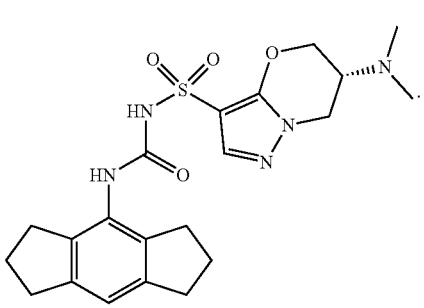 [SMILES: CN(C)[C@H]1COc2c(S(=O)(=O)NC(=O)Nc3c4c(cc5c3CCC5)CCC4)cnn2C1]
72. The compound of claim 1, wherein the compound is
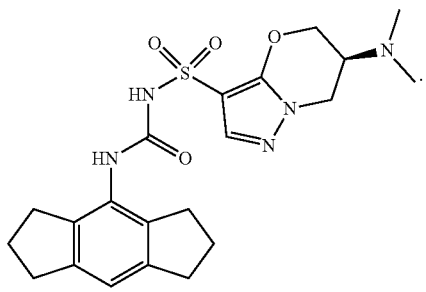 [SMILES: CN(C)[C@@H]1COc2c(S(=O)(=O)NC(=O)Nc3c4c(cc5c3CCC5)CCC4)cnn2C1]
73. The compound of claim 1, wherein the compound is
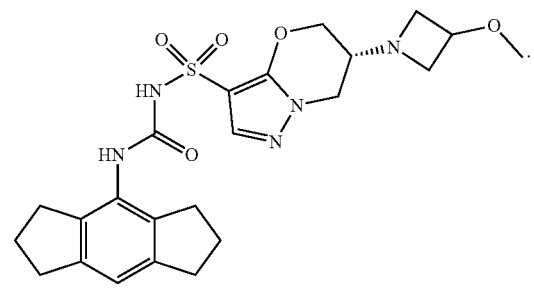 [SMILES: COC1CN([C@H]2COc3c(S(=O)(=O)NC(=O)Nc4c5c(cc6c4CCC6)CCC5)cnn3C2)C1]
74. The compound of claim 1, wherein the compound is
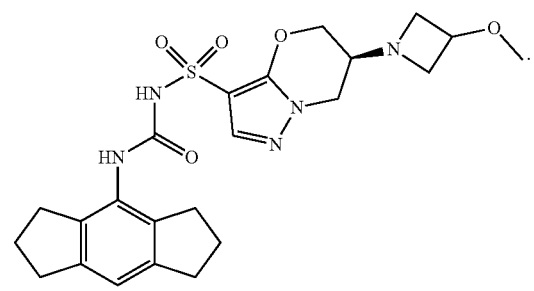 [SMILES: COC1CN([C@@H]2COc3c(S(=O)(=O)NC(=O)Nc4c5c(cc6c4CCC6)CCC5)cnn3C2)C1]
\* \* \* \* \*

UNITED STATES PATENT AND TRADEMARK OFFICE
CERTIFICATE OF CORRECTION

PATENT NO. : 11,040,985 B2
APPLICATION NO. : 16/513621
DATED : June 22, 2021
INVENTOR(S) : Jeffrey A. Stafford et al.

It is certified that error appears in the above-identified patent and that said Letters Patent is hereby corrected as shown below:

In the Claims

Claim 1, Column 463, Line 46, please delete:
"-N($C_1$-$C_6$alkyl);"
And insert:
-- -N($C_1$-$C_6$alkyl)$_2$; --

Claim 2, Column 465, Line 8, please delete:

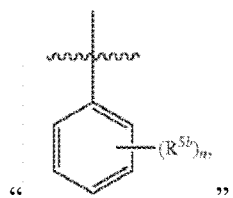
"                              "

And insert:

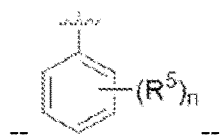
--                              --

Claim 2, Column 465, Line 14, please delete:
"-$OR^6$, -$NR^6R^7$,"
And insert:
-- -$OR^6$, -$NHR^6$, -$NR^6R^7$, --

Claim 8, Column 466, Line 17, please delete:
"$NO_2$, $OR^6$,"
And insert:
-- -$NO_2$, -$OR^6$, --

Signed and Sealed this
Twenty-sixth Day of September, 2023

*Katherine Kelly Vidal*
*Director of the United States Patent and Trademark Office*

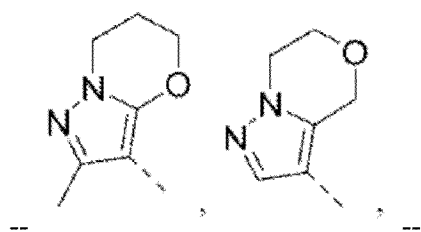

Claim 12, Column 467, Line 27, please delete:
"-NR⁶"
And insert:
-- -NHR⁶ --
Claim 20, Column 469, Line 35, please delete:
"-NH2,"
And insert:
-- -NH$_2$, --
Claim 20, Column 469, Line 44, please delete:
"-NH2,"
And insert:
-- -NH$_2$, --
Claim 23, Column 470, Line 18, please delete:
"-NH2,"
And insert:
-- -NH$_2$, --
Claim 26, Column 471, Lines 55-60, please delete:
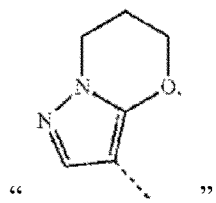
And insert: